United States Patent
Mitra et al.

(10) Patent No.: US 11,365,233 B2
(45) Date of Patent: Jun. 21, 2022

(54) ACTIVATABLE CYTOKINE CONSTRUCTS AND RELATED COMPOSITIONS AND METHODS

(71) Applicant: CytomX Therapeutics, Inc., South San Francisco, CA (US)

(72) Inventors: Sayantan Mitra, Mountain View, CA (US); Nicole G. Lapuyade, San Francisco, CA (US); Hikmat Haizar Assi, San Pablo, CA (US); Madan M. Paidhungat, San Francisco, CA (US); Dylan L. Daniel, San Francisco, CA (US); Erwan Le Scolan, San Francisco, CA (US); Walter A. Bogdanoff, Rio Vista, CA (US); Na Cai, San Mateo, CA (US); Hsin Wang, San Mateo, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/227,017

(22) Filed: Apr. 9, 2021

(65) Prior Publication Data
US 2021/0317177 A1 Oct. 14, 2021

Related U.S. Application Data

(60) Provisional application No. 63/008,542, filed on Apr. 10, 2020, provisional application No. 63/161,889, filed on Mar. 16, 2021, provisional application No. 63/164,849, filed on Mar. 23, 2021.

(51) Int. Cl.
*C07K 14/56* (2006.01)

(52) U.S. Cl.
CPC ......... *C07K 14/56* (2013.01); *C07K 2319/02* (2013.01); *C07K 2319/30* (2013.01)

(58) Field of Classification Search
CPC . C07K 14/56; C07K 2319/02; C07K 2319/30
See application file for complete search history.

(56) References Cited

U.S. PATENT DOCUMENTS

| | | | |
|---|---|---|---|
| 5,030,719 A | 7/1991 | Umemeto et al. | |
| 5,731,168 A | 3/1998 | Carter et al. | |
| 7,465,790 B2 | 12/2008 | Waldmann et al. | |
| 7,695,936 B2 | 4/2010 | Carter et al. | |
| 8,399,219 B2 | 3/2013 | Stagliano et al. | |
| 8,513,390 B2 | 8/2013 | Stagliano et al. | |
| 8,518,404 B2 | 8/2013 | Daugherty et al. | |
| 8,529,898 B2 | 9/2013 | Daugherty et al. | |
| 8,541,203 B2 | 9/2013 | Daugherty et al. | |
| 8,563,269 B2 | 10/2013 | Stagliano et al. | |
| 8,734,774 B2 | 5/2014 | Frelinger et al. | |
| 8,809,504 B2 | 8/2014 | Lauermann | |
| 8,993,266 B2 | 3/2015 | Stagliano et al. | |
| 9,169,321 B2 | 10/2015 | Daugherty et al. | |
| 9,453,078 B2 | 9/2016 | Stagliano et al. | |
| 9,644,016 B2 | 5/2017 | Stagliano et al. | |
| 9,675,672 B2 | 6/2017 | Tagaya | |
| 10,059,762 B2 | 8/2018 | Stagliano et al. | |
| 10,077,300 B2 | 9/2018 | Daugherty et al. | |
| 10,118,961 B2 | 11/2018 | Stagliano et al. | |
| 10,513,549 B2 | 12/2019 | Stagliano et al. | |
| 10,683,368 B2 | 6/2020 | Moessner et al. | |
| 10,696,723 B2 | 6/2020 | Winston et al. | |
| 10,696,724 B2 | 6/2020 | Winston et al. | |
| 10,875,913 B2 | 12/2020 | Stagliano et al. | |
| 11,028,162 B2 | 6/2021 | Daugherty et al. | |
| 2004/0109855 A1 | 6/2004 | Waldmann et al. | |
| 2006/0024272 A1 | 2/2006 | Reinl et al. | |
| 2006/0269516 A1* | 11/2006 | Presta ..................... | A61P 31/18 424/85.4 |

(Continued)

FOREIGN PATENT DOCUMENTS

| | | |
|---|---|---|
| EP | 1523503 | 4/2009 |
| EP | 1324771 | 6/2011 |

(Continued)

OTHER PUBLICATIONS

Wagner B et al: "Horse cytokine/IgG fusion proteins—mammalian expression of biologically active cytokines and a system to verify antibody specificity to equine cytokines", Veterinary Immunology and Immunopathology, Elsevier BV, Amsterdam, NL, vol. 105, No. 1-2, May 1, 2005 (May 1, 2005), pp. 1-14, XP027671923.

Jazayeri, J A et al: "Fc-based cytokines: Prospects for engineering superior therapeutics", Biodrugs, ADIS International Ltd, NZ, vol. 22, No. 1, Jan. 1, 2008 (Jan. 1, 2008), pp. 11-26, XP009148905.

Le Scolan, Erwan: "Conditional Cytokine Therapeutics for Tumor-Selective Biological Activity—Preclinical characterization of a dual-masked IFN[alpha]-2b", , Mar. 24, 2021 (Mar. 24, 2021), pp. 1-14, XP055819390.

Written Opinion and International Search Report issued in PCT/US2021/026675 dated Sep. 2, 2021, 26 pages.

Akbar, A. N., Lord, J. M. and Salmon, M. (2000) 'IFN-α and IFN-β: A link between immune memory and chronic inflammation', Immunology Today, 21(7), pp. 337-342. doi: 10.1016/S0167-5699(00)01652-2.

(Continued)

*Primary Examiner* — Ruixiang Li
(74) *Attorney, Agent, or Firm* — Rothwell, Figg, Ernst & Manbeck, P.C.

(57) ABSTRACT

Provided herein are activatable cytokine constructs that include: (a) a first monomer construct comprising a first mature cytokine protein (CP1), a first cleavable moiety (CM1), and a first dimerization domain (DD1), wherein the CM1 is positioned between the CP1 and the DD1; and (b) a second monomer construct comprising a second mature cytokine protein (CP2), a second cleavable moiety (CM2), and a second dimerization domain (DD2), where the CM2 is positioned between the CP2 and the DD2, where: the CM1 and the CM2 function as a substrate for a protease; the DD1 and the DD2 bind each other; and where the ACC is characterized by a reduction in at least one activity of the CP1 and/or CP2 as compared to a control level of the at least one activity of the CP1 and/or CP2.

29 Claims, 34 Drawing Sheets

Specification includes a Sequence Listing.

(56) References Cited

U.S. PATENT DOCUMENTS

| | | |
|---|---|---|
| 2009/0025106 A1 | 1/2009 | Reinl et al. |
| 2009/0304719 A1 | 12/2009 | Daugherty et al. |
| 2010/0189651 A1 | 7/2010 | Stagliano et al. |
| 2010/0297081 A1 | 11/2010 | Huang et al. |
| 2012/0149061 A1 | 6/2012 | Stagliano et al. |
| 2012/0207756 A1 | 8/2012 | Stagliano et al. |
| 2012/0237512 A1 | 9/2012 | Daugherty et al. |
| 2012/0244154 A1 | 9/2012 | Daugherty et al. |
| 2013/0309230 A1 | 11/2013 | Stagliano et al. |
| 2014/0024810 A1 | 1/2014 | Stagliano et al. |
| 2014/0045195 A1 | 2/2014 | Daugherty et al. |
| 2016/0122425 A1 | 5/2016 | Daugherty et al. |
| 2016/0228546 A1 | 8/2016 | Stagliano et al. |
| 2016/0289324 A1 | 10/2016 | Moore et al. |
| 2017/0051015 A1 | 2/2017 | Tagaya et al. |
| 2017/0081397 A1 | 3/2017 | Stagliano et al. |
| 2019/0119370 A1 | 4/2019 | Stagliano et al. |
| 2019/0211089 A1 | 7/2019 | Daugherty et al. |
| 2019/0216898 A1 | 7/2019 | Wang et al. |
| 2019/0284283 A1 | 9/2019 | Moore et al. |
| 2019/0315883 A1 | 10/2019 | Ast et al. |
| 2020/0040052 A1 | 2/2020 | Winston et al. |
| 2020/0283490 A1 | 9/2020 | Winston et al. |
| 2020/0392235 A1 | 12/2020 | Lu et al. |
| 2021/0002343 A1 | 1/2021 | Karow et al. |
| 2021/0115102 A1 | 4/2021 | Winston et al. |
| 2021/0130430 A1 | 5/2021 | Winston et al. |
| 2021/0139553 A1 | 5/2021 | Li et al. |
| 2021/0187027 A1 | 6/2021 | Wu et al. |
| 2021/0188934 A1 | 6/2021 | Wu et al. |
| 2021/0237977 A1 | 8/2021 | Lindley et al. |

FOREIGN PATENT DOCUMENTS

| | | |
|---|---|---|
| WO | 1994011026 | 5/1994 |
| WO | 200191798 | 6/2001 |
| WO | 02/02143 A2 | 1/2002 |
| WO | 2002030460 A2 | 4/2002 |
| WO | 02/055098 A2 | 7/2002 |
| WO | 2004009638 A1 | 1/2004 |
| WO | 2007105027 | 9/2007 |
| WO | 2009025846 A2 | 2/2009 |
| WO | 2010081173 | 7/2010 |
| WO | 2010096838 A2 | 8/2010 |
| WO | 2012072815 A1 | 6/2012 |
| WO | 2015048329 | 4/2015 |
| WO | 2015116933 | 8/2015 |
| WO | 2015/198072 A1 | 12/2015 |
| WO | 2015198072 | 12/2015 |
| WO | 2016/118629 A1 | 7/2016 |
| WO | 2017190684 A1 | 11/2017 |
| WO | 2018/071919 A1 | 4/2018 |
| WO | 2018/236701 A1 | 12/2018 |
| WO | 2018236701 A1 | 12/2018 |
| WO | 2019091384 A1 | 5/2019 |
| WO | 2019092181 A1 | 5/2019 |
| WO | 2019126240 A1 | 7/2019 |
| WO | 2019173832 A2 | 9/2019 |
| WO | 2019222294 A1 | 11/2019 |
| WO | 2019222295 A2 | 11/2019 |
| WO | 2019222296 A1 | 11/2019 |
| WO | 2019/246392 A1 | 12/2019 |
| WO | 2019230868 A1 | 12/2019 |
| WO | 2019246392 A1 | 12/2019 |
| WO | 2020/023702 A1 | 1/2020 |
| WO | 2020023702 A1 | 1/2020 |
| WO | 2020/041758 A1 | 2/2020 |
| WO | 2020041758 A1 | 2/2020 |
| WO | 2020065096 A1 | 4/2020 |
| WO | 2020069398 A1 | 4/2020 |
| WO | 2020086758 A1 | 4/2020 |
| WO | 2020113403 A1 | 6/2020 |
| WO | 2020118109 | 6/2020 |
| WO | 2020123980 A1 | 8/2020 |
| WO | 2020214690 A1 | 10/2020 |
| WO | 2020232305 A1 | 11/2020 |
| WO | 2020242884 A1 | 12/2020 |
| WO | 2020246567 A1 | 12/2020 |
| WO | 2020252264 A1 | 12/2020 |
| WO | 2021011353 A1 | 1/2021 |
| WO | 2021016599 A1 | 1/2021 |
| WO | 2021016640 A1 | 1/2021 |
| WO | 2021/030483 A1 | 2/2021 |
| WO | 2021/035188 A1 | 2/2021 |
| WO | 2021/062406 A1 | 4/2021 |
| WO | 2021097376 A1 | 5/2021 |
| WO | 2021/113577 A1 | 6/2021 |
| WO | 2021/127487 A2 | 6/2021 |
| WO | 2021113577 A1 | 6/2021 |
| WO | 2021119516 A1 | 6/2021 |
| WO | 2021127487 A2 | 6/2021 |
| WO | 2021127495 A1 | 6/2021 |
| WO | 2021/146455 A1 | 7/2021 |
| WO | 2021/189139 A1 | 9/2021 |
| WO | 2021/202354 A1 | 10/2021 |
| WO | 2021/202673 A2 | 10/2021 |
| WO | 2021/202675 A1 | 10/2021 |
| WO | 2021/202678 A1 | 10/2021 |
| WO | 2021/222762 A2 | 11/2021 |
| WO | 2021/236676 A1 | 11/2021 |

OTHER PUBLICATIONS

Altrock, B. W. et al. (1986) 'Antiviral and Antitumor Effects of a Human Interferon Analog, IFN-αCon1, Assessed in Hamsters', Journal of Interferon Research, 6(4), pp. 405-415. doi: 10.1089/jir.1986.6.405.

Altschul, S. F. et al. (1990) 'Basic local alignment search tool', Journal of Molecular Biology, 215(3), pp. 403-410. doi: 10.1016/S0022-2836(05)80360-2.

Arenas-Ramirez, N. et al. (2016) 'Improved cancer immunotherapy by a CD25-mimobody conferring selectivity to human interleukin-2', Science Translational Medicine, 8(367), pp. 1-13. doi: 10.1126/scitranslmed.aag3187.

Arndt, B. et al. (2015) 'CD8 + CD122 + PD-1—effector cells promote the development of diabetes in NOD mice', Journal of Leukocyte Biology, 97(1), pp. 111-120. doi: 10.1189/jlb.3a0613-344rr.

Atkins, M. B. et al. (2018) 'Pembrolizumab plus pegylated interferon alfa-2b or ipilimumab for advanced melanoma or renal cell carcinoma: dose-finding results from the phase Ib KEYNOTE-029 Study', Clinical Cancer Research, 24(8), pp. 1805-1815. doi: 10.1158/1078-0432.CCR-17-3436.

Bacher, N. et al. (2011) 'Interferon-α abrogates tolerance induction by human tolerogenic dendritic cells', PLoS ONE, 6(7). doi: 10.1371/journal.pone.0022763.

Bacher, N. et al. (2013) 'Interferon-a suppresses cAMP to disarm human regulatory T cells', Cancer Research, 73(18), pp. 5647-5656. doi: 10.1158/0008-5472.CAN-12-3788.

Baechler, E. C. et al. (2003) 'Interferon-inducible gene expression signature in peripheral blood cells of patients with severe lupus', Proceedings of the National Academy of Sciences of the United States of America, 100(5), pp. 2610-2615. doi: 10.1073/pnas.0337679100.

Bekisz, J. et al. (2004) 'Human interferons alpha, beta and omega', Growth Factors, 22(4), pp. 243-251. doi: 10.1080/08977190400000833.

Belardelli, F. et al. (1998) 'The induction of in vivo proliferation of long-lived CD44(hi) CD8+ T cells after the injection of tumor cells expressing IFN-α1 into syngeneic mice', Cancer Research, 58(24), pp. 5795-5802.

Benci, J. L. et al. (2016) 'Tumor Interferon Signaling Regulates a Multigenic Resistance Program to Immune Checkpoint Blockade', Cell, 167(6), pp. 1540-1554.e12. doi: 10.1016/j.cell.2016.11.022.

Benci, J. L. et al. (2019) 'Opposing Functions of Interferon Coordinate Adaptive and Innate Immune Responses to Cancer Immune Checkpoint Blockade', Cell, 178(4), pp. 933-948.e14. doi: 10.1016/j.cell.2019.07.019.

Boorjian, S. A. et al. (2021) 'Intravesical nadofaragene firadenovec gene therapy for BCG-unresponsive non-muscle-invasive bladder

(56) References Cited

OTHER PUBLICATIONS cancer: a single-arm, open-label, repeat-dose clinical trial', The Lancet Oncology, 22(1), pp. 107-117. doi: 10.1016/81470-2045(20)30540-4.

Borden, E. C. (2019) 'Interferons α and β in cancer: therapeutic opportunities from new insights', Nature Reviews Drug Discovery, 18(3), pp. 219-234. doi: 10.1038/s41573-018-0011-2.

Bossen, C. et al. (2006) 'Interactions of tumor necrosis factor (TNF) and TNF receptor family members in the mouse and human', Journal of Biological Chemistry, 281(20), pp. 13964-13971. doi: 10.1074/jbc.M601553200.

Brierley, M. M. and Fish, E. N. (2002) 'IFN-α/βreceptor interactions to biologic outcomes: Understanding the circuitry', Journal of Interferon and Cytokine Research, 22(8), pp. 835-845. doi: 10.1089/107999002760274845.

Brosjö, O. et al. (1985) 'Influence of Human β-Interferon on Four Human Osteosarcoma Xenografts in Nude Mice', Cancer Research, 45(November), pp. 5598-5602.

Bruno, R. et al. (2012) 'Comparison of peginterferon pharmacokinetic and pharmacodynamic profiles', Journal of Viral Hepatitis, 19(SUPPL. 1), pp. 33-36. doi: 10.1111/j.1365-2893.2011.01519.x.

Budhwani, M., Mazzieri, R. and Dolcetti, R. (2018) 'Plasticity of type I interferon-mediated responses in cancer therapy: From antitumor immunity to resistance', Frontiers in Oncology, 8(AUG). doi: 10.3389/fonc.2018.00322.

Burnette, B. C. et al. (2011) 'The efficacy of radiotherapy relies upon induction of type I interferon-dependent innate and adaptive immunity', Cancer Research, 71(7), pp. 2488-2496. doi: 10.1158/0008-5472.CAN-10-2820.

Cameron, R. B., McIntosh, J. K. and Rosenberg, S. A. (1988) 'Synergistic antitumor effects of combination immunotherapy with recombinant interleukin-2 and a recombinant hybrid α-interferon in the treatment of established murine hepatic metastases', Cancer Research, 48(20), pp. 5810-5817.

Carmenate, T. et al. (2013) 'Human IT-2 Mutein with Higher Antitumor Efficacy Than Wild Type IL-2', The Journal of Immunology, 190(12), pp. 6230-6238. doi: 10.4049/jimmunol.1201895.

Cheetham, B. F. et al. (1991) 'Structure-function studies of human interferons-α: Enhanced activity on human and murine cells', Antiviral Research, 15(1), pp. 27-39. doi: 10.1016/0166-3542(91)90038-S.

Chen, J., Baig, E. and Fish, E. N. (2004) 'Diversity and relatedness among the type I interferons', Journal of Interferon and Cytokine Research, 24(12), pp. 687-698. doi: 10.1089/jir.2004.24.687.

Chen, W. et al. (2017) Establishing a safe, rapid, convenient and low-cost antiviral assay of interferon bioactivity based on recombinant VSV expressing GFP, Journal of Virological Methods. Elsevier B.V. doi: 10.1016/j.jviromet.2017.08.007.

Da Silva, A. J. et al. (2002) 'Comparison of gene expression patterns induced by treatment of human umbilical vein endothelial cells with IFN-α2b vs. IFN-β1a: Understanding the functional relationship between distinct type I interferons that act through a common receptor', Journal of Interferon and Cytokine Research, 22(2), pp. 173-188. doi: 10.1089/107999002753536149.

Daud, A. et al. (2012) 'Management of pegylated interferon alpha toxicity in adjuvant therapy of melanoma', Expert Opinion on Biological Therapy, 12(8), pp. 1087-1099. doi: 10.1517/14712598.2012.694421.

Daud, A. I. et al. (2011) 'Pharmacokinetic/pharmacodynamic analysis of adjuvant pegylated interferon α-2b in patients with resected high-risk melanoma', Cancer Chemotherapy and Pharmacology, 67(3), pp. 657-666. doi: 10.1007/s00280-010-1326-9.

Davar, D. et al. (2018) 'Phase Ib/II study of pembrolizumab and pegylated-interferon alfa-2b in advanced melanoma', Journal of Clinical Oncology, 36(35), pp. 3450-3458. doi: 10.1200/JCO.18.00632.

De Paula, V. S. et al. (2020) 'Interleukin-2 druggability is modulated by global conformational transitions controlled by a helical capping switch', Proceedings of the National Academy of Sciences of the United States of America, 117(13), pp. 7183-7192. doi: 10.1073/pnas.2000419117.

De Weerd, N. A. et al. (2013) 'Structural basis of a unique interferon-β signaling axis mediated via the receptor IFNAR1', Nature Immunology, 14(9), pp. 901-907. doi: 10.103 8/ni.2667.

De Weerd, N. A., Samarajiwa, S. A. and Hertzog, P. J. (2007) 'Type I interferon receptors: Biochemistry and biological functions', Journal of Biological Chemistry, 282(28), pp. 20053-20057. doi: 10.1074/jbc.R700006200.

Demers, G. W. et al. (2002) 'Tumor growth inhibition by interferon-α using PEGylated protein or adenovirus gene transfer with constitutive or regulated expression', Molecular Therapy, 6(1), pp. 50-56. doi: 10.1006/mthe.2002.0629.

Diamond, M. S. et al. (2011) 'Type I interferon is selectively required by dendritic cells for immune rejection of tumors', Journal of Experimental Medicine, 208(10), pp. 1989-2003. doi: 10.1084/jem.20101158.

Doctoral_Thesis_Kuen_Martin "Antibody masked cytokines as new approach in targeted tumor therapy" (2015).

Dubrot, J. et al. (2011) 'Intratumoral injection of interferon-α and systemic delivery of agonist anti-CD137 monoclonal antibodies synergize for immunotherapy', International Journal of Cancer, 128(1), pp. 105-118. doi: 10.1002/ijc.25333.

Dunn, G. P. et al. (2005) 'A critical function for type I interferons in cancer immunoediting', Nature Immunology, 6(7), pp. 722-729. doi: 10.1038/ni1213.

Eggermont, A. M. M. et al. (2012) 'Long-term results of the randomized phase III trial EORTC 18991 of adjuvant therapy with pegylated interferon alfa-2b versus observation in resected stage III melanoma', Journal of Clinical Oncology, 30(31), pp. 3810-3818. doi: 10.1200/JCO.2011.41.3799.

Elsadek, B. and Kratz, F. (2012) 'Impact of albumin on drug delivery—New applications on the horizon', Journal of Controlled Release, 157(1), pp. 4-28. doi: 10.1016/j.jconrel.2011.09.069.

Escudier, B. et al. (2010) 'Phase III trial of bevacizumab plus interferon alfa-2a in patients with metastatic renal cell carcinoma (AVOREN): Final analysis of overall survival', Journal of Clinical Oncology, 28(13), pp. 2144-2150. doi: 10.1200/JCO.2009.26.7849.

Faries, M. B. (2016) 'Intralesional immunotherapy for metastatic melanoma: The oldest and newest treatment in oncology', Critical Reviews in Oncogenesis, 21(1-2), pp. 65-73. doi: 10.1615/CritRevOncog.2016017124.

Ferrantini, M., Capone, I. and Belardelli, F. (2007) 'Interferon-α and cancer: Mechanisms of action and new perspectives of clinical use', Biochimie, 89(6-7), pp. 884-893. doi: 10.1016/j.biochi.2007.04.006.

Fitzgerald-Bocarsly, P. (2007) 'The role of type I interferon production by dendritic cells in host defense', Biochimie, 89, pp. 843-855. doi: 10.1016/j.biochi.2007.04.018.The.

Flores, M. V. et al. (2012) 'Preclinical studies of PF-04849285, an interferon-α8 fusion protein for the treatment of HCV', Antiviral Therapy, 17(5), pp. 869-881. doi: 10.3851/IMP2099.

Foster, G. R. and Finter, N. B. (1998) 'Are all Type I human interferons equivalent?', Journal of Viral Hepatitis, 5(3), pp. 143-152. doi: 10.1046/j.1365-2893.1998.00103.x.

Foster, G. R. et al. (2004) 'IFN-α Subtypes Differentially Affect Human T Cell Motility', The Journal of Immunology, 173(3), pp. 1663-1670. doi: 10.4049/jimmunol.173.3.1663.

Fuertes, M. B. et al. (2011) 'Host type I IFN signals are required for antitumor CD8+ T cell responses through CD8α+ dendritic cells', Journal of Experimental Medicine, 208(10), pp. 2005-2016. doi: 10.1084/jem.20101159.

Fuertes, M. B. et al. (2013) 'Type I interferon response and innate immune sensing of cancer', Trends in Immunology, 34(2), pp. 67-73. doi: 10.1016/j.it.2012.10.004.

Fujimura, T. et al. (2017) 'Phase I study of nivolumab combined with IFN-β for patients with advanced melanoma', Oncotarget, 8(41), pp. 71181-71187. doi: 10.18632/oncotarget.17090.

Furse, R. K. and Malek, T. R. (1993) 'Selection of internalization-deficient cells by interleukin-2-Pseudomonas exotoxin chimeric protein: the cytoplasmic domain of the interleukin-2 receptor β

(56) References Cited

OTHER PUBLICATIONS chain does not contribute to internalization of interleukin-2', European Journal of Immunology, 23(12), pp. 3181-3188. doi: 10.1002/eji.1830231221.
Ghaffar, A. et al. (1992) 'Cross-Species Antiviral Activity of a Recombinant Human Alpha-Interferon Hybrid', Annals of the New York Academy of Sciences, 653(1), pp. 314-322. doi: 10.1111/j.1749-6632.1992.tb19658.x.
Glue, P. et al. (2000) 'Pegylated interferon-α2b: Pharmacokinetics, pharmacodynamics, safety, and preliminary efficacy data', Clinical Pharmacology and Therapeutics, 68(5), pp. 556-567. doi: 10.1067/mcp.2000.110973.
Gogas, H. Ioannovich, J., Dafni, U., Stavropoulou-Giokas, C., Frangia, K., Tsoutsos, D., Panagiotou, P., Polyzos, A., Papadopoulos, O., Stratigos, A., Markopoulos, C., Bafaloukos, D., Pectasides, D., Fountzilas, G., & Kirkwood, J. M. (2006) 'Prognostic Significance of Autoimmunity during Treatment of Melanoma with Interferon', N Engl J Med, pp. 709-718.
Grace, M. et al. (2001) 'Structural and biologic characterization of pegylated recombinant IFN-β2b', Journal of Interferon and Cytokine Research, 21(12), pp. 1103-1115. doi: 10.1089/107999001317205240.
Grace, M. J. et al. (2005) 'Site of pegylation and polyethylene glycol molecule size attenuate interferon-α antiviral and antiproliferative activities through the JAK/STAT signaling pathway', Journal of Biological Chemistry, 280(8), pp. 6327-6336. doi: 10.1074/jbc.M412134200.
Gresser, I. (1989) 'Antitumor effects of interferon', Acta Oncologica, 28(3), pp. 347-353. doi: 10.3109/02841868909111205.
Grob, J. J. et al. (2013) 'Adjuvant therapy with pegylated interferon alfa-2b (36 months) versus low-dose interferon alfa-2b (18 months) in melanoma patients without macrometastatic nodes: An open-label, randomised, phase 3 European Association for Dermato-Oncology (EADO) study', European Journal of Cancer, 49(1), pp. 166-174. doi: 10.1016/j.ejca.2012.07.018.
Gui, J. et al. (2016) 'Therapeutic Elimination of the Type 1 Interferon Receptor for Treating Psoriatic Skin Inflammation', Journal of Investigative Dermatology, 136(10), pp. 1990-2002. doi: 10.1016/j.jid.2016.06.608.
Guo, J. et al. (2019) 'Empowering therapeutic antibodies with IFN-α for cancer immunotherapy', PLoS ONE, 14(8), pp. 1-13. doi: 10.1371/journal.pone.0219829.
Gutterman, J. U. (1994) 'Cytokine therapeutics: Lessons from interferon α', Proceedings of the National Academy of Sciences of the United States of America, 91(4), pp. 1198-1205. doi: 10.1073/pnas.91.4.1198.
Hagiwara, S. et al. (2007) 'Combination therapy with PEG-IFN-α and 5-FU inhibits HepG2 tumour cell growth in nude mice by apoptosis of p53', British Journal of Cancer, 97(11), pp. 1532-1537. doi: 10.1038/sj.bjc.6604058.
Harari, D. et al. (2014) 'Bridging the species divide: Transgenic mice humanized for type-I interferon response', PLoS ONE, 9(1), pp. 1-12. doi: 10.1371/journal.pone.0084259.
Harcourt, J. L. and Offermann, M. K. (2000) 'Interferon-α synergistically enhances induction of interleukin-6 by double stranded RNA in HeLa cells', European Journal of Biochemistry, 267(9), pp. 2768-2777. doi: 10.1046/j.1432-1327.2000.01300.x.
Harris, K. E. et al. (2021) 'A bispecific antibody agonist of the IL-2 heterodimeric receptor preferentially promotes in vivo expansion of CD8 and NK cells', Scientific Reports, 11(1), pp. 1-15. doi: 10.1038/s41598-021-90096-8.
Hashimoto, H. et al. (2014) 'Type i IFN gene delivery suppresses regulatory T cells within tumors', Cancer Gene Therapy, 21(12), pp. 532-541. doi: 10.1038/cgt.2014.60.
Hervas-Stubbs, S. et al. (2011) 'Direct effects of type I interferons on cells of the immune system', Clinical Cancer Research, 17(9), pp. 2619-2627. doi: 10.1158/1078-0432.CCR-10-1114.
Herzer, K. et al. (2009) 'IFN-α-induced apoptosis in hepatocellular carcinoma involves promyelocytic leukemia protein and TRAIL independently of p53', Cancer Research, 69(3), pp. 855-862. doi: 10.1158/0008-5472.CAN-08-2831.

Hilkens, C. M. U., Schlaak, J. F. and Kerr, I. M. (2003) 'Differential Responses to IFN-α Subtypes in Human T Cells and Dendritic Cells', The Journal of Immunology, 171(10), pp. 5255-5263. doi: 10.4049/jimmunol.171.10.5255.
Huang, T.-H., Chintalacharuvu, K. R. and Morrison, S. L. (2007) 'Targeting IFN-α to B Cell Lymphoma by a Tumor-Specific Antibody Elicits Potent Antitumor Activities', The Journal of Immunology, 179(10), pp. 6881-6888. doi: 10.4049/jimmunol.179.10.6881.
Iigo, M et al. (1988) 'In Vivo Antitumor Activity of Multiple Injections of Recombinant Interleukin 2 , Â §', Cancer Research, 48(2), pp. 260-264.
INFERGEN (Interferon alfacon-1) Label_copyright 1997-1998.
Isaacs A, L. J. (1957) 'Virus interference . I . The interferon', Proc R Soc Lond B Biol Sci, 147(927), pp. 258-267.
Islam, M. et al. (2002) 'Differential effect of IFNα-2b on the cytochrome P450 enzyme system: A potential basis of IFN toxicity and its modulation by other drugs', Clinical Cancer Research, 8(8), pp. 2480-2487.
Ito, N. et al. (1996) 'Induction of interleukin-6 by interferon alfa and its abrogation by a serine protease inhibitor in patients with chronic hepatitis C', Hepatology, 23(4), pp. 669-675. doi: 10.1053/jhep.1996.v23.pm0008666316.
Ivashkiv, L. B. and Donlin, L. T. (2014) 'Regulation of type i interferon responses', Nature Reviews Immunology, 14(1), pp. 36-49. doi: 10.1038/nri3581.
Jablonska, J. et al. (2010) 'Neutrophils responsive to endogenous IFN-β regulate tumor angiogenesis and growth in a mouse tumor model', Journal of Clinical Investigation, 120(4), pp. 1151-1164. doi: 10.1172/JCI37223.
Jacquelot, N. et al. (2019) 'Sustained Type I interferon signaling as a mechanism of resistance to PD-1 blockade', Cell Research, 29(10), pp. 846-861. doi: 10.1038/s41422-019-0224-x.
Jaitin, D. A. et al. (2006) 'Inquiring into the Differential Action of Interferons (IFNs): an IFN-α2 Mutant with Enhanced Affinity to IFNAR1 Is Functionally Similar to IFN-β', Molecular and Cellular Biology, 26(5), pp. 1888-1897. doi: 10.1128/mcb.26.5.1888-1897.2006.
Jeon, S. et al. (2013) 'Saturable human neopterin response to interferon-α assessed by a pharmacokinetic-pharmacodynamic model', Journal of Translational Medicine, 11(1), p. 1. doi: 10.1186/1479-5876-11-240.
Jia, H. et al. (2016) 'Elimination of N-glycosylation by site mutation further prolongs the half-life of IFN-α/Fc fusion proteins expressed in Pichia pastoris', Microbial Cell Factories, 15(1), pp. 1-9. doi: 10.1186/s12934-016-0601-9.
Jones, T. D. et al. (2004) 'The Development of a Modified Human IFN-α2b Linked to the Fc Portion of Human IgG1 as a Novel Potential Therapeutic for the Treatment of Hepatitis C Virus Infection', Journal of Interferon & Cytokine Research, 24(9), pp. 560-572. doi: 10.1089/1079990041992686.
Kalie, E. et al. (2007) 'An interferon α2 mutant optimized by phage display for IFNAR1 binding confers specifically enhanced antitumor activities', Journal of Biological Chemistry, 282(15), pp. 11602-11611. doi: 10.1074/jbc.M610115200.
Kang, J. H., Bluestone, J. A. and Young, A. (2021) 'Predicting and Preventing Immune Checkpoint Inhibitor Toxicity: Targeting Cytokines', Trends in Immunology, 42(4), pp. 293-311. doi: 10.1016/j.it.2021.02.006.
Klatte, T. et al. (2008) 'Pretreatment with interferon-αmodulates perioperative immunodysfunction in patients with renal cell carcinoma', Onkologie, 31(1-2), pp. 28-34. doi: 10.1159/000112214.
Koltchev, D. H. et al. (2008) 'Biological activities and detection of cynomolgus interferon-α subtypes', PBL InterferonSource Poster.
Kono, T., Minami, Y. and Taniguchi, T. (1993) 'The interleukin-2 receptor complex and signal transduction: Role of the β-chain', Seminars in Immunology, pp. 299-307. doi: 10.1006/smim.1993.1036.
Kotredes, K. P. and Gamero, A. M. (2013) 'Interferons as inducers of apoptosis in malignant cells', Journal of Interferon and Cytokine Research, 33(4), pp. 162-170. doi: 10.1089/jir.2012.0110.
Krepler, C. et al. (2004) 'Pegylated and conventional interferon-α induce comparable transcriptional responses and inhibition of tumor growth in a human melanoma SCID mouse xenotransplantation

(56) References Cited

OTHER PUBLICATIONS model', Journal of Investigative Dermatology, 123(4), pp. 664-669. doi: 10.1111/j.0022-202X.2004.23433.x.
Kuruganti, S., Accavitti-Loper, M. A. and Walter, M. R. (2017) 'Production and characterization of thirteen human Type-I interferon-α subtypes', Protein Expr Purif. Nov. 2014;103:75-83. doi: 10.1016/j.pep.2014.08.010.
Kusano, H. et al. (2013) 'Pegylated interferon-α2a inhibits proliferation of human liver cancer cells in vitro and in vivo', PLoS ONE, 8(12), pp. 1-10. doi: 10.1371/journal.pone.0083195.
Lazear, H. M., Schoggins, J. W. and Diamond, M. S. (2019) 'Shared and Distinct Functions of Type I and Type 111 Interferons', Immunity, 50(4), pp. 907-923. doi: 10.1016/j.immuni.2019.03.025.
Le Bon, A. et al. (2001) 'Type I interferons potently enhance humoral immunity and can promote isotype switching by stimulating dendritic cells in vivo', Immunity, 14(4), pp. 461-470. doi: 10.1016/S1074-7613(01)00126-1.
Leavy, O. (2011) 'Cytokines: Structuring the type I IFN response', Nature Reviews Immunology, 11(10), pp. 640-641. doi: 10.1038/nri3067.
Li, S. F. et al. (2018) 'Type i interferons: Distinct biological activities and current applications for viral infection', Cellular Physiology and Biochemistry, 51(5), pp. 2377-2396. doi: 10.1159/000495897.
Liang, Y. et al. (2018) 'Targeting IFNα to tumor by anti-PD-L1 creates feedforward antitumor responses to overcome checkpoint blockade resistance', Nature Communications, 9(1), pp. 1-11. doi: 10.1038/s41467-018-06890-y.
Liang, Y. et al. (2018) 'Targeting IFNα to tumor by anti-PD-L1 creates feedforward antitumor responses to overcome checkpoint blockade resistance', Nature Communications, 9(1), Supplements pp. 1-12.
Liu, H. et al. (2018) 'Tumor-derived IFN triggers chronic pathway agonism and sensitivity to ADAR loss', Nature Medicine, 25(1), pp. 95-102. doi: 10.1038/s41591-018-0302-5.
Liu, Y. Z. et al. (2012) 'Pegylated interferon a enhances recovery of memory T cells in e antigen positive chronic hepatitis B patients', Virology Journal, 9(1), p. 1. doi: 10.1186/1743-422X-9-274.
Loignon, M. et al. (2008) 'Stable high volumetric production of glycosylated human recombinant IFNalpha2b in HF.K293 cells', BMC Biotechnology, 8, pp. 1-16. doi: 10.1186/1472-6750-8-65.
Lopes, J. E. et al. (2020) 'ALKS 4230: A novel engineered IL-2 fusion protein with an improved cellular selectivity profile for cancer immunotherapy', Journal for ImmunoTherapy of Cancer, 8(1), pp. 1-13. doi: 10.1136/jitc-2020-000673.
Malek, T. R. et al. (1998) 'Monoclonal antibodies to the common γ-chain as cytokine receptor antagonists in vivo: Effect on intrathymic and intestinal intraepithelial T lymphocyte development', Journal of Leukocyte Biology, 63(6), pp. 643-649. doi: 10.1002/jlb.63.6.643.
Marchant, D. J. et al. (2014) 'A new transcriptional role for matrix metalloproteinase-12 in antiviral immunity', Nature Medicine, 20(5), pp. 493-502. doi: 10.1038/nm.3508.
Martinović, K. M. et al. (2019) 'Effect of cytokines on NK cell activity and activating receptor expression in high-risk cutaneous melanoma patients', European Cytokine Network, 30(4), pp. 160-167. doi: 10.1684/ecn.2019.0440.
Massoud, R. et al. (2015) 'Common y-chain blocking peptide reduces in vitro immune activation markers in HTLV-1-associated myelopathy/tropical spastic paraparesis', Proceedings of the National Academy of Sciences of the United States of America, 112(35), pp. 11030-11035. doi: 10.1073/pnas.1412626112.
Meager, A. (2002) 'Biological assays for interferons', Journal of Immunological Methods, 261(1-2), pp. 21-36. doi: 10.1016/80022-1759(01)00570-1.
Meager, A. et al. (2001) 'Establishment of new and replacement World Health Organization International Biological Standards for human interferon alpha and omega', Journal of Immunological Methods, 257(1-2), pp. 17-33. doi: 10.1016/S0022-1759(01)00460-4.

Medrano, R. F. V. et al. (2017) Immunomodulatory and antitumor effects of type I interferons and their application in cancer therapy, Oncotarget. doi: 10.18632/oncotarget.19531.
Minn, A. J. and Wherry, E. J. (2016) 'Combination Cancer Therapies with Immune Checkpoint Blockade: Convergence on Interferon Signaling', Cell, 165(2), pp. 272-275. doi: 10.1016/j.cell.2016.03.031.
Moll, H. P. et al. (2011) 'The differential activity of interferon-α subtypes is consistent among distinct target genes and cell types', Cytokine, 53(1), pp. 52-59. doi: 10.1016/j.cyto.2010.09.006.
Moraga, I. et al. (2009) 'Receptor Density Is Key to the Alpha2/Beta Interferon Differential Activities', Molecular and Cellular Biology, 29(17), pp. 4778-4787. doi: 10.1128/mcb.01808-08.
Moraga, I. et al. (2017) 'Synthekines are surrogate cytokine and growth factor agonists that compel signaling through non-natural receptor dimers', eLife, 6, pp. 1-22. doi: 10.7554/eLife.22882.
Moriya, F. et al. (2008) 'Growth inhibitory effects of pegylated IFN-α2b and 5-fluorouracil in combination on renal cell carcinoma cell lines in vitro and in vivo', International Journal of Oncology, 35, pp. 547-557. doi: 10.3892/ijo.
Mundy-Bosse, B. L. and Young, G. S. (2012) 'cells from patients with GI malignancy', 60(9), pp. 1269-1279. doi: 10.1007/s00262-011-1029-z.Distinct.
Nakajima, S. et al. (1990) 'Changes in interferon receptors on peripheral blood mononuclear cells from patients with chronic hepatitis B being treated with interferon', Hepatology, 12(6), pp. 1261-1265. doi: 10.1002/hep.1840120602.
Nakamura, Y. et al. (1994) 'Heterodimerization of the IT-2 receptor β- And γ-chain cytoplasmic domains is required for signalling', Nature, 369(6478), pp. 330-333. doi: 10.1038/369330a0.
Nederman, T., Karlström, E. and Sjödin, L. (1990) 'An in vitro bioassay for quantitation of human interferons by measurements of antiproliferative activity on a continuous human lymphoma cell line', Biologicals, 18(1), pp. 29-34. doi: 10.1016/1045-1056(90)90066-9.
Nelson, B. H. et al. (1997) 'Requirement for an initial signal from the membrane-proximal region of the interleukin 2 receptor γc chain for Janus kinase activation leading to T cell proliferation', Proceedings of the National Academy of Sciences of the United States of America, 94(5), pp. 1878-1883. doi: 10.1073/pnas.94.5.1878.
Nelson, B. H., Lord, J. D. and Greenberg, P. D. (1994) 'signal for T-cell proliferation', Nature, 369(6478), pp. 333-336.
Nelson, B. H., Lord, J. D. and Greenberg, P. D. (1996) 'A membrane-proximal region of the interleukin-2 receptor gamma c chain sufficient for Jak kinase activation and induction of proliferation in T cells', Molecular and Cellular Biology, 16(1), pp. 309-317. doi: 10.1128/mcb.16.1.309.
Nuara, A. A. et al. (2008) 'Structure and mechanism of IFN-γantagonism by an orthopoxvirus IFN-γ-binding protein', Proceedings of the National Academy of Sciences of the United States of America, 105(6), pp. 1861-1866. doi: 10.1073/pnas.0705753105.
O'Connell, P. et al. (2019) 'SLAMF7 Is a Critical Negative Regulator of IFN-α-Mediated CXCL10 Production in Chronic HIV Infection', The Journal of Immunology, 202(1), pp. 228-238. doi: 10.4049/jimmunol.1800847.
O'Neil, J. et al. (2021) 'XTX202, a protein-engineered IT-2, in mice without peripheral toxicities in nonhuman primates.', ASCO Poster, doi: 10.1200/jco.2021.39.15_suppl.2563.
Ohdo, S. et al. (1997) 'Circadian rhythm of fever induced by interferon-alpha in mice', Life sciences, 61(8), pp. 95-100.
Okanoue, T. (2006) 'Side effects of interferon therapy for chronic hepatitis C', Nippon rinsho. Japanese journal of clinical medicine, 64(7), pp. 1363-1367.
Osborn, B. L. et al. (2002) 'Pharmacokinetic and pharmacodynamic studies of a human serum albumin-interferon-α fusion protein in cynomolgus monkeys', Journal of Pharmacology and Experimental Therapeutics, 303(2), pp. 540-548. doi: 10.1124/jpet.102.037002.
Ozzello, L. et al. (1988) 'Treatment of Human Breast Cancer Xenografts Using Natural Interferons-α and -γ Injected Singly or in Combination', Journal of Interferon Research, 8(5), pp. 679-690. doi: 10.1089/jir.1988.8.679.

(56) References Cited

OTHER PUBLICATIONS

Pace, L. et al. (2010) 'APC Activation by IFN-α Decreases Regulatory T Cell and Enhances Th Cell Functions', The Journal of Immunology, 184(11), pp. 5969-5979. doi: 10.4049/jimmunol.0900526.

Pan, M. et al. (2008) 'Mutation of the IFNAR-1 receptor binding site of human IFN-α2 generates type I IFN competitive antagonists', Biochemistry, 47(46), p. 12018-12027. doi: 10.1021/bi801588g.

Parisi, G. et al. (2020) 'Persistence of adoptively transferred T cells with a kinetically engineered IL-2 receptor agonist', Nature Communications, 11(1), pp. 1-12. doi: 10.1038/s41467-019-12901-3.

Paulson, M. et al. (1999) 'Stat protein transactivation domains recruit p300/CBP through widely divergent sequences', Journal of Biological Chemistry, 274(36), pp. 25343-25349. doi: 10.1074/jbc.274.36.25343.

Pfeffer, L. M. et al. (1998) 'Biological Properties of Recombinant α-Interferons : 40th Anniversary of the Discovery of Interferons Biological Properties of Recombinant Â «-InterfÂ © rons : 40th Anniversary of the Discovery of Interferons 1', Cancer Research, 58(12), pp. 2489-2499.

Piehler, J., Roisman, L. C. and Schreiber, G. (2000) 'New structural and functional aspects of the type I interferon-receptor interaction revealed by comprehensive mutational analysis of the binding interface', Journal of Biological Chemistry, 275(51), p. 40425-40433. doi: 10.1074/jbc.M006854200.

Piehler, J., Thomas, C. and Garcia, K. C. (2012) 'Imr_12001 317..334', pp. 1-18. Available at: papers://1825b63a-f617-4840-9a49-fa78b8732348/Paper/p1187.

Platanias, L. C. (2005) 'Mechanisms of type-I- and type-II-interferon-mediated signalling', Nature Reviews Immunology, 5(5), pp. 375-386. doi: 10.1038/nri1604.

Plote, D. et al. (2019) 'Inhibition of urothelial carcinoma through targeted type I interferon-mediated immune activation', OncoImmunology, 8(5), pp. 1-17. doi: 10.1080/2162402X.2019.1577125.

Pogue, S. L. et al. (2016) 'Targeting attenuated interferon-α to myeloma cells with a CD38 antibody induces potent tumor regression with reduced off-target activity', PLoS ONE, 11(9), pp. 1-20. doi: 10.1371/journal.pone.0162472.

Price-Troska, T. et al. (2019) 'Inhibiting IT-2 signaling and the regulatory T-cell pathway using computationally designed peptides', Investigational New Drugs, 37(1), pp. 9-16. doi: 10.1007/s10637-018-0606-9.

Quadt-Akabayov, S. R. et al. (2006) 'Determination of the human type I interferon receptor binding site on human interferon-α2 by cross saturation and an NMR-based model of the complex', Protein Science, 15(11), pp. 2656-2668. doi: 10.1110/ps.062283006.

Radhakrishnan, R. et al. (1996) 'Zinc mediated dimer of human interferon-α(2b) revealed by X-ray crystallography', Structure, 4(12), pp. 1453-1463. doi: 10.1016/S0969-2126(96)00152-9.

Rath, P. C. and Aggarwal, B. B. (2001) 'Antiproliferative effects of IFN-α correlate with the downregulation of nuclear factor-κB in human Burkitt lymphoma Daudi cells', Journal of Interferon and Cytokine Research, 21(7), pp. 523-528. doi: 10.1089/10799900152434402.

Reading, J. L. and Quezada, S. A. (2016) 'Too Much of a Good Thing? Chronic IFN Fuels Resistance to Cancer Immunotherapy', Immunity, 45(6), pp. 1181-1183. doi: 10.1016/j.immuni.2016.12.004.

Reder, A. T. and Feng, X. (2014) 'How type i interferons work in multiple sclerosis and other diseases: Some unexpected mechanisms', Journal of Interferon and Cytokine Research, 34(8), pp. 589-599. doi: 10.1089/jir.2013.0158.

Rehberg, E. et al. (1982) 'Specific molecular activities of recombinant and hybrid leukocyte interferons', Journal of Biological Chemistry, 257(19), p. 11497-11502. doi: 10.1016/s0021-9258(18)33788-8.

Richter, D. et al. (2017) 'Ligand-induced type II interleukin-4 receptor dimers are sustained by rapid re-association within plasma membrane microcompartments', Nature Communications, 8(May). doi: 10.1038/ncomms15976.

Rivero-Juarez, A. et al. (2017) 'KIR2DS2 as predictor of thrombocytopenia secondary to pegylated interferon-alpha therapy', Pharmacogenomics Journal, 17(4), pp. 360-365. doi: 10.1038/tpj.2016.19.

Roisman, L. C. et al. (2005) 'Mutational analysis of the IFNAR1 binding site on IFNα2 reveals the architecture of a weak ligand-receptor binding-site', Journal of Molecular Biology, 353(2), pp. 271-281. doi: 10.1016/j.jmb.2005.08.042.

Rossmann, C. et al. (1996) 'Expression and purification of recombinant, glycosylated human interferon alpha 2b in murine myeloma NSo cells', Protein Expression and Purification, 7(4), pp. 335-342. doi: 10.1006/prep.1996.0050.

Rozera, C. et al. (1999) 'Murine interferon-α1 gene-transduced ESb tumor cells are rejected by host-mediated mechanisms despite resistance of the parental tumor to interferon-α/α therapy', Cancer Gene Therapy, 6(3), pp. 246-253. doi: 10.103 8/sj.cgt.7700051.

Runkel, L. et al. (2000) 'Systematic Mutational Mapping of Sites on Human Interferon-β-1a That Are Important for Receptor Binding and Functional Activity', Biochemistry, 39(10), pp. 2538-2551. Available at: http://pubs.acs.org/doi/abs/10.1021/bi991631c.

Ryan, C. W. et al. (2007) 'Sorafenib with interferon alfa-2b as first-line treatment of advanced renal carcinoma: A phase II study of the southwest oncology group', Journal of Clinical Oncology, 25(22), pp. 3296-3301. doi: 10.1200/JCO.2007.11.1047.

Samarajiwa, S. A. et al. (2009) 'INTERFEROME: The database of interferon regulated genes', Nucleic Acids Research, 37(SUPPL. 1), pp. 852-857. doi: 10.1093/nar/gkn732.

Sandler, N. G. et al. (2014) 'prevent SIV infection and slow disease progression', Nature, 511(7511), pp. 601-605. doi: 10.1038/nature13554.Type.

Santini, S. M. et al. (2000) 'Type I interferon as a powerful adjuvant for monocyte-derived dendritic cell development and activity in vitro and in Hu-PBL-SCID mice', Journal of Experimental Medicine, 191(10), pp. 1777-1788. doi: 10.1084/jem.191.10.1777.

Schlaak, J. F. et al. (2002) 'Cell-type and donor-specific transcriptional responses to interferon-α: Use of customized gene arrays', Journal of Biological Chemistry, 277(51), pp. 49428-49437. doi: 10.1074/jbc.M205571200.

Schreiber, G. (2017) 'The molecular basis for differential type i interferon signaling', Journal of Biological Chemistry, 292(18), pp. 7285-7294. doi: 10.1074/jbc.R116.774562.

Schreiber, G. and Piehler, J. (2015) 'The molecular basis for functional plasticity in type I interferon signaling', Trends in Immunology, 36(3), pp. 139-149. doi: 10.1016/j.it.2015.01.002.

Schwarzmeier, J. D. et al. (1996) 'Inadequate production of hematopoietic growth factors in hairy cell leukemia: Up-regulation of interleukin 6 by recombinant IFN-α in vitro', Cancer Research, 56(20), pp. 4679-4685.

Seeds, R. E. and Miller, J. L. (2011) 'Measurement of type I interferon production', Current Protocols in Immunology, (SUPPL. 92), pp. 1-11. doi: 10.1002/0471142735.im1421s92.

Sharma, M. et al. (2020) 'Bempegaldesleukin selectively depletes intratumoral Tregs and potentiates T cell-mediated cancer therapy', Nature Communications, 11(1). doi: 10.1038/s41467-020-14471-1.

Shire, S. J. (1983) 'pH-Dependent Polymerization of a Human Leukocyte Interferon Produced by Recombinant Deoxyribonucleic Acid Technology', Biochemistry, 22(11), pp. 2664-2671. doi: 10.1021/bi00280a012.

Siurala, M. et al. (2016) 'Syngeneic Syrian hamster tumors feature tumor-infiltrating lymphocytes allowing adoptive cell therapy enhanced by oncolytic adenovirus in a replication permissive setting', OncoImmunology, 5(5). doi: 10.1080/2162402X.2015.1136046.

Slutzki, M. et al. (2006) 'Variations in the Unstructured C-terminal Tail of Interferons Contribute to Differential Receptor Binding and Biological Activity', Journal of Molecular Biology, 360(5), pp. 1019-1030. doi: 10.1016/j.jmb.2006.05.069.

Sonnenfeld, G. et al. (2001) 'Efficacy and safety of orally/sublingually, intranasally, and intraperitoneally administered recombinant murine interferon in the treatment of murine encephalomyocarditis

(56) References Cited

OTHER PUBLICATIONS virus', Journal of Interferon and Cytokine Research, 21(7), pp. 539-545. doi: 10.1089/10799900152434420.
Spangler, J. B. et al. (2015) 'Antibodies to Interleukin-2 Elicit Selective T Cell Subset Potentiation through Distinct Conformational Mechanisms', Immunity, 42(5), pp. 815-825. doi: 10.1016/j.immuni. 2015.04.015.
Spangler, J. B. et al. (2019) 'A strategy for the selection of monovalent antibodies that span protein dimer interfaces', Journal of Biological Chemistry, 294(38), pp. 13876-13886. doi: 10.1074/jbc.RA119.009213.
Stagg, J. et al. (2011) 'Anti-ErbB-2 mAb therapy requires type I and II interferons and synergizes with anti-PD-1 or anti-CD137 mAb therapy', Proceedings of the National Academy of Sciences of the United States of America, 108(17), pp. 7142-7147. doi: 10.1073/pnas.1016569108.
Stauber, D. J. et al. (2006) 'Crystal structure of the IT-2 signaling complex: Paradigm for a heterotrimeric cytokine receptor', Proceedings of the National Academy of Sciences of the United States of America, 103(8), pp. 2788-2793. doi: 10.1073/pnas.0511161103.
Stetson, D. B. and Medzhitov, R. (2006) 'Type I Interferons in Host Defense', Immunity, 25(3), pp. 373-381. doi: 10.1016/j.immuni. 2006.08.007.
Su, S. S. et al. (2014) 'Regulatory phenotype, PD-1 and TLR3 expression in T cells and monocytes from HCV patients undergoing antiviral therapy: A randomized clinical trial', PLoS ONE, 9(4). doi: 10.1371/journal.pone.0093620.
Subramanian, G. M. et al. (2007) 'Albinterferon $\alpha$-2b: A genetic fusion protein for the treatment of chronic hepatitis C', Nature Biotechnology, 25(12), pp. 1411-1419. doi: 10.1038/nbt1364.
Sugyiama, K. et al. (1993) 'Expression of human interferon-60 2 in Sf9 cells', European Journal of Biochemistry, 217(3), pp. 921-927. Available at: https://doi.org/10.1111/j.1432-1033.1993.tb18322.x.
Swann, J. B. et al. (2007) 'Type I IFN Contributes to NK Cell Homeostasis, Activation, and Antitumor Function', The Journal of Immunology, 178(12), pp. 7540-7549. doi: 10.4049/jimmunol.178. 12.7540.
Talpaz, M. et al. (2013) 'Re-emergence of interferon-$\alpha$ in the treatment of chronic myeloid leukemia', Leukemia, 27(4), pp. 803-812. doi: 10.1038/leu.2012.313.
Tanaka, T. et al. (1991) 'A novel monoclonal antibody against murine IL-2 receptor beta-chain. Characterization of receptor expression in normal lymphoid cells and EL-4 cells.', Journal of immunology (Baltimore, Md.: 1950), 147(7), pp. 2222-2228. Available at: http://www.ncbi.nlm.nih.gov/pubmed/1918958.
Tanimoto, T. et al. (2007) 'The combination of IFN-$\alpha$2 and IFN-$\alpha$8 exhibits synergistic antiproliferative activity on renal cell carcinoma (RCC) cell lines through increased binding affinity for IFNAR-2', Journal of Interferon and Cytokine Research, 27(6), pp. 517-523. doi: 10.1089/jir.2007.0155.
Taylor, M. W. et al. (2004) 'Global Effect of PEG-IFN-$\alpha$ and Ribavirin on Gene Expression in PBMC in Vitro', Journal of Interferon and Cytokine Research, 24(2), pp. 107-118. doi: 10.1089/107999004322813354.
Teijaro, J. R. et al. (2013) 'Persistent LCMV infection is controlled by blockade of type I interferon signaling', Science, 340(6129), pp. 207-211. doi: 10.1126/science.1235214.
Thomas, C. et al. (2011) 'Structural linkage between ligand discrimination and receptor activation by Type i interferons', Cell, 146(4), pp. 621-632. doi: 10.1016/j.cell.2011.06.048.
Trinchieri, G. (2010) 'Type I interferon: Friend or foe?', Journal of Experimental Medicine, 207(10), pp. 2053-2063. doi: 10.1084/jem. 20101664.
Uno, K. et al. (1988) 'Effect of recombinant human interferon-$\alpha$a/d on in vivo murine tumor cell growth', Cancer Research, 48(9), pp. 2366-2371.
Van Pesch, V. et al. (2004) 'Characterization of the Murine Alpha Interferon Gene Family', Journal of Virology, 78(15), pp. 8219-8228. doi: 10.1128/jvi.78.15.8219-8228.2004.

Villarreal, D. O. et al. (2017) 'Targeting of CD122 enhances antitumor immunity by altering the tumor immune environment', Oncotarget, 8(65), pp. 109151-109160. doi: 10.18632/oncotarget. 22642.
Von Wussow, P. et al. (1988) 'Intralesional interferon-alpha therapy in advanced malignant melanoma', Cancer, 61(6), pp. 1071-1074. doi: 10.1002/1097-0142(19880315)61:6<1071::AID-CNCR2820610603>3.0.CO;2-T.
Walter, M. R. et al. (1998) 'Review of recent developments in the molecular characterization of recombinant alfa interferons on the 40th anniversary of the discovery of interferon', Cancer Biotherapy and Radiopharmaceuticals, 13(3), pp. 143-154. doi: 10.1089/cbr. 1998.13.143.
Watermann, I. et al. (2007) 'Activation of CD95L fusion protein prodrugs by tumor-associated proteases', Cell Death and Differentiation, 14(4), pp. 765-774. doi: 10.103 8/sj.cdd.4402051.
Weber, H. et al. (1987) 'Single amino acid changes that render human IFN-alpha 2 biologically active on mouse cells.', The EMBO journal, 6(3), pp. 591-598. doi: 10.1002/j.1460-2075.1987.tb04795. x.
Week, P. K. et al. (1981) 'Comparison of the antiviral activities of various cloned human interferon-$\alpha$ subtypes in mammalian cell cultures', Journal of General Virology, 57(1), pp. 233-237. doi: 10.1099/0022-1317-57-1-233.
Weidle, U. H., Tiefenthaler, G. and Georges, G. (2014) 'Proteases as activators for cytotoxic prodrugs in antitumor therapy', Cancer Genomics and Proteomics, 11(2), pp. 67-80.
Wilmes, S. et al. (2020) 'Mechanism of homodimeric cytokine receptor activation and dysregulation by oncogenic mutations', Science, 367(6478), pp. 643-652. doi: 10.1126/science.aaw3242.
Wilson, E. B. et al. (2013) 'Blockade of chronic type I interferon signaling to control persistent LCMV infection', Science, 340(6129), pp. 202-207. doi: 10.1126/science.1235208.
Xuan, C. et al. (2010) 'Targeted delivery of interferon-alpha via fusion to anti-CD20 results in potent antitumor activity against B-cell lymphoma', Blood, 115(14), pp. 2864-2871. doi: 10.1182/blood-2009-10-250555.
Yamaji, K. et al. (2006) 'Interferon-$\alpha$/$\beta$ upregulate IL-15 expression in vitro and in vivo: Analysis in human hepatocellular carcinoma cell lines and in chronic hepatitis C patients during interferon-$\alpha$/$\beta$ treatment', Cancer Immunology, Immunotherapy, 55(4), pp. 394-403. doi: 10.1007/s00262-005-0005-x.
Yang, X. et al. (2014) 'Targeting the tumor microenvironment with interferon-bridges innate and adaptive immune responses', Cancer Cell, 25(1), pp. 37-48. doi: 10.1016/j.ccr.2013.12.004.
Youngster, S. et al. (2015) 'Structure, Biology, and Therapeutic Implications of Pegylated Interferon', pp. 2139-2157.
Zhang, K. J. et al. (2017) 'A potent in Vivo antitumor efficacy of novel recombinant type i interferon', Clinical Cancer Research, 23(8), pp. 2038-2049. doi: 10.1158/1078-0432.CCR-16-1386.
Zibelman, M. and Plimack, E. R. (2019) 'Pembrolizumab plus ipilimumab or pegylated interferon alfa-2b for patients with melanoma or renal cell carcinoma: take new drugs but keep the old?', Annals of Translational Medicine, 7(S3), pp. S95-S95. doi: 10.21037/atm.2019.04.57.
Zimmerer, J. M. et al. (2008) 'Gene expression profiling reveals similarities between the in vitro and in vivo responses of immune effector cells to IFN-$\alpha$', Clinical Cancer Research, 14(18), pp. 5900-5906. doi: 10.1158/1078-0432.CCR-08-0846.
Zitvogel, L. et al. (2015) 'Type I interferons in anticancer immunity', Nature Reviews Immunology, 15(7), pp. 405-414. doi: 10.1038/nri3845.
Chernajovsky et al., Response under 37 C.F.R. §1.111 filed in U.S. Appl. No. 15/322,129, filed Feb. 25, 2019, 27 pages.
Gull et al., "Development of latent Interferon alpha 2b as a safe therapeutic for treatment of Hepatitis C virus infection", Scientific Reports, (2019) 9:10867, 12 pages.
Wagner et al., "Evolution of the six horse IGHG genes and corresponding immunoglobulin gamma heavy chains", Immunogenetics (2002) 54: pp. 353-364.
Irving, "Probodies Empower a New Generation of Antibody Immunotherapies," presented at Keystone Symposia on Molecular and Cellular Biology, Feb. 2015, 25 pages.

(56) References Cited

OTHER PUBLICATIONS

La Rocca et al., "Zymographic Detection and Clinical Correlations of MMP-2 and MMP-9 in Breast Cancer sera", Br. J. Cancer (2004) 90(7): 1414-1421.
Ramakrishnan et al., "Comparison of the Selective Cytotoxic Effects of Immunotoxins Containing Ricin A Chain or Pokeweed Antiviral Protein and Anti-Thy 1.1 Monoclonal Antibodies", Cancer Res. (1984) 44:201-208.
Vitetta et al., "Redesigning Nature's Poisons to Create Anti-Tumor Reagents", Science (1987) 238:1098.
Uccellini et al., "ISRE-Reporter Mouse Reveals High Basal and Induced Type I IFN Responses in Inflammatory Monocytes", Cell Rep. (2018); 25(10): 2784-2796.
Rivero-Juarez et al., "KIR2DS2 as predictor of thrombocytopenia secondary to pegylated interferon-alpha therapy", The Pharmacogenomics Journal (2017) 17, 360-365.
Breznik et al., "Proteases and cytokines as mediators of interactions between cancer and stromal cells in tumours", Biol. Chem. (2017); 398(7): 709-719.
Chen et al., "Type I IFN protects cancer cells from CD8+ T cell-mediated cytotoxicity after radiation", The Journal of Clinical Investigation vol. 129, No. 10, (2019), 4224-4238.

\* cited by examiner

*METDTLLLWVLLLWVPGST*GCDLPQTHSLGSRRTLMLLAQMRRISLFS
CLKDRHDFGFPQEEFGNQFQKAETIPVLHEMIQQIFNLFSTKDSSAAW
DETLLDKFYTELYQQLNDLEACVIQGVGVTETPLMKEDSILAVRKYFQ
RITLYLKEKKYSPCAWEVVRAEIMRSFSLSTNLQESLRSKESGRSDNI
*GGGS*ESKYGPPCPPCPAPEFLGGPSVFLFPPKPKDTLMISRTPEVTCV
VVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFL
YSRLTVDKSRWQQGNVFSCSVMHEALHNHYTQKSLSLS (SEQ ID NO:309)

FIGURE 3

*METDTLLLWVLLLWVPGSTG*CDLPQTHSLGSRRTLMLLAQMRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMRSFSLSTNLQESLRSKEISSGLLSGRSDNI*GGGS*ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQQGNVFSCSVMHEALHNHYTQKSLSLS (SEQ ID NO:311)

FIGURE 4

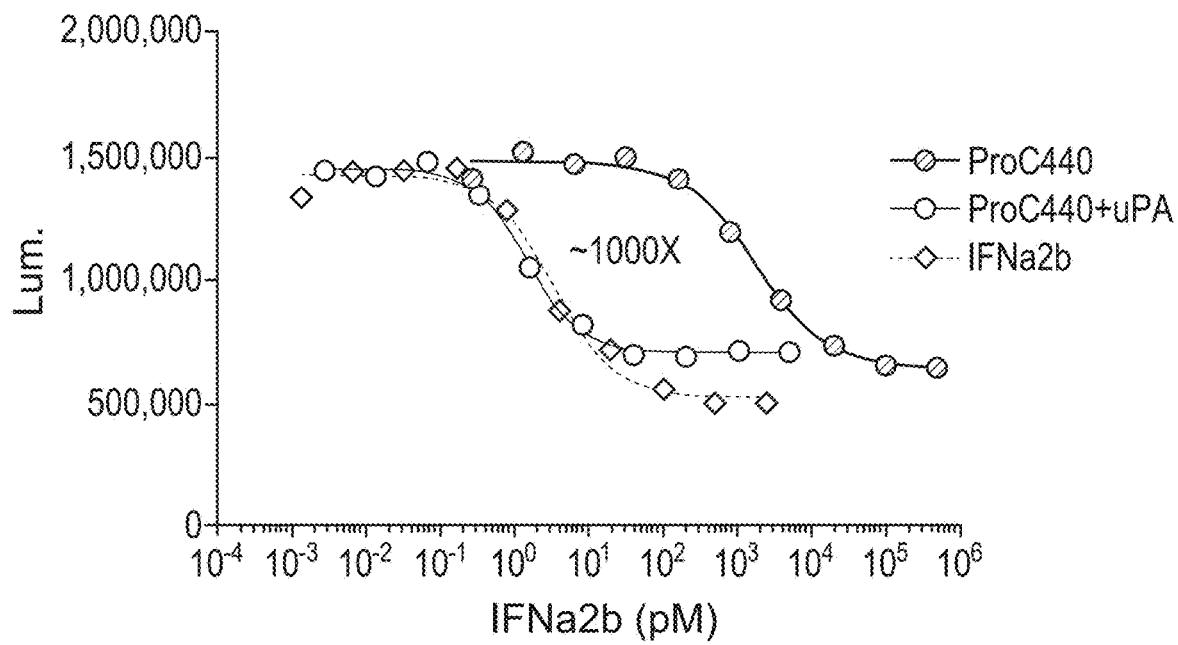
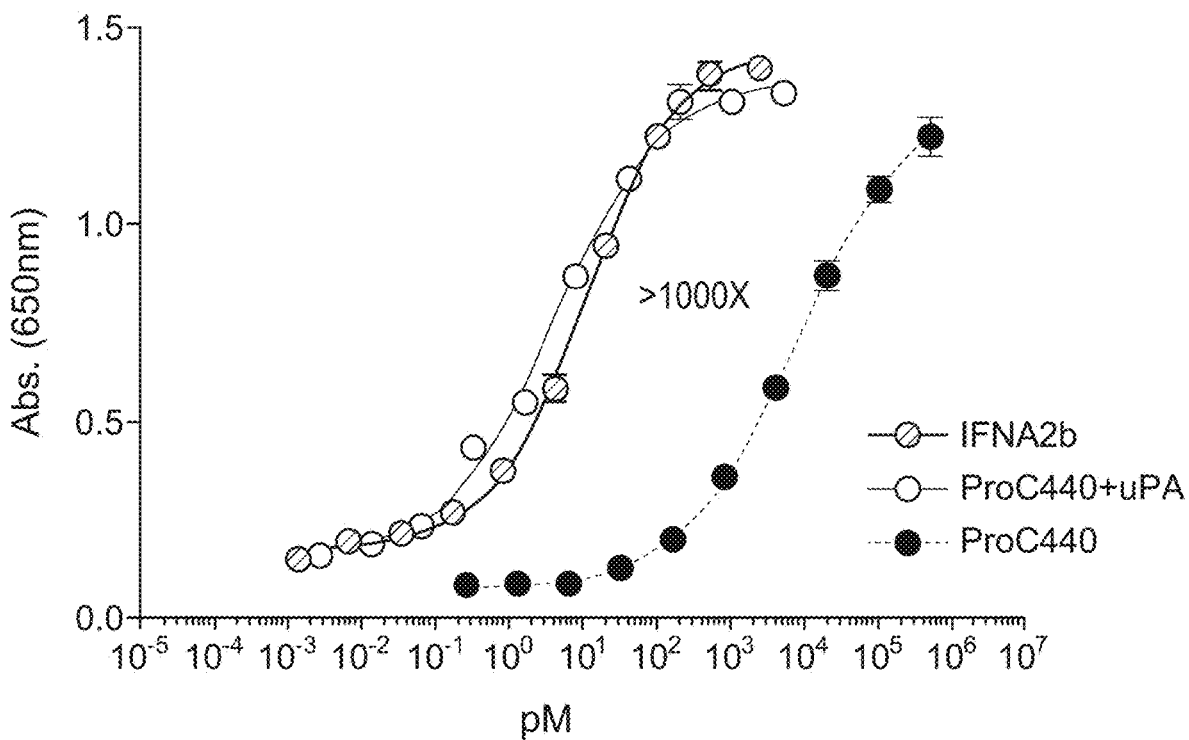
FIGURE 13

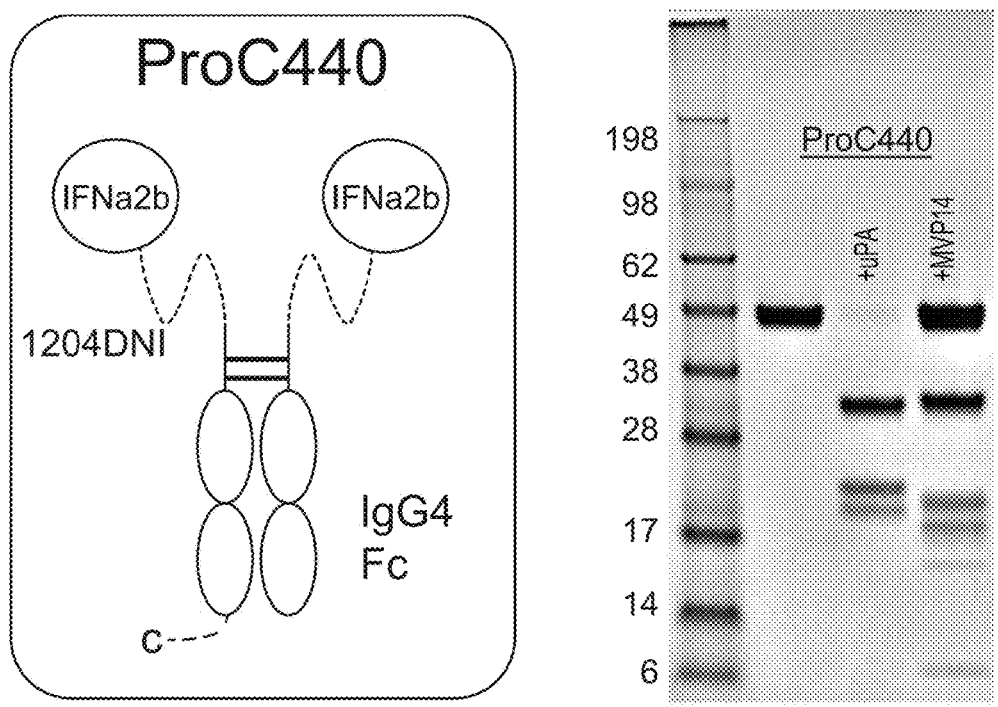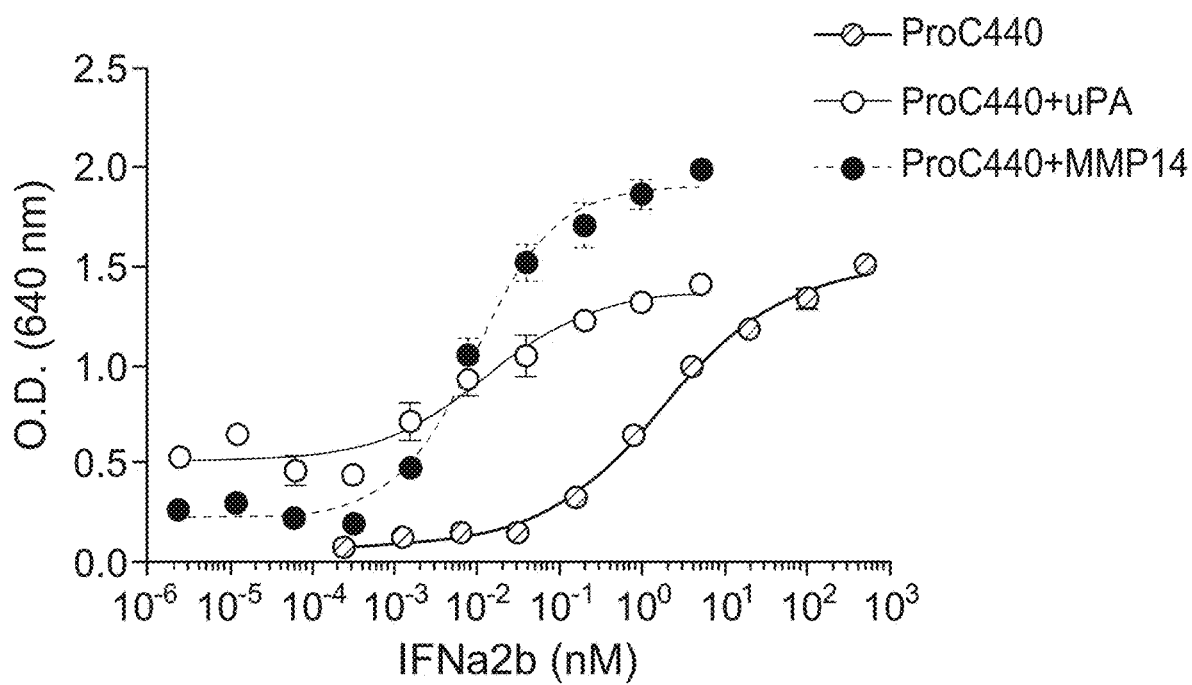
FIGURE 14A

ProC440 LC-MS data:

MMP14 cleavage
L161 uPA cleavage: 25145.1 Da
S169

CDLPQTHSLGSRTLMLLAQMRRISLFSCLKDRHDFGFPQEEFGNQFQKAETIPVLHEMIQQIFNLFSTKDSSA
AWDETLLDKFYTELYQQLNDLEACVIQGVGVTETPLMKEDSILAVRKYFQRTLYLKEKKYSPCAWEVVRAEIM
RSFSLSTNLQESLRSKESGRSDNICPPCAPEFLGGPSVFLPPKPKDTLMISRTPEVTCVVVDVSQEDPEVQ
FNWYVDGVEVHNAKTKPREEQFNSTYRVVSVLTVLHQDWLNGKEYKCKVSNKGLPSSIEKTISKAKGQPREP
QVYTLPPSQEEMTKNQVSLTCLVKGFYPSDIAVEWESNGQPENNYKTTPPVLDSDGSFFLYSRLTVDKSRWQ
QGNVFSCSVMHEALHNHYTQKSLSLS

FIGURE 14B

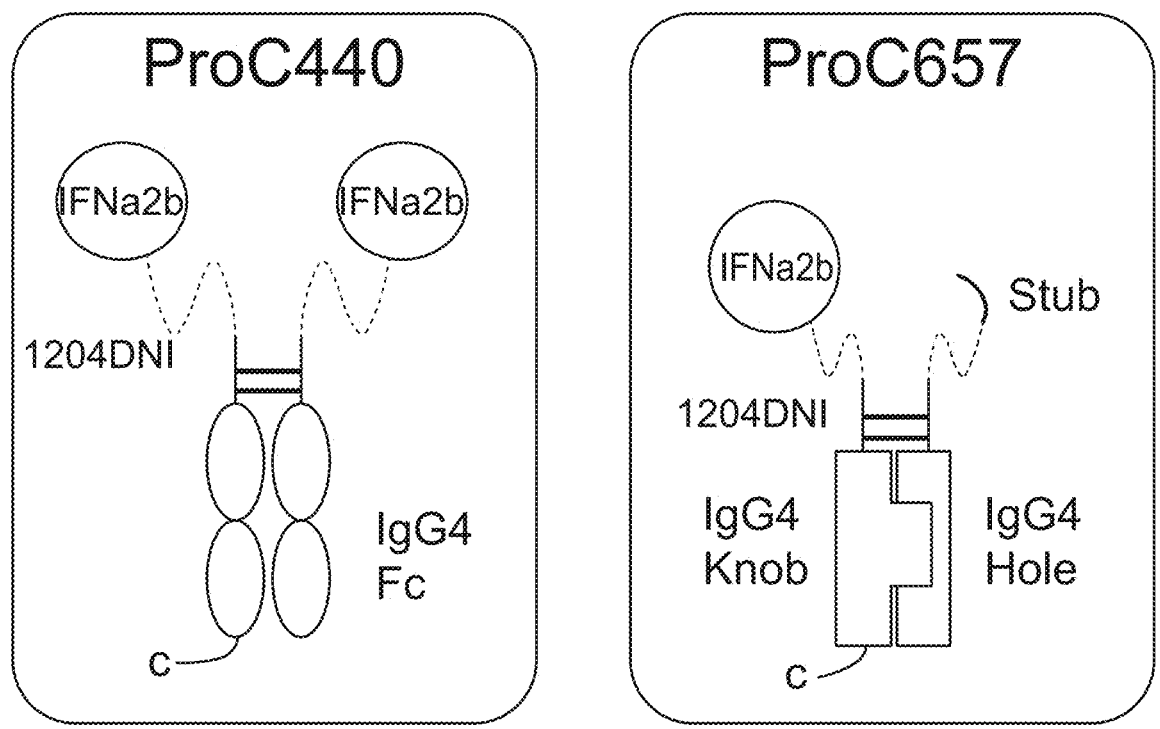
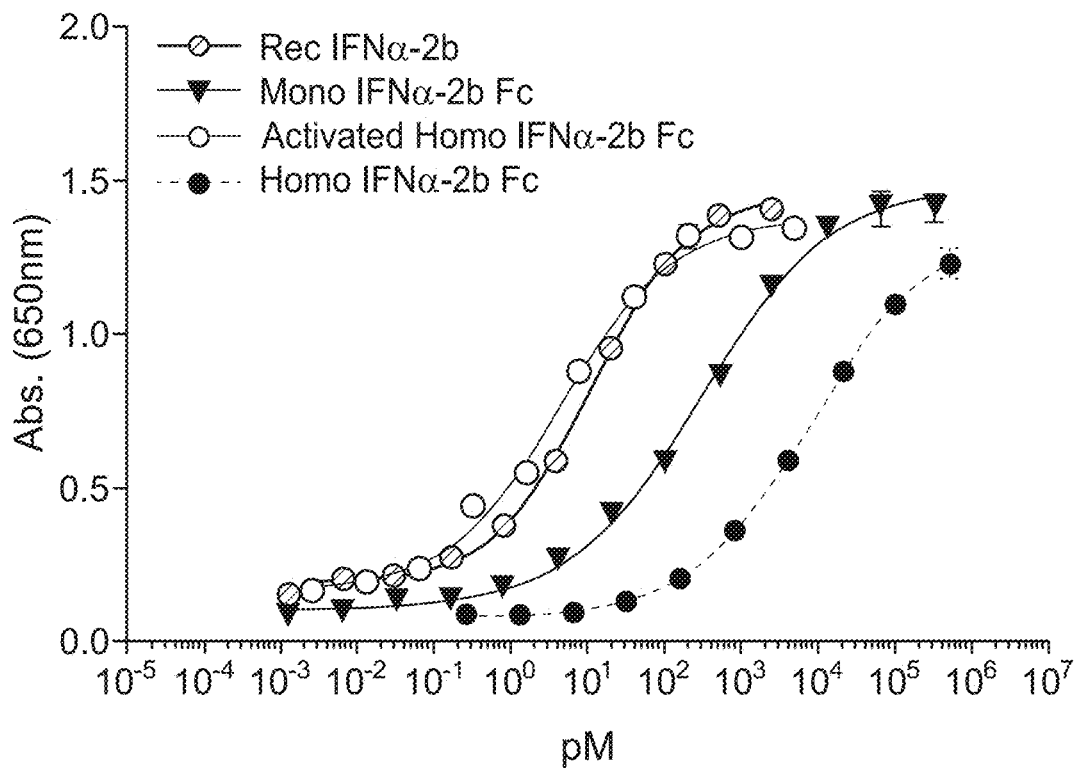
FIGURE 15

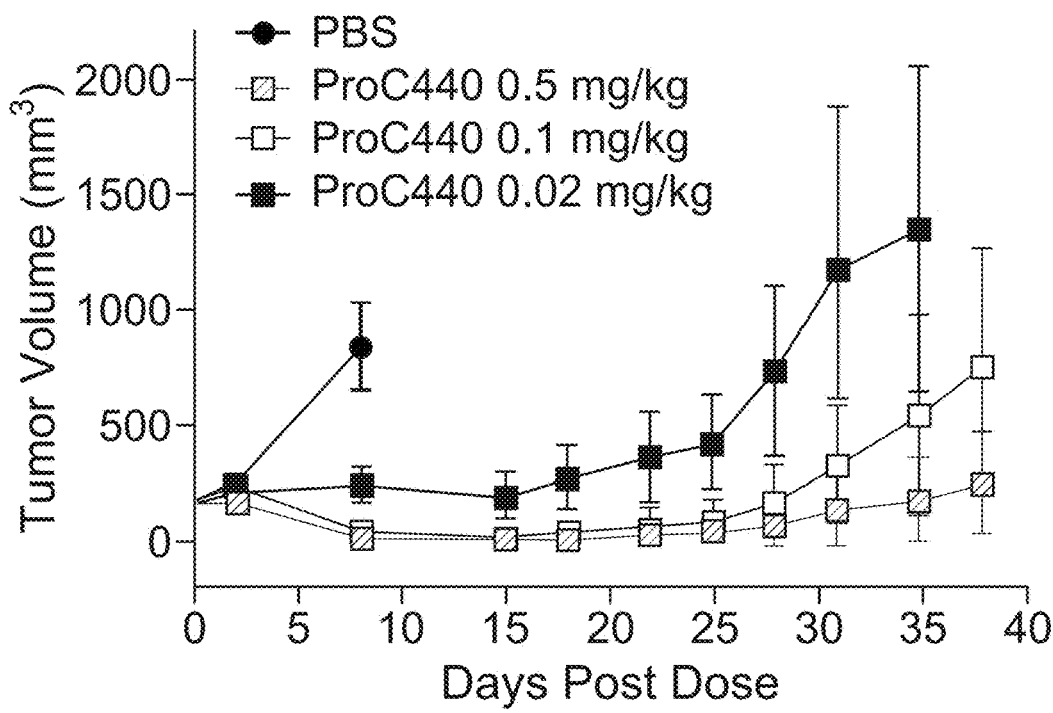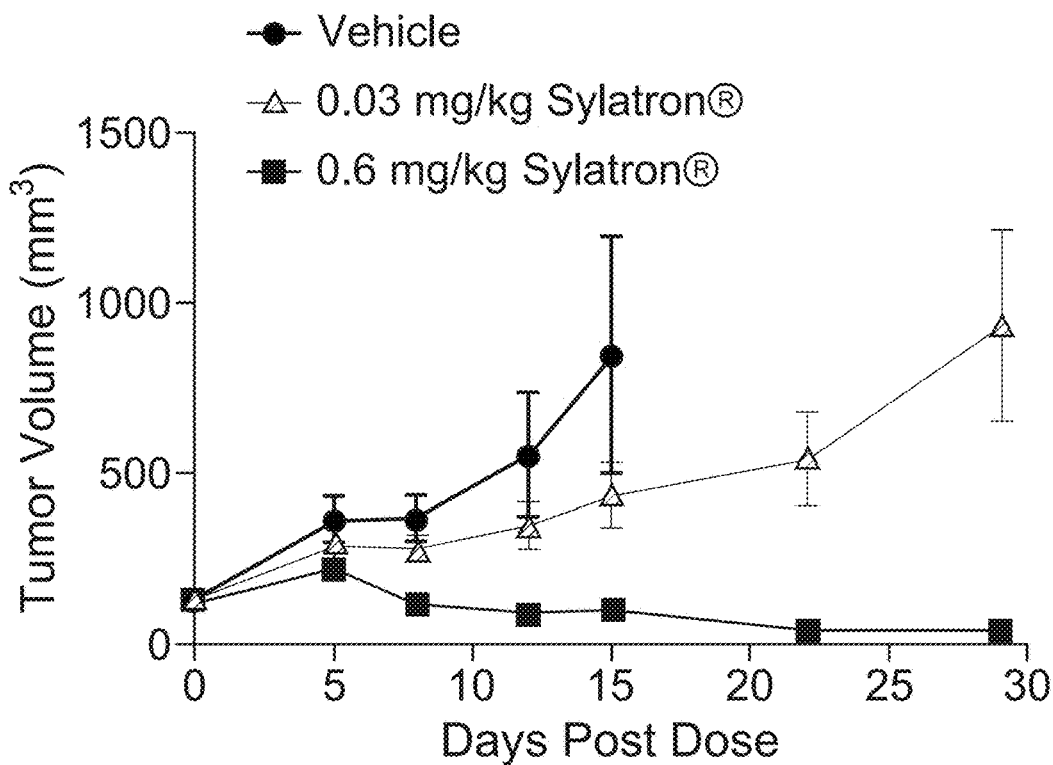
FIGURE 16

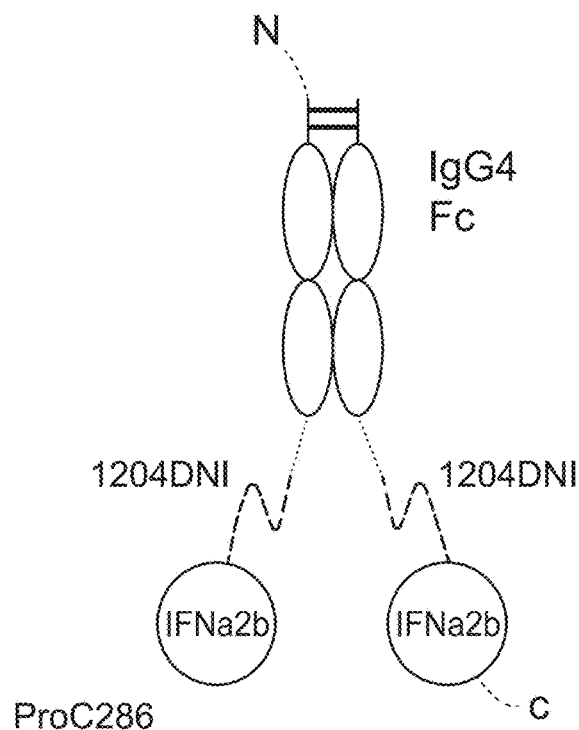
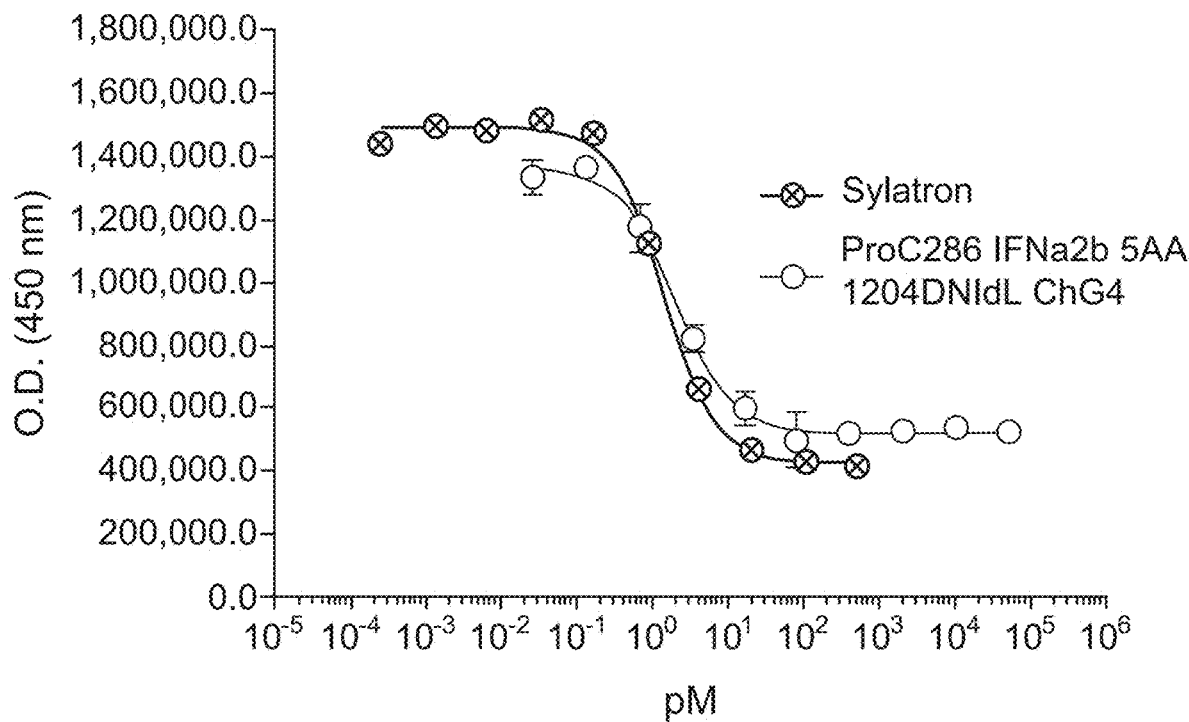
FIGURE 17A

|  | IFNa-con | ProC440+uPA | PEG-IFNa2b (Sylatron) | ProC440 |
|---|---|---|---|---|
| Specific activity | $1-2 \times 10^9$ U/mg | $3.5 \times 10^8$ U/mg | $0.7 \times 10^8$ U/mg | $1.3 \times 10^7$ U/mg |
| Anticipated toxic dose | 0.1 mpk* | 0.288 mpk | 1.43 mpk | 7.68 mpk |

FIGURE 18

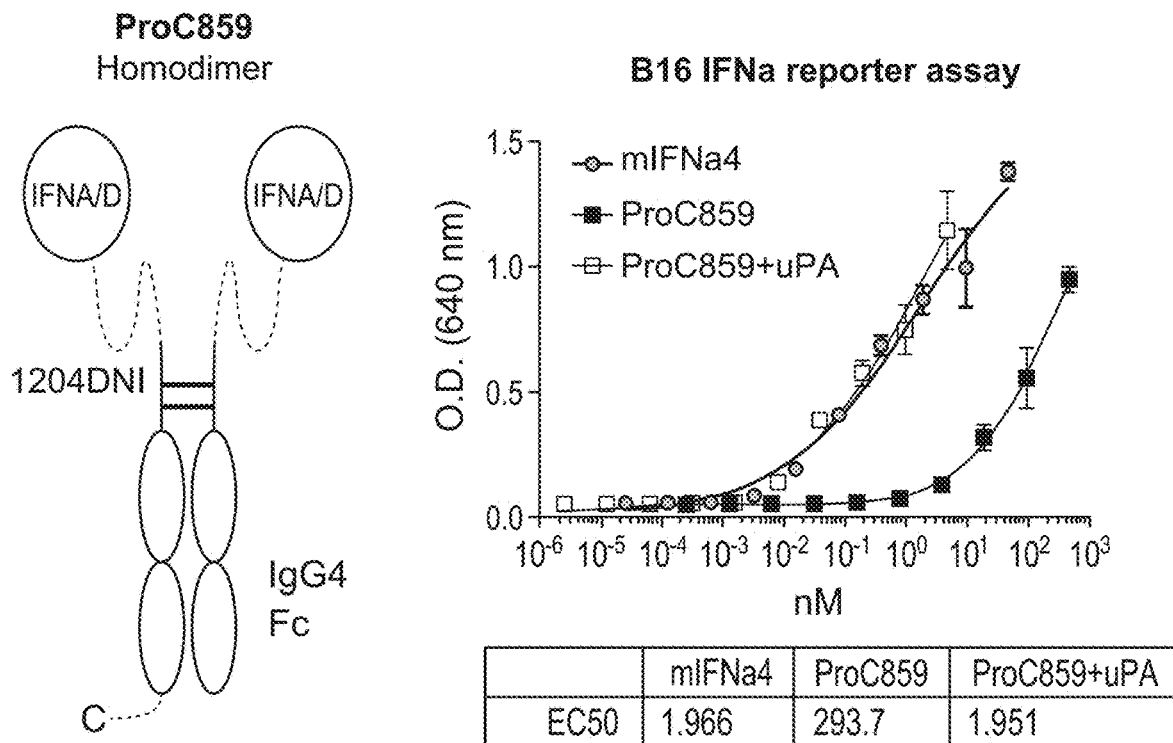
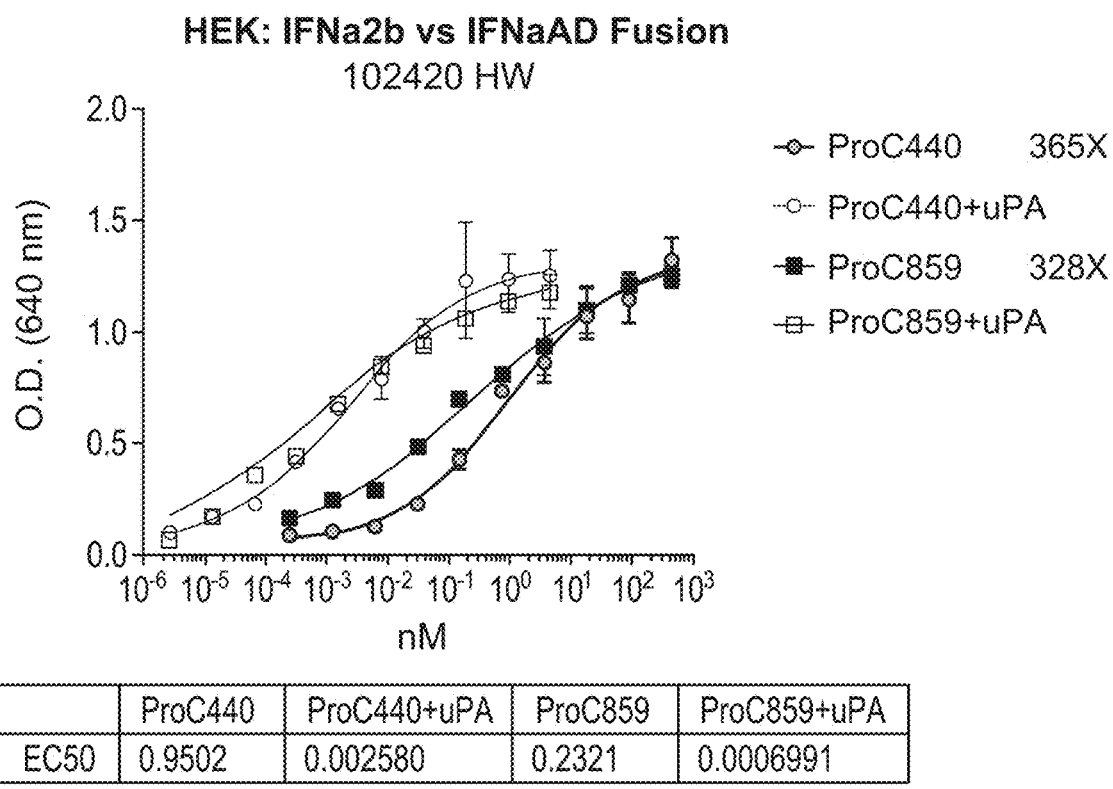
FIGURE 19

```
                              SEQUENCE LISTING

<160> NUMBER OF SEQ ID NOS: 518

<210> SEQ ID NO 1
<211> LENGTH: 165
<212> TYPE: PRT
<213> ORGANISM: Artificial Sequence
<220> FEATURE:
<223> OTHER INFORMATION: Synthetic

<400> SEQUENCE: 1

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Gly Gly Gly Ser
1

<210> SEQ ID NO 3
<211> LENGTH: 219
<212> TYPE: PRT
<213> ORGANISM: Artificial Sequence
<220> FEATURE:
<223> OTHER INFORMATION: Synthetic

<400> SEQUENCE: 3

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
```

```
            20                  25                  30
Glu Val Thr Cys Val Val Asp Val Ser Gln Glu Asp Pro Glu Val
        35                  40                  45
Gln Phe Asn Trp Tyr Val Asp Gly Val Glu Val His Asn Ala Lys Thr
    50                  55                  60
Lys Pro Arg Glu Glu Gln Phe Asn Ser Thr Tyr Arg Val Val Ser Val
65                  70                  75                  80
Leu Thr Val Leu His Gln Asp Trp Leu Asn Gly Lys Glu Tyr Lys Cys
                85                  90                  95
Lys Val Ser Asn Lys Gly Leu Pro Ser Ser Ile Glu Lys Thr Ile Ser
                100                 105                 110
Lys Ala Lys Gly Gln Pro Arg Glu Pro Gln Val Tyr Thr Leu Pro Pro
            115                 120                 125
Ser Gln Glu Glu Met Thr Lys Asn Gln Val Ser Leu Thr Cys Leu Val
            130                 135                 140
Lys Gly Phe Tyr Pro Ser Asp Ile Ala Val Glu Trp Glu Ser Asn Gly
145                 150                 155                 160
Gln Pro Glu Asn Asn Tyr Lys Thr Thr Pro Pro Val Leu Asp Ser Asp
                165                 170                 175
Gly Ser Phe Phe Leu Tyr Ser Arg Leu Thr Val Asp Lys Ser Arg Trp
                180                 185                 190
Gln Gln Gly Asn Val Phe Ser Cys Ser Val Met His Glu Ala Leu His
            195                 200                 205
Asn His Tyr Thr Gln Lys Ser Leu Ser Leu Ser
            210                 215

<210> SEQ ID NO 4
<211> LENGTH: 226
<212> TYPE: PRT
<213> ORGANISM: Artificial Sequence
<220> FEATURE:
<223> OTHER INFORMATION: Synthetic

<400> SEQUENCE: 4

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
                100                 105                 110
Ser Ile Glu Lys Thr Ile Ser Lys Ala Lys Gly Gln Pro Arg Glu Pro
            115                 120                 125
Gln Val Tyr Thr Leu Pro Pro Ser Gln Glu Glu Met Thr Lys Asn Gln
            130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
```

```
                    165                 170                 175
Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser
225

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Leu Ser Gly Arg Ser Asp Asn His
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Thr Gly Arg Gly Pro Ser Trp Val
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Pro Leu Thr Gly Arg Ser Gly Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Thr Ala Arg Gly Pro Ser Phe Lys
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Asn Thr Leu Ser Gly Arg Ser Glu Asn His Ser Gly
1               5                   10
```

```
<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Asn Thr Leu Ser Gly Arg Ser Gly Asn His Gly Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Thr Ser Thr Ser Gly Arg Ser Ala Asn Pro Arg Gly
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Thr Ser Gly Arg Ser Ala Asn Pro
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Val His Met Pro Leu Gly Phe Leu Gly Pro
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Ala Val Gly Leu Leu Ala Pro Pro
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Ala Gln Asn Leu Leu Gly Met Val
1               5
```

```
<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gln Asn Gln Ala Leu Arg Met Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Leu Ala Ala Pro Leu Gly Leu Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Ser Thr Phe Pro Phe Gly Met Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Ile Ser Ser Gly Leu Leu Ser Ser
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Pro Ala Gly Leu Trp Leu Asp Pro
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Val Ala Gly Arg Ser Met Arg Pro
1               5

<210> SEQ ID NO 22
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 22

Val Val Pro Glu Gly Arg Arg Ser
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Ile Leu Pro Arg Ser Pro Ala Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Met Val Leu Gly Arg Ser Leu Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Gln Gly Arg Ala Ile Thr Phe Ile
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Ser Pro Arg Ser Ile Met Leu Ala
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Ser Met Leu Arg Ser Met Pro Leu
1               5

<210> SEQ ID NO 28
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 28

Ile Ser Ser Gly Leu Leu Ser Gly Arg Ser Asp Asn His
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Synthetic

<400> SEQUENCE: 29

Ala Val Gly Leu Leu Ala Pro Pro Gly Gly Leu Ser Gly Arg Ser Asp
1               5                   10                  15

Asn His

<210> SEQ ID NO 30
<211> LENGTH: 22
<212> TYPE: PRT
<213> ORGANISM: Artificial Sequence
<220> FEATURE:
<223> OTHER INFORMATION: Synthetic

<400> SEQUENCE: 30

Ile Ser Ser Gly Leu Leu Ser Ser Gly Gly Ser Gly Gly Ser Leu Ser
1               5                   10                  15

Gly Arg Ser Asp Asn His
            20

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Leu Ser Gly Arg Ser Gly Asn His
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Ser Gly Arg Ser Ala Asn Pro Arg Gly
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Leu Ser Gly Arg Ser Asp Asp His
1               5
```

```
<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Leu Ser Gly Arg Ser Asp Ile His
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Leu Ser Gly Arg Ser Asp Gln His
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Leu Ser Gly Arg Ser Asp Thr His
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Leu Ser Gly Arg Ser Asp Tyr His
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Leu Ser Gly Arg Ser Asp Asn Pro
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

Leu Ser Gly Arg Ser Ala Asn Pro
1               5
```

```
<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Leu Ser Gly Arg Ser Ala Asn Ile
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Leu Ser Gly Arg Ser Asp Asn Ile
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Met Ile Ala Pro Val Ala Tyr Arg
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic

<400> SEQUENCE: 43

Arg Pro Ser Pro Met Trp Ala Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Trp Ala Thr Pro Arg Pro Met Arg
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

Phe Arg Leu Leu Asp Trp Gln Trp
1               5
```

```
<210> SEQ ID NO 46
<211> LENGTH: 5
<212> TYPE: PRT
<213> ORGANISM: Artificial Sequence
<220> FEATURE:
<223> OTHER INFORMATION: Synthetic

<400> SEQUENCE: 46

Ile Ser Ser Gly Leu
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Ile Ser Ser Gly Leu Leu Ser
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic

<400> SEQUENCE: 48

Ile Ser Ser Gly Leu Leu
1               5

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

Ile Ser Ser Gly Leu Leu Ser Gly Arg Ser Ala Asn Pro Arg Gly
1               5                   10                  15

<210> SEQ ID NO 50
<211> LENGTH: 18
<212> TYPE: PRT
<213> ORGANISM: Artificial Sequence
<220> FEATURE:
<223> OTHER INFORMATION: Synthetic

<400> SEQUENCE: 50

Ala Val Gly Leu Leu Ala Pro Pro Thr Ser Gly Arg Ser Ala Asn Pro
1               5                   10                  15

Arg Gly

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Ala Val Gly Leu Leu Ala Pro Pro Ser Gly Arg Ser Ala Asn Pro Arg
1               5                   10                  15
```

Gly

<210> SEQ ID NO 52
<211> LENGTH: 13
<212> TYPE: PRT
<213> ORGANISM: Artificial Sequence
<220> FEATURE:
<223> OTHER INFORMATION: Synthetic

<400> SEQUENCE: 52

Ile Ser Ser Gly Leu Leu Ser Gly Arg Ser Asp Asp His
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic

<400> SEQUENCE: 53

Ile Ser Ser Gly Leu Leu Ser Gly Arg Ser Asp Ile His
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic

<400> SEQUENCE: 54

Ile Ser Ser Gly Leu Leu Ser Gly Arg Ser Asp Gln His
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic

<400> SEQUENCE: 55

Ile Ser Ser Gly Leu Leu Ser Gly Arg Ser Asp Thr His
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic

<400> SEQUENCE: 56

Ile Ser Ser Gly Leu Leu Ser Gly Arg Ser Asp Tyr His
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic

<400> SEQUENCE: 57

Ile Ser Ser Gly Leu Leu Ser Gly Arg Ser Asp Asn Pro
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic

<400> SEQUENCE: 58

Ile Ser Ser Gly Leu Leu Ser Gly Arg Ser Ala Asn Pro
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic

<400> SEQUENCE: 59

Ile Ser Ser Gly Leu Leu Ser Gly Arg Ser Ala Asn Ile
1               5                   10

<210> SEQ ID NO 60
<211> LENGTH: 18
<212> TYPE: PRT
<213> ORGANISM: Artificial Sequence
<220> FEATURE:
<223> OTHER INFORMATION: Synthetic

<400> SEQUENCE: 60

Ala Val Gly Leu Leu Ala Pro Pro Gly Gly Leu Ser Gly Arg Ser Asp
1               5                   10                  15

Asp His

<210> SEQ ID NO 61
<211> LENGTH: 18
<212> TYPE: PRT
<213> ORGANISM: Artificial Sequence
<220> FEATURE:
<223> OTHER INFORMATION: Synthetic

<400> SEQUENCE: 61

Ala Val Gly Leu Leu Ala Pro Pro Gly Gly Leu Ser Gly Arg Ser Asp
1               5                   10                  15

Ile His

<210> SEQ ID NO 62
<211> LENGTH: 18
<212> TYPE: PRT
<213> ORGANISM: Artificial Sequence
<220> FEATURE:
<223> OTHER INFORMATION: Synthetic

<400> SEQUENCE: 62

Ala Val Gly Leu Leu Ala Pro Pro Gly Gly Leu Ser Gly Arg Ser Asp
1               5                   10                  15

Gln His

<210> SEQ ID NO 63
<211> LENGTH: 18
<212> TYPE: PRT
<213> ORGANISM: Artificial Sequence
<220> FEATURE:
<223> OTHER INFORMATION: Synthetic -continued

<400> SEQUENCE: 63

Ala Val Gly Leu Leu Ala Pro Pro Gly Gly Leu Ser Gly Arg Ser Asp
1               5                   10                  15

Thr His

<210> SEQ ID NO 64
<211> LENGTH: 18
<212> TYPE: PRT
<213> ORGANISM: Artificial Sequence
<220> FEATURE:
<223> OTHER INFORMATION: Synthetic

<400> SEQUENCE: 64

Ala Val Gly Leu Leu Ala Pro Pro Gly Gly Leu Ser Gly Arg Ser Asp
1               5                   10                  15

Tyr His

<210> SEQ ID NO 65
<211> LENGTH: 18
<212> TYPE: PRT
<213> ORGANISM: Artificial Sequence
<220> FEATURE:
<223> OTHER INFORMATION: Synthetic

<400> SEQUENCE: 65

Ala Val Gly Leu Leu Ala Pro Pro Gly Gly Leu Ser Gly Arg Ser Asp
1               5                   10                  15

Asn Pro

<210> SEQ ID NO 66
<211> LENGTH: 18
<212> TYPE: PRT
<213> ORGANISM: Artificial Sequence
<220> FEATURE:
<223> OTHER INFORMATION: Synthetic

<400> SEQUENCE: 66

Ala Val Gly Leu Leu Ala Pro Pro Gly Gly Leu Ser Gly Arg Ser Ala
1               5                   10                  15

Asn Pro

<210> SEQ ID NO 67
<211> LENGTH: 18
<212> TYPE: PRT
<213> ORGANISM: Artificial Sequence
<220> FEATURE:
<223> OTHER INFORMATION: Synthetic

<400> SEQUENCE: 67

Ala Val Gly Leu Leu Ala Pro Pro Gly Gly Leu Ser Gly Arg Ser Ala
1               5                   10                  15

Asn Ile

<210> SEQ ID NO 68
<211> LENGTH: 13
<212> TYPE: PRT
<213> ORGANISM: Artificial Sequence
<220> FEATURE:
<223> OTHER INFORMATION: Synthetic

<400> SEQUENCE: 68

Ile Ser Ser Gly Leu Leu Ser Gly Arg Ser Asp Asn Ile

-continued

```
1               5                   10

<210> SEQ ID NO 69
<211> LENGTH: 18
<212> TYPE: PRT
<213> ORGANISM: Artificial Sequence
<220> FEATURE:
<223> OTHER INFORMATION: Synthetic

<400> SEQUENCE: 69

Ala Val Gly Leu Leu Ala Pro Pro Gly Gly Leu Ser Gly Arg Ser Asp
1               5                   10                  15

Asn Ile

<210> SEQ ID NO 70
<211> LENGTH: 19
<212> TYPE: PRT
<213> ORGANISM: Artificial Sequence
<220> FEATURE:
<223> OTHER INFORMATION: Synthetic

<400> SEQUENCE: 70

Gly Leu Ser Gly Arg Ser Asp Asn His Gly Gly Ala Val Gly Leu Leu
1               5                   10                  15

Ala Pro Pro

<210> SEQ ID NO 71
<211> LENGTH: 21
<212> TYPE: PRT
<213> ORGANISM: Artificial Sequence
<220> FEATURE:
<223> OTHER INFORMATION: Synthetic

<400> SEQUENCE: 71

Gly Leu Ser Gly Arg Ser Asp Asn His Gly Gly Val His Met Pro Leu
1               5                   10                  15

Gly Phe Leu Gly Pro
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic

<400> SEQUENCE: 72

Leu Ser Gly Arg Ser Asp Asn His Gly Gly Val His Met Pro Leu Gly
1               5                   10                  15

Phe Leu Gly Pro
            20

<210> SEQ ID NO 73
<211> LENGTH: 7
<212> TYPE: PRT
<213> ORGANISM: Artificial Sequence
<220> FEATURE:
<223> OTHER INFORMATION: Synthetic

<400> SEQUENCE: 73

Ile Ser Ser Gly Leu Ser Ser
1               5

<210> SEQ ID NO 74
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 74

Pro Val Gly Tyr Thr Ser Ser Leu
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic

<400> SEQUENCE: 75

Asp Trp Leu Tyr Trp Pro Gly Ile
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Leu Lys Ala Ala Pro Arg Trp Ala
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic

<400> SEQUENCE: 77

Gly Pro Ser His Leu Val Leu Thr
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Leu Pro Gly Gly Leu Ser Pro Trp
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic

<400> SEQUENCE: 79

Met Gly Leu Phe Ser Glu Ala Gly
1               5

<210> SEQ ID NO 80
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 80

Ser Pro Leu Pro Leu Arg Val Pro
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic

<400> SEQUENCE: 81

Arg Met His Leu Arg Ser Leu Gly
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic

<400> SEQUENCE: 82

Leu Leu Ala Pro Ser His Arg Ala
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic

<400> SEQUENCE: 83

Gly Pro Arg Ser Phe Gly Leu
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic

<400> SEQUENCE: 84

Gly Pro Arg Ser Phe Gly
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic

<400> SEQUENCE: 85

Ser Ala Arg Gly Pro Ser Arg Trp
1               5

<210> SEQ ID NO 86
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 86

Gly Gly Trp His Thr Gly Arg Asn
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

His Thr Gly Arg Ser Gly Ala Leu
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Ala Ala Arg Gly Pro Ala Ile His
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic

<400> SEQUENCE: 89

Arg Gly Pro Ala Phe Asn Pro Met
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic

<400> SEQUENCE: 90

Ser Ser Arg Gly Pro Ala Tyr Leu
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic

<400> SEQUENCE: 91

Arg Gly Pro Ala Thr Pro Ile Met
1               5

<210> SEQ ID NO 92
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 92

Arg Gly Pro Ala
1

<210> SEQ ID NO 93
<211> LENGTH: 10
<212> TYPE: PRT
<213> ORGANISM: Artificial Sequence
<220> FEATURE:
<223> OTHER INFORMATION: Synthetic

<400> SEQUENCE: 93

Gly Gly Gln Pro Ser Gly Met Trp Gly Trp
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic

<400> SEQUENCE: 94

Phe Pro Arg Pro Leu Gly Ile Thr Gly Leu
1               5                   10

<210> SEQ ID NO 95
<211> LENGTH: 8
<212> TYPE: PRT
<213> ORGANISM: Artificial Sequence
<220> FEATURE:
<223> OTHER INFORMATION: Synthetic

<400> SEQUENCE: 95

Ser Pro Leu Thr Gly Arg Ser Gly
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Ser Ala Gly Phe Ser Leu Pro Ala
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic

<400> SEQUENCE: 97

Leu Ala Pro Leu Gly Leu Gln Arg Arg
1               5

<210> SEQ ID NO 98
<211> LENGTH: 8
<212> TYPE: PRT
<213> ORGANISM: Artificial Sequence
<220> FEATURE:
```

<223> OTHER INFORMATION: Synthetic

<400> SEQUENCE: 98

Ser Gly Gly Pro Leu Gly Val Arg
1               5

<210> SEQ ID NO 99
<211> LENGTH: 4
<212> TYPE: PRT
<213> ORGANISM: Artificial Sequence
<220> FEATURE:
<223> OTHER INFORMATION: Synthetic

<400> SEQUENCE: 99

Pro Leu Gly Leu
1

<210> SEQ ID NO 100
<211> LENGTH: 7
<212> TYPE: PRT
<213> ORGANISM: Artificial Sequence
<220> FEATURE:
<223> OTHER INFORMATION: Synthetic

<400> SEQUENCE: 100

Ser Gly Arg Ser Asp Asn Ile
1               5

<210> SEQ ID NO 101
<211> LENGTH: 165
<212> TYPE: PRT
<213> ORGANISM: Artificial Sequence
<220> FEATURE:
<223> OTHER INFORMATION: Synthetic

<400> SEQUENCE: 101

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 102
<211> LENGTH: 169

```
<212> TYPE: PRT
<213> ORGANISM: Artificial Sequence
<220> FEATURE:
<223> OTHER INFORMATION: Synthetic

<400> SEQUENCE: 102

Cys Asp Leu Pro His Thr His Asn Leu Arg Asn Lys Arg Ala Phe Thr
1               5                   10                  15

Leu Leu Ala Gln Met Arg Arg Leu Ser Pro Val Ser Cys Leu Lys Asp
            20                  25                  30

Arg Lys Asp Phe Gly Phe Pro Leu Glu Lys Val Asp Gly Gln Gln Ile
        35                  40                  45

Gln Lys Ala Gln Ala Ile Pro Val Leu His Glu Leu Thr Gln Gln Ile
    50                  55                  60

Leu Ser Leu Phe Thr Ser Lys Glu Ser Ser Thr Ala Trp Asp Ala Ser
65                  70                  75                  80

Leu Leu Asp Ser Phe Cys Asn Asp Leu Gln Gln Gln Leu Ser Gly Leu
                85                  90                  95

Gln Ala Cys Leu Met Gln Gln Val Gly Val Gln Glu Ser Pro Leu Thr
            100                 105                 110

Gln Glu Asp Ser Leu Leu Ala Val Arg Glu Tyr Phe His Arg Ile Thr
        115                 120                 125

Val Tyr Leu Arg Glu Lys Lys His Ser Pro Cys Ala Trp Glu Val Val
    130                 135                 140

Arg Ala Glu Val Trp Arg Ala Leu Ser Ser Ala Asn Leu Leu Gly
145                 150                 155                 160

Arg Leu Arg Glu Glu Arg Asn Glu Ser
                165

<210> SEQ ID NO 103
<211> LENGTH: 167
<212> TYPE: PRT
<213> ORGANISM: Artificial Sequence
<220> FEATURE:
<223> OTHER INFORMATION: Synthetic

<400> SEQUENCE: 103

Cys Asp Leu Pro His Thr Tyr Asn Leu Arg Asn Lys Arg Ala Leu Lys
1               5                   10                  15

Val Leu Ala Gln Met Arg Arg Leu Pro Phe Leu Ser Cys Leu Lys Asp
            20                  25                  30

Arg Gln Asp Phe Gly Phe Pro Leu Glu Lys Val Asp Asn Gln Gln Ile
        35                  40                  45

Gln Lys Ala Gln Ala Ile Pro Val Leu Arg Asp Leu Thr Gln Gln Thr
    50                  55                  60

Leu Asn Leu Phe Thr Ser Lys Ala Ser Ser Ala Ala Trp Asn Ala Thr
65                  70                  75                  80

Leu Leu Asp Ser Phe Cys Asn Asp Leu His Gln Gln Leu Asn Asp Leu
                85                  90                  95

Gln Thr Cys Leu Met Gln Gln Val Gly Val Gln Glu Pro Pro Leu Thr
            100                 105                 110

Gln Glu Asp Ala Leu Leu Ala Val Arg Lys Tyr Phe His Arg Ile Thr
        115                 120                 125

Val Tyr Leu Arg Glu Lys Lys His Ser Pro Cys Ala Trp Glu Val Val
    130                 135                 140

Arg Ala Glu Val Trp Arg Ala Leu Ser Ser Ser Val Asn Leu Leu Pro
145                 150                 155                 160
```

Arg Leu Ser Glu Glu Lys Glu
            165

<210> SEQ ID NO 104
<211> LENGTH: 165
<212> TYPE: PRT
<213> ORGANISM: Artificial Sequence
<220> FEATURE:
<223> OTHER INFORMATION: Synthetic

<400> SEQUENCE: 104

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 105
<211> LENGTH: 495
<212> TYPE: PRT
<213> ORGANISM: Artificial Sequence
<220> FEATURE:
<223> OTHER INFORMATION: Synthetic

<400> SEQUENCE: 105

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu

```
            115                 120                 125
Tyr Leu Lys Glu Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Cys Asp Leu Pro Gln Thr His Ser Leu Gly Ser
                165                 170                 175

Arg Arg Thr Leu Met Leu Leu Ala Gln Met Arg Arg Ile Ser Leu Phe
                180                 185                 190

Ser Cys Leu Lys Asp Arg His Asp Phe Gly Phe Pro Gln Glu Glu Phe
                195                 200                 205

Gly Asn Gln Phe Gln Lys Ala Glu Thr Ile Pro Val Leu His Glu Met
                210                 215                 220

Ile Gln Gln Ile Phe Asn Leu Phe Ser Thr Lys Asp Ser Ser Ala Ala
225                 230                 235                 240

Trp Asp Glu Thr Leu Leu Asp Lys Phe Tyr Thr Glu Leu Tyr Gln Gln
                245                 250                 255

Leu Asn Asp Leu Glu Ala Cys Val Ile Gln Gly Val Gly Val Thr Glu
                260                 265                 270

Thr Pro Leu Met Asn Glu Asp Ser Ile Leu Ala Val Arg Lys Tyr Phe
                275                 280                 285

Gln Arg Ile Thr Leu Tyr Leu Lys Glu Lys Lys Tyr Ser Pro Cys Ala
                290                 295                 300

Trp Glu Val Val Arg Ala Glu Ile Met Arg Ser Phe Ser Leu Ser Thr
305                 310                 315                 320

Asn Leu Gln Glu Ser Leu Arg Ser Lys Glu Cys Asp Leu Pro Gln Thr
                325                 330                 335

His Ser Leu Gly Ser Arg Arg Thr Leu Met Leu Leu Ala Gln Met Arg
                340                 345                 350

Arg Ile Ser Leu Phe Ser Cys Leu Lys Asp Arg His Asp Phe Gly Phe
                355                 360                 365

Pro Gln Glu Glu Phe Gly Asn Gln Phe Gln Lys Ala Glu Thr Ile Pro
370                 375                 380

Val Leu His Glu Met Ile Gln Gln Ile Phe Asn Leu Phe Ser Thr Lys
385                 390                 395                 400

Asp Ser Ser Ala Ala Trp Asp Glu Thr Leu Leu Asp Lys Phe Tyr Thr
                405                 410                 415

Glu Leu Tyr Gln Gln Leu Asn Asp Leu Glu Ala Cys Val Ile Gln Gly
                420                 425                 430

Val Gly Val Thr Glu Thr Pro Leu Met Asn Glu Asp Ser Ile Leu Ala
                435                 440                 445

Val Arg Lys Tyr Phe Gln Arg Ile Thr Leu Tyr Leu Lys Glu Lys Lys
                450                 455                 460

Tyr Ser Pro Cys Ala Trp Glu Val Val Arg Ala Glu Ile Met Arg Ser
465                 470                 475                 480

Phe Ser Leu Ser Thr Asn Leu Gln Glu Ser Leu Arg Ser Lys Glu
                485                 490                 495

<210> SEQ ID NO 106
<211> LENGTH: 166
<212> TYPE: PRT
<213> ORGANISM: Artificial Sequence
<220> FEATURE:
<223> OTHER INFORMATION: Synthetic
```

<400> SEQUENCE: 106

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 107
<211> LENGTH: 165
<212> TYPE: PRT
<213> ORGANISM: Artificial Sequence
<220> FEATURE:
<223> OTHER INFORMATION: Synthetic

<400> SEQUENCE: 107

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Thr Gly Trp Asn Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

```
<210> SEQ ID NO 108
<211> LENGTH: 182
<212> TYPE: PRT
<213> ORGANISM: Artificial Sequence
<220> FEATURE:
<223> OTHER INFORMATION: Synthetic

<400> SEQUENCE: 108
```

| Met<br>1 | Asn | Asn | Arg | Trp<br>5 | Ile | Leu | His | Ala | Ala<br>10 | Phe | Leu | Leu | Cys | Phe<br>15 | Ser |
|---|---|---|---|---|---|---|---|---|---|---|---|---|---|---|---|

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
        115                 120                 125

Trp Glu Met Ser Ser Thr Ala Leu His Leu Lys Ser Tyr Tyr Trp Arg
    130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn
            180

```
<210> SEQ ID NO 109
<211> LENGTH: 184
<212> TYPE: PRT
<213> ORGANISM: Artificial Sequence
<220> FEATURE:
<223> OTHER INFORMATION: Synthetic

<400> SEQUENCE: 109
```

Met Ala Asn Arg Trp Thr Leu His Ile Ala Phe Leu Leu Cys Phe Ser
1               5                   10                  15

Thr Thr Ala Leu Ser Ile Asp Tyr Lys Gln Leu Gln Phe Arg Gln Ser
            20                  25                  30

Thr Ser Ile Arg Thr Cys Gln Lys Leu Leu Arg Gln Leu Asn Gly Arg
        35                  40                  45

Leu Asn Leu Ser Tyr Arg Thr Asp Phe Lys Ile Pro Met Glu Val Met
    50                  55                  60

His Pro Ser Gln Met Glu Lys Ser Tyr Thr Ala Phe Ala Ile Gln Val
65                  70                  75                  80

Met Leu Gln Asn Val Phe Leu Val Phe Arg Ser Asn Phe Ser Ser Thr
                85                  90                  95

Gly Trp Asn Glu Thr Ile Val Glu Ser Leu Leu Asp Glu Leu His Gln
            100                 105                 110

Gln Thr Glu Leu Leu Glu Ile Ile Leu Lys Glu Lys Gln Glu Glu Arg
        115                 120                 125

```
Leu Thr Trp Val Thr Ser Thr Thr Leu Gly Leu Lys Ser Tyr Tyr
    130                 135                 140

Trp Arg Val Gln Arg Tyr Leu Lys Asp Lys Tyr Asn Ser Tyr Ala
145                 150                 155                 160

Trp Met Val Val Arg Ala Glu Val Phe Arg Asn Phe Ser Ile Ile Leu
                165                 170                 175

Arg Leu Asn Arg Asn Phe Gln Asn
            180

<210> SEQ ID NO 110
<211> LENGTH: 173
<212> TYPE: PRT
<213> ORGANISM: Artificial Sequence
<220> FEATURE:
<223> OTHER INFORMATION: Synthetic

<400> SEQUENCE: 110

Met Cys Asp Leu Pro Gln Asn His Gly Leu Leu Ser Arg Asn Thr Leu
1               5                   10                  15

Val Leu Leu His Gln Met Arg Arg Ile Ser Pro Phe Leu Cys Leu Lys
                20                  25                  30

Asp Arg Arg Asp Phe Arg Phe Pro Gln Glu Met Val Lys Gly Ser Gln
            35                  40                  45

Leu Gln Lys Ala His Val Met Ser Val Leu His Glu Met Leu Gln Gln
50                  55                  60

Ile Phe Ser Leu Phe His Thr Glu Arg Ser Ser Ala Ala Trp Asn Met
65                  70                  75                  80

Thr Leu Leu Asp Gln Leu His Thr Gly Leu His Gln Gln Leu Gln His
                85                  90                  95

Leu Glu Thr Cys Leu Leu Gln Val Val Gly Glu Gly Glu Ser Ala Gly
            100                 105                 110

Ala Ile Ser Ser Pro Ala Leu Thr Leu Arg Arg Tyr Phe Gln Gly Ile
        115                 120                 125

Arg Val Tyr Leu Lys Glu Lys Lys Tyr Ser Asp Cys Ala Trp Glu Val
130                 135                 140

Val Arg Met Glu Ile Met Lys Ser Leu Phe Leu Ser Thr Asn Met Gln
145                 150                 155                 160

Glu Arg Leu Arg Ser Lys Asp Arg Asp Leu Gly Ser Ser
                165                 170

<210> SEQ ID NO 111
<211> LENGTH: 271
<212> TYPE: PRT
<213> ORGANISM: Artificial Sequence
<220> FEATURE:
<223> OTHER INFORMATION: Synthetic

<400> SEQUENCE: 111

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
                20                  25                  30

Lys Ser Phe Tyr His Val Ser Tyr Gly Pro Leu His Glu Gly Cys Met
            35                  40                  45

Asp Gln Ser Val Ser Leu Ser Ile Ser Glu Thr Ser Lys Thr Ser Lys
50                  55                  60

Leu Thr Phe Lys Glu Ser Met Val Val Ala Thr Asn Gly Lys Val
65                  70                  75                  80
```

```
Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Val Lys Tyr Asn Phe Met Arg
            115                 120                 125

Ile Ile Lys Tyr Glu Phe Ile Leu Asn Asp Ala Leu Asn Gln Ser Ile
        130                 135                 140

Ile Arg Ala Asn Asp Gln Tyr Leu Thr Ala Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
            195                 200                 205

Glu Ile Pro Lys Thr Ile Thr Gly Ser Glu Thr Asn Leu Leu Phe Phe
        210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 112
<211> LENGTH: 270
<212> TYPE: PRT
<213> ORGANISM: Artificial Sequence
<220> FEATURE:
<223> OTHER INFORMATION: Synthetic

<400> SEQUENCE: 112

Met Ala Lys Val Pro Asp Leu Phe Glu Asp Leu Lys Asn Cys Tyr Ser
1               5                   10                  15

Glu Asn Glu Asp Tyr Ser Ser Ala Ile Asp His Leu Ser Leu Asn Gln
            20                  25                  30

Lys Ser Phe Tyr Asp Ala Ser Tyr Gly Ser Leu His Glu Thr Cys Thr
        35                  40                  45

Asp Gln Phe Val Ser Leu Arg Thr Ser Glu Thr Ser Lys Met Ser Asn
    50                  55                  60

Phe Thr Phe Lys Glu Ser Arg Val Thr Val Ser Ala Thr Ser Ser Asn
65                  70                  75                  80

Gly Lys Ile Leu Lys Lys Arg Leu Ser Phe Ser Glu Thr Phe Thr
                85                  90                  95

Glu Asp Asp Leu Gln Ser Ile Thr His Asp Leu Glu Glu Thr Ile Gln
            100                 105                 110

Pro Arg Ser Ala Pro Tyr Thr Tyr Gln Ser Asp Leu Arg Tyr Lys Leu
        115                 120                 125

Met Lys Leu Val Arg Gln Lys Phe Val Met Asn Asp Ser Leu Asn Gln
    130                 135                 140

Thr Ile Tyr Gln Asp Val Asp Lys His Tyr Leu Ser Thr Thr Trp Leu
145                 150                 155                 160

Asn Asp Leu Gln Gln Glu Val Lys Phe Asp Met Tyr Ala Tyr Ser Ser
                165                 170                 175
```

-continued

Gly Gly Asp Asp Ser Lys Tyr Pro Val Thr Leu Lys Ile Ser Asp Ser
                180                 185                 190

Gln Leu Phe Val Ser Ala Gln Gly Glu Asp Gln Pro Val Leu Leu Lys
            195                 200                 205

Glu Leu Pro Glu Thr Pro Lys Leu Ile Thr Gly Ser Glu Thr Asp Leu
210                 215                 220

Ile Phe Phe Trp Lys Ser Ile Asn Ser Lys Asn Tyr Phe Thr Ser Ala
225                 230                 235                 240

Ala Tyr Pro Glu Leu Phe Ile Ala Thr Lys Glu Gln Ser Arg Val His
                245                 250                 255

Leu Ala Arg Gly Leu Pro Ser Met Thr Asp Phe Gln Ile Ser
            260                 265                 270

<210> SEQ ID NO 113
<211> LENGTH: 269
<212> TYPE: PRT
<213> ORGANISM: Artificial Sequence
<220> FEATURE:
<223> OTHER INFORMATION: Synthetic

<400> SEQUENCE: 113

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
            130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 114
<211> LENGTH: 269
<212> TYPE: PRT
<213> ORGANISM: Artificial Sequence
<220> FEATURE:
<223> OTHER INFORMATION: Synthetic

<400> SEQUENCE: 114

Met Ala Thr Val Pro Glu Leu Asn Cys Glu Met Pro Pro Phe Asp Ser
1               5                   10                  15

Asp Glu Asn Asp Leu Phe Phe Glu Val Asp Gly Pro Gln Lys Met Lys
            20                  25                  30

Gly Cys Phe Gln Thr Phe Asp Leu Gly Cys Pro Asp Glu Ser Ile Gln
        35                  40                  45

Leu Gln Ile Ser Gln Gln His Ile Asn Lys Ser Phe Arg Gln Ala Val
    50                  55                  60

Ser Leu Ile Val Ala Val Glu Lys Leu Trp Gln Leu Pro Val Ser Phe
65                  70                  75                  80

Pro Trp Thr Phe Gln Asp Glu Asp Met Ser Thr Phe Ser Phe Ile
                85                  90                  95

Phe Glu Glu Glu Pro Ile Leu Cys Asp Ser Trp Asp Asp Asp Asn
            100                 105                 110

Leu Leu Val Cys Asp Val Pro Ile Arg Gln Leu His Tyr Arg Leu Arg
        115                 120                 125

Asp Glu Gln Gln Lys Ser Leu Val Leu Ser Asp Pro Tyr Glu Leu Lys
    130                 135                 140

Ala Leu His Leu Asn Gly Gln Asn Ile Asn Gln Gln Val Ile Phe Ser
145                 150                 155                 160

Met Ser Phe Val Gln Gly Glu Pro Ser Asn Asp Lys Ile Pro Val Ala
                165                 170                 175

Leu Gly Leu Lys Gly Lys Asn Leu Tyr Leu Ser Cys Val Met Lys Asp
            180                 185                 190

Gly Thr Pro Thr Leu Gln Leu Glu Ser Val Asp Pro Lys Gln Tyr Pro
        195                 200                 205

Lys Lys Lys Met Glu Lys Arg Phe Val Phe Asn Lys Ile Glu Val Lys
    210                 215                 220

Ser Lys Val Glu Phe Glu Ser Ala Glu Phe Pro Asn Trp Tyr Ile Ser
225                 230                 235                 240

Thr Ser Gln Ala Glu His Lys Pro Val Phe Leu Gly Asn Asn Ser Gly
                245                 250                 255

Gln Asp Ile Ile Asp Phe Thr Met Glu Ser Val Ser Ser
            260                 265

<210> SEQ ID NO 115
<211> LENGTH: 177
<212> TYPE: PRT
<213> ORGANISM: Artificial Sequence
<220> FEATURE:
<223> OTHER INFORMATION: Synthetic

<400> SEQUENCE: 115

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe

```
            35                  40                  45
Tyr Leu Arg Asn Asn Gln Leu Val Ala Gly Tyr Leu Gln Gly Pro Asn
 50                  55                  60

Val Asn Leu Glu Glu Lys Ile Asp Val Val Pro Ile Glu Pro His Ala
 65                  70                  75                  80

Leu Phe Leu Gly Ile His Gly Gly Lys Met Cys Leu Ser Cys Val Lys
                     85                  90                  95

Ser Gly Asp Glu Thr Arg Leu Gln Leu Glu Ala Val Asn Ile Thr Asp
                100                 105                 110

Leu Ser Glu Asn Arg Lys Gln Asp Lys Arg Phe Ala Phe Ile Arg Ser
            115                 120                 125

Asp Ser Gly Pro Thr Thr Ser Phe Glu Ser Ala Ala Cys Pro Gly Trp
        130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 116
<211> LENGTH: 178
<212> TYPE: PRT
<213> ORGANISM: Artificial Sequence
<220> FEATURE:
<223> OTHER INFORMATION: Synthetic

<400> SEQUENCE: 116

Met Glu Ile Cys Trp Gly Pro Tyr Ser His Leu Ile Ser Leu Leu Leu
1               5                   10                  15

Ile Leu Leu Phe His Ser Glu Ala Ala Cys Arg Pro Ser Gly Lys Arg
                 20                  25                  30

Pro Cys Lys Met Gln Ala Phe Arg Ile Trp Asp Thr Asn Gln Lys Thr
             35                  40                  45

Phe Tyr Leu Arg Asn Asn Gln Leu Ile Ala Gly Tyr Leu Gln Gly Pro
         50                  55                  60

Asn Ile Lys Leu Glu Glu Lys Ile Asp Met Val Pro Ile Asp Leu His
 65                  70                  75                  80

Ser Val Phe Leu Gly Ile His Gly Gly Lys Leu Cys Leu Ser Cys Ala
                 85                  90                  95

Lys Ser Gly Asp Asp Ile Lys Leu Gln Leu Glu Glu Val Asn Ile Thr
                100                 105                 110

Asp Leu Ser Lys Asn Lys Glu Glu Asp Lys Arg Phe Thr Phe Ile Arg
            115                 120                 125

Ser Glu Lys Gly Pro Thr Thr Ser Phe Glu Ser Ala Ala Cys Pro Gly
        130                 135                 140

Trp Phe Leu Cys Thr Thr Leu Glu Ala Asp Arg Pro Val Ser Leu Thr
145                 150                 155                 160

Asn Thr Pro Glu Glu Pro Leu Ile Val Thr Lys Phe Tyr Phe Gln Glu
                165                 170                 175

Asp Gln

<210> SEQ ID NO 117
<211> LENGTH: 193
<212> TYPE: PRT
<213> ORGANISM: Artificial Sequence
<220> FEATURE:
```

<223> OTHER INFORMATION: Synthetic

<400> SEQUENCE: 117

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

<210> SEQ ID NO 118
<211> LENGTH: 192
<212> TYPE: PRT
<213> ORGANISM: Artificial Sequence
<220> FEATURE:
<223> OTHER INFORMATION: Synthetic

<400> SEQUENCE: 118

```
Met Ala Ala Met Ser Glu Asp Ser Cys Val Asn Phe Lys Glu Met Met
1               5                   10                  15

Phe Ile Asp Asn Thr Leu Tyr Phe Ile Pro Glu Glu Asn Gly Asp Leu
            20                  25                  30

Glu Ser Asp Asn Phe Gly Arg Leu His Cys Thr Thr Ala Val Ile Arg
        35                  40                  45

Asn Ile Asn Asp Gln Val Leu Phe Val Asp Lys Arg Gln Pro Val Phe
    50                  55                  60

Glu Asp Met Thr Asp Ile Asp Gln Ser Ala Ser Glu Pro Gln Thr Arg
65                  70                  75                  80

Leu Ile Ile Tyr Met Tyr Lys Asp Ser Glu Val Arg Gly Leu Ala Val
                85                  90                  95

Thr Leu Ser Val Lys Asp Ser Lys Met Ser Thr Leu Ser Cys Lys Asn
            100                 105                 110

Lys Ile Ile Ser Phe Glu Glu Met Asp Pro Pro Glu Asn Ile Asp Asp
        115                 120                 125

Ile Gln Ser Asp Leu Ile Phe Phe Gln Lys Arg Val Pro Gly His Asn
    130                 135                 140
```

```
Lys Met Glu Phe Glu Ser Ser Leu Tyr Glu Gly His Phe Leu Ala Cys
145                 150                 155                 160

Gln Lys Glu Asp Asp Ala Phe Lys Leu Ile Leu Lys Lys Lys Asp Glu
            165                 170                 175

Asn Gly Asp Lys Ser Val Met Phe Thr Leu Thr Asn Leu His Gln Ser
        180                 185                 190
```

<210> SEQ ID NO 119
<211> LENGTH: 150
<212> TYPE: PRT
<213> ORGANISM: Artificial Sequence
<220> FEATURE:
<223> OTHER INFORMATION: Synthetic

<400> SEQUENCE: 119

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser
145                 150
```

<210> SEQ ID NO 120
<211> LENGTH: 169
<212> TYPE: PRT
<213> ORGANISM: Artificial Sequence
<220> FEATURE:
<223> OTHER INFORMATION: Synthetic

<400> SEQUENCE: 120

```
Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
            85                  90                  95

Leu Gly Pro Leu Arg His Val Leu Asp Leu Thr Gln Ser Lys Ser Phe
            100                 105                 110
```

```
Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165
```

```
<210> SEQ ID NO 121
<211> LENGTH: 153
<212> TYPE: PRT
<213> ORGANISM: Artificial Sequence
<220> FEATURE:
<223> OTHER INFORMATION: Synthetic

<400> SEQUENCE: 121
```

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

```
<210> SEQ ID NO 122
<211> LENGTH: 140
<212> TYPE: PRT
<213> ORGANISM: Artificial Sequence
<220> FEATURE:
<223> OTHER INFORMATION: Synthetic

<400> SEQUENCE: 122
```

```
Met Gly Leu Asn Pro Gln Leu Val Val Ile Leu Leu Phe Phe Leu Glu
1               5                   10                  15

Cys Thr Arg Ser His Ile His Gly Cys Asp Lys Asn His Leu Arg Glu
            20                  25                  30

Ile Ile Gly Ile Leu Asn Glu Val Thr Gly Glu Gly Thr Pro Cys Thr
        35                  40                  45

Glu Met Asp Val Pro Asn Val Leu Thr Ala Thr Lys Asn Thr Thr Glu
    50                  55                  60

Ser Glu Leu Val Cys Arg Ala Ser Lys Val Leu Arg Ile Phe Tyr Leu
65                  70                  75                  80

Lys His Gly Lys Thr Pro Cys Leu Lys Lys Asn Ser Ser Val Leu Met
```

```
                85                  90                  95
Glu Leu Gln Arg Leu Phe Arg Ala Phe Arg Cys Leu Asp Ser Ser Ile
            100                 105                 110

Ser Cys Thr Met Asn Glu Ser Lys Ser Thr Ser Leu Lys Asp Phe Leu
        115                 120                 125

Glu Ser Leu Lys Ser Ile Met Gln Met Asp Tyr Ser
130                 135                 140
```

<210> SEQ ID NO 123
<211> LENGTH: 177
<212> TYPE: PRT
<213> ORGANISM: Artificial Sequence
<220> FEATURE:
<223> OTHER INFORMATION: Synthetic

<400> SEQUENCE: 123

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 124
<211> LENGTH: 154
<212> TYPE: PRT
<213> ORGANISM: Artificial Sequence
<220> FEATURE:
<223> OTHER INFORMATION: Synthetic

<400> SEQUENCE: 124

```
Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30

Glu Gly Lys Ala Tyr Glu Ser Val Leu Met Ile Ser Ile Asp Glu Leu
        35                  40                  45

Asp Lys Met Thr Gly Thr Asp Ser Asn Cys Pro Asn Asn Glu Pro Asn
    50                  55                  60

Phe Phe Arg Lys His Val Cys Asp Asp Thr Lys Glu Ala Ala Phe Leu
```

```
                65                  70                  75                  80

Asn Arg Ala Ala Arg Lys Leu Lys Gln Phe Leu Lys Met Asn Ile Ser
                85                  90                  95

Glu Glu Phe Asn Val His Leu Leu Thr Val Ser Gln Gly Thr Gln Thr
                100                 105                 110

Leu Val Asn Cys Thr Ser Lys Glu Glu Lys Asn Val Lys Glu Gln Lys
                115                 120                 125

Lys Asn Asp Ala Cys Phe Leu Lys Arg Leu Leu Arg Glu Ile Lys Thr
                130                 135                 140

Cys Trp Asn Lys Ile Leu Lys Gly Ser Ile
145                 150

<210> SEQ ID NO 125
<211> LENGTH: 144
<212> TYPE: PRT
<213> ORGANISM: Artificial Sequence
<220> FEATURE:
<223> OTHER INFORMATION: Synthetic

<400> SEQUENCE: 125

Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
                20                  25                  30

Leu Ile Asn Lys Met Gln Glu Asp Pro Ala Ser Lys Cys His Cys Ser
                35                  40                  45

Ala Asn Val Thr Ser Cys Leu Cys Leu Gly Ile Pro Ser Asp Asn Cys
                50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
                100                 105                 110

Cys Asn Gln Thr Thr Ala Gly Asn Ala Leu Thr Phe Leu Lys Ser Leu
                115                 120                 125

Leu Glu Ile Phe Gln Lys Glu Lys Met Arg Gly Met Arg Gly Lys Ile
                130                 135                 140

<210> SEQ ID NO 126
<211> LENGTH: 144
<212> TYPE: PRT
<213> ORGANISM: Artificial Sequence
<220> FEATURE:
<223> OTHER INFORMATION: Synthetic

<400> SEQUENCE: 126

Met Leu Val Thr Tyr Ile Leu Ala Ser Val Leu Leu Phe Ser Ser Val
1               5                   10                  15

Leu Gly Gln Arg Cys Ser Thr Thr Trp Gly Ile Arg Asp Thr Asn Tyr
                20                  25                  30

Leu Ile Glu Asn Leu Lys Asp Asp Pro Pro Ser Lys Cys Ser Cys Ser
                35                  40                  45

Gly Asn Val Thr Ser Cys Leu Cys Leu Ser Val Pro Thr Asp Asp Cys
                50                  55                  60

Thr Thr Pro Cys Tyr Arg Glu Gly Leu Leu Gln Leu Thr Asn Ala Thr
65                  70                  75                  80
```

```
Gln Lys Ser Arg Leu Leu Pro Val Phe His Arg Val Lys Arg Ile Val
                85                  90                  95

Glu Val Leu Lys Asn Ile Thr Cys Pro Ser Phe Ser Cys Glu Lys Pro
            100                 105                 110

Cys Asn Gln Thr Met Ala Gly Asn Thr Leu Ser Phe Leu Lys Ser Leu
        115                 120                 125

Leu Gly Thr Phe Gln Lys Thr Glu Met Gln Arg Gln Lys Ser Arg Pro
    130                 135                 140
```

<210> SEQ ID NO 127
<211> LENGTH: 146
<212> TYPE: PRT
<213> ORGANISM: Artificial Sequence
<220> FEATURE:
<223> OTHER INFORMATION: Synthetic

<400> SEQUENCE: 127

```
Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
                20                  25                  30

Ser Pro Gly Pro Val Pro Pro Ser Thr Ala Leu Arg Glu Leu Ile Glu
            35                  40                  45

Glu Leu Val Asn Ile Thr Gln Asn Gln Lys Ala Pro Leu Cys Asn Gly
        50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
                100                 105                 110

Phe Ser Ser Leu His Val Arg Asp Thr Lys Ile Glu Val Ala Gln Phe
            115                 120                 125

Val Lys Asp Leu Leu Leu His Leu Lys Lys Leu Phe Arg Glu Gly Arg
        130                 135                 140

Phe Asn
145
```

<210> SEQ ID NO 128
<211> LENGTH: 131
<212> TYPE: PRT
<213> ORGANISM: Artificial Sequence
<220> FEATURE:
<223> OTHER INFORMATION: Synthetic

<400> SEQUENCE: 128

```
Met Ala Leu Trp Val Thr Ala Val Leu Ala Leu Ala Cys Leu Gly Gly
1               5                   10                  15

Leu Ala Ala Pro Gly Pro Val Pro Arg Ser Val Ser Leu Pro Leu Thr
                20                  25                  30

Leu Lys Glu Leu Ile Glu Glu Leu Ser Asn Ile Thr Gln Asp Gln Thr
                35                  40                  45

Pro Leu Cys Asn Gly Ser Met Val Trp Ser Val Asp Leu Ala Ala Gly
            50                  55                  60

Gly Phe Cys Val Ala Leu Asp Ser Leu Thr Asn Ile Ser Asn Cys Asn
65                  70                  75                  80

Ala Ile Tyr Arg Thr Gln Arg Ile Leu His Gly Leu Cys Asn Arg Lys
                85                  90                  95
```

```
Ala Pro Thr Thr Val Ser Ser Leu Pro Asp Thr Lys Ile Glu Val Ala
                100                 105                 110

His Phe Ile Thr Lys Leu Leu Ser Tyr Thr Lys Gln Leu Phe Arg His
            115                 120                 125

Gly Pro Phe
    130
```

<210> SEQ ID NO 129
<211> LENGTH: 162
<212> TYPE: PRT
<213> ORGANISM: Artificial Sequence
<220> FEATURE:
<223> OTHER INFORMATION: Synthetic

<400> SEQUENCE: 129

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser
```

<210> SEQ ID NO 130
<211> LENGTH: 162
<212> TYPE: PRT
<213> ORGANISM: Artificial Sequence
<220> FEATURE:
<223> OTHER INFORMATION: Synthetic

<400> SEQUENCE: 130

```
Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95
```

```
Val Ile Leu His Glu Tyr Ser Asn Met Thr Leu Asn Glu Thr Val Arg
                100                 105                 110

Asn Val Leu Tyr Leu Ala Asn Ser Thr Leu Ser Ser Asn Lys Asn Val
            115                 120                 125

Ala Glu Ser Gly Cys Lys Glu Cys Glu Leu Glu Lys Thr Phe
130                 135                 140

Thr Glu Phe Leu Gln Ser Phe Ile Arg Ile Val Gln Met Phe Ile Asn
145                 150                 155                 160

Thr Ser

<210> SEQ ID NO 131
<211> LENGTH: 152
<212> TYPE: PRT
<213> ORGANISM: Artificial Sequence
<220> FEATURE:
<223> OTHER INFORMATION: Synthetic

<400> SEQUENCE: 131

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 132
<211> LENGTH: 166
<212> TYPE: PRT
<213> ORGANISM: Artificial Sequence
<220> FEATURE:
<223> OTHER INFORMATION: Synthetic

<400> SEQUENCE: 132

Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Gly Arg
            20                  25                  30

Asp Thr His Arg Leu Thr Arg Thr Leu Asn Cys Ser Ser Ile Val Lys
        35                  40                  45

Glu Ile Ile Gly Lys Leu Pro Glu Pro Glu Leu Lys Thr Asp Asp Glu
    50                  55                  60

Gly Pro Ser Leu Arg Asn Lys Ser Phe Arg Arg Val Asn Leu Ser Lys
65                  70                  75                  80
```

Phe Val Glu Ser Gln Gly Val Asp Pro Glu Asp Arg Tyr Val Ile
            85                  90                  95

Lys Ser Asn Leu Gln Lys Leu Asn Cys Cys Leu Pro Thr Ser Ala Asn
            100                 105                 110

Asp Ser Ala Leu Pro Gly Val Phe Ile Arg Asp Leu Asp Asp Phe Arg
            115                 120                 125

Lys Lys Leu Arg Phe Tyr Met Val His Leu Asn Asp Leu Glu Thr Val
        130                 135                 140

Leu Thr Ser Arg Pro Pro Gln Pro Ala Ser Gly Ser Val Ser Pro Asn
145                 150                 155                 160

Arg Gly Thr Val Glu Cys
                165

<210> SEQ ID NO 133
<211> LENGTH: 134
<212> TYPE: PRT
<213> ORGANISM: Artificial Sequence
<220> FEATURE:
<223> OTHER INFORMATION: Synthetic

<400> SEQUENCE: 133

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
            35                  40                  45

Thr Leu Arg Ile Pro Val Pro Val His Lys Asn His Gln Leu Cys Thr
        50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
            85                  90                  95

Tyr Ile Asp Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
            130

<210> SEQ ID NO 134
<211> LENGTH: 133
<212> TYPE: PRT
<213> ORGANISM: Artificial Sequence
<220> FEATURE:
<223> OTHER INFORMATION: Synthetic

<400> SEQUENCE: 134

Met Arg Arg Met Leu Leu His Leu Ser Val Leu Thr Leu Ser Cys Val
1               5                   10                  15

Trp Ala Thr Ala Met Glu Ile Pro Met Ser Thr Val Val Lys Glu Thr
            20                  25                  30

Leu Thr Gln Leu Ser Ala His Arg Ala Leu Leu Thr Ser Asn Glu Thr
            35                  40                  45

Met Arg Leu Pro Val Pro Thr His Lys Asn His Gln Leu Cys Ile Gly
        50                  55                  60

Glu Ile Phe Gln Gly Leu Asp Ile Leu Lys Asn Gln Thr Val Arg Gly

```
                65                   70                   75                   80
Gly Thr Val Glu Met Leu Phe Gln Asn Leu Ser Leu Ile Lys Lys Tyr
                    85                   90                   95

Ile Asp Arg Gln Lys Glu Lys Cys Gly Glu Glu Arg Arg Thr Arg
                100                 105                 110

Gln Phe Leu Asp Tyr Leu Gln Glu Phe Leu Gly Val Met Ser Thr Glu
                115                 120                 125

Trp Ala Met Glu Gly
    130
```

<210> SEQ ID NO 135
<211> LENGTH: 144
<212> TYPE: PRT
<213> ORGANISM: Artificial Sequence
<220> FEATURE:
<223> OTHER INFORMATION: Synthetic

<400> SEQUENCE: 135

```
Met Trp Leu Gln Ser Leu Leu Leu Gly Thr Val Ala Cys Ser Ile
1               5                  10                  15

Ser Ala Pro Ala Arg Ser Pro Ser Thr Gln Pro Trp Glu His
                20                  25                  30

Val Asn Ala Ile Gln Glu Ala Arg Arg Leu Leu Asn Leu Ser Arg Asp
                35                  40                  45

Thr Ala Ala Glu Met Asn Glu Thr Val Glu Val Ile Ser Glu Met Phe
50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
                115                 120                 125

Asp Phe Leu Leu Val Ile Pro Phe Asp Cys Trp Glu Pro Val Gln Glu
                130                 135                 140
```

<210> SEQ ID NO 136
<211> LENGTH: 141
<212> TYPE: PRT
<213> ORGANISM: Artificial Sequence
<220> FEATURE:
<223> OTHER INFORMATION: Synthetic

<400> SEQUENCE: 136

```
Met Trp Leu Gln Asn Leu Leu Phe Leu Gly Ile Val Val Tyr Ser Leu
1               5                  10                  15

Ser Ala Pro Thr Arg Ser Pro Ile Thr Val Thr Arg Pro Trp Lys His
                20                  25                  30

Val Glu Ala Ile Lys Glu Ala Leu Asn Leu Asp Asp Met Pro Val
                35                  40                  45

Thr Leu Asn Glu Glu Val Glu Val Val Ser Asn Glu Phe Ser Phe Lys
50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95
```

```
Tyr Tyr Gln Thr Tyr Cys Pro Pro Thr Pro Glu Thr Asp Cys Glu Thr
                100                 105                 110

Gln Val Thr Thr Tyr Ala Asp Phe Ile Asp Ser Leu Lys Thr Phe Leu
                115                 120                 125

Thr Asp Ile Pro Phe Glu Cys Lys Lys Pro Gly Gln Lys
            130                 135                 140

<210> SEQ ID NO 137
<211> LENGTH: 212
<212> TYPE: PRT
<213> ORGANISM: Artificial Sequence
<220> FEATURE:
<223> OTHER INFORMATION: Synthetic

<400> SEQUENCE: 137

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 138
<211> LENGTH: 211
<212> TYPE: PRT
<213> ORGANISM: Artificial Sequence
<220> FEATURE:
<223> OTHER INFORMATION: Synthetic

<400> SEQUENCE: 138

Met Lys Phe Leu Ser Ala Arg Asp Phe His Pro Val Ala Phe Leu Gly
1               5                   10                  15

Leu Met Leu Val Thr Thr Thr Ala Phe Pro Thr Ser Gln Val Arg Arg
                20                  25                  30

Gly Asp Phe Thr Glu Asp Thr Thr Pro Asn Arg Pro Val Tyr Thr Thr
            35                  40                  45
```

Ser Gln Val Gly Gly Leu Ile Thr His Val Leu Trp Glu Ile Val Glu
    50                  55                  60

Met Arg Lys Glu Leu Cys Asn Gly Asn Ser Asp Cys Met Asn Asn Asp
65                  70                  75                  80

Asp Ala Leu Ala Glu Asn Asn Leu Lys Leu Pro Glu Ile Gln Arg Asn
                85                  90                  95

Asp Gly Cys Tyr Gln Thr Gly Tyr Asn Gln Glu Ile Cys Leu Leu Lys
            100                 105                 110

Ile Ser Ser Gly Leu Leu Glu Tyr His Ser Tyr Leu Glu Tyr Met Lys
        115                 120                 125

Asn Asn Leu Lys Asp Asn Lys Lys Asp Lys Ala Arg Val Leu Gln Arg
    130                 135                 140

Asp Thr Glu Thr Leu Ile His Ile Phe Asn Gln Glu Val Lys Asp Leu
145                 150                 155                 160

His Lys Ile Val Leu Pro Thr Pro Ile Ser Asn Ala Leu Leu Thr Asp
                165                 170                 175

Lys Leu Glu Ser Gln Lys Glu Trp Leu Arg Thr Lys Thr Ile Gln Phe
            180                 185                 190

Ile Leu Lys Ser Leu Glu Glu Phe Leu Lys Val Thr Leu Arg Ser Thr
        195                 200                 205

Arg Gln Thr
    210

<210> SEQ ID NO 139
<211> LENGTH: 199
<212> TYPE: PRT
<213> ORGANISM: Artificial Sequence
<220> FEATURE:
<223> OTHER INFORMATION: Synthetic

<400> SEQUENCE: 139

Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

```
Leu Leu Leu Lys Thr Arg Leu
        195

<210> SEQ ID NO 140
<211> LENGTH: 199
<212> TYPE: PRT
<213> ORGANISM: Artificial Sequence
<220> FEATURE:
<223> OTHER INFORMATION: Synthetic

<400> SEQUENCE: 140

Met Asn Cys Val Cys Arg Leu Val Leu Val Val Leu Ser Leu Trp Pro
1               5                   10                  15

Asp Arg Val Val Ala Pro Gly Pro Pro Ala Gly Ser Pro Arg Val Ser
            20                  25                  30

Ser Asp Pro Arg Ala Asp Leu Asp Ser Ala Val Leu Leu Thr Arg Ser
        35                  40                  45

Leu Leu Ala Asp Thr Arg Gln Leu Ala Ala Gln Met Arg Asp Lys Phe
    50                  55                  60

Pro Ala Asp Gly Asp His Ser Leu Asp Ser Leu Pro Thr Leu Ala Met
65                  70                  75                  80

Ser Ala Gly Thr Leu Gly Ser Leu Gln Leu Pro Gly Val Leu Thr Arg
                85                  90                  95

Leu Arg Val Asp Leu Met Ser Tyr Leu Arg His Val Gln Trp Leu Arg
            100                 105                 110

Arg Ala Gly Gly Pro Ser Leu Lys Thr Leu Glu Pro Glu Leu Gly Ala
        115                 120                 125

Leu Gln Ala Arg Leu Glu Arg Leu Leu Arg Arg Leu Gln Leu Leu Met
    130                 135                 140

Ser Arg Leu Ala Leu Pro Gln Ala Ala Pro Asp Gln Pro Val Ile Pro
145                 150                 155                 160

Leu Gly Pro Pro Ala Ser Ala Trp Gly Ser Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
        195

<210> SEQ ID NO 141
<211> LENGTH: 207
<212> TYPE: PRT
<213> ORGANISM: Artificial Sequence
<220> FEATURE:
<223> OTHER INFORMATION: Synthetic

<400> SEQUENCE: 141

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
```

```
                    85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
            115                 120                 125

Ser Pro Glu Leu Gly Pro Thr Leu Asp Thr Leu Gln Leu Asp Val Ala
            130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
                180                 185                 190

Phe Leu Glu Val Ser Tyr Arg Val Leu Arg His Leu Ala Gln Pro
                195                 200                 205

<210> SEQ ID NO 142
<211> LENGTH: 208
<212> TYPE: PRT
<213> ORGANISM: Artificial Sequence
<220> FEATURE:
<223> OTHER INFORMATION: Synthetic

<400> SEQUENCE: 142

Met Ala Gln Leu Ser Ala Gln Arg Arg Met Lys Leu Met Ala Leu Gln
1               5                   10                  15

Leu Leu Leu Trp Gln Ser Ala Leu Trp Ser Gly Arg Glu Ala Val Pro
            20                  25                  30

Leu Val Thr Val Ser Ala Leu Pro Pro Ser Leu Pro Leu Pro Arg Ser
            35                  40                  45

Phe Leu Leu Lys Ser Leu Glu Gln Val Arg Lys Ile Gln Ala Ser Gly
        50                  55                  60

Ser Val Leu Leu Glu Gln Leu Cys Ala Thr Tyr Lys Leu Cys His Pro
65                  70                  75                  80

Glu Glu Leu Val Leu Leu Gly His Ser Leu Gly Ile Pro Lys Ala Ser
                85                  90                  95

Leu Ser Gly Cys Ser Ser Gln Ala Leu Gln Gln Thr Gln Cys Leu Ser
            100                 105                 110

Gln Leu His Ser Gly Leu Cys Leu Tyr Gln Gly Leu Leu Gln Ala Leu
            115                 120                 125

Ser Gly Ile Ser Pro Ala Leu Ala Pro Thr Leu Asp Leu Leu Gln Leu
            130                 135                 140

Asp Val Ala Asn Phe Ala Thr Thr Ile Trp Gln Gln Met Glu Asn Leu
145                 150                 155                 160

Gly Val Ala Pro Thr Val Gln Pro Thr Gln Ser Ala Met Pro Ala Phe
                165                 170                 175

Thr Ser Ala Phe Gln Arg Arg Ala Gly Gly Val Leu Ala Ile Ser Tyr
                180                 185                 190

Leu Gln Gly Phe Leu Glu Thr Ala Arg Leu Ala Leu His His Leu Ala
                195                 200                 205

<210> SEQ ID NO 143
<211> LENGTH: 219
<212> TYPE: PRT
<213> ORGANISM: Artificial Sequence
<220> FEATURE:
<223> OTHER INFORMATION: Synthetic
```

<400> SEQUENCE: 143

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
                100                 105                 110

Ser Arg Lys Thr Ser Phe Met Met Ala Leu Cys Leu Ser Ser Ile Tyr
            115                 120                 125

Glu Asp Leu Lys Met Tyr Gln Val Glu Phe Lys Thr Met Asn Ala Lys
130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
            195                 200                 205

Ile Asp Arg Val Met Ser Tyr Leu Asn Ala Ser
            210                 215

<210> SEQ ID NO 144
<211> LENGTH: 328
<212> TYPE: PRT
<213> ORGANISM: Artificial Sequence
<220> FEATURE:
<223> OTHER INFORMATION: Synthetic

<400> SEQUENCE: 144

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
            165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Ser Leu Pro Ile
            195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
            325

<210> SEQ ID NO 145
<211> LENGTH: 335
<212> TYPE: PRT
<213> ORGANISM: Artificial Sequence
<220> FEATURE:
<223> OTHER INFORMATION: Synthetic

<400> SEQUENCE: 145

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
            35                  40                  45

Thr Cys Asp Thr Pro Glu Glu Asp Ile Thr Trp Thr Ser Asp Gln
        50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
            85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
            115                 120                 125

Glu Ala Pro Asn Tyr Ser Gly Arg Phe Thr Cys Ser Trp Leu Val Gln
130                 135                 140

Arg Asn Met Asp Leu Lys Phe Asn Ile Lys Ser Ser Ser Ser Ser Pro
145                 150                 155                 160

```
Asp Ser Arg Ala Val Thr Cys Gly Met Ala Ser Leu Ser Ala Glu Lys
            165                 170                 175

Val Thr Leu Asp Gln Arg Asp Tyr Glu Lys Tyr Ser Val Ser Cys Gln
        180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
                260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
        290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 146
<211> LENGTH: 215
<212> TYPE: PRT
<213> ORGANISM: Artificial Sequence
<220> FEATURE:
<223> OTHER INFORMATION: Synthetic

<400> SEQUENCE: 146

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190
```

Ile Leu Leu His Ala Phe Ser Thr Arg Val Val Thr Ile Asn Arg Val
            195                 200                 205

Met Gly Tyr Leu Ser Ser Ala
    210                 215

<210> SEQ ID NO 147
<211> LENGTH: 202
<212> TYPE: PRT
<213> ORGANISM: Artificial Sequence
<220> FEATURE:
<223> OTHER INFORMATION: Synthetic

<400> SEQUENCE: 147

Met Lys Val Leu Ala Ala Gly Val Val Pro Leu Leu Val Leu His
1               5                   10                  15

Trp Lys His Gly Ala Gly Ser Pro Leu Pro Ile Thr Pro Val Asn Ala
                20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
        195                 200

<210> SEQ ID NO 148
<211> LENGTH: 203
<212> TYPE: PRT
<213> ORGANISM: Artificial Sequence
<220> FEATURE:
<223> OTHER INFORMATION: Synthetic

<400> SEQUENCE: 148

Met Lys Val Leu Ala Ala Gly Ile Val Pro Leu Leu Leu Val Leu
1               5                   10                  15

His Trp Lys His Gly Ala Gly Ser Pro Leu Pro Ile Thr Pro Val Asn
                20                  25                  30

Ala Thr Cys Ala Ile Arg His Pro Cys His Gly Asn Leu Met Asn Gln
            35                  40                  45

Ile Lys Asn Gln Leu Ala Gln Leu Asn Gly Ser Ala Asn Ala Leu Phe
        50                  55                  60

Ile Ser Tyr Tyr Thr Ala Gln Gly Glu Pro Phe Pro Asn Asn Val Glu
65                  70                  75                  80

```
Lys Leu Cys Ala Pro Asn Met Thr Asp Phe Pro Ser Phe His Gly Asn
                85                  90                  95

Gly Thr Glu Lys Thr Lys Leu Val Glu Leu Tyr Arg Met Val Ala Tyr
            100                 105                 110

Leu Ser Ala Ser Leu Thr Asn Ile Thr Arg Asp Gln Lys Val Leu Asn
            115                 120                 125

Pro Thr Ala Val Ser Leu Gln Val Lys Leu Asn Ala Thr Ile Asp Val
        130                 135                 140

Met Arg Gly Leu Leu Ser Asn Val Leu Cys Arg Leu Cys Asn Lys Tyr
145                 150                 155                 160

Arg Val Gly His Val Asp Val Pro Val Pro Asp His Ser Asp Lys
                165                 170                 175

Glu Ala Phe Gln Arg Lys Lys Leu Gly Cys Gln Leu Leu Gly Thr Tyr
            180                 185                 190

Lys Gln Val Ile Ser Val Val Val Gln Ala Phe
        195                 200

<210> SEQ ID NO 149
<211> LENGTH: 252
<212> TYPE: PRT
<213> ORGANISM: Artificial Sequence
<220> FEATURE:
<223> OTHER INFORMATION: Synthetic

<400> SEQUENCE: 149

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
                20                  25                  30

Lys Glu Tyr Arg Val Leu Leu Gly Gln Leu Gln Lys Gln Thr Asp Leu
            35                  40                  45

Met Gln Asp Thr Ser Arg Leu Leu Asp Pro Tyr Ile Arg Ile Gln Gly
        50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
210                 215                 220

His Gln Ala Leu Arg Lys Gly Val Arg Arg Thr Arg Pro Ser Arg Lys
225                 230                 235                 240
```

```
Gly Lys Arg Leu Met Thr Arg Gly Gln Leu Pro Arg
            245                 250

<210> SEQ ID NO 150
<211> LENGTH: 263
<212> TYPE: PRT
<213> ORGANISM: Artificial Sequence
<220> FEATURE:
<223> OTHER INFORMATION: Synthetic

<400> SEQUENCE: 150

Met Gln Thr Arg Leu Leu Arg Thr Leu Leu Ser Leu Thr Leu Ser Leu
1               5                   10                  15

Leu Ile Leu Ser Met Ala Leu Ala Asn Arg Gly Cys Ser Asn Ser Ser
            20                  25                  30

Ser Gln Leu Leu Ser Gln Leu Gln Asn Gln Ala Asn Leu Thr Gly Asn
        35                  40                  45

Thr Glu Ser Leu Leu Glu Pro Tyr Ile Arg Leu Gln Asn Leu Asn Thr
    50                  55                  60

Pro Asp Leu Arg Ala Ala Cys Thr Gln His Ser Val Ala Phe Pro Ser
65                  70                  75                  80

Glu Asp Thr Leu Arg Gln Leu Ser Lys Pro His Phe Leu Ser Thr Val
                85                  90                  95

Tyr Thr Thr Leu Asp Arg Val Leu Tyr Gln Leu Asp Ala Leu Arg Gln
            100                 105                 110

Lys Phe Leu Lys Thr Pro Ala Phe Pro Lys Leu Asp Ser Ala Arg His
        115                 120                 125

Asn Ile Leu Gly Ile Arg Asn Asn Val Phe Cys Met Ala Arg Leu Leu
130                 135                 140

Asn His Ser Leu Glu Ile Pro Glu Pro Thr Gln Thr Asp Ser Gly Ala
145                 150                 155                 160

Ser Arg Ser Thr Thr Thr Pro Asp Val Phe Asn Thr Lys Ile Gly Ser
                165                 170                 175

Cys Gly Phe Leu Trp Gly Tyr His Arg Phe Met Gly Ser Val Gly Arg
            180                 185                 190

Val Phe Arg Glu Trp Asp Asp Gly Ser Thr Arg Ser Arg Arg Gln Ser
        195                 200                 205

Pro Leu Arg Ala Arg Arg Lys Gly Thr Arg Ile Arg Val Arg His
210                 215                 220

Lys Gly Thr Arg Arg Ile Arg Val Arg Arg Lys Gly Thr Arg Arg Ile
225                 230                 235                 240

Trp Val Arg Arg Lys Gly Ser Arg Lys Ile Arg Pro Ser Arg Ser Thr
                245                 250                 255

Gln Ser Pro Thr Thr Arg Ala
            260

<210> SEQ ID NO 151
<211> LENGTH: 178
<212> TYPE: PRT
<213> ORGANISM: Artificial Sequence
<220> FEATURE:
<223> OTHER INFORMATION: Synthetic

<400> SEQUENCE: 151

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
```

```
                    20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
        50                  55                  60

Leu Leu Lys Glu Ser Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 152
<211> LENGTH: 178
<212> TYPE: PRT
<213> ORGANISM: Artificial Sequence
<220> FEATURE:
<223> OTHER INFORMATION: Synthetic

<400> SEQUENCE: 152

Met Pro Gly Ser Ala Leu Leu Cys Cys Leu Leu Leu Leu Thr Gly Met
1               5                   10                  15

Arg Ile Ser Arg Gly Gln Tyr Ser Arg Glu Asp Asn Asn Cys Thr His
            20                  25                  30

Phe Pro Val Gly Gln Ser His Met Leu Leu Glu Leu Arg Thr Ala Phe
        35                  40                  45

Ser Gln Val Lys Thr Phe Phe Gln Thr Lys Asp Gln Leu Asp Asn Ile
    50                  55                  60

Leu Leu Thr Asp Ser Leu Met Gln Asp Phe Lys Gly Tyr Leu Gly Cys
65                  70                  75                  80

Gln Ala Leu Ser Glu Met Ile Gln Phe Tyr Leu Val Glu Val Met Pro
                85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
        115                 120                 125

Phe Leu Pro Cys Glu Asn Lys Ser Lys Ala Val Glu Gln Val Lys Ser
    130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser

<210> SEQ ID NO 153
<211> LENGTH: 176
```

```
<212> TYPE: PRT
<213> ORGANISM: Artificial Sequence
<220> FEATURE:
<223> OTHER INFORMATION: Synthetic

<400> SEQUENCE: 153

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
                20                  25                  30

Cys Val Ile Ala Thr Asn Leu Gln Glu Ile Arg Asn Gly Phe Ser Glu
            35                  40                  45

Ile Arg Gly Ser Val Gln Ala Lys Asp Gly Asn Ile Asp Ile Arg Ile
        50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys His Ala
            115                 120                 125

His Met Thr Cys His Cys Gly Glu Glu Ala Met Lys Lys Tyr Ser Gln
        130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175

<210> SEQ ID NO 154
<211> LENGTH: 176
<212> TYPE: PRT
<213> ORGANISM: Artificial Sequence
<220> FEATURE:
<223> OTHER INFORMATION: Synthetic

<400> SEQUENCE: 154

Met Lys Gly Phe Gly Leu Ala Phe Gly Leu Phe Ser Ala Val Gly Phe
1               5                   10                  15

Leu Leu Trp Thr Pro Leu Thr Gly Leu Lys Thr Leu His Leu Gly Ser
                20                  25                  30

Cys Val Ile Thr Ala Asn Leu Gln Ala Ile Gln Lys Glu Phe Ser Glu
            35                  40                  45

Ile Arg Asp Ser Val Gln Ala Glu Asp Thr Asn Ile Asp Ile Arg Ile
        50                  55                  60

Leu Arg Thr Thr Glu Ser Leu Lys Asp Ile Lys Ser Leu Asp Arg Cys
65                  70                  75                  80

Cys Phe Leu Arg His Leu Val Arg Phe Tyr Leu Asp Arg Val Phe Lys
                85                  90                  95

Val Tyr Gln Thr Pro Asp His His Thr Leu Arg Lys Ile Ser Ser Leu
                100                 105                 110

Ala Asn Ser Phe Leu Ile Ile Lys Lys Asp Leu Ser Val Cys His Ser
            115                 120                 125

His Met Ala Cys His Cys Gly Glu Glu Ala Met Glu Lys Tyr Asn Gln
        130                 135                 140

Ile Leu Ser His Phe Ile Glu Leu Glu Leu Gln Ala Ala Val Val Lys
145                 150                 155                 160
```

```
Ala Leu Gly Glu Leu Gly Ile Leu Leu Arg Trp Met Glu Met Leu
            165                 170                 175
```

<210> SEQ ID NO 155
<211> LENGTH: 546
<212> TYPE: PRT
<213> ORGANISM: Artificial Sequence
<220> FEATURE:
<223> OTHER INFORMATION: Synthetic

<400> SEQUENCE: 155

```
Met Lys Asn Gln Asp Lys Lys Asn Gly Ala Ala Lys Gln Ser Asn Pro
1               5                   10                  15

Lys Ser Ser Pro Gly Gln Pro Glu Ala Gly Pro Gly Ala Gln Glu
            20                  25                  30

Arg Pro Ser Gln Ala Ala Pro Ala Val Glu Ala Glu Gly Pro Gly Ser
        35                  40                  45

Ser Gln Ala Pro Arg Lys Pro Glu Gly Ala Gln Ala Arg Thr Ala Gln
    50                  55                  60

Ser Gly Ala Leu Arg Asp Val Ser Glu Glu Leu Ser Arg Gln Leu Glu
65                  70                  75                  80

Asp Ile Leu Ser Thr Tyr Cys Val Asp Asn Gln Gly Gly Pro Gly
                85                  90                  95

Glu Asp Gly Ala Gln Gly Glu Pro Ala Glu Pro Glu Asp Ala Glu Lys
            100                 105                 110

Ser Arg Thr Tyr Val Ala Arg Asn Gly Glu Pro Glu Pro Thr Pro Val
        115                 120                 125

Val Asn Gly Glu Lys Glu Pro Ser Lys Gly Asp Pro Asn Thr Glu Glu
    130                 135                 140

Ile Arg Gln Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
            180                 185                 190

Cys Lys Lys Tyr Ala Glu Leu Leu Glu Glu His Arg Asn Ser Gln Lys
        195                 200                 205

Gln Met Lys Leu Leu Gln Lys Lys Gln Ser Gln Leu Val Gln Glu Lys
    210                 215                 220

Asp His Leu Arg Gly Glu His Ser Lys Ala Val Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Lys Arg Lys Glu
            260                 265                 270

Val Thr Ser His Phe Gln Val Thr Leu Asn Asp Ile Gln Leu Gln Met
        275                 280                 285

Glu Gln His Asn Glu Arg Asn Ser Lys Leu Arg Gln Glu Asn Met Glu
    290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
            340                 345                 350
```

```
Glu Arg His Gln Arg Glu Lys Asp Phe Leu Leu Lys Glu Ala Val Glu
            355                 360                 365

Ser Gln Arg Met Cys Glu Leu Met Lys Gln Gln Glu Thr His Leu Lys
    370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
                420                 425                 430

Arg Ser Arg Trp Glu Ser Ser Asn Lys Ala Leu Leu Glu Met Ala Glu
            435                 440                 445

Glu Lys Thr Val Arg Asp Lys Glu Leu Glu Gly Leu Gln Val Lys Ile
            450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gln Gly Ser Leu
                485                 490                 495

Thr Asp Ser Gly Pro Glu Arg Arg Pro Glu Gly Pro Ala Gln Ala
            500                 505                 510

Pro Ser Ser Pro Arg Val Thr Glu Ala Pro Cys Tyr Pro Gly Ala Pro
            515                 520                 525

Ser Thr Glu Ala Ser Gly Gln Thr Gly Pro Gln Glu Pro Thr Ser Ala
            530                 535                 540

Arg Ala
545

<210> SEQ ID NO 156
<211> LENGTH: 554
<212> TYPE: PRT
<213> ORGANISM: Artificial Sequence
<220> FEATURE:
<223> OTHER INFORMATION: Synthetic

<400> SEQUENCE: 156

Met Lys Asn Gln Asp Lys Lys Asn Gly Pro Ala Lys His Ser Asn Ser
1               5                   10                  15

Lys Gly Ser Pro Gly Gln Arg Glu Ala Gly Pro Glu Gly Ala His Gly
            20                  25                  30

Arg Pro Arg Gln Thr Ala Pro Gly Ala Glu Ala Glu Gly Ser Thr Ser
            35                  40                  45

Gln Ala Pro Gly Lys Thr Glu Gly Ala Arg Ala Lys Ala Ala Gln Pro
    50                  55                  60

Gly Ala Leu Cys Asp Val Ser Glu Glu Leu Arg Gln Leu Glu Asp
65                  70                  75                  80

Ile Leu Ser Thr Tyr Cys Val Asp Asn Gln Gly Gly Pro Ala Glu
                85                  90                  95

Glu Gly Ala Gln Gly Glu Pro Thr Glu Pro Glu Asp Thr Glu Lys Ser
            100                 105                 110

Arg Thr Tyr Ala Ala Arg Asn Gly Glu Pro Glu Pro Gly Ile Pro Val
            115                 120                 125

Val Asn Gly Glu Lys Glu Thr Ser Lys Gly Glu Pro Gly Thr Glu Glu
            130                 135                 140

Ile Arg Ala Ser Asp Glu Val Gly Asp Arg Asp His Arg Arg Pro Gln
145                 150                 155                 160
```

```
Glu Lys Lys Lys Ala Lys Gly Leu Gly Lys Glu Ile Thr Leu Leu Met
                165                 170                 175
Gln Thr Leu Asn Thr Leu Ser Thr Pro Glu Lys Leu Ala Ala Leu
            180                 185                 190
Cys Lys Lys Tyr Ala Glu Leu Leu Glu Glu His Arg Asn Ser Gln Lys
                195                 200                 205
Gln Met Lys Leu Leu Gln Lys Gln Ser Gln Leu Val Gln Glu Lys
        210                 215                 220
Asp His Leu Arg Gly Glu His Ser Lys Ala Val Leu Ala Arg Ser Lys
225                 230                 235                 240
Leu Glu Ser Leu Cys Arg Glu Leu Gln Arg His Asn Arg Ser Leu Lys
                245                 250                 255
Glu Glu Gly Val Gln Arg Ala Arg Glu Glu Glu Lys Arg Lys Glu
            260                 265                 270
Val Thr Ser His Phe Gln Val Thr Leu Asn Asp Ile Gln Leu Gln Met
    275                 280                 285
Glu Gln His Asn Glu Arg Asn Ser Lys Leu Arg Gln Glu Asn Met Glu
290                 295                 300
Leu Ala Glu Arg Leu Lys Lys Leu Ile Glu Gln Tyr Glu Leu Arg Glu
305                 310                 315                 320
Glu His Ile Asp Lys Val Phe Lys His Lys Asp Leu Gln Gln Gln Leu
                325                 330                 335
Val Asp Ala Lys Leu Gln Gln Ala Gln Glu Met Leu Lys Glu Ala Glu
                340                 345                 350
Glu Arg His Gln Arg Glu Lys Glu Phe Leu Leu Lys Glu Ala Val Glu
                355                 360                 365
Ser Gln Arg Met Cys Glu Leu Met Lys Gln Gln Glu Thr His Leu Lys
        370                 375                 380
Gln Gln Leu Ala Leu Tyr Thr Glu Lys Phe Glu Glu Phe Gln Asn Thr
385                 390                 395                 400
Leu Ser Lys Ser Ser Glu Val Phe Thr Thr Phe Lys Gln Glu Met Glu
                405                 410                 415
Lys Met Thr Lys Lys Ile Lys Lys Leu Glu Lys Glu Thr Thr Met Tyr
                420                 425                 430
Arg Ser Arg Trp Glu Ser Ser Asn Lys Ala Leu Leu Glu Met Ala Glu
            435                 440                 445
Glu Lys Thr Val Arg Asp Lys Glu Leu Glu Gly Leu Gln Val Lys Ile
        450                 455                 460
Gln Arg Leu Glu Lys Leu Cys Arg Ala Leu Gln Thr Glu Arg Asn Asp
465                 470                 475                 480
Leu Asn Lys Arg Val Gln Asp Leu Thr Ala Gly Gly Ile Thr Asp Ile
                485                 490                 495
Gly Ser Glu Arg Arg Pro Glu Ala Thr Thr Ala Ser Lys Glu Gln Gly
            500                 505                 510
Val Glu Ser Pro Gly Ala Gln Pro Ala Ser Ser Pro Arg Ala Thr Asp
        515                 520                 525
Ala Pro Cys Cys Ser Gly Ala Pro Ser Thr Gly Thr Ala Gly Gln Thr
        530                 535                 540
Gly Pro Gly Glu Pro Thr Pro Ala Thr Ala
545                 550

<210> SEQ ID NO 157
<211> LENGTH: 1331
```

```
<212> TYPE: PRT
<213> ORGANISM: Artificial Sequence
<220> FEATURE:
<223> OTHER INFORMATION: Synthetic

<400> SEQUENCE: 157
```

| | | | | | | | | | | | | | | | |
|---|---|---|---|---|---|---|---|---|---|---|---|---|---|---|---|
| Met | Glu | Ser | His | Ser | Arg | Ala | Gly | Lys | Ser | Arg | Lys | Ser | Ala | Lys | Phe |
| 1 | | | | 5 | | | | | 10 | | | | | 15 | |
| Arg | Ser | Ile | Ser | Arg | Ser | Leu | Met | Leu | Cys | Asn | Ala | Lys | Thr | Ser | Asp |
| | | | 20 | | | | | 25 | | | | | 30 | | |
| Asp | Gly | Ser | Ser | Pro | Asp | Glu | Lys | Tyr | Pro | Asp | Pro | Phe | Glu | Ile | Ser |
| | | | 35 | | | | | 40 | | | | | 45 | | |
| Leu | Ala | Gln | Gly | Lys | Glu | Gly | Ile | Phe | His | Ser | Ser | Val | Gln | Leu | Ala |
| | 50 | | | | | 55 | | | | | 60 | | | | |
| Asp | Thr | Ser | Glu | Ala | Gly | Pro | Ser | Ser | Val | Pro | Asp | Leu | Ala | Leu | Ala |
| 65 | | | | | 70 | | | | | 75 | | | | | 80 |
| Ser | Glu | Ala | Ala | Gln | Leu | Gln | Ala | Ala | Gly | Asn | Asp | Arg | Gly | Lys | Thr |
| | | | | 85 | | | | | 90 | | | | | 95 | |
| Cys | Arg | Arg | Ile | Phe | Phe | Met | Lys | Glu | Ser | Ser | Thr | Ala | Ser | Ser | Arg |
| | | | 100 | | | | | 105 | | | | | 110 | | |
| Glu | Lys | Pro | Gly | Lys | Leu | Glu | Ala | Gln | Ser | Ser | Asn | Phe | Leu | Phe | Pro |
| | | | 115 | | | | | 120 | | | | | 125 | | |
| Lys | Ala | Cys | His | Gln | Arg | Ala | Arg | Ser | Asn | Ser | Thr | Ser | Val | Asn | Pro |
| | 130 | | | | | 135 | | | | | 140 | | | | |
| Tyr | Cys | Thr | Arg | Glu | Ile | Asp | Phe | Pro | Met | Thr | Lys | Lys | Ser | Ala | Ala |
| 145 | | | | | 150 | | | | | 155 | | | | | 160 |
| Pro | Thr | Asp | Arg | Gln | Pro | Tyr | Ser | Leu | Cys | Ser | Asn | Arg | Lys | Ser | Leu |
| | | | | 165 | | | | | 170 | | | | | 175 | |
| Ser | Gln | Gln | Leu | Asp | Cys | Pro | Ala | Gly | Lys | Ala | Ala | Gly | Thr | Ser | Arg |
| | | | 180 | | | | | 185 | | | | | 190 | | |
| Pro | Thr | Arg | Ser | Leu | Ser | Thr | Ala | Gln | Leu | Val | Gln | Pro | Ser | Gly | Gly |
| | | | 195 | | | | | 200 | | | | | 205 | | |
| Leu | Gln | Ala | Ser | Val | Ile | Ser | Asn | Ile | Val | Leu | Met | Lys | Gly | Gln | Ala |
| | 210 | | | | | 215 | | | | | 220 | | | | |
| Lys | Gly | Leu | Gly | Phe | Ser | Ile | Val | Gly | Gly | Lys | Asp | Ser | Ile | Tyr | Gly |
| 225 | | | | | 230 | | | | | 235 | | | | | 240 |
| Pro | Ile | Gly | Ile | Tyr | Val | Lys | Thr | Ile | Phe | Ala | Gly | Gly | Ala | Ala | Ala |
| | | | | 245 | | | | | 250 | | | | | 255 | |
| Ala | Asp | Gly | Arg | Leu | Gln | Glu | Gly | Asp | Glu | Ile | Leu | Glu | Leu | Asn | Gly |
| | | | 260 | | | | | 265 | | | | | 270 | | |
| Glu | Ser | Met | Ala | Gly | Leu | Thr | His | Gln | Asp | Ala | Leu | Gln | Lys | Phe | Lys |
| | | | 275 | | | | | 280 | | | | | 285 | | |
| Gln | Ala | Lys | Lys | Gly | Leu | Leu | Thr | Leu | Thr | Val | Arg | Thr | Arg | Leu | Thr |
| | 290 | | | | | 295 | | | | | 300 | | | | |
| Ala | Pro | Pro | Ser | Leu | Cys | Ser | His | Leu | Ser | Pro | Leu | Cys | Arg | Ser |
| 305 | | | | | 310 | | | | | 315 | | | | | 320 |
| Leu | Ser | Ser | Ser | Thr | Cys | Ile | Thr | Lys | Asp | Ser | Ser | Phe | Ala | Leu |
| | | | | 325 | | | | | 330 | | | | | 335 | |
| Glu | Ser | Pro | Ser | Ala | Pro | Ile | Ser | Thr | Ala | Lys | Pro | Asn | Tyr | Arg | Ile |
| | | | 340 | | | | | 345 | | | | | 350 | | |
| Met | Val | Glu | Val | Ser | Leu | Gln | Lys | Glu | Ala | Gly | Val | Gly | Leu | Gly | Ile |
| | | | 355 | | | | | 360 | | | | | 365 | | |
| Gly | Leu | Cys | Ser | Val | Pro | Tyr | Phe | Gln | Cys | Ile | Ser | Gly | Ile | Phe | Val |
| | 370 | | | | | 375 | | | | | 380 | | | | |

```
His Thr Leu Ser Pro Gly Ser Val Ala His Leu Asp Gly Arg Leu Arg
385                 390                 395                 400

Cys Gly Asp Glu Ile Val Glu Ile Ser Asp Ser Pro Val His Cys Leu
            405                 410                 415

Thr Leu Asn Glu Val Tyr Thr Ile Leu Ser His Cys Asp Pro Gly Pro
            420                 425                 430

Val Pro Ile Ile Val Ser Arg His Pro Asp Pro Gln Val Ser Glu Gln
            435                 440                 445

Gln Leu Lys Glu Ala Val Ala Gln Ala Val Glu Asn Thr Lys Phe Gly
            450                 455                 460

Lys Glu Arg His Gln Trp Ser Leu Glu Gly Val Lys Arg Leu Glu Ser
465                 470                 475                 480

Ser Trp His Gly Arg Pro Thr Leu Glu Lys Glu Arg Glu Lys Asn Ser
            485                 490                 495

Ala Pro Pro His Arg Arg Ala Gln Lys Val Met Ile Arg Ser Ser Ser
            500                 505                 510

Asp Ser Ser Tyr Met Ser Gly Ser Pro Gly Ser Pro Gly Ser Gly
            515                 520                 525

Ser Ala Glu Lys Pro Ser Ser Asp Val Asp Ile Ser Thr His Ser Pro
            530                 535                 540

Ser Leu Pro Leu Ala Arg Glu Pro Val Val Leu Ser Ile Ala Ser Ser
545                 550                 555                 560

Arg Leu Pro Gln Glu Ser Pro Leu Pro Glu Ser Arg Asp Ser His
            565                 570                 575

Pro Pro Leu Arg Leu Lys Lys Ser Phe Glu Ile Val Arg Lys Pro Met
            580                 585                 590

Ser Ser Lys Pro Lys Pro Pro Arg Lys Tyr Phe Lys Ser Asp Ser
            595                 600                 605

Asp Pro Gln Lys Ser Leu Glu Glu Arg Glu Asn Ser Ser Cys Ser Ser
            610                 615                 620

Gly His Thr Pro Pro Thr Cys Gly Gln Glu Ala Arg Glu Leu Leu Pro
625                 630                 635                 640

Leu Leu Leu Pro Gln Glu Asp Thr Ala Gly Arg Ser Pro Ser Ala Ser
            645                 650                 655

Ala Gly Cys Pro Gly Pro Gly Ile Gly Pro Gln Thr Lys Ser Ser Thr
            660                 665                 670

Glu Gly Glu Pro Gly Trp Arg Ala Ser Pro Val Thr Gln Thr Ser
            675                 680                 685

Pro Ile Lys His Pro Leu Leu Lys Arg Gln Ala Arg Met Asp Tyr Ser
            690                 695                 700

Phe Asp Thr Thr Ala Glu Asp Pro Trp Val Arg Ile Ser Asp Cys Ile
705                 710                 715                 720

Lys Asn Leu Phe Ser Pro Ile Met Ser Glu Asn His Gly His Met Pro
            725                 730                 735

Leu Gln Pro Asn Ala Ser Leu Asn Glu Glu Gly Thr Gln Gly His
            740                 745                 750

Pro Asp Gly Thr Pro Pro Lys Leu Asp Thr Ala Asn Gly Thr Pro Lys
            755                 760                 765

Val Tyr Lys Ser Ala Asp Ser Ser Thr Val Lys Lys Gly Pro Pro Val
            770                 775                 780

Ala Pro Lys Pro Ala Trp Phe Arg Gln Ser Leu Lys Gly Leu Arg Asn
785                 790                 795                 800

Arg Ala Ser Asp Pro Arg Gly Leu Pro Asp Pro Ala Leu Ser Thr Gln
```

-continued

```
                805                 810                 815
Pro Ala Pro Ala Ser Arg Glu His Leu Gly Ser His Ile Arg Ala Ser
            820                 825                 830
Ser Ser Ser Ser Ser Ile Arg Gln Arg Ile Ser Phe Glu Thr Phe
            835                 840                 845
Gly Ser Ser Gln Leu Pro Asp Lys Gly Ala Gln Arg Leu Ser Leu Gln
        850                 855                 860
Pro Ser Ser Gly Glu Ala Ala Lys Pro Leu Gly Lys His Glu Gly
865                 870                 875                 880
Arg Phe Ser Gly Leu Leu Gly Arg Gly Ala Ala Pro Thr Leu Val Pro
                885                 890                 895
Gln Gln Pro Glu Gln Val Leu Ser Ser Gly Ser Pro Ala Ala Ser Glu
            900                 905                 910
Ala Arg Asp Pro Gly Val Ser Glu Ser Pro Pro Gly Arg Gln Pro
            915                 920                 925
Asn Gln Lys Thr Leu Pro Pro Gly Pro Asp Pro Leu Leu Arg Leu Leu
            930                 935                 940
Ser Thr Gln Ala Glu Glu Ser Gln Gly Pro Val Leu Lys Met Pro Ser
945                 950                 955                 960
Gln Arg Ala Arg Ser Phe Pro Leu Thr Arg Ser Gln Ser Cys Glu Thr
                965                 970                 975
Lys Leu Leu Asp Glu Lys Thr Ser Lys Leu Tyr Ser Ile Ser Ser Gln
            980                 985                 990
Val Ser Ser Ala Val Met Lys Ser Leu Leu Cys Leu Pro Ser Ser Ile
            995                 1000                1005
Ser Cys Ala Gln Thr Pro Cys Ile Pro Lys Glu Gly Ala Ser Pro
    1010                1015                1020
Thr Ser Ser Ser Asn Glu Asp Ser Ala Ala Asn Gly Ser Ala Glu
    1025                1030                1035
Thr Ser Ala Leu Asp Thr Gly Phe Ser Leu Asn Leu Ser Glu Leu
    1040                1045                1050
Arg Glu Tyr Thr Glu Gly Leu Thr Glu Ala Lys Glu Asp Asp Asp
    1055                1060                1065
Gly Asp His Ser Ser Leu Gln Ser Gly Gln Ser Val Ile Ser Leu
    1070                1075                1080
Leu Ser Ser Glu Glu Leu Lys Lys Leu Ile Glu Glu Val Lys Val
    1085                1090                1095
Leu Asp Glu Ala Thr Leu Lys Gln Leu Asp Gly Ile His Val Thr
    1100                1105                1110
Ile Leu His Lys Glu Glu Gly Ala Gly Leu Gly Phe Ser Leu Ala
    1115                1120                1125
Gly Gly Ala Asp Leu Glu Asn Lys Val Ile Thr Val His Arg Val
    1130                1135                1140
Phe Pro Asn Gly Leu Ala Ser Gln Glu Gly Thr Ile Gln Lys Gly
    1145                1150                1155
Asn Glu Val Leu Ser Ile Asn Gly Lys Ser Leu Lys Gly Thr Thr
    1160                1165                1170
His His Asp Ala Leu Ala Ile Leu Arg Gln Ala Arg Glu Pro Arg
    1175                1180                1185
Gln Ala Val Ile Val Thr Arg Lys Leu Thr Pro Glu Ala Met Pro
    1190                1195                1200
Asp Leu Asn Ser Ser Thr Asp Ser Ala Ala Ser Ala Ser Ala Ala
    1205                1210                1215
```

Ser Asp Val Ser Val Glu Ser Thr Ala Glu Ala Thr Val Cys Thr
    1220                1225                1230

Val Thr Leu Glu Lys Met Ser Ala Gly Leu Gly Phe Ser Leu Glu
    1235                1240                1245

Gly Gly Lys Gly Ser Leu His Gly Asp Lys Pro Leu Thr Ile Asn
    1250                1255                1260

Arg Ile Phe Lys Gly Ala Ala Ser Glu Gln Ser Glu Thr Val Gln
    1265                1270                1275

Pro Gly Asp Glu Ile Leu Gln Leu Gly Gly Thr Ala Met Gln Gly
    1280                1285                1290

Leu Thr Arg Phe Glu Ala Trp Asn Ile Ile Lys Ala Leu Pro Asp
    1295                1300                1305

Gly Pro Val Thr Ile Val Ile Arg Arg Lys Ser Leu Gln Ser Lys
    1310                1315                1320

Glu Thr Thr Ala Ala Gly Asp Ser
    1325                1330

<210> SEQ ID NO 158
<211> LENGTH: 1322
<212> TYPE: PRT
<213> ORGANISM: Artificial Sequence
<220> FEATURE:
<223> OTHER INFORMATION: Synthetic

<400> SEQUENCE: 158

Met Glu Pro His Gly His Ser Gly Lys Ser Arg Lys Ser Thr Lys Phe
1               5                   10                  15

Arg Ser Ile Ser Arg Ser Leu Ile Leu Cys Asn Ala Lys Thr Ser Asp
                20                  25                  30

Asp Gly Ser Ser Pro Asp Glu Lys Tyr Pro Asp Pro Phe Glu Thr Ser
            35                  40                  45

Leu Cys Gln Gly Lys Glu Gly Phe Phe His Ser Met Gln Leu Ala
        50                  55                  60

Asp Thr Phe Glu Ala Gly Leu Ser Asn Ile Pro Asp Leu Ala Leu Ala
65                  70                  75                  80

Ser Asp Ser Ala Gln Leu Ala Ala Gly Ser Asp Arg Gly Lys His
                85                  90                  95

Cys Arg Lys Met Phe Phe Met Lys Glu Ser Ser Ser Thr Ser Ser Lys
                100                 105                 110

Glu Lys Ser Gly Lys Pro Glu Ala Gln Ser Ser Ser Phe Leu Phe Pro
            115                 120                 125

Lys Ala Cys His Gln Arg Thr Arg Ser Asn Ser Thr Ser Val Asn Pro
        130                 135                 140

Tyr Ser Ala Gly Glu Ile Asp Phe Pro Met Thr Lys Lys Ser Ala Ala
145                 150                 155                 160

Pro Thr Asp Arg Gln Pro Tyr Ser Leu Cys Ser Asn Arg Lys Ser Leu
                165                 170                 175

Ser Gln Gln Leu Asp Tyr Pro Ile Leu Gly Thr Ala Arg Pro Thr Arg
            180                 185                 190

Ser Leu Ser Thr Ala Gln Leu Gly Gln Leu Ser Gly Gly Leu Gln Ala
        195                 200                 205

Ser Val Ile Ser Asn Ile Val Leu Met Lys Gly Gln Ala Lys Gly Leu
    210                 215                 220

Gly Phe Ser Ile Val Gly Gly Lys Asp Ser Ile Tyr Gly Pro Ile Gly
225                 230                 235                 240

-continued

```
Ile Tyr Val Lys Ser Ile Phe Ala Gly Gly Ala Ala Ala Asp Gly
            245                 250                 255

Arg Leu Gln Glu Gly Asp Glu Ile Leu Glu Leu Asn Gly Glu Ser Met
        260                 265                 270

Ala Gly Leu Thr His Gln Asp Ala Leu Gln Lys Phe Lys Gln Ala Lys
        275                 280                 285

Lys Gly Leu Leu Thr Leu Thr Val Arg Thr Arg Leu Thr Thr Pro Pro
    290                 295                 300

Ser Leu Cys Ser His Leu Ser Pro Pro Leu Cys Arg Ser Leu Ser Ser
305                 310                 315                 320

Ser Thr Cys Gly Ala Gln Asp Ser Ser Pro Phe Ser Leu Glu Ser Pro
            325                 330                 335

Ala Ser Pro Ala Ser Thr Ala Lys Pro Asn Tyr Arg Ile Met Val Glu
        340                 345                 350

Val Ser Leu Lys Lys Glu Ala Gly Val Gly Leu Gly Ile Gly Leu Cys
        355                 360                 365

Ser Ile Pro Tyr Phe Gln Cys Ile Ser Gly Ile Phe Val His Thr Leu
    370                 375                 380

Ser Pro Gly Ser Val Ala His Leu Asp Gly Arg Leu Arg Cys Gly Asp
385                 390                 395                 400

Glu Ile Val Glu Ile Asn Asp Ser Pro Val His Cys Leu Thr Leu Asn
            405                 410                 415

Glu Val Tyr Thr Ile Leu Ser His Cys Asp Pro Gly Pro Val Pro Ile
        420                 425                 430

Ile Val Ser Arg His Pro Asp Pro Gln Val Ser Glu Gln Leu Lys
        435                 440                 445

Glu Ala Val Ala Gln Ala Val Glu Gly Val Lys Phe Gly Lys Asp Arg
    450                 455                 460

His Gln Trp Ser Leu Glu Gly Val Lys Arg Leu Glu Ser Ser Trp His
465                 470                 475                 480

Gly Arg Pro Thr Leu Glu Lys Glu Arg Glu Lys His Ser Ala Pro Pro
            485                 490                 495

His Arg Arg Ala Gln Lys Ile Met Val Arg Ser Ser Ser Asp Ser Ser
        500                 505                 510

Tyr Met Ser Gly Ser Pro Gly Gly Ser Pro Cys Ser Ala Gly Ala Glu
        515                 520                 525

Pro Gln Pro Ser Glu Arg Glu Gly Ser Thr His Ser Pro Ser Leu Ser
    530                 535                 540

Pro Gly Glu Glu Gln Glu Pro Cys Pro Gly Val Pro Ser Arg Pro Gln
545                 550                 555                 560

Gln Glu Ser Pro Pro Leu Pro Glu Ser Leu Glu Arg Glu Ser His Pro
            565                 570                 575

Pro Leu Arg Leu Lys Lys Ser Phe Glu Ile Leu Val Arg Lys Pro Thr
        580                 585                 590

Ser Ser Lys Pro Lys Pro Pro Arg Lys Tyr Phe Lys Asn Asp Ser
        595                 600                 605

Glu Pro Gln Lys Lys Leu Glu Glu Lys Glu Lys Val Thr Asp Pro Ser
    610                 615                 620

Gly His Thr Leu Pro Thr Cys Ser Gln Glu Thr Arg Glu Leu Leu Pro
625                 630                 635                 640

Leu Leu Leu Gln Glu Asp Thr Ala Gly Arg Ala Pro Cys Thr Ala Ala
            645                 650                 655
```

```
Cys Cys Pro Gly Pro Ala Ala Ser Thr Gln Thr Ser Ser Thr Glu
            660                 665                 670

Gly Glu Ser Arg Arg Ser Ala Ser Pro Glu Thr Pro Ala Ser Pro Gly
    675                 680                 685

Lys His Pro Leu Leu Lys Arg Gln Ala Arg Met Asp Tyr Ser Phe Asp
    690                 695                 700

Ile Thr Ala Glu Asp Pro Trp Val Arg Ile Ser Asp Cys Ile Lys Asn
705                 710                 715                 720

Leu Phe Ser Pro Ile Met Ser Glu Asn His Ser His Thr Pro Leu Gln
                725                 730                 735

Pro Asn Thr Ser Leu Gly Glu Glu Asp Gly Thr Gln Gly Cys Pro Glu
            740                 745                 750

Gly Gly Leu Ser Lys Met Asp Ala Ala Asn Gly Ala Pro Arg Val Tyr
        755                 760                 765

Lys Ser Ala Asp Gly Ser Thr Val Lys Lys Gly Pro Pro Val Ala Pro
    770                 775                 780

Lys Pro Ala Trp Phe Arg Gln Ser Leu Lys Gly Leu Arg Asn Arg Ala
785                 790                 795                 800

Pro Asp Pro Arg Arg Pro Pro Glu Val Ala Ser Ala Ile Gln Pro Thr
                805                 810                 815

Pro Val Ser Arg Asp Pro Pro Gly Pro Gln Pro Gln Ala Ser Ser Ser
            820                 825                 830

Ile Arg Gln Arg Ile Ser Ser Phe Glu Asn Phe Gly Ser Ser Gln Leu
        835                 840                 845

Pro Asp Arg Gly Val Gln Arg Leu Ser Leu Gln Pro Ser Ser Gly Glu
    850                 855                 860

Thr Thr Lys Phe Pro Gly Lys Gln Asp Gly Gly Arg Phe Ser Gly Leu
865                 870                 875                 880

Leu Gly Gln Gly Ala Thr Val Thr Ala Lys His Arg Gln Thr Glu Val
                885                 890                 895

Glu Ser Met Ser Thr Thr Phe Pro Asn Ser Ser Glu Val Arg Asp Pro
            900                 905                 910

Gly Leu Pro Glu Ser Pro Pro Gly Gln Arg Pro Ser Thr Lys Ala
        915                 920                 925

Leu Ser Pro Asp Pro Leu Leu Arg Leu Leu Thr Thr Gln Ser Glu Asp
    930                 935                 940

Thr Gln Gly Pro Gly Leu Lys Met Pro Ser Gln Arg Ala Arg Ser Phe
945                 950                 955                 960

Pro Leu Thr Arg Thr Gln Ser Cys Glu Thr Lys Leu Leu Asp Glu Lys
                965                 970                 975

Ala Ser Lys Leu Tyr Ser Ile Ser Ser Gln Leu Ser Ser Ala Val Met
            980                 985                 990

Lys Ser Leu Leu Cys Leu Pro Ser  Ser Val Ser Cys Gly  Gln Ile Thr
        995                 1000                1005

Cys Ile  Pro Lys Glu Arg Val  Ser Pro Lys Ser Pro  Cys Asn Asn
    1010                1015                1020

Ser Ser  Ala Ala Glu Gly Phe  Gly Glu Ala Met Ala  Ser Asp Thr
    1025                1030                1035

Gly Phe  Ser Leu Asn Leu Ser  Glu Leu Arg Glu Tyr  Ser Glu Gly
    1040                1045                1050

Leu Thr  Glu Pro Gly Glu Thr  Glu Asp Arg Asn His  Cys Ser Ser
    1055                1060                1065

Gln Ala  Gly Gln Ser Val Ile  Ser Leu Leu Ser Ala  Glu Glu Leu
```

-continued

```
            1070                1075                1080

Glu Lys Leu Ile Glu Glu Val Arg Val Leu Asp Glu Ala Thr Leu
        1085                1090                1095

Lys Gln Leu Asp Ser Ile His Val Thr Ile Leu His Lys Glu Glu
        1100                1105                1110

Gly Ala Gly Leu Gly Phe Ser Leu Ala Gly Gly Ala Asp Leu Glu
        1115                1120                1125

Asn Lys Val Ile Thr Val His Arg Val Phe Pro Asn Gly Leu Ala
        1130                1135                1140

Ser Gln Glu Gly Thr Ile Gln Lys Gly Asn Glu Val Leu Ser Ile
        1145                1150                1155

Asn Gly Lys Ser Leu Lys Gly Ala Thr His Asn Asp Ala Leu Ala
        1160                1165                1170

Ile Leu Arg Gln Ala Arg Asp Pro Arg Gln Ala Val Ile Val Thr
        1175                1180                1185

Arg Arg Thr Thr Val Glu Ala Thr His Asp Leu Asn Ser Ser Thr
        1190                1195                1200

Asp Ser Ala Ala Ser Ala Ser Ala Ala Ser Asp Ile Ser Val Glu
        1205                1210                1215

Ser Lys Glu Ala Thr Val Cys Thr Val Thr Leu Glu Lys Thr Ser
        1220                1225                1230

Ala Gly Leu Gly Phe Ser Leu Glu Gly Gly Lys Gly Ser Leu His
        1235                1240                1245

Gly Asp Lys Pro Leu Thr Ile Asn Arg Ile Phe Lys Gly Thr Glu
        1250                1255                1260

Gln Gly Glu Met Val Gln Pro Gly Asp Glu Ile Leu Gln Leu Ala
        1265                1270                1275

Gly Thr Ala Val Gln Gly Leu Thr Arg Phe Glu Ala Trp Asn Val
        1280                1285                1290

Ile Lys Ala Leu Pro Asp Gly Pro Val Thr Ile Val Ile Arg Arg
        1295                1300                1305

Thr Ser Leu Gln Cys Lys Gln Thr Thr Ala Ser Ala Asp Ser
        1310                1315                1320

<210> SEQ ID NO 159
<211> LENGTH: 155
<212> TYPE: PRT
<213> ORGANISM: Artificial Sequence
<220> FEATURE:
<223> OTHER INFORMATION: Synthetic

<400> SEQUENCE: 159

Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
                35                  40                  45

Leu Asn Ile His Asn Arg Asn Thr Asn Thr Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
```

```
                100             105                 110
Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
            130                 135             140

Thr Cys Val Thr Pro Ile Val His His Val Ala
145                 150                 155

<210> SEQ ID NO 160
<211> LENGTH: 158
<212> TYPE: PRT
<213> ORGANISM: Artificial Sequence
<220> FEATURE:
<223> OTHER INFORMATION: Synthetic

<400> SEQUENCE: 160

Met Ser Pro Gly Arg Ala Ser Val Ser Leu Met Leu Leu Leu Leu Leu
1               5                   10                  15

Leu Ser Leu Ala Ala Thr Val Lys Ala Ala Ile Ile Pro Gln Ser
            20                  25                  30

Ser Ala Cys Pro Asn Thr Glu Ala Lys Asp Phe Leu Gln Asn Val Lys
            35                  40                  45

Val Asn Leu Lys Val Phe Asn Ser Leu Gly Ala Lys Val Ser Ser Arg
50                  55                  60

Arg Pro Ser Asp Tyr Leu Asn Arg Ser Thr Ser Pro Trp Thr Leu His
65                  70                  75                  80

Arg Asn Glu Asp Pro Asp Arg Tyr Pro Ser Val Ile Trp Glu Ala Gln
            85                  90                  95

Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
            115                 120                 125

Pro Glu Ser Cys Pro Phe Thr Phe Arg Val Glu Lys Met Leu Val Gly
            130                 135                 140

Val Gly Cys Thr Cys Val Ala Ser Ile Val Arg Gln Ala Ala
145                 150                 155

<210> SEQ ID NO 161
<211> LENGTH: 261
<212> TYPE: PRT
<213> ORGANISM: Artificial Sequence
<220> FEATURE:
<223> OTHER INFORMATION: Synthetic

<400> SEQUENCE: 161

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
            85                  90                  95
```

```
Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 162
<211> LENGTH: 260
<212> TYPE: PRT
<213> ORGANISM: Artificial Sequence
<220> FEATURE:
<223> OTHER INFORMATION: Synthetic

<400> SEQUENCE: 162

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190
```

```
Trp Leu Lys Pro Ser Ser Gly Ser Glu Arg Ile Leu Leu Lys Ala Ala
            195                 200                 205

Asn Thr His Ser Ser Ser Gln Leu Cys Glu Gln Gln Ser Val His Leu
        210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 163
<211> LENGTH: 244
<212> TYPE: PRT
<213> ORGANISM: Artificial Sequence
<220> FEATURE:
<223> OTHER INFORMATION: Synthetic

<400> SEQUENCE: 163

Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly

<210> SEQ ID NO 164
<211> LENGTH: 306
<212> TYPE: PRT
<213> ORGANISM: Artificial Sequence
<220> FEATURE:
<223> OTHER INFORMATION: Synthetic
```

<400> SEQUENCE: 164

```
Met Gly Thr Arg Gly Leu Gln Gly Leu Gly Arg Pro Gln Gly Arg
1               5                   10                  15

Gly Cys Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Arg Arg Val Glu Lys Ile Ile Gly Ser Gly Ala Gln
    50                  55                  60

Ala Gln Lys Arg Leu Asp Asp Ser Lys Pro Ser Cys Ile Leu Pro Ser
65                  70                  75                  80

Pro Ser Ser Leu Ser Glu Thr Pro Asp Pro Arg Leu His Pro Gln Arg
                85                  90                  95

Ser Asn Ala Ser Arg Asn Leu Ala Ser Thr Ser Gln Gly Pro Val Ala
            100                 105                 110

Gln Ser Ser Arg Glu Ala Ser Ala Trp Met Thr Ile Leu Ser Pro Ala
        115                 120                 125

Ala Asp Ser Thr Pro Asp Pro Gly Val Gln Gln Leu Pro Lys Gly Glu
    130                 135                 140

Pro Glu Thr Asp Leu Asn Pro Glu Leu Pro Ala Ala His Leu Ile Gly
145                 150                 155                 160

Ala Trp Met Ser Gly Gln Gly Leu Ser Trp Glu Ala Ser Gln Glu Glu
                165                 170                 175

Ala Phe Leu Arg Ser Gly Ala Gln Phe Ser Pro Thr His Gly Leu Ala
            180                 185                 190

Leu Pro Gln Asp Gly Val Tyr Tyr Leu Tyr Cys His Val Gly Tyr Arg
        195                 200                 205

Gly Arg Thr Pro Pro Ala Gly Arg Ser Arg Ala Arg Ser Leu Thr Leu
    210                 215                 220

Arg Ser Ala Leu Tyr Arg Ala Gly Gly Ala Tyr Gly Arg Gly Ser Pro
225                 230                 235                 240

Glu Leu Leu Leu Glu Gly Ala Glu Thr Val Thr Pro Val Val Asp Pro
                245                 250                 255

Ile Gly Tyr Gly Ser Leu Trp Tyr Thr Ser Val Gly Phe Gly Gly Leu
            260                 265                 270

Ala Gln Leu Arg Ser Gly Glu Arg Val Tyr Val Asn Ile Ser His Pro
        275                 280                 285

Asp Met Val Asp Tyr Arg Arg Gly Lys Thr Phe Phe Gly Ala Val Met
    290                 295                 300

Val Gly
305
```

<210> SEQ ID NO 165
<211> LENGTH: 232
<212> TYPE: PRT
<213> ORGANISM: Artificial Sequence
<220> FEATURE:
<223> OTHER INFORMATION: Synthetic

<400> SEQUENCE: 165

```
Ser Thr Glu Ser Met Ile Arg Asp Val Glu Leu Ala Glu Glu Ala Leu
1               5                   10                  15

Pro Lys Lys Thr Gly Gly Pro Gln Gly Ser Arg Arg Cys Leu Phe Leu
            20                  25                  30
```

Ser Leu Phe Ser Phe Leu Ile Val Ala Gly Ala Thr Thr Leu Phe Cys
            35                  40                  45

Leu Leu His Phe Gly Val Ile Gly Pro Gln Arg Glu Glu Phe Pro Arg
 50                  55                  60

Asp Leu Ser Leu Ile Ser Pro Leu Ala Gln Ala Val Arg Ser Ser Ser
65                  70                  75                  80

Arg Thr Pro Ser Asp Lys Pro Val Ala His Val Val Ala Asn Pro Gln
                85                  90                  95

Ala Glu Gly Gln Leu Gln Trp Leu Asn Arg Arg Ala Asn Ala Leu Leu
            100                 105                 110

Ala Asn Gly Val Glu Leu Arg Asp Asn Gln Leu Val Val Pro Ser Glu
        115                 120                 125

Gly Leu Tyr Leu Ile Tyr Ser Gln Val Leu Phe Lys Gly Gln Gly Cys
    130                 135                 140

Pro Ser Thr His Val Leu Leu Thr His Thr Ile Ser Arg Ile Ala Val
145                 150                 155                 160

Ser Tyr Gln Thr Lys Val Asn Leu Leu Ser Ala Ile Lys Ser Pro Cys
                165                 170                 175

Gln Arg Glu Thr Pro Glu Gly Ala Glu Ala Lys Pro Trp Tyr Glu Pro
            180                 185                 190

Ile Tyr Leu Gly Gly Val Phe Gln Leu Glu Lys Gly Asp Arg Leu Ser
        195                 200                 205

Ala Glu Ile Asn Arg Pro Asp Tyr Leu Asp Phe Ala Glu Ser Gly Gln
    210                 215                 220

Val Tyr Phe Gly Ile Ile Ala Leu
225                 230

<210> SEQ ID NO 166
<211> LENGTH: 138
<212> TYPE: PRT
<213> ORGANISM: Artificial Sequence
<220> FEATURE:
<223> OTHER INFORMATION: Synthetic

<400> SEQUENCE: 166

Asn His Gln Val Glu Glu Gln Leu Glu Trp Leu Ser Gln Arg Ala Asn
1               5                   10                  15

Ala Leu Leu Ala Asn Gly Met Asp Leu Lys Asp Asn Gln Leu Val Val
            20                  25                  30

Pro Ala Asp Gly Leu Tyr Leu Val Tyr Ser Gln Val Leu Phe Lys Gly
        35                  40                  45

Gln Gly Cys Pro Asp Tyr Val Leu Leu Thr His Thr Val Ser Arg Phe
    50                  55                  60

Ala Ile Ser Tyr Gln Glu Lys Val Asn Leu Leu Ser Ala Val Lys Ser
65                  70                  75                  80

Pro Cys Pro Lys Asp Thr Pro Glu Gly Ala Glu Leu Lys Pro Trp Tyr
                85                  90                  95

Glu Pro Ile Tyr Leu Gly Gly Val Phe Gln Leu Glu Lys Gly Asp Gln
            100                 105                 110

Leu Ser Ala Glu Val Asn Leu Pro Lys Tyr Leu Asp Phe Ala Glu Ser
        115                 120                 125

Gly Gln Val Tyr Phe Gly Val Ile Ala Leu
    130                 135

<210> SEQ ID NO 167
<211> LENGTH: 205

<212> TYPE: PRT
<213> ORGANISM: Artificial Sequence
<220> FEATURE:
<223> OTHER INFORMATION: Synthetic

<400> SEQUENCE: 167

```
Met Thr Pro Pro Glu Arg Leu Phe Leu Pro Arg Val Cys Gly Thr Thr
1               5                   10                  15
Leu His Leu Leu Leu Leu Gly Leu Leu Val Leu Leu Pro Gly Ala
            20                  25                  30
Gln Gly Leu Pro Gly Val Gly Leu Thr Pro Ser Ala Ala Gln Thr Ala
        35                  40                  45
Arg Gln His Pro Lys Met His Leu Ala His Ser Thr Leu Lys Pro Ala
    50                  55                  60
Ala His Leu Ile Gly Asp Pro Ser Lys Gln Asn Ser Leu Leu Trp Arg
65                  70                  75                  80
Ala Asn Thr Asp Arg Ala Phe Leu Gln Asp Gly Phe Ser Leu Ser Asn
                85                  90                  95
Asn Ser Leu Leu Val Pro Thr Ser Gly Ile Tyr Phe Val Tyr Ser Gln
            100                 105                 110
Val Val Phe Ser Gly Lys Ala Tyr Ser Pro Lys Ala Thr Ser Ser Pro
        115                 120                 125
Leu Tyr Leu Ala His Glu Val Gln Leu Phe Ser Ser Gln Tyr Pro Phe
    130                 135                 140
His Val Pro Leu Leu Ser Ser Gln Lys Met Val Tyr Pro Gly Leu Gln
145                 150                 155                 160
Glu Pro Trp Leu His Ser Met Tyr His Gly Ala Ala Phe Gln Leu Thr
                165                 170                 175
Gln Gly Asp Gln Leu Ser Thr His Thr Asp Gly Ile Pro His Leu Val
            180                 185                 190
Leu Ser Pro Ser Thr Val Phe Phe Gly Ala Phe Ala Leu
        195                 200                 205
```

<210> SEQ ID NO 168
<211> LENGTH: 254
<212> TYPE: PRT
<213> ORGANISM: Artificial Sequence
<220> FEATURE:
<223> OTHER INFORMATION: Synthetic

<400> SEQUENCE: 168

```
Met Glu Tyr Ala Ser Asp Ala Ser Leu Asp Pro Glu Ala Pro Trp Pro
1               5                   10                  15
Pro Ala Pro Arg Ala Arg Ala Cys Arg Val Leu Pro Trp Ala Leu Val
            20                  25                  30
Ala Gly Leu Leu Leu Leu Leu Leu Ala Ala Ala Cys Ala Val Phe
        35                  40                  45
Leu Ala Cys Pro Trp Ala Val Ser Gly Ala Arg Ala Ser Pro Gly Ser
    50                  55                  60
Ala Ala Ser Pro Arg Leu Arg Glu Gly Pro Glu Leu Ser Pro Asp Asp
65                  70                  75                  80
Pro Ala Gly Leu Leu Asp Leu Arg Gln Gly Met Phe Ala Gln Leu Val
                85                  90                  95
Ala Gln Asn Val Leu Leu Ile Asp Gly Pro Leu Ser Trp Tyr Ser Asp
            100                 105                 110
Pro Gly Leu Ala Gly Val Ser Leu Thr Gly Gly Leu Ser Tyr Lys Glu
        115                 120                 125
```

```
Asp Thr Lys Glu Leu Val Val Ala Lys Ala Gly Val Tyr Tyr Val Phe
            130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 169
<211> LENGTH: 309
<212> TYPE: PRT
<213> ORGANISM: Artificial Sequence
<220> FEATURE:
<223> OTHER INFORMATION: Synthetic

<400> SEQUENCE: 169

Met Asp Gln His Thr Leu Asp Val Glu Asp Thr Ala Asp Ala Arg His
1               5                   10                  15

Pro Ala Gly Thr Ser Cys Pro Ser Asp Ala Ala Leu Leu Arg Asp Thr
                20                  25                  30

Gly Leu Leu Ala Asp Ala Ala Leu Leu Ser Asp Thr Val Arg Pro Thr
            35                  40                  45

Asn Ala Ala Leu Pro Thr Asp Ala Ala Tyr Pro Ala Val Asn Val Arg
        50                  55                  60

Asp Arg Glu Ala Ala Trp Pro Pro Ala Leu Asn Phe Cys Ser Arg His
65                  70                  75                  80

Pro Lys Leu Tyr Gly Leu Val Ala Leu Val Leu Leu Leu Ile Ala
                85                  90                  95

Ala Cys Val Pro Ile Phe Thr Arg Thr Glu Pro Arg Pro Ala Leu Thr
                100                 105                 110

Ile Thr Thr Ser Pro Asn Leu Gly Thr Arg Glu Asn Asn Ala Asp Gln
            115                 120                 125

Val Thr Pro Val Ser His Ile Gly Cys Pro Asn Thr Thr Gln Gln Gly
130                 135                 140

Ser Pro Val Phe Ala Lys Leu Leu Ala Lys Asn Gln Ala Ser Leu Cys
145                 150                 155                 160

Asn Thr Thr Leu Asn Trp His Ser Gln Asp Gly Ala Gly Ser Ser Tyr
                165                 170                 175

Leu Ser Gln Gly Leu Arg Tyr Glu Glu Asp Lys Lys Glu Leu Val Val
                180                 185                 190

Asp Ser Pro Gly Leu Tyr Tyr Val Phe Leu Glu Leu Lys Leu Ser Pro
            195                 200                 205

Thr Phe Thr Asn Thr Gly His Lys Val Gln Gly Trp Val Ser Leu Val
        210                 215                 220

Leu Gln Ala Lys Pro Gln Val Asp Asp Phe Asp Asn Leu Ala Leu Thr
225                 230                 235                 240
```

```
Val Glu Leu Phe Pro Cys Ser Met Glu Asn Lys Leu Val Asp Arg Ser
                245                 250                 255

Trp Ser Gln Leu Leu Leu Lys Ala Gly His Arg Leu Ser Val Gly
        260                 265                 270

Leu Arg Ala Tyr Leu His Gly Ala Gln Asp Ala Tyr Arg Asp Trp Glu
            275                 280                 285

Leu Ser Tyr Pro Asn Thr Thr Ser Phe Gly Leu Phe Leu Val Lys Pro
        290                 295                 300

Asp Asn Pro Trp Glu
305

<210> SEQ ID NO 170
<211> LENGTH: 146
<212> TYPE: PRT
<213> ORGANISM: Artificial Sequence
<220> FEATURE:
<223> OTHER INFORMATION: Synthetic

<400> SEQUENCE: 170

Ala Val Leu Thr Gln Lys Gln Lys Gln His Ser Val Leu His Leu
1               5                   10                  15

Val Pro Ile Asn Ala Thr Ser Lys Asp Asp Ser Asp Val Thr Glu Val
            20                  25                  30

Met Trp Gln Pro Ala Leu Arg Arg Gly Arg Gly Leu Gln Ala Gln Gly
        35                  40                  45

Tyr Gly Val Arg Ile Gln Asp Ala Gly Val Tyr Leu Leu Tyr Ser Gln
    50                  55                  60

Val Leu Phe Gln Asp Val Thr Phe Thr Met Gly Gln Val Val Ser Arg
65                  70                  75                  80

Glu Gly Gln Gly Arg Gln Glu Thr Leu Phe Arg Cys Ile Arg Ser Met
                85                  90                  95

Pro Ser His Pro Asp Arg Ala Tyr Asn Ser Cys Tyr Ser Ala Gly Val
            100                 105                 110

Phe His Leu His Gln Gly Asp Ile Leu Ser Val Ile Ile Pro Arg Ala
        115                 120                 125

Arg Ala Lys Leu Asn Leu Ser Pro His Gly Thr Phe Leu Gly Phe Val
    130                 135                 140

Lys Leu
145

<210> SEQ ID NO 171
<211> LENGTH: 241
<212> TYPE: PRT
<213> ORGANISM: Artificial Sequence
<220> FEATURE:
<223> OTHER INFORMATION: Synthetic

<400> SEQUENCE: 171

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
```

```
                65                  70                  75                  80
Val Leu Glu Ala Trp Lys Asp Gly Ala Lys Ser Arg Arg Arg Ala
                    85                  90                  95
Val Leu Thr Gln Lys His Lys Lys His Ser Val Leu His Leu Val
                    100                 105                 110
Pro Val Asn Ile Thr Ser Lys Ala Asp Ser Asp Val Thr Glu Val Met
                    115                 120                 125
Trp Gln Pro Val Leu Arg Arg Gly Arg Gly Leu Glu Ala Gln Gly Asp
                130                 135                 140
Ile Val Arg Val Trp Asp Thr Gly Ile Tyr Leu Leu Tyr Ser Gln Val
145                 150                 155                 160
Leu Phe His Asp Val Thr Phe Thr Met Gly Gln Val Val Ser Arg Glu
                    165                 170                 175
Gly Gln Gly Arg Arg Glu Thr Leu Phe Arg Cys Ile Arg Ser Met Pro
                180                 185                 190
Ser Asp Pro Asp Arg Ala Tyr Asn Ser Cys Tyr Ser Ala Gly Val Phe
                    195                 200                 205
His Leu His Gln Gly Asp Ile Ile Thr Val Lys Ile Pro Arg Ala Asn
                    210                 215                 220
Ala Lys Leu Ser Leu Ser Pro His Gly Thr Phe Leu Gly Phe Val Lys
225                 230                 235                 240
Leu

<210> SEQ ID NO 172
<211> LENGTH: 193
<212> TYPE: PRT
<213> ORGANISM: Artificial Sequence
<220> FEATURE:
<223> OTHER INFORMATION: Synthetic

<400> SEQUENCE: 172

Met Pro Glu Glu Gly Ser Gly Cys Ser Val Arg Arg Arg Pro Tyr Gly
1               5                   10                  15
Cys Val Leu Arg Ala Ala Leu Val Pro Leu Val Ala Gly Leu Val Ile
                20                  25                  30
Cys Leu Val Val Cys Ile Gln Arg Phe Ala Gln Ala Gln Gln Gln Leu
                35                  40                  45
Pro Leu Glu Ser Leu Gly Trp Asp Val Ala Glu Leu Gln Leu Asn His
                50                  55                  60
Thr Gly Pro Gln Gln Asp Pro Arg Leu Tyr Trp Gln Gly Gly Pro Ala
65                  70                  75                  80
Leu Gly Arg Ser Phe Leu His Gly Pro Glu Leu Asp Lys Gly Gln Leu
                85                  90                  95
Arg Ile His Arg Asp Gly Ile Tyr Met Val His Ile Gln Val Thr Leu
                100                 105                 110
Ala Ile Cys Ser Ser Thr Thr Ala Ser Arg His His Pro Thr Thr Leu
                115                 120                 125
Ala Val Gly Ile Cys Ser Pro Ala Ser Arg Ser Ile Ser Leu Leu Arg
                130                 135                 140
Leu Ser Phe His Gln Gly Cys Thr Ile Ala Ser Gln Arg Leu Thr Pro
145                 150                 155                 160
Leu Ala Arg Gly Asp Thr Leu Cys Thr Asn Leu Thr Gly Thr Leu Leu
                165                 170                 175
Pro Ser Arg Asn Thr Asp Glu Thr Phe Phe Gly Val Gln Trp Val Arg
                180                 185                 190
```

Pro

<210> SEQ ID NO 173
<211> LENGTH: 195
<212> TYPE: PRT
<213> ORGANISM: Artificial Sequence
<220> FEATURE:
<223> OTHER INFORMATION: Synthetic

<400> SEQUENCE: 173

```
Met Pro Glu Glu Gly Arg Pro Cys Pro Trp Val Arg Trp Ser Gly Thr
1               5                   10                  15

Ala Phe Gln Arg Gln Trp Pro Trp Leu Leu Leu Val Val Phe Ile Thr
            20                  25                  30

Val Phe Cys Cys Trp Phe His Cys Ser Gly Leu Leu Ser Lys Gln Gln
        35                  40                  45

Gln Arg Leu Leu Glu His Pro Glu Pro His Thr Ala Glu Leu Gln Leu
    50                  55                  60

Asn Leu Thr Val Pro Arg Lys Asp Pro Thr Leu Arg Trp Gly Ala Gly
65                  70                  75                  80

Pro Ala Leu Gly Arg Ser Phe Thr His Gly Pro Glu Leu Glu Glu Gly
                85                  90                  95

His Leu Arg Ile His Gln Asp Gly Leu Tyr Arg Leu His Ile Gln Val
            100                 105                 110

Thr Leu Ala Asn Cys Ser Ser Pro Gly Ser Thr Leu Gln His Arg Ala
        115                 120                 125

Thr Leu Ala Val Gly Ile Cys Ser Pro Ala Ala His Gly Ile Ser Leu
    130                 135                 140

Leu Arg Gly Arg Phe Gly Gln Asp Cys Thr Val Ala Leu Gln Arg Leu
145                 150                 155                 160

Thr Tyr Leu Val His Gly Asp Val Leu Cys Thr Asn Leu Thr Leu Pro
                165                 170                 175

Leu Leu Pro Ser Arg Asn Ala Asp Glu Thr Phe Phe Gly Val Gln Trp
            180                 185                 190

Ile Cys Pro
        195
```

<210> SEQ ID NO 174
<211> LENGTH: 234
<212> TYPE: PRT
<213> ORGANISM: Artificial Sequence
<220> FEATURE:
<223> OTHER INFORMATION: Synthetic

<400> SEQUENCE: 174

```
Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95
```

```
Lys Ser Trp Ala Tyr Leu Gln Val Ala Lys His Leu Asn Lys Thr Lys
                100                 105                 110

Leu Ser Trp Asn Lys Asp Gly Ile Leu His Gly Val Arg Tyr Gln Asp
            115                 120                 125

Gly Asn Leu Val Ile Gln Phe Pro Gly Leu Tyr Phe Ile Ile Cys Gln
130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
            195                 200                 205

Asp Thr Phe Gln Tyr Ile Asp Thr Ser Thr Phe Pro Leu Glu Asn Val
210                 215                 220

Leu Ser Ile Phe Leu Tyr Ser Asn Ser Asp
225                 230

<210> SEQ ID NO 175
<211> LENGTH: 239
<212> TYPE: PRT
<213> ORGANISM: Artificial Sequence
<220> FEATURE:
<223> OTHER INFORMATION: Synthetic

<400> SEQUENCE: 175

Met Glu Pro Gly Leu Gln Gln Ala Gly Ser Cys Gly Ala Pro Ser Pro
1               5                   10                  15

Asp Pro Ala Met Gln Val Gln Pro Gly Ser Val Ala Ser Pro Trp Arg
            20                  25                  30

Ser Thr Arg Pro Trp Arg Ser Thr Ser Arg Ser Tyr Phe Tyr Leu Ser
        35                  40                  45

Thr Thr Ala Leu Val Cys Leu Val Val Ala Val Ala Ile Ile Leu Val
    50                  55                  60

Leu Val Val Gln Lys Lys Asp Ser Thr Pro Asn Thr Glu Lys Ala
65                  70                  75                  80

Pro Leu Lys Gly Gly Asn Cys Ser Glu Asp Leu Phe Cys Thr Leu Lys
                85                  90                  95

Ser Thr Pro Ser Lys Lys Ser Trp Ala Tyr Leu Gln Val Ser Lys His
            100                 105                 110

Leu Asn Asn Thr Lys Leu Ser Trp Asn Glu Asp Gly Thr Ile His Gly
        115                 120                 125

Leu Ile Tyr Gln Asp Gly Asn Leu Ile Val Gln Phe Pro Gly Leu Tyr
    130                 135                 140

Phe Ile Val Cys Gln Leu Gln Phe Leu Val Gln Cys Ser Asn His Ser
145                 150                 155                 160

Val Asp Leu Thr Leu Gln Leu Leu Ile Asn Ser Lys Ile Lys Lys Gln
                165                 170                 175

Thr Leu Val Thr Val Cys Glu Ser Gly Val Gln Ser Lys Asn Ile Tyr
            180                 185                 190

Gln Asn Leu Ser Gln Phe Leu Leu His Tyr Leu Gln Val Asn Ser Thr
        195                 200                 205

Ile Ser Val Arg Val Asp Asn Phe Gln Tyr Val Asp Thr Asn Thr Phe
    210                 215                 220
```

```
Pro Leu Asp Asn Val Leu Ser Val Phe Leu Tyr Ser Ser Ser Asp
225                 230                 235
```

<210> SEQ ID NO 176
<211> LENGTH: 281
<212> TYPE: PRT
<213> ORGANISM: Artificial Sequence
<220> FEATURE:
<223> OTHER INFORMATION: Synthetic

<400> SEQUENCE: 176

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro
        35                  40                  45

Pro Pro Pro Pro Pro Leu Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280
```

<210> SEQ ID NO 177
<211> LENGTH: 279
<212> TYPE: PRT
<213> ORGANISM: Artificial Sequence
<220> FEATURE:
<223> OTHER INFORMATION: Synthetic

<400> SEQUENCE: 177

```
Met Gln Gln Pro Met Asn Tyr Pro Cys Pro Gln Ile Phe Trp Val Asp
```

```
            1               5                  10                 15
         Ser Ser Ala Thr Ser Ser Trp Ala Pro Pro Gly Ser Val Phe Pro Cys
                         20                 25                 30

Pro Ser Cys Gly Pro Arg Gly Pro Asp Gln Arg Arg Pro Pro Pro
                     35                 40                 45

Pro Pro Pro Val Ser Pro Leu Pro Pro Ser Gln Pro Leu Pro Leu
                 50                 55                 60

Pro Pro Leu Thr Pro Leu Lys Lys Lys Asp His Asn Thr Asn Leu Trp
         65                 70                 75                 80

Leu Pro Val Val Phe Phe Met Val Leu Val Ala Leu Val Gly Met Gly
                             85                 90                 95

Leu Gly Met Tyr Gln Leu Phe His Leu Gln Lys Glu Leu Ala Glu Leu
                         100                105                110

Arg Glu Phe Thr Asn Gln Ser Leu Lys Val Ser Ser Phe Glu Lys Gln
                     115                120                125

Ile Ala Asn Pro Ser Thr Pro Ser Glu Lys Lys Glu Pro Arg Ser Val
         130                135                140

Ala His Leu Thr Gly Asn Pro His Ser Arg Ser Ile Pro Leu Glu Trp
         145                150                155                160

Glu Asp Thr Tyr Gly Thr Ala Leu Ile Ser Gly Val Lys Tyr Lys Lys
                         165                170                175

Gly Gly Leu Val Ile Asn Glu Thr Gly Leu Tyr Phe Val Tyr Ser Lys
                     180                185                190

Val Tyr Phe Arg Gly Gln Ser Cys Asn Asn Gln Pro Leu Asn His Lys
                     195                200                205

Val Tyr Met Arg Asn Ser Lys Tyr Pro Glu Asp Leu Val Leu Met Glu
                 210                215                220

Glu Lys Arg Leu Asn Tyr Cys Thr Thr Gly Gln Ile Trp Ala His Ser
         225                230                235                240

Ser Tyr Leu Gly Ala Val Phe Asn Leu Thr Ser Ala Asp His Leu Tyr
                         245                250                255

Val Asn Ile Ser Gln Leu Ser Leu Ile Asn Phe Glu Glu Ser Lys Thr
                     260                265                270

Phe Phe Gly Leu Tyr Lys Leu
                     275

<210> SEQ ID NO 178
<211> LENGTH: 199
<212> TYPE: PRT
<213> ORGANISM: Artificial Sequence
<220> FEATURE:
<223> OTHER INFORMATION: Synthetic

<400> SEQUENCE: 178

Met Thr Leu His Pro Ser Pro Ile Thr Cys Glu Phe Leu Phe Ser Thr
         1               5                  10                 15

Ala Leu Ile Ser Pro Lys Met Cys Leu Ser His Leu Glu Asn Met Pro
                         20                 25                 30

Leu Ser His Ser Arg Thr Gln Gly Ala Gln Arg Ser Ser Trp Lys Leu
                     35                 40                 45

Trp Leu Phe Cys Ser Ile Val Met Leu Leu Phe Leu Cys Ser Phe Ser
                 50                 55                 60

Trp Leu Ile Phe Ile Phe Leu Gln Leu Glu Thr Ala Lys Glu Pro Cys
         65                 70                 75                 80

Met Ala Lys Phe Gly Pro Leu Pro Ser Lys Trp Gln Met Ala Ser Ser
```

```
                    85                  90                  95
Glu Pro Pro Cys Val Asn Lys Val Ser Asp Trp Lys Leu Glu Ile Leu
              100                 105                 110

Gln Asn Gly Leu Tyr Leu Ile Tyr Gly Gln Val Ala Pro Asn Ala Asn
          115                 120                 125

Tyr Asn Asp Val Ala Pro Phe Glu Val Arg Leu Tyr Lys Asn Lys Asp
      130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
              165                 170                 175

Glu His Gln Val Leu Lys Asn Asn Thr Tyr Trp Gly Ile Ile Leu Leu
          180                 185                 190

Ala Asn Pro Gln Phe Ile Ser
          195

<210> SEQ ID NO 179
<211> LENGTH: 173
<212> TYPE: PRT
<213> ORGANISM: Artificial Sequence
<220> FEATURE:
<223> OTHER INFORMATION: Synthetic

<400> SEQUENCE: 179

Met Glu Glu Met Pro Leu Arg Glu Ser Ser Pro Gln Arg Ala Glu Arg
1               5                   10                  15

Cys Lys Lys Ser Trp Leu Leu Cys Ile Val Ala Leu Leu Leu Met Leu
              20                  25                  30

Leu Cys Ser Leu Gly Thr Leu Ile Tyr Thr Ser Leu Lys Pro Thr Ala
          35                  40                  45

Ile Glu Ser Cys Met Val Lys Phe Glu Leu Ser Ser Ser Lys Trp His
      50                  55                  60

Met Thr Ser Pro Lys Pro His Cys Val Asn Thr Thr Ser Asp Gly Lys
65                  70                  75                  80

Leu Lys Ile Leu Gln Ser Gly Thr Tyr Leu Ile Tyr Gly Gln Val Ile
              85                  90                  95

Pro Val Asp Lys Lys Tyr Ile Lys Asp Asn Ala Pro Phe Val Val Gln
          100                 105                 110

Ile Tyr Lys Lys Asn Asp Val Leu Gln Thr Leu Met Asn Asp Phe Gln
      115                 120                 125

Ile Leu Pro Ile Gly Gly Val Tyr Glu Leu His Ala Gly Asp Asn Ile
  130                 135                 140

Tyr Leu Lys Phe Asn Ser Lys Asp His Ile Gln Lys Thr Asn Thr Tyr
145                 150                 155                 160

Trp Gly Ile Ile Leu Met Pro Asp Leu Pro Phe Ile Ser
              165                 170

<210> SEQ ID NO 180
<211> LENGTH: 240
<212> TYPE: PRT
<213> ORGANISM: Artificial Sequence
<220> FEATURE:
<223> OTHER INFORMATION: Synthetic

<400> SEQUENCE: 180

Met Glu Glu Ser Val Val Arg Pro Ser Val Phe Val Val Asp Gly Gln
1               5                   10                  15
```

```
Thr Asp Ile Pro Phe Thr Arg Leu Gly Arg Ser His Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
 50                  55                  60

Leu Gly Glu Met Val Thr Arg Leu Pro Asp Gly Pro Ala Gly Ser Trp
 65                  70                  75                  80

Glu Gln Leu Ile Gln Glu Arg Ser His Glu Val Asn Pro Ala Ala
            85                  90                  95

His Leu Thr Gly Ala Asn Ser Ser Leu Thr Gly Ser Gly Gly Pro Leu
        100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Ile Tyr
        130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
        165                 170                 175

Leu Glu Leu Leu Val Ser Gln Gln Ser Pro Cys Gly Arg Ala Thr Ser
        180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
210                 215                 220

Val Arg Leu Arg Asp Gly Thr Arg Ser Tyr Phe Gly Ala Phe Met Val
225                 230                 235                 240

<210> SEQ ID NO 181
<211> LENGTH: 239
<212> TYPE: PRT
<213> ORGANISM: Artificial Sequence
<220> FEATURE:
<223> OTHER INFORMATION: Synthetic

<400> SEQUENCE: 181

Met Glu Ser Val Val Gln Pro Ser Val Phe Val Val Asp Gly Gln Thr
1               5                   10                  15

Asp Ile Pro Phe Arg Arg Leu Glu Gln Asn His Arg Arg Arg Cys
            20                  25                  30

Gly Thr Val Gln Val Ser Leu Ala Leu Val Leu Leu Leu Gly Ala Gly
        35                  40                  45

Leu Ala Thr Gln Gly Trp Phe Leu Leu Arg Leu His Gln Arg Leu Gly
 50                  55                  60

Asp Ile Val Ala His Leu Pro Asp Gly Lys Gly Ser Trp Glu Lys
 65                  70                  75                  80

Leu Ile Gln Asp Gln Arg Ser His Gln Ala Asn Pro Ala Ala His Leu
            85                  90                  95

Thr Gly Ala Asn Ala Ser Leu Ile Gly Ile Gly Gly Pro Leu Leu Trp
        100                 105                 110

Glu Thr Arg Leu Gly Leu Ala Phe Leu Arg Gly Leu Thr Tyr His Asp
        115                 120                 125

Gly Ala Leu Val Thr Met Glu Pro Gly Tyr Tyr Tyr Val Tyr Ser Lys
        130                 135                 140
```

Val Gln Leu Ser Gly Val Gly Cys Pro Gln Gly Leu Ala Asn Gly Leu
145                 150                 155                 160

Pro Ile Thr His Gly Leu Tyr Lys Arg Thr Ser Arg Tyr Pro Lys Glu
            165                 170                 175

Leu Glu Leu Leu Val Ser Arg Arg Ser Pro Cys Gly Arg Ala Asn Ser
        180                 185                 190

Ser Arg Val Trp Trp Asp Ser Ser Phe Leu Gly Gly Val Val His Leu
        195                 200                 205

Glu Ala Gly Glu Glu Val Val Arg Val Pro Gly Asn Arg Leu Val
        210                 215                 220

Arg Pro Arg Asp Gly Thr Arg Ser Tyr Phe Gly Ala Phe Met Val
225                 230                 235

<210> SEQ ID NO 182
<211> LENGTH: 183
<212> TYPE: PRT
<213> ORGANISM: Artificial Sequence
<220> FEATURE:
<223> OTHER INFORMATION: Synthetic

<400> SEQUENCE: 182

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 183
<211> LENGTH: 197
<212> TYPE: PRT
<213> ORGANISM: Artificial Sequence
<220> FEATURE:
<223> OTHER INFORMATION: Synthetic

<400> SEQUENCE: 183

Met Glu Gly Glu Gly Val Gln Pro Leu Asp Glu Asn Leu Glu Asn Gly
1               5                   10                  15

Ser Arg Pro Arg Phe Lys Trp Lys Lys Thr Leu Arg Leu Val Val Ser
            20                  25                  30

```
Gly Ile Lys Gly Ala Gly Met Leu Leu Cys Phe Ile Tyr Val Cys Leu
            35                  40                  45

Gln Leu Ser Ser Ser Pro Ala Lys Asp Pro Pro Ile Gln Arg Leu Arg
 50                  55                  60

Gly Ala Val Thr Arg Cys Glu Asp Gly Gln Leu Phe Ile Ser Ser Tyr
 65                  70                  75                  80

Lys Asn Glu Tyr Gln Thr Met Glu Val Gln Asn Asn Ser Val Val Ile
                85                  90                  95

Lys Cys Asp Gly Leu Tyr Ile Ile Tyr Leu Lys Gly Ser Phe Phe Gln
            100                 105                 110

Glu Val Lys Ile Asp Leu His Phe Arg Glu Asp His Asn Pro Ile Ser
        115                 120                 125

Ile Pro Met Leu Asn Asp Gly Arg Arg Ile Val Phe Thr Val Val Ala
    130                 135                 140

Ser Leu Ala Phe Lys Asp Lys Val Tyr Leu Thr Val Asn Ala Pro Asp
145                 150                 155                 160

Thr Leu Cys Glu His Leu Gln Ile Asn Asp Gly Glu Leu Ile Val Val
                165                 170                 175

Gln Leu Thr Pro Gly Tyr Cys Ala Pro Glu Gly Ser Tyr His Ser Thr
            180                 185                 190

Val Asn Gln Val Pro
        195

<210> SEQ ID NO 184
<211> LENGTH: 285
<212> TYPE: PRT
<213> ORGANISM: Artificial Sequence
<220> FEATURE:
<223> OTHER INFORMATION: Synthetic

<400> SEQUENCE: 184

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190
```

-continued

```
Phe Phe Ile Tyr Gly Gln Val Leu Tyr Thr Asp Lys Thr Tyr Ala Met
            195                 200                 205
Gly His Leu Ile Gln Arg Lys Lys Val His Val Phe Gly Asp Glu Leu
        210                 215                 220
Ser Leu Val Thr Leu Phe Arg Cys Ile Gln Asn Met Pro Glu Thr Leu
225                 230                 235                 240
Pro Asn Asn Ser Cys Tyr Ser Ala Gly Ile Ala Lys Leu Glu Glu Gly
                245                 250                 255
Asp Glu Leu Gln Leu Ala Ile Pro Arg Glu Asn Ala Gln Ile Ser Leu
            260                 265                 270
Asp Gly Asp Val Thr Phe Phe Gly Ala Leu Lys Leu Leu
                275                 280                 285

<210> SEQ ID NO 185
<211> LENGTH: 249
<212> TYPE: PRT
<213> ORGANISM: Artificial Sequence
<220> FEATURE:
<223> OTHER INFORMATION: Synthetic

<400> SEQUENCE: 185

Met Ala Met Ala Phe Cys Pro Lys Asp Gln Tyr Trp Asp Ser Ser Arg
1               5                   10                  15
Lys Ser Cys Val Ser Cys Ala Leu Thr Cys Ser Gln Arg Ser Gln Arg
            20                  25                  30
Thr Cys Thr Asp Phe Cys Lys Phe Ile Asn Cys Arg Lys Glu Gln Gly
        35                  40                  45
Arg Tyr Tyr Asp His Leu Leu Gly Ala Cys Val Ser Cys Asp Ser Thr
    50                  55                  60
Cys Thr Gln His Pro Gln Gln Cys Ala His Phe Cys Glu Lys Arg Pro
65                  70                  75                  80
Arg Ser Gln Ala Asn Leu Gln Pro Glu Leu Gly Arg Pro Gln Ala Gly
                85                  90                  95
Glu Val Glu Val Arg Ser Asp Asn Ser Gly Arg His Gln Gly Ser Glu
            100                 105                 110
His Gly Pro Gly Leu Arg Leu Ser Ser Asp Gln Leu Thr Leu Tyr Cys
        115                 120                 125
Thr Leu Gly Val Cys Leu Cys Ala Ile Phe Cys Cys Phe Leu Val Ala
    130                 135                 140
Leu Ala Ser Phe Leu Arg Arg Arg Gly Glu Pro Leu Pro Ser Gln Pro
145                 150                 155                 160
Ala Gly Pro Arg Gly Ser Gln Ala Asn Ser Pro His Ala His Arg Pro
                165                 170                 175
Val Thr Glu Ala Cys Asp Glu Val Thr Ala Ser Pro Gln Pro Val Glu
            180                 185                 190
Thr Cys Ser Phe Cys Phe Pro Glu Arg Ser Ser Pro Thr Gln Glu Ser
        195                 200                 205
Ala Pro Arg Ser Leu Gly Ile His Gly Phe Ala Gly Thr Ala Ala Pro
    210                 215                 220
Gln Pro Cys Met Arg Ala Thr Val Gly Gly Leu Gly Val Leu Arg Ala
225                 230                 235                 240
Ser Thr Gly Asp Ala Arg Pro Ala Thr
                245

<210> SEQ ID NO 186
```

-continued

```
<211> LENGTH: 281
<212> TYPE: PRT
<213> ORGANISM: Artificial Sequence
<220> FEATURE:
<223> OTHER INFORMATION: Synthetic

<400> SEQUENCE: 186

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 187
<211> LENGTH: 291
<212> TYPE: PRT
<213> ORGANISM: Artificial Sequence
<220> FEATURE:
<223> OTHER INFORMATION: Synthetic

<400> SEQUENCE: 187

Met Pro Ser Ser Gly Ala Leu Lys Asp Leu Ser Phe Ser Gln His Phe
1               5                   10                  15

Arg Met Met Val Ile Cys Ile Val Leu Leu Gln Val Leu Leu Gln Ala
            20                  25                  30

Val Ser Val Ala Val Thr Tyr Met Tyr Phe Thr Asn Glu Met Lys Gln
```

```
              35                  40                  45
Leu Gln Asp Asn Tyr Ser Lys Ile Gly Leu Ala Cys Phe Ser Lys Thr
     50                  55                  60

Asp Glu Asp Phe Trp Asp Ser Thr Asp Gly Glu Ile Leu Asn Arg Pro
 65                  70                  75                  80

Cys Leu Gln Val Lys Arg Gln Leu Tyr Gln Leu Ile Glu Glu Val Thr
                 85                  90                  95

Leu Arg Thr Phe Gln Asp Thr Ile Ser Thr Val Pro Glu Lys Gln Leu
            100                 105                 110

Ser Thr Pro Pro Leu Pro Arg Gly Gly Arg Pro Gln Lys Val Ala Ala
        115                 120                 125

His Ile Thr Gly Ile Thr Arg Arg Ser Asn Ser Ala Leu Ile Pro Ile
    130                 135                 140

Ser Lys Asp Gly Lys Thr Leu Gly Leu Gln Lys Ile Glu Ser Trp Glu Ser
145                 150                 155                 160

Ser Arg Lys Gly His Ser Phe Leu Asn His Val Leu Phe Arg Asn Gly
                165                 170                 175

Glu Leu Val Ile Glu Gln Gly Leu Tyr Tyr Ile Tyr Ser Gln Thr
            180                 185                 190

Tyr Phe Arg Phe Gln Glu Ala Glu Asp Ala Ser Lys Met Val Ser Lys
                195                 200                 205

Asp Lys Val Arg Thr Lys Gln Leu Val Gln Tyr Ile Tyr Lys Tyr Thr
        210                 215                 220

Ser Tyr Pro Asp Pro Ile Val Leu Met Lys Ser Ala Arg Asn Ser Cys
225                 230                 235                 240

Trp Ser Arg Asp Ala Glu Tyr Gly Leu Tyr Ser Ile Tyr Gln Gly Gly
                245                 250                 255

Leu Phe Glu Leu Lys Lys Asn Asp Arg Ile Phe Val Ser Val Thr Asn
            260                 265                 270

Glu His Leu Met Asp Leu Asp Gln Glu Ala Ser Phe Phe Gly Ala Phe
        275                 280                 285

Leu Ile Asn
    290

<210> SEQ ID NO 188
<211> LENGTH: 249
<212> TYPE: PRT
<213> ORGANISM: Artificial Sequence
<220> FEATURE:
<223> OTHER INFORMATION: Synthetic

<400> SEQUENCE: 188

Met Ala Ala Arg Arg Ser Gln Arg Arg Gly Arg Arg Gly Glu Pro
 1               5                  10                  15

Gly Thr Ala Leu Leu Val Pro Leu Ala Leu Gly Leu Gly Leu Ala Leu
             20                  25                  30

Ala Cys Leu Gly Leu Leu Leu Ala Val Val Ser Leu Gly Ser Arg Ala
         35                  40                  45

Ser Leu Ser Ala Gln Glu Pro Ala Gln Glu Glu Leu Val Ala Glu Glu
     50                  55                  60

Asp Gln Asp Pro Ser Glu Leu Asn Pro Gln Thr Glu Glu Ser Gln Asp
 65                  70                  75                  80

Pro Ala Pro Phe Leu Asn Arg Leu Val Arg Pro Arg Arg Ser Ala Pro
                 85                  90                  95

Lys Gly Arg Lys Thr Arg Ala Arg Arg Ala Ile Ala Ala His Tyr Glu
```

```
                100               105               110
Val His Pro Arg Pro Gly Gln Asp Gly Ala Gln Ala Gly Val Asp Gly
            115               120               125

Thr Val Ser Gly Trp Glu Glu Ala Arg Ile Asn Ser Ser Ser Pro Leu
        130               135               140

Arg Tyr Asn Arg Gln Ile Gly Glu Phe Ile Val Thr Arg Ala Gly Leu
145               150               155               160

Tyr Tyr Leu Tyr Cys Gln Val His Phe Asp Glu Gly Lys Ala Val Tyr
                165               170               175

Leu Lys Leu Asp Leu Leu Val Asp Gly Val Leu Ala Leu Arg Cys Leu
            180               185               190

Glu Glu Phe Ser Ala Thr Ala Ala Ser Ser Leu Gly Pro Gln Leu Arg
        195               200               205

Leu Cys Gln Val Ser Gly Leu Leu Ala Leu Arg Pro Gly Ser Ser Leu
    210               215               220

Arg Ile Arg Thr Leu Pro Trp Ala His Leu Lys Ala Ala Pro Phe Leu
225               230               235               240

Thr Tyr Phe Gly Leu Phe Gln Val His
                245

<210> SEQ ID NO 189
<211> LENGTH: 129
<212> TYPE: PRT
<213> ORGANISM: Artificial Sequence
<220> FEATURE:
<223> OTHER INFORMATION: Synthetic

<400> SEQUENCE: 189

Met Ala Ser Ala Trp Pro Arg Ser Leu Pro Gln Ile Leu Val Leu Gly
1               5                   10                  15

Phe Gly Leu Val Leu Met Arg Ala Ala Ala Gly Glu Gln Ala Pro Gly
                20                  25                  30

Thr Ser Pro Cys Ser Ser Gly Ser Ser Trp Ser Ala Asp Leu Asp Lys
            35                  40                  45

Cys Met Asp Cys Ala Ser Cys Pro Ala Arg Pro His Ser Asp Phe Cys
        50                  55                  60

Leu Gly Cys Ala Ala Ala Pro Pro Ala His Phe Arg Leu Leu Trp Pro
65                  70                  75                  80

Ile Leu Gly Gly Ala Leu Ser Leu Val Leu Val Leu Ala Leu Val Ser
                85                  90                  95

Ser Phe Leu Val Trp Arg Arg Cys Arg Arg Arg Glu Lys Phe Thr Thr
                100                 105                 110

Pro Ile Glu Glu Thr Gly Gly Glu Gly Cys Pro Gly Val Ala Leu Ile
            115                 120                 125

Gln

<210> SEQ ID NO 190
<211> LENGTH: 317
<212> TYPE: PRT
<213> ORGANISM: Artificial Sequence
<220> FEATURE:
<223> OTHER INFORMATION: Synthetic

<400> SEQUENCE: 190

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
```

```
            20                  25                  30
Pro Pro Pro Ala Pro His Gln Pro Pro Ala Ala Ser Arg Ser Met
        35                  40                  45
Phe Val Ala Leu Leu Gly Leu Gly Leu Gly Gln Val Val Cys Ser Val
    50                  55                  60
Ala Leu Phe Phe Tyr Phe Arg Ala Gln Met Asp Pro Asn Arg Ile Ser
65                  70                  75                  80
Glu Asp Gly Thr His Cys Ile Tyr Arg Ile Leu Arg Leu His Glu Asn
                85                  90                  95
Ala Asp Phe Gln Asp Thr Thr Leu Glu Ser Gln Asp Thr Lys Leu Ile
            100                 105                 110
Pro Asp Ser Cys Arg Arg Ile Lys Gln Ala Phe Gln Gly Ala Val Gln
            115                 120                 125
Lys Glu Leu Gln His Ile Val Gly Ser Gln His Ile Arg Ala Glu Lys
        130                 135                 140
Ala Met Val Asp Gly Ser Trp Leu Asp Leu Ala Lys Arg Ser Lys Leu
145                 150                 155                 160
Glu Ala Gln Pro Phe Ala His Leu Thr Ile Asn Ala Thr Asp Ile Pro
                165                 170                 175
Ser Gly Ser His Lys Val Ser Leu Ser Ser Trp Tyr His Asp Arg Gly
            180                 185                 190
Trp Ala Lys Ile Ser Asn Met Thr Phe Ser Asn Gly Lys Leu Ile Val
        195                 200                 205
Asn Gln Asp Gly Phe Tyr Tyr Leu Tyr Ala Asn Ile Cys Phe Arg His
    210                 215                 220
His Glu Thr Ser Gly Asp Leu Ala Thr Glu Tyr Leu Gln Leu Met Val
225                 230                 235                 240
Tyr Val Thr Lys Thr Ser Ile Lys Ile Pro Ser Ser His Thr Leu Met
                245                 250                 255
Lys Gly Gly Ser Thr Lys Tyr Trp Ser Gly Asn Ser Glu Phe His Phe
            260                 265                 270
Tyr Ser Ile Asn Val Gly Gly Phe Phe Lys Leu Arg Ser Gly Glu Glu
        275                 280                 285
Ile Ser Ile Glu Val Ser Asn Pro Ser Leu Leu Asp Pro Asp Gln Asp
    290                 295                 300
Ala Thr Tyr Phe Gly Ala Phe Lys Val Arg Asp Ile Asp
305                 310                 315

<210> SEQ ID NO 191
<211> LENGTH: 316
<212> TYPE: PRT
<213> ORGANISM: Artificial Sequence
<220> FEATURE:
<223> OTHER INFORMATION: Synthetic

<400> SEQUENCE: 191

Met Arg Arg Ala Ser Arg Asp Tyr Gly Lys Tyr Leu Arg Ser Ser Glu
1               5                   10                  15
Glu Met Gly Ser Gly Pro Gly Val Pro His Glu Gly Pro Leu His Pro
            20                  25                  30
Ala Pro Ser Ala Pro Ala Pro Pro Ala Ala Ser Arg Ser
        35                  40                  45
Met Phe Leu Ala Leu Leu Gly Leu Gly Leu Gly Gln Val Val Cys Ser
    50                  55                  60
Ile Ala Leu Phe Leu Tyr Phe Arg Ala Gln Met Asp Pro Asn Arg Ile
```

```
                65                  70                  75                  80
Ser Glu Asp Ser Thr His Cys Phe Tyr Arg Ile Leu Arg Leu His Glu
                    85                  90                  95

Asn Ala Asp Leu Gln Asp Ser Thr Leu Glu Ser Glu Asp Thr Leu Pro
                100                 105                 110

Asp Ser Cys Arg Arg Met Lys Gln Ala Phe Gln Gly Ala Val Gln Lys
                115                 120                 125

Glu Leu Gln His Ile Val Gly Pro Gln Arg Phe Ser Gly Ala Pro Ala
            130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                    165                 170                 175

Gly Ser His Lys Val Thr Leu Ser Ser Trp Tyr His Asp Arg Gly Trp
                180                 185                 190

Ala Lys Ile Ser Asn Met Thr Leu Ser Asn Gly Lys Leu Arg Val Asn
            195                 200                 205

Gln Asp Gly Phe Tyr Tyr Leu Tyr Ala Asn Ile Cys Phe Arg His His
            210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
                245                 250                 255

Gly Gly Ser Thr Lys Asn Trp Ser Gly Asn Ser Glu Phe His Phe Tyr
                260                 265                 270

Ser Ile Asn Val Gly Gly Phe Phe Lys Leu Arg Ala Gly Glu Glu Ile
            275                 280                 285

Ser Ile Gln Val Ser Asn Pro Ser Leu Leu Asp Pro Asp Gln Asp Ala
            290                 295                 300

Thr Tyr Phe Gly Ala Phe Lys Val Gln Asp Ile Asp
305                 310                 315

<210> SEQ ID NO 192
<211> LENGTH: 390
<212> TYPE: PRT
<213> ORGANISM: Artificial Sequence
<220> FEATURE:
<223> OTHER INFORMATION: Synthetic

<400> SEQUENCE: 192

Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65              70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
                100                 105                 110

Met Val Glu Thr His Asn Glu Ile Tyr Asp Lys Phe Lys Gln Ser Thr
```

```
                115                 120                 125
His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 193
<211> LENGTH: 390
<212> TYPE: PRT
<213> ORGANISM: Artificial Sequence
<220> FEATURE:
<223> OTHER INFORMATION: Synthetic

<400> SEQUENCE: 193

Met Pro Pro Ser Gly Leu Arg Leu Leu Pro Leu Leu Leu Pro Leu Pro
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Asp Pro Glu
```

```
                    85                  90                  95
Pro Glu Pro Glu Ala Asp Tyr Tyr Ala Lys Glu Val Thr Arg Val Leu
            100                 105                 110

Met Val Asp Arg Asn Asn Ala Ile Tyr Glu Lys Thr Lys Asp Ile Ser
            115                 120                 125

His Ser Ile Tyr Met Phe Phe Asn Thr Ser Asp Ile Arg Glu Ala Val
    130                 135                 140

Pro Glu Pro Pro Leu Leu Ser Arg Ala Glu Leu Arg Leu Gln Arg Leu
145                 150                 155                 160

Lys Ser Ser Val Glu Gln His Val Glu Leu Tyr Gln Lys Tyr Ser Asn
                165                 170                 175

Asn Ser Trp Arg Tyr Leu Gly Asn Arg Leu Leu Thr Pro Thr Asp Thr
            180                 185                 190

Pro Glu Trp Leu Ser Phe Asp Val Thr Gly Val Val Arg Gln Trp Leu
            195                 200                 205

Asn Gln Gly Asp Gly Ile Gln Gly Phe Arg Phe Ser Ala His Cys Ser
    210                 215                 220

Cys Asp Ser Lys Asp Asn Lys Leu His Val Glu Ile Asn Gly Ile Ser
225                 230                 235                 240

Pro Lys Arg Arg Gly Asp Leu Gly Thr Ile His Asp Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Tyr Cys Phe Ser Ser
    275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ser Pro Cys Cys Val Pro Gln Ala Leu Glu Pro Leu Pro Ile Val Tyr
    355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 194
<211> LENGTH: 414
<212> TYPE: PRT
<213> ORGANISM: Artificial Sequence
<220> FEATURE:
<223> OTHER INFORMATION: Synthetic

<400> SEQUENCE: 194

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
            35                  40                  45

Lys Leu Thr Ser Pro Pro Glu Asp Tyr Pro Glu Pro Glu Glu Val Pro
```

```
            50                  55                  60
Pro Glu Val Ile Ser Ile Tyr Asn Ser Thr Arg Asp Leu Leu Gln Glu
 65                  70                  75                  80

Lys Ala Ser Arg Arg Ala Ala Cys Glu Arg Glu Arg Ser Asp Glu
                 85                  90                  95

Glu Tyr Tyr Ala Lys Glu Val Tyr Lys Ile Asp Met Pro Pro Phe Phe
                100                 105                 110

Pro Ser Glu Asn Ala Ile Pro Pro Thr Phe Tyr Arg Pro Tyr Phe Arg
            115                 120                 125

Ile Val Arg Phe Asp Val Ser Ala Met Glu Lys Asn Ala Ser Asn Leu
            130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
            195                 200                 205

Glu Trp Leu His His Lys Asp Arg Asn Leu Gly Phe Lys Ile Ser Leu
            210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Met Leu Leu Pro Ser
            275                 280                 285

Tyr Arg Leu Glu Ser Gln Gln Thr Asn Arg Arg Lys Lys Arg Ala Leu
            290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
            325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
            355                 360                 365

Thr Ile Asn Pro Glu Ala Ser Ala Ser Pro Cys Cys Val Ser Gln Asp
370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
                405                 410

<210> SEQ ID NO 195
<211> LENGTH: 414
<212> TYPE: PRT
<213> ORGANISM: Artificial Sequence
<220> FEATURE:
<223> OTHER INFORMATION: Synthetic

<400> SEQUENCE: 195

Met His Tyr Cys Val Leu Ser Thr Phe Leu Leu Leu His Leu Val Pro
```

| | | | | | | | | | | | | | | | |
|---|---|---|---|---|---|---|---|---|---|---|---|---|---|---|---|
| 1 | | | | 5 | | | | | 10 | | | | | 15 | |
| Val | Ala | Leu | Ser | Leu | Ser | Thr | Cys | Ser | Thr | Leu | Asp | Met | Asp | Gln | Phe |
| | | | 20 | | | | | 25 | | | | | 30 | | |
| Met | Arg | Lys | Arg | Ile | Glu | Ala | Ile | Arg | Gly | Gln | Ile | Leu | Ser | Lys | Leu |
| | | | 35 | | | | | 40 | | | | | 45 | | |
| Lys | Leu | Thr | Ser | Pro | Pro | Glu | Asp | Tyr | Pro | Glu | Pro | Asp | Glu | Val | Pro |
| | | | 50 | | | | | 55 | | | | | 60 | | |
| Pro | Glu | Val | Ile | Ser | Ile | Tyr | Asn | Ser | Thr | Arg | Asp | Leu | Leu | Gln | Glu |
| 65 | | | | | 70 | | | | | 75 | | | | | 80 |
| Lys | Ala | Ser | Arg | Arg | Ala | Ala | Ala | Cys | Glu | Arg | Glu | Arg | Ser | Asp | Glu |
| | | | | 85 | | | | | 90 | | | | | 95 | |
| Glu | Tyr | Tyr | Ala | Lys | Glu | Val | Tyr | Lys | Ile | Asp | Met | Pro | Ser | His | Leu |
| | | | | 100 | | | | | 105 | | | | | 110 | |
| Pro | Ser | Glu | Asn | Ala | Ile | Pro | Pro | Thr | Phe | Tyr | Arg | Pro | Tyr | Phe | Arg |
| | | | | 115 | | | | | 120 | | | | | 125 | |
| Ile | Val | Arg | Phe | Asp | Val | Ser | Thr | Met | Glu | Lys | Asn | Ala | Ser | Asn | Leu |
| | | 130 | | | | | 135 | | | | | 140 | | | |
| Val | Lys | Ala | Glu | Phe | Arg | Val | Phe | Arg | Leu | Gln | Asn | Pro | Lys | Ala | Arg |
| 145 | | | | | 150 | | | | | 155 | | | | | 160 |
| Val | Ala | Glu | Gln | Arg | Ile | Glu | Leu | Tyr | Gln | Ile | Leu | Lys | Ser | Lys | Asp |
| | | | | 165 | | | | | 170 | | | | | 175 | |
| Leu | Thr | Ser | Pro | Thr | Gln | Arg | Tyr | Ile | Asp | Ser | Lys | Val | Val | Lys | Thr |
| | | | | 180 | | | | | 185 | | | | | 190 | |
| Arg | Ala | Glu | Gly | Glu | Trp | Leu | Ser | Phe | Asp | Val | Thr | Asp | Ala | Val | Gln |
| | | | 195 | | | | | 200 | | | | | 205 | | |
| Glu | Trp | Leu | His | His | Lys | Asp | Arg | Asn | Leu | Gly | Phe | Lys | Ile | Ser | Leu |
| | | 210 | | | | | 215 | | | | | 220 | | | |
| His | Cys | Pro | Cys | Cys | Thr | Phe | Val | Pro | Ser | Asn | Asn | Tyr | Ile | Ile | Pro |
| 225 | | | | | 230 | | | | | 235 | | | | | 240 |
| Asn | Lys | Ser | Glu | Glu | Leu | Glu | Ala | Arg | Phe | Ala | Gly | Ile | Asp | Gly | Thr |
| | | | | 245 | | | | | 250 | | | | | 255 | |
| Ser | Thr | Tyr | Ala | Ser | Gly | Asp | Gln | Lys | Thr | Ile | Lys | Ser | Thr | Arg | Lys |
| | | | | 260 | | | | | 265 | | | | | 270 | |
| Lys | Thr | Ser | Gly | Lys | Thr | Pro | His | Leu | Leu | Leu | Met | Leu | Leu | Pro | Ser |
| | | 275 | | | | | 280 | | | | | 285 | | | |
| Tyr | Arg | Leu | Glu | Ser | Gln | Gln | Ser | Ser | Arg | Arg | Lys | Lys | Arg | Ala | Leu |
| | | 290 | | | | | 295 | | | | | 300 | | | |
| Asp | Ala | Ala | Tyr | Cys | Phe | Arg | Asn | Val | Gln | Asp | Asn | Cys | Cys | Leu | Arg |
| 305 | | | | | 310 | | | | | 315 | | | | | 320 |
| Pro | Leu | Tyr | Ile | Asp | Phe | Lys | Arg | Asp | Leu | Gly | Trp | Lys | Trp | Ile | His |
| | | | | 325 | | | | | 330 | | | | | 335 | |
| Glu | Pro | Lys | Gly | Tyr | Asn | Ala | Asn | Phe | Cys | Ala | Gly | Ala | Cys | Pro | Tyr |
| | | | 340 | | | | | 345 | | | | | 350 | | |
| Leu | Trp | Ser | Ser | Asp | Thr | Gln | His | Thr | Lys | Val | Leu | Ser | Leu | Tyr | Asn |
| | | | 355 | | | | | 360 | | | | | 365 | | |
| Thr | Ile | Asn | Pro | Glu | Ala | Ser | Ala | Ser | Pro | Cys | Cys | Val | Ser | Gln | Asp |
| | | 370 | | | | | 375 | | | | | 380 | | | |
| Leu | Glu | Pro | Leu | Thr | Ile | Leu | Tyr | Tyr | Ile | Gly | Asn | Thr | Pro | Lys | Ile |
| 385 | | | | | 390 | | | | | 395 | | | | | 400 |
| Glu | Gln | Leu | Ser | Asn | Met | Ile | Val | Lys | Ser | Cys | Lys | Cys | Ser | | |
| | | | | 405 | | | | | 410 | | | | | | |

<210> SEQ ID NO 196

```
<211> LENGTH: 412
<212> TYPE: PRT
<213> ORGANISM: Artificial Sequence
<220> FEATURE:
<223> OTHER INFORMATION: Synthetic

<400> SEQUENCE: 196

Met Lys Met His Leu Gln Arg Ala Leu Val Leu Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Lys Arg Val Glu Ala Ile Arg Gly Gln Ile Leu
                35                  40                  45

Ser Lys Leu Arg Leu Thr Ser Pro Pro Glu Pro Thr Val Met Thr His
50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
                115                 120                 125

Ser Lys Val Phe Arg Phe Asn Val Ser Val Glu Lys Asn Arg Thr
                130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
                180                 185                 190

Thr Arg Gly Thr Ala Glu Trp Leu Ser Phe Asp Val Thr Asp Thr Val
                195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
                260                 265                 270

His His Asn Pro His Leu Ile Leu Met Met Ile Pro Pro His Arg Leu
                275                 280                 285

Asp Asn Pro Gly Gln Gly Gly Gln Arg Lys Lys Arg Ala Leu Asp Thr
                290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
                355                 360                 365

Asn Pro Glu Ala Ser Ala Ser Pro Cys Cys Val Pro Gln Asp Leu Glu
                370                 375                 380
```

```
Pro Leu Thr Ile Leu Tyr Tyr Val Gly Arg Thr Pro Lys Val Glu Gln
385                 390                 395                 400

Leu Ser Asn Met Val Lys Ser Cys Lys Cys Ser
            405                 410

<210> SEQ ID NO 197
<211> LENGTH: 410
<212> TYPE: PRT
<213> ORGANISM: Artificial Sequence
<220> FEATURE:
<223> OTHER INFORMATION: Synthetic

<400> SEQUENCE: 197

Met His Leu Gln Arg Ala Leu Val Val Leu Ala Leu Asn Leu Ala
1               5                   10                  15

Thr Ile Ser Leu Ser Leu Ser Thr Cys Thr Thr Leu Asp Phe Gly His
                20                  25                  30

Ile Lys Lys Lys Arg Val Glu Ala Ile Arg Gly Gln Ile Leu Ser Lys
            35                  40                  45

Leu Arg Leu Thr Ser Pro Pro Glu Pro Ser Val Met Thr His Val Pro
50                  55                  60

Tyr Gln Val Leu Ala Leu Tyr Asn Ser Thr Arg Glu Leu Leu Glu Glu
65                  70                  75                  80

Met His Gly Glu Arg Glu Glu Gly Cys Thr Gln Glu Thr Ser Glu Ser
                85                  90                  95

Glu Tyr Tyr Ala Lys Glu Ile His Lys Phe Asp Met Ile Gln Gly Leu
            100                 105                 110

Ala Glu His Asn Glu Leu Ala Val Cys Pro Lys Gly Ile Thr Ser Lys
            115                 120                 125

Val Phe Arg Phe Asn Val Ser Ser Val Glu Lys Asn Gly Thr Asn Leu
            130                 135                 140

Phe Arg Ala Glu Phe Arg Val Leu Arg Val Pro Asn Pro Ser Ser Lys
145                 150                 155                 160

Arg Thr Glu Gln Arg Ile Glu Leu Phe Gln Ile Leu Arg Pro Asp Glu
                165                 170                 175

His Ile Ala Lys Gln Arg Tyr Ile Gly Gly Lys Asn Leu Pro Thr Arg
            180                 185                 190

Gly Thr Ala Glu Trp Leu Ser Phe Asp Val Thr Asp Thr Val Arg Glu
            195                 200                 205

Trp Leu Leu Arg Arg Glu Ser Asn Leu Gly Leu Glu Ile Ser Ile His
210                 215                 220

Cys Pro Cys His Thr Phe Gln Pro Asn Gly Asp Ile Leu Glu Asn Val
225                 230                 235                 240

His Glu Val Met Glu Ile Lys Phe Lys Gly Val Asp Asn Glu Asp Asp
                245                 250                 255

His Gly Arg Gly Asp Leu Gly Arg Leu Lys Lys Gln Lys Asp His His
            260                 265                 270

Asn Pro His Leu Ile Leu Met Met Ile Pro Pro His Arg Leu Asp Ser
            275                 280                 285

Pro Gly Gln Gly Ser Gln Arg Lys Lys Arg Ala Leu Asp Thr Asn Tyr
290                 295                 300

Cys Phe Arg Asn Leu Glu Glu Asn Cys Cys Val Arg Pro Leu Tyr Ile
305                 310                 315                 320

Asp Phe Arg Gln Asp Leu Gly Trp Lys Trp Val His Glu Pro Lys Gly
                325                 330                 335
```

```
Tyr Tyr Ala Asn Phe Cys Ser Gly Pro Cys Pro Tyr Leu Arg Ser Ala
                340             345                 350

Asp Thr Thr His Ser Thr Val Leu Gly Leu Tyr Asn Thr Leu Asn Pro
            355                 360                 365

Glu Ala Ser Ala Ser Pro Cys Cys Val Pro Gln Asp Leu Glu Pro Leu
370                 375                 380

Thr Ile Leu Tyr Tyr Val Gly Arg Thr Pro Lys Val Glu Gln Leu Ser
385                 390                 395                 400

Asn Met Val Val Lys Ser Cys Lys Cys Ser
                405                 410

<210> SEQ ID NO 198
<211> LENGTH: 193
<212> TYPE: PRT
<213> ORGANISM: Artificial Sequence
<220> FEATURE:
<223> OTHER INFORMATION: Synthetic

<400> SEQUENCE: 198

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 199
<211> LENGTH: 192
<212> TYPE: PRT
<213> ORGANISM: Artificial Sequence
<220> FEATURE:
<223> OTHER INFORMATION: Synthetic

<400> SEQUENCE: 199

Met Gly Val Pro Glu Arg Pro Thr Leu Leu Leu Leu Leu Ser Leu Leu
1               5                   10                  15

Leu Ile Pro Leu Gly Leu Pro Val Leu Cys Ala Pro Pro Arg Leu Ile
                20                  25                  30
```

```
Cys Asp Ser Arg Val Leu Glu Arg Tyr Ile Leu Glu Ala Lys Glu Ala
         35                  40                  45

Glu Asn Val Thr Met Gly Cys Ala Glu Gly Pro Arg Leu Ser Glu Asn
 50                  55                  60

Ile Thr Val Pro Asp Thr Lys Val Asn Phe Tyr Ala Trp Lys Arg Met
 65                  70                  75                  80

Glu Val Glu Glu Gln Ala Ile Glu Val Trp Gln Gly Leu Ser Leu Leu
                 85                  90                  95

Ser Glu Ala Ile Leu Gln Ala Gln Ala Leu Leu Ala Asn Ser Ser Gln
            100                 105                 110

Pro Pro Glu Thr Leu Gln Leu His Ile Asp Lys Ala Ile Ser Gly Leu
            115                 120                 125

Arg Ser Leu Thr Ser Leu Leu Arg Val Leu Gly Ala Gln Lys Glu Leu
130                 135                 140

Met Ser Pro Pro Asp Thr Thr Pro Pro Ala Pro Leu Arg Thr Leu Thr
145                 150                 155                 160

Val Asp Thr Phe Cys Lys Leu Phe Arg Val Tyr Ala Asn Phe Leu Arg
                    165                 170                 175

Gly Lys Leu Lys Leu Tyr Thr Gly Glu Val Cys Arg Arg Gly Asp Arg
            180                 185                 190

<210> SEQ ID NO 200
<211> LENGTH: 353
<212> TYPE: PRT
<213> ORGANISM: Artificial Sequence
<220> FEATURE:
<223> OTHER INFORMATION: Synthetic

<400> SEQUENCE: 200

Met Glu Leu Thr Glu Leu Leu Leu Val Val Met Leu Leu Leu Thr Ala
 1               5                  10                  15

Arg Leu Thr Leu Ser Ser Pro Ala Pro Pro Ala Cys Asp Leu Arg Val
             20                  25                  30

Leu Ser Lys Leu Leu Arg Asp Ser His Val Leu His Ser Arg Leu Ser
         35                  40                  45

Gln Cys Pro Glu Val His Pro Leu Pro Thr Pro Val Leu Leu Pro Ala
 50                  55                  60

Val Asp Phe Ser Leu Gly Glu Trp Lys Thr Gln Met Glu Glu Thr Lys
 65                  70                  75                  80

Ala Gln Asp Ile Leu Gly Ala Val Thr Leu Leu Leu Glu Gly Val Met
                 85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
            115                 120                 125

Leu Gly Thr Gln Leu Pro Pro Gln Gly Arg Thr Thr Ala His Lys Asp
130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                    165                 170                 175

Pro Pro Thr Thr Ala Val Pro Ser Arg Thr Ser Leu Val Leu Thr Leu
            180                 185                 190

Asn Glu Leu Pro Asn Arg Thr Ser Gly Leu Leu Glu Thr Asn Phe Thr
            195                 200                 205
```

```
Ala Ser Ala Arg Thr Thr Gly Ser Gly Leu Leu Lys Trp Gln Gln Gly
    210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
            245                 250                 255

Thr Arg Gly Leu Phe Pro Gly Pro Ser Arg Arg Thr Leu Gly Ala Pro
                260                 265                 270

Asp Ile Ser Ser Gly Thr Ser Asp Thr Gly Ser Leu Pro Pro Asn Leu
            275                 280                 285

Gln Pro Gly Tyr Ser Pro Ser Pro Thr His Pro Pro Thr Gly Gln Tyr
    290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
            325                 330                 335

Pro Leu Leu Asn Thr Ser Tyr Thr His Ser Gln Asn Leu Ser Gln Glu
                340                 345                 350

Gly
```

<210> SEQ ID NO 201
<211> LENGTH: 356
<212> TYPE: PRT
<213> ORGANISM: Artificial Sequence
<220> FEATURE:
<223> OTHER INFORMATION: Synthetic

<400> SEQUENCE: 201

```
Met Glu Leu Thr Asp Leu Leu Ala Ala Met Leu Leu Ala Val Ala
1               5                   10                  15

Arg Leu Thr Leu Ser Ser Pro Val Ala Pro Ala Cys Asp Pro Arg Leu
                20                  25                  30

Leu Asn Lys Leu Leu Arg Asp Ser His Leu Leu His Ser Arg Leu Ser
            35                  40                  45

Gln Cys Pro Asp Val Asp Pro Leu Ser Ile Pro Val Leu Leu Pro Ala
    50                  55                  60

Val Asp Phe Ser Leu Gly Glu Trp Lys Thr Gln Thr Glu Gln Ser Lys
65                  70                  75                  80

Ala Gln Asp Ile Leu Gly Ala Val Ser Leu Leu Leu Glu Gly Val Met
                85                  90                  95

Ala Ala Arg Gly Gln Leu Glu Pro Ser Cys Leu Ser Ser Leu Leu Gly
                100                 105                 110

Gln Leu Ser Gly Gln Val Arg Leu Leu Leu Gly Ala Leu Gln Gly Leu
            115                 120                 125

Leu Gly Thr Gln Leu Pro Leu Gln Gly Arg Thr Thr Ala His Lys Asp
    130                 135                 140

Pro Asn Ala Leu Phe Leu Ser Leu Gln Gln Leu Leu Arg Gly Lys Val
145                 150                 155                 160

Arg Phe Leu Leu Leu Val Glu Gly Pro Thr Leu Cys Val Arg Arg Thr
                165                 170                 175

Leu Pro Thr Thr Ala Val Pro Ser Ser Thr Ser Gln Leu Leu Thr Leu
            180                 185                 190

Asn Lys Phe Pro Asn Arg Thr Ser Gly Leu Leu Glu Thr Asn Phe Ser
    195                 200                 205
```

Val Thr Ala Arg Thr Ala Gly Pro Gly Leu Leu Ser Arg Leu Gln Gly
210                 215                 220

Phe Arg Val Lys Ile Thr Pro Gly Gln Leu Asn Gln Thr Ser Arg Ser
225                 230                 235                 240

Pro Val Gln Ile Ser Gly Tyr Leu Asn Arg Thr His Gly Pro Val Asn
            245                 250                 255

Gly Thr His Gly Leu Phe Ala Gly Thr Ser Leu Gln Thr Leu Glu Ala
            260                 265                 270

Ser Asp Ile Ser Pro Gly Ala Phe Asn Lys Gly Ser Leu Ala Phe Asn
            275                 280                 285

Leu Gln Gly Gly Leu Pro Pro Ser Pro Ser Leu Ala Pro Asp Gly His
290                 295                 300

Thr Pro Phe Pro Pro Ser Pro Ala Leu Pro Thr Thr His Gly Ser Pro
305                 310                 315                 320

Pro Gln Leu His Pro Leu Phe Pro Asp Pro Ser Thr Thr Met Pro Asn
            325                 330                 335

Ser Thr Ala Pro His Pro Val Thr Met Tyr Pro His Pro Arg Asn Leu
            340                 345                 350

Ser Gln Glu Thr
            355

<210> SEQ ID NO 202
<211> LENGTH: 235
<212> TYPE: PRT
<213> ORGANISM: Artificial Sequence
<220> FEATURE:
<223> OTHER INFORMATION: Synthetic

<400> SEQUENCE: 202

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
            180                 185                 190

Pro Val Gly Leu Leu Leu Leu Ala Ala Ala Trp Cys Leu His Trp Gln
        195                 200                 205

```
Arg Thr Arg Arg Arg Thr Pro Arg Pro Gly Glu Gln Val Pro Pro Val
    210                 215                 220

Pro Ser Pro Gln Asp Leu Leu Leu Val Glu His
225                 230                 235

<210> SEQ ID NO 203
<211> LENGTH: 232
<212> TYPE: PRT
<213> ORGANISM: Artificial Sequence
<220> FEATURE:
<223> OTHER INFORMATION: Synthetic

<400> SEQUENCE: 203

Met Thr Val Leu Ala Pro Ala Trp Ser Pro Asn Ser Ser Leu Leu Leu
1               5                   10                  15

Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
        35                  40                  45

Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gly Leu Leu Leu
            180                 185                 190

Leu Leu Leu Leu Leu Leu Pro Leu Thr Leu Val Leu Leu Ala Ala Ala
        195                 200                 205

Trp Gly Leu Arg Trp Gln Arg Ala Arg Arg Arg Gly Glu Leu His Pro
    210                 215                 220

Gly Val Pro Leu Pro Ser His Pro
225                 230

<210> SEQ ID NO 204
<211> LENGTH: 273
<212> TYPE: PRT
<213> ORGANISM: Artificial Sequence
<220> FEATURE:
<223> OTHER INFORMATION: Synthetic

<400> SEQUENCE: 204

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45
```

Lys Asp Tyr Met Ile Thr Leu Lys Tyr Val Pro Gly Met Asp Val Leu
 50                  55                  60

Pro Ser His Cys Trp Ile Ser Glu Met Val Val Gln Leu Ser Asp Ser
 65                  70                  75                  80

Leu Thr Asp Leu Leu Asp Lys Phe Ser Asn Ile Ser Glu Gly Leu Ser
                 85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
            115                 120                 125

Ser Pro Glu Pro Arg Leu Phe Thr Pro Glu Gly Phe Phe Arg Ile Phe
        130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
                180                 185                 190

Leu Arg Asn Asp Ser Ser Ser Asn Arg Lys Ala Lys Asn Pro Pro
        195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
            260                 265                 270

Val

<210> SEQ ID NO 205
<211> LENGTH: 273
<212> TYPE: PRT
<213> ORGANISM: Artificial Sequence
<220> FEATURE:
<223> OTHER INFORMATION: Synthetic

<400> SEQUENCE: 205

Met Lys Lys Thr Gln Thr Trp Ile Ile Thr Cys Ile Tyr Leu Gln Leu
 1                   5                  10                  15

Leu Leu Phe Asn Pro Leu Val Lys Thr Lys Glu Ile Cys Gly Asn Pro
                 20                  25                  30

Val Thr Asp Asn Val Lys Asp Ile Thr Lys Leu Val Ala Asn Leu Pro
             35                  40                  45

Asn Asp Tyr Met Ile Thr Leu Asn Tyr Val Ala Gly Met Asp Val Leu
 50                  55                  60

Pro Ser His Cys Trp Leu Arg Asp Met Val Ile Gln Leu Ser Leu Ser
 65                  70                  75                  80

Leu Thr Thr Leu Leu Asp Lys Phe Ser Asn Ile Ser Glu Gly Leu Ser
                 85                  90                  95

Asn Tyr Ser Ile Ile Asp Lys Leu Gly Lys Ile Val Asp Asp Leu Val
            100                 105                 110

Leu Cys Met Glu Glu Asn Ala Pro Lys Asn Ile Lys Glu Ser Pro Lys
            115                 120                 125

-continued

Arg Pro Glu Thr Arg Ser Phe Thr Pro Glu Glu Phe Ser Ile Phe
    130                 135                 140

Asn Arg Ser Ile Asp Ala Phe Lys Asp Phe Met Val Ala Ser Asp Thr
145                 150                 155                 160

Ser Asp Cys Val Leu Ser Ser Thr Leu Gly Pro Glu Lys Asp Ser Arg
                165                 170                 175

Val Ser Val Thr Lys Pro Phe Met Leu Pro Pro Val Ala Ala Ser Ser
                180                 185                 190

Leu Arg Asn Asp Ser Ser Ser Asn Arg Lys Ala Ala Lys Ala Pro
                195                 200                 205

Glu Asp Ser Gly Leu Gln Trp Thr Ala Met Ala Leu Pro Ala Leu Ile
    210                 215                 220

Ser Leu Val Ile Gly Phe Ala Phe Gly Ala Leu Tyr Trp Lys Lys Lys
225                 230                 235                 240

Gln Ser Ser Leu Thr Arg Ala Val Glu Asn Ile Gln Ile Asn Glu Glu
                245                 250                 255

Asp Asn Glu Ile Ser Met Leu Gln Gln Lys Glu Arg Glu Phe Gln Glu
                260                 265                 270

Val

<210> SEQ ID NO 206
<211> LENGTH: 554
<212> TYPE: PRT
<213> ORGANISM: Artificial Sequence
<220> FEATURE:
<223> OTHER INFORMATION: Synthetic

<400> SEQUENCE: 206

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
                20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
        50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
                100                 105                 110

Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
        130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
                180                 185                 190

Tyr Pro Lys Ala Ile Pro Ser Ser Asp Pro Ala Ser Val Ser Pro His
            195                 200                 205

Gln Pro Leu Ala Pro Ser Met Ala Pro Val Ala Gly Leu Thr Trp Glu

```
                210                 215                 220
Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
                260                 265                 270

Thr Ile Gly Gly Ser Pro Gln Pro Arg Pro Ser Val Gly Ala Phe Asn
                275                 280                 285

Pro Gly Met Glu Asp Ile Leu Asp Ser Ala Met Gly Thr Asn Trp Val
                290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
                340                 345                 350

Ser Ala Lys Gly Gln Gln Pro Ala Asp Val Thr Gly Thr Ala Leu Pro
                355                 360                 365

Arg Val Gly Pro Val Arg Pro Thr Gly Gln Asp Trp Asn His Thr Pro
                370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
                420                 425                 430

Ser Val Leu Pro Leu Gly Glu Leu Glu Gly Arg Arg Ser Thr Arg Asp
                435                 440                 445

Arg Arg Ser Pro Ala Glu Pro Glu Gly Gly Pro Ala Ser Glu Gly Ala
                450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
                485                 490                 495

Val Phe His Leu Leu Val Pro Ser Val Ile Leu Val Leu Leu Ala Val
                500                 505                 510

Gly Gly Leu Leu Phe Tyr Arg Trp Arg Arg Ser His Gln Glu Pro
                515                 520                 525

Gln Arg Ala Asp Ser Pro Leu Glu Gln Pro Glu Gly Ser Pro Leu Thr
                530                 535                 540

Gln Asp Asp Arg Gln Val Glu Leu Pro Val
545                 550

<210> SEQ ID NO 207
<211> LENGTH: 552
<212> TYPE: PRT
<213> ORGANISM: Artificial Sequence
<220> FEATURE:
<223> OTHER INFORMATION: Synthetic

<400> SEQUENCE: 207

Met Thr Ala Arg Gly Ala Ala Gly Arg Cys Pro Ser Ser Thr Trp Leu
1               5                   10                  15

Gly Ser Arg Leu Leu Leu Val Cys Leu Leu Met Ser Arg Ser Ile Ala
```

```
                20                  25                  30
        Lys Glu Val Ser Glu His Cys Ser His Met Ile Gly Asn Gly His Leu
                    35                  40                  45

Lys Val Leu Gln Gln Leu Ile Asp Ser Gln Met Glu Thr Ser Cys Gln
                    50                  55                  60

Ile Ala Phe Glu Phe Val Asp Gln Glu Gln Leu Asp Asp Pro Val Cys
         65                  70                  75                  80

Tyr Leu Lys Lys Ala Phe Phe Leu Val Gln Asp Ile Ile Asp Glu Thr
                        85                  90                  95

Met Arg Phe Lys Asp Asn Thr Pro Asn Ala Asn Ala Thr Glu Arg Leu
                        100                 105                 110

Gln Glu Leu Ser Asn Asn Leu Asn Ser Cys Phe Thr Lys Asp Tyr Glu
                    115                 120                 125

Glu Gln Asn Lys Ala Cys Val Arg Thr Phe His Glu Thr Pro Leu Gln
                    130                 135                 140

Leu Leu Glu Lys Ile Lys Asn Phe Phe Asn Glu Thr Lys Asn Leu Leu
        145                 150                 155                 160

Glu Lys Asp Trp Asn Ile Phe Thr Lys Asn Cys Asn Asn Ser Phe Ala
                        165                 170                 175

Lys Cys Ser Ser Arg Asp Val Val Thr Lys Pro Asp Cys Asn Cys Leu
                    180                 185                 190

Tyr Pro Lys Ala Thr Pro Ser Ser Asp Pro Ala Ser Ala Ser Pro His
                    195                 200                 205

Gln Pro Pro Ala Pro Ser Met Ala Pro Leu Ala Gly Leu Ala Trp Asp
                    210                 215                 220

Asp Ser Gln Arg Thr Glu Gly Ser Ser Leu Leu Pro Ser Glu Leu Pro
        225                 230                 235                 240

Leu Arg Ile Glu Asp Pro Gly Ser Ala Lys Gln Arg Pro Pro Arg Ser
                        245                 250                 255

Thr Cys Gln Thr Leu Glu Ser Thr Glu Gln Pro Asn His Gly Asp Arg
                    260                 265                 270

Leu Thr Glu Asp Ser Gln Pro His Pro Ser Ala Gly Gly Pro Val Pro
                    275                 280                 285

Gly Val Glu Asp Ile Leu Glu Ser Ser Leu Gly Thr Asn Trp Val Leu
                    290                 295                 300

Glu Glu Ala Ser Gly Glu Ala Ser Glu Gly Phe Leu Thr Gln Glu Ala
        305                 310                 315                 320

Lys Phe Ser Pro Ser Thr Pro Val Gly Gly Ser Ile Gln Ala Glu Thr
                        325                 330                 335

Asp Arg Pro Arg Ala Leu Ser Ala Ser Pro Phe Pro Lys Ser Thr Glu
                    340                 345                 350

Asp Gln Lys Pro Val Asp Ile Thr Asp Arg Pro Leu Thr Glu Val Asn
                    355                 360                 365

Pro Met Arg Pro Ile Gly Gln Thr Gln Asn Asn Thr Pro Glu Lys Thr
                    370                 375                 380

Asp Gly Thr Ser Thr Leu Arg Glu Asp His Gln Glu Pro Gly Ser Pro
        385                 390                 395                 400

His Ile Ala Thr Pro Asn Pro Gln Arg Val Ser Asn Ser Ala Thr Pro
                        405                 410                 415

Val Ala Gln Leu Leu Leu Pro Lys Ser His Ser Trp Gly Ile Val Leu
                    420                 425                 430

Pro Leu Gly Glu Leu Glu Gly Lys Arg Ser Thr Arg Asp Arg Arg Ser
                    435                 440                 445
```

```
Pro Ala Glu Leu Glu Gly Gly Ser Ala Ser Glu Gly Ala Ala Arg Pro
    450                 455                 460

Val Ala Arg Phe Asn Ser Ile Pro Leu Thr Asp Thr Gly His Val Glu
465                 470                 475                 480

Gln His Glu Gly Ser Ser Asp Pro Gln Ile Pro Glu Ser Val Phe His
                485                 490                 495

Leu Leu Val Pro Gly Ile Ile Leu Val Leu Thr Val Gly Gly Leu
            500                 505                 510

Leu Phe Tyr Lys Trp Lys Trp Arg Ser His Arg Asp Pro Gln Thr Leu
        515                 520                 525

Asp Ser Ser Val Gly Arg Pro Glu Asp Ser Ser Leu Thr Gln Asp Glu
    530                 535                 540

Asp Arg Gln Val Glu Leu Pro Val
545                 550

<210> SEQ ID NO 208
<211> LENGTH: 711
<212> TYPE: PRT
<213> ORGANISM: Artificial Sequence
<220> FEATURE:
<223> OTHER INFORMATION: Synthetic

<400> SEQUENCE: 208

Met Gly Trp Leu Pro Leu Leu Leu Leu Thr Gln Cys Leu Gly Val
1               5                   10                  15

Pro Gly Gln Arg Ser Pro Leu Asn Asp Phe Gln Val Leu Arg Gly Thr
            20                  25                  30

Glu Leu Gln His Leu Leu His Ala Val Val Pro Gly Pro Trp Gln Glu
        35                  40                  45

Asp Val Ala Asp Ala Glu Glu Cys Ala Gly Arg Cys Gly Pro Leu Met
    50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Thr Val Gly Gly
        115                 120                 125

Leu Pro Cys Gln Ala Trp Ser His Lys Phe Pro Asn Asp His Lys Tyr
    130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
            180                 185                 190

Trp Cys Asn Gly Glu Glu Tyr Arg Gly Ala Val Asp Arg Thr Glu Ser
        195                 200                 205

Gly Arg Glu Cys Gln Arg Trp Asp Leu Gln His Pro His Gln His Pro
    210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255
```

-continued

```
Gln Ile Glu Arg Glu Phe Cys Asp Leu Pro Arg Cys Gly Ser Glu Ala
            260                 265                 270

Gln Pro Arg Gln Glu Ala Thr Thr Val Ser Cys Phe Arg Gly Lys Gly
        275                 280                 285

Glu Gly Tyr Arg Gly Thr Ala Asn Thr Thr Ala Gly Val Pro Cys
    290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
            340                 345                 350

Ala Phe Cys Tyr Gln Ile Arg Arg Cys Thr Asp Asp Val Arg Pro Gln
        355                 360                 365

Asp Cys Tyr His Gly Ala Gly Glu Gln Tyr Arg Gly Thr Val Ser Lys
    370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
            420                 425                 430

Thr Met Asp Pro Arg Thr Pro Phe Asp Tyr Cys Ala Leu Arg Arg Cys
        435                 440                 445

Ala Asp Asp Gln Pro Pro Ser Ile Leu Asp Pro Asp Gln Val Gln
    450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
                485                 490                 495

Ser Leu Arg Asn Arg Gln Gly Gln His Phe Cys Gly Gly Ser Leu Val
            500                 505                 510

Lys Glu Gln Trp Ile Leu Thr Ala Arg Gln Cys Phe Ser Ser Cys His
        515                 520                 525

Met Pro Leu Thr Gly Tyr Glu Val Trp Leu Gly Thr Leu Phe Gln Asn
    530                 535                 540

Pro Gln His Gly Glu Pro Ser Leu Gln Arg Val Pro Val Ala Lys Met
545                 550                 555                 560

Val Cys Gly Pro Ser Gly Ser Gln Leu Val Leu Leu Lys Leu Glu Arg
                565                 570                 575

Ser Val Thr Leu Asn Gln Arg Val Ala Leu Ile Cys Leu Pro Pro Glu
            580                 585                 590

Trp Tyr Val Val Pro Pro Gly Thr Lys Cys Glu Ile Ala Gly Trp Gly
        595                 600                 605

Glu Thr Lys Gly Thr Gly Asn Asp Thr Val Leu Asn Val Ala Leu Leu
    610                 615                 620

Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala
                645                 650                 655

Cys Glu Gly Asp Tyr Gly Gly Pro Leu Ala Cys Phe Thr His Asn Cys
            660                 665                 670
```

```
Trp Val Leu Glu Gly Ile Ile Ile Pro Asn Arg Val Cys Ala Arg Ser
            675                 680                 685

Arg Trp Pro Ala Val Phe Thr Arg Val Ser Val Phe Val Asp Trp Ile
            690                 695                 700

His Lys Val Met Arg Leu Gly
705                 710

<210> SEQ ID NO 209
<211> LENGTH: 1378
<212> TYPE: PRT
<213> ORGANISM: Artificial Sequence
<220> FEATURE:
<223> OTHER INFORMATION: Synthetic

<400> SEQUENCE: 209

Met Gly Leu Pro Leu Pro Leu Leu Gln Ser Ser Leu Leu Met Leu
1               5                   10                  15

Leu Leu Arg Leu Ser Ala Ala Ser Thr Asn Leu Asn Trp Gln Cys Pro
            20                  25                  30

Arg Ile Pro Tyr Ala Ala Ser Arg Asp Phe Ser Val Lys Tyr Val Val
            35                  40                  45

Pro Ser Phe Ser Ala Gly Gly Arg Val Gln Ala Thr Ala Ala Tyr Glu
50                  55                  60

Asp Ser Thr Asn Ser Ala Val Phe Val Ala Thr Arg Asn His Leu His
65                  70                  75                  80

Val Leu Gly Pro Asp Leu Gln Phe Ile Glu Asn Leu Thr Thr Gly Pro
                85                  90                  95

Ile Gly Asn Pro Gly Cys Gln Thr Cys Ala Ser Cys Gly Pro Gly Pro
            100                 105                 110

His Gly Pro Pro Lys Asp Thr Asp Thr Leu Val Leu Val Met Glu Pro
            115                 120                 125

Gly Leu Pro Ala Leu Val Ser Cys Gly Ser Thr Leu Gln Gly Arg Cys
130                 135                 140

Phe Leu His Glu Leu Glu Pro Arg Gly Lys Ala Leu His Leu Ala Ala
145                 150                 155                 160

Pro Ala Cys Leu Phe Ser Ala Asn Asn Asn Lys Pro Glu Ala Cys Thr
                165                 170                 175

Asp Cys Val Ala Ser Pro Leu Gly Thr Arg Val Thr Val Val Glu Gln
            180                 185                 190

Gly His Ala Ser Tyr Phe Tyr Val Ala Ser Ser Leu Asp Pro Glu Leu
            195                 200                 205

Ala Ala Ser Phe Ser Pro Arg Ser Val Ser Ile Arg Arg Leu Lys Ser
210                 215                 220

Asp Thr Ser Gly Phe Gln Pro Gly Phe Pro Ser Leu Ser Val Leu Pro
225                 230                 235                 240

Lys Tyr Leu Ala Ser Tyr Leu Ile Lys Tyr Val Tyr Ser Phe His Ser
                245                 250                 255

Gly Asp Phe Val Tyr Phe Leu Thr Val Gln Pro Ile Ser Val Thr Ser
            260                 265                 270

Pro Pro Ser Ala Leu His Thr Arg Leu Val Arg Leu Asn Ala Val Glu
            275                 280                 285

Pro Glu Ile Gly Asp Tyr Arg Glu Leu Val Leu Asp Cys His Phe Ala
            290                 295                 300

Pro Lys Arg Arg Arg Arg Gly Ala Pro Glu Gly Thr Gln Pro Tyr Pro
305                 310                 315                 320
```

-continued

Val Leu Gln Ala Ala His Ser Ala Pro Val Asp Ala Lys Leu Ala Val
            325                 330                 335

Glu Leu Ser Ile Ser Glu Gly Gln Glu Val Leu Phe Gly Val Phe Val
            340                 345                 350

Thr Val Lys Asp Gly Gly Ser Gly Met Gly Pro Asn Ser Val Val Cys
            355                 360                 365

Ala Phe Pro Ile Tyr His Leu Asn Ile Leu Glu Glu Gly Val Glu
370                 375                 380

Tyr Cys Cys His Ser Ser Asn Ser Ser Ser Leu Leu Ser Arg Gly Leu
385                 390                 395                 400

Asp Phe Phe Gln Thr Pro Ser Phe Cys Pro Asn Pro Pro Gly Gly Glu
            405                 410                 415

Ala Ser Gly Pro Ser Ser Arg Cys His Tyr Phe Pro Leu Met Val His
            420                 425                 430

Ala Ser Phe Thr Arg Val Asp Leu Phe Asn Gly Leu Leu Gly Ser Val
            435                 440                 445

Lys Val Thr Ala Leu His Val Thr Arg Leu Gly Asn Val Thr Val Ala
            450                 455                 460

His Met Gly Thr Val Asp Gly Arg Val Leu Gln Val Glu Ile Ala Arg
465                 470                 475                 480

Ser Leu Asn Tyr Leu Leu Tyr Val Ser Asn Phe Ser Leu Gly Ser Ser
            485                 490                 495

Gly Gln Pro Val His Arg Asp Val Ser Arg Leu Gly Asn Asp Leu Leu
            500                 505                 510

Phe Ala Ser Gly Asp Gln Val Phe Lys Val Pro Ile Gln Gly Pro Gly
            515                 520                 525

Cys Arg His Phe Leu Thr Cys Trp Arg Cys Leu Arg Ala Gln Arg Phe
            530                 535                 540

Met Gly Cys Gly Trp Cys Gly Asp Arg Cys Asp Arg Gln Lys Glu Cys
545                 550                 555                 560

Pro Gly Ser Trp Gln Gln Asp His Cys Pro Pro Glu Ile Ser Glu Phe
            565                 570                 575

Tyr Pro His Ser Gly Pro Leu Arg Gly Thr Thr Arg Leu Thr Leu Cys
            580                 585                 590

Gly Ser Asn Phe Tyr Leu Arg Pro Asp Asp Val Val Pro Glu Gly Thr
            595                 600                 605

His Gln Ile Thr Val Gly Gln Ser Pro Cys Arg Leu Leu Pro Lys Asp
            610                 615                 620

Ser Ser Ser Pro Arg Pro Gly Ser Leu Lys Glu Phe Ile Gln Glu Leu
625                 630                 635                 640

Glu Cys Glu Leu Glu Pro Leu Val Thr Gln Ala Val Gly Thr Thr Asn
            645                 650                 655

Ile Ser Leu Val Ile Thr Asn Met Pro Ala Gly Lys His Phe Arg Val
            660                 665                 670

Glu Gly Ile Ser Val Gln Glu Gly Phe Ser Phe Val Glu Pro Val Leu
            675                 680                 685

Thr Ser Ile Lys Pro Asp Phe Gly Pro Arg Ala Gly Gly Thr Tyr Leu
            690                 695                 700

Thr Leu Glu Gly Gln Ser Leu Ser Val Gly Thr Ser Arg Ala Val Leu
705                 710                 715                 720

Val Asn Gly Thr Gln Cys Arg Leu Glu Gln Val Asn Glu Glu Gln Ile
            725                 730                 735

Leu Cys Val Thr Pro Pro Gly Ala Gly Thr Ala Arg Val Pro Leu His

-continued

```
                740                 745                 750
Leu Gln Ile Gly Gly Ala Glu Val Pro Gly Ser Trp Thr Phe His Tyr
            755                 760                 765
Lys Glu Asp Pro Ile Val Leu Asp Ile Ser Pro Lys Cys Gly Tyr Ser
            770                 775                 780
Gly Ser His Ile Met Ile His Gly Gln His Leu Thr Ser Ala Trp His
785                 790                 795                 800
Phe Thr Leu Ser Phe His Asp Gly Gln Ser Thr Val Glu Ser Arg Cys
                805                 810                 815
Ala Gly Gln Phe Val Glu Gln Gln Arg Arg Cys Arg Leu Pro Glu
                820                 825                 830
Tyr Val Val Arg Asn Pro Gln Gly Trp Ala Thr Gly Asn Leu Ser Val
            835                 840                 845
Trp Gly Asp Gly Ala Ala Gly Phe Thr Leu Pro Gly Phe Arg Phe Leu
            850                 855                 860
Pro Pro Pro Ser Pro Leu Arg Ala Gly Leu Val Glu Leu Lys Pro Glu
865                 870                 875                 880
Glu His Ser Val Lys Val Glu Tyr Val Gly Leu Gly Ala Val Ala Asp
                885                 890                 895
Cys Val Thr Val Asn Met Thr Val Gly Gly Glu Val Cys Gln His Glu
                900                 905                 910
Leu Arg Gly Asp Val Val Ile Cys Pro Leu Pro Pro Ser Leu Gln Leu
            915                 920                 925
Gly Lys Asp Gly Val Pro Leu Gln Val Cys Val Asp Gly Gly Cys His
        930                 935                 940
Ile Leu Ser Gln Val Val Arg Ser Ser Pro Gly Arg Ala Ser Gln Arg
945                 950                 955                 960
Ile Leu Leu Ile Ala Leu Leu Val Leu Ile Leu Val Ala Val Leu
                965                 970                 975
Ala Val Ala Leu Ile Phe Asn Ser Arg Arg Arg Lys Lys Gln Leu Gly
            980                 985                 990
Ala His Ser Leu Ser Pro Thr Thr Leu Ser Asp Ile Asn Asp Thr Ala
        995                 1000                1005
Ser Gly Ala Pro Asn His Glu Glu Ser Glu Ser Arg Asp Gly
    1010                1015                1020
Thr Ser Val Pro Leu Leu Arg Thr Glu Ser Ile Arg Leu Gln Asp
    1025                1030                1035
Leu Asp Arg Met Leu Leu Ala Glu Val Lys Asp Val Leu Ile Pro
    1040                1045                1050
His Glu Gln Val Val Ile His Thr Asp Gln Val Ile Gly Lys Gly
    1055                1060                1065
His Phe Gly Val Val Tyr His Gly Glu Tyr Thr Asp Gly Ala Gln
    1070                1075                1080
Asn Gln Thr His Cys Ala Ile Lys Ser Leu Ser Arg Ile Thr Glu
    1085                1090                1095
Val Gln Glu Val Glu Ala Phe Leu Arg Glu Gly Leu Leu Met Arg
    1100                1105                1110
Gly Leu His His Pro Asn Ile Leu Ala Leu Ile Gly Ile Met Leu
    1115                1120                1125
Pro Pro Glu Gly Leu Pro Val Leu Leu Pro Tyr Met Arg His
    1130                1135                1140
Gly Asp Leu Leu His Phe Ile Arg Ser Pro Gln Arg Asn Pro Thr
    1145                1150                1155
```

```
Val Lys Asp Leu Val Ser Phe Gly Leu Gln Val Ala Cys Gly Met
    1160                1165                1170

Glu Tyr Leu Ala Glu Gln Lys Phe Val His Arg Asp Leu Ala Ala
    1175                1180                1185

Arg Asn Cys Met Leu Asp Glu Ser Phe Thr Val Lys Val Ala Asp
    1190                1195                1200

Phe Gly Leu Ala Arg Gly Val Leu Asp Lys Glu Tyr Tyr Ser Val
    1205                1210                1215

Arg Gln His Arg His Ala Arg Leu Pro Val Lys Trp Met Ala Leu
    1220                1225                1230

Glu Ser Leu Gln Thr Tyr Arg Phe Thr Thr Lys Ser Asp Val Trp
    1235                1240                1245

Ser Phe Gly Val Leu Leu Trp Glu Leu Leu Thr Arg Gly Ala Pro
    1250                1255                1260

Pro Tyr Pro His Ile Asp Pro Phe Asp Leu Ser His Phe Leu Ala
    1265                1270                1275

Gln Gly Arg Arg Leu Pro Gln Pro Glu Tyr Cys Pro Asp Ser Leu
    1280                1285                1290

Tyr His Val Met Leu Arg Cys Trp Glu Ala Asp Pro Ala Ala Arg
    1295                1300                1305

Pro Thr Phe Arg Ala Leu Val Leu Glu Val Lys Gln Val Val Ala
    1310                1315                1320

Ser Leu Leu Gly Asp His Tyr Val Gln Leu Thr Ala Ala Tyr Val
    1325                1330                1335

Asn Val Gly Pro Arg Ala Val Asp Asp Gly Ser Val Pro Pro Glu
    1340                1345                1350

Gln Val Gln Pro Ser Pro Gln His Cys Arg Ser Thr Ser Lys Pro
    1355                1360                1365

Arg Pro Leu Ser Glu Pro Pro Leu Pro Thr
    1370                1375

<210> SEQ ID NO 210
<211> LENGTH: 11
<212> TYPE: PRT
<213> ORGANISM: Artificial Sequence
<220> FEATURE:
<223> OTHER INFORMATION: Synthetic

<400> SEQUENCE: 210

Gly Ser Ser Gly Gly Ser Gly Gly Ser Gly Gly
1               5                   10

<210> SEQ ID NO 211
<211> LENGTH: 8
<212> TYPE: PRT
<213> ORGANISM: Artificial Sequence
<220> FEATURE:
<223> OTHER INFORMATION: Synthetic

<400> SEQUENCE: 211

Gly Gly Gly Ser Gly Gly Gly Ser
1               5

<210> SEQ ID NO 212
<211> LENGTH: 12
<212> TYPE: PRT
<213> ORGANISM: Artificial Sequence
<220> FEATURE:
<223> OTHER INFORMATION: Synthetic
```

-continued

<400> SEQUENCE: 212

Gly Gly Gly Ser Gly Gly Gly Ser Gly Gly Gly Ser
1               5                   10

<210> SEQ ID NO 213
<211> LENGTH: 15
<212> TYPE: PRT
<213> ORGANISM: Artificial Sequence
<220> FEATURE:
<223> OTHER INFORMATION: Synthetic

<400> SEQUENCE: 213

Gly Gly Gly Gly Ser Gly Gly Gly Gly Ser Gly Gly Gly Gly Ser
1               5                   10                  15

<210> SEQ ID NO 214
<211> LENGTH: 25
<212> TYPE: PRT
<213> ORGANISM: Artificial Sequence
<220> FEATURE:
<223> OTHER INFORMATION: Synthetic

<400> SEQUENCE: 214

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 215
<211> LENGTH: 10
<212> TYPE: PRT
<213> ORGANISM: Artificial Sequence
<220> FEATURE:
<223> OTHER INFORMATION: Synthetic

<400> SEQUENCE: 215

Gly Gly Gly Gly Ser Gly Gly Gly Gly Ser
1               5                   10

<210> SEQ ID NO 216
<211> LENGTH: 5
<212> TYPE: PRT
<213> ORGANISM: Artificial Sequence
<220> FEATURE:
<223> OTHER INFORMATION: Synthetic

<400> SEQUENCE: 216

Gly Gly Gly Gly Ser
1               5

<210> SEQ ID NO 217
<211> LENGTH: 7
<212> TYPE: PRT
<213> ORGANISM: Artificial Sequence
<220> FEATURE:
<223> OTHER INFORMATION: Synthetic

<400> SEQUENCE: 217

Gly Gly Gly Gly Ser Gly Ser
1               5

<210> SEQ ID NO 218
<211> LENGTH: 17
<212> TYPE: PRT
<213> ORGANISM: Artificial Sequence
<220> FEATURE:
<223> OTHER INFORMATION: Synthetic

<400> SEQUENCE: 218

Gly Gly Gly Gly Ser Gly Gly Gly Ser Gly Gly Gly Ser Gly
1               5                   10                  15

Ser

<210> SEQ ID NO 219
<211> LENGTH: 12
<212> TYPE: PRT
<213> ORGANISM: Artificial Sequence
<220> FEATURE:
<223> OTHER INFORMATION: Synthetic

<400> SEQUENCE: 219

Gly Gly Ser Leu Asp Pro Lys Gly Gly Gly Ser
1               5                   10

<210> SEQ ID NO 220
<211> LENGTH: 20
<212> TYPE: PRT
<213> ORGANISM: Artificial Sequence
<220> FEATURE:
<223> OTHER INFORMATION: Synthetic

<400> SEQUENCE: 220

Pro Lys Ser Cys Asp Lys Thr His Thr Cys Pro Pro Cys Pro Ala Pro
1               5                   10                  15

Glu Leu Leu Gly
            20

<210> SEQ ID NO 221
<211> LENGTH: 17
<212> TYPE: PRT
<213> ORGANISM: Artificial Sequence
<220> FEATURE:
<223> OTHER INFORMATION: Synthetic

<400> SEQUENCE: 221

Ser Lys Tyr Gly Pro Pro Cys Pro Pro Cys Pro Ala Pro Glu Phe Leu
1               5                   10                  15

Gly

<210> SEQ ID NO 222
<211> LENGTH: 12
<212> TYPE: PRT
<213> ORGANISM: Artificial Sequence
<220> FEATURE:
<223> OTHER INFORMATION: Synthetic

<400> SEQUENCE: 222

Gly Lys Ser Ser Gly Ser Gly Ser Glu Ser Lys Ser
1               5                   10

<210> SEQ ID NO 223
<211> LENGTH: 14
<212> TYPE: PRT
<213> ORGANISM: Artificial Sequence
<220> FEATURE:
<223> OTHER INFORMATION: Synthetic

<400> SEQUENCE: 223

Gly Ser Thr Ser Gly Ser Gly Lys Ser Ser Glu Gly Lys Gly
1               5                   10

```
<210> SEQ ID NO 224
<211> LENGTH: 18
<212> TYPE: PRT
<213> ORGANISM: Artificial Sequence
<220> FEATURE:
<223> OTHER INFORMATION: Synthetic

<400> SEQUENCE: 224

Gly Ser Thr Ser Gly Ser Gly Lys Ser Ser Glu Gly Ser Gly Ser Thr
1               5                   10                  15

Lys Gly

<210> SEQ ID NO 225
<211> LENGTH: 18
<212> TYPE: PRT
<213> ORGANISM: Artificial Sequence
<220> FEATURE:
<223> OTHER INFORMATION: Synthetic

<400> SEQUENCE: 225

Gly Ser Thr Ser Gly Ser Gly Lys Pro Gly Ser Gly Glu Gly Ser Thr
1               5                   10                  15

Lys Gly

<210> SEQ ID NO 226
<211> LENGTH: 16
<212> TYPE: PRT
<213> ORGANISM: Artificial Sequence
<220> FEATURE:
<223> OTHER INFORMATION: Synthetic

<400> SEQUENCE: 226

Gly Ser Thr Ser Gly Ser Gly Lys Pro Gly Ser Ser Glu Gly Ser Thr
1               5                   10                  15

<210> SEQ ID NO 227
<211> LENGTH: 5
<212> TYPE: PRT
<213> ORGANISM: Artificial Sequence
<220> FEATURE:
<223> OTHER INFORMATION: Synthetic

<400> SEQUENCE: 227

Gly Ser Gly Gly Ser
1               5

<210> SEQ ID NO 228
<211> LENGTH: 4
<212> TYPE: PRT
<213> ORGANISM: Artificial Sequence
<220> FEATURE:
<223> OTHER INFORMATION: Synthetic

<400> SEQUENCE: 228

Gly Gly Gly Ser
1

<210> SEQ ID NO 229
<211> LENGTH: 4
<212> TYPE: PRT
<213> ORGANISM: Artificial Sequence
<220> FEATURE:
<223> OTHER INFORMATION: Synthetic

<400> SEQUENCE: 229
```

Gly Gly Ser Gly
1

<210> SEQ ID NO 230
<211> LENGTH: 5
<212> TYPE: PRT
<213> ORGANISM: Artificial Sequence
<220> FEATURE:
<223> OTHER INFORMATION: Synthetic

<400> SEQUENCE: 230

Gly Gly Ser Gly Gly
1               5

<210> SEQ ID NO 231
<211> LENGTH: 5
<212> TYPE: PRT
<213> ORGANISM: Artificial Sequence
<220> FEATURE:
<223> OTHER INFORMATION: Synthetic

<400> SEQUENCE: 231

Gly Ser Gly Ser Gly
1               5

<210> SEQ ID NO 232
<211> LENGTH: 5
<212> TYPE: PRT
<213> ORGANISM: Artificial Sequence
<220> FEATURE:
<223> OTHER INFORMATION: Synthetic

<400> SEQUENCE: 232

Gly Ser Gly Gly Gly
1               5

<210> SEQ ID NO 233
<211> LENGTH: 5
<212> TYPE: PRT
<213> ORGANISM: Artificial Sequence
<220> FEATURE:
<223> OTHER INFORMATION: Synthetic

<400> SEQUENCE: 233

Gly Gly Gly Ser Gly
1               5

<210> SEQ ID NO 234
<211> LENGTH: 5
<212> TYPE: PRT
<213> ORGANISM: Artificial Sequence
<220> FEATURE:
<223> OTHER INFORMATION: Synthetic

<400> SEQUENCE: 234

Gly Ser Ser Ser Gly
1               5

<210> SEQ ID NO 235

<400> SEQUENCE: 235

000

<210> SEQ ID NO 236

```
<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245
<211> LENGTH: 8
<212> TYPE: PRT
<213> ORGANISM: Artificial Sequence
<220> FEATURE:
<223> OTHER INFORMATION: Synthetic

<400> SEQUENCE: 245

Gly Pro Gln Gly Thr Ala Gly Gln
1               5

<210> SEQ ID NO 246

<400> SEQUENCE: 246

000
```

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250
<211> LENGTH: 7
<212> TYPE: PRT
<213> ORGANISM: Artificial Sequence
<220> FEATURE:
<223> OTHER INFORMATION: Synthetic

<400> SEQUENCE: 250

Tyr Gly Ala Gly Leu Gly Trp
1               5

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

```
<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263
<211> LENGTH: 11
<212> TYPE: PRT
<213> ORGANISM: Artificial Sequence
<220> FEATURE:
<223> OTHER INFORMATION: Synthetic

<400> SEQUENCE: 263

Ala Pro Arg Ser Ala Leu Ala His Gly Leu Phe
1               5                   10

<210> SEQ ID NO 264
<211> LENGTH: 8
<212> TYPE: PRT
<213> ORGANISM: Artificial Sequence
<220> FEATURE:
<223> OTHER INFORMATION: Synthetic

<400> SEQUENCE: 264

Ala Gln Asn Leu Leu Gly Met Tyr
1               5

<210> SEQ ID NO 265
<211> LENGTH: 18
<212> TYPE: PRT
<213> ORGANISM: Artificial Sequence
<220> FEATURE:
<223> OTHER INFORMATION: Synthetic

<400> SEQUENCE: 265

Leu Ser Gly Arg Ser Asp Asn His Gly Gly Ala Val Gly Leu Leu Ala
1               5                   10                  15
```

Pro Pro

<210> SEQ ID NO 266
<211> LENGTH: 20
<212> TYPE: PRT
<213> ORGANISM: Artificial Sequence
<220> FEATURE:
<223> OTHER INFORMATION: Synthetic

<400> SEQUENCE: 266

Val His Met Pro Leu Gly Phe Leu Gly Pro Gly Gly Leu Ser Gly Arg
1               5                   10                  15

Ser Asp Asn His
            20

<210> SEQ ID NO 267
<211> LENGTH: 20
<212> TYPE: PRT
<213> ORGANISM: Artificial Sequence
<220> FEATURE:
<223> OTHER INFORMATION: Synthetic

<400> SEQUENCE: 267

Leu Ser Gly Arg Ser Asp Asn His Gly Gly Val His Met Pro Leu Gly
1               5                   10                  15

Phe Leu Gly Pro
            20

<210> SEQ ID NO 268
<211> LENGTH: 22
<212> TYPE: PRT
<213> ORGANISM: Artificial Sequence
<220> FEATURE:
<223> OTHER INFORMATION: Synthetic

<400> SEQUENCE: 268

Leu Ser Gly Arg Ser Asp Asn His Gly Gly Ser Gly Gly Ser Ile Ser
1               5                   10                  15

Ser Gly Leu Leu Ser Ser
            20

<210> SEQ ID NO 269
<211> LENGTH: 22
<212> TYPE: PRT
<213> ORGANISM: Artificial Sequence
<220> FEATURE:
<223> OTHER INFORMATION: Synthetic

<400> SEQUENCE: 269

Ile Ser Ser Gly Leu Leu Ser Ser Gly Gly Ser Gly Gly Ser Leu Ser
1               5                   10                  15

Gly Arg Ser Gly Asn His
            20

<210> SEQ ID NO 270
<211> LENGTH: 22
<212> TYPE: PRT
<213> ORGANISM: Artificial Sequence
<220> FEATURE:
<223> OTHER INFORMATION: Synthetic

<400> SEQUENCE: 270

Leu Ser Gly Arg Ser Asp Asn His Gly Gly Ser Gly Gly Ser Gln Asn
1               5                   10                  15

Gln Ala Leu Arg Met Ala
            20

<210> SEQ ID NO 271
<211> LENGTH: 22
<212> TYPE: PRT
<213> ORGANISM: Artificial Sequence
<220> FEATURE:
<223> OTHER INFORMATION: Synthetic

<400> SEQUENCE: 271

Gln Asn Gln Ala Leu Arg Met Ala Gly Gly Ser Gly Gly Ser Leu Ser
1               5                   10                  15

Gly Arg Ser Asp Asn His
            20

<210> SEQ ID NO 272
<211> LENGTH: 22
<212> TYPE: PRT
<213> ORGANISM: Artificial Sequence
<220> FEATURE:
<223> OTHER INFORMATION: Synthetic

<400> SEQUENCE: 272

Leu Ser Gly Arg Ser Gly Asn His Gly Gly Ser Gly Gly Ser Gln Asn
1               5                   10                  15

Gln Ala Leu Arg Met Ala
            20

<210> SEQ ID NO 273
<211> LENGTH: 22
<212> TYPE: PRT
<213> ORGANISM: Artificial Sequence
<220> FEATURE:
<223> OTHER INFORMATION: Synthetic

<400> SEQUENCE: 273

Gln Asn Gln Ala Leu Arg Met Ala Gly Gly Ser Gly Gly Ser Leu Ser
1               5                   10                  15

Gly Arg Ser Gly Asn His
            20

<210> SEQ ID NO 274
<211> LENGTH: 13
<212> TYPE: PRT
<213> ORGANISM: Artificial Sequence
<220> FEATURE:
<223> OTHER INFORMATION: Synthetic

<400> SEQUENCE: 274

Ile Ser Ser Gly Leu Leu Ser Gly Arg Ser Gly Asn His
1               5                   10

<210> SEQ ID NO 275
<211> LENGTH: 22
<212> TYPE: PRT
<213> ORGANISM: Artificial Sequence
<220> FEATURE:
<223> OTHER INFORMATION: Synthetic

<400> SEQUENCE: 275

Ala Val Gly Leu Leu Ala Pro Pro Gly Gly Thr Ser Thr Ser Gly Arg
1               5                   10                  15

Ser Ala Asn Pro Arg Gly
            20

<210> SEQ ID NO 276
<211> LENGTH: 22
<212> TYPE: PRT
<213> ORGANISM: Artificial Sequence
<220> FEATURE:
<223> OTHER INFORMATION: Synthetic

<400> SEQUENCE: 276

Thr Ser Thr Ser Gly Arg Ser Ala Asn Pro Arg Gly Gly Ala Val
1               5                   10                  15

Gly Leu Leu Ala Pro Pro
            20

<210> SEQ ID NO 277
<211> LENGTH: 24
<212> TYPE: PRT
<213> ORGANISM: Artificial Sequence
<220> FEATURE:
<223> OTHER INFORMATION: Synthetic

<400> SEQUENCE: 277

Val His Met Pro Leu Gly Phe Leu Gly Pro Gly Gly Thr Ser Thr Ser
1               5                   10                  15

Gly Arg Ser Ala Asn Pro Arg Gly
            20

<210> SEQ ID NO 278
<211> LENGTH: 24
<212> TYPE: PRT
<213> ORGANISM: Artificial Sequence
<220> FEATURE:
<223> OTHER INFORMATION: Synthetic

<400> SEQUENCE: 278

Thr Ser Thr Ser Gly Arg Ser Ala Asn Pro Arg Gly Gly Val His
1               5                   10                  15

Met Pro Leu Gly Phe Leu Gly Pro
            20

<210> SEQ ID NO 279
<211> LENGTH: 22
<212> TYPE: PRT
<213> ORGANISM: Artificial Sequence
<220> FEATURE:
<223> OTHER INFORMATION: Synthetic

<400> SEQUENCE: 279

Leu Ser Gly Arg Ser Gly Asn His Gly Gly Ser Gly Gly Ser Ile Ser
1               5                   10                  15

Ser Gly Leu Leu Ser Ser
            20

<210> SEQ ID NO 280
<211> LENGTH: 8
<212> TYPE: PRT
<213> ORGANISM: Artificial Sequence
<220> FEATURE:
<223> OTHER INFORMATION: Synthetic

<400> SEQUENCE: 280

Pro Arg Phe Lys Ile Ile Gly Gly
1               5

```
<210> SEQ ID NO 281
<211> LENGTH: 8
<212> TYPE: PRT
<213> ORGANISM: Artificial Sequence
<220> FEATURE:
<223> OTHER INFORMATION: Synthetic

<400> SEQUENCE: 281

Pro Arg Phe Arg Ile Ile Gly Gly
1               5

<210> SEQ ID NO 282
<211> LENGTH: 9
<212> TYPE: PRT
<213> ORGANISM: Artificial Sequence
<220> FEATURE:
<223> OTHER INFORMATION: Synthetic

<400> SEQUENCE: 282

Ser Ser Arg His Arg Arg Ala Leu Asp
1               5

<210> SEQ ID NO 283
<211> LENGTH: 14
<212> TYPE: PRT
<213> ORGANISM: Artificial Sequence
<220> FEATURE:
<223> OTHER INFORMATION: Synthetic

<400> SEQUENCE: 283

Arg Lys Ser Ser Ile Ile Ile Arg Met Arg Asp Val Val Leu
1               5                   10

<210> SEQ ID NO 284
<211> LENGTH: 15
<212> TYPE: PRT
<213> ORGANISM: Artificial Sequence
<220> FEATURE:
<223> OTHER INFORMATION: Synthetic

<400> SEQUENCE: 284

Ser Ser Ser Phe Asp Lys Gly Lys Tyr Lys Lys Gly Asp Asp Ala
1               5                   10                  15

<210> SEQ ID NO 285
<211> LENGTH: 15
<212> TYPE: PRT
<213> ORGANISM: Artificial Sequence
<220> FEATURE:
<223> OTHER INFORMATION: Synthetic

<400> SEQUENCE: 285

Ser Ser Ser Phe Asp Lys Gly Lys Tyr Lys Arg Gly Asp Asp Ala
1               5                   10                  15

<210> SEQ ID NO 286
<211> LENGTH: 4
<212> TYPE: PRT
<213> ORGANISM: Artificial Sequence
<220> FEATURE:
<223> OTHER INFORMATION: Synthetic

<400> SEQUENCE: 286

Ile Glu Gly Arg
1

<210> SEQ ID NO 287
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 287

Ile Asp Gly Arg
1

<210> SEQ ID NO 288
<211> LENGTH: 7
<212> TYPE: PRT
<213> ORGANISM: Artificial Sequence
<220> FEATURE:
<223> OTHER INFORMATION: Synthetic

<400> SEQUENCE: 288

Gly Gly Ser Ile Asp Gly Arg
1               5

<210> SEQ ID NO 289
<211> LENGTH: 6
<212> TYPE: PRT
<213> ORGANISM: Artificial Sequence
<220> FEATURE:
<223> OTHER INFORMATION: Synthetic

<400> SEQUENCE: 289

Pro Leu Gly Leu Trp Ala
1               5

<210> SEQ ID NO 290
<211> LENGTH: 8
<212> TYPE: PRT
<213> ORGANISM: Artificial Sequence
<220> FEATURE:
<223> OTHER INFORMATION: Synthetic

<400> SEQUENCE: 290

Gly Pro Gln Gly Ile Ala Gly Gln
1               5

<210> SEQ ID NO 291
<211> LENGTH: 8
<212> TYPE: PRT
<213> ORGANISM: Artificial Sequence
<220> FEATURE:
<223> OTHER INFORMATION: Synthetic

<400> SEQUENCE: 291

Gly Pro Gln Gly Leu Leu Gly Ala
1               5

<210> SEQ ID NO 292
<211> LENGTH: 5
<212> TYPE: PRT
<213> ORGANISM: Artificial Sequence
<220> FEATURE:
<223> OTHER INFORMATION: Synthetic

<400> SEQUENCE: 292

Gly Ile Ala Gly Gln
1               5

<210> SEQ ID NO 293
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 293

Gly Pro Leu Gly Ile Ala Gly Ile
1               5

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Gly Pro Glu Gly Leu Arg Val Gly
1               5

<210> SEQ ID NO 295
<211> LENGTH: 8
<212> TYPE: PRT
<213> ORGANISM: Artificial Sequence
<220> FEATURE:
<223> OTHER INFORMATION: Synthetic

<400> SEQUENCE: 295

Tyr Gly Ala Gly Leu Gly Val Val
1               5

<210> SEQ ID NO 296
<211> LENGTH: 8
<212> TYPE: PRT
<213> ORGANISM: Artificial Sequence
<220> FEATURE:
<223> OTHER INFORMATION: Synthetic

<400> SEQUENCE: 296

Ala Gly Leu Gly Val Val Glu Arg
1               5

<210> SEQ ID NO 297
<211> LENGTH: 8
<212> TYPE: PRT
<213> ORGANISM: Artificial Sequence
<220> FEATURE:
<223> OTHER INFORMATION: Synthetic

<400> SEQUENCE: 297

Ala Gly Leu Gly Ile Ser Ser Thr
1               5

<210> SEQ ID NO 298
<211> LENGTH: 8
<212> TYPE: PRT
<213> ORGANISM: Artificial Sequence
<220> FEATURE:
<223> OTHER INFORMATION: Synthetic

<400> SEQUENCE: 298

Glu Pro Gln Ala Leu Ala Met Ser
1               5

<210> SEQ ID NO 299
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 299

Gln Ala Leu Ala Met Ser Ala Ile
1               5

<210> SEQ ID NO 300
<211> LENGTH: 8
<212> TYPE: PRT
<213> ORGANISM: Artificial Sequence
<220> FEATURE:
<223> OTHER INFORMATION: Synthetic

<400> SEQUENCE: 300

Ala Ala Tyr His Leu Val Ser Gln
1               5

<210> SEQ ID NO 301
<211> LENGTH: 8
<212> TYPE: PRT
<213> ORGANISM: Artificial Sequence
<220> FEATURE:
<223> OTHER INFORMATION: Synthetic

<400> SEQUENCE: 301

Met Asp Ala Phe Leu Glu Ser Ser
1               5

<210> SEQ ID NO 302
<211> LENGTH: 8
<212> TYPE: PRT
<213> ORGANISM: Artificial Sequence
<220> FEATURE:
<223> OTHER INFORMATION: Synthetic

<400> SEQUENCE: 302

Glu Ser Leu Pro Val Val Ala Val
1               5

<210> SEQ ID NO 303
<211> LENGTH: 8
<212> TYPE: PRT
<213> ORGANISM: Artificial Sequence
<220> FEATURE:
<223> OTHER INFORMATION: Synthetic

<400> SEQUENCE: 303

Ser Ala Pro Ala Val Glu Ser Glu
1               5

<210> SEQ ID NO 304
<211> LENGTH: 8
<212> TYPE: PRT
<213> ORGANISM: Artificial Sequence
<220> FEATURE:
<223> OTHER INFORMATION: Synthetic

<400> SEQUENCE: 304

Asp Val Ala Gln Phe Val Leu Thr
1               5

<210> SEQ ID NO 305
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 305

Val Ala Gln Phe Val Leu Thr
1               5

<210> SEQ ID NO 306
<211> LENGTH: 8
<212> TYPE: PRT
<213> ORGANISM: Artificial Sequence
<220> FEATURE:
<223> OTHER INFORMATION: Synthetic

<400> SEQUENCE: 306

Val Ala Gln Phe Val Leu Thr Glu
1               5

<210> SEQ ID NO 307
<211> LENGTH: 8
<212> TYPE: PRT
<213> ORGANISM: Artificial Sequence
<220> FEATURE:
<223> OTHER INFORMATION: Synthetic

<400> SEQUENCE: 307

Ala Gln Phe Val Leu Thr Glu Gly
1               5

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Pro Val Gln Pro Ile Gly Pro Gln
1               5

<210> SEQ ID NO 309
<211> LENGTH: 422
<212> TYPE: PRT
<213> ORGANISM: Artificial Sequence
<220> FEATURE:
<223> OTHER INFORMATION: Synthetic

<400> SEQUENCE: 309

Met Glu Thr Asp Thr Leu Leu Leu Trp Val Leu Leu Leu Trp Val Pro
1               5                   10                  15

Gly Ser Thr Gly Cys Asp Leu Pro Gln Thr His Ser Leu Gly Ser Arg
            20                  25                  30

Arg Thr Leu Met Leu Leu Ala Gln Met Arg Arg Ile Ser Leu Phe Ser
        35                  40                  45

Cys Leu Lys Asp Arg His Asp Phe Gly Phe Pro Gln Glu Glu Phe Gly
    50                  55                  60

Asn Gln Phe Gln Lys Ala Glu Thr Ile Pro Val Leu His Glu Met Ile
65                  70                  75                  80

Gln Gln Ile Phe Asn Leu Phe Ser Thr Lys Asp Ser Ser Ala Ala Trp
                85                  90                  95

Asp Glu Thr Leu Leu Asp Lys Phe Tyr Thr Glu Leu Tyr Gln Gln Leu
            100                 105                 110

Asn Asp Leu Glu Ala Cys Val Ile Gln Gly Val Gly Val Thr Glu Thr
```

```
                115                 120                 125
Pro Leu Met Lys Glu Asp Ser Ile Leu Ala Val Arg Lys Tyr Phe Gln
    130                 135                 140

Arg Ile Thr Leu Tyr Leu Lys Glu Lys Tyr Ser Pro Cys Ala Trp
145                 150                 155                 160

Glu Val Val Arg Ala Glu Ile Met Arg Ser Phe Ser Leu Ser Thr Asn
                165                 170                 175

Leu Gln Glu Ser Leu Arg Ser Lys Glu Ser Gly Arg Ser Asp Asn Ile
            180                 185                 190

Gly Gly Gly Ser Glu Ser Lys Tyr Gly Pro Pro Cys Pro Pro Cys Pro
        195                 200                 205

Ala Pro Glu Phe Leu Gly Gly Pro Ser Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Arg Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser
            420

<210> SEQ ID NO 310
<211> LENGTH: 1269
<212> TYPE: DNA
<213> ORGANISM: Artificial Sequence
<220> FEATURE:
<223> OTHER INFORMATION: Synthetic

<400> SEQUENCE: 310
atggaaaccg acacactgct gctgtgggtg ctgcttttgt gggtgccagg atccacaggc      60
tgtgatctgc ctcaaacgca ttcattgggg tccaggcgca cgcttatgtt gcttgcacag    120
atgaggagaa tatcactttt ctcttgcttg aaggaccgcc acgatttggg ctttccgcag    180
gaagagttcg gtaaccagtt ccaaaaggca gagacaatcc ccgttttgca tgagatgatc    240
caacagatct ttaacctgtt ttcaaccaag gatagcagcg cagcgtggga tgagacactg    300
```

-continued

```
cttgacaagt tttacaccga gctctatcag caacttaatg atctcgaagc ctgcgtaatt      360
caaggagtag gcgttacaga gacacctttg atgaaggagg attccatcct tgcagtaaga      420
aaatacttcc agaggatcac cctctacctc aaagaaaaga atactcccc atgcgcgtgg       480 gaagtagtgc gagctgaaat aatgcggagc ttttctttgt caactaatct ccaagaatct      540
ctgagaagca aggagtcagg taggtctgat aatatcgggg gaggttctga atctaagtac      600
ggccctcctt gtcctccatg tcctgctcca gagtttctcg gaggccctc cgtgttcctg       660 tttcctccaa agcctaagga caccctgatg atcagcagaa cccctgaagt gacctgcgtg      720
gtggtcgacg tttcacaaga ggaccccgag gtgcagttca attggtacgt ggacggcgtg      780
gaagtgcaca acgccaagac caagcctaga gaggaacagt tcaacagcac ctacagagtg      840
gtgtccgtgc tgaccgtgct gcaccaggat tggctgaacg gcaaagagta caagtgcaag      900
gtgtccaaca agggcctgcc tagcagcatc gagaaaacca tcagcaaggc caagggccag      960
ccaagggaac cccaggttta cacactgcca cctagccaag aggaaatgac caagaaccag     1020
gtgtccctga cctgcctggt caagggcttt taccctccg atatcgccgt ggaatgggag      1080
agcaatggcc agcctgagaa caactacaag accacacctc ctgtgctgga cagcgacggc     1140
tcattcttcc tgtacagcag actgaccgtg gacaagagca gatggcagca gggcaacgtg     1200
ttcagctgca gcgtgatgca cgaggccctg cacaaccact acacccagaa gtctctgagc     1260
ctgagctga                                                             1269
```

<210> SEQ ID NO 311
<211> LENGTH: 428
<212> TYPE: PRT
<213> ORGANISM: Artificial Sequence
<220> FEATURE:
<223> OTHER INFORMATION: Synthetic

<400> SEQUENCE: 311

```
Met Glu Thr Asp Thr Leu Leu Leu Trp Val Leu Leu Leu Trp Val Pro
1               5                   10                  15

Gly Ser Thr Gly Cys Asp Leu Pro Gln Thr His Ser Leu Gly Ser Arg
            20                  25                  30

Arg Thr Leu Met Leu Leu Ala Gln Met Arg Arg Ile Ser Leu Phe Ser
        35                  40                  45

Cys Leu Lys Asp Arg His Asp Phe Gly Phe Pro Gln Glu Glu Phe Gly
    50                  55                  60

Asn Gln Phe Gln Lys Ala Glu Thr Ile Pro Val Leu His Glu Met Ile
65                  70                  75                  80

Gln Gln Ile Phe Asn Leu Phe Ser Thr Lys Asp Ser Ser Ala Ala Trp
                85                  90                  95

Asp Glu Thr Leu Leu Asp Lys Phe Tyr Thr Glu Leu Tyr Gln Gln Leu
            100                 105                 110

Asn Asp Leu Glu Ala Cys Val Ile Gln Gly Val Gly Val Thr Glu Thr
        115                 120                 125

Pro Leu Met Lys Glu Asp Ser Ile Leu Ala Val Arg Lys Tyr Phe Gln
    130                 135                 140

Arg Ile Thr Leu Tyr Leu Lys Glu Lys Lys Tyr Ser Pro Cys Ala Trp
145                 150                 155                 160

Glu Val Val Arg Ala Glu Ile Met Arg Ser Phe Ser Leu Ser Thr Asn
                165                 170                 175

Leu Gln Glu Ser Leu Arg Ser Lys Glu Ile Ser Ser Gly Leu Leu Ser
            180                 185                 190
```

```
Gly Arg Ser Asp Asn Ile Gly Gly Ser Glu Ser Lys Tyr Gly Pro
        195                 200                 205
Pro Cys Pro Pro Cys Pro Ala Pro Glu Phe Leu Gly Gly Pro Ser Val
    210                 215                 220
Phe Leu Phe Pro Pro Lys Pro Lys Asp Thr Leu Met Ile Ser Arg Thr
225                 230                 235                 240
Pro Glu Val Thr Cys Val Val Val Asp Val Ser Gln Glu Asp Pro Glu
                245                 250                 255
Val Gln Phe Asn Trp Tyr Val Asp Gly Val Glu Val His Asn Ala Lys
            260                 265                 270
Thr Lys Pro Arg Glu Glu Gln Phe Asn Ser Thr Tyr Arg Val Val Ser
        275                 280                 285
Val Leu Thr Val Leu His Gln Asp Trp Leu Asn Gly Lys Glu Tyr Lys
    290                 295                 300
Cys Lys Val Ser Asn Lys Gly Leu Pro Ser Ser Ile Glu Lys Thr Ile
305                 310                 315                 320
Ser Lys Ala Lys Gly Gln Pro Arg Glu Pro Gln Val Tyr Thr Leu Pro
                325                 330                 335
Pro Ser Gln Glu Glu Met Thr Lys Asn Gln Val Ser Leu Thr Cys Leu
            340                 345                 350
Val Lys Gly Phe Tyr Pro Ser Asp Ile Ala Val Glu Trp Glu Ser Asn
        355                 360                 365
Gly Gln Pro Glu Asn Asn Tyr Lys Thr Thr Pro Pro Val Leu Asp Ser
    370                 375                 380
Asp Gly Ser Phe Phe Leu Tyr Ser Arg Leu Thr Val Asp Lys Ser Arg
385                 390                 395                 400
Trp Gln Gln Gly Asn Val Phe Ser Cys Ser Val Met His Glu Ala Leu
                405                 410                 415
His Asn His Tyr Thr Gln Lys Ser Leu Ser Leu Ser
            420                 425
```

<210> SEQ ID NO 312
<211> LENGTH: 1287
<212> TYPE: DNA
<213> ORGANISM: Artificial Sequence
<220> FEATURE:
<223> OTHER INFORMATION: Synthetic

<400> SEQUENCE: 312

| | | | | | |
|---|---|---|---|---|---|
| atggaaaccg | acacactgct | gctgtgggtg | ctgcttttgt | gggtgccagg | atccacaggc | 60 |
| tgtgatctgc | ctcaaacgca | ttcattgggg | tccaggcgca | cgcttatgtt | gcttgcacag | 120 |
| atgaggagaa | tatcactttt | ctcttgcttg | aaggaccgcc | acgattttgg | ctttccgcag | 180 |
| gaagagttcg | gtaaccagtt | ccaaaaggca | gagacaatcc | ccgttttgca | tgagatgatc | 240 |
| caacagatct | ttaacctgtt | tcaaccaag | gatagcagcg | cagcgtggga | tgagacactg | 300 |
| cttgacaagt | tttacaccga | gctctatcag | caacttaatg | atctcgaagc | tgcgtaatt | 360 |
| caaggagtag | gcgttacaga | gacacctttg | atgaaggagg | attccatcct | gcagtaaga | 420 |
| aaatacttcc | agaggatcac | cctctacctc | aaagaaaaga | atactccccc | atgcgcgtgg | 480 |
| gaagtagtgc | gagctgaaat | aatgcggagc | ttttctttgt | caactaatct | ccaagaatct | 540 |
| ctgagaagca | aggagattag | ttctggcctg | ctgtcaggta | ggtctgataa | atcgggga | 600 |
| ggttctgaat | ctaagtacgg | ccctccttgt | cctccatgtc | ctgctccaga | gtttctcgga | 660 |
| ggcccctccg | tgttcctgtt | tcctccaaag | cctaaggaca | ccctgatgat | cagcagaacc | 720 |

```
cctgaagtga cctgcgtggt ggtcgacgtt tcacaagagg accccgaggt gcagttcaat    780
tggtacgtgg acggcgtgga agtgcacaac gccaagacca agcctagaga ggaacagttc    840
aacagcacct acagagtggt gtccgtgctg accgtgctgc accaggattg gctgaacggc    900
aaagagtaca agtgcaaggt gtccaacaag ggcctgccta gcagcatcga aaaaccatc     960 agcaaggcca agggccagcc aagggaaccc caggtttaca cactgccacc tagccaagag   1020
gaaatgacca gaaccaggt gtccctgacc tgcctggtca agggcttta ccctccgat      1080 atcgccgtgg aatgggagag caatggccag cctgagaaca actacaagac cacacctcct   1140
gtgctggaca gcgacggctc attcttcctg tacagcagac tgaccgtgga caagagcaga   1200
tggcagcagg gcaacgtgtt cagctgcagc gtgatgcacg aggccctgca caaccactac   1260
acccagaagt ctctgagcct gagctga                                       1287
```

<210> SEQ ID NO 313
<211> LENGTH: 391
<212> TYPE: PRT
<213> ORGANISM: Artificial Sequence
<220> FEATURE:
<223> OTHER INFORMATION: Synthetic

<400> SEQUENCE: 313

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Ser Gly Arg Ser Asp Asn Ile Cys Pro Pro Cys
                165                 170                 175

Pro Ala Pro Glu Phe Leu Gly Gly Pro Ser Val Phe Leu Phe Pro Pro
            180                 185                 190

Lys Pro Lys Asp Thr Leu Met Ile Ser Arg Thr Pro Glu Val Thr Cys
        195                 200                 205

Val Val Val Asp Val Ser Gln Glu Asp Pro Glu Val Gln Phe Asn Trp
    210                 215                 220

Tyr Val Asp Gly Val Glu Val His Asn Ala Lys Thr Lys Pro Arg Glu
225                 230                 235                 240

Glu Gln Phe Asn Ser Thr Tyr Arg Val Val Ser Val Leu Thr Val Leu
                245                 250                 255
```

His Gln Asp Trp Leu Asn Gly Lys Glu Tyr Lys Cys Lys Val Ser Asn
                260                 265                 270

Lys Gly Leu Pro Ser Ser Ile Glu Lys Thr Ile Ser Lys Ala Lys Gly
            275                 280                 285

Gln Pro Arg Glu Pro Gln Val Tyr Thr Leu Pro Pro Ser Gln Glu Glu
        290                 295                 300

Met Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Arg Leu Thr Val Asp Lys Ser Arg Trp Gln Gln Gly Asn
        355                 360                 365

Val Phe Ser Cys Ser Val Met His Glu Ala Leu His Asn His Tyr Thr
370                 375                 380

Gln Lys Ser Leu Ser Leu Ser
385                 390

<210> SEQ ID NO 314
<211> LENGTH: 393
<212> TYPE: PRT
<213> ORGANISM: Artificial Sequence
<220> FEATURE:
<223> OTHER INFORMATION: Synthetic

<400> SEQUENCE: 314

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Ser Gly Arg Ser Asp Asn Ile Cys Pro Pro Cys
                165                 170                 175

Pro Ala Pro Glu Phe Glu Gly Gly Pro Ser Val Phe Leu Phe Pro Pro
            180                 185                 190

Lys Pro Lys Asp Thr Leu Met Ile Ser Arg Thr Pro Glu Val Thr Cys
        195                 200                 205

Val Val Val Asp Val Ser Gln Glu Asp Pro Glu Val Gln Phe Asn Trp
    210                 215                 220

Tyr Val Asp Gly Val Glu Val His Asn Ala Lys Thr Lys Pro Arg Glu
225                 230                 235                 240

Glu Gln Phe Asn Ser Thr Tyr Arg Val Val Ser Val Leu Thr Val Leu
            245                 250                 255

His Gln Asp Trp Leu Asn Gly Lys Glu Tyr Lys Cys Lys Val Ser Asn
        260                 265                 270

Lys Gly Leu Pro Ser Ser Ile Glu Lys Thr Ile Ser Lys Ala Lys Gly
    275                 280                 285

Gln Pro Arg Glu Pro Gln Val Tyr Thr Leu Pro Pro Cys Gln Glu Glu
290                 295                 300

Met Thr Lys Asn Gln Val Ser Leu Trp Cys Leu Val Lys Gly Phe Tyr
305                 310                 315                 320

Pro Ser Asp Ile Ala Val Glu Trp Glu Ser Asn Gly Gln Pro Glu Asn
            325                 330                 335

Asn Tyr Lys Thr Thr Pro Pro Val Leu Asp Ser Asp Gly Ser Phe Phe
        340                 345                 350

Leu Tyr Ser Arg Leu Thr Val Asp Lys Ser Arg Trp Gln Glu Gly Asn
    355                 360                 365

Val Phe Ser Cys Ser Val Met His Glu Ala Leu His Asn His Tyr Thr
370                 375                 380

Gln Lys Ser Leu Ser Leu Ser Leu Gly
385                 390

<210> SEQ ID NO 315
<211> LENGTH: 221
<212> TYPE: PRT
<213> ORGANISM: Artificial Sequence
<220> FEATURE:
<223> OTHER INFORMATION: Synthetic

<400> SEQUENCE: 315

Cys Pro Pro Cys Pro Ala Pro Glu Phe Glu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Cys Gln Glu Glu Met Thr Lys Asn Gln Val Ser Leu Trp Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
            195                 200                 205

Asn His Tyr Thr Gln Lys Ser Leu Ser Leu Ser Leu Gly
    210                 215                 220

<210> SEQ ID NO 316
<211> LENGTH: 221
<212> TYPE: PRT
<213> ORGANISM: Artificial Sequence
<220> FEATURE:
<223> OTHER INFORMATION: Synthetic

<400> SEQUENCE: 316

Cys Pro Pro Cys Pro Ala Pro Glu Phe Glu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Cys Thr Leu Pro Pro
        115                 120                 125

Ser Gln Glu Glu Met Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn Arg Phe Thr Gln Lys Ser Leu Ser Leu Ser Leu Gly
    210                 215                 220

<210> SEQ ID NO 317
<211> LENGTH: 4
<212> TYPE: PRT
<213> ORGANISM: Artificial Sequence
<220> FEATURE:
<223> OTHER INFORMATION: Synthetic

<400> SEQUENCE: 317

Ser Asp Asn Ile
1

<210> SEQ ID NO 318
<211> LENGTH: 6
<212> TYPE: PRT
<213> ORGANISM: Artificial Sequence
<220> FEATURE:
<223> OTHER INFORMATION: Synthetic

```
<400> SEQUENCE: 318

Gly Ser Ser Gly Gly Ser
1               5

<210> SEQ ID NO 319
<211> LENGTH: 4
<212> TYPE: PRT
<213> ORGANISM: Artificial Sequence
<220> FEATURE:
<223> OTHER INFORMATION: Synthetic

<400> SEQUENCE: 319

Glu Ser Lys Tyr
1

<210> SEQ ID NO 320
<211> LENGTH: 407
<212> TYPE: PRT
<213> ORGANISM: Artificial Sequence
<220> FEATURE:
<223> OTHER INFORMATION: Synthetic

<400> SEQUENCE: 320

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Gly Gly Gly Gly Ser Gly Arg Ser Asp Asn Ile Gly Gly
225                 230                 235                 240

Gly Ser Cys Asp Leu Pro Gln Thr His Ser Leu Gly Ser Arg Arg Thr
                245                 250                 255

Leu Met Leu Leu Ala Gln Met Arg Arg Ile Ser Leu Phe Ser Cys Leu
            260                 265                 270
```

```
Lys Asp Arg His Asp Phe Gly Phe Pro Gln Glu Glu Phe Gly Asn Gln
            275                 280                 285

Phe Gln Lys Ala Glu Thr Ile Pro Val Leu His Glu Met Ile Gln Gln
        290                 295                 300

Ile Phe Asn Leu Phe Ser Thr Lys Asp Ser Ser Ala Ala Trp Asp Glu
305                 310                 315                 320

Thr Leu Leu Asp Lys Phe Tyr Thr Glu Leu Tyr Gln Gln Leu Asn Asp
                325                 330                 335

Leu Glu Ala Cys Val Ile Gln Gly Val Gly Val Thr Glu Thr Pro Leu
                340                 345                 350

Met Lys Glu Asp Ser Ile Leu Ala Val Arg Lys Tyr Phe Gln Arg Ile
            355                 360                 365

Thr Leu Tyr Leu Lys Glu Lys Lys Tyr Ser Pro Cys Ala Trp Glu Val
        370                 375                 380

Val Arg Ala Glu Ile Met Arg Ser Phe Ser Leu Ser Thr Asn Leu Gln
385                 390                 395                 400

Glu Ser Leu Arg Ser Lys Glu
                405

<210> SEQ ID NO 321
<211> LENGTH: 4
<212> TYPE: PRT
<213> ORGANISM: Artificial Sequence
<220> FEATURE:
<223> OTHER INFORMATION: Synthetic

<400> SEQUENCE: 321

Ser Gly Gly Gly
1

<210> SEQ ID NO 322
<211> LENGTH: 225
<212> TYPE: PRT
<213> ORGANISM: Artificial Sequence
<220> FEATURE:
<223> OTHER INFORMATION: Synthetic

<400> SEQUENCE: 322

Ser Asp Asn Ile Cys Pro Pro Cys Pro Ala Pro Glu Phe Glu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser Gln Glu
        35                  40                  45

Asp Pro Glu Val Gln Phe Asn Trp Tyr Val Asp Gly Val Glu Val His
    50                  55                  60

Asn Ala Lys Thr Lys Pro Arg Glu Glu Gln Phe Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Gly Leu Pro Ser Ser Ile Glu
            100                 105                 110

Lys Thr Ile Ser Lys Ala Lys Gly Gln Pro Arg Glu Pro Gln Val Cys
        115                 120                 125

Thr Leu Pro Pro Ser Gln Glu Glu Met Thr Lys Asn Gln Val Ser Leu
    130                 135                 140

Ser Cys Ala Val Lys Gly Phe Tyr Pro Ser Asp Ile Ala Val Glu Trp
145                 150                 155                 160
```

```
Glu Ser Asn Gly Gln Pro Glu Asn Asn Tyr Lys Thr Thr Pro Pro Val
                165                 170                 175

Leu Asp Ser Asp Gly Ser Phe Phe Leu Val Ser Arg Leu Thr Val Asp
            180                 185                 190

Lys Ser Arg Trp Gln Glu Gly Asn Val Phe Ser Cys Ser Val Met His
        195                 200                 205

Glu Ala Leu His Asn Arg Phe Thr Gln Lys Ser Leu Ser Leu Ser Leu
    210                 215                 220

Gly
225

<210> SEQ ID NO 323
<211> LENGTH: 392
<212> TYPE: PRT
<213> ORGANISM: Artificial Sequence
<220> FEATURE:
<223> OTHER INFORMATION: Synthetic

<400> SEQUENCE: 323

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Thr Thr Lys Asp Ser Ser Ala Ala Trp Asp Glu Asp Leu
65                  70                  75                  80

Leu Asp Lys Phe Cys Thr Glu Leu Tyr Gln Gln Leu Asn Asp Leu Glu
                85                  90                  95

Ala Cys Val Met Gln Glu Glu Arg Val Gly Glu Thr Pro Leu Met Asn
            100                 105                 110

Val Asp Ser Ile Leu Ala Val Lys Lys Tyr Phe Arg Arg Ile Thr Leu
        115                 120                 125

Tyr Leu Thr Glu Lys Lys Tyr Ser Pro Cys Ala Trp Glu Val Val Arg
    130                 135                 140

Ala Glu Ile Met Arg Ser Leu Ser Leu Ser Thr Asn Leu Gln Glu Arg
145                 150                 155                 160

Leu Arg Arg Lys Glu Leu Ser Gly Arg Ser Asp Asn Ile Cys Pro Pro
                165                 170                 175

Cys Pro Ala Pro Glu Phe Leu Gly Gly Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Ser Gln Glu Asp Pro Glu Val Gln Phe Asn
    210                 215                 220

Trp Tyr Val Asp Gly Val Glu Val His Asn Ala Lys Thr Lys Pro Arg
225                 230                 235                 240

Glu Glu Gln Phe Asn Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Gly Leu Pro Ser Ser Ile Glu Lys Thr Ile Ser Lys Ala Lys
        275                 280                 285
```

Gly Gln Pro Arg Glu Pro Gln Val Tyr Thr Leu Pro Pro Ser Gln Glu
            290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Arg Leu Thr Val Asp Lys Ser Arg Trp Gln Gln Gly
            355                 360                 365

Asn Val Phe Ser Cys Ser Val Met His Glu Ala Leu His Asn His Tyr
            370                 375                 380

Thr Gln Lys Ser Leu Ser Leu Ser
385                 390

<210> SEQ ID NO 324
<211> LENGTH: 165
<212> TYPE: PRT
<213> ORGANISM: Artificial Sequence
<220> FEATURE:
<223> OTHER INFORMATION: Synthetic

<400> SEQUENCE: 324

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Thr Thr Lys Asp Ser Ser Ala Ala Trp Asp Glu Asp Leu
65                  70                  75                  80

Leu Asp Lys Phe Cys Thr Glu Leu Tyr Gln Gln Leu Asn Asp Leu Glu
                85                  90                  95

Ala Cys Val Met Gln Glu Glu Arg Val Gly Glu Thr Pro Leu Met Asn
            100                 105                 110

Val Asp Ser Ile Leu Ala Val Lys Lys Tyr Phe Arg Arg Ile Thr Leu
        115                 120                 125

Tyr Leu Thr Glu Lys Lys Tyr Ser Pro Cys Ala Trp Glu Val Val Arg
    130                 135                 140

Ala Glu Ile Met Arg Ser Leu Ser Leu Ser Thr Asn Leu Gln Glu Arg
145                 150                 155                 160

Leu Arg Arg Lys Glu
                165

<210> SEQ ID NO 325
<211> LENGTH: 166
<212> TYPE: PRT
<213> ORGANISM: Artificial Sequence
<220> FEATURE:
<223> OTHER INFORMATION: Synthetic

<400> SEQUENCE: 325

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu

```
                    20                  25                  30

Lys Asp Arg Met Asn Phe Asp Ile Pro Glu Glu Ile Lys Gln Leu Gln
                35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 326
<211> LENGTH: 203
<212> TYPE: PRT
<213> ORGANISM: Artificial Sequence
<220> FEATURE:
<223> OTHER INFORMATION: Synthetic

<400> SEQUENCE: 326

Met Thr Ala Asn His Gln Ser Pro Gly Met His Ser Ile Leu Leu Leu
1               5                   10                  15

Leu Leu Leu Pro Ala Leu Thr Thr Thr Phe Ser Cys Asn His Leu Arg
                20                  25                  30

His Gln Asp Ala Asn Phe Ser Trp Lys Ser Leu Gln Leu Leu Gln Asn
            35                  40                  45

Thr Ala Pro Pro Pro Gln Pro Cys Pro Gln Gln Asp Val Thr Phe
        50                  55                  60

Pro Phe Pro Glu Thr Leu Leu Lys Ser Lys Asp Lys Lys Gln Ala Ala
65                  70                  75                  80

Ile Thr Thr Leu Arg Ile Leu Gln His Leu Phe Asn Met Leu Ser Ser
                85                  90                  95

Pro His Thr Pro Lys His Trp Ile Asp Arg Thr Arg His Ser Leu Leu
            100                 105                 110

Asn Gln Ile Gln His Tyr Ile His His Leu Glu Gln Cys Phe Val Asn
        115                 120                 125

Gln Gly Thr Arg Ser Gln Arg Gly Pro Arg Asn Ala His Leu Ser
    130                 135                 140

Ile Asn Lys Tyr Phe Arg Ser Ile His Asn Phe Leu Gln His Asn Asn
145                 150                 155                 160

Tyr Ser Ala Cys Thr Trp Asp His Val Arg Leu Gln Ala Arg Asp Cys
                165                 170                 175

Phe Arg His Val Asp Thr Leu Ile Gln Trp Met Lys Ser Arg Ala Pro
            180                 185                 190

Leu Thr Ala Ser Ser Lys Arg Leu Asn Thr Gln
        195                 200
```

```
<210> SEQ ID NO 327
<211> LENGTH: 187
<212> TYPE: PRT
<213> ORGANISM: Artificial Sequence
<220> FEATURE:
<223> OTHER INFORMATION: Synthetic

<400> SEQUENCE: 327
```

Met Ala Leu Pro Cys Ser Phe Ser Val Ala Leu Val Leu Leu Ser Cys
1               5                   10                  15

His Ser Leu Cys Cys Leu Ala Cys His Leu Pro Asp Thr His Ser Leu
            20                  25                  30

Arg Asn Trp Arg Val Leu Thr Leu Leu Gly Gln Met Arg Arg Leu Ser
        35                  40                  45

Ala Ser Ser Cys Asp His Tyr Thr Thr Asp Phe Ala Phe Pro Lys Glu
    50                  55                  60

Leu Phe Asp Gly Gln Arg Leu Gln Glu Ala Gln Ala Leu Ser Val Val
65                  70                  75                  80

His Val Met Thr Gln Lys Val Phe His Leu Phe Cys Thr Asn Thr Ser
                85                  90                  95

Ser Ala Pro Trp Asn Met Thr Leu Leu Glu Glu Leu Cys Ser Gly Leu
            100                 105                 110

Ser Glu Gln Leu Asp Asp Leu Asp Ala Cys Pro Leu Gln Glu Ala Gly
        115                 120                 125

Leu Ala Glu Thr Pro Leu Met His Glu Asp Ser Thr Leu Arg Thr Tyr
    130                 135                 140

Phe Gln Arg Ile Ser Leu Tyr Leu Gln Asp Arg Asn His Ser Pro Cys
145                 150                 155                 160

Ala Trp Glu Met Val Arg Ala Glu Ile Gly Arg Ser Phe Phe Ser Leu
                165                 170                 175

Thr Ile Leu Gln Glu Arg Val Arg Arg Lys
            180                 185

```
<210> SEQ ID NO 328
<211> LENGTH: 191
<212> TYPE: PRT
<213> ORGANISM: Artificial Sequence
<220> FEATURE:
<223> OTHER INFORMATION: Synthetic

<400> SEQUENCE: 328
```

Met Pro Gly Pro Ser Ala Pro Pro Pro Ala Ile Tyr Ser Ala Leu
1               5                   10                  15

Ala Leu Leu Leu Leu Thr Pro Pro Ala Asn Ala Phe Ser Cys Ser
            20                  25                  30

Pro Leu Arg Leu His Asp Ser Ala Phe Ala Trp Asp Ser Leu Gln Leu
        35                  40                  45

Leu Arg Asn Met Ala Pro Ser Pro Thr Gln Pro Cys Pro Gln Gln His
    50                  55                  60

Ala Pro Cys Ser Phe Pro Asp Thr Leu Leu Asp Thr Asn Asp Thr Gln
65                  70                  75                  80

Gln Ala Ala His Thr Ala Leu His Leu Leu Gln His Leu Phe Asp Thr
                85                  90                  95

Leu Ser Ser Pro Ser Thr Pro Ala His Trp Leu His Thr Ala Arg His
            100                 105                 110

Asp Leu Leu Asn Gln Leu Gln His His Ile His His Leu Glu Arg Cys
        115                 120                 125

Phe Pro Ala Asp Ala Ala Arg Leu His Arg Arg Gly Pro Arg Asn Leu
            130                 135                 140

His Leu Ser Ile Asn Lys Tyr Phe Gly Cys Ile Gln His Phe Leu Gln
145                 150                 155                 160

Asn His Thr Tyr Ser Pro Cys Ala Trp Asp His Val Arg Leu Glu Ala
                165                 170                 175

His Ala Cys Phe Gln Arg Ile His Arg Leu Thr Arg Thr Met Arg
            180                 185                 190

<210> SEQ ID NO 329
<211> LENGTH: 189
<212> TYPE: PRT
<213> ORGANISM: Artificial Sequence
<220> FEATURE:
<223> OTHER INFORMATION: Synthetic

<400> SEQUENCE: 329

Met Ala Pro Ala Trp Ser Phe Leu Leu Ala Leu Leu Leu Leu Ser Cys
1               5                   10                  15

Asn Ala Ile Cys Ser Leu Gly Cys His Leu Pro His Thr His Ser Leu
            20                  25                  30

Pro Asn Arg Arg Val Leu Thr Leu Leu Arg Gln Leu Arg Arg Val Ser
        35                  40                  45

Pro Ser Ser Cys Leu Gln Asp Arg Asn Asp Phe Ala Phe Pro Gln Glu
    50                  55                  60

Ala Leu Gly Gly Ser Gln Leu Gln Lys Ala Gln Ala Ile Ser Val Leu
65                  70                  75                  80

His Glu Val Thr Gln His Thr Phe Gln Leu Phe Ser Thr Glu Gly Ser
                85                  90                  95

Ala Ala Ala Trp Asp Glu Ser Leu Leu Asp Lys Leu Arg Ala Ala Leu
            100                 105                 110

Asp Gln Gln Leu Thr Asp Leu Gln Ala Cys Leu Arg Gln Glu Glu Gly
        115                 120                 125

Leu Arg Gly Ala Pro Leu Leu Lys Glu Asp Ala Ser Leu Ala Val Arg
    130                 135                 140

Lys Tyr Phe His Arg Leu Thr Leu Tyr Leu Arg Glu Lys Arg His Asn
145                 150                 155                 160

Pro Cys Ala Trp Glu Val Val Arg Ala Glu Val Met Arg Ala Phe Ser
                165                 170                 175

Ser Ser Thr Asn Leu Gln Glu Arg Phe Arg Arg Lys Asp
            180                 185

<210> SEQ ID NO 330
<211> LENGTH: 193
<212> TYPE: PRT
<213> ORGANISM: Artificial Sequence
<220> FEATURE:
<223> OTHER INFORMATION: Synthetic

<400> SEQUENCE: 330

Met Ala Val Pro Ala Ser Pro Gln His Pro Arg Gly Tyr Gly Ile Leu
1               5                   10                  15

Leu Leu Thr Leu Leu Leu Lys Ala Leu Ala Thr Thr Ala Ser Ala Cys
            20                  25                  30

Asn His Leu Arg Pro Gln Asp Ala Thr Phe Ser His Asp Ser Leu Gln
        35                  40                  45

Leu Leu Arg Asp Met Ala Pro Thr Leu Pro Gln Leu Cys Pro Gln His
    50                  55                  60

Asn Ala Ser Cys Ser Phe Asn Asp Thr Ile Leu Asp Thr Ser Asn Thr
65                  70                  75                  80

Arg Gln Ala Asp Lys Thr Thr His Asp Ile Leu Gln His Leu Phe Lys
                85                  90                  95

Ile Leu Ser Ser Pro Ser Thr Pro Ala His Trp Asn Asp Ser Gln Arg
            100                 105                 110

Gln Ser Leu Leu Asn Arg Ile His Arg Tyr Thr Gln His Leu Glu Gln
        115                 120                 125

Cys Leu Asp Ser Ser Asp Thr Arg Ser Arg Thr Arg Trp Pro Arg Asn
    130                 135                 140

Leu His Leu Thr Ile Lys Lys His Phe Ser Cys Leu His Thr Phe Leu
145                 150                 155                 160

Gln Asp Asn Asp Tyr Ser Ala Cys Ala Trp Glu His Val Arg Leu Gln
                165                 170                 175

Ala Arg Ala Trp Phe Leu His Ile His Asn Leu Thr Gly Asn Thr Arg
            180                 185                 190

Thr

<210> SEQ ID NO 331
<211> LENGTH: 194
<212> TYPE: PRT
<213> ORGANISM: Artificial Sequence
<220> FEATURE:
<223> OTHER INFORMATION: Synthetic

<400> SEQUENCE: 331

Met Ala Leu Pro Ser Ser Phe Leu Val Ala Leu Val Ala Leu Gly Cys
1               5                   10                  15

Asn Ser Val Cys Ser Leu Gly Cys Asp Leu Pro Gln Thr His Gly Leu
                20                  25                  30

Leu Asn Arg Arg Ala Leu Thr Leu Leu Gly Gln Met Arg Arg Leu Pro
            35                  40                  45

Ala Ser Ser Cys Gln Lys Asp Arg Asn Asp Phe Ala Phe Pro Gln Asp
        50                  55                  60

Val Phe Gly Gly Asp Gln Ser His Lys Ala Gln Ala Leu Ser Val Val
65                  70                  75                  80

His Val Thr Asn Gln Lys Ile Phe His Phe Phe Cys Thr Glu Ala Ser
                85                  90                  95

Ser Ser Ala Ala Trp Asn Thr Thr Leu Leu Glu Glu Phe Cys Thr Gly
            100                 105                 110

Leu Asp Arg Gln Leu Thr Arg Leu Glu Ala Cys Val Leu Gln Glu Val
        115                 120                 125

Glu Glu Gly Glu Ala Pro Leu Thr Asn Glu Asp Ile His Pro Glu Asp
    130                 135                 140

Ser Ile Leu Arg Asn Tyr Phe Gln Arg Leu Ser Leu Tyr Leu Gln Glu
145                 150                 155                 160

Lys Lys Tyr Ser Pro Cys Ala Trp Glu Ile Val Arg Ala Glu Ile Met
                165                 170                 175

Arg Ser Leu Tyr Tyr Ser Ser Thr Ala Leu Gln Lys Arg Leu Arg Ser
            180                 185                 190

Glu Lys

<210> SEQ ID NO 332
<211> LENGTH: 186
<212> TYPE: PRT

<213> ORGANISM: Artificial Sequence
<220> FEATURE:
<223> OTHER INFORMATION: Synthetic

<400> SEQUENCE: 332

```
Met Ala Asn Lys Cys Ile Leu Gln Ile Ala Leu Leu Met Cys Phe Ser
1               5                   10                  15

Thr Thr Ala Leu Ser Met Ser Tyr Asp Val Leu Arg Tyr Gln Gln Arg
            20                  25                  30

Ser Ser Asn Leu Ala Cys Gln Lys Leu Leu Gly Gln Leu Pro Gly Thr
        35                  40                  45

Pro Gln Tyr Cys Leu Glu Asp Arg Met Asn Phe Glu Val Pro Glu Glu
    50                  55                  60

Ile Met Gln Pro Pro Gln Phe Gln Lys Glu Asp Ala Val Leu Ile Ile
65                  70                  75                  80

His Glu Met Leu Gln Gln Ile Phe Gly Ile Leu Arg Arg Asn Phe Ser
                85                  90                  95

Ser Thr Gly Trp Asn Glu Thr Val Ile Lys Thr Ile Leu Val Glu Leu
            100                 105                 110

Asp Gly Gln Met Asp Asp Leu Glu Thr Ile Leu Glu Glu Ile Met Glu
        115                 120                 125

Glu Glu Asn Phe Pro Arg Gly Asp Met Thr Ile Leu His Leu Lys Lys
    130                 135                 140

Tyr Tyr Leu Ser Ile Leu Gln Tyr Leu Lys Ser Lys Glu Tyr Arg Ser
145                 150                 155                 160

Cys Ala Trp Thr Val Val Gln Val Glu Ile Leu Arg Asn Phe Ser Phe
                165                 170                 175

Leu Asn Arg Leu Thr Asp Tyr Leu Arg Asn
            180                 185
```

<210> SEQ ID NO 333
<211> LENGTH: 186
<212> TYPE: PRT
<213> ORGANISM: Artificial Sequence
<220> FEATURE:
<223> OTHER INFORMATION: Synthetic

<400> SEQUENCE: 333

```
Met Thr His Arg Cys Leu Leu Gln Met Val Leu Leu Cys Phe Ser
1               5                   10                  15

Thr Thr Ala Leu Ser Arg Ser Tyr Ser Leu Leu Arg Phe Gln Gln Arg
            20                  25                  30

Arg Ser Leu Ala Leu Cys Gln Lys Leu Leu Arg Gln Leu Pro Ser Thr
        35                  40                  45

Pro Gln His Cys Leu Glu Ala Arg Met Asp Phe Gln Met Pro Glu Glu
    50                  55                  60

Met Lys Gln Ala Gln Gln Phe Gln Lys Glu Asp Ala Ile Leu Val Ile
65                  70                  75                  80

Tyr Glu Met Leu Gln Gln Ile Phe Asn Ile Leu Thr Arg Asp Phe Ser
                85                  90                  95

Ser Thr Gly Trp Ser Glu Thr Ile Ile Glu Asp Leu Leu Glu Glu Leu
            100                 105                 110

Tyr Glu Gln Met Asn His Leu Glu Pro Ile Gln Lys Glu Ile Met Gln
        115                 120                 125

Lys Gln Asn Ser Thr Met Gly Asp Thr Thr Val Leu His Leu Arg Lys
    130                 135                 140
```

```
Tyr Tyr Phe Asn Leu Val Gln Tyr Leu Lys Ser Lys Glu Tyr Asn Arg
145                 150                 155                 160

Cys Ala Trp Thr Val Val Arg Val Gln Ile Leu Arg Asn Phe Ser Phe
                165                 170                 175

Leu Thr Arg Leu Thr Gly Tyr Leu Arg Glu
            180                 185

<210> SEQ ID NO 334
<211> LENGTH: 165
<212> TYPE: PRT
<213> ORGANISM: Artificial Sequence
<220> FEATURE:
<223> OTHER INFORMATION: Synthetic

<400> SEQUENCE: 334

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Asn
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 335
<211> LENGTH: 5
<212> TYPE: PRT
<213> ORGANISM: Artificial Sequence
<220> FEATURE:
<223> OTHER INFORMATION: Synthetic

<400> SEQUENCE: 335

Ser Gly Gly Gly Gly
1               5

<210> SEQ ID NO 336
<211> LENGTH: 396
<212> TYPE: PRT
<213> ORGANISM: Artificial Sequence
<220> FEATURE:
<223> OTHER INFORMATION: Synthetic

<400> SEQUENCE: 336

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
```

```
            20                  25                  30
Arg His Asp Phe Gly Phe Pro Gln Glu Glu Phe Gly Asn Gln Phe Gln
            35                  40                  45
Lys Ala Glu Thr Ile Pro Val Leu His Glu Met Ile Gln Gln Ile Phe
 50                  55                  60
Asn Leu Phe Ser Thr Lys Asp Ser Ser Ala Ala Trp Asp Glu Thr Leu
 65                  70                  75                  80
Leu Asp Lys Phe Tyr Thr Glu Leu Tyr Gln Gln Leu Asn Asp Leu Glu
                85                  90                  95
Ala Cys Val Ile Gln Gly Val Gly Val Thr Glu Thr Pro Leu Met Lys
                100                 105                 110
Glu Asp Ser Ile Leu Ala Val Arg Lys Tyr Phe Gln Arg Ile Thr Leu
                115                 120                 125
Tyr Leu Lys Glu Lys Lys Tyr Ser Pro Cys Ala Trp Glu Val Val Arg
            130                 135                 140
Ala Glu Ile Met Arg Ser Phe Ser Leu Ser Thr Asn Leu Gln Glu Ser
145                 150                 155                 160
Leu Arg Ser Lys Glu Ser Gly Gly Gly Ser Gly Arg Ser Asp Asn
                    165                 170                 175
Ile Cys Pro Pro Cys Pro Ala Pro Glu Phe Leu Gly Gly Pro Ser Val
                180                 185                 190
Phe Leu Phe Pro Pro Lys Pro Lys Asp Thr Leu Met Ile Ser Arg Thr
            195                 200                 205
Pro Glu Val Thr Cys Val Val Val Asp Val Ser Gln Glu Asp Pro Glu
        210                 215                 220
Val Gln Phe Asn Trp Tyr Val Asp Gly Val Glu Val His Asn Ala Lys
225                 230                 235                 240
Thr Lys Pro Arg Glu Glu Gln Phe Asn Ser Thr Tyr Arg Val Val Ser
                    245                 250                 255
Val Leu Thr Val Leu His Gln Asp Trp Leu Asn Gly Lys Glu Tyr Lys
                260                 265                 270
Cys Lys Val Ser Asn Lys Gly Leu Pro Ser Ser Ile Glu Lys Thr Ile
            275                 280                 285
Ser Lys Ala Lys Gly Gln Pro Arg Glu Pro Gln Val Tyr Thr Leu Pro
        290                 295                 300
Pro Ser Gln Glu Glu Met Thr Lys Asn Gln Val Ser Leu Thr Cys Leu
305                 310                 315                 320
Val Lys Gly Phe Tyr Pro Ser Asp Ile Ala Val Glu Trp Glu Ser Asn
                    325                 330                 335
Gly Gln Pro Glu Asn Asn Tyr Lys Thr Thr Pro Pro Val Leu Asp Ser
                340                 345                 350
Asp Gly Ser Phe Phe Leu Tyr Ser Arg Leu Thr Val Asp Lys Ser Arg
            355                 360                 365
Trp Gln Gln Gly Asn Val Phe Ser Cys Ser Val Met His Glu Ala Leu
        370                 375                 380
His Asn His Tyr Thr Gln Lys Ser Leu Ser Leu Ser
385                 390                 395

<210> SEQ ID NO 337
<211> LENGTH: 399
<212> TYPE: PRT
<213> ORGANISM: Artificial Sequence
<220> FEATURE:
<223> OTHER INFORMATION: Synthetic
```

<400> SEQUENCE: 337

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Ser Gly Gly Gly Ser Gly Arg Ser Asp Asn
                165                 170                 175

Ile Gly Pro Pro Cys Pro Pro Cys Pro Ala Pro Glu Phe Leu Gly Gly
            180                 185                 190

Pro Ser Val Phe Leu Phe Pro Pro Lys Pro Lys Asp Thr Leu Met Ile
        195                 200                 205

Ser Arg Thr Pro Glu Val Thr Cys Val Val Val Asp Val Ser Gln Glu
210                 215                 220

Asp Pro Glu Val Gln Phe Asn Trp Tyr Val Asp Gly Val Glu Val His
225                 230                 235                 240

Asn Ala Lys Thr Lys Pro Arg Glu Glu Gln Phe Asn Ser Thr Tyr Arg
                245                 250                 255

Val Val Ser Val Leu Thr Val Leu His Gln Asp Trp Leu Asn Gly Lys
            260                 265                 270

Glu Tyr Lys Cys Lys Val Ser Asn Lys Gly Leu Pro Ser Ser Ile Glu
        275                 280                 285

Lys Thr Ile Ser Lys Ala Lys Gly Gln Pro Arg Glu Pro Gln Val Tyr
290                 295                 300

Thr Leu Pro Pro Ser Gln Glu Glu Met Thr Lys Asn Gln Val Ser Leu
305                 310                 315                 320

Thr Cys Leu Val Lys Gly Phe Tyr Pro Ser Asp Ile Ala Val Glu Trp
                325                 330                 335

Glu Ser Asn Gly Gln Pro Glu Asn Asn Tyr Lys Thr Thr Pro Pro Val
            340                 345                 350

Leu Asp Ser Asp Gly Ser Phe Phe Leu Tyr Ser Arg Leu Thr Val Asp
        355                 360                 365

Lys Ser Arg Trp Gln Gln Gly Asn Val Phe Ser Cys Ser Val Met His
370                 375                 380

Glu Ala Leu His Asn His Tyr Thr Gln Lys Ser Leu Ser Leu Ser
385                 390                 395
```

<210> SEQ ID NO 338

```
<211> LENGTH: 403
<212> TYPE: PRT
<213> ORGANISM: Artificial Sequence
<220> FEATURE:
<223> OTHER INFORMATION: Synthetic

<400> SEQUENCE: 338
```

| | | | | | | | | | | | | | | |
|---|---|---|---|---|---|---|---|---|---|---|---|---|---|---|
| Cys | Asp | Leu | Pro | Gln | Thr | His | Ser | Leu | Gly | Ser | Arg | Arg | Thr | Leu | Met |
| 1 | | | | 5 | | | | | 10 | | | | | 15 | |

| Leu | Leu | Ala | Gln | Met | Arg | Arg | Ile | Ser | Leu | Phe | Ser | Cys | Leu | Lys | Asp |
| | | | 20 | | | | | 25 | | | | | 30 | | |

| Arg | His | Asp | Phe | Gly | Phe | Pro | Gln | Glu | Glu | Phe | Gly | Asn | Gln | Phe | Gln |
| | | 35 | | | | | 40 | | | | | 45 | | | |

| Lys | Ala | Glu | Thr | Ile | Pro | Val | Leu | His | Glu | Met | Ile | Gln | Gln | Ile | Phe |
| | 50 | | | | | 55 | | | | | 60 | | | | |

| Asn | Leu | Phe | Ser | Thr | Lys | Asp | Ser | Ser | Ala | Ala | Trp | Asp | Glu | Thr | Leu |
| 65 | | | | | 70 | | | | | 75 | | | | | 80 |

| Leu | Asp | Lys | Phe | Tyr | Thr | Glu | Leu | Tyr | Gln | Gln | Leu | Asn | Asp | Leu | Glu |
| | | | | 85 | | | | | 90 | | | | | 95 | |

| Ala | Cys | Val | Ile | Gln | Gly | Val | Gly | Val | Thr | Glu | Thr | Pro | Leu | Met | Lys |
| | | | | 100 | | | | | 105 | | | | | 110 | |

| Glu | Asp | Ser | Ile | Leu | Ala | Val | Arg | Lys | Tyr | Phe | Gln | Arg | Ile | Thr | Leu |
| | | | 115 | | | | | 120 | | | | | 125 | | |

| Tyr | Leu | Lys | Glu | Lys | Lys | Tyr | Ser | Pro | Cys | Ala | Trp | Glu | Val | Val | Arg |
| | 130 | | | | | 135 | | | | | 140 | | | | |

| Ala | Glu | Ile | Met | Arg | Ser | Phe | Ser | Leu | Ser | Thr | Asn | Leu | Gln | Glu | Ser |
| 145 | | | | | 150 | | | | | 155 | | | | | 160 |

| Leu | Arg | Ser | Lys | Glu | Ser | Gly | Gly | Gly | Ser | Gly | Arg | Ser | Asp | Asn |
| | | | | 165 | | | | | 170 | | | | | 175 |

| Ile | Glu | Ser | Lys | Tyr | Gly | Pro | Pro | Cys | Pro | Cys | Pro | Ala | Pro | Glu |
| | | | 180 | | | | | 185 | | | | | 190 | |

| Phe | Leu | Gly | Gly | Pro | Ser | Val | Phe | Leu | Phe | Pro | Pro | Lys | Pro | Lys | Asp |
| | | | 195 | | | | | 200 | | | | | 205 | | |

| Thr | Leu | Met | Ile | Ser | Arg | Thr | Pro | Glu | Val | Thr | Cys | Val | Val | Val | Asp |
| | 210 | | | | | 215 | | | | | 220 | | | | |

| Val | Ser | Gln | Glu | Asp | Pro | Glu | Val | Gln | Phe | Asn | Trp | Tyr | Val | Asp | Gly |
| 225 | | | | | 230 | | | | | 235 | | | | | 240 |

| Val | Glu | Val | His | Asn | Ala | Lys | Thr | Lys | Pro | Arg | Glu | Glu | Gln | Phe | Asn |
| | | | | 245 | | | | | 250 | | | | | 255 | |

| Ser | Thr | Tyr | Arg | Val | Val | Ser | Val | Leu | Thr | Val | Leu | His | Gln | Asp | Trp |
| | | | 260 | | | | | 265 | | | | | 270 | | |

| Leu | Asn | Gly | Lys | Glu | Tyr | Lys | Cys | Lys | Val | Ser | Asn | Lys | Gly | Leu | Pro |
| | 275 | | | | | 280 | | | | | 285 | | | | |

| Ser | Ser | Ile | Glu | Lys | Thr | Ile | Ser | Lys | Ala | Lys | Gly | Gln | Pro | Arg | Glu |
| 290 | | | | | 295 | | | | | 300 | | | | | |

| Pro | Gln | Val | Tyr | Thr | Leu | Pro | Pro | Ser | Gln | Glu | Glu | Met | Thr | Lys | Asn |
| 305 | | | | | 310 | | | | | 315 | | | | | 320 |

| Gln | Val | Ser | Leu | Thr | Cys | Leu | Val | Lys | Gly | Phe | Tyr | Pro | Ser | Asp | Ile |
| | | | | 325 | | | | | 330 | | | | | 335 | |

| Ala | Val | Glu | Trp | Glu | Ser | Asn | Gly | Gln | Pro | Glu | Asn | Asn | Tyr | Lys | Thr |
| | | | 340 | | | | | 345 | | | | | 350 | | |

| Thr | Pro | Pro | Val | Leu | Asp | Ser | Asp | Gly | Ser | Phe | Phe | Leu | Tyr | Ser | Arg |
| | | 355 | | | | | 360 | | | | | 365 | | | |

| Leu | Thr | Val | Asp | Lys | Ser | Arg | Trp | Gln | Gln | Gly | Asn | Val | Phe | Ser | Cys |
| | 370 | | | | | 375 | | | | | 380 | | | | |

Ser Val Met His Glu Ala Leu His Asn His Tyr Thr Gln Lys Ser Leu
385                 390                 395                 400

Ser Leu Ser

<210> SEQ ID NO 339
<211> LENGTH: 407
<212> TYPE: PRT
<213> ORGANISM: Artificial Sequence
<220> FEATURE:
<223> OTHER INFORMATION: Synthetic

<400> SEQUENCE: 339

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Ser Gly Gly Gly Gly Ser Gly Arg Ser Asp Asn
                165                 170                 175

Ile Gly Gly Gly Ser Glu Ser Lys Tyr Gly Pro Pro Cys Pro Pro Cys
            180                 185                 190

Pro Ala Pro Glu Phe Leu Gly Gly Pro Ser Val Phe Leu Phe Pro Pro
        195                 200                 205

Lys Pro Lys Asp Thr Leu Met Ile Ser Arg Thr Pro Glu Val Thr Cys
210                 215                 220

Val Val Val Asp Val Ser Gln Glu Asp Pro Glu Val Gln Phe Asn Trp
225                 230                 235                 240

Tyr Val Asp Gly Val Glu Val His Asn Ala Lys Thr Lys Pro Arg Glu
                245                 250                 255

Glu Gln Phe Asn Ser Thr Tyr Arg Val Val Ser Val Leu Thr Val Leu
            260                 265                 270

His Gln Asp Trp Leu Asn Gly Lys Glu Tyr Lys Cys Lys Val Ser Asn
        275                 280                 285

Lys Gly Leu Pro Ser Ser Ile Glu Lys Thr Ile Ser Lys Ala Lys Gly
    290                 295                 300

Gln Pro Arg Glu Pro Gln Val Tyr Thr Leu Pro Pro Ser Gln Glu Glu
305                 310                 315                 320

Met Thr Lys Asn Gln Val Ser Leu Thr Cys Leu Val Lys Gly Phe Tyr
                325                 330                 335

```
Pro Ser Asp Ile Ala Val Glu Trp Glu Ser Asn Gly Gln Pro Glu Asn
            340                 345                 350

Asn Tyr Lys Thr Thr Pro Pro Val Leu Asp Ser Asp Gly Ser Phe Phe
            355                 360                 365

Leu Tyr Ser Arg Leu Thr Val Asp Lys Ser Arg Trp Gln Gln Gly Asn
    370                 375                 380

Val Phe Ser Cys Ser Val Met His Glu Ala Leu His Asn His Tyr Thr
385                 390                 395                 400

Gln Lys Ser Leu Ser Leu Ser
                405

<210> SEQ ID NO 340
<211> LENGTH: 237
<212> TYPE: PRT
<213> ORGANISM: Artificial Sequence
<220> FEATURE:
<223> OTHER INFORMATION: Synthetic

<400> SEQUENCE: 340

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Ser Gly Arg Ser Asp Asn Ile Gly Pro Pro Cys
                165                 170                 175

Pro Pro Cys Pro Ala Pro Glu Phe Leu Gly Gly Pro Ser Val Phe Leu
            180                 185                 190

Phe Pro Pro Lys Pro Lys Asp Thr Leu Met Ile Ser Arg Thr Pro Glu
        195                 200                 205

Val Thr Cys Val Val Val Asp Val Ser Gln Glu Asp Pro Glu Val Gln
    210                 215                 220

Phe Asn Trp Tyr Val Asp Gly Val Glu Val His Asn Ala
225                 230                 235

<210> SEQ ID NO 341
<211> LENGTH: 398
<212> TYPE: PRT
<213> ORGANISM: Artificial Sequence
<220> FEATURE:
<223> OTHER INFORMATION: Synthetic

<400> SEQUENCE: 341
```

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu Ser Gly Arg Ser Asp Asn Ile Glu Ser Lys Tyr
                165                 170                 175

Gly Pro Pro Cys Pro Pro Cys Pro Ala Pro Glu Phe Leu Gly Gly Pro
            180                 185                 190

Ser Val Phe Leu Phe Pro Pro Lys Pro Lys Asp Thr Leu Met Ile Ser
            195                 200                 205

Arg Thr Pro Glu Val Thr Cys Val Val Val Asp Val Ser Gln Glu Asp
210                 215                 220

Pro Glu Val Gln Phe Asn Trp Tyr Val Asp Gly Val Glu Val His Asn
225                 230                 235                 240

Ala Lys Thr Lys Pro Arg Glu Glu Gln Phe Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Gly Leu Pro Ser Ser Ile Glu Lys
        275                 280                 285

Thr Ile Ser Lys Ala Lys Gly Gln Pro Arg Glu Pro Gln Val Tyr Thr
290                 295                 300

Leu Pro Pro Ser Gln Glu Glu Met Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Arg Leu Thr Val Asp Lys
        355                 360                 365

Ser Arg Trp Gln Gln Gly Asn Val Phe Ser Cys Ser Val Met His Glu
370                 375                 380

Ala Leu His Asn His Tyr Thr Gln Lys Ser Leu Ser Leu Ser
385                 390                 395

<210> SEQ ID NO 342
<211> LENGTH: 402

```
<212> TYPE: PRT
<213> ORGANISM: Artificial Sequence
<220> FEATURE:
<223> OTHER INFORMATION: Synthetic

<400> SEQUENCE: 342

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Ser Gly Arg Ser Asp Asn Ile Gly Gly Gly Ser
                165                 170                 175

Glu Ser Lys Tyr Gly Pro Pro Cys Pro Pro Cys Pro Ala Pro Glu Phe
            180                 185                 190

Leu Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
210                 215                 220

Ser Gln Glu Asp Pro Glu Val Gln Phe Asn Trp Tyr Val Asp Gly Val
225                 230                 235                 240

Glu Val His Asn Ala Lys Thr Lys Pro Arg Glu Glu Gln Phe Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Gly Leu Pro Ser
        275                 280                 285

Ser Ile Glu Lys Thr Ile Ser Lys Ala Lys Gly Gln Pro Arg Glu Pro
290                 295                 300

Gln Val Tyr Thr Leu Pro Pro Ser Gln Glu Glu Met Thr Lys Asn Gln
305                 310                 315                 320

Val Ser Leu Thr Cys Leu Val Lys Gly Phe Tyr Pro Ser Asp Ile Ala
                325                 330                 335

Val Glu Trp Glu Ser Asn Gly Gln Pro Glu Asn Asn Tyr Lys Thr Thr
            340                 345                 350

Pro Pro Val Leu Asp Ser Asp Gly Ser Phe Phe Leu Tyr Ser Arg Leu
        355                 360                 365

Thr Val Asp Lys Ser Arg Trp Gln Gln Gly Asn Val Phe Ser Cys Ser
370                 375                 380
```

Val Met His Glu Ala Leu His Asn His Tyr Thr Gln Lys Ser Leu Ser
385                 390                 395                 400

Leu Ser

<210> SEQ ID NO 343
<211> LENGTH: 17
<212> TYPE: PRT
<213> ORGANISM: Artificial Sequence
<220> FEATURE:
<223> OTHER INFORMATION: Synthetic

<400> SEQUENCE: 343

Met Arg Ala Trp Ile Phe Phe Leu Leu Cys Leu Ala Gly Arg Ala Leu
1               5                   10                  15

Ala

<210> SEQ ID NO 344
<211> LENGTH: 23
<212> TYPE: PRT
<213> ORGANISM: Artificial Sequence
<220> FEATURE:
<223> OTHER INFORMATION: Synthetic

<400> SEQUENCE: 344

Met Ala Leu Thr Phe Ala Leu Leu Val Ala Leu Leu Val Leu Ser Cys
1               5                   10                  15

Lys Ser Ser Cys Ser Val Gly
            20

<210> SEQ ID NO 345
<211> LENGTH: 20
<212> TYPE: PRT
<213> ORGANISM: Artificial Sequence
<220> FEATURE:
<223> OTHER INFORMATION: Synthetic

<400> SEQUENCE: 345

Met Glu Thr Asp Thr Leu Leu Leu Trp Val Leu Leu Leu Trp Val Pro
1               5                   10                  15

Gly Ser Thr Gly
            20

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

```
<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
```

```
<400> SEQUENCE: 372
000

<210> SEQ ID NO 373
<400> SEQUENCE: 373
000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377
<400> SEQUENCE: 377
000

<210> SEQ ID NO 378
<400> SEQUENCE: 378
000

<210> SEQ ID NO 379
<400> SEQUENCE: 379
000

<210> SEQ ID NO 380
<400> SEQUENCE: 380
000

<210> SEQ ID NO 381
<400> SEQUENCE: 381
000

<210> SEQ ID NO 382
<400> SEQUENCE: 382
000

<210> SEQ ID NO 383
<400> SEQUENCE: 383
```

000

<210> SEQ ID NO 384
<400> SEQUENCE: 384
000

<210> SEQ ID NO 385
<400> SEQUENCE: 385
000

<210> SEQ ID NO 386
<400> SEQUENCE: 386
000

<210> SEQ ID NO 387
<400> SEQUENCE: 387
000

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<400> SEQUENCE: 392
000

<210> SEQ ID NO 393
<400> SEQUENCE: 393
000

<210> SEQ ID NO 394
<400> SEQUENCE: 394
000

```
<210> SEQ ID NO 395
<400> SEQUENCE: 395
000

<210> SEQ ID NO 396
<400> SEQUENCE: 396
000

<210> SEQ ID NO 397
<400> SEQUENCE: 397
000

<210> SEQ ID NO 398
<400> SEQUENCE: 398
000

<210> SEQ ID NO 399
<400> SEQUENCE: 399
000

<210> SEQ ID NO 400
<400> SEQUENCE: 400
000

<210> SEQ ID NO 401
<400> SEQUENCE: 401
000

<210> SEQ ID NO 402
<400> SEQUENCE: 402
000

<210> SEQ ID NO 403
<400> SEQUENCE: 403
000

<210> SEQ ID NO 404
<400> SEQUENCE: 404
000

<210> SEQ ID NO 405
<400> SEQUENCE: 405
000

<210> SEQ ID NO 406
```

```
<400> SEQUENCE: 406
000

<210> SEQ ID NO 407
<400> SEQUENCE: 407
000

<210> SEQ ID NO 408
<400> SEQUENCE: 408
000

<210> SEQ ID NO 409
<400> SEQUENCE: 409
000

<210> SEQ ID NO 410
<400> SEQUENCE: 410
000

<210> SEQ ID NO 411
<400> SEQUENCE: 411
000

<210> SEQ ID NO 412
<400> SEQUENCE: 412
000

<210> SEQ ID NO 413
<400> SEQUENCE: 413
000

<210> SEQ ID NO 414
<400> SEQUENCE: 414
000

<210> SEQ ID NO 415
<400> SEQUENCE: 415
000

<210> SEQ ID NO 416
<400> SEQUENCE: 416
000

<210> SEQ ID NO 417
<400> SEQUENCE: 417
```

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

-continued

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

```
<210> SEQ ID NO 440
<400> SEQUENCE: 440
000

<210> SEQ ID NO 441
<400> SEQUENCE: 441
000

<210> SEQ ID NO 442
<400> SEQUENCE: 442
000

<210> SEQ ID NO 443
<400> SEQUENCE: 443
000

<210> SEQ ID NO 444
<400> SEQUENCE: 444
000

<210> SEQ ID NO 445
<400> SEQUENCE: 445
000

<210> SEQ ID NO 446
<400> SEQUENCE: 446
000

<210> SEQ ID NO 447
<400> SEQUENCE: 447
000

<210> SEQ ID NO 448
<400> SEQUENCE: 448
000

<210> SEQ ID NO 449
<400> SEQUENCE: 449
000

<210> SEQ ID NO 450
<400> SEQUENCE: 450
000

<210> SEQ ID NO 451
```

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

```
<400> SEQUENCE: 485
000

<210> SEQ ID NO 486
<400> SEQUENCE: 486
000

<210> SEQ ID NO 487
<400> SEQUENCE: 487
000

<210> SEQ ID NO 488
<400> SEQUENCE: 488
000

<210> SEQ ID NO 489
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
<400> SEQUENCE: 496
```

000

<210> SEQ ID NO 497
<400> SEQUENCE: 497

000

<210> SEQ ID NO 498
<400> SEQUENCE: 498

000

<210> SEQ ID NO 499
<400> SEQUENCE: 499

000

<210> SEQ ID NO 500
<400> SEQUENCE: 500

000

<210> SEQ ID NO 501
<400> SEQUENCE: 501

000

<210> SEQ ID NO 502
<400> SEQUENCE: 502

000

<210> SEQ ID NO 503
<400> SEQUENCE: 503

000

<210> SEQ ID NO 504
<211> LENGTH: 6
<212> TYPE: PRT
<213> ORGANISM: Artificial Sequence
<220> FEATURE:
<223> OTHER INFORMATION: Synthetic

<400> SEQUENCE: 504

Gln Gly Gln Ser Gly Ser
1               5

<210> SEQ ID NO 505
<211> LENGTH: 5
<212> TYPE: PRT
<213> ORGANISM: Artificial Sequence
<220> FEATURE:
<223> OTHER INFORMATION: Synthetic

<400> SEQUENCE: 505

Gly Gln Ser Gly Ser
1               5

```
<210> SEQ ID NO 506
<211> LENGTH: 4
<212> TYPE: PRT
<213> ORGANISM: Artificial Sequence
<220> FEATURE:
<223> OTHER INFORMATION: Synthetic

<400> SEQUENCE: 506

Gln Ser Gly Ser
1

<210> SEQ ID NO 507
<211> LENGTH: 7
<212> TYPE: PRT
<213> ORGANISM: Artificial Sequence
<220> FEATURE:
<223> OTHER INFORMATION: Synthetic

<400> SEQUENCE: 507

Gln Gly Gln Ser Gly Gln Gly
1               5

<210> SEQ ID NO 508
<211> LENGTH: 6
<212> TYPE: PRT
<213> ORGANISM: Artificial Sequence
<220> FEATURE:
<223> OTHER INFORMATION: Synthetic

<400> SEQUENCE: 508

Gly Gln Ser Gly Gln Gly
1               5

<210> SEQ ID NO 509
<211> LENGTH: 5
<212> TYPE: PRT
<213> ORGANISM: Artificial Sequence
<220> FEATURE:
<223> OTHER INFORMATION: Synthetic

<400> SEQUENCE: 509

Gln Ser Gly Gln Gly
1               5

<210> SEQ ID NO 510
<211> LENGTH: 4
<212> TYPE: PRT
<213> ORGANISM: Artificial Sequence
<220> FEATURE:
<223> OTHER INFORMATION: Synthetic

<400> SEQUENCE: 510

Ser Gly Gln Gly
1

<210> SEQ ID NO 511
<211> LENGTH: 6
<212> TYPE: PRT
<213> ORGANISM: Artificial Sequence
<220> FEATURE:
<223> OTHER INFORMATION: Synthetic

<400> SEQUENCE: 511

Gln Gly Gln Ser Gly Gln
1               5

<210> SEQ ID NO 512
```

```
<211> LENGTH: 5
<212> TYPE: PRT
<213> ORGANISM: Artificial Sequence
<220> FEATURE:
<223> OTHER INFORMATION: Synthetic

<400> SEQUENCE: 512

Gly Gln Ser Gly Gln
1               5

<210> SEQ ID NO 513
<211> LENGTH: 4
<212> TYPE: PRT
<213> ORGANISM: Artificial Sequence
<220> FEATURE:
<223> OTHER INFORMATION: Synthetic

<400> SEQUENCE: 513

Gln Ser Gly Gln
1

<210> SEQ ID NO 514
<211> LENGTH: 5
<212> TYPE: PRT
<213> ORGANISM: Artificial Sequence
<220> FEATURE:
<223> OTHER INFORMATION: Synthetic

<400> SEQUENCE: 514

Gln Gly Gln Ser Gly
1               5

<210> SEQ ID NO 515
<211> LENGTH: 4
<212> TYPE: PRT
<213> ORGANISM: Artificial Sequence
<220> FEATURE:
<223> OTHER INFORMATION: Synthetic

<400> SEQUENCE: 515

Gln Gly Gln Ser
1

<210> SEQ ID NO 516
<211> LENGTH: 10
<212> TYPE: PRT
<213> ORGANISM: Artificial Sequence
<220> FEATURE:
<223> OTHER INFORMATION: N-terminal deletion sequence in an Fc

<400> SEQUENCE: 516

Glu Pro Lys Ser Cys Asp Lys Thr His Thr
1               5                   10

<210> SEQ ID NO 517
<211> LENGTH: 12
<212> TYPE: PRT
<213> ORGANISM: Artificial Sequence
<220> FEATURE:
<223> OTHER INFORMATION: N-terminal deletion in an Fc

<400> SEQUENCE: 517

Glu Leu Lys Thr Pro Leu Gly Asp Thr Thr His Thr
1               5                   10

<210> SEQ ID NO 518
<211> LENGTH: 7
```

```
<212> TYPE: PRT
<213> ORGANISM: Artificial Sequence
<220> FEATURE:
<223> OTHER INFORMATION: N-terminal deletion sequence in an Fc

<400> SEQUENCE: 518

Glu Ser Lys Tyr Gly Pro Pro
1               5
```

ACTIVATABLE CYTOKINE CONSTRUCTS AND RELATED COMPOSITIONS AND METHODS

CROSS-REFERENCE TO RELATED APPLICATIONS

This application claims priority benefit of U.S. provisional application Nos. 63/008,542, filed Apr. 10, 2020, 63/161,889, filed Mar. 16, 2021, and 63/164,849, filed Mar. 23, 2021, the entire contents of which are incorporated herein by reference.

REFERENCE TO SEQUENCE LISTING

The present application includes a Sequence Listing filed in electronic format. The "Sequence Listing" submitted electronically concurrently herewith pursuant 37 C.F.R. § 1.821 in computer readable form (CRF) via EFS-Web is entitled "CYTX-071-PCT_ST25.txt," was created on Apr. 7, 2021, and is 379,000 bytes in size. The information in the electronic format of the Sequence Listing is part of the present application and is incorporated herein by reference in its entirety.

TECHNICAL FIELD

The present disclosure relates to the field of biotechnology, and more specifically, to activatable cytokine constructs.

BACKGROUND

Cytokines are a family of naturally-occurring small proteins and glycoproteins produced and secreted by most nucleated cells in response to viral infection and/or other antigenic stimuli. Interferons are a subclass of cytokines. Interferons are presently grouped into three major classes: interferon type I, interferon type II, and interferon type III. Interferons exert their cellular activities by binding to specific membrane receptors on a cell surface.

Interferon therapy has many clinical benefits. For example, interferons are known to up-regulate the immune system and also to have antiviral and anti-proliferative properties. These biological properties have led to the clinical use of interferons as therapeutic agents for the treatment of viral infections and malignancies. Further, interferons are useful for recruiting a patient's innate immune system to identify and attack cancer cells. Accordingly, interferon therapy has been extensively used in cancer and antiviral therapy, including for the treatment of hepatitis, Kaposi sarcoma, hairy cell leukemia, chronic myeloid leukemia (CML), follicular lymphoma, renal cell cancer (RCC), melanoma, and other disease states. However, systemic administration of interferons is accompanied by dose-dependent toxicities, including strong flu-like symptoms, neurological symptoms, hepatotoxicity, bone marrow suppression, and arrythmia, among others. In a Melanoma patient study, the combination of Pembrolizumab and Pegylated IFNa led to an ORR of 60.5%. The combination treatment was also associated with 49% of G3/G4 adverse events which required dose reduction of Pegylated IFNa (Davar et al., J. Clin. Oncol., 2018). These undesired side-effects have limited the dosage of interferon therapies and sometimes leads to discontinuation or delay of interferon treatment.

Interleukins are another subclass of cytokines. Interleukins regulate cell growth, differentiation, and motility. They are particularly important in stimulating immune responses, such as inflammation. Interleukins have been used for treatment of cancer, autoimmune disorders, and other disorders. For example, interleukin-2 (IL2) is indicated for treatment of melamona, graft-versus-host disease (GVHD), neuroblastoma, renal cell cancer (RCC), and is also considered useful for conditions including acute coronary syndrome, acute myeloid syndrome, atopic dermatitis, autoimmune liver diseases, basal cell carcinoma, bladder cancer, breast cancer, candidiasis, colorectal cancer, cutaneous T-cell lymphoma, endometriomas, HIV invention, ischemic heart disease, rheumatoid arthritis, nasopharyngeal adenocarcimoa, non-small cell lung cancer (NSCLC), ovarian cancer, pancreatic cancer, systemic lupus erythematosus, tuberculosis, and other disorders. Other interleukins, such as IL-6, IL-7, IL-12, and IL-21, among others, are potential treatments for cancers and other disorders. Interleukin therapy is often accompanied by undesired side effects, including flu-like symptoms, nausea, vomiting, diarrhea, low blood pressure, and arrhythmia, among others.

Thus, the need and desire for improved specificity and selectivity of cytokine therapy to the desired target is of great interest. Increased targeting of cytokine therapeutics to the disease site could reduce systemic mechanism-based toxicities and lead to broader therapeutic utility.

SUMMARY

The present disclosure provides activatable cytokine constructs (ACCs) that include: (a) a first monomer comprising a first mature cytokine protein (CP1), a first cleavable moiety (CM1), and a first dimerization domain (DD1), wherein the CM1 is positioned between the CP1 and the DD1; and (b) a second monomer comprising a second mature cytokine protein (CP2), a second cleavable moiety (CM2), and a second dimerization domain (DD2), wherein the CM2 is positioned between the CP2 and the DD2, where: the CM1 and the CM2 function as a substrate for a protease; the DD1 and the DD2 bind each other; and where the ACC is characterized by a reduction in at least one activity of the CP1 and/or CP2 as compared to a control level of the at least one activity of the CP1 and/or CP2. The protease(s) that cleave the CM1 and CM2 may be over-expressed in diseased tissue (e.g., tumor tissue) relative to healthy tissue. The ACC may be activated upon cleavage of the CM1 and/or CM2 so that the cytokine may exert its activity in the diseased tissue (e.g., in a tumor microenvironment) while the cytokine activity is attenuated in the context of healthy tissue. Thus, the ACCs provided herein may provide reduced toxicity relative to traditional cytokine therapeutics, enable higher effective dosages of cytokine, and/or increase the therapeutic window for the cytokine.

Provided herein are activatable cytokine constructs (ACC) that include a first monomer construct and a second monomer construct, wherein: (a) the first monomer construct comprises a first mature cytokine protein (CP1), a first cleavable moiety (CM1), and a first dimerization domain (DD1), wherein the CM1 is positioned between the CP1 and the DD1; and (b) the second monomer construct comprises a second mature cytokine protein (CP2), a second cleavable moiety (CM2), and a second dimerization domain (DD2), wherein the CM2 is positioned between the CP2 and the DD2; wherein the DD1 and the DD2 bind each other thereby forming a dimer of the first monomer construct and the second monomer construct; and wherein the ACC is characterized by having a reduced level of at least one CP1 and/or CP2 activity as compared to a control level of the at least one CP1 and/or CP2 activity.

The present disclosure provides activatable cytokine constructs (ACCs) that include: (a) a first monomer comprising a first mature cytokine protein (CP1), a first dimerization domain (DD1); and (b) a second monomer comprising a second mature cytokine protein (CP2), a cleavable moiety (CM), and a second dimerization domain (DD2), wherein the CM is positioned between the CP2 and the DD2, where: the CM functions as a substrate for a protease; the DD1 and the DD2 bind each other; and where the ACC is characterized by a reduction in at least one activity of the CP1 and/or CP2 as compared to a control level of the at least one activity of the CP1 and/or CP2.

The present disclosure provides activatable cytokine constructs (ACCs) that include: (a) a first monomer comprising a first mature cytokine protein (CP1), a cleavable moiety (CM), and a first dimerization domain (DD1), wherein the CM is positioned between the CP1 and the DD1; and (b) a second monomer comprising a second mature cytokine protein (CP2), and a second dimerization domain (DD2), where: the CM functions as a substrate for a protease; the DD1 and the DD2 bind each other; and where the ACC is characterized by a reduction in at least one activity of the CP1 and/or CP2 as compared to a control level of the at least one activity of the CP1 and/or CP2.

The present disclosure provides activatable cytokine constructs (ACCs) that include: (a) a first monomer comprising a first mature cytokine protein (CP1), and a first dimerization domain (DD1); and (b) a second monomer comprising a second mature cytokine protein (CP2), and a second dimerization domain (DD2), wherein the CP1, the CP2, or both CP1 and CP2 include(s) an amino acid sequence that functions as a substrate for a protease; the DD1 and the DD2 bind each other; and where the ACC is characterized by a reduction in at least one activity of the CP1 and/or CP2 as compared to a control level of the at least one activity of the CP1 and/or CP2.

The ACCs of the present disclosure are characterized in that CP1 and CP2 are not connected to peptide masks, for example, affinity masking moieties.

In some embodiments, the first monomer construct comprises a first polypeptide that comprises the CP1, the CM1, and the DD1. In some embodiments, the second monomer construct comprises a second polypeptide that comprises the CP2, the CM2, and the DD2. In some embodiments, the DD1 and the DD2 are a pair selected from the group consisting of: a pair of Fc domains, a sushi domain from an alpha chain of human IL-15 receptor (IL15Rα) and a soluble IL-15; barnase and barnstar; a protein kinase A (PKA) and an A-kinase anchoring protein (AKAP); adapter/docking tag modules based on mutated RNase I fragments; an epitope and single domain antibody (sdAb); an epitope and single chain variable fragment (scFv); and soluble N-ethyl-maleimide sensitive factor attachment protein receptors (SNARE) modules based on interactions of the proteins syntaxin, synaptotagmin, synaptobrevin, and SNAP25, an antigen-binding domain and an epitope.

In some embodiments, the DD1 and the DD2 are a pair of Fc domains. In some embodiments, the pair of Fc domains is a pair of human Fc domains. In some embodiments, the human Fc domains are human IgG1 Fc domains, human IgG2 Fc domains, human IgG3 Fc domains, or human IgG4 Fc domains. In some embodiments, the human Fc domains are human IgG4 Fc domains. In some embodiments, the human Fc domains comprise a sequence that is at least 80% identical to SEQ ID NO: 3. In some embodiments, the human Fc domains each comprise a sequence that is at least 90%, 95%, 96%, 97%, 98%, or 99% identical to SEQ ID NO: 3. In some embodiments, the human Fc domains each comprise SEQ ID NO: 3. In some embodiments, the DD1 and the DD2 are the same. For example, DD1 and the DD2 may be a pair of identical human IgG4 Fc domains. In some embodiments, the dimerization domains have amino acid sequences of SEQ ID NOs: 315 and 316, respectively. In some embodiments, the human Fc domains include mutations to eliminate glycosylation and/or to reduce Fc-gamma receptor binding. In some embodiments, the human Fc domains comprise the mutation N297Q, N297A, or N297G; in some embodiments the human Fc domains comprise a mutation at position 234 and/or 235, for example L235E, or L234A and L235A (in IgG1), or F234A and L235A (in IgG4); in some embodiments the human Fc domains are IgG2 Fc domains that comprise the mutations V234A, G237A, P238S, H268Q/A, V309L, A330S, or P331S, or a combination thereof (all according to EU numbering).

Additional examples of engineered human Fc domains are known to those skilled in the art. Examples of Ig heavy chain constant region amino acids in which mutations in at least one amino acid leads to reduced Fc function include, but are not limited to, mutations in amino acid 228, 233, 234, 235, 236, 237, 239, 252, 254, 256, 265, 270, 297, 318, 320, 322, 327, 329, 330, and 331 of the heavy constant region (according to EU numbering). Examples of combinations of mutated amino acids are also known in the art, such as, but not limited to a combination of mutations in amino acids 234, 235, and 331, such as L234F, L235E, and P331S or a combination of amino acids 318, 320, and 322, such as E318A, K320A, and K322A.

Further examples of engineered Fc domains include F243L/R292P/Y300L/V305I/P396 IgG1; S239D/I332E IgG1; S239D/I332E/A330L IgG1; S298A/E333A/K334A; in one heavy chain, L234Y/L235Q/G236W/S239M/H268D/D270E/S298A IgG1, and in the opposing heavy chain, D270E/K326D, A330M/K334E IgG; G236A/S239D/I332E IgG1; K326W/E333S IgG1; S267E/H268F/S324T IgG1; E345R/E430G/S440Y IgG1; N297A or N297Q or N297G IgG1; L235E IgG1; L234A/L235A IgG1; F234A/L235A IgG4; H268Q/V309L/A330S/P331S IgG2; V234A/G237A/P238S/H268A/V309L/A330S/P331S IgG2; M252Y/S254T/T256E IgG1; M428L/N434S IgG1; S267E/L328F IgG1; N325S/L328F IgG1, and the like. In some embodiments, the engineered Fc domain comprises one or more substitutions selected from the group consisting of N297A IgG1, N297Q IgG1, and S228P IgG4.

In some embodiments, DD1 comprises an antigen-binding domain and DD2 comprises a corresponding epitope. In some embodiments, the antigen-binding domain is an anti-His tag antigen-binding domain and wherein the DD2 comprises a His tag. In some embodiments, the antigen-binding domain is a single chain variable fragment (scFv). In some embodiments, the antigen-binding domain is a single domain antibody (sdAb). In some embodiments, at least one of DD1 and DD2 comprises a dimerization domain substituent selected from the group consisting of a non-polypeptide polymer and a small molecule. In some embodiments, DD1 and DD2 comprise non-polypeptide polymers covalently bound to each other. In some embodiments, the non-polypeptide polymer is a sulfur-containing polyethylene glycol, and wherein DD1 and DD2 are covalently bound to each other via one or more disulfide bonds. In some embodiments, at least one of DD1 and DD2 comprises a small molecule. In some embodiments, the small molecule is biotin. In some embodiments, DD1 comprises biotin and DD2 comprises an avidin.

In some embodiments, the CP1 and the CP2 are mature cytokines. In some embodiments, each of the CP1 and the CP2 comprise a mature cytokine sequence and further comprise a signal peptide (also referred to herein as a "signal sequence"). In some embodiments, the CP1 and/or the CP2 is/are each individually selected from the group consisting of: an interferon, an interleukin, GM-CSF, G-CSF, LIF, OSM, CD154, LT-β, TNF-α, TNF-β, 4-1BBL, APRIL, CD70, CD153, CD178, GITRL, LIGHT, OX40L, TALL-1, TRAIL, TWEAK, TRANCE, TGF-β1, TGF-β1, TGF-β3, Epo, Tpo, Flt-3L, SCF, M-CSF, and MSP. The CP1 and/or CP2 may be a wild-type human or non-human animal sequence, a mutant sequence, a truncated sequence, a hybrid sequence, or sequence comprising insertions. In some embodiments, the CP1 and the CP2 are the same. In some embodiments, the CP1 and the CP2 are different and this disclosure includes selection and combination of any two of the cytokine proteins listed herein. In some embodiments, the CP1 and/or the CP2 is/are an interferon. In some embodiments, the CP1 and the CP2 both are an interferon. In some embodiments, the CP1 and the CP2 are different interferons. In some embodiments, the CP1 and the CP2 are the same interferon. In some embodiments, the CP1 or the CP2 is an interferon. In some embodiments, one of the CP1 and the CP2 is an interferon, and the other of CP1 or CP2 is a cytokine other than an interferon. In some aspects, one or both cytokines are monomeric cytokines. In some aspects, one or both interferons are monomeric inteferons. In some aspects, either CP1 or CP2 is a monomeric interferon and the other CP1 or CP2 is a different cytokine. In some aspects, the CP1 and/or the CP2 include a mutant cytokine sequence. In some aspects, the CP1 and/or the CP2 include a universal cytokine sequence. In some aspects, the CP1 and/or the CP2 include a truncated sequence that retains cytokine activity.

In some embodiments, the interferon(s) is/are a human wildtype mature interferon. In some embodiments, the interferon(s) may be type I and type II interferons, for example including, but not limited to interferon-alpha, interferon-beta, interferon-omega, interferon-gamma, and interferon-tau. In some embodiments, the interferons is/are an interferon-alpha. In some embodiments, the interferon(s) is/are selected from the group consisting of: interferon alpha-2a, interferon alpha-2b, and interferon alpha-n3. In some embodiments, the interferon(s) is/are interferon alpha-2b. In some embodiments, the interferon(s) is/are a mutant interferon. In some embodiments, the interferon(s) is/are a mutant interferon wherein an endogenous protease cleavage site has been rendered disfunctional by substitution, deletion, or insertion of one or more amino acids. In some embodiments, the interferon(s) is/are a universal cytokine molecule, e.g., having a hybrid sequence of different cytokine subtypes or a chimeric cytokine sequence or a humanized cytokine sequence. In some embodiments, the interferon(s) is/are a universal interferon molecule. In some embodiments, the interferon(s) is/are a universal interferon alpha, e.g., a hybrid of interferon alpha 1 and interferon alpha 2b. In some embodiments, the CP1 and/or CP2 comprises a sequence that is at least 80% identical to SEQ ID NO: 1. In some embodiments, the CP1 and/or CP2 comprises a sequence that is at least 90%, 95%, 96%, 97%, 98%, or 99% identical to SEQ ID NO: 1. In some embodiments, the CP1 and/or CP2 comprises a sequence of SEQ ID NO: 1. In some embodiments, the interferon is an interferon beta. In some embodiments, the interferon beta is selected from the group consisting of interferon beta-1a, and interferon beta-1b. In some embodiments, the CP1 and/or the CP2 comprises an IFab domain. In some embodiments, the CP1 and/or the CP2 comprises an interleukin. In some embodiments, the interleukin is selected from the group consisting of IL-1α, IL-1β, IL-1RA, IL-18, IL-2, IL-4, IL-7, IL-9, IL-13, IL-15, IL-3, IL-5, IL-6, IL-11, IL-12, IL-10, IL-20, IL-14, IL-16, and IL-17.

In some embodiments, the CM1 and/or the CM2 comprise a total of about 3 amino acids to about 15 amino acids. In some embodiments, the CM1 and the CM2 comprise substrates for different proteases. In some embodiments, the CM1 and the CM2 are of the same length and comprise the same amino acid sequence. In some embodiments, wherein the CM1 and the CM2 comprise substrates for the same protease. In some embodiments, the protease(s) is/are selected from the group consisting of: ADAM8, ADAM8, ADAM10, ADAM12, ADAM15, ADAM17/TACE, ADAM-DEC1, ADAMTS1, ADAMTS4, ADAMTS5, BACE, Renin, Cathepsin D, Cathepsin E, Caspase 1, Caspase 2, Caspase 3, Caspase 4, Caspase 5, Caspase 6, Caspase 7, Caspase 8, Caspase 9, Caspase 10, Caspase 14, Cathepsin B, Cathepsin C, Cathepsin K, Cathespin L, Cathepsin S, Cathepsin V/L2, Cathepsin X/Z/P, Cruzipain, Legumain, Otubain-2, KLK4, KLK5, KLK6, KLK7, KLK8, KLK10, KLK11, KLK13, KLK14, Meprin, Neprilysin, PSMA, BMP-1, matrix metalloproteinases (e.g., MMP-1, MMP-2, MMP-3, MMP-7, MMP-9, MMP-10, MMP-11, MMP-12, MMP-13, MMP-14, MMP-15, MMP-16, MMP-17, MMP-19, MMP-20, MMP-23, MMP-24, MMP-26, MMP-27), activated protein C, cathepsin A, cathepsin G, Chymase, FVIIa, FIXa, FXa, FXIa, FXIIa, Elastase, Granzyme B, Guanidinobenzoatase, HtrA1, human neutrophil lyase, lactoferrin, marapsin, NS3/4A, PACE4, Plasmin, PSA, tPA, thrombin, tryptase, uPA, DESC1, DPP-4, FAP, Hepsin, Matriptase-2, MT-SP1/Matripase, TMPRSS2, TMPRSS3, and TMPRSS4. In some embodiments, the protease(s) is/are selected from the group consisting of: uPA, legumain, MT-SP1, ADAM17, BMP-1, TMPRSS3, TMPRSS4, MMP-2, MMP-9, MMP-12, MMP-13, and MMP-14.

Suitable cleavable moieties have been disclosed in WO 2010/081173, WO 2015/048329, WO 2015/116933, WO 2016/118629, and WO 2020/118109, the disclosures of which are incorporated herein by reference in their entireties.

In some embodiments, the CM1 and/or the CM2 comprise a sequence selected from the group consisting of: LSGRSDNH (SEQ ID NO: 5), TGRGPSWV (SEQ ID NO: 6), PLTGRSGG (SEQ ID NO: 7), TARGPSFK (SEQ ID NO: 8), NTLSGRSENHSG (SEQ ID NO: 9), NTLSGRSGNHGS (SEQ ID NO: 10), TSTSGRSANPRG (SEQ ID NO: 11), TSGRSANP (SEQ ID NO: 12), VHMPLGFLGP (SEQ ID NO: 13), AVGLLAPP (SEQ ID NO: 14), AQNLLGMV (SEQ ID NO: 15), QNQALRMA (SEQ ID NO: 16), LAAPLGLL (SEQ ID NO: 17), STFPFGMF (SEQ ID NO: 18), ISSGLLSS (SEQ ID NO: 19), PAGLWLDP (SEQ ID NO: 20), VAGRSMRP (SEQ ID NO: 21), VVPEGRRS (SEQ ID NO: 22), ILPRSPAF (SEQ ID NO: 23), MVLGRSLL (SEQ ID NO: 24), QGRAITFI (SEQ ID NO: 25), SPRSIMLA (SEQ ID NO: 26), SMLRSMPL (SEQ ID NO: 27), ISSGLLSGRSDNH (SEQ ID NO: 28), AVGLLAPPGGLSGRSDNH (SEQ ID NO: 29), ISSGLLSSGGSGGSLSGRSDNH (SEQ ID NO: 30), LSGRSGNH (SEQ ID NO: 31), SGRSANPRG (SEQ ID NO: 32), LSGRSDDH (SEQ ID NO: 33), LSGRSDIH (SEQ ID NO: 34), LSGRSDQH (SEQ ID NO: 35), LSGRSDTH (SEQ ID NO: 36), LSGRSDYH (SEQ ID NO: 37), LSGRSDNP (SEQ ID NO: 38), LSGRSANP (SEQ ID NO: 39), LSGRSANI (SEQ ID NO: 40), LSGRSDNI (SEQ ID NO: 41), MIAPVAYR (SEQ ID NO: 42), RPSPMWAY (SEQ ID NO: 43), WATPRPMR (SEQ ID NO: 44), FRLL-DWQW (SEQ ID NO: 45), ISSGL (SEQ ID NO: 46), ISSGLLS (SEQ ID NO: 47), ISSGLL (SEQ ID NO: 48), ISSGLLSGRSANPRG (SEQ ID NO: 49), AVGLLAPPTS-GRSANPRG (SEQ ID NO: 50), AVGLLAPPSGRSANPRG (SEQ ID NO: 51), ISSGLLSGRSDDH (SEQ ID NO: 52), ISSGLLSGRSDIH (SEQ ID NO: 53), ISSGLLSGRSDQH (SEQ ID NO: 54), ISSGLLSGRSDTH (SEQ ID NO: 55), ISSGLLSGRSDYH (SEQ ID NO: 56), ISSGLLSGRSDNP (SEQ ID NO: 57), ISSGLLSGRSANP (SEQ ID NO: 58), ISSGLLSGRSANI (SEQ ID NO: 59), AVGLLAPPGGLS-GRSDDH (SEQ ID NO: 60), AVGLLAPPGGLSGRSDIH (SEQ ID NO: 61), AVGLLAPPGGLSGRSDQH (SEQ ID NO: 62), AVGLLAPPGGLSGRSDTH (SEQ ID NO: 63), AVGLLAPPGGLSGRSDYH (SEQ ID NO: 64), AVGL-LAPPGGLSGRSDNP (SEQ ID NO: 65), AVGLLAPPG-GLSGRSANP (SEQ ID NO: 66), AVGLLAPPGGLSGR-SANI (SEQ ID NO: 67), ISSGLLSGRSDNI (SEQ ID NO: 68), AVGLLAPPGGLSGRSDNI (SEQ ID NO: 69), GLS-GRSDNHGGAVGLLAPP (SEQ ID NO: 70), GLS-GRSDNHGGVHMPLGFLGP (SEQ ID NO: 71), LSGRSDNHGGVHMPLGFLGP (SEQ ID NO: 72), ISSGLSS (SEQ ID NO: 73), PVGYTSSL (SEQ ID NO: 74), DWLYWPGI (SEQ ID NO: 75), LKAAPRWA (SEQ ID NO: 76), GPSHLVLT (SEQ ID NO: 77), LPGGLSPW (SEQ ID NO: 78), MGLFSEAG (SEQ ID NO: 79), SPLPLRVP (SEQ ID NO: 80), RMHLRSLG (SEQ ID NO: 81), LLAP-SHRA (SEQ ID NO: 82), GPRSFGL (SEQ ID NO: 83), GPRSFG (SEQ ID NO: 84), SARGPSRW (SEQ ID NO: 85), GGWHTGRN (SEQ ID NO: 86), HTGRSGAL (SEQ ID NO: 87), AARGPAIH (SEQ ID NO: 88), RGPAFNPM (SEQ ID NO: 89), SSRGPAYL (SEQ ID NO: 90), RGPAT-PIM (SEQ ID NO: 91), RGPA (SEQ ID NO: 92), GGQPSGMWGW (SEQ ID NO: 93), FPRPLGITGL (SEQ ID NO: 94), SPLTGRSG (SEQ ID NO: 95), SAGFSLPA (SEQ ID NO: 96), LAPLGLQRR (SEQ ID NO: 97), SGG-PLGVR (SEQ ID NO: 98), PLGL (SEQ ID NO: 99), and SGRSDNI (SEQ ID NO: 100). In some embodiments, the CM comprises a sequence selected from the group consisting of: ISSGLLSGRSDNH (SEQ ID NO: 28), LSGRSDDH (SEQ ID NO: 33), ISSGLLSGRSDQH (SEQ ID NO: 54), SGRSDNI (SEQ ID NO: 100), and ISSGLLSGRSDNI (SEQ ID NO: 68). In some embodiments, the protease(s) is/are produced by a tumor in the subject, e.g., the protease(s) are produced in greater amounts in the tumor than in healthy tissues of the subject. In some embodiments, the subject has been diagnosed or identified as having a cancer.

In some embodiments, the CP1 and the CM1 directly abut each other in the first monomer construct. In some embodiments, the CM1 and the DD1 directly abut each other in the first monomer construct. In some embodiments, the CP2 and the CM2 directly abut each other in the second monomer construct. In some embodiments, the CM2 and the DD2 directly abut each other in the second monomer construct. In some embodiments, the first monomer construct comprises the CP1 directly abutting the CM1, and the CM1 directly abutting the DD1, wherein the CM1 comprises a sequence that is selected from the group consisting of SEQ ID Nos 5-100. In some embodiments, the second monomer construct comprises the CP2 directly abutting the CM2, and the CM2 directly abutting the DD2, wherein the CM2 comprises a sequence that is selected from the group consisting of SEQ ID Nos 5-100. In some embodiments, the first monomer construct comprises the CP1 directly abutting the CM1, and the CM1 directly abutting the DD1, wherein the CM1 comprises a sequence that is no more than 13, 12, 11, 10, 9, 8, 7, 6, 5 or 4 amino acids in length. In some embodiments, the second monomer construct comprises the CP2 directly abutting the CM2, and the CM2 directly abutting the DD2, wherein the CM2 comprises a sequence that is no more than 13, 12, 11, 10, 9, 8, 7, 6, 5 or 4 amino acids in length. In some embodiments, the first and second monomer construct each are configured such that the cytokine (CM1 and CM2, respectively) directly abuts a cleavable moiety (CM1 and CM2, respectively) that is no more than 10, 9, 8, 7, 6, 5, or 4 amino acids in length, and the cleavable moiety directly abuts a dimerization domain (DD1 and DD2, respectively) that is the Fc region of a human IgG, wherein the N-terminus of the Fc region is the first cysteine residue in the hinge region reading in the N- to C-direction (e.g., Cysteine 226 of human IgG1, using EU numbering). In some aspects, the dimerization domain is an IgG Fc region wherein the upper hinge residues have been deleted. For example, the Fc is a variant wherein N-terminal sequences EPKSCDKTHT (SEQ ID NO: 516), ERK, ELKTPLGDTTHT (SEQ ID NO: 517), or ESKYGPP (SEQ ID NO: 518) have been deleted.

In some embodiments, the first monomer construct comprises at least one linker. In some embodiments, the at least one linker is a linker L1 disposed between the CP1 and the CM1 and/or a linker L2 disposed between the CM1 and the DD1. In some embodiments, the second monomer construct comprises at least one linker. In some embodiments, the at least one linker is a linker L3 disposed between the CP2 and the CM2 and/or a linker L4 disposed between the CM2 and the DD2. In some embodiments, the first monomer construct comprises a linker L1 and the second monomer construct comprises a linker L3. In some embodiments, L1 and L3 are the same. In some embodiments, the first monomer construct comprises a linker L2 and the second monomer construct comprises a linker L4. In some embodiments, L2 and L4 are the same. In some embodiments, each linker has a total length of 1 amino acid to about 15 amino acids. In some embodiments, each linker has a total length of at least 5 amino acids. As used herein, the term "linker" refers to a peptide, the amino acid sequence of which is not a substrate for a protease.

In some embodiments, the first monomer construct comprises at least one linker, wherein each linker is independently selected from the group consisting of GSSGGSGGSGG (SEQ ID NO: 210); GGGS (SEQ ID NO: 2); GGGSGGGS (SEQ ID NO: 211); GGGSGGGSGGGS (SEQ ID NO: 212); GGGGSGGGGSGGGGS (SEQ ID NO: 213); GGGGSGGGGSGGGGSGGGGSGGGGS (SEQ ID NO: 214); GGGGSGGGGS (SEQ ID NO: 215); GGGGS (SEQ ID NO: 216); GS; GGGGSGS (SEQ ID NO: 217); GGGGSGGGGSGGGGSGS (SEQ ID NO: 218); GGSLDPKGGGGS (SEQ ID NO: 219); PKSCDKTH-TCPPCPAPELLG (SEQ ID NO: 220); SKYGPPCPPCPA-PEFLG (SEQ ID NO: 221); GKSSGSGSESKS (SEQ ID NO: 222); GSTSGSGKSSEGKG (SEQ ID NO: 223); GST-SGSGKSSEGSGSTKG (SEQ ID NO: 224); GST-SGSGKPGSGEGSTKG (SEQ ID NO: 225); GST-SGSGKPGSSEGST (SEQ ID NO: 226); (GS)n, (GGS)n, (GSGGS)n (SEQ ID NO: 227), (GGGS)n (SEQ ID NO: 228), (GGGGS)n (SEQ ID NO: 216), wherein each n is an integer of at least one; GGSG (SEQ ID NO: 229); GGSGG (SEQ ID NO: 230); GSGSG (SEQ ID NO: 231); GSGGG (SEQ ID NO: 232); GGGSG (SEQ ID NO: 233); GSSSG (SEQ ID NO: 234); GGGGSGGGGSGGGGS (SEQ ID NO: 213); GGGGSGGGGSGGGGSGGGGS (SEQ ID NO: 214);

and GSTSGSGKPGSSEGST (SEQ ID NO: 226). In some embodiments, the linker comprises a sequence of GGGS (SEQ ID NO: 2).

As used herein, the term "spacer" refers herein to an amino acid residue or a peptide incorporated at a free terminus of the mature ACC, for example between the signal peptide and the N-terminus of the mature ACC. In some aspects, a spacer (or "header") may contain glutamine (Q) residues. In some aspects, residues in the spacer minimize aminopeptidase and/or exopeptidase action to prevent cleavage of N-terminal amino acids. Illustrative and non-limiting spacer amino acid sequences may comprise or consist of any of the following exemplary amino acid sequences: QGQSGS (SEQ ID NO: 504); GQSGS (SEQ ID NO: 505); QSGS (SEQ ID NO: 506); SGS; GS; S; QGQSGQG (SEQ ID NO: 507); GQSGQG (SEQ ID NO: 508); QSGQG (SEQ ID NO: 509); SGQG (SEQ ID NO: 510); GQG; QG; G; QGQSGQ (SEQ ID NO: 511); GQSGQ (SEQ ID NO: 512); QSGQ (SEQ ID NO: 513); QGQSG (SEQ ID NO: 514); QGQS (SEQ ID NO: 515); SGQ; GQ; and Q. In some embodiments, spacer sequences may be omitted.

In some embodiments, the first monomer construct, comprises in a N- to C-terminal direction, the CP1, the CM1, and, linked directly or indirectly to the C-terminus of the CM1, the DD1. In some embodiments, the first polypeptide comprises in a C- to N-terminal direction, the CP1, the CM1, and, linked directly or indirectly to the N-terminus of the CM1, the DD1. In some embodiments, the second polypeptide comprises in a N- to C-terminal direction, the CP2, CM2, and, linked directly or indirectly to the C-terminus of the CM2, the DD2. In some embodiments, the second polypeptide comprises in a C- to N-terminal direction, the CP2, CM2, and, linked directly or indirectly to the CM2, the DD2.

In some embodiments, the first monomer construct comprises in an N- to C-terminal direction, the CP1, an optional linker, the CM1, an optional linker, and the DD1, wherein DD1 is an Fc region of an IgG, wherein the N-terminus of the Fc region is the first cysteine residue in the hinge region reading in the N- to C-direction (e.g., Cysteine 226 of human IgG1 or IgG4, using EU numbering), and wherein the CM1 and any linker(s) interposed between the CP1 and the N-terminal cysteine of the DD1 have a combined total length of no more than 15, 14, 13, 12, 11, 10, 9, 8, 7, 6, 5, or 4 amino acids, preferably no more than 10 amino acids, especially preferably no more than 7 amino acids. In some embodiments, the second monomer construct comprises in an N- to C-terminal direction, the CP2, an optional linker, the CM2, an optional linker, and the DD2, wherein DD2 is an Fc region of an IgG, wherein the N-terminus of the Fc region is the first cysteine residue in the hinge region reading in the N- to C-direction (e.g., Cysteine 226 of human IgG1 or IgG4, using EU numbering), and wherein the CM2 and any linker(s) interposed between the CP2 and the N-terminal cysteine of the DD2 have a combined total length of no more than 15, 14, 13, 12, 11, 10, 9, 8, 7, 6, 5, or 4 amino acids, preferably no more than 10 amino acids, especially preferably no more than 7 amino acids.

In some embodiments, the ACC is a homodimer in which the first monomer construct and the second monomer construct are identical and comprise the amino acid sequence of SEQ ID NO: 313. In some embodiments, the first monomer construct and the second monomer construct each comprise an amino acid sequence that is at least 90%, 95%, 96%, 97%, 98%, or 99% identical to SEQ ID NO: 313. In some embodiments, the first monomer construct and the second monomer construct each comprise, in an N- to C-terminal direction, SEQ ID NO:1; a CM comprising an amino acid sequence selected from the group consisting of SEQ ID NO: 41, SEQ ID NO: 68, and SEQ ID NO: 100; and a dimerization domain.

In some embodiments, the at least one CP1 and/or CP2 activity is a binding affinity ($K_D$) of the CP1 and/or the CP2 for its cognate receptor as determined using surface plasmon resonance. For example, where the CP1 or CP2 is an interferon, the cognate receptor may be the interferon-alpha/beta receptor (IFNAR). In some embodiments, the at least one CP1 and/or CP2 activity is a level of proliferation of lymphoma cells. In some embodiments, the at least one CP1 and/or CP2 activity is the level of JAK/STAT/ISGF3 pathway activation in a lymphoma cell. In some embodiments, the at least one activity is a level of secreted alkaline phosphatase (SEAP) production in a lymphoma cell. In some embodiments, the ACC (prior to exposure to proteases) is characterized by at least a 2-fold reduction in at least one CP1 and/or CP2 activity as compared to the control level. In some embodiments, the ACC is characterized by at least a 5-fold reduction in at least one CP1 and/or CP2 activity as compared to the control level. In some embodiments, the ACC is characterized by at least a 10-fold reduction in at least one activity of the CP1 and/or CP2 as compared to the control level. In some embodiments, the ACC is characterized by at least a 20-fold, 50-fold, 100-fold, 200-fold, 300-fold, 400-fold, 500-fold, 600-fold, 700-fold, 800-fold, 900-fold, 1000-fold, 1100-fold, 1200-fold, 1300-fold, 1400-fold, 1500-fold, 1600-fold, 1700-fold, 1800-fold, 1900-fold, 2000-fold reduction in at least one CP1 and/or CP2 activity as compared to the control level. In some embodiments, the control level of the at least one activity of the CP1 and/or CP2, is the activity of the CP1 and/or CP2 in the ACC following exposure of the ACC to the protease(s). In some embodiments, the control level of the at least one CP1 and/or CP2, is the corresponding CP1 and/or CP2 activity of a corresponding wildtype mature cytokine.

In some embodiments, the ACC is characterized by generating a cleavage product following exposure to the protease(s), wherein the cleavage product comprises the at least one activity of the CP1 and/or CP2. In some embodiments, the at least one activity of the CP1 and/or CP2 is anti-proliferation activity. In some embodiments, the control level is an EC50 value of the wildtype mature cytokine, and wherein ratio of EC50 (cleavage product) to EC50 (wildtype control level) is less than about 10, or less than about 9, or less than about 8, or less than about 7, or less than about 6, or less than about 5, or less than about 4, or less than about 3, or less than about 2, or less than about 1.5, or equal to about 1. In some embodiments, the EC50 of the cleavage product is approximately the same as the EC50 of the wildtype mature cytokine, demonstrating that the following cleavage, the activity of the CP1 and/or CP2 is fully recovered, or nearly fully recovered.

Provided herein are compositions comprising any one of the ACCs described herein. In some embodiments, the composition is a pharmaceutical composition. Also provided herein are kits comprising at least one dose of any one of the compositions described herein.

Provided herein are methods of treating a subject in need thereof comprising administering to the subject a therapeutically effective amount of any one of the ACCs described herein or any one of the compositions described herein. In some embodiments, the subject has been identified or diagnosed as having a cancer. In some non-limiting embodiments, the cancer is Kaposi sarcoma, hairy cell leukemia, chronic myeloid leukemia (CML), follicular lymphoma, renal cell cancer (RCC), melanoma, neuroblastoma, basal cell carcinoma, bladder cancer, breast cancer, colorectal cancer, cutaneous T-cell lymphoma, nasopharyngeal adenocarcimoa, non-small cell lung cancer (NSCLC), ovarian cancer, pancreatic cancer. In some non-limiting embodiments, the cancer is a lymphoma. In some non-limiting embodiments, the lymphoma is Burkitt's lymphoma.

Provided herein are nucleic acids encoding a polypeptide that comprises the CP1 and CM1 of any one of the ACCs described herein. In some embodiments, the polypeptide further comprises any one of the DD1 described herein. Also provided herein are nucleic acids encoding a polypeptide that comprises the CP2 and CM2 of any one of the ACCs described herein. When the monomers are identical, then the present disclosure provides a single nucleic acid encoding the monomer that dimerizes to form ACC. In some embodiments, the polypeptide further comprises any one of the DD2 described herein. Also provided herein are vectors comprising any one of the nucleic acids described herein. In some embodiments, the vector is an expression vector. Also provided herein are cells comprising any one of the nucleic acids described herein or any one of the vectors described herein.

Provided herein are pairs of nucleic acids that together encode a polypeptide that comprises the CP1 and CM1 of the first monomer construct and a polypeptide that comprises the CP2 and CM2 of the second monomer construct of any one of the ACCs described herein. Also provided herein are pairs of vectors that together comprise any of one of the pair of nucleic acids described herein. In some embodiments, the pair of vectors is a pair of expression vectors. Also provided herein are cells comprising any one of the pairs of nucleic acids described herein or any one of the pairs of vectors described herein. In other embodiments, the present invention provides a vector comprising the pair of vectors.

Provided herein are methods of producing an ACC comprising: culturing any one of the cells described herein in a liquid culture medium under conditions sufficient to produce the ACC; and recovering the ACC from the cell or the liquid culture medium. In some embodiments, the method further comprises: isolating the ACC recovered from the cell or the liquid culture medium. In some embodiments, the method further comprises: formulating isolated ACC into a pharmaceutical composition.

Provided herein are ACCs produced by any one of the methods described herein. Also provided herein are compositions comprising any one the ACCs described herein. Also provided herein are compositions of any one of the compositions described herein, wherein the composition is a pharmaceutical composition. Also provided herein are kits comprising at least one dose of any one of the compositions described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

The term "a" and "an" refers to one or more (i.e., at least one) of the grammatical object of the article. By way of example, "a cell" encompasses one or more cells.

As used herein, the terms "about" and "approximately," when used to modify an amount specified in a numeric value or range, indicate that the numeric value as well as reasonable deviations from the value known to the skilled person in the art. For example ±20%, ±10%, or ±5%, are within the intended meaning of the recited value where appropriate.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of," as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" or "consisting of" would find direct support due to this definition for any elements disclosed throughout this disclosure. Based on this definition, any element disclosed herein or incorporated by reference may be included in or excluded from the claimed invention.

As used herein, a plurality of compounds, elements, or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain molecules, constructs, compositions, elements, moieties, excipients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date. For example, a list of constructs, molecules, method steps, kits, or compositions described with respect to a construct, composition, or method is intended to and does find direct support for embodiments related to constructs, compositions, formulations, and methods described in any other part of this disclosure, even if those method steps, active agents, kits, or compositions are not re-listed in the context or section of that embodiment or aspect.

Unless otherwise specified, a "nucleic acid sequence encoding a protein" includes all nucleotide sequences that are degenerate versions of each other and thus encode the same amino acid sequence.

The term "N-terminally positioned" when referring to a position of a first domain or sequence relative to a second domain or sequence in a polypeptide primary amino acid sequence means that the first domain or sequence is located closer to the N-terminus of the polypeptide primary amino acid sequence than the second domain or sequence. In some embodiments, there may be additional sequences and/or domains between the first domain or sequence and the second domain or sequence.

The term "C-terminally positioned" when referring to a position of a first domain or sequence relative to a second domain or sequence in a polypeptide primary amino acid sequence means that the first domain or sequence is located closer to the C-terminus of the polypeptide primary amino acid sequence than the second domain or sequence. In some embodiments, there may be additional sequences and/or domains between the first domain or sequence and the second domain or sequence.

The term "exogenous" refers to any material introduced from or originating from outside a cell, a tissue, or an organism that is not produced by or does not originate from the same cell, tissue, or organism in which it is being introduced.

The term "transduced," "transfected," or "transformed" refers to a process by which an exogenous nucleic acid is introduced or transferred into a cell. A "transduced," "transfected," or "transformed" cell (e.g., mammalian cell) is one that has been transduced, transfected, or transformed with exogenous nucleic acid (e.g., a vector) that includes an exogenous nucleic acid encoding any of the activatable cytokine constructs described herein.

The term "nucleic acid" refers to a deoxyribonucleic acid (DNA) or ribonucleic acid (RNA), or a combination thereof, in either a single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the nucleic acids described herein, the nucleic acid is DNA. In some embodiments of any of the nucleic acids described herein, the nucleic acid is RNA.

Modifications can be introduced into a nucleotide sequence by standard techniques known in the art, such as site-directed mutagenesis and polymerase chain reaction (PCR)-mediated mutagenesis. Conservative amino acid substitutions are ones in which the amino acid residue is replaced with an amino acid residue having a similar side chain. Families of amino acid residues having similar side chains have been defined in the art. These families include: amino acids with acidic side chains (e.g., aspartate and glutamate), amino acids with basic side chains (e.g., lysine, arginine, and histidine), non-polar amino acids (e.g., alanine, valine, leucine, isoleucine, proline, phenylalanine, methionine, and tryptophan), uncharged polar amino acids (e.g., glycine, asparagine, glutamine, cysteine, serine, threonine and tyrosine), hydrophilic amino acids (e.g., arginine, asparagine, aspartate, glutamine, glutamate, histidine, lysine, serine, and threonine), hydrophobic amino acids (e.g., alanine, cysteine, isoleucine, leucine, methionine, phenylalanine, proline, tryptophan, tyrosine, and valine). Other families of amino acids include: aliphatic-hydroxy amino acids (e.g., serine and threonine), amide family (e.g., asparagine and glutamine), alphatic family (e.g., alanine, valine, leucine and isoleucine), aromatic family (e.g., phenylalanine, tryptophan, and tyrosine).

As used herein the phrase "specifically binds," or "immunoreacts with" means that the activatable antigen-binding protein complex reacts with one or more antigenic determinants of the desired target antigen and does not react with other polypeptides, or binds at much lower affinity, e.g., about or greater than $10^{-6}$ M.

The term "treatment" refers to ameliorating at least one symptom of a disorder. In some embodiments, the disorder being treated is a cancer and to ameliorate at least one symptom of a cancer.

BRIEF DESCRIPTION OF DRAWINGS

FIG. 3 provides the amino acid sequence of an illustrative activatable cytokine construct IFN-α2b-1204dL-hIgG4 (SEQ ID NO:309), wherein the first and second monomer constructs have an identical amino acid sequence. From N-terminus to C-terminus, the amino acid sequence of the first and second monomer constructs encodes: a mouse signal peptide (italicized text, not bolded); mature human interferon-α2b (underscored text); cleavable moiety 1204dL (bolded text); a linker (italicized and bolded text); and a human IgG4 Fc domain (text that is not italicized, bolded, or underscored).

FIG. 4 provides the amino acid sequence of an illustrative activatable cytokine construct IFN-α2b-1490DNI-hIgG4 (SEQ ID NO:311), wherein the first and second monomer constructs have an identical amino acid sequence. From N-terminus to C-terminus, the amino acid sequence encodes: a mouse signal peptide (italicized text, not bolded); mature human interferon-α2b (underscored text); cleavable moiety 1490DNI (bolded text, not italicized); a linker (italicized and bolded text); and a human IgG4 Fc domain (text that is not italicized, bolded, or underscored).

FIG. 13 depicts the results of a Daudi lymphoma cell-based assay for measuring the anti-proliferation activity (top) and the results of an HEK293 cell-based reporter assay for measuring the activity (bottom) of an ACC (ProC440), a protease-treated ACC (ProC440+uPA), and stem cell IFNα2b. The results indicated that activity was reduced 1000× by making the ACC structure of the present disclosure and, following treatment of the ACC with a protease, the activity of the cytokine in the ACC was restored to a level comparable to the recombinant parental cytokine.

FIG. 14A depicts the structure of ProC440, and shows that cleavage with uPa at the expected site in the CM was confirmed by Mass spectrometry analysis. In addition to sensitivity to uPa activation, ProC440 is cleaved by MMP4. FIG. 14B shows the analysis by Mass spectrometry identified a MMP14 cleavage site at the C-terminal extremity of IFNa (at L161) near the cleavable moiety. Protease activation with MMP14 restored activity to a level that is comparable to the recombinant cytokine.

FIG. 15 depicts the structures of ProC440 and ProC657 (N IFNα2b 0AA 1204DNIdL 0AA IgG4 KiHSS). The activities of the ACCs ProC440 and ProC657, a protease-treated ACC (ProC440+uPA), and stem cell IFNα2b were tested using IFN-responsive HEK293 cells. The results indicated that activity of ProC657 was reduced as compared to Stem Cell IFNα-2b or uPa-activated ProC440 but increased as compared to ProC440.

FIG. 16 (top) depicts anti-proliferative effects of ACC ProC440 in vivo using the Daudi xenograft tumor model. ACC ProC440 induced complete tumor regression at a dose as low as 0.1 mg/kg and slowed-down tumor growth at a dose of 0.02 mg/kg.

FIG. 16 (bottom) depicts anti-proliferative effects of Sylatron® in vivo using the Daudi xenograft tumor model.

FIG. 17A depicts the structure of ProC286 and the activity of ProC286 compared to the activity of Sylatron® in the Daudi apotosis assay. ProC286 and Sylatron® showed similar levels of activity indicating that ProC286 could be used as surrogate Sylatron® control to evaluate the tolerability of IFNα-2b in the hamster study.

FIG. 18 depicts the specific activity of IFNα-con (recombinant interferon alpha, a non-naturally occurring type-I interferon), ProC440+uPA, PEG-IFNα2b (Sylatron), and ProC440 and anticipated toxic doses in a dose-escalation study in vivo, e.g., at escalating doses of 0.08, 0.4, 2, 10, 15 mg/kg ("mpk").

FIG. 19 depicts the structure of ACC ProC859 universal interferon (top), the anti-proliferative effects of ACC ProC859 in a B16 mouse melanoma cell assay and the activity of ACC ProC859 in the IFN-responsive HEK293 assay.

DETAILED DESCRIPTION

Figure 1A:
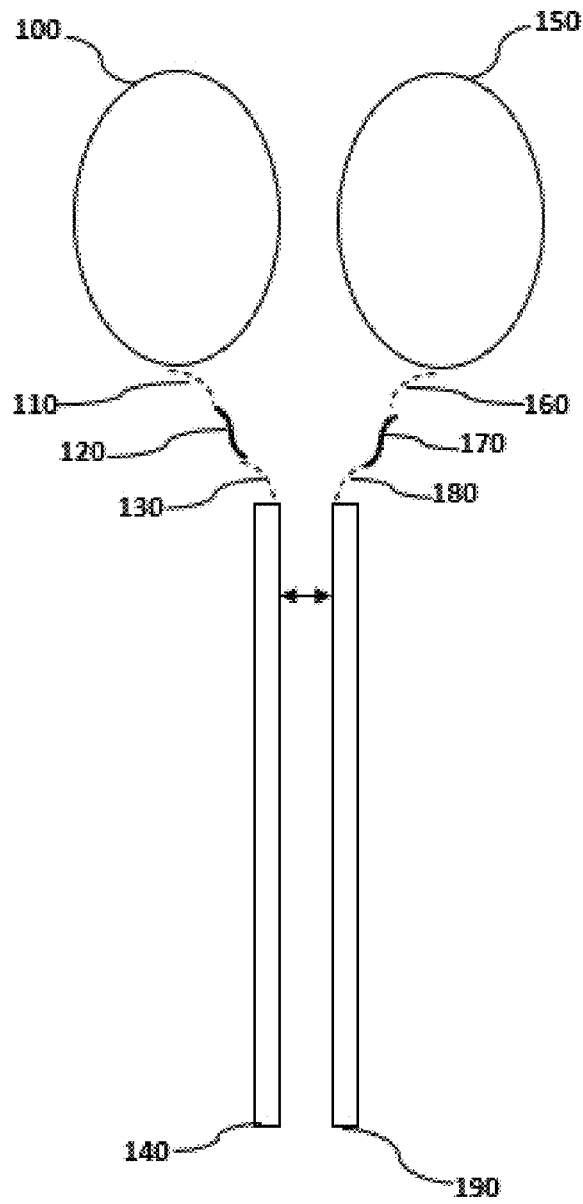
FIG. 1A is a schematic of an illustrative activatable cytokine construct comprising a first and second monomer construct that bind to each other either covalently or non-covalently via first and second dimerization domains DD1 140 and DD2 190, respectively. The first monomer construct comprises, from N-terminus to C-terminus, a first mature cytokine protein CP1 100, a first optional linker 110, a first cleavable moiety CM1 120, a second optional linker 130, and a first dimerization domain DD1 140. The second monomer construct comprises, from N-terminus to C-terminus, a second mature cytokine protein CP2 150, a third optional linker 160, a second cleavable moiety CM2 170, a fourth optional linker 180, and a second dimerization domain DD2 190.

Provided herein are activatable cytokine constructs (ACCs) that exhibit a reduced level of at least one activity of the corresponding cytokine, but which, after exposure to an activation condition, yield a cytokine product having substantially restored activity. Activatable cytokine constructs of the present invention may be designed to selectively activate upon exposure to diseased tissue, and not in normal tissue. As such, these compounds have the potential for conferring the benefit of a cytokine-based therapy, with potentially less of the toxicity associated with certain cytokine-based therapies.

Also provided herein are related intermediates, compositions, kits, nucleic acids, and recombinant cells, as well as related methods, including methods of using and methods of producing any of the activatable cytokine constructs described herein.

The inventors have surprisingly found that ACCs having the specific elements and structural orientations described herein appear potentially effective in improving the safety and therapeutic index of cytokines in therapy, particularly for treating cancers. While cytokines are regulators of innate and adaptive immune system and have broad anti-tumor activity in pre-clinical models, their clinical success has been limited by systemic toxicity and poor systemic exposure to target tissues. The inventors have surprisingly found that ACCs having the specific elements and structural orientations described herein appear to reduce the systemic toxicity associated with cytokine therapeutics and improve targeting and exposure to target issues. As such, the present disclosure provides a method of reducing target-mediated drug disposition (TMDD) of cytokine therapeutics by administering ACCs having the specific elements and structural orientations described herein to a subject. As such, the invention solves the problem of sequestration of a significant fraction of the administered cytokine dose by normal tissues, which is a problem that limits the fraction of the dose available in the systemic circulation to reach the target tissues, e.g., cancerous tissue, in conventional cytokine therapeutics. The present cytokine construct localizes target binding to tumor tissues, thereby maintaining potency, reducing side effects, enabling new target opportunities, improving the therapeutic window for validated targets, creating a therapeutic window for undruggable targets, and providing multiple binding modalities. The present disclosure enables safe and effective systemic delivery, thereby avoiding the dose-dependent toxicities of conventional systemic cytokine therapies, and also avoids a requirement for intra-tumoral injection. The present disclosure provides a means for imparting localized anti-viral activity, immunomodulatory activity, antiproliferative activity and pro-apoptotic activity. The inventors surprisingly found that dimerization of the first and second monomer constructs achieves high reduction of cytokine activity, particularly higher reduction than when a single cytokine is attached to a dimerization domain. See FIG. 15.

Additionally, the inventors have discovered that the degree of reduction of cytokine activity can be adjusted by varying the flexible linker length or the linking region length. The inventors surprisingly found that reduction of cytokine activity on the order of 1,000 fold or more can be achieved by attaching a cytokine via a short protease cleavable sequence to a sterically constrained dimerization domain (such as an Fc domain of a human IgG that is truncated at the first cysteine in the hinge region, e.g., Cys226 as numbered by EU numbering). Surprisingly, protease cleavage occurs despite the steric constraint, and full cytokine activity is regained upon cleavage of the cytokine from the dimerization domain.

Applicant's U.S. Provisional App. No. 63/008,542, filed Apr. 10, 2020, which describes certain activatable cytokine constructs, is incorporated herein by reference in its entirety.

Activatable Cytokine Constructs

Activatable cytokine constructs of the present invention are dimer complexes comprising a first monomer construct and a second monomer construct. Dimerization of the monomeric components is facilitated by a pair of dimerization domains. In one aspect, each monomer construct includes a cytokine protein, a cleavable moiety, and a dimerization domain (DD). In one aspect, one monomer construct includes a cytokine protein, a cleavable moiety, and a DD, whereas the other monomer construct includes a cytokine protein and a DD, but not a cleavable moiety. In one aspect, one monomer construct includes a cytokine protein, a cleavable moiety, and a DD, whereas the other monomer construct includes a protein or peptide that lacks cytokine activity and a DD, but not a cleavable moiety. In a specific embodiment, the present invention provides an activatable cytokine construct (ACC) that includes a first monomer construct and a second monomer construct, wherein:

(a) the first monomer construct comprises a first mature cytokine protein (CP1), a first cleavable moiety (CM1), and a first dimerization domain (DD1),
   wherein the CM1 is positioned between the CP1 and the DD1; and
(b) the second monomer construct comprises a second mature cytokine protein (CP2), a second cleavable moiety (CM2), and a second dimerization domain (DD2),
   wherein the CM2 is positioned between the CP2 and the DD2;
wherein the DD1 and the DD2 bind each other thereby forming a dimer of the first monomer construct and the second monomer construct; and
wherein the ACC is characterized by having a reduced level of at least one CP1 and/or CP2 activity as compared to a control level of the at least one CP1 and/or CP2 activity.

The term "activatable" when used in reference to a cytokine construct, refers to a cytokine construct that exhibits a first level of one or more activities, whereupon exposure to a condition that causes cleavage of one or both cleavable moieties results in the generation of a cytokine construct that exhibits a second level of the one or more activities, where the second level of activity is greater than the first level of activity. Non-limiting examples of an activities include any of the exemplary activities of a cytokine described herein or known in the art.

The term "mature cytokine protein" refers herein to a cytokine protein that lacks a signal sequence. A cytokine protein (CP) may be a mature cytokine protein or a cytokine protein with a signal peptide. Thus, the ACCs of the present disclosure may include a mature cytokine protein sequence in some aspects. In some aspects, the ACCs of the present disclosure may include a mature cytokine protein sequence and, additionally, a signal sequence. In some aspects, the ACCs of the present disclosure may include sequences disclosed herein, including or lacking the signal sequences recited herein.

The terms "cleavable moiety" and "CM" are used interchangeably herein to refer to a peptide, the amino acid sequence of which comprises a substrate for a sequence-specific protease. Cleavable moieties that are suitable for use as CM1 and/or CM2 include any of the protease substrates that are known the art. Exemplary cleavable moieties are described in more detail below.

The terms "dimerization domain" and "DD" are used interchangeably herein to refer to one member of a pair of dimerization domains, wherein each member of the pair is capable of binding to the other via one or more covalent or non-covalent interactions. The first DD and the second DD may be the same or different. Exemplary DDs suitable for use as DD1 and or DD2 are described in more detail herein below.

As used herein, a polypeptide, such as a cytokine or an Fc domain, may be a wild-type polypeptide (e.g., a naturally-existing polypeptide) or a variant of the wild-type polypeptide. A variant may be a polypeptide modified by substitution, insertion, deletion and/or addition of one or more amino acids of the wild-type polypeptide, provided that the variant retains the basic function or activity of the wild-type polypeptide. In some examples, a variant may have altered (e.g., increased or decreased) function or activity comparing with the wild-type polypeptide. In some aspects, the variant may be a functional fragment of the wild-type polypeptide. The term "functional fragment" means that the sequence of the polypeptide (e.g., cytokine) may include fewer amino acids than the full-length polypeptide sequence, but sufficient polypeptide chain length to confer activity (e.g., cytokine activity).

The first and second monomer constructs may further comprise additional elements, such as, for example, one or more linkers, and the like. The additional elements are described below in more detail. The organization of the CP, CM, and DD components in each of the first and second monomer constructs may be arranged in the same order in each monomer construct. The CP1, CM1, and DD1 components may be the same or different as compared to the corresponding CP2, CM2, and DD2, in terms of, for example, molecular weight, size, amino acid sequence of the CP and CM components (and the DD components in embodiments where the DD components are polypeptides), and the like. Thus, the resulting dimer may have symmetrical or asymmetrical monomer construct components.

In some embodiments, the first monomer construct comprises, from N- to C-terminus of the CP and CM components, the CP1, the CM1, and, linked directly or indirectly (via a linker) to the C-terminus of the CM1, the DD1. In other embodiments, the first monomer construct comprises from C- to N-terminus of the CP and CM components, the CP1, the CM1, and, linked directly or indirectly (via a linker) to the N-terminus of the CM1, the DD1. In some embodiments, the second monomer construct comprises, from N- to C-terminal terminus of the CP and CM components, the CP2, the CM2, and, linked directly or indirectly (via a linker) to the C-terminus of the CM2, the DD2. In other embodiments, the second monomer construct comprises, from C- to N-terminus of the CP and CM components, the CP2, the CM2, and, linked directly or indirectly (via a linker) to the N-terminus of the CM2, the DD2.

In certain embodiments, the first and second monomeric constructs are oriented such that the components in each member of the dimer are organized in the same order from N-terminus to C-terminus of the CP and CM components. A schematic of an illustrative ACC is provided in FIG. 1A. With reference to FIG. 1A, the ACC comprises, from N-terminus to C-terminus of the CP and CM components: (1) a first monomer construct having a CP1 100; a CM1 120 C-terminally positioned relative to the CP1 100; an optional linker 110, which, if present, is positioned between the C-terminus of the CP1 100 and the N-terminus of the CM1 120; a DD1 140; and an optional linker 130, which, if present, is positioned between the C-terminus of the CM1 120; and the DD1 140; (2) a second monomeric construct having a CP2 150; a CM2 170 that is C-terminally positioned relative to the CP2 150; an optional linker 160, which, if present, is positioned between the C-terminus of the CP2 150 and the N-terminus of the CM2 170; a DD2 190; and an optional linker 180, which, if present, is positioned between the C-terminus of the CM2 170 and the DD2 190; and (3) one or more covalent or non-covalent bonds (←→).

Figure 1B:
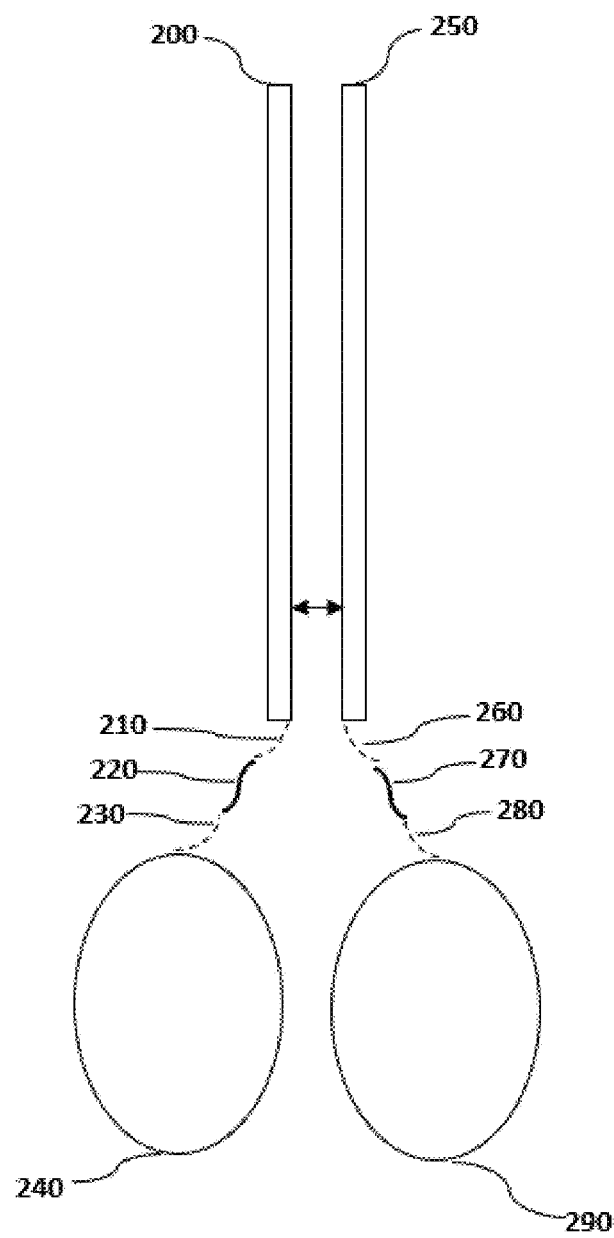
FIG. 1B is a schematic of an illustrative activatable cytokine construct comprising a first and second monomer construct that bind to each other either covalently or non-covalently via first and second dimerization domains DD1 200 and DD2 250, respectively. The first monomer construct comprises, from N-terminus to C-terminus, a first dimerization domain DD1 200, a second optional linker 210, a first cleavable moiety CM1 220, a first optional linker 230, and a first mature cytokine protein CP1 240. The second monomer construct comprises, from N-terminus to C-terminus, a second dimerization domain DD2 250, a fourth optional linker 260, a second cleavable moiety CM2 270, a third optional linker 280, and a second mature cytokine protein CP2 290.

A schematic of a further illustrative ACC, with its components organized in the reverse orientation of the ACC is provided in FIG. 1B. With reference to FIG. 1B, the ACC comprises, from N-terminus to C-terminus of the CP and CM components: (1) a first monomeric construct having a DD1 200; a CM1 220; an optional linker 210, which, if present, is positioned between the DD1 200 and the N-terminus of the CM1 220; a CP1 240 C-terminally positioned relative to the CM1 220; and an optional linker 230, which, if present, is positioned between the C-terminus of the CM1 220 and the N-terminus of the CP1 240; (2) a second monomeric construct having a DD2 250; a CM2 270; an optional linker 260, which, if present, is positioned between the DD2 250 and the N-terminus of the CM2 270; a CP2 290 C-terminally positioned relative to the CM2 270; and an optional linker 280, which, if present, is positioned between the C-terminus of the CM2 290 and the N-terminus of the CP2 290; and (3) one or more covalent or non-covalent bonds (←→).

Figure 2A:
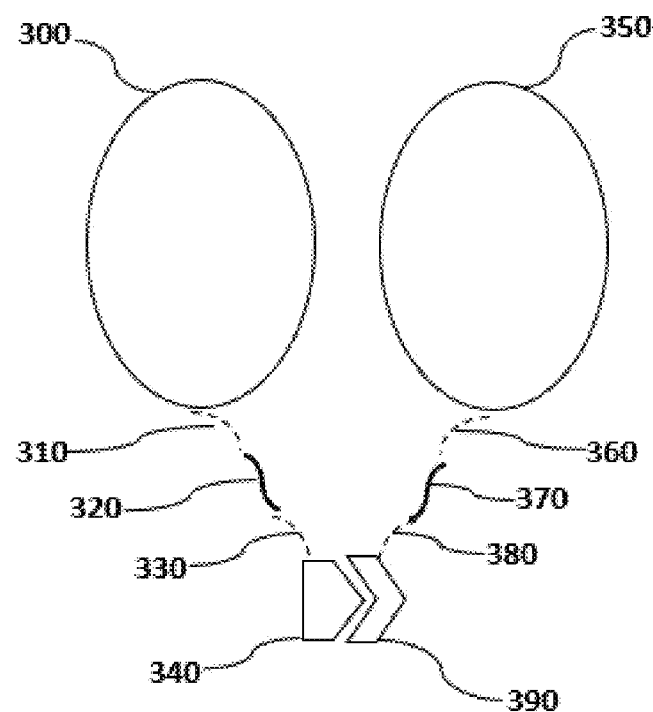
FIG. 2A is a schematic of an illustrative activatable cytokine construct comprising a first and second monomer construct that bind to each other by non-covalent means via first and second dimerization domains DD1 340 and DD2 390, respectively. The first monomer construct comprises, from N-terminus to C-terminus, a first mature cytokine protein CP1 300, a first optional linker 310, a first cleavable moiety CM1 320, a second optional linker 330, and a first dimerization domain DD1 340. The second monomer construct comprises, from N-terminus to C-terminus, a second mature cytokine protein CP2 350, a third optional linker 360, a second cleavable moiety CM2 370, a fourth optional linker 380, and a second dimerization domain DD2 390.
Figure 2B:
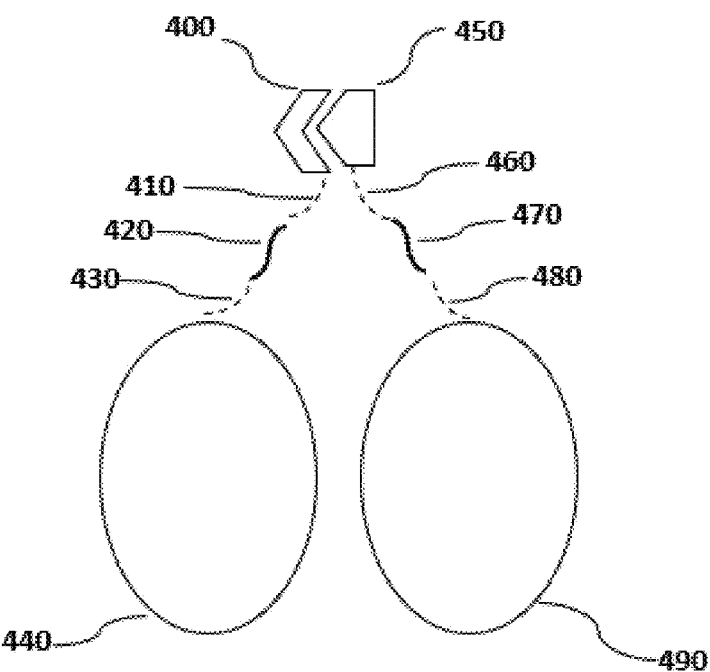
FIG. 2B is a schematic of an illustrative activatable cytokine construct comprising a first and second monomer construct that bind to each other by non-covalent means via first and second dimerization domains DD1 400 and DD2 450, respectively. The first monomer construct comprises, from N-terminus to C-terminus, a first dimerization domain DD1 400, a second optional linker 410, a first cleavable moiety CM1 420, a first optional linker 430, and a first mature cytokine protein CP1 440. The second monomer construct comprises, from N-terminus to C-terminus, a second dimerization domain DD2 450, a fourth optional linker 460, a second cleavable moiety CM2 470, a third optional linker 480, and a second mature cytokine protein CP2 490.
Figure 5:
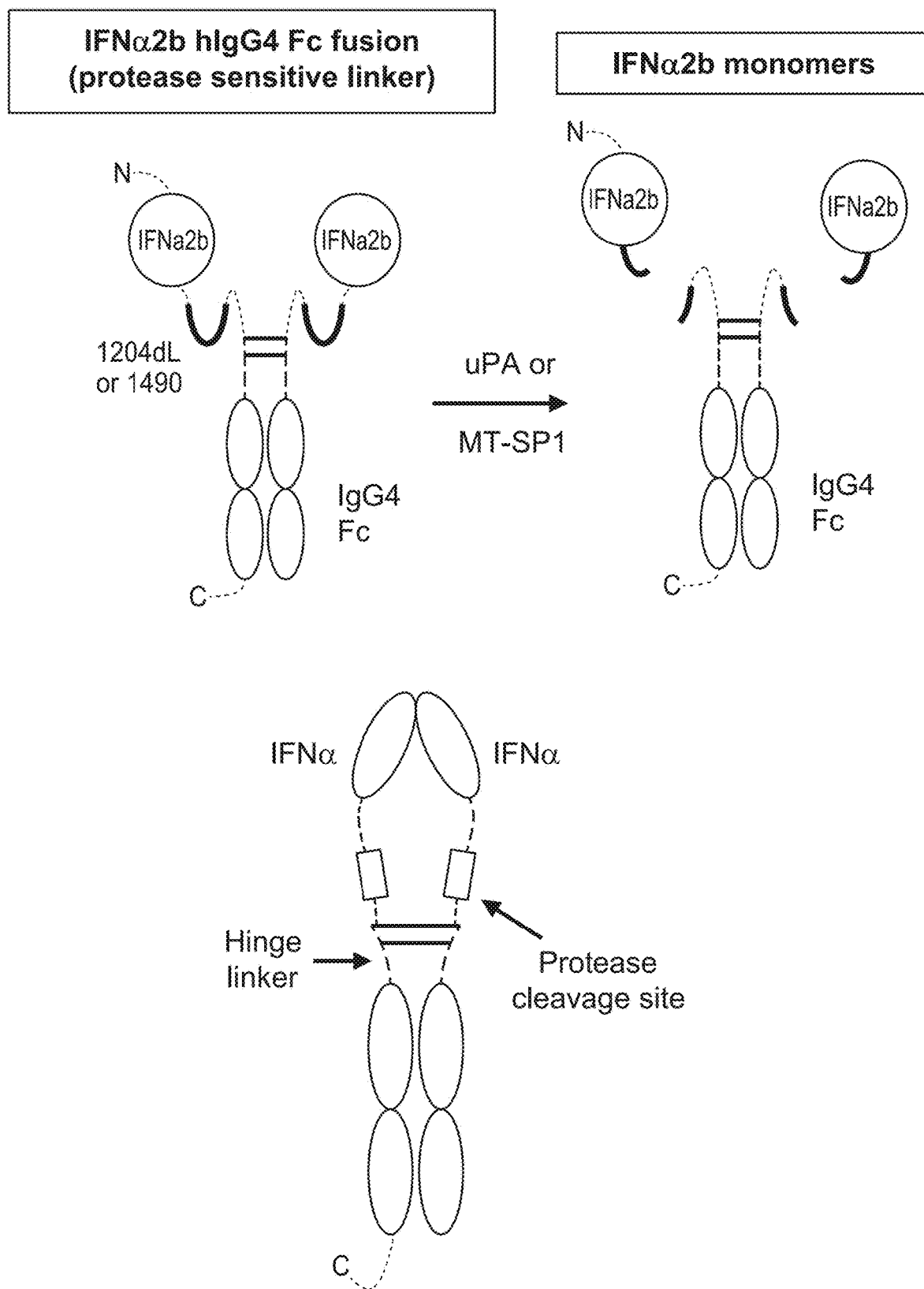
FIG. 5 depicts the cleavage reaction of activatable cytokine construct IFNα-2b-hIgG4 Fc (with either cleavable moiety 1204dL or cleavable moiety 1490) and a protease (either uPA or MT-SP1), which generates monomeric mature IFNα-2b.

FIG. 2A is a schematic of an illustrative activatable cytokine construct comprising a first and second monomer construct that bind to each other by non-covalent means via first and second dimerization domains DD1 340 and DD2 390, respectively. The first monomer construct comprises, from N-terminus to C-terminus of the CP and CM components, a first mature cytokine protein CP1 300, a first optional linker 310, a first cleavable moiety CM1 320, a second optional linker 330, and a first dimerization domain DD1 340. The second monomer construct comprises, from N-terminus to C-terminus, a second mature cytokine protein CP2 350, a third optional linker 360, a second cleavable moiety CM2 370, a fourth optional linker 380, and a second dimerization domain DD2 390.

FIG. 2B is a schematic of an illustrative activatable cytokine construct comprising a first and second monomer construct that bind to each other by non-covalent means via first and second dimerization domains DD1 400 and DD2 450, respectively. The first monomer construct comprises, from N-terminus to C-terminus of the CP and CM components, a first dimerization domain DD1 400, a second optional linker 410, a first cleavable moiety CM1 420, a first optional linker 430, and a first mature cytokine protein CP1 440. The second monomer construct comprises, from N-terminus to C-terminus of the CP and CM components, a second dimerization domain DD2 450, a fourth optional linker 460, a second cleavable moiety CM2 470, a third optional linker 480, and a second mature cytokine protein CP2 490. In alternative aspects, one of the two moieties depicted as CP1 440 and CP2 490 is a truncated cytokine protein that lacks cytokine activity. For example, either CP1 or CP2 may be a truncated interferon alpha 2b having the first 151 amino acids of wild-type interferon alpha 2b. In alternative aspects, one of the two moieties depicted as CP1 440 and CP2 490 is a mutated cytokine protein that lacks cytokine activity. For example, either CP1 or CP2 may be a truncated interferon alpha 2b having a L130P mutation. In alternative aspects, one of the two moieties depicted as CP1 440 and CP2 490 is a polypeptide sequence that lacks cytokine activity, e.g., a signal moiety and/or a stub sequence. In alternative aspects, a first one of the two moieties depicted as CP1 440 and CP2 490 is a polypeptide sequence that binds with high affinity to a second one of the two moieties depicted as CP1 440 and CP2 490 and reduces the cytokine activity of the second moiety as compared to the control level of the second moiety.

The ACC structure was discovered to be highly effective at reducing activity of the mature cytokine protein components in a way that does not lead to substantially impaired cytokine activity after activation. The activation condition for the ACCs described herein is exposure to a protease that can cleave at least one of the cleavable moieties (CMs) in the ACC. As demonstrated in the Examples, activation of the ACC resulted in substantial recovery of cytokine activity. The results suggest that conformation of the cytokine components was not irreversibly altered within the context of the ACC. Significantly, the ACC does not rely on having to identify and utilize a peptide mask that has binding affinity for the cytokine protein component to achieve a masking effect. Thus, the ACC does not comprise a peptide mask having binding affinity for the cytokine protein component. The present inventors unexpectedly found that the ACC structure is sufficient to avoid off-target and undesired activity and/or toxic side effects of cytokines without use of any masking moieties having binding affinity for the cytokine protein component. Thus, the ACCs described herein are characterized in that they lack affinity masking moieties or peptide masking moieties.

The ACC may employ any of a variety of mature cytokine proteins, cleavable moieties, and DDs as the CP1, CP2, CM1, CM2, DD1, and DD2, respectively. For example, any of a variety of mature cytokine proteins that are known in the art or sequence and/or truncation variants thereof, may be suitable for use as either or both CP1 and CP2 components of the ACC. The mature cytokine proteins, CP1 and CP2 may be the same or different. In certain specific embodiments, CP1 and CP2 are the same. In other embodiments, CP1 and CP2 are different. The ACC may comprise additional amino acid residues at either or both N- and/or C-terminal ends of the CP1 and/or CP2.

In some embodiments, the CP1 and/or the CP2 may each independently comprise a mature cytokine protein selected from the group of: an interferon (such as, for example, an interferon alpha, an interferon beta, an interferon gamma, an interferon tau, and an interferon omega), an interleukin (such as, for example, IL-1α, IL-1β, IL-1RA, IL-18, IL-2, IL-4, IL-7, IL-9, IL-13, IL-15, IL-3, IL-5, GM-CSF, IL-6, IL-11, IL-21), G-CSF, IL-12, LIF, OSM, IL-10, IL-20, IL-14, IL-16, IL-17, CD154, LT-0, TNF-α, TNF-β, 4-1BBL, APRIL, CD70, CD153, CD178, GITRL, LIGHT, OX40L, TALL-1, TRAIL, TWEAK, TRANCE, TGF-β1, TGF-β1, TGF-β3, EPOo, TPO, Flt-3L, SCF, M-CSF, and MSP, and the like, as well as sequence and truncation variants thereof. For example, sequences of such proteins include those exemplified herein and additional sequences can be obtained from ncbi.nlm.nih.gov/protein. Truncation variants that are suitable for use in the ACCs of the present invention include any N- or C-terminally truncated cytokine that retains a cytokine activity. Exemplary truncation variants employed in the present invention include any of the truncated cytokine polypeptides that are known in the art (see, e.g., Slutzki et al., *J. Mol. Biol.* 360:1019-1030, 2006, and US 2009/0025106), as well as cytokine polypeptides that are N- and/or C-terminally truncated by 1 to about 40 amino acids, 1 to about 35 amino acids, 1 to about 30 amino acids, 1 to about 25 amino acids, 1 to about 20 amino acids, 1 to about 15 amino acids, 1 to about 10 amino acids, 1 to about 8 amino acids, 1 to about 6 amino acids, 1 to about 4 amino acids, that retain a cytokine activity. In some of the foregoing embodiments, the truncated CP is an N-terminally truncated CP. In other embodiments, the truncated CP is a C-terminally truncated CP. In certain embodiments, the truncated CP is a C- and an N-terminally truncated CP.

In some embodiments, the CP1 and/or the CP2 each independently comprise an amino acid sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100% identical) to a cytokine reference sequence selected from the group consisting of: SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 12, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, and SEQ ID NO: 209. The percentage of sequence identity refers to the level of amino acid sequence identity between two or more peptide sequences when aligned using a sequence alignment program, e.g., the suite of BLAST programs, publicly available on the Internet at the NCBI website. See also Altschul et al., J. Mol. Biol. 215:403-10, 1990. In some aspects, the ACC includes an interferon alpha 2b mutant, for example, an interferon alpha 2b molecule having a mutation at position L130, e.g., L130P mutation, as either CP1 or CP2. In some aspects, the ACC includes an interferon alpha 2b mutant having a mutation at position 124, F64, 160, 163, F64, W76, 1116, L117, F123, or L128, or a combination thereof. For example, the interferon alpha 2b mutant may include mutations 1116 to T, N. or R; L128 to N, H, or R; 124 to P or Q; L117H; or L128T, or a combination thereof. In some aspects, the interferon alpha 2b mutant may include mutations 124Q, 160T, F64A, W76H, 1116R, and L128N, or a subset thereof. In some aspects, the ACC includes as one of CP1 and CP2 a truncated interferon alpha 2b molecule that lacks cytokine activity. For example, the truncated interferon alpha 2b may consist of 151 or fewer amino acids of interferon alpha 2b, e.g., any one of amino acids in the wild-type interferon alpha 2b sequence from N to C-terminus: 1 to 151, 1 to 150, 1 to 149, 1 to 148, . . . 1 to 10, 1 to 9, 1 to 8, 1 to 7, 1 to 6, or 2 to 151, 3 to 151, 4 to 151, 5 to 150, 6 to 149, 7 to 148, 8 to 147, or any intervening sequence of amino acids or mutants thereof.

In certain specific embodiments, the CP1 and/or the CP2 comprise an interferon. Interferons that are suitable for use in the constructs of the present invention as CP1 and/or CP2 include, for example, an interferon-alpha, an interferon-beta, an interferon-omega, and an interferon-tau. In some embodiments, when the interferon is an interferon alpha, it may be an interferon alpha-2α, an interferon alpha-2b, or an interferon alpha-n3. Further examples of interferon alpha include interferon alpha-1, interferon alpha-4, interferon alpha-5, interferon alpha-6, interferon alpha-7, interferon alpha-8, interferon alpha-10, interferon alpha-13, interferon alpha-14, interferon alpha-16, interferon alpha-17, and interferon alpha-21. In some embodiments, the interferon is a recombinant or purified interferon alpha. In certain embodiments, when the interferon is an interferon-beta, it is selected from the group consisting of an interferon beta-1a and an interferon beta-1b. In some embodiments, the CP1 and/or the CP2 comprises an IFab domain of an interferon alpha or an interferon beta. The IFab domain is responsible for the cytokine release and antivirus functions of interferons. Exemplary IFab sequences are provided in SEQ ID Nos: 325-334.

In some embodiments, the CP1 and/or the CP2 exhibit(s) an interferon activity and include(s) an amino acid sequence that is at least 80% identical, at least 82% identical, at least 84% identical, at least 86% identical, at least 88% identical, at least 90% identical, at least 92% identical, at least 94% identical, at least 96% identical, at least 98% identical, or at least 99% identical, or 100% identical to an interferon alpha reference sequence selected from the group consisting of SEQ ID NO: 1, SEQ ID NO: 101, SEQ ID NO: 102, SEQ ID NO: 103, SEQ ID NO: 104, and SEQ ID NO: 105. In certain specific embodiments, the interferon alpha reference sequence is SEQ ID NO: 1 (human interferon alpha-2b). In some embodiments, the CP1 and/or the CP2 comprise a mature alpha interferon having an amino acid sequence selected from the group consisting of SEQ ID NO: 1, SEQ ID NO: 101, SEQ ID NO: 102, SEQ ID NO: 103, SEQ ID NO: 104, and SEQ ID NO: 105. In certain embodiments, the CP1 and/or the CP2 comprise a mature human alpha interferon having the amino acid sequence of SEQ ID NO: 1. In some of the above-described embodiments, the CP1 and the CP2 comprise the same amino acid sequence.

In other embodiments, the CP1 and/or the CP2 exhibit(s) an interferon activity and include(s) an amino acid sequence that is at least 80% identical, at least 82% identical, at least 84% identical, at least 86% identical, at least 88% identical, at least 90% identical, at least 92% identical, at least 94% identical, at least 96% identical, at least 98% identical, or at least 99% identical, or 100% identical to an interferon beta reference sequence selected from the group consisting of SEQ ID NO: 106, SEQ ID NO: 107, SEQ ID NO: 108, and SEQ ID NO: 109. In certain embodiments, the interferon beta reference sequence is a human interferon beta reference sequence selected from the group consisting of SEQ ID NO: 106 and SEQ ID NO: 107. In some embodiments, the CP1 and/or the CP2 comprise a mature beta interferon having an amino acid sequence selected from the group consisting of SEQ ID NO: 106, SEQ ID NO: 107, SEQ ID NO: 108, and SEQ ID NO: 109. In some of the above-described embodiments, the CP1 and the CP2 comprise the same amino acid sequence.

In some embodiments, the CP1 and/or CP2 exhibit(s) an interferon activity and include(s) an amino acid sequence that is at least 80% identical, at least 82% identical, at least 84% identical, at least 86% identical, at least 88% identical, at least 90% identical, at least 92% identical, at least 94% identical, at least 96% identical, at least 98% identical, or at least 99% identical, or 100% identical to an interferon omega reference sequence corresponding to SEQ ID NO: 110 (human interferon omega). In certain specific embodiments, the CP1 and/or CP2 comprise a mature human omega interferon having the amino acid sequence of SEQ ID NO: 110. In some of the above-described embodiments, the CP1 and the CP2 comprise the same amino acid sequence.

In some embodiments, the CP1 and/or the CP2 exhibit(s) an interleukin activity and include(s) an amino acid sequence that is at least 80% identical, at least 82%, at least 84%, at least 86%, at least 88%, at least 90%, at least 92%, at least 94%, at least 95%, at least 96%, at least 97%, at least 98%, or at least 99% identical or 100% identical to an interleukin reference sequence selected from the group consisting of: SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 12, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 143, SEQ ID NO: 144, SEQ ID NO: 145, SEQ ID NO: 146, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, and SEQ ID NO: 160. In some embodiments, CP1 and/or CP2 comprises a mature interleukin having an amino acid sequence selected from the group consisting of: SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 12, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 143, SEQ ID NO: 144, SEQ ID NO: 145, SEQ ID NO: 146, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, and SEQ ID NO: 160. In some of the above-described embodiments, the CP1 and the CP2 comprise the same amino acid sequence.

In some embodiments, CP1 and/or CP2 exhibit(s) an interleukin activity and include(s) an amino acid sequence that is at least 80% identical, at least 82%, at least 84%, at least 86%, at least 88%, at least 90%, at least 92%, at least 94%, at least 95%, at least 96%, at least 97%, at least 98%, or at least 99% identical to an interleukin reference sequence selected from the group consisting of SEQ ID NO: 111 (human IL-1 alpha), SEQ ID NO: 113 (human IL-1 beta), SEQ ID NO: 115 (human IL-1RA), SEQ ID NO: 117 (human IL-18), SEQ ID NO: 119 (human IL-2), SEQ ID NO: 121 (human IL-4), SEQ ID NO: 123 (human IL-7), SEQ ID NO: 125 (human IL-9), SEQ ID NO: 127 (human IL-13), SEQ ID NO: 129 (human IL-15), SEQ ID NO: 131 (human IL-3), SEQ ID NO: 133 (human IL-5), SEQ ID NO: 137 (human IL-6), SEQ ID NO: 139 (human IL-11), SEQ ID NO: 143 (human IL-12 alpha), SEQ ID NO: 144 (human IL-12 beta), SEQ ID NO: 151 (human IL-10), SEQ ID NO: 153 (human IL-20); SEQ ID NO: 155 (human IL-14), SEQ ID NO: 157 (human IL-16), and SEQ ID NO: 159 (human IL-17). In certain of these embodiments, CP1 and/or CP2 comprise an amino acid sequence from the group consisting of SEQ ID NO: 111 (human IL-1 alpha), SEQ ID NO: 113 (human IL-1 beta), SEQ ID NO: 115 (human IL-1RA), SEQ ID NO: 117 (human IL-18), SEQ ID NO: 119 (human IL-2), SEQ ID NO: 121, SEQ ID NO: 123 (human IL-7), SEQ ID NO: 125 (human IL-9), SEQ ID NO: 127 (human IL-13), SEQ ID NO: 129 (human IL-15), SEQ ID NO: 131 (human IL-3), SEQ ID NO: 133 (human IL-5), SEQ ID NO: 137 (human IL-6), SEQ ID NO: 139 (human IL-11), SEQ ID NO: 143 (human IL-12 alpha), SEQ ID NO: 144 (human IL-12 beta), SEQ ID NO: 151 (human IL-10), SEQ ID NO: 153 (human IL-20); SEQ ID NO: 155 (human IL-14), SEQ ID NO: 157 (human IL-16), and SEQ ID NO: 159 (human IL-17). In some of the above-described embodiments, the CP1 and the CP2 comprise the same amino acid sequence.

The number of amino acids in the sequence of the cytokine proteins employed may vary, depending on the specific cytokine protein employed. In some embodiments, the CP1 and/or the CP2 includes a total of about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, about 10 amino acids to about 80 amino acids, about 10 amino acids to about 60 amino acids, about 10 amino acids to about 40 amino acids, about 10 amino acids to about 20 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 250 amino acids, about 20 amino acids to about 200 amino acids, about 20 amino acids to about 150 amino acids, about 20 amino acids to about 100 amino acids, about 20 amino acids to about 80 amino acids, about 20 amino acids to about 60 amino acids, about 20 amino acids to about 40 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 250 amino acids, about 40 amino acids to about 200 amino acids, about 40 amino acids to about 150 amino acids, about 40 amino acids to about 100 amino acids, about 40 amino acids to about 80 amino acids, about 40 amino acids to about 60 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 250 amino acids, about 60 amino acids to about 200 amino acids, about 60 amino acids to about 150 amino acids, about 60 amino acids to about 100 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 250 amino acids, about 80 amino acids to about 200 amino acids, about 80 amino acids to about 150 amino acids, about 80 amino acids to about 100 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 700 amino acids, about 500 amino acids to about 650 amino acids, about 500 amino acids to about 600 amino acids, about 500 amino acids to about 550 amino acids, about 550 amino acids to about 700 amino acids, about 550 amino acids to about 650 amino acids, about 550 amino acids to about 600 amino acids, about 600 amino acids to about 700 amino acids, about 600 amino acids to about 650 amino acids, or about 650 amino acids to about 700 amino acids. In some embodiments, CP1 and/or the CP2 is a mature wildtype human cytokine protein.

Each monomer construct of the ACC may employ any of a variety of dimerization domains. Suitable DDs include both polymeric (e.g., a synthetic polymer, a polypeptide, a polynucleotide, and the like) and small molecule (non-polymeric moieties having a molecular weight of less than about 1 kilodalton, and sometimes less than about 800 daltons) types of moieties. The pair of DDs may be any pair of moieties that are known in the art to bind to each other.

For example, in some embodiments, the DD1 and the DD2 are members of a pair selected from the group of: a sushi domain from an alpha chain of human IL-15 receptor (IL15Rα) and a soluble IL-15; barnase and barnstar; a PKA and an AKAP; adapter/docking tag molecules based on mutated RNase I fragments; a pair of antigen-binding domains (e.g., a pair of single domain antibodies); soluble N-ethyl-maleimide sensitive factor attachment protein receptors (SNARE) modules based on interactions of the proteins syntaxin, synaptotagmin, synaptobrevin, and SNAP25; a single domain antibody (sdAb) and corresponding epitope; an antigen-binding domain (e.g., a single chain antibody such as a single chain variable fragment (scFv), a single domain antibody, and the like) and a corresponding epitope; coiled coil polypeptide structions (e.g., Fos-Jun coiled coil structures, acid/base coiled-coil helices, Glu-Lys coiled coil helices, leucine zipper structures), small molecule binding pairs such as biotin and avidin or streptavidin, amine/aldehyde, lectin/carbohydrate; a pair of polymers that can bind each other, such as, for example, a pair of sulfur- or thiol-containing polymers (e.g., a pair of Fc domains, a pair of thiolized-human serum albumin polypeptides, and the like); and the like.

In some embodiments, the DD1 and DD2 are non-polypeptide polymers. The non-polypeptide polymers may covalently bound to each other. In some examples, the non-polypeptide polymers may be a sulfur-containing polymer, e.g., sulfur-containing polyethylene glycol. In such cases, the DD1 and DD2 may be covalently bound to each other via one or more disulfide bonds.

When the pair of DD1 and DD2 are members of a pair of epitope and antigen-binding domain, the epitope may be a naturally or non-naturally occurring epitope. Exemplary non-naturally occurring epitopes include, for example, a non-naturally occurring peptide, such as, for example, a poly-His peptide (e.g., a His tag, and the like).

In certain specific embodiments, the DD1 and the DD2 are a pair of Fc domains. As used herein, an "Fc domain" refers to a contiguous amino acid sequence of a single heavy chain of an immunoglobulin. A pair of Fc domains associate together to form an Fc region of an immunoglobulin.

In some embodiments, the pair of Fc domains is a pair of human Fc domains (e.g., a pair of wildtype human Fc domains). In some embodiments, the human Fc domains are human IgG1 Fc domains (e.g., wildtype human IgG1 Fc domains), human IgG2 Fc domains (e.g., wildtype human IgG2 Fc domains), human IgG3 Fc domains (e.g., wildtype human IgG3 Fc domains), or human IgG4 Fc domains (e.g., wildtype human IgG4 Fc domains). In some embodiments, the human Fc domains comprise a sequence that is at least 80% identical (e.g., at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 3.

In some embodiments, the pair of Fc domains comprise a knob mutant and a hole mutant of a Fc domain. The knob and hole mutants may interact with each other to facilitate the dimerization. In some embodiments, the knob and hole mutants may comprise one or more amino acid modifications within the interface between two Fc domains (e.g., in the CH3 domain). In one example, the modifications comprise amino acid substitution T366W and optionally the amino acid substitution S354C in one of the antibody heavy chains, and the amino acid substitutions T366S, L368A, Y407V and optionally Y349C in the other one of the antibody heavy chains (numbering according to EU index of Kabat numbering system). Examples of the knob and hole mutants include Fc mutants of SEQ ID NOs: 315 and 316, as well as those described in U.S. Pat. Nos. 5,731,168; 7,695,936; and 10,683,368, which are incorporated herein by reference in their entireties. In some embodiments, the dimerization domains comprise a sequence that is at least 80% identical (e.g., at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NOs: 315 and 316, respectively.

In some embodiments, DD1 and/or DD2 can further include a serum half-life extending moiety (e.g., polypeptides that bind serum proteins, such as immunoglobulin (e.g., IgG) or serum albumin (e.g., human serum albumin (HSA)). Examples of half-life extending moieties include hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, and VSV Epitope.

In some embodiments, DD1 and/or DD2 each include a total of about 5 amino acids to about 250 amino acids, about 5 amino acids to about 200 amino acids, about 5 amino acids to about 180 amino acids, about 5 amino acids to about 160 amino acids, about 5 amino acids to about 140 amino acids, about 5 amino acids to about 120 amino acids, about 5 amino acids to about 100 amino acids, about 5 amino acids to about 80 amino acids, about 5 amino acids to about 60 amino acids, about 5 amino acids to about 40 amino acids, about 5 amino acids to about 20 amino acids, about 5 amino acids to about 10 amino acids, about 10 amino acids to about 250 amino acids, about 10 amino acids to about 200 amino acids, about 10 amino acids to about 180 amino acids, about 10 amino acids to about 160 amino acids, about 10 amino acids to about 140 amino acids, about 10 amino acids to about 120 amino acids, about 10 amino acids to about 100 amino acids, about 10 amino acids to about 80 amino acids, about 10 amino acids to about 60 amino acids, about 10 amino acids to about 40 amino acids, about 10 amino acids to about 20 amino acids, about 20 amino acids to about 250 amino acids, about 20 amino acids to about 200 amino acids, about 20 amino acids to about 180 amino acids, about 20 amino acids to about 160 amino acids, about 20 amino acids to about 140 amino acids, about 20 amino acids to about 120 amino acids, about 20 amino acids to about 100 amino acids, about 20 amino acids to about 80 amino acids, about 20 amino acids to about 60 amino acids, about 20 amino acids to about 40 amino acids, about 40 amino acids to about 250 amino acids, about 40 amino acids to about 200 amino acids, about 40 amino acids to about 180 amino acids, about 40 amino acids to about 160 amino acids, about 40 amino acids to about 140 amino acids, about 40 amino acids to about 120 amino acids, about 40 amino acids to about 100 amino acids, about 40 amino acids to about 80 amino acids, about 40 amino acids to about 60 amino acids, about 60 amino acids to about 250 amino acids, about 60 amino acids to about 200 amino acids, about 60 amino acids to about 180 amino acids, about 60 amino acids to about 160 amino acids, about 60 amino acids to about 140 amino acids, about 60 amino acids to about 120 amino acids, about 60 amino acids to about 100 amino acids, about 60 amino acids to about 80 amino acids, about 80 amino acids to about 250 amino acids, about 80 amino acids to about 200 amino acids, about 80 amino acids to about 180 amino acids, about 80 amino acids to about 160 amino acids, about 80 amino acids to about 140 amino acids, about 80 amino acids to about 120 amino acids, about 80 amino acids to about 100 amino acids, about 100 amino acids to about 250 amino acids, about 100 amino acids to about 200 amino acids, about 100 amino acids to about 180 amino acids, about 100 amino acids to about 160 amino acids, about 100 amino acids to about 140 amino acids, about 100 amino acids to about 120 amino acids, about 120 amino acids to about 250 amino acids, about 120 amino acids to about 200 amino acids, about 120 amino acids to about 180 amino acids, about 120 amino acids to about 160 amino acids, about 120 amino acids to about 140 amino acids, about 140 amino acids to about 250 amino acids, about 140 amino acids to about 200 amino acids, about 140 amino acids to about 180 amino acids, about 140 amino acids to about 160 amino acids, about 160 amino acids to about 250 amino acids, about 160 amino acids to about 200 amino acids, about 160 amino acids to about 180 amino acids, about 180 amino acids to about 250 amino acids, about 180 amino acids to about 200 amino acids, or about 200 amino acids to about 250 amino acids. In some embodiments, DD1 and DD2 are each an Fc domain that comprises a portion of the hinge region that includes two cysteine residues, a CH2 domain, and a CH3 domain. In some embodiments, DD1 and DD2 are each an Fc domain whose N-terminus is the first cysteine residue in the hinge region reading in the N- to C-direction (e.g., Cysteine 226 of human IgG1 or IgG4, using EU numbering).

In some aspects, positioned between the CP and the DD components, either directly or indirectly (e.g., via a linker), is a cleavable moiety that comprises a substrate for a protease. In some embodiments, the CM1 and CM2 may each independently comprise a substrate for a protease selected from the group consisting of ADAM8, ADAM8, ADAM10, ADAM12, ADAM15, ADAM17/TACE, ADEMDEC1, ADAMTS1, ADAMTS4, ADAMTS5, BACE, Renin, Cathepsin D, Cathepsin E, Caspase 1, Caspase 2, Caspase 3, Caspase 4, Caspase 5, Caspase 6, Caspase 7, Caspase 8, Caspase 9, Caspase 10, Caspase 14, Cathepsin A, Cathepsin B, Cathepsin C, Cathepsin G, Cathepsin K, Cathepsin L, Cathepsin S, Cathepsin V/L2, Cathepsin X/Z/P, Chymase, Cruzipain, DESC1, DPP-4, FAP, Legumain, Otubain-2, Elastase, FVIIa, FiXA, FXa, FXIa, FXIIa, Granzyme B, Guanidinobenzoatase, Hepsin, HtrA1, Human Neutrophil Elastase, KLK4, KLK5, KLK6, KLK7, KLK8, KLK10, KLK11, KLK13, KLK14, Lactoferrin, Marapsin, Matriptase-2, Meprin, MT-SP1/Matriptase, Neprilysin, NS3/4A, PACE4, Plasmin, PSMA, PSA, BMP-1, MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, MMP27, TMPRSS2, TMPRSS3, TMPRSS4, tPA, Thrombin, Tryptase, and uPA.

In some embodiments of any of the ACCs described herein, the protease that cleaves any of the CMs described herein can be ADAM8, ADAM8, ADAM10, ADAM12, ADAM15, ADAM17/TACE, ADAMDEC1, ADAMTS1, ADAMTS4, ADAMTS5, BACE, Renin, Cathepsin D, Cathepsin E, Caspase 1, Caspase 2, Caspase 3, Caspase 4, Caspase 5, Caspase 6, Caspase 7, Caspase 8, Caspase 9, Caspase 10, Caspase 14, Cathepsin B, Cathepsin C, Cathepsin K, Cathespin L, Cathepsin S, Cathepsin V/L2, Cathepsin X/Z/P, Cruzipain, Legumain, Otubain-2, KLK4, KLK5, KLK6, KLK7, KLK8, KLK10, KLK11, KLK13, KLK14, Meprin, Neprilysin, PSMA, BMP-1, MMP-1, MMP-2, MMP-3, MMP-7, MMP-9, MMP-10, MMP-11, MMP-12, MMP-13, MMP-14, MMP-15, MMP-16, MMP-17, MMP-19, MMP-20, MMP-23, MMP-24, MMP-26, MMP-27, activated protein C, cathepsin A, cathepsin G, Chymase, FVIIa, FIXa, FXa, FXIa, FXIIa, Elastase, Granzyme B, Guanidinobenzoatase, HtrA1, human neutrophil lyase, lactoferrin, marapsin, NS3/4A, PACE4, Plasmin, PSA, tPA, thrombin, tryptase, uPA, DESC1, DPP-4, FAP, Hepsin, Matriptase-2, MT-SP1/Matripase, TMPRSS2, TMPRSS3, and TMPRSS4.

In some embodiments of any of the ACCs described herein, the protease is selected from the group of: uPA, legumain, MT-SP1, ADAM17, BMP-1, TMPRSS3, TMPRSS4, MMP-2, MMP-9, MMP-12, MMP-13, and MMP-14.

Increased levels of proteases having known substrates have been reported in a number of cancers. See, e.g., La Roca et al., *British J. Cancer* 90(7):1414-1421, 2004. Substrates suitable for use in the CM1 and/or CM2 components employed herein include those which are more prevalently found in cancerous cells and tissue. Thus, in certain embodiments, CM1 and/or CM2 each independently comprise a substrate for a protease that is more prevalently found in diseased tissue associated with a cancer. In some embodiments, the cancer is selected from the group of: gastric cancer, breast cancer, osteosarcoma, and esophageal cancer. In some embodiments, the cancer is breast cancer. In some embodiments, the cancer is a HER2-positive cancer. In some embodiments, the cancer is Kaposi sarcoma, hairy cell leukemia, chronic myeloid leukemia (CML), follicular lymphoma, renal cell cancer (RCC), melanoma, neuroblastoma, basal cell carcinoma, cutaneous T-cell lymphoma, nasopharyngeal adenocarcimoa, breast cancer, ovarian cancer, bladder cancer, BCG-resistant non-muscle invasive bladder cancer (NMIBC), endometrial cancer, pancreatic cancer, non-small cell lung cancer (NSCLC), colorectal cancer, esophageal cancer, gallbladder cancer, glioma, head and neck carcinoma, uterine cancer, cervical cancer, or testicular cancer, and the like. In some of the above-described embodiments, the CM components comprise substrates for protease(s) that is/are more prevalent in tumor tissue.

In some embodiments, CM1 and/or CM2 each independently include(s) a sequence selected from the group consisting of SEQ ID NO: 5 to SEQ ID NO: 100, as well as C-terminal and N-terminal truncation variants thereof.

In some embodiments, the CM includes a sequence selected from the group of:

```
                              (SEQ ID NO: 28)
    ISSGLLSGRSDNH, (SEQ ID NO: 33)
    LSGRSDDH,
```

ISSGLLSGRSDQH, (SEQ ID NO: 54)
and

ISSGLLSGRSDNI. (SEQ ID NO: 68)

In certain embodiments, CM1 and/or CM2 include(s) a sequence selected from the group of: APRSALAHGLF (SEQ ID NO: 263), AQNLLGMY (SEQ ID NO: 264), LSGRSDNHGGAVGLLAPP (SEQ ID NO: 265), VHMPLGFLGPGGLSGRSDNH (SEQ ID NO: 266), LSGRSDNHGGVHMPLGFLGP (SEQ ID NO: 267), LSGRSDNHGGSGGSISSGLLSS (SEQ ID NO: 268), ISSGLLSSGGSGGSLSGRSGNH (SEQ ID NO: 269), LSGRSDNHGGSGGSQNQALRMA (SEQ ID NO: 270), QNQALRMAGGSGGSLSGRSDNH (SEQ ID NO:271), LSGRSGNHGGSGGSQNQALRMA (SEQ ID NO: 272), QNQALRMAGGSGGSLSGRSGNH (SEQ ID NO: 273), ISSGLLSGRSGNH (SEQ ID NO: 274), as well as C-terminal and N-terminal truncation variants thereof. Examples of CM also include those described in U.S. Patent Application Publication Nos. 2016/0289324, 2019/0284283, and in publication numbers WO 2010/081173, WO 2015/048329, WO 2015/116933, WO 2016/118629, and WO 2020/118109, which are incorporated herein by reference in their entireties.

Truncation variants of the aforementioned amino acid sequences that are suitable for use in a CM1 and/or CM2 are any that retain the recognition site for the corresponding protease. These include C-terminal and/or N-terminal truncation variants comprising at least 3 contiguous amino acids of the above-described amino acid sequences, or at least 4, or at least 5, or at least 6, or at least 7 amino acids of the foregoing amino acid sequences that retain a recognition site for a protease. In certain embodiments, the truncation variant of the above-described amino acid sequences is an amino acid sequence corresponding to any of the above, but that is C- and/or N-terminally truncated by 1 to about 10 amino acids, 1 to about 9 amino acids, 1 to about 8 amino acids, 1 to about 7 amino acids, 1 to about 6 amino acids, 1 to about 5 amino acids, 1 to about 4 amino acids, or 1 to about 3 amino acids, and which: (1) has at least three amino acid residues; and (2) retains a recognition site for a protease. In some of the foregoing embodiments, the truncated CM is an N-terminally truncated CM. In some embodiments, the truncated CM is a C-terminally truncated CM. In some embodiments, the truncated C is a C- and an N-terminally truncated CM.

In some embodiments of any of the activatable cytokine constructs described herein, the CM1 and/or the CM2 comprise a total of about 3 amino acids to about 25 amino acids. In some embodiments, the CM1 and/or CM2 comprise a total of about 3 amino acids to about 25 amino acids, about 3 amino acids to about 20 amino acids, about 3 amino acids to about 15 amino acids, about 3 amino acids to about 10 amino acids, about 3 amino acids to about 5 amino acids, about 5 amino acids to about 25 amino acids, about 5 amino acids to about 20 amino acids, about 5 amino acids to about 15 amino acids, about 5 amino acids to about 10 amino acids, about 10 amino acids to about 25 amino acids, about 10 amino acids to about 20 amino acids, about 10 amino acids to about 15 amino acids, about 15 amino acids to about 25 amino acids, about 15 amino acids to about 20 amino acids, or about 20 amino acids to about 25 amino acids.

In some embodiments, the ACC may comprise multiple CMs that comprise substrates for different proteases. In some embodiments, the CM1 and the CM2 comprise substrates for different proteases. In some embodiments, the CM1 and the CM2 comprise substrates for the same protease.

The first and second monomer constructs may comprise one or more additional components including one or more linkers, and the like. In some embodiments, the first monomer can include a linker disposed between the CP1 and the CM1. In some embodiments, the CP1 and the CM1 directly abut each other in the first monomer. In some embodiments, the first monomer comprises a linker disposed between the CM1 and the DD1. In some embodiments, the linker has a total length of 1 amino acid to about 15 amino acids. In some embodiments, the CM1 and the DD1 directly abut each other in the first monomer. In some embodiments, the CM and any linkers disposed between the CP1 and DD1 have a combined total length of 3 to 15 amino acids, or 3 to 10 amino acids, or 3 to 7 amino acids.

In some embodiments, the second monomer comprises a linker disposed between the CP2 and the CM2. In some embodiments, the CP2 and the CM2 directly abut each other in the second monomer. In some embodiments, the second monomer comprises a linker disposed between the CM2 and the DD2. In some embodiments, the linker has a total length of 1 amino acid to about 15 amino acids. In some embodiments, the linker comprises a sequence of GGGS (SEQ ID NO: 2). In some embodiments, the CM2 (e.g., any of the cleavable moieties described herein) and the DD2 (e.g., any of the DDs described herein) directly abut each other in the second monomer. In some embodiments, the CM and any linkers disposed between the CP2 and DD2 have a combined total length of 3 to 15 amino acids, or 3 to 10 amino acids, or 3 to 7 amino acids.

In some embodiments, the first monomer and/or the second monomer can include a total of about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 800 amino acids, about 250 amino acids to about 750 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 800 amino acids, about 600 amino acids to about 750 amino acids, about 600 amino acids to about 700 amino acids, about 600 amino acids to about 650 amino acids, about 650 amino acids to about 800 amino acids, about 650 amino acids to about 750 amino acids, about 650 amino acids to about 700 amino acids, about 700 amino acids to about 800 amino acids, about 700 amino acids to about 750 amino acids, or about 750 amino acids to about 800 amino acids.

In some embodiments of any of the ACCs described herein, one or more linkers (e.g., flexible linkers) can be introduced into the activatable cytokine construct to provide flexibility at one or more of the junctions between domains, between moieties, between moieties and domains, or at any other junctions where a linker would be beneficial. In some embodiments, where the ACC is provided as a conformationally constrained construct, a flexible linker can be inserted to facilitate formation and maintenance of a structure in the uncleaved activatable cytokine construct. Any of the linkers described herein can provide the desired flexibility to facilitate the inhibition of the binding of a target (e.g., a receptor of a cytokine), or to facilitate cleavage of a CM by a protease. In some embodiments, linkers are included in the ACC that are all or partially flexible, such that the linker can include a flexible linker as well as one or more portions that confer less flexible structure to provide for a desired ACC. Some linkers may include cysteine residues, which may form disulfide bonds and reduce flexibility of the construct. In some embodiments, reducing the length of the linkers or Linking Region reduces the activity of the mature cytokine protein in the ACCs (see, e.g., FIGS. 8A-8B and 10A-10B). In most instances, linker length is determined by counting, in a N- to C-direction, the number of amino acids from the N-terminus of the linker adjacent to the C-terminal amino acid of the preceding component, to the C-terminus of the linker adjacent to the N-terminal amino acid of the following component (i.e., where the linker length does not include either the C-terminal amino acid of the preceding component or the N-terminal amino acid of the following component). In embodiments in which a linker is employed at the N-terminus of a DD that comprises an Fc domain, linker length is determined by counting the number of amino acids from the N-terminus of the linker adjacent to the C-terminal amino acid of the preceding component to C-terminus of the linker adjacent to the first cysteine of an Fc hinge region (i.e., where the linker length does not include the C-terminal amino acid of the preceding component or the first cysteine of the Fc hinge region).

Figure 25:
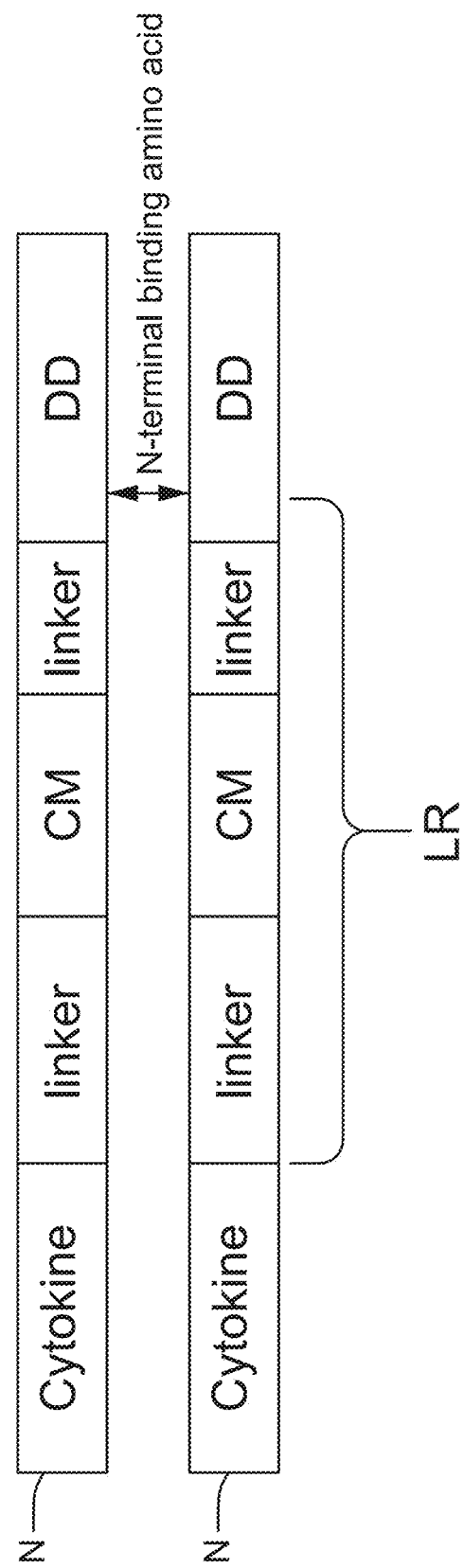
FIG. 25 schematically shows an embodiment of an ACC denoting its Linking Region (LR).

As apparent from the present disclosure and FIG. 25, ACCs of the present disclosure include a stretch of amino acids between the CP and the proximal point of interaction between the dimerization domains. That stretch of amino acids may be referred to as a Linking Region (LR). As used herein, the term "Linking Region" or "LR" refers to the stretch of amino acid residues between the C-terminus of the cytokine and the amino acid residue that is N-terminally adjacent to the proximal point of interaction between the dimerization domains (i.e., the linking region does not include the C-terminal amino acid of the cytokine or the N-terminal amino acid of the DD that forms the proximal point of interaction to the DD of the corresponding second monomer). For example, when the DDs are a pair of Fc domains, the linking region is the stretch of amino acid residues between the C-terminus of the cytokine and the first N-terminal cysteine residue that participates in the disulfide linkage of the Fc (e.g., Cysteine 226 of an IgG1 or IgG4 Fc domain, according to EU numbering). When the dimerization domain is not a peptide, then the linking region is the stretch of amino acid residues following the C-terminus of the cytokine until the last amino acid. For example, when the DDs are a biotin-streptavidin pair, the linking region of the biotin-containing monomer is the stretch of amino acid residues between the C-terminus of the cytokine and the biotin molecule, and the linking region of the streptavidin-containing monomer is the stretch of amino acid residues between the C-terminus of the cytokine and the streptavidin molecule. In some aspects, the Linking Region may comprise no more than 24, 18, 14, 12, 11, 10, 9, 8, 7, 6, 5, or 4 amino acids, e.g., 5 to 14, 7 to 12, or 8 to 11 amino acids.

In some embodiments, additional amino acid sequences may be positioned N-terminally or C-terminally to any of the domains of any of the ACCs. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HSA)).

In some embodiments of any of the activatable cytokine constructs described herein, a linker can include a total of about 1 amino acid to about 25 amino acids (e.g., about 1 amino acid to about 24 amino acids, about 1 amino acid to about 22 amino acids, about 1 amino acid to about 20 amino acids, about 1 amino acid to about 18 amino acids, about 1 amino acid to about 16 amino acids, about 1 amino acid to about 15 amino acids, about 1 amino acid to about 14 amino acids, about 1 amino acid to about 12 amino acids, about 1 amino acid to about 10 amino acids, about 1 amino acid to about 8 amino acids, about 1 amino acid to about 6 amino acids, about 1 amino acid to about 5 amino acids, about 1 amino acid to about 4 amino acids, about 1 amino acid to about 3 amino acids, about 1 amino acid to about 2 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 15 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 5 amino acids, about 2 amino acids to about 4 amino acids, about 2 amino acids to about 3 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 15 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 4 amino acids to about 5 amino acids, about 5 amino acids to about 25 amino acids, about 5 amino acids to about 24 amino acids, about 5 amino acids to about 22 amino acids, about 5 amino acids to about 20 amino acids, about 5 amino acids to about 18 amino acids, about 5 amino acids to about 16 amino acids, about 5 amino acids to about 15 amino acids, about 5 amino acids to about 14 amino acids, about 5 amino acids to about 12 amino acids, about 5 amino acids to about 10 amino acids, about 5 amino acids to about 8 amino acids, about 5 amino acids to about 6 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 15 amino acids, about 6 amino acids to about 14 amino acids, about 6 amino acids to about 12 amino acids, about 6 amino acids to about 10 amino acids, about 6 amino acids to about 8 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 15 amino acids, about 8 amino acids to about 14 amino acids, about 8 amino acids to about 12 amino acids, about 8 amino acids to about 10 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 15 amino acids, about 10 amino acids to about 14 amino acids, about 10 amino acids to about 12 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 15 amino acids, about 12 amino acids to about 14 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 14 amino acids to about 15 amino acids, about 15 amino acids to about 25 amino acids, about 15 amino acids to about 24 amino acids, about 15 amino acids to about 22 amino acids, about 15 amino acids to about 20 amino acids, about 15 amino acids to about 18 amino acids, about 15 amino acids to about 16 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 25 amino acids, about 18 amino acids to about 24 amino acids, about 18 amino acids to about 22 amino acids, about 18 amino acids to about 20 amino acids, about 20 amino acids to about 25 amino acids, about 20 amino acids to about 24 amino acids, about 20 amino acids to about 22 amino acids, about 22 amino acid to about 25 amino acids, about 22 amino acid to about 24 amino acids, or about 24 amino acid to about 25 amino acids).

In some embodiments of any of the ACCs described herein, the linker includes a total of about 1 amino acid, about 2 amino acids, about 3 amino acids, about 4 amino acids, about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, about 20 amino acids, about 21 amino acids, about 22 amino acids, about 23 amino acids, about 24 amino acids, or about 25 amino acids.

Surprisingly, the inventors have discovered that ACCs that do not comprise any linkers between the CP and the DD exhibit the most significant reduction in cytokine activity relative to the wildtype mature cytokine. See FIGS. 8A and 10A. Further, a configuration in which there are no linkers between the CP and the DD still allows effective cleavage of a CM positioned between the CP and the DD. See FIGS. 12-14. Thus, in some embodiments, the ACC does not comprise any linkers between the CP and the DD, and the CM between the CP and the DD comprises not more than 10, 9, 8, 7, 6, 5, 4, or 3 amino acids. In some embodiments the total number of amino acids in the LR comprises not more than 25 amino acids, e.g., not more than 25, 24, 23, 22, 21, 20, 19, 18, 17, 16, 15, 14, 13, 12, 11, 10, 9, 8, 7, 6, 5, 4, or 3 amino acids, or 3 to 10 amino acids or 5 to 15 amino acids, or 7 to 12 amino acids, or any range or specific number of amino acids selected from the range encompassed by 3 to 25 amino acids.

In some embodiments of any of the ACCs described herein, a linker can be rich in glycine (Gly or G) residues. In some embodiments, the linker can be rich in serine (Ser or S) residues. In some embodiments, the linker can be rich in glycine and serine residues. In some embodiments, the linker has one or more glycine-serine residue pairs (GS) (e.g., 1, 2, 3, 4, 5, 6, 7, 8, 9, or 10 or more GS pairs). In some embodiments, the linker has one or more Gly-Gly-Gly-Ser (GGGS) sequences (e.g., 1, 2, 3, 4, 5, 6, 7, 8, 9, or 10 or more GGGS sequences). In some embodiments, the linker has one or more Gly-Gly-Gly-Gly-Ser (GGGGS) sequences (e.g., 1, 2, 3, 4, 5, 6, 7, 8, 9, or 10 or more GGGGS sequences). In some embodiments, the linker has one or more Gly-Gly-Ser-Gly (GGSG) sequences (e.g., 1, 2, 3, 4, 5, 6, 7, 8, 9, or 10 or more GGSG sequences).

In some embodiments of any of the ACCs described herein, a linker includes any one of or a combination of one or more of: GSSGGSGGSGG (SEQ ID NO: 210), GGGS (SEQ ID NO: 2), GGGSGGGS (SEQ ID NO: 211), GGGSGGGSGGGS (SEQ ID NO: 212), GGGGSGGGGSGGGGS (SEQ ID NO: 213), GGGGSGGGGSGGGGSGGGGSGGGGS (SEQ ID NO: 214), GGGGSGGGGS (SEQ ID NO: 215), GGGGS (SEQ ID NO: 216), GS, GGGGSGS (SEQ ID NO: 217), GGGGSGGGGSGGGGSGS (SEQ ID NO: 218), GGSLDPKGGGGS (SEQ ID NO: 219), PKSCDKTHTCPPCPAPELLG (SEQ ID NO: 220), SKYGPPCPPCPAPEFLG (SEQ ID NO: 221), GKSSGSGSESKS (SEQ ID NO: 222), GSTSGSGKSSEGKG (SEQ ID NO: 223), GSTSGSGKSSEGSGSTKG (SEQ ID NO: 224), and GSTSGSGKPGSGEGSTKG (SEQ ID NO: 225).

Non-limiting examples of linkers can include a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to GGGS (SEQ ID NO: 2), GSSGGSGGSGG (SEQ ID NO: 210), GGGGSGGGGSGGGGS (SEQ ID NO: 213), GGGGSGS (SEQ ID NO: 217), GGGGSGGGGSGGGGSGS (SEQ ID NO: 218), GGGGSGGGGSGGGGSGGGGS (SEQ ID NO: 214), GGSLDPKGGGGS (SEQ ID NO: 215), and GSTSGSGKPGSSEGST (SEQ ID NO: 226).

In some embodiments, the linker includes a sequence selected from the group of: GGSLDPKGGGGS (SEQ ID NO: 219), GGGGSGGGGSGGGGSGS (SEQ ID NO: 218), GGGGSGS (SEQ ID NO: 217), GS, (GS)n, (GGS)n, (GSGGS)n (SEQ ID NO: 227) and (GGGS)n (SEQ ID NO: 228), GGSG (SEQ ID NO: 229), GGSGG (SEQ ID NO: 230), GSGSG (SEQ ID NO: 231), GSGGG (SEQ ID NO: 232), GGGSG (SEQ ID NO: 233), GSSSG (SEQ ID NO: 234), GGGGSGGGGSGGGGS (SEQ ID NO: 213), GGGGSGGGGSGGGGSGGGGS (SEQ ID NO: 214), GSTSGSGKPGSSEGST (SEQ ID NO: 226), (GGGGS)n (SEQ ID NO: 216), wherein n is an integer of at least one. In some embodiments, the linker includes a sequence selected from the group consisting of: GGSLDPKGGGGS (SEQ ID NO: 219), GGGGSGGGGSGGGGSGS (SEQ ID NO: 218), GGGGSGS (SEQ ID NO: 217), and GS. In some embodiments of any of the ACCs described herein, the linker includes a sequence selected from the group of: GGGGSGGGGSGGGGS (SEQ ID NO: 213), GGGGSGGGGSGGGGSGGGGS (SEQ ID NO: 214), and GSTSGSGKPGSSEGST (SEQ ID NO: 226). In some embodiments of any of the activatable cytokine constructs described herein, the linker includes a sequence selected from the group of: GGGGSGGGGSGGGGS (SEQ ID NO: 213) or GGGGS (SEQ ID NO: 216). In some embodiments, the linker comprises a sequence of GGGS (SEQ ID NO: 2).

In some embodiments, an ACC can include one, two, three, four, five, six, seven, eight, nine, or ten linker sequence(s) (e.g., the same or different linker sequences of any of the exemplary linker sequences described herein or known in the art). In some embodiments, a linker comprises sulfo-SIAB, SMPB, and sulfo-SMPB, wherein the linkers react with primary amines sulfhydryls.

In some embodiments of any of the ACCs described herein, the ACC is characterized by a reduction in at least one activity of the CP1 and/or CP2 as compared to a control level of the at least one activity of the CP1 and/or CP2. In some embodiments, a control level can be the level of the activity for a recombinant CP1 and/or CP2 (e.g., a commercially available recombinant CP1 and/or CP2, a recombinant wildtype CP1 and/or CP2, and the like). In some embodiments, a control level can be the level of the activity of a cleaved (activated) form of the ACC. In certain embodiments, a control level can be the level of the activity of a pegylated CP1 and/or CP2.

In some embodiments, the at least one activity is the binding affinity ($K_D$) of the CP1 and/or the CP2 for its cognate receptor as determined using surface plasmon resonance (e.g., performed in phosphate buffered saline at 25° C.). In certain embodiments, the at least one activity is the level of proliferation of lymphoma cells. In other embodiments, the at least one activity is the level of JAK/STAT/ISGF3 pathway activation in a lymphoma cell. In some embodiments, the at least one activity is a level of SEAP production in a lymphoma cell. In a further embodiment, the at least one activity of the CP1 and/or CP2 is level of cytokine-stimulated gene induction using, for example RNAseq methods (see, e.g., Zimmerer et al., *Clin. Cancer Res.* 14(18):5900-5906, 2008; Hilkens et al., *J. Immunol.* 171:5255-5263, 2003).

In some embodiments, the ACC is characterized by at least a 2-fold reduction in at least one CP1 and/or CP2 activity as compared to the control level of the at least one CP1 and/or CP2 activity. In some embodiments, the ACC is characterized by at least a 5-fold reduction in at least one activity of the CP1 and/or CP2 as compared to the control level of the at least one activity of the CP1 and/or CP2. In some embodiments, the ACC is characterized by at least a 10-fold reduction in at least one activity of the CP1 and/or CP2 as compared to the control level of the at least one activity of the CP1 and/or CP2. In some embodiments, the ACC is characterized by at least a 20-fold reduction in at least one activity of the CP1 and/or CP2 as compared to the control level of the at least one activity of the CP1 and/or CP2. In some embodiments, the ACC is characterized by at least a 30-fold, 40-fold, 50-fold, 60-fold, 70-fold, 80-fold, 90-fold, 100-fold, 500-fold, or 1000-fold reduction in at least one activity of the CP1 and/or CP2 as compared to the control level of the at least one activity of the CP1 and/or CP2. In some embodiments, ACC is characterized by at least a 1- to 20-fold reduction, a 200- to 500-fold reduction, a 300- to 500-fold reduction, a 400- to 500-fold reduction, a 500- to 600-fold reduction, a 600- to 700-fold reduction, a 150- to 1000-fold reduction, a 100- to 1500-fold reduction, a 200- to 1500-fold reduction, a 300- to 1500-fold reduction, a 400- to 1500-fold reduction, a 500- to 1500-fold reduction, a 1000- to 1500-fold reduction, a 100- to 1000-fold reduction, a 200- to 1000-fold reduction, a 300- to 1000-fold reduction, a 400- to 1000-fold reduction, a 500- to 1000-fold reduction, a 100- to 500-fold reduction, a 20- to 50-fold reduction, a 30- to 50-fold reduction, a 40- to 50-fold reduction, a 100- to 400-fold reduction, a 200- to 400-fold reduction, or a 300- to 400-fold reduction, a 100- to 300-fold reduction, a 200- to 300-fold reduction, or a 100- to 200-fold reduction in at least one activity of the CP1 and/or CP2 as compared to the control level of the at least one activity of the CP1 and/or CP2.

In some embodiments, the control level of the at least one activity of the CP1 and/or CP2 is the activity of the CP1 and/or CP2 released from the ACC following cleavage of CM1 and CM2 by the protease(s) (the "cleavage product"). In some embodiments, the control level of the at least one activity of the CP1 and/or CP2 is the activity of a corresponding wildtype mature cytokine (e.g., recombinant wildtype mature cytokine).

In some embodiments, incubation of the ACC with the protease yields an activated cytokine product(s), where one or more activities of CP1 and/or CP2 of the activated cytokine product(s) is greater than the one or more activities of CP1 and/or CP2 of the intact ACC. In some embodiments, one or more activities of CP1 and/or CP2 of the activated cytokine product(s) is at least 1-fold greater than the one or more activities of CP1 and/or CP2 of the ACC. In some embodiments, one or more activities of CP1 and/or CP2 of the activated cytokine product(s) is at least 2-fold greater than the one or more activities of CP1 and/or CP2 of the ACC. In some embodiments, one or more activities of CP1 and/or CP2 of the activated cytokine product(s) is at least 5-fold greater than the one or more activities of CP1 and/or CP2 of the ACC. In some embodiments, one or more activities of CP1 and/or CP2 of the activated cytokine product(s) is at least 10-fold greater than the one or more activities of CP1 and/or CP2 of the ACC. In some embodiments, one or more activities of CP1 and/or CP2 of the activated cytokine product(s) is at least 20-fold greater than the one or more activities of CP1 and/or CP2 of the ACC. In some embodiments, one or more activities of CP1 and/or CP2 of the activated cytokine product(s) is at least 1- to 20-fold greater, 2- to 20-fold greater, 3- to 20-fold greater, 4- to 20-fold greater, 5- to 20-fold greater, 10- to 20-fold greater, 15- to 20-fold greater, 1- to 15-fold greater, 2- to 15-fold greater, 3- to 15-fold greater, 4- to 15-fold greater, 5- to 15-fold greater, 10- to 15-fold greater, 1- to 10-fold greater, 2- to 10-fold greater, 3- to 10-fold greater, 4- to 10-fold greater, 5- to 10-fold greater, 1- to 5-fold greater, 2- to 5-fold greater, 3- to 5-fold greater, 4- to 5-fold greater, 1- to 4-fold greater, 2- to 4-fold greater, 3- to 4-fold greater, 1- to 3-fold greater, 2- to 3-fold greater, or 1- to 2-fold greater than the one or more activities of CP1 and/or CP2 of the ACC.

In some embodiments, an ACC can include a sequence that is at least 80% (e.g., at least 82%, at least 84%, at least 86%, at least 88%, at least 90%, at least 92%, at least 94%, at least 96%, at least 98%, at least 99%, or 100%) identical to SEQ ID NO: 309 or 311. In some embodiments, an ACC can be encoded by a nucleic acid including a sequence that is at least 80% (e.g., at least 82%, at least 84%, at least 86%, at least 88%, at least 90%, at least 92%, at least 94%, at least 96%, at least 98%, at least 99%, or 100%) identical to SEQ ID NO: 310 or 312. In some aspects, an ACC may include such sequences but either without the signal sequences of those sequences. Signal sequences are not particularly limited. Some non-limiting examples of signal sequences include, e.g., residues 1-20 of SEQ ID NO: 309 and corresponding residues and nucleotides in the other sequences, or substituted with a signal sequence from another species or cell line. Other examples of signal sequences include MRAWIFFLLCLAGRALA (SEQ ID NO: 343) and MALTFALLVALLVLSCKSSCSVG (SEQ ID NO: 344).

Various exemplary aspects of these activatable cytokine constructs are described below and can be used in any combination in the methods provided herein without limitation. Exemplary aspects of the activatable cytokine constructs and methods of making activatable cytokine constructs are described below.

In some embodiments, the CM is selected for use with a specific protease. The protease may be one produced by a tumor cell (e.g., the tumor cell may express greater amounts of the protease than healthy tissues). In some embodiments, the CM is a substrate for at least one protease selected from the group of an ADAM 17, a BMP-1, a cysteine protease such as a cathepsin, a HtrA1, a legumain, a matriptase (MT-SP1), a matrix metalloprotease (MMP), a neutrophil elastase, a TMPRSS, such as TMPRSS3 or TMPRSS4, a thrombin, and a u-type plasminogen activator (uPA, also referred to as urokinase).

In some embodiments, a CM is a substrate for at least one matrix metalloprotease (MMP). Examples of MMPs include MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, and MMP27. In some embodiments, the CM is a substrate for MMP9, MMP14, MMP1, MMP3, MMP13, MMP17, MMP11, and MMP19. In some embodiments, the CM is a substrate for MMP7. In some embodiments, the CM is a substrate for MMP9. In some embodiments, the CM is a substrate for MMP14. In some embodiments, the CM is a substrate for two or more MMPs. In some embodiments, the CM is a substrate for at least MMP9 and MMP14. In some embodiments, the CM includes two or more substrates for the same MMP. In some embodiments, the CM includes at least two or more MMP9 substrates. In some embodiments, the CM includes at least two or more MMP14 substrates.

In some embodiments, a CM is a substrate for an MMP and includes the sequence ISSGLLSS (SEQ ID NO: 19); QNQALRMA (SEQ ID NO: 16); AQNLLGMV (SEQ ID NO: 15); STFPFGMF (SEQ ID NO: 18); PVGYTSSL (SEQ ID NO: 74); DWLYWPGI (SEQ ID NO: 75); MIAPVAYR (SEQ ID NO: 42); RPSPMWAY (SEQ ID NO: 43); WATPRPMR (SEQ ID NO: 44); FRLLDWQW (SEQ ID NO: 45); LKAAPRWA (SEQ ID NO: 76); GPSHLVLT (SEQ ID NO: 77); LPGGLSPW (SEQ ID NO: 78); MGLFSEAG (SEQ ID NO: 79); SPLPLRVP (SEQ ID NO: 80); RMHLRSLG (SEQ ID NO: 81); LAAPLGLL (SEQ ID NO: 17); AVGLLAPP (SEQ ID NO: 14); LLAPSHRA (SEQ ID NO: 82); PAGLWLDP (SEQ ID NO: 20); and/or ISSGLSS (SEQ ID NO: 73).

In some embodiments, a CM is a substrate for thrombin. In some embodiments, the CM is a substrate for thrombin and includes the sequence GPRSFGL (SEQ ID NO: 83) or GPRSFG (SEQ ID NO: 84).

In some embodiments, a CM includes an amino acid sequence selected from the group of NTLSGRSENHSG (SEQ ID NO: 9); NTLSGRSGNHGS (SEQ ID NO: 10); TSTSGRSANPRG (SEQ ID NO: 11); TSGRSANP (SEQ ID NO: 12); VAGRSMRP (SEQ ID NO: 21); VVPEGRRS (SEQ ID NO: 22); ILPRSPAF (SEQ ID NO: 23); MVL-GRSLL (SEQ ID NO: 24); QGRAITFI (SEQ ID NO: 25); SPRSIMLA (SEQ ID NO: 26); and SMLRSMPL (SEQ ID NO: 27).

In some embodiments, a CM is a substrate for a neutrophil elastase. In some embodiments, a CM is a substrate for a serine protease. In some embodiments, a CM is a substrate for uPA. In some embodiments, a CM is a substrate for legumain. In some embodiments, the CM is a substrate for matriptase. In some embodiments, the CM is a substrate for a cysteine protease. In some embodiments, the CM is a substrate for a cysteine protease, such as a cathepsin.

In some embodiments, a CM includes a sequence of ISSGLLSGRSDNH (SEQ ID NO: 28); ISSGLLSSGGSGGSLSGRSDNH (SEQ ID NO: 30); AVGLLAPPGGTSTSGRSANPRG (SEQ ID NO: 275); TSTSGRSANPRGGGAVGLLAPP (SEQ ID NO: 276); VHMPLGFLGPGGTSTSGRSANPRG (SEQ ID NO: 277); TSTSGRSANPRGGGVHMPLGFLGP (SEQ ID NO: 278); AVGLLAPPGGLSGRSDNH (SEQ ID NO: 29); LSGRSDNHGGAVGLLAPP (SEQ ID NO: 70); VHMPLGFLGPGGLSGRSDNH (SEQ ID NO: 266); LSGRSDNHGGVHMPLGFLGP (SEQ ID NO: 267); LSGRSDNHGGSGGSISSGLLSS (SEQ ID NO: 268); LSGRSGNHGGSGGSISSGLLSS (SEQ ID NO: 279); ISSGLLSSGGSGGSLSGRSGNH (SEQ ID NO: 269); LSGRSDNHGGSGGSQNQALRMA (SEQ ID NO: 270); QNQALRMAGGSGGSLSGRSDNH (SEQ ID NO: 271); LSGRSGNHGGSGGSQNQALRMA (SEQ ID NO: 272); QNQALRMAGGSGGSLSGRSGNH (SEQ ID NO: 273), and/or ISSGLLSGRSGNH (SEQ ID NO: 274).

In some embodiments, the CM1 and/or the CM2 comprise a sequence selected from the group consisting of: SEQ ID NO: 5 through SEQ ID NO: 100. In some embodiments, the CM comprises a sequence selected from the group of:

```
                        (SEQ ID NO: 28)
ISSGLLSGRSDNH, (SEQ ID NO: 33)
LSGRSDDH, (SEQ ID NO: 54)
ISSGLLSGRSDQH, (SEQ ID NO: 100)
SGRSDNI,
and (SEQ ID NO: 68)
ISSGLLSGRSDNI.
```

In some aspects, the ACC includes a CP1 selected from SEQ ID Nos: 1 and 101-209, a CM1 selected from SEQ ID Nos: 5-100 and 263-308, and a DD1 dimerized with a CP2 selected from SEQ ID Nos: 1 and 101-209, a CM2 selected from SEQ ID Nos: 5-100 and 263-308, and a DD2. In some aspects, the ACC may include, between CP1 and CM1 and/or between CM1 and DD1, a linker selected from SEQ ID Nos: 2 and 210-234, 245, or 250, and between CP2 and CM2 and/or between CM2 and DD2, a linker selected from SEQ ID Nos: 2 and 210-234, 245, or 250. In some embodiments, the ACC includes a DD1 and/or a DD2 that has an amino acid sequence that is at least 80% identical (e.g., at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 3 or SEQ ID NO: 4. In some embodiments, the ACC includes a DD1 that has an amino acid sequence that is at least 80% identical (e.g., at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 315 or SEQ ID NO: 316. In some embodiments, the ACC includes a DD2 that has an amino acid sequence that is at least 80% identical (e.g., at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 315 or SEQ ID NO: 316.

Conjugation to Agents

This disclosure also provides methods and materials for including additional elements in any of the ACCs described herein including, for example, a targeting moiety to facilitate delivery to a cell or tissue of interest, an agent (e.g., a therapeutic agent, an antineoplastic agent), a toxin, or a fragment thereof.

In some embodiments of any of the ACCs described herein, the ACC can be conjugated to a cytotoxic agent, including, without limitation, a toxin (e.g., an enzymatically active toxin of bacterial, fungal, plant, or animal origin, or fragments thereof) or a radioactive isotope. In some embodiments of any of the ACCs described herein, the activatable cytokine construct can be conjugated to a cytotoxic agent including, without limitation, a toxin (e.g., an enzymatically active toxin of bacterial, fungal, plant, or animal origin, or fragments thereof), or a radioactive isotope.

Non-limiting exemplary cytotoxic agents that can be conjugated to any of the ACCs described herein include: dolastatins and derivatives thereof (e.g., auristatin E, AFP, monomethyl auristatin D (MMAD), monomethyl auristatin F (MMAF), monomethyl auristatin E (MMAE), desmethyl auristatin E (DMAE), auristatin F, desmethyl auristatin F (DMAF), dolastatin 16 (DmJ), dolastatin 16 (Dpv), auristatin derivatives (e.g., auristatin tyramine, auristatin quinolone), maytansinoids (e.g., DM-1, DM-4), maytansinoid derivatives, duocarmycin, alpha-amanitin, turbostatin, phenstatin, hydroxyphenstatin, spongistatin 5, spongistatin 7, halistatin 1, halistatin 2, halistatin 3, halocomstatin, pyrrolobenzimidazoles (PBI), cibrostatin6, doxaliform, cemadotin analogue (CemCH2-SH), *Pseudomonas* toxin A (PES8) variant, Pseudomonase toxin A (ZZ-PE38) variant, ZJ-101, anthracycline, doxorubicin, daunorubicin, bryostatin, camptothecin, 7-substituted campothecin, 10, 11-difluoromethylenedioxycamptothecin, combretastatins, debromoaplysiatoxin, KahaMide-F, discodermolide, and Ecteinascidins.

Non-limiting exemplary enzymatically active toxins that can be conjugated to any of the ACCs described herein include: diphtheria toxin, exotoxin A chain from *Pseudomonas aeruginosa*, ricin A chain, abrin A chain, modeccin A chain, alpha-sarcin, *Aleuriies fordii* proteins, dianfhin proteins, *Phytoiaca Americana* proteins (e.g., PAPI, PAPII, and PAP-8), *Momordica charantia* inhibitor, curcin, crotirs, *Sapaonaria officinalis* inhibitor, geionin, mitogeliin, restrictocin, phenomycin, neomycin, and tricothecenes.

Non-limiting exemplary anti-neoplastics that can be conjugated to any of the ACCs described herein include: adriamycin, cerubidine, bleomycin, alkeran, velban, oncovin, fluorouracil, methotrexate, thiotepa, bisantrene, novantrone, thioguanine, procarabizine, and cytarabine.

Non-limiting exemplary antivirals that can be conjugated to any of the ACCs described herein include: acyclovir, vira A, and symmetrel.

Non-limiting exemplary antifungals that can be conjugated to any of the ACCs described herein include: nystatin.

Non-limiting exemplary conjugatable detection reagents that can be conjugated to any of the ACCs described herein include: fluorescein and derivatives thereof, fluorescein isothiocyanate (FITC).

Non-limiting exemplary antibacterials that can be conjugated to any of the activatable cytokine constructs described herein include: aminoglycosides, streptomycin, neomycin, kanamycin, amikacin, gentamicin, and tobramycin.

Non-limiting exemplary 3beta, 16beta, 17alpha-trihydroxycholest-5-en-22-one 16-O-(2-O-4-methoxybenzoyl-beta-D-xylopyranosyl)-(1→3)-(2-O-acetyl-alpha-L-arabinopyranoside) (OSW-1) that can be conjugated to any of the activatable cytokine constructs described herein include: s-nitrobenzyloxycarbonyl derivatives of 06-benzylguanine, toposisomerase inhibitors, hemiasterlin, cephalotaxine, homoharringionine, pyrrol obenzodiazepine dimers (PBDs), functionalized pyrrolobenzodiazepenes, calcicheamicins, podophyiitoxins, taxanes, and *Vinca* alkoids.

Non-limiting exemplary radiopharmaceuticals that can be conjugated to any of the activatable cytokine constructs described herein include: $^{123}$I, $^{89}$Zr, $^{125}$I, $^{131}$I, $^{99}$mTc, $^{201}$Tl, $^{62}$Cu, $^{18}$F, $^{68}$Ga, $^{13}$N, $^{15}$O, $^{38}$K, $^{82}$Rb, $^{111}$In, $^{133}$Xe, $^{11}$C, and $^{99}$mTc (Technetium).

Non-limiting exemplary heavy metals that can be conjugated to any of the ACCs described herein include: barium, gold, and platinum.

Non-limiting exemplary anti-mycoplasmals that can be conjugated to any of the ACCs described herein include: tylosine, spectinomycin, streptomycin B, ampicillin, sulfanilamide, polymyxin, and chloramphenicol.

Those of ordinary skill in the art will recognize that a large variety of possible moieties can be conjugated to any of the activatable cytokine constructs described herein. Conjugation can include any chemical reaction that will bind the two molecules so long as the ACC and the other moiety retain their respective activities. Conjugation can include many chemical mechanisms, e.g., covalent binding, affinity binding, intercalation, coordinate binding, and complexation. In some embodiments, the preferred binding is covalent binding. Covalent binding can be achieved either by direct condensation of existing side chains or by the incorporation of external bridging molecules. Many bivalent or polyvalent linking agents are useful in conjugating any of the activatable cytokine constructs described herein. For example, conjugation can include organic compounds, such as thioesters, carbodiimides, succinimide esters, glutaraldehyde, diazobenzenes, and hexamethylene diamines. In some embodiments, the activatable cytokine construct can include, or otherwise introduce, one or more non-natural amino acid residues to provide suitable sites for conjugation.

In some embodiments of any of the ACCs described herein, an agent and/or conjugate is attached by disulfide bonds (e.g., disulfide bonds on a cysteine molecule) to the antigen-binding domain. Since many cancers naturally release high levels of glutathione, a reducing agent, glutathione present in the cancerous tissue microenvironment can reduce the disulfide bonds, and subsequently release the agent and/or the conjugate at the site of delivery.

In some embodiments of any of the ACCs described herein, when the conjugate binds to its target in the presence of complement within the target site (e.g., diseased tissue (e.g., cancerous tissue)), the amide or ester bond attaching the conjugate and/or agent to the linker is cleaved, resulting in the release of the conjugate and/or agent in its active form. These conjugates and/or agents when administered to a subject, will accomplish delivery and release of the conjugate and/or the agent at the target site (e.g., diseased tissue (e.g., cancerous tissue)). These conjugates and/or agents are particularly effective for the in vivo delivery of any of the conjugates and/or agents described herein.

In some embodiments, the linker is not cleavable by enzymes of the complement system. For example, the conjugate and/or agent is released without complement activation since complement activation ultimately lyses the target cell. In such embodiments, the conjugate and/or agent is to be delivered to the target cell (e.g., hormones, enzymes, corticosteroids, neurotransmitters, or genes). Furthermore, the linker is mildly susceptible to cleavage by serum proteases, and the conjugate and/or agent is released slowly at the target site.

In some embodiments of any of the ACCs described herein, the conjugate and/or agent is designed such that the conjugate and/or agent is delivered to the target site (e.g., disease tissue (e.g., cancerous tissue)) but the conjugate and/or agent is not released.

In some embodiments of any of the ACCs described herein, the conjugate and/or agent is attached to an antigen-binding domain either directly or via a non-cleavable linker. Exemplary non-cleavable linkers include amino acids (e.g., D-amino acids), peptides, or other organic compounds that may be modified to include functional groups that can subsequently be utilized in attachment to antigen-binding domains by methods described herein.

In some embodiments of any of the ACCs described herein, an ACC includes at least one point of conjugation for an agent. In some embodiments, all possible points of conjugation are available for conjugation to an agent. In some embodiments, the one or more points of conjugation include, without limitation, sulfur atoms involved in disulfide bonds, sulfur atoms involved in interchain disulfide bonds, sulfur atoms involved in interchain sulfide bonds but not sulfur atoms involved in intrachain disulfide bonds, and/or sulfur atoms of cysteine or other amino acid residues containing a sulfur atom. In such cases, residues may occur naturally in the protein construct structure or may be incorporated into the protein construct using methods including, without limitation, site-directed mutagenesis, chemical conversion, or mis-incorporation of non-natural amino acids.

This disclosure also provides methods and materials for preparing an ACC for conjugation. In some embodiments of any of the ACCs described herein, an ACC is modified to include one or more interchain disulfide bonds. For example, disulfide bonds in the ACC can undergo reduction following exposure to a reducing agent such as, without limitation, TCEP, DTT, or β-mercaptoethanol. In some cases, the reduction of the disulfide bonds is only partial. As used herein, the term partial reduction refers to situations where an ACC is contacted with a reducing agent and a fraction of all possible sites of conjugation undergo reduction (e.g., not all disulfide bonds are reduced). In some embodiments, an activatable cytokine construct is partially reduced following contact with a reducing agent if less than 99%, (e.g., less than 98%, 97%, 96%, 95%, 90%, 85%, 80%, 75%, 70%, 65%, 60%, 55%, 50%, 45%, 40%, 35%, 30%, 25%, 20%, 15%, 10% or less than 5%) of all possible sites of conjugation are reduced. In some embodiments, the ACC having a reduction in one or more interchain disulfide bonds is conjugated to a drug reactive with free thiols.

This disclosure also provides methods and materials for conjugating a therapeutic agent to a particular location on an ACC. In some embodiments of any of the ACC described herein, an ACC is modified so that the therapeutic agents can be conjugated to the ACC at particular locations on the ACC. For example, an ACC can be partially reduced in a manner that facilitates conjugation to the ACC. In such cases, partial reduction of the ACC occurs in a manner that conjugation sites in the ACC are not reduced. In some embodiments, the conjugation site(s) on the ACC are selected to facilitate conjugation of an agent at a particular location on the protein construct. Various factors can influence the "level of reduction" of the ACC upon treatment with a reducing agent. For example, without limitation, the ratio of reducing agent to ACC, length of incubation, incubation temperature, and/or pH of the reducing reaction solution can require optimization in order to achieve partial reduction of the ACC with the methods and materials described herein. Any appropriate combination of factors (e.g., ratio of reducing agent to ACC, the length and temperature of incubation with reducing agent, and/or pH of reducing agent) can be used to achieve partial reduction of the ACC (e.g., general reduction of possible conjugation sites or reduction at specific conjugation sites).

An effective ratio of reducing agent to ACC can be any ratio that at least partially reduces the ACC in a manner that allows conjugation to an agent (e.g., general reduction of possible conjugation sites or reduction at specific conjugation sites). In some embodiments, the ratio of reducing agent to ACC will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

An effective incubation time and temperature for treating an ACC with a reducing agent can be any time and temperature that at least partially reduces the ACC in a manner that allows conjugation of an agent to an ACC (e.g., general reduction of possible conjugation sites or reduction at specific conjugation sites). In some embodiments, the incubation time and temperature for treating an ACC will be in a range from about 1 hour at 37° C. to about 12 hours at 37° C. (or any subranges therein).

An effective pH for a reduction reaction for treating an ACC with a reducing agent can be any pH that at least partially reduces the ACC in a manner that allows conjugation of the ACC to an agent (e.g., general reduction of possible conjugation sites or reduction at specific conjugation sites).

When a partially-reduced ACC is contacted with an agent containing thiols, the agent can conjugate to the interchain thiols in the ACC. An agent can be modified in a manner to include thiols using a thiol-containing reagent (e.g., cysteine or N-acetyl cysteine). For example, the ACC can be partially reduced following incubation with reducing agent (e.g., TEPC) for about 1 hour at about 37° C. at a desired ratio of reducing agent to ACC. An effective ratio of reducing agent to ACC can be any ratio that partially reduces at least two interchain disulfide bonds located in the ACC in a manner that allows conjugation of a thiol-containing agent (e.g., general reduction of possible conjugation sites or reduction at specific conjugation sites).

In some embodiments of any of the ACCs described herein, an ACC is reduced by a reducing agent in a manner that avoids reducing any intrachain disulfide bonds. In some embodiments of any of the ACCs described herein, an ACC is reduced by a reducing agent in a manner that avoids reducing any intrachain disulfide bonds and reduces at least one interchain disulfide bond.

In some embodiments of any of the ACCs described herein, the ACC can also include an agent conjugated to the ACC. In some embodiments, the conjugated agent is a therapeutic agent.

In some embodiments, the agent (e.g., agent conjugated to an activatable cytokine construct) is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

In some embodiments, the agent (e.g., cytotoxic agent conjugated to an activatable cytokine construct) is linked to the ACC using a carbohydrate moiety, sulfhydryl group, amino group, or carboxylate group.

In some embodiments of any of the ACCs described herein conjugated to an agent, the agent (e.g., cytotoxic agent conjugated to an activatable cytokine construct) is conjugated to the ACC via a linker and/or a CM (also referred to as a cleavable sequence). In some embodiments, the agent (e.g., cytotoxic agent conjugated to an activatable cytokine construct) is conjugated to a cysteine or a lysine in the ACC. In some embodiments, the agent (e.g., cytotoxic agent conjugated to an activatable cytokine construct) is conjugated to another residue of the ACC, such as those residues disclosed herein. In some embodiments, the linker is a thiol-containing linker. In some embodiments, the linker is a non-cleavable linker. Some non-limiting examples of cleavable moieties and linkers are provided in Table 1.

TABLE 1

| Types of CMs | Amino Acid Sequence |
|---|---|
| Plasmin CMs | |
| Pro-urokinase | PRFKIIGG (SEQ ID NO: 280) |
|  | PRFRIIGG (SEQ ID NO: 281) |
| TGFP | SSRHRRALD (SEQ ID NO: 282) |
| Plasminogen | RKSSIIRMRDVVL (SEQ ID NO: 283) |
| Staphylokinase | SSSFDKGKYKKGDDA (SEQ ID NO: 284) |
| SSSFDKGKYKRGDDA | (SEQ ID NO: 285) |

TABLE 1-continued

| Types of CMs | Amino Acid Sequence |
|---|---|
| Factor Xa CMs | IEGR (SEQ ID NO: 286) |
| | IDGR (SEQ ID NO: 287) |
| | GGSIDGR (SEQ ID NO: 288) |
| MMPCMs | |
| Gelatinase A | PLGLWA (SEQ ID NO: 289) |
| Collagenase CMs | |
| Calf skin collagen (α1(I) chain) | GPQGIAGQ (SEQ ID NO: 290) |
| Calf skin collagen (α2(I) chain) | GPQGLLGA (SEQ ID NO: 291) |
| Bovine cartilage collagen (α1(II) chain) | GIAGQ (SEQ ID NO: 292) |
| Human liver collagen (α1(III) chain) | GPLGIAGI (SEQ ID NO: 293) |
| Human α$_2$M | GPEGLRVG (SEQ ID NO: 294) |
| Human PZP | YGAGLGVV (SEQ ID NO: 295) |
| | AGLGVVER (SEQ ID NO: 296) |
| | AGLGISST (SEQ ID NO: 297) |
| Rat α$_1$M | EPQALAMS (SEQ ID NO: 298) |
| | QALAMSAI (SEQ ID NO: 299) |
| Rat α$_2$M | AAYHLVSQ (SEQ ID NO: 300) |
| | MDAFLESS (SEQ ID NO: 301) |
| Rat α$_1$I$_3$(2J) | ESLPVVAV (SEQ ID NO: 302) |
| Rat α$_1$I$_3$(27J) | SAPAVESE (SEQ ID NO: 303) |
| Human fibroblast collagenase | DVAQFVLT (SEQ ID NO: 304) |
| (autolytic cleavages) | VAQFVLT (SEQ ID NO: 305) |
| | VAQFVLTE (SEQ ID NO: 306) |
| | AQFVLTEG (SEQ ID NO: 307) |
| | PVQPIGPQ (SEQ ID NO: 308) |

Those of ordinary skill in the art will recognize that a large variety of possible moieties can be coupled to the ACCs of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference). In general, an effective conjugation of an agent (e.g., cytotoxic agent) to an ACC can be accomplished by any chemical reaction that will bind the agent to the ACC while also allowing the agent and the ACC to retain functionality.

In some embodiments of any of the ACCs conjugated to an agent, a variety of bifunctional protein-coupling agents can be used to conjugate the agent to the ACC including, without limitation, N-succinimidyl-3-(2-pyridyldithiol) propionate (SPDP), iminothiolane (IT), bifunctional derivatives of imidoesters (e.g., dimethyl adipimidate HCL), active esters (e.g., disuccinimidyl suberate), aldehydes (e.g., glutareldehyde), bis-azido compounds (e.g., bis (p-azidobenzoyl) hexanediamine), bis-diazonium derivatives (e.g., bis-(p-diazoniumbenzoyl)-ethylenediamine), diisocyanates (e.g., tolyene 2,6-diisocyanate), and bis-active fluorine compounds (e.g., 1,5-difluoro-2,4-dinitrobenzene). For example, a ricin immunotoxin can be prepared as described in Vitetta et al., Science 238: 1098 (1987). In some embodiments, a carbon-14-labeled 1-isothiocyanatobenzyl-3-methyldiethylene triaminepentaacetic acid (MX-DTPA) chelating agent can be used to conjugate a radionucleotide to the ACC. (See, e.g., WO94/11026).

Suitable linkers and CMs are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an ACC by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC, sulfo-SMCC, SPDB, or sulfo-SPDB.

The CMs and linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically-hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments of any of the ACCs, an agent can be conjugated to the ACC using a modified amino acid sequence included in the amino acid sequence of the ACC. By inserting conjugation-enabled amino acids at specific locations within the amino acid sequence of the ACC, the protein construct can be designed for controlled placement and/or dosage of the conjugated agent (e.g., cytotoxic agent). For example, the ACC can be modified to include a cysteine amino acid residue at positions on the first monomer, the second monomer, the third monomer, and/or the fourth monomer that provide reactive thiol groups and does not negatively impact protein folding and/or assembly and does not alter antigen-binding properties. In some embodiments, the ACC can be modified to include one or more non-natural amino acid residues within the amino acid sequence of the ACC to provide suitable sites for conjugation. In some embodiments, the ACC can be modified to include enzymatically activatable peptide sequences within the amino acid sequence of the ACC.

Nucleic Acids

Provided herein are nucleic acids including sequences that encode the first monomer construct (or the protein portion of the first monomer construct) (e.g., any of the first monomers constructs described herein) and the second monomer construct (or the protein portion of the second monomer construct) (e.g., any of the second monomer constructs described herein) of any of the ACCs described herein. In some embodiments, a pair of nucleic acids together encode the first monomer construct (or the protein portion of the first monomer construct) and the second monomer construct (or the protein portion of the second monomer construct). In some embodiments, the nucleic acid sequence encoding the first monomer construct (or the protein portion of the first monomer construct) is at least 70% identical (e.g., at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical) to the nucleic acid sequence encoding the second monomer construct (or the protein portion of the second monomer construct).

In some embodiments, the nucleic acid encoding the protein portion of a first monomer construct encodes a polypeptide comprising the CP1 and CM1 moieties. In some embodiments, the nucleic acid encoding the protein portion of a second monomer encodes a polypeptide comprising the CP2 and CM2 moieties. In some embodiments, a pair of nucleic acids together encode the protein portion of a first monomer construct and the protein portion of the second monomer construct, wherein the protein portions are then conjugated to the DD1 and DD2 moieties, respectively (in a subsequent conjugation step).

In some embodiments, the nucleic acid encoding the first monomer construct encodes a polypeptide comprising the DD1 moiety. In some embodiments, the nucleic acid encoding the second monomer construct encodes a polypeptide comprising the DD2 moiety.

Vectors

Provided herein are vectors and sets of vectors including any of the nucleic acids described herein. One skilled in the art will be capable of selecting suitable vectors or sets of vectors (e.g., expression vectors) for making any of the ACCs described herein, and using the vectors or sets of vectors to express any of the ACCs described herein. For example, in selecting a vector or a set of vectors, the cell must be considered because the vector(s) may need to be able to integrate into a chromosome of the cell and/or replicate in it. Exemplary vectors that can be used to produce an ACC are also described below.

As used herein, the term "vector" refers to a polynucleotide capable of inducing the expression of a recombinant protein (e.g., a first or second monomer) in a cell (e.g., any of the cells described herein). A "vector" is able to deliver nucleic acids and fragments thereof into a host cell, and includes regulatory sequences (e.g., promoter, enhancer, poly(A) signal). Exogenous polynucleotides may be inserted into the expression vector in order to be expressed. The term "vector" also includes artificial chromosomes, plasmids, retroviruses, and baculovirus vectors.

Methods for constructing suitable vectors that include any of the nucleic acids described herein, and suitable for transforming cells (e.g., mammalian cells) are well-known in the art. See, e.g., Sambrook et al., Eds. "Molecular Cloning: A Laboratory Manual," $2^{nd}$ Ed., Cold Spring Harbor Press, 1989 and Ausubel et al., Eds. "Current Protocols in Molecular Biology," Current Protocols, 1993.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, for example, include sufficient cis-acting elements for expression; other elements for expression can be supplied by the host mammalian cell or in an in vitro expression system. Skilled practitioners will be capable of selecting suitable vectors and mammalian cells for making any of the ACCs described herein.

In some embodiments of any of the ACCs described herein, the ACC may be made biosynthetically using recombinant DNA technology and expression in eukaryotic or prokaryotic species.

In some embodiments, the vector includes a nucleic acid encoding the first monomer and the second monomer of any of the ACCs described herein. In some embodiments, the vector is an expression vector.

In some embodiments, a pair of vectors together include a pair of nucleic acids that together encode the first monomer and the second monomer of any of the ACCs described herein. In some embodiments, the pair of vectors is a pair of expression vectors.

Cells

Also provided herein are host cells including any of the vector or sets of vectors described herein including any of the nucleic acids described herein.

Any of the ACCs described herein can be produced by any cell (e.g., a mammalian cell). In some embodiments, a host cell is a mammalian cell (e.g., a human cell), a rodent cell (e.g., a mouse cell, a rat cell, a hamster cell, or a guinea pig cell), or a non-human primate cell.

Methods of introducing nucleic acids and vectors (e.g., any of the vectors or any of the sets of vectors described herein) into a cell are known in the art. Non-limiting examples of methods that can be used to introducing a nucleic acid into a cell include: lipofection, transfection, calcium phosphate transfection, cationic polymer transfection, viral transduction (e.g., adenoviral transduction, lentiviral transduction), nanoparticle transfection, and electroporation.

In some embodiments, the introducing step includes introducing into a cell a vector (e.g., any of the vectors or sets of vectors described herein) including a nucleic acid encoding the monomers that make up any of the ACCs described herein.

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary (CHO) cells and human embryonic kidney cells (e.g., HEK293 cells).

In some embodiments, the cell contains the nucleic acid encoding the first monomer and the second monomer of any one of the ACCs described herein. In some embodiments, the cell contains the pair of nucleic acids that together encode the first monomer and the second monomer of any of the ACCs described herein.

Methods of Producing Activatable Cytokine Constructs

Provided herein are methods of producing any of the ACCs described herein that include: (a) culturing any of the recombinant host cells described herein in a liquid culture medium under conditions sufficient to produce the ACC; and (b) recovering the ACC from the host cell and/or the liquid culture medium.

Methods of culturing cells are well known in the art. Cells can be maintained in vitro under conditions that favor cell proliferation, cell differentiation and cell growth. For example, cells can be cultured by contacting a cell (e.g., any of the cells described herein) with a cell culture medium that includes the necessary growth factors and supplements sufficient to support cell viability and growth.

In some embodiments of any of the methods described herein, the method further includes isolating the recovered ACC. Non-limiting examples of methods of isolation include: ammonium sulfate precipitation, polyethylene glycol precipitation, size exclusion chromatography, ligand-affinity chromatography, ion-exchange chromatography (e.g., anion or cation), and hydrophobic interaction chromatography.

In some embodiments, the cells can produce a protein portion of a first monomer construct that includes the CP1 and the CM1, and a protein portion of a second monomer construct that includes the CP2 and the CM2, and then the protein portions are subsequently conjugated to the DD1 and DD2 moieties, respectively.

Compositions and methods described herein may involve use of non-reducing or partially-reducing conditions that allow disulfide bonds to form between the dimerization domains to form and maintain dimerization of the ACCs.

In some embodiments of any of the methods described herein, the method further includes formulating the isolated ACC into a pharmaceutical composition. Various formulations are known in the art and are described herein. Any of the isolated ACCs described herein can be formulated for any route of administration (e.g., intravenous, intratumoral, subcutaneous, intradermal, oral (e.g., inhalation), transdermal (e.g., topical), transmucosal, or intramuscular).

Also provided herein are ACCs produced by any of the methods described herein. Also provided are compositions (e.g., pharmaceutical compositions) that include any of the ACCs produced by any of the methods described herein. Also provided herein are kits that include at least one dose of any of the compositions (e.g., pharmaceutical compositions) described herein.

Methods of Treatment

Provided herein are methods of treating a disease (e.g., a cancer (e.g., any of the cancers described herein)) in a subject including administering a therapeutically effective amount of any of the ACCs described herein to the subject.

As used herein, the term "subject" refers to any mammal. In some embodiments, the subject is a feline (e.g., a cat), a canine (e.g., a dog), an equine (e.g., a horse), a rabbit, a pig, a rodent (e.g., a mouse, a rat, a hamster or a guinea pig), a non-human primate (e.g., a simian (e.g., a monkey (e.g., a baboon, a marmoset), or an ape (e.g., a chimpanzee, a gorilla, an orangutan, or a gibbon)), or a human. In some embodiments, the subject is a human.

In some embodiments, the subject has been previously identified or diagnosed as having the disease (e.g., cancer (e.g., any of the cancers described herein)).

As used herein, the term "treat" includes reducing the severity, frequency or the number of one or more (e.g., 1, 2, 3, 4, or 5) symptoms or signs of a disease (e.g., a cancer (e.g., any of the cancers described herein)) in the subject (e.g., any of the subjects described herein). In some embodiments where the disease is cancer, treating results in reducing cancer growth, inhibiting cancer progression, inhibiting cancer metastasis, or reducing the risk of cancer recurrence in a subject having cancer.

In some embodiments of any of the methods described herein, the disease is a cancer. Also provided herein are methods of treating a subject in need thereof (e.g., any of the exemplary subjects described herein or known in the art) that include administering to the subject a therapeutically effective amount of any of the ACCs described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, a lymphoma (e.g., B-cell lymphoma, B-cell non-Hodgkin's lymphoma, Hodgkin's lymphoma, cutaneous T-cell lymphoma), a leukemia (e.g., hairy cell leukemia, chronic lymphocytic leukemia (CLL), acute myeloid leukemia (AML), chronic myeloid leukemia (CML), acute lymphocytic leukemia (ALL)), myelodysplastic syndromes (MDS), Kaposi sarcoma, retinoblastoma, stomach cancer, urothelial carcinoma, lung cancer, renal cell carcinoma, gastric and esophageal cancer, pancreatic cancer, prostate cancer, brain cancer, colon cancer, bone cancer, lung cancer, breast cancer, colorectal cancer, ovarian cancer, nasopharyngeal adenocarcimoa, non-small cell lung carcinoma (NSCLC), squamous cell head and neck carcinoma, endometrial cancer, bladder cancer, cervical cancer, liver cancer, and hepatocellular carcinoma. In some embodiments, the cancer is a lymphoma. In some embodiments, the lymphoma is Burkitt's lymphoma. In some aspects, the subject has been identified or diagnosed as having familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood;

Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

Further exemplary cancers include diffuse large B-cell lymphoma (DLBCL) and mantle cell lymphoma (MCL).

Metastases of the aforementioned cancers can also be treated or prevented in accordance with the methods described herein.

In some embodiments, these methods can result in a reduction in the number, severity, or frequency of one or more symptoms of the cancer in the subject (e.g., as compared to the number, severity, or frequency of the one or more symptoms of the cancer in the subject prior to treatment).

In some embodiments of any of the methods described herein, the methods further include administering to a subject an additional therapeutic agent (e.g., one or more of the therapeutic agents listed in Table 2).

TABLE 2

| Additional Therapeutic Agents | |
|---|---|
| Antibody Trade Name (antibody name) | Target |
| Raptiva ™ (efalizumab) | CD11a |
| Arzerra ™ (ofatumumab) | CD20 |
| Bexxar ™ (tositumomab) | CD20 |
| Gazyva ™ (obinutuzumab) | CD20 |
| Ocrevus ™ (ocrelizumab) | CD20 |
| Rituxan ™ (rituximab) | CD20 |
| Zevalin ™ (ibritumomab tiuxetan) | CD20 |
| Adcetris ™ (brentuximab vedotin) | CD30 |
| Myelotarg ™ (gemtuzumab) | CD33 |
| Mylotarg ™ (gemtuzumab ozogamicin) | CD33 |
| (vadastuximab) | CD33 |
| (vadastuximab talirine) | CD33 |
| Campath ™ (alemtuzumab) | CD52 |
| Lemtrada ™ (alemtuzumab) | CD52 |
| Tactress ™ (tamtuvetmab) | CD52 |
| Soliris ™ (eculizumab) | Complement C5 |
| Ultomiris ™ (ravulizumab) | Complement C5 |
| (olendalizumab) | Complement C5 |
| Yervoy ™ (ipilimumab) | CTLA-4 |
| (tremelimumab) | CTLA-4 |
| Orencia ™ (abatacept) | CTLA-4 |
| Hu5c8 | CD40L |
| (letolizumab) | CD40L |
| Rexomun ™ (ertumaxomab) | CD3/Her2 |
| Erbitux ™ (cetuximab) | EGFR |
| Portrazza ™ (necitumumab) | EGFR |
| Vectibix ™ (panitumumab) | EGFR |
| CH806 | EGFR |
| (depatuxizumab) | EGFR |
| (depatuxizumab mafodotin) | EGFR |
| (futuximab:modotuximab) | EGFR |
| ICR62 (imgatuzumab) | EGFR |
| (laprituximab) | EGFR |
| (losatuxizumab) | EGFR |
| (losatuxizumab vedotin) | EGFR |
| mAb 528 | EGFR |
| (matuzumab) | EGFR |
| (nimotuzumab) | EGFR |
| (tomuzotuximab) | EGFR |
| (zalutumumab) | EGFR |
| MDX-447 | EGFR/CD64 |
| (adecatumumab) | EpCAM |
| Panorex ™ (edrecolomab) | EpCAM |
| Vicinium ™ | EpCAM |
| Synagis ™ (palivizumab) | F protein of RSV |
| ReoPro ™ (abiciximab) | Glycoprotein receptor IIb/IIIa |
| Herceptin ™ (trastuzumab) | Her2 |
| Herceptin ™ Hylecta (trastuzumab; Hyaluronidase) | Her2 |
| (trastuzumab deruxtecan) | Her2 |
| (hertuzumab verdotin) | Her2 |
| Kadcyla ™ (trastuzumab emtansine) | Her2 |
| (margetuximab) | Her2 |
| (timigutuzumab) | Her2 |
| Xolair ™ (omalizumab) | IgE |
| (ligelizumab) | IgE |
| (figitumumab) | IGF1R |
| (teprotumumab) | IGF1R |
| Simulect ™ (basiliximab) | IL2R |
| Zenapax ™ (daclizumab) | IL2R |
| Zinbryta ™ (daclizumab) | IL2R |
| Actemra ™ (tocilizumab) | IL-6 receptor |
| Kevzara ™ (sarilumab) | IL-6 receptor |
| (vobarilizumab) | IL-6 receptor |
| Stelara ™ (ustekinumab) | IL-12/IL-23 |
| Tysabri ™ (natalizumab) | Integrinα4 |
| (abrilumab) | Integrinα4 |
| | Jagged 1 or Jagged 2 |
| (fasinumab) | NGF |
| (fulranumab) | NGF |
| (tanezumab) | NGF |
| | Notch, e.g., Notch 1 |
| Pidilizumab | Delta like-1 (PD-1 pathway inhibitor) |
| Opdivo ® (nivolumab) | PD1 |
| Keytruda ® (pembrolizumab) | PD1 |
| Libtayo ® (cemiplimab) | PD1 |

TABLE 2-continued

Additional Therapeutic Agents

| Antibody Trade Name (antibody name) | Target |
| --- | --- |
| BGB-A317 (tislelizumab) | PD1 |
| PDR001 (spartalizumab) | PD1 |
| JNJ-63723283 (cetrelimab) | PD1 |
| TSR042 (dostarlimab) | PD1 |
| AGEN2034 (balstilimab) | PD1 |
| JS001 (toripalimab) | PD1 |
| IOBI308 (sintilimab) | PD1 |
| BCD100 (prolgolimab) | PD1 |
| CBT-501 (genolimzumab) | PD1 |
| ABBV181 (budigalimab) | PD1 |
| AK105 | PD1 |
| BI-754091 | PD1 |
| INCSHR-1210 | PD1 |
| MEDI0680 | PD1 |
| MGA012 | PD1 |
| SHR-1210 | PD1 |
| Imfinzi ™ (durvalumab) | PD-L1 |
| Tecentriq ® (atezolizumab) | PD-L1 |
| Bavencio ® (avelumab) | PD-L1 |
| KN035 (envafolimab) | PD-L1 |
| BMS936559 (MDX1105) | PD-L1 |
| BGBA 333 | PD-L1 |
| FAZ053 | PD-L1 |
| LY-3300054 | PD-L1 |
| SH-1316 | PD-L1 |
| AMP-224 | PD-L2 |
| (bavituximab) | Phosphatidylserine |
| huJ591 | PSMA |
| RAV12 | RAAG12 |
| Prolia ™ (denosumab) | RANKL |
| GC1008 (fresolimumab) | TGFbeta |
| Cimzia ™ (Certolizumab Pegol) | TNFα |
| Remicade ™ (infliximab) | TNFα |
| Humira ™ (adalimumab) | TNFα |
| Simponi ™ (golimumab) | TNFα |
| Enbrel ™ (etanercept) | TNF-R |
| (mapatumumab) | TRAIL-R1 |
| Avastin ™ (bevacizumab) | VEGF |
| Lucentis ™ (ranibizumab) | VEGF |
| (brolucizumab) | VEGF |
| (vanucizumab) | VEGF |

Compositions/Kits

Also provided herein are compositions (e.g., pharmaceutical compositions) including any of the ACCs described herein and one or more (e.g., 1, 2, 3, 4, or 5) pharmaceutically acceptable carriers (e.g., any of the pharmaceutically acceptable carriers described herein), diluents, or excipients.

In some embodiments, the compositions (e.g. pharmaceutical compositions) that include any of the ACCs described herein can be disposed in a sterile vial or a pre-loaded syringe.

In some embodiments, the compositions (e.g. pharmaceutical compositions) that include any of the ACCs described herein can be formulated for different routes of administration (e.g., intravenous, subcutaneous, intramuscular, intraperitoneal, or intratumoral).

In some embodiments, any of the pharmaceutical compositions described herein can include one or more buffers (e.g., a neutral-buffered saline, a phosphate-buffered saline (PBS), amino acids (e.g., glycine), one or more carbohydrates (e.g., glucose, mannose, sucrose, dextran, or mannitol), one or more antioxidants, one or more chelating agents (e.g., EDTA or glutathione), one or more preservatives, and/or a pharmaceutically acceptable carrier (e.g., bacteriostatic water, PBS, or saline).

As used herein, the phrase "pharmaceutically acceptable carrier" refers to any and all solvents, dispersion media, coatings, antibacterial agents, antimicrobial agents, isotonic and absorption delaying agents, and the like, compatible with pharmaceutical administration. Suitable carriers include, but are not limited to: water, saline, ringer's solutions, dextrose solution, and about 5% human serum albumin.

In some embodiments of any of the pharmaceutical compositions described herein, any of the ACCs described herein are prepared with carriers that protect against rapid elimination from the body, e.g., sustained and controlled release formulations, including implants and microencapsulated delivery systems. Biodegradable, biocompatible polymers can be used, e.g., ethylene vinyl acetate, polyanhydrides, polyglycolic acid, collage, polyorthoesters, and polylactic acid. Methods for preparation of such pharmaceutical compositions and formulations are apparent to those skilled in the art.

Also provided herein are kits that include any of the ACCs described herein, any of the compositions that include any of the ACCs described herein, or any of the pharmaceutical compositions that include any of the ACCs described herein. Also provided are kits that include one or more second therapeutic agent(s) selected from Table 2 in addition to an ACC described herein. The second therapeutic agent(s) may be provided in a dosage administration form that is separate from the ACC. Alternatively, the second therapeutic agent(s) may be formulated together with the ACC.

Any of the kits described herein can include instructions for using any of the compositions (e.g., pharmaceutical compositions) and/or any of the ACCs described herein. In some embodiments, the kits can include instructions for performing any of the methods described herein. In some embodiments, the kits can include at least one dose of any of the compositions (e.g., pharmaceutical compositions) described herein. In some embodiments, the kits can provide a syringe for administering any of the pharmaceutical compositions described herein.

The present disclosure includes the following non-limiting aspects:

1. An activatable cytokine construct (ACC) that includes a first monomer construct and a second monomer construct, wherein:
   (a) the first monomer construct comprises a first mature cytokine protein (CP1), a first cleavable moiety (CM1), and a first dimerization domain (DD1), wherein the CM1 is positioned between the CP1 and the DD1; and
   (b) the second monomer construct comprises a second mature cytokine protein (CP2), a second cleavable moiety (CM2), and a second dimerization domain (DD2), wherein the CM2 is positioned between the CP2 and the DD2; or
   (a) the first monomer construct comprises a first mature cytokine protein (CP1), a first dimerization domain (DD1), and
   (b) the second monomer construct comprises a second mature cytokine protein (CP2), a cleavable moiety (CM), and a second dimerization domain (DD2), wherein the CM is positioned between the CP2 and the DD2, wherein the CM functions as a substrate for a protease; or
   (a) the first monomer construct comprises a first mature cytokine protein (CP1), a cleavable moiety (CM), and a first dimerization domain (DD1), wherein the CM is positioned between the CP1 and the DD1, and
   (b) the second monomer construct comprises a second mature cytokine protein (CP2), and a second dimerization domain (DD2), wherein the CM functions as a substrate for a protease; or
   (a) the first monomer construct comprises a first mature cytokine protein (CP1), and a first dimerization domain (DD1), and
   (b) the second monomer construct comprises a second mature cytokine protein (CP2), and a second dimerization domain (DD2), wherein the CP1, the CP2, or both CP1 and CP2 include(s) an amino acid sequence that functions as a substrate for a protease;
   further wherein:
   (c) the DD1 and the DD2 bind each other thereby forming a dimer of the first monomer construct and the second monomer construct; and
   (d) the ACC is characterized by having a reduced level of at least one CP1 and/or CP2 activity as compared to a control level of the at least one CP1 and/or CP2 activity.

2. The ACC of aspect 1, wherein the first monomer construct comprises a first polypeptide that comprises the CP1, the CM1, and the DD1.

3. The ACC of any one or combination of aspect 1 or 2, wherein the second monomer construct comprises a second polypeptide that comprises the CP2, the CM2, and the DD2.

4. The ACC of any one or combination of aspects 1-3, wherein the DD1 and the DD2 are a pair selected from the group consisting of: a pair of Fc domains, a sushi domain from an alpha chain of human IL-15 receptor (IL15Rα) and a soluble IL-15; barnase and barnstar; a PKA and an AKAP; adapter/docking tag modules based on mutated RNase I fragments; an epitope and sdAb; an epitope and scFv; and SNARE modules based on interactions of the proteins syntaxin, synaptotagmin, synaptobrevin, and SNAP25, an antigen-binding domain and an epitope.

5. The ACC of aspect 4, wherein the DD1 and the DD2 are a pair of Fc domains.

6. The ACC of aspect 5, wherein the pair of Fc domains is a pair of human Fc domains.

7. The ACC of aspect 6, wherein the human Fc domains are human IgG1 Fc domains, human IgG2 Fc domains, human IgG3 Fc domains, or human IgG4 Fc domains.

8. The ACC of aspect 7, wherein the human Fc domains are human IgG4 Fc domains.

9. The ACC of aspect 8, wherein the human Fc domains comprise a sequence that is at least 80%, 85%, 90%, 95%, 96%, 97%, 98%, or 99% identical to SEQ ID NO: 3, SEQ ID NO: 315, or SEQ ID NO: 316.

10. The ACC of aspect 9, wherein the human Fc domains comprise a sequence that is at least 90% identical to SEQ ID NO: 3, SEQ ID NO: 315, or SEQ ID NO: 316.

11. The ACC of aspect 10, wherein the human Fc domains comprise SEQ ID NO: 3, SEQ ID NO: 315, or SEQ ID NO: 316.

12. The ACC of any one or combination of aspects 1-3 and 5-11, wherein the DD1 and the DD2 are the same.

13. The ACC of aspect 4, wherein DD1 comprises an antigen-binding domain and DD2 comprises a corresponding epitope.

14. The ACC of aspect 13, wherein the antigen-binding domain is an anti-His tag antigen-binding domain and wherein the DD2 comprises a His tag.

15. The ACC of aspect 13, wherein the antigen-binding domain is a single chain variable fragment (scFv).

16. The ACC of aspect 13, wherein the antigen-binding domain is a single domain antibody (sdAb).

17. The ACC of aspect 1, wherein at least one of DD1 and DD2 comprises a dimerization domain substituent selected from the group consisting of a non-polypeptide polymer and a small molecule.

18. The ACC of aspect 17, wherein DD1 and DD2 comprise non-polypeptide polymers covalently bound to each other.

19. The ACC of aspect 18, wherein the non-polypeptide polymer is a sulfur-containing polyethylene glycol, and wherein DD1 and DD2 are covalently bound to each other via one or more disulfide bonds.

20. The ACC of aspect 17, wherein at least one of DD1 and DD2 comprises a small molecule.

21. The ACC of aspect 20, wherein the small molecule is biotin.

22. The ACC of aspect 20, wherein DD1 comprises biotin and DD2 comprises an avidin.

23. The ACC of any one or combination of aspects 1-22, wherein the CP1 and/or the CP2 is/are each individually selected from the group consisting of: an interferon, an interleukin, GM-CSF, G-CSF, LIF, OSM, CD154, LT-β, TNF-α, TNF-β, 4-1BBL, APRIL, CD70, CD153, CD178, GITRL, LIGHT, OX40L, TALL-1, TRAIL, TWEAK, TRANCE, TGF-β1, TGF-β1, TGF-β3, Epo, Tpo, Flt-3L, SCF, M-CSF, and MSP.

24. The ACC of any one or combination of aspects 1-23, wherein the CP1 and the CP2 are the same.

25. The ACC of any one or combination of aspects 1-23 wherein the CP1 and the CP2 are different.

26. The ACC of any one or combination of aspects 1-23, wherein the CP1 and/or the CP2 is/are an interferon.
27. The ACC of aspect 26, wherein the CP1 and the CP2 are an interferon.
28. The ACC of aspect 26, wherein the CP1 and the CP2 are different interferons.
29. The ACC of aspect 26, wherein the CP1 and the CP2 are the same interferon.
30. The ACC of aspect 26, wherein the CP1 or the CP2 is an interferon.
31. The ACC of any one or combination of aspects 26-30, wherein the interferon(s) is/are a human wildtype mature interferon.
32. The ACC of any one or combination of aspects 26-31, wherein the interferon(s) is/are selected from the group consisting of: interferon-alpha, interferon-beta, interferon-omega, and interferon-tau.
33. The ACC of aspect 32, wherein the interferons is/are an interferon-alpha.
34. The ACC of aspect 33, wherein the interferon(s) is/are selected from the group consisting of: interferon alpha-2α, interferon alpha-2b, and interferon alpha-n3.
35. The ACC of aspect 34, wherein the interferon(s) is/are interferon alpha-2b.
36. The ACC of aspect 35, wherein the CP1 and/or CP2 comprises a sequence that is at least 80% identical to SEQ ID NO: 1.
37. The ACC of aspect 36, wherein the CP1 and/or CP2 comprises a sequence that is at least 90% identical to SEQ ID NO: 1.
38. The ACC of aspect 37, wherein the CP1 and/or CP2 comprises a sequence of SEQ ID NO: 1.
39. The ACC of aspect 32, wherein the interferon is an interferon beta.
40. The ACC of aspect 39, wherein the interferon beta is selected from the group consisting of interferon beta-1a, and interferon beta-1b.
41. The ACC of any one of aspects 1-40, wherein the CP1 and/or the CP2 comprises an IFab domain.
42. The ACC of aspect 41, wherein the CP1 and/or the CP2 comprises an interleukin.
43. The ACC of aspect 42, wherein the interleukin is selected from the group consisting of IL-1α, IL-1β, IL-1RA, IL-18, IL-2, IL-4, IL-7, IL-9, IL-13, IL-15, IL-3, IL-5, IL-6, IL-11, IL-12, IL-10, IL-20, IL-14, IL-16, and IL-17.
44. The ACC of any one or combination of aspects 1-43, wherein the CM1 and/or the CM2 comprise a total of about 3 amino acids to about 15 amino acids.
45. The ACC of any one or combination of aspects 1-44, wherein the CM1 and the CM2 comprise substrates for different proteases.
46. The ACC of any one or combination of aspects 1-44, wherein the CM1 and the CM2 comprise substrates for the same protease.
47. The ACC of any one or combination of aspects 1-46, wherein the protease(s) is/are selected from the group consisting of: ADAM8, ADAM8, ADAM10, ADAM12, ADAM15, ADAM17/TACE, ADAMDEC1, ADAMTS1, ADAMTS4, ADAMTS5, BACE, Renin, Cathepsin D, Cathepsin E, Caspase 1, Caspase 2, Caspase 3, Caspase 4, Caspase 5, Caspase 6, Caspase 7, Caspase 8, Caspase 9, Caspase 10, Caspase 14, Cathepsin B, Cathepsin C, Cathepsin K, Cathespin L, Cathepsin S, Cathepsin V/L2, Cathepsin X/Z/P, Cruzipain, Legumain, Otubain-2, KLK4, KLK5, KLK6, KLK7, KLK8, KLK10, KLK11, KLK13, KLK14, Meprin, Neprilysin, PSMA, BMP-1, MMP-1, MMP-2, MMP-3, MMP-7, MMP-9, MMP-10, MMP-11, MMP-12, MMP-13, MMP-14, MMP-15, MMP-16, MMP-17, MMP-19, MMP-20, MMP-23, MMP-24, MMP-26, MMP-27, activated protein C, cathepsin A, cathepsin G, Chymase, FVIIa, FIXa, FXa, FXIa, FXIIa, Elastase, Granzyme B, Guanidinobenzoatase, HtrA1, human neutrophil lyase, lactoferrin, marapsin, NS3/4A, PACE4, Plasmin, PSA, tPA, thrombin, tryptase, uPA, DESC1, DPP-4, FAP, Hepsin, Matriptase-2, MT-SP1/Matripase, TMPRSS2, TMPRSS3, and TMPRSS4.
48. The ACC of aspect 47, wherein the protease(s) is/are selected from the group consisting of: uPA, legumain, MT-SP1, ADAM17, BMP-1, TMPRSS3, TMPRSS4, MMP-2, MMP-9, MMP-12, MMP-13, and MMP-14.
49. The ACC of aspect 47, wherein the CM1 and/or the CM2 comprise a sequence selected from the group consisting of: LSGRSDNH (SEQ ID NO: 5), TGRGPSWV (SEQ ID NO: 6), PLTGRSGG (SEQ ID NO: 7), TARGPSFK (SEQ ID NO: 8), NTLSGRSENHSG (SEQ ID NO: 9), NTLSGRSGNHGS (SEQ ID NO: 10), TSTSGRSANPRG (SEQ ID NO: 11), TSGRSANP (SEQ ID NO: 12), VHMPLGFLGP (SEQ ID NO: 13), AVGLLAPP (SEQ ID NO: 14), AQNLLGMV (SEQ ID NO: 15), QNQALRMA (SEQ ID NO: 16), LAAPLGLL (SEQ ID NO: 17), STFPFGMF (SEQ ID NO: 18), ISSGLLSS (SEQ ID NO: 19), PAGLWLDP (SEQ ID NO: 20), VAGRSMRP (SEQ ID NO: 21), VVPEGRRS (SEQ ID NO: 22), ILPRSPAF (SEQ ID NO: 23), MVLGRSLL (SEQ ID NO: 24), QGRAITFI (SEQ ID NO: 25), SPRSIMLA (SEQ ID NO: 26), SMLRSMPL (SEQ ID NO: 27), ISSGLLSGRSDNH (SEQ ID NO: 28), AVGLLAPPGGLSGRSDNH (SEQ ID NO: 29), ISSGLLSSGGSGGSLSGRSDNH (SEQ ID NO: 30), LSGRSGNH (SEQ ID NO: 31), SGRSANPRG (SEQ ID NO: 32), LSGRSDDH (SEQ ID NO: 33), LSGRSDIH (SEQ ID NO: 34), LSGRSDQH (SEQ ID NO: 35), LSGRSDTH (SEQ ID NO: 36), LSGRSDYH (SEQ ID NO: 37), LSGRSDNP (SEQ ID NO: 38), LSGRSANP (SEQ ID NO: 39), LSGRSANI (SEQ ID NO: 40), LSGRSDNI (SEQ ID NO: 41), MIAPVAYR (SEQ ID NO: 42), RPSPMWAY (SEQ ID NO: 43), WATPRPMR (SEQ ID NO: 44), FRLLDWQW (SEQ ID NO: 45), ISSGL (SEQ ID NO: 46), ISSGLLS (SEQ ID NO: 47), ISSGLL (SEQ ID NO: 48), ISSGLLSGRSANPRG (SEQ ID NO: 49), AVGLLAPPTSGRSANPRG (SEQ ID NO: 50), AVGLLAPPSGRSANPRG (SEQ ID NO: 51), ISSGLLSGRSDDH (SEQ ID NO: 52), ISSGLLSGRSDIH (SEQ ID NO: 53), ISSGLLSGRSDQH (SEQ ID NO: 54), ISSGLLSGRSDTH (SEQ ID NO: 55), ISSGLLSGRSDYH (SEQ ID NO: 56), ISSGLLSGRSDNP (SEQ ID NO: 57), ISSGLLSGRSANP (SEQ ID NO: 58), ISSGLLSGRSANI (SEQ ID NO: 59), AVGLLAPPGGLSGRSDDH (SEQ ID NO: 60), AVGLLAPPGGLSGRSDIH (SEQ ID NO: 61), AVGLLAPPGGLSGRSDQH (SEQ ID NO: 62), AVGLLAPPGGLSGRSDTH (SEQ ID NO: 63), AVGLLAPPGGLSGRSDYH (SEQ ID NO: 64), AVGLLAPPGGLSGRSDNP (SEQ ID NO: 65), AVGLLAPPGGLSGRSANP (SEQ ID NO: 66), AVGLLAPPGGLSGRSANI (SEQ ID NO: 67), ISSGLLSGRSDNI (SEQ ID NO: 68), AVGLLAPPGGLSGRSDNI (SEQ ID NO: 69), GLSGRSDNHGGAVGLLAPP (SEQ ID NO: 70), GLSGRSDNHGGVHMPLGFLGP (SEQ ID NO: 71), LSGRSDNHGGVHMPLGFLGP (SEQ ID NO: 72), ISSGLSS (SEQ ID NO: 73), PVGYTSSL (SEQ ID NO: 74), DWLYWPGI (SEQ ID NO: 75), LKAAPRWA (SEQ ID NO: 76), GPSHLVLT (SEQ ID NO: 77), LPGGLSPW (SEQ ID NO: 78), MGLFSEAG (SEQ ID NO: 79), SPLPLRVP (SEQ ID NO: 80), RMHLRSLG (SEQ ID NO: 81), LLAPSHRA (SEQ ID NO: 82), GPRSFGL (SEQ ID NO: 83), GPRSFG (SEQ ID NO: 84), SARGPSRW (SEQ ID NO: 85), GGWHTGRN (SEQ ID NO: 86), HTGRSGAL (SEQ ID NO: 87), AARGPAIH (SEQ ID NO: 88), RGPAFNPM (SEQ ID NO: 89), SSRGPAYL (SEQ ID NO: 90), RGPATPIM (SEQ ID NO: 91), RGPA (SEQ ID NO: 92), GGQPSGMWGW (SEQ ID NO: 93), FPRPLGITGL (SEQ ID NO: 94), SPLTGRSG (SEQ ID NO: 95), SAGFSLPA (SEQ ID NO: 96), LAPLGLQRR (SEQ ID NO: 97), SGGPLGVR (SEQ ID NO: 98), PLGL (SEQ ID NO: 99), and SGRSDNI (SEQ ID NO: 100).

50. The ACC of aspect 47, wherein the CM1 and/or the CM2 comprises a sequence selected from the group consisting of: ISSGLLSGRSDNH (SEQ ID NO: 28), LSGRSDDH (SEQ ID NO: 33), ISSGLLSGRSDQH (SEQ ID NO: 54), SGRSDNI (SEQ ID NO: 100), and ISSGLLSGRSDNI (SEQ ID NO: 68).

51. The ACC of any one or combination of aspects 1-50, wherein the protease(s) is/are produced by a tumor in a subject.

52. The ACC of aspect 51, wherein the subject has been diagnosed or identified as having a cancer.

53. The ACC of any one or combination of aspects 1-52, wherein the CP1 and the CM1 directly abut each other in the first monomer construct.

54. The ACC of any one or combination of aspects 1-53, wherein the CM1 and the DD1 directly abut each other in the first monomer construct.

55. The ACC of any one or combination of aspects 1-54, wherein the CP2 and the CM2 directly abut each other in the second monomer construct.

56. The ACC of any one or combination of aspects 1-55, wherein the CM2 and the DD2 directly abut each other in the second monomer construct.

57. The ACC of any one or combination of aspects 1-56, wherein the first monomer construct comprises at least one linker.

58. The ACC of aspect 57, wherein the at least one linker is a linker L1 disposed between the CP1 and the CM1 and/or a linker L2 disposed between the CM1 and the DD1.

59. The ACC of aspect 58, wherein the second monomer construct comprises at least one linker.

60. The ACC of aspect 59, wherein the at least one linker is a linker L3 disposed between the CP2 and the CM2 and/or a linker L4 disposed between the CM2 and the DD2.

61. The ACC of aspect 60, wherein the first monomer construct comprises a linker L1 and the second monomer construct comprises a linker L3.

62. The ACC of aspect 61, wherein L1 and L3 are the same.

63. The ACC of aspect 62, wherein the second monomer construct comprises a linker L2 and the second monomer construct comprises a linker L4.

64. The ACC of aspect 63, wherein L2 and L4 are the same.

65. The ACC of aspect 64, wherein each linker has a total length of 1 amino acid to about 15 amino acids.

66. The ACC of aspect 65, wherein each linker has a total length of at least 5 amino acids.

67. The ACC of any one or combination of aspects 1-66, wherein the first monomer construct comprises at least one linker, wherein each linker is independently selected from the group consisting of GSSGGSGGSGG (SEQ ID NO: 210); GGGS (SEQ ID NO: 2); GGGSGGGS (SEQ ID NO: 211); GGGSGGGSGGGS (SEQ ID NO: 212); GGGGSGGGGSGGGGS (SEQ ID NO: 213); GGGGSGGGGSGGGGSGGGGSGGGGS (SEQ ID NO: 214); GGGGSGGGGS (SEQ ID NO: 215); GGGGS (SEQ ID NO: 216); GS; GGGGSGS (SEQ ID NO: 217); GGGGSGGGGSGGGGSGS (SEQ ID NO: 218); GGSLDPKGGGGS (SEQ ID NO: 219); PKSCDKTH-TCPPCPAPELLG (SEQ ID NO: 220); SKY-GPPCPPCPAPEFLG (SEQ ID NO: 221); GKSSGSGS-ESKS (SEQ ID NO: 222); GSTSGSGKSSEGKG (SEQ ID NO: 223); GSTSGSGKSSEGSGSTKG (SEQ ID NO: 224); GSTSGSGKPGSGEGSTKG (SEQ ID NO: 225); GSTSGSGKPGSSEGST (SEQ ID NO: 226); (GS)n, (GGS)n, (GSGGS)n (SEQ ID NO: 227), (GGGS)n (SEQ ID NO: 228), (GGGGS)n (SEQ ID NO: 216), wherein each n is an integer of at least one; GGSG (SEQ ID NO: 229); GGSGG (SEQ ID NO: 230); GSGSG (SEQ ID NO: 231; GSGGG (SEQ ID NO: 232); GGGSG (SEQ ID NO: 233); GSSSG (SEQ ID NO: 234); GGGGSGGGGSGGGGS (SEQ ID NO: 213); GGGGSGGGGSGGGGSGGGGS (SEQ ID NO: 214); and GSTSGSGKPGSSEGST (SEQ ID NO: 226).

68. The ACC of aspect 67, wherein the linker comprises a sequence of GGGS (SEQ ID NO: 2).

69. The ACC of any one or combination of aspects 1-68, wherein the first monomer construct, comprises in a N- to C-terminal direction, the CP1, the CM1, and, linked directly or indirectly to the C-terminus of the CM1, the DD1.

70. The ACC of any one or combination of aspects 1-69, wherein the first polypeptide comprises in a C- to N-terminal direction, the CP1, the CM1, and, linked directly or indirectly to the N-terminus of the CM1, the DD1.

71. The ACC of any one or combination of aspects 1-70, wherein the second polypeptide comprises in a N- to C-terminal direction, the CP2, CM2, and, linked directly or indirectly to the C-terminus of the CM2, the DD2.

72. The ACC of any one or combination of aspects 1-71, wherein the second polypeptide comprises in a C- to N-terminal direction, the CP2, CM2, and, linked directly or indirectly to the CM2, the DD2.

73. The ACC of aspect 69, wherein the first monomer construct comprises, in the N to C-terminal direction, the CP1, the CM1, and the DD1, wherein the CP1 and the CM1 directly abut each other, wherein the CM1 and the DD1 directly abut each other, wherein the CM1 is a peptide of not more than 10 amino acids, wherein the second monomer construct is the same as the first monomer construct, and wherein the first and second monomer constructs are covalently bound to each other via at least two disulfide bonds.

74. The ACC of aspect 73, wherein CP1 is an interferon.

75. The ACC of aspect 74, wherein CP1 is an interferon-alpha.

76. The ACC of any one or combination of aspects 1-75, wherein the at least one CP1 and/or CP2 activity is a binding affinity ($K_D$) of the CP1 and/or the CP2 for its cognate receptor as determined using surface plasmon resonance.

77. The ACC of any one or combination of aspects 1-75, wherein the at least one CP1 and/or CP2 activity is a level of proliferation of lymphoma cells.

78. The ACC of any one or combination of aspects 1-75, wherein the at least one CP1 and/or CP2 activity is a level of JAK/STAT/ISGF3 pathway activation in a lymphoma cell.

79. The ACC of any one or combination of aspects 1-75, wherein the at least one activity is a level of SEAP production in a lymphoma cell.

80. The ACC of any one or combination aspects 1-79, wherein the ACC is characterized by at least a 20-fold reduction in at least one CP1 and/or CP2 activity as compared to the control level.
81. The ACC of aspect 80, wherein the ACC is characterized by at least a 50-fold reduction in at least one CP1 and/or CP2 activity as compared to the control level.
82. The ACC of aspect 81, wherein the ACC is characterized by at least a 100-fold reduction in at least one activity of the CP1 and/or CP2 as compared to the control level.
83. The ACC of aspect 82, wherein the ACC is characterized by at least a 500-fold reduction in at least one CP1 and/or CP2 activity as compared to the control level.
84. The ACC of any one or combination of aspects 1-83, wherein the control level of the at least one activity of the CP1 and/or CP2, is the activity of the CP1 and/or CP2 in the ACC following exposure of the ACC to the protease(s).
85. The ACC of any one or combination of aspects 1-83, wherein the control level of the at least one CP1 and/or CP2, is the corresponding CP1 and/or CP2 activity of a corresponding wildtype mature cytokine.
86. The ACC of any one or combination of aspects 1-85, wherein the ACC is characterized by generating a cleavage product following exposure to the protease(s), wherein the cleavage product comprises the at least one activity of the CP1 and/or CP2.
87. The ACC of aspect 86, wherein the at least one activity of the CP1 and/or CP2 is anti-proliferation activity.
88. The ACC of aspect 87, wherein the control level is an EC50 value, and wherein ratio of EC50 (cleavage product) to EC50 (control level) is less than about 10, or less than about 9, or less than about 8, or less than about 7, or less than about 6, or less than about 5, or less than about 4, or less than about 3, or less than about 2, or less than about 1.5.
89. A composition comprising an ACC of any one or combination of aspects 1-88.
90. The composition of aspect 89, wherein the composition is a pharmaceutical composition.
91. A container, vial, syringe, injector pen, or kit comprising at least one dose of the composition of aspect 89 or 90.
92. A method of treating a subject in need thereof comprising administering to the subject a therapeutically effective amount of the ACC of any one or combination of aspects 1-88 or the composition of aspects 89 or 90.
93. The method of aspect 92, wherein the subject has been identified or diagnosed as having a cancer.
94. The method of aspect 93, wherein the cancer is a lymphoma, solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, bladder cancer, stomach cancer, urothelial carcinoma, lung cancer, colon cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, or hepatocellular carcinoma.
95. The method of aspect 94, wherein the lymphoma is Burkitt's lymphoma.
96. A nucleic acid encoding a polypeptide that comprises the CP1 and CM1 of the ACC of any one or combination of aspects 1-88.
97. The nucleic acid of aspect 96, wherein the polypeptide further comprises a DD1 of any one or combination of aspects 1-16 or aspects 23-88.
98. A nucleic acid encoding a polypeptide that comprises the CP2 and CM2 of the ACC of any one or combination of aspects 1-88.
99. The nucleic acid of aspect 98, wherein the polypeptide further comprises the DD2 of any one or combination of aspects 1-16 or aspects 23-88.
100. A vector comprising the nucleic acid of any one or combination of aspects 96-99.
101. The vector of aspect 100, wherein the vector is an expression vector.
102. A cell comprising the nucleic acid of any one or combination of aspects 96-99 or the vector of aspect 100 or 101.
103. A pair of nucleic acids that together encode a polypeptide that comprises the CP1 and CM1 of the first monomer construct and a polypeptide that comprises the CP2 and CM2 of the second monomer construct of any one or combination of aspects 1-88.
104. A pair of vectors that together comprise the pair of nucleic acids of aspect 103.
105. The pair of vectors of aspect 104, wherein the pair of vectors is a pair of expression vectors.
106. A cell comprising the pair of nucleic acids of aspect 103 or the pair of vectors of aspects 104 or 105.
107. A method of producing an ACC comprising:
    culturing a cell of aspect 102 or 106 in a liquid culture medium under conditions sufficient to produce the ACC; and
    recovering the ACC from the cell or the liquid culture medium.
108. The method of aspect 107, further comprising:
    isolating the ACC recovered from the cell or the liquid culture medium.
109. The method of aspect 108, further comprising:
    formulating isolated ACC into a pharmaceutical composition.
110. An ACC produced by the method of aspect 107.
111. A composition comprising an ACC of aspect 110.
112. The composition of aspect 111, wherein the composition is a pharmaceutical composition.
113. A container, vial, syringe, injector pen, or kit comprising at least one dose of the composition of aspect 111 or 112.
114. An activatable cytokine construct (ACC) comprising a first monomer construct and a second monomer construct, wherein:
    (a) the first monomer construct comprises a first mature cytokine protein (CP1), a first cleavable moiety (CM1), and a first dimerization domain (DD1);
    (b) the second monomer construct comprises a second mature cytokine protein (CP2), a second cleavable moiety (CM2), and a second dimerization domain (DD2);
    (c) the first monomer construct is a polypeptide comprising, in an N- to C-terminal direction, the CP1, the CM1, and the DD1, further wherein:
    (i) each of the first monomer and the second monomer comprises a Linking Region comprising no more than 24 amino acids; and
    (ii) the CP1 is a mature interferon;

(d) further wherein:
  (i) the second monomer construct is the same as the first monomer construct,
  (ii) the first and second monomer constructs are covalently bound to each other via at least one disulfide bond, and
  (iii) the DD1 and the DD2 are a pair of human IgG Fc domains;
(e) the DD1 and the DD2 bind each other thereby forming a dimer of the first monomer construct and the second monomer construct; and
(f) the ACC is characterized by having a reduced level of interferon activity as compared to a corresponding control interferon.

115. The ACC of aspect 114, wherein the CP1 is a mature human interferon alpha.

116. The ACC of any one or combination of aspects 114-115, wherein the mature interferon is mature interferon alpha-2b.

117. The ACC of any one or combination of aspects 114-116, wherein the mature interferon is a truncated form of a wild type mature interferon alpha-2b.

118. The ACC of any one or combination of aspects 114-116, wherein the mature interferon comprises a sequence that is at least 95% identical to SEQ ID NO: 1.

119. The ACC of any one or combination of aspects 114-116, wherein the mature interferon alpha comprises the sequence of SEQ ID NO: 1.

120. The ACC of any one or combination of aspects 114-119, wherein the CP1 and the CM1 directly abut each other, the CM1 and the DD1 directly abut each other, and the CM1 and the CM2 each comprises no more than 10 amino acids, optionally no more than 7 amino acids.

121. The ACC of any one or combination of aspects 114-120, wherein the CM1 and the CM2 each independently functions as a substrate of urokinase (uPa) and/or a matrix metalloproteinase (MMP).

122. The ACC of any one or combination of aspects 114-121, wherein the CM1 and the CM2 each independently functions as a substrate of urokinase (uPa) and/or MMP-14.

123. The ACC of any one or combination of aspects 114-122, wherein the CM1 and the CM2 each comprises a sequence that is at least 85% identical to SEQ ID NO: 100.

124. The ACC of any one or combination of aspects 114-123, wherein the CM1 and the CM2 each comprises a sequence selected from the group consisting of SEQ ID NO: 41, SEQ ID NO: 68, and SEQ ID NO: 100.

125. The ACC of any one or combination of aspects 114-124, wherein the DD1 and the DD2 are a pair of human IgG1 Fc domains or a pair of human IgG4 Fc domains.

126. The ACC of aspect 125, wherein the DD1 and the DD2 are a pair of human IgG1 Fc domains truncated at N-terminus to Cysteine 226 as numbered by EU numbering or a pair of human IgG4 Fc domains truncated at N-terminus to Cysteine 226 as numbered by EU numbering.

127. The ACC of aspect 125 or 126, wherein the DD1 and the DD2 are a pair of human IgG4 Fc domains that comprise a S228P mutation as numbered by EU numbering.

128. The ACC of any one or combination of aspects 114-127, wherein the DD1 and the DD2 each comprises a sequence that is at least 95% identical to SEQ ID NO: 3.

129. The ACC of any one or combination of aspects 114-128, wherein the DD1 and the DD2 each comprises a sequence of SEQ ID NO: 3.

130. The ACC of any one or combination of aspects 114-129, wherein the first and second monomer constructs are covalently bound to each other via at least two disulfide bonds.

131. The ACC of any one or combination of aspects 114-130, wherein the first and second monomer constructs are covalently bound to each other via at least three disulfide bonds.

132. The ACC of any one or combination of aspects 114-131, wherein the first and second monomer constructs are covalently bound to each other via at least four disulfide bonds.

133. The ACC of any one or combination of aspects 114-132, wherein the first monomer construct further comprises a signal sequence directly abutting the N-terminus of the CM1.

134. The ACC of aspect 133, wherein the signal sequence comprises a sequence that is at least 95% identical to SEQ ID NO: 345.

135. The ACC of aspect 133, wherein the signal sequence comprises the sequence of SEQ ID NO: 345.

136. The ACC of any one or combination of aspects 114-135 comprising a Linking Region comprising no more than 18 amino acids, or no more than 12 amino acids.

137. The ACC of aspect 136, wherein the Linking Region comprises 7 to 12 amino acids.

138. The ACC of aspect 136, wherein the Linking Region comprises 7 amino acids.

139. The ACC of any one or combination of aspects 114-138, wherein the ACC is characterized by at least a 500-fold reduction in interferon activity as compared to a corresponding control interferon.

140. The ACC of any one or combination of aspects 114-139, wherein the CP1 is an interferon alpha and the control interferon is a recombinant interferon alpha.

141. The ACC of any one or combination of aspects 114-139, wherein the CP1 is an interferon alpha-2b and the control interferon is pegylated interferon alpha-2b.

142. The ACC of any one or combination of aspects 114-141, wherein the interferon activity is an anti-proliferation activity in lymphoma cells.

143. The ACC of any one or combination of aspects 114-141, wherein the interferon activity is induction of secreted embryonic alkaline phosphatase production in interferon-responsive HEK293 cells.

144. The ACC of any of aspects 114-143, wherein the ACC is further characterized by generating a cleavage product following exposure to the protease for which CM1 functions as a substrate, wherein the ratio of the interferon activity of the control interferon to the cleavage product is less than about 2, and wherein the control interferon is a corresponding recombinant wildtype interferon or a corresponding pegylated interferon.

145. The ACC of aspect 144, wherein the EC50 of the cleavage product is approximately the same as the EC50 of the corresponding recombinant wildtype interferon.

146. The ACC of aspect 114, wherein the first and second monomer constructs each comprises a sequence that is at least 95% identical to SEQ ID NO: 313.

147. The ACC of aspect 146, wherein the ACC is characterized by at least a 500-fold reduction in interferon activity as compared to wild type interferon alpha-2b, and wherein the ACC is further characterized by generating a cleavage product following exposure to uPA, wherein the cleavage product has approximately the same interferon activity as wildtype interferon alpha-2b, wherein interferon activity is measured in an anti-proliferation assay in lymphoma cells or in an assay of induction of secreted embryonic alkaline phosphatase production in interferon-responsive HEK293 cells.
148. The ACC of aspect 146, wherein the ACC exhibits lower toxicity in vivo compared to either wildtype interferon alpha-2b or PEGylated interferon alpha-2b.
149. An activatable cytokine construct (ACC) comprising a first monomer construct and a second monomer construct, wherein:
   (a) the first monomer construct comprises a first mature cytokine protein (CP1), a first cleavable moiety (CM1), and a first dimerization domain (DD1);
   (b) the second monomer construct comprises a second mature cytokine protein (CP2), a second cleavable moiety (CM2), and a second dimerization domain (DD2);
   (c) the first monomer construct is a polypeptide comprising, in an N- to C-terminal direction, the CP1, the CM1, and the DD1, further wherein:
      (i) the CP1 and the CM1 directly abut each other,
      (ii) the CM1 and the DD1 directly abut each other,
      (iii) the CP1 comprises a sequence that is at least 85% identical to SEQ ID NO: 1,
      (iv) the CM1 comprises a sequence that is at least 85% identical to SEQ ID: 100,
   (d) further wherein:
      (i) the second monomer construct is the same as the first monomer construct,
      (ii) the first and second monomer constructs are covalently bound to each other via at least one disulfide bond, and
      (iii) the DD1 and DD2 are a pair of human IgG4 Fc domains;
   (e) the DD1 and the DD2 bind each other thereby forming a dimer of the first monomer construct and the second monomer construct; and
   (f) the ACC is characterized by having a reduced level of interferon alpha activity as compared to the interferon alpha activity of PEGylated interferon alpha-2b.
150. A composition comprising the ACC of any one or combination of aspects 114-149.
151. The composition of aspect 150, where the composition is a pharmaceutical composition.
152. A container, vial, syringe, injector pen, or kit comprising at least one dose of the composition of aspect 150 or 151.
153. A method of treating a subject in need thereof comprising administering to the subject a therapeutically effective amount of the ACC of any one or combination of aspects 114-149 or the composition of aspect 150 or 151.
154. The method of aspect 153, wherein the subject has been identified or diagnosed as having a cancer.
155. A nucleic acid encoding a polypeptide that comprises the first monomer of the ACC of any one or combination of aspects 114-149.
156. A vector comprising the nucleic acid of aspect 155.
157. The vector of aspect 156, wherein the vector is an expression vector.
158. A mammalian cell comprising the nucleic acid of aspect 155 or the vector of aspect 156 or 157.
159. The mammalian cell of aspect 158, wherein the mammalian cell is an HEK293 cell or a CHO cell.
160. A method of manufacturing an ACC, the method comprising:
   a. expressing the ACC in the mammalian cell of aspect 158 or 159; and
   b. purifying the expressed ACC.
161. The ACC of any one or combination of aspects 114-149, wherein the CM1 functions as a substrate for a protease that is over-expressed in a tumor tissue.

EXAMPLES

The invention is further described in the following examples, which do not limit the scope of the invention described in the claims.

Example 1: Production of Activatable Cytokine Constructs

Activatable cytokine construct IFN-α2b-1204DNIdl-hIgG4 was prepared by recombinant methods. The 1$^{st}$ and 2$^{nd}$ monomer constructs of this ACC were identical, with each being a polypeptide having the amino acid sequence shown in FIG. 3 (SEQ ID NO:309). Each of the 1$^{st}$ and 2$^{nd}$ monomer constructs comprises, from N-terminus to C-terminus, a signal sequence from a mouse IgG kappa signal sequence (residues 1-20 of SEQ ID NO:309), a mature cytokine protein that corresponds to human interferon alpha-2b (SEQ ID NO:1), a cleavable moiety having the amino acid sequence of SEQ ID NO:99, a linker having the amino acid sequence, GGGS (SEQ ID NO:2), and a DD corresponding to human IgG Fc (SEQ ID NO:4). The polypeptide was prepared by transforming a host cell with a polynucleotide having the sequence of SEQ ID NO: 310, followed by cultivation of the resulting recombinant host cells. Dimerization of the resulting expressed polypeptides yielded activatable cytokine construct, IFN-α2b 1204DNIdl hIgG4.

Activatable cytokine construct IFN-α-2b 1490DNI-hIgG4 was also prepared by recombinant methods. The 1$^{st}$ and 2$^{nd}$ monomer constructs of this ACC were also identical, with each being a polypeptide having the amino acid sequence shown in FIG. 4 (SEQ ID NO:311). Each of the 1$^{st}$ and 2$^{nd}$ monomer constructs comprises, from N-terminus to C-terminus, a signal sequence from a mouse IgG kappa signal sequence (residues 1-20 of SEQ ID NO:309), a mature cytokine protein that corresponds to human interferon alpha-2b (SEQ ID NO:1), a cleavable moiety having the amino acid sequence of SEQ ID NO:68, a linker having the amino acid sequence, GGGS (SEQ ID NO:2), and a DD corresponding to human IgG Fc (SEQ ID NO:4). The polypeptide was prepared by transforming a host cell with a polynucleotide having the sequence of SEQ ID NO: 312, followed by cultivation of the resulting recombinant host cells. Dimerization of the resulting expressed polypeptides yielded activatable cytokine construct, IFN-α2b 1204dl hIgG4.

Additional activatable cytokine constructs were prepared that included an additional five amino acid residues in the linkers.

Figure 6:
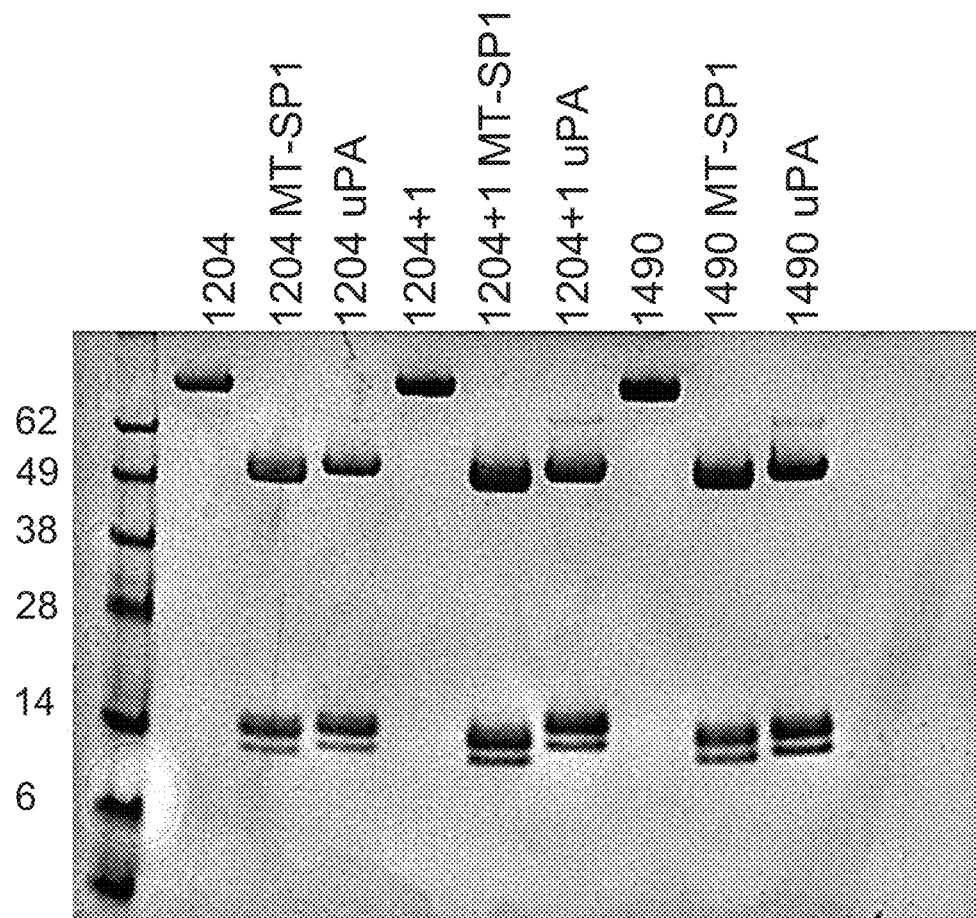
FIG. 6 is image of a gel loaded with: (1) ACC with cleavable moiety 1204 (1204); (2) product of protease membrane type serine protease 1 (MT-SP1) and ACC IFNα-2b-hIgG4 Fc with cleavable moiety 1204 (1204 MT-SP1); (3) product of ACC IFNα-2b-hIgG4 Fc with cleavable moiety 1204 and protease uPA (1204 uPA); (4) ACC IFNα-2b-hIgG4 Fc with cleavable moiety 1204 fused to a 5 amino acid linker (1204+1); (5) product of IFNα-2b-hIgG4 Fc 1204+1 and MT-SP1 (1204+1 MT-SP1); (6) ACC IFNα-2b-hIgG4 Fc with cleavable moiety 1490; (7) product of MT-SP1 and ACC IFNα-2b-hIgG4 Fc with cleavable moiety 1490; product of uPA and ACC IFNα-2b-hIgG4 Fc with cleavable moiety 1490 (1490 uPA).

Electrophoresis was performed on the activatable cytokine constructs and protease-treated activatable cytokine constructs. FIG. 6 depicts the gel, which shows the results for (from left to right): (1) ACC IFN-α2b-1204DNIdl-hIgG4 ("1204"), (2) MT-SP1-treated IFN-α2b-1204DNIdl-hIgG4 ("1204 MT-SP1"); (3) uPA-treated IFN-α2b-1204DNIdl-hIgG4 ("1204 uPA"); (4) IFN-α2b-1204DNIdl-hIgG4 with five amino acid residues added to the linker ("1204+1"); (5) MT-SP1-treated IFN-α2b-1204DNIdl-hIgG4 ("1204+1 MT-SP1"); (6) uPA-treated IFN-α2b-1204DNIdl-hIgG4 ("1204+1 uPA"); (7) IFN-α-2b 1490DNI-hIgG4 ("1490"), (8) MT-SP1-treated IFN-α-2b 1490DNI-hIgG4 ("1490 MT- SP1"); and (9) uPA-treated IFN-α-2b 1490DNI-hIgG4 ("1490 uPA"). The results suggest that the proteases were effective at cleaving the cleavable moieties in the activatable cytokine constructs.

Example 2. IFN-alpha-2b Activity of Activatable Cytokine Constructs

A cell-based reporter assay for human type I interferons was used to test the activity of the ACCs described in Example 1.

Figure 7:
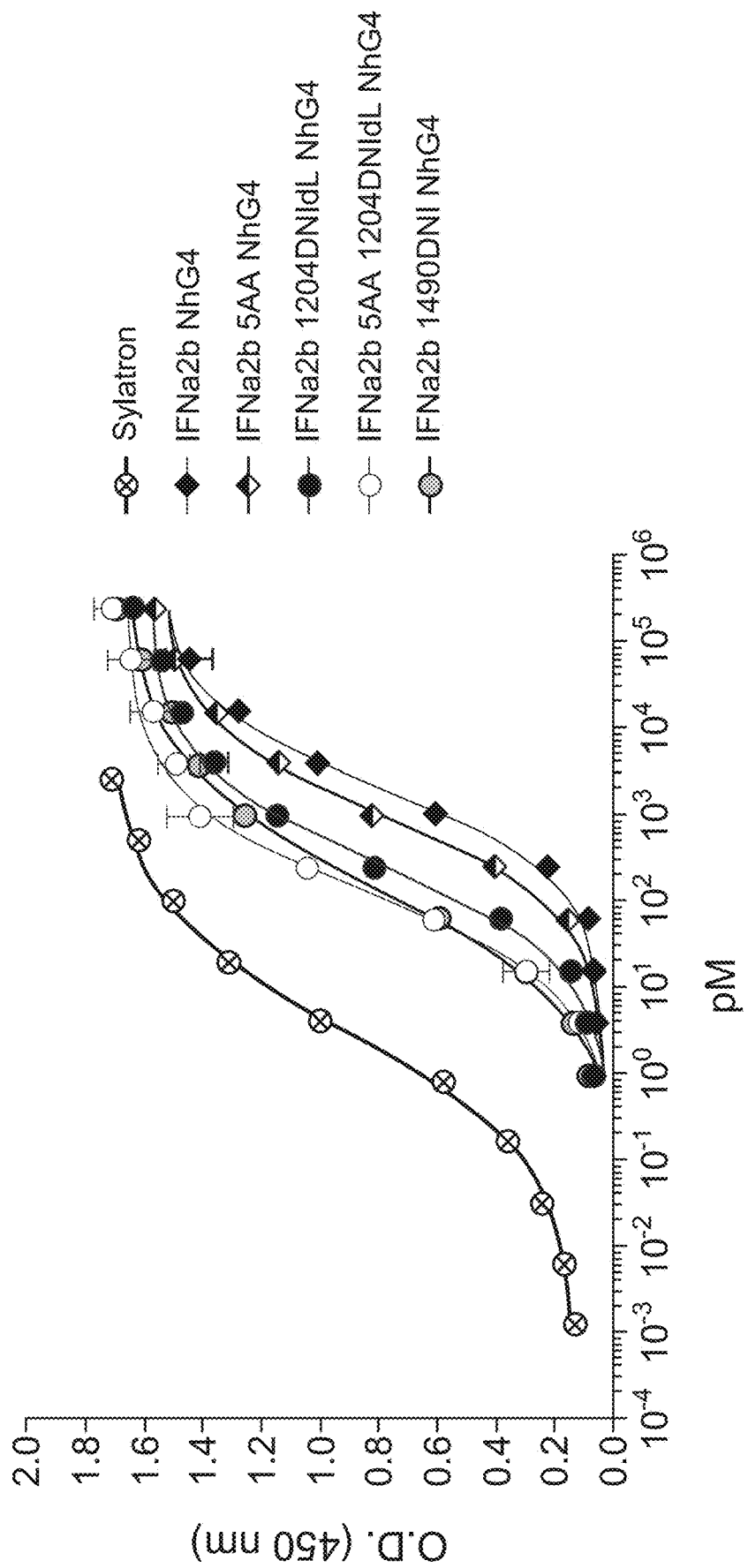
FIG. 7 provides the results from an HEK293 cell-based reporter assay to assess interferon-α2b activity of Sylatron® (peginterferon alfa-2b) and various interferon α-2b (IFNa2b) fusions: human IgG4 N-terminally fused to IFNa2b (IFNa2b NhG4); Human IgG4 N-terminally fused to IFNa2b via a five amino acid linker (IFNa2b 5AA NhG4); activatable cytokine construct IFN-α2b-1204dL-hIgG4 (IFNa2b 1204DNIdL NhG4); an activatable cytokine construct that includes the same components as IFN-α2b-1204dL-hIgG4, but which also has a 5 amino acid linker positioned between the mature cytokine protein component and the cleavable moiety (IFNa2b 5AA 1204DNIdL NhG4); and activatable cytokine construct IFN-α2b-1490DNI-hIgG4 (IFNa2b 1490DNI NhG4).

IFN-responsive HEK293 cells were generated by stable transfection with the human STAT2 and IRF9 genes to obtain a fully active type I IFN signaling pathway. The cells also feature an inducible SEAP (secreted embryonic alkaline phosphatase) reporter gene under the control of the IFNα/β inducible ISG54 promoter. To maintain transgene expression, cells were cultured in DMEM GlutaMax media supplemented with 10% FBS, Pen/Strep, 30 μg/mL of blasticidin, 100 μg/ml of zeocin and 100 μg/mL of normocin. The addition of type I IFN to these cells activates the JAK/STAT/ISGF3 pathway and subsequently induces the production of SEAP which can be readily assessed in the supernatant using Quanti-Blue solution, a colorimetric detection for alkaline phosphatase activity. Using this reporter assay, the activity of IFNα-2b containing ACCs was compared to the activity of Sylatron® (Peginterferon alfa-2b). The data in FIG. 7 show that IFNα-2b activity of the ACCs was significantly reduced as compared to the IFNα-2b activity of Sylatron® (Peginterferon alfa-2b).

Figure 8A:
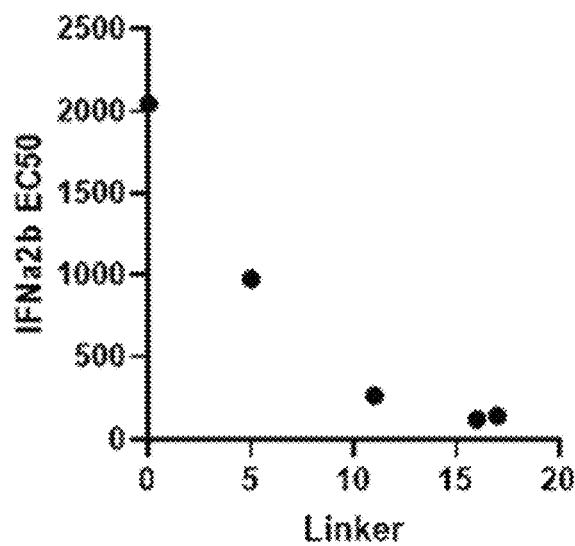
FIG. 8A depicts the effect of length of a flexible linker in an interferon-α2b-Fc fusion on EC50 as determined by an HEK293 cell-based reporter assay.
Figure 8B:
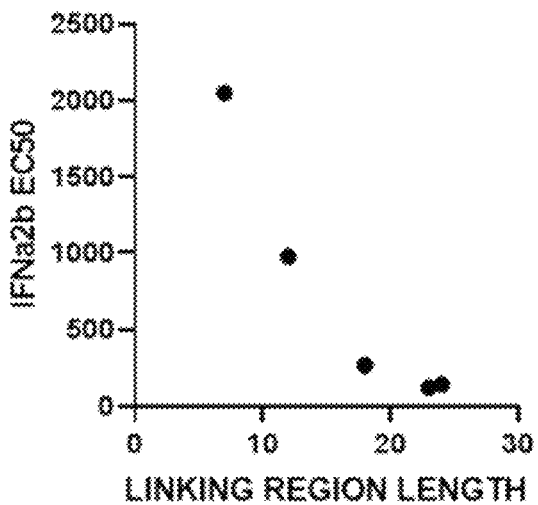
FIG. 8B depicts the effect of length of a Linking Region (LR) in an interferon-α2b-Fc fusion on EC50 as determined by an HEK293 cell-based reporter assay.

Furthermore, the data in FIGS. 8A and 8B show that the activity of the (uncleaved) ACCs could be modulated by varying the length of the linker or Linking Region. The data in FIG. 8A-8B show the results of IFNα-2b-hIgG4 Fc fusion constructs with varying linker lengths, or without a linker between the IFNα-2b and the hIgG4 Fc as tested in the HEK293 reporter assay. The fusion proteins tested in this experiment include, in an N- to C-terminal direction, the mature IFNalpha-2b cytokine sequence, an optional linker and/or cleavable moiety, and the Fc domain of human IgG4 of SEQ ID NO: 4 (including the full hinge region such that the N-terminus of the Fc sequence begins with the amino acid sequence ESKYGPPCPPC . . . ). The first construct (Linking Region=7) has no linker or cleavable moiety; its sequence in the N- to C-terminal direction consists of SEQ ID NO: 1 fused to SEQ ID NO: 4. The second construct (Linking Region=12) has a 5 amino acid linker SGGGG (SEQ ID NO: 335); its sequence in the N- to C-terminal direction consists of SEQ ID NO: 1 fused to SEQ ID NO: 335 fused to SEQ ID NO: 4. The third construct (Linking Region=18) includes a 7 amino acid CM (SGRSDNI) and a 4 amino acid linker GGGS; its sequence in the N- to C-terminal direction consists of SEQ ID NO: 1 fused to SEQ ID NO: 100 fused to SEQ ID NO: 2 fused to SEQ ID NO: 4. The fourth construct (Linking Region=23) includes a 5 amino acid linker, a 7 amino acid CM, and a 4 amino acid linker; its sequence in the N to C-terminal direction consists of SEQ ID NO: 1 fused to SEQ ID NO: 335 fused to SEQ ID NO: 100 fused to SEQ ID NO: 2 fused to SEQ ID NO: 4. The fifth construct (Linking Region=24) includes a 13 amino acid CM (ISSGLLSGRSDNI) and a 4 amino acid linker; its sequence in the N- to C-terminal direction consists of SEQ ID NO: 1 fused to SEQ ID NO: 68 fused to SEQ ID NO: 2 fused to SEQ ID NO: 4.

Example 3: In Vitro Anti-Proliferative Effect of ACCs on Cancer Cells

The anti-proliferative effects of IFNα-2b and IFNα-2b-containing ACCs were tested in vitro using Daudi cells, a cell line of human B-cell lymphoblastic origin. Daudi cells were prepared at a concentration of 2×10$^5$ cells/mL in RPMI-1640 media supplemented with 10% FBS and 50 μL aliquots were pipetted into wells of a white flat-bottom 96-well plate (10K/well). The tested ACCs or controls were diluted in RPMI 1640 media supplemented with 10% FBS. Duplicate five-fold serial dilutions were generated from which 50 μL was added to the each well. After 3 days of incubation at 37° C., a viability kit was used to measure the levels of intracellular ATP as an indirect estimate of the number of viable cells remaining. 100 μL of cell-titer go was directly added to the plates which were then placed on an orbital shaker for 10 minutes. Following this incubation, the luminescent signal was directly measured using an Envision plate reader. Dose-response curves were generated and EC50 values were obtained by sigmoidal fit non-linear regression using Graph Pad Prism software. Specific activities were determined by comparison of EC50 values with recombinant IFNα2b or pharmaceutical-grade Sylatron® (Peginterferon alfa-2b).

Figure 9:
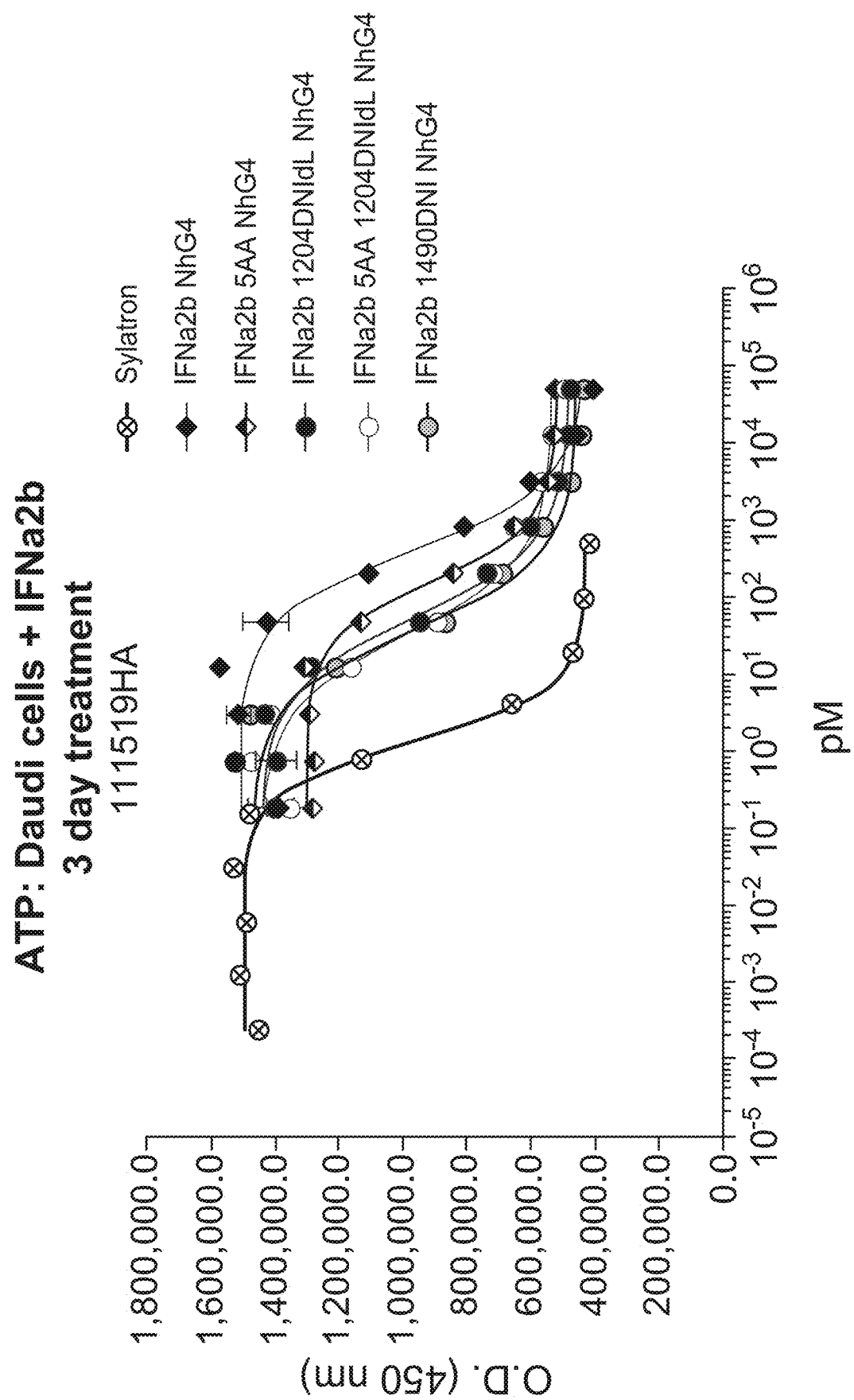
FIG. 9 provides the results of a Daudi apoptosis assay to determine the anti-proliferative activity of Sylatron® and various IFNa2b fusions: human IgG4 N-terminally fused to IFNa2b (IFNa2b NhG4); Human IgG4 N-terminally fused to IFNa2b via a five amino acid linker (IFNa2b 5AA NhG4); activatable cytokine construct IFN-α2b-1204dL-hIgG4 (IFNa2b 1204DNIdL NhG4); an activatable cytokine construct that includes the same components as IFN-α2b-1204dL-hIgG4, but which also has a 5 amino acid linker positioned between the mature cytokine protein component and the cleavable moiety (IFNa2b 5AA 1204DNIdL NhG4); and activatable cytokine construct IFN-α2b-1490DNI-hIgG4 (IFNa2b 1490DNI NhG4).

The anti-proliferative activity of IFNα-2b-containing ACCs in Daudi lymphoma cells indicated that the IFNα-2b activity of the uncleaved ACCs was decreased compared to Sylatron® (Peginterferon alfa-2b) (FIG. 9).

Figure 10A:
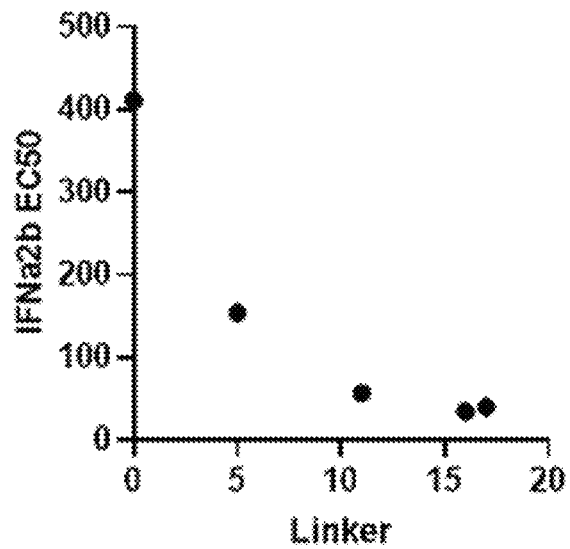
FIG. 10A depicts the effect of length of a linker in an interferon-α2b-Fc fusion protein on EC50 as determined from a Daudi apoptosis assay.
Figure 10B:
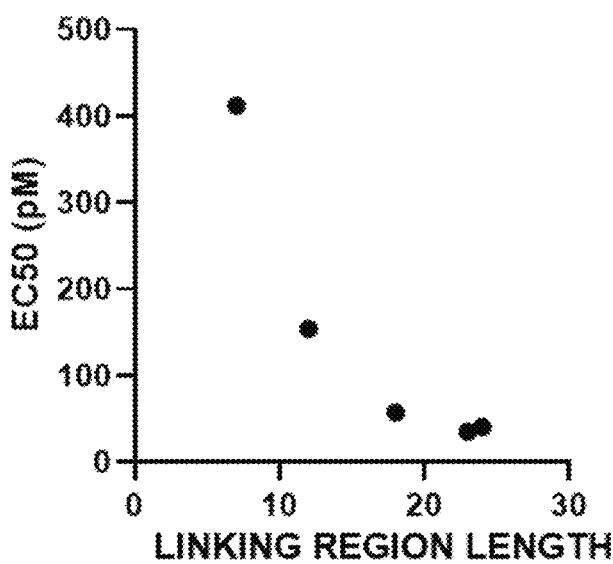
FIG. 10B depicts the effect of length of a Linking Region (LR) in an interferon-α2b-Fc fusion on EC50 as determined from an Daudi apoptosis assay.
Figure 11:
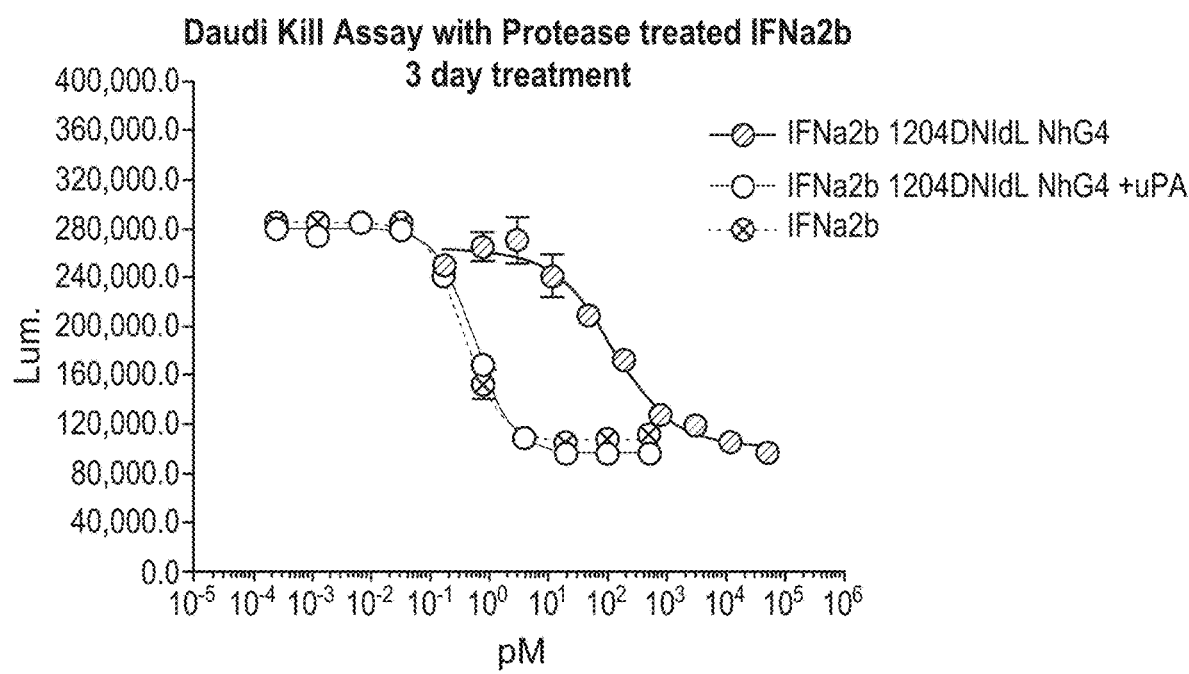
FIG. 11 provides the results of a Daudi lymphoma cell-based assay for measuring the anti-proliferation activity of an ACC (IFNa2b 1204DNIdL NhG4); protease-treated ACC (IFNa2b 1204DNIdL NhG4+uPA); and the recombinant parental cytokine (IFNa2b). The results indicated that, following treatment of the ACC with a protease, the activity of the cytokine in the ACC could be restored to a level comparable to the recombinant parental cytokine.
Figure 12:
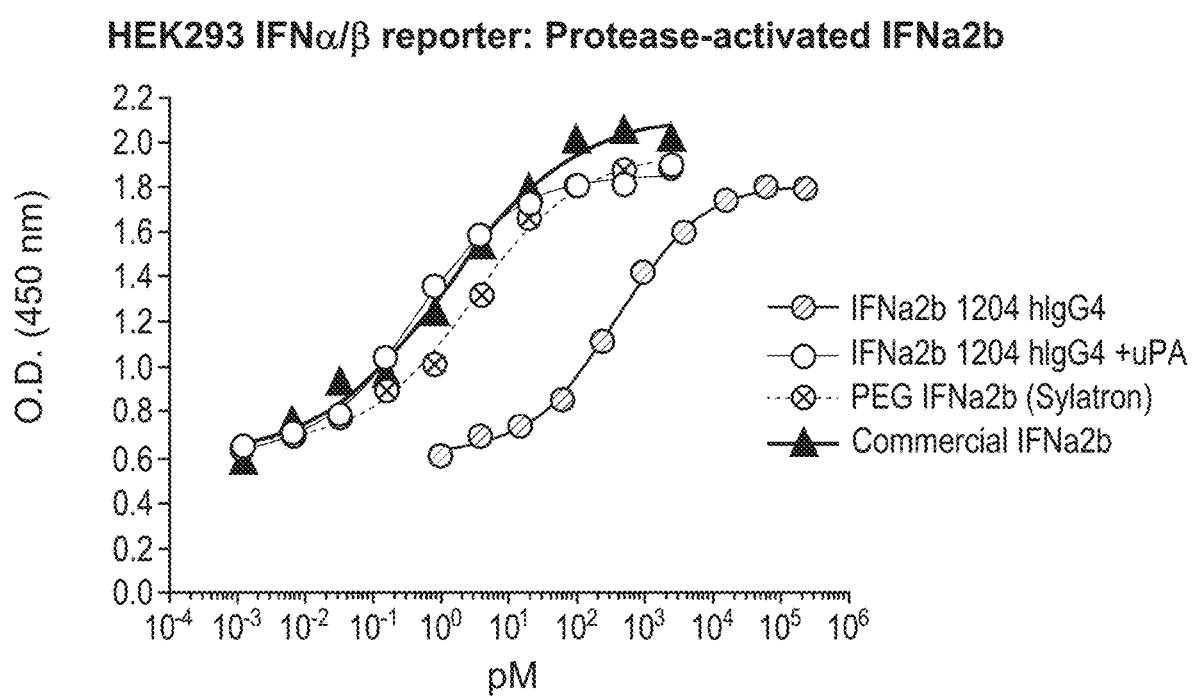
FIG. 12 depicts the results of an HEK293 cell-based reporter assay to assess the activity of an ACC (IFNa2b 1204DNIdL NhG4); a protease-treated (activated) ACC (IFNα-2b 1204DNIdL NhG4+uPA); Sylatron®; and the recombinant parental cytokine (IFNα2b). The results indicated that, following treatment of the ACC with a protease, the activity of the cytokine in the ACC could be restored to a level comparable to the recombinant parental cytokine.

The data in FIGS. 10A-10B also shows that the activity of the (uncleaved) ACCs could be modulated by varying the length of the linker. The anti-proliferative effects of IFNα-2b-hIgG4 Fc fusion protein constructs with varying linker lengths or without a linker between the IFNα-2b and the hIgG4 Fc were tested in vitro using Daudi cells. The data indicate that the length of the flexible linkers and the length of the Linking Region (LR) between the cytokine and the Fc domain had an impact on the activity of the (uncleaved) ACCs. Constructs with zero linkers, or short linkers, and a correspondingly short LR display reduced cytokine activity, whereas constructs with longer linkers and thus a longer LR have a higher level of cytokine activity. The results are shown in FIGS. 10A-10B. The fusion protein constructs are the same as those described above in Example 2 with respect to FIGS. 8A and 8B.

Example 4: Activity of Protease-Treated ACCs

Protease treated IFNα-2b-containing ACCs were tested for anti-proliferative responses in Daudi lympho cells and in the cell-based reporter assay to determine if the activity could be restored.

To cleave the dimerizing domain, IFNα-2b-containing ACCs were treated overnight at 37° C. with recombinant human proteases such at urokinase-type plasminogen activator (uPA), or matriptase (MT-SP1). A cocktail of protease inhibitors were added to neutralize the proteases prior to testing for activity as described in Example 2 and 3. The results from these assays indicate that the treatment of IFNα-2b-containing ACCs with proteases could restore activity to a level that is comparable to the recombinant cytokine. EC50 values for ACC IFNα-2b-1204DNIdl-hIgG4, ACC IFNα-2b-1204DNIdl-hIgG4+uPA, and Stem Cell IFNα-2b (human recombinant IFN-alpha 2b, available from StemCell Technologies, Catalog #78077.1) were computed from the Daudi apoptosis assay results, and are provided below in Table 3.

TABLE 3

| EC50: Daudi Apoptosis Assay | | |
| --- | --- | --- |
| IFNα-2b-1204DNIdl-hIgG4 (ACC) | IFNα-2b-1204DNIdl-hIgG4 (ACC) + uPA | Stem Cell IFNα-2b |
| EC50 131.8 | 0.5701 | 0.3664 |

EC50 values for ACC IFNα-2b-1204DNIdl-hIgG4, ACC IFNα-2b-1204DNIdl-hIgG4+uPA, and Stem Cell IFNα-2b were computed from the IFNα/β assay results, and are provided below in Table 4.

TABLE 4

| EC50: IFNα/β Reporter Assay | | | |
| --- | --- | --- | --- |
| IFNα-2b-1204DNIdl-hIgG4 (ACC) | IFNα-2b-1204DNIdl-hIgG4 (ACC) + uPA | Sylatron ® | Commercial IFNα-2b |
| EC50 393.1 | 0.4611 | 3.019 | 1.280 |

These results show that without the presence of an activating protease, the activity of IFNα-2b-1204DNIdl-hIgG4 is significantly decreased relative to the IFNα-2b control.

Example 5: Universal ProIFN

An ACC according to the present disclosure was prepared by recombinant methods having a universal interferon sequence (ProC859) (IFNaAD 0AA 1204DNIdL 0AA IgG4) having activity on both human and mouse cells. The 1$^{st}$ and 2$^{nd}$ monomer constructs of this ACC were identical, with each being a polypeptide having the amino acid sequence (SEQ ID NO: 323 and a signal sequence at its N-terminus). Each of the 1$^{st}$ and 2$^{nd}$ monomer constructs comprises, from N-terminus to C-terminus, a signal sequence, a mature cytokine protein that corresponds to a universal interferon molecule that is a hybrid of IFN alpha 1 and IFN alpha 2a (SEQ ID NO: 324), a cleavable moiety having the amino acid sequence of SEQ ID NO: 100, and a dimerization domain corresponding to human IgG Fc (SEQ ID NO: 3). The activity of the universal ProIFN was tested in vitro using IFN-responsive HEK293 cells and B16 mouse melanoma cells.

The activity of ProC859 was reduced at least 150× as compare to mouse IFNα4. Protease activation with uPa restored activity to a level that is comparable to mouse IFNα4 as shown in FIG. 19). EC50 values for ACC ProC859, ACC ProC859+uPA, and mouse IFNα4 were computed from the assay results and are provided in FIG. 19.

| EC50: B16 IFNα/β Reporter Assay | | |
| --- | --- | --- |
| ProC859 (ACC) | ProC859 (ACC) + uPA | IFNa4 |
| EC50 293.7 | 1.951 | 1.966 |

Example 6: In Vitro Characterization of Lead ACC ProC440

Activatable cytokine construct ProC 440 (N IFNα2b 0 1204DNIdL 0AA Fc) was also prepared by recombinant methods. The 1$^{st}$ and 2$^{nd}$ monomer constructs of this ACC were identical, with each being a polypeptide having the amino acid sequence of SEQ ID NO: 313 and a signal sequence at its N-terminus. Each of the 1$^{st}$ and 2$^{nd}$ monomer constructs comprises, from N-terminus to C-terminus, a signal sequence, a mature cytokine protein that corresponds to human interferon alpha-2b (SEQ ID NO: 1), a cleavable moiety having the amino acid sequence of SEQ ID NO: 100, and a dimerization domain corresponding to human IgG Fc (SEQ ID NO: 3).

The activity of ProC440 was tested in vitro using IFN-responsive HEK293 cells and Daudi cells as previously described. In both assays, the activity of ProC440 was reduced at least 1,000× as compared to Stem Cell IFNα-2b (FIG. 13). Protease activation with uPa restored activity to a level that is comparable to the recombinant cytokine (IFNα2b as shown in FIG. 13). EC50 values for ACC ProC440, ACC ProC440+uPA, and Stem Cell IFNα-2b were computed from the IFNα/β assay results and are provided below in Table 5.

TABLE 5

| EC50: IFNα/β Reporter Assay | | | |
|---|---|---|---|
| | ProC440 (ACC) | ProC440 (ACC) + uPA | Stem Cell IFNα-2b |
| EC50 | 7643 | 4.333 | 10.88 |

EC50 values for ACC ProC440, ACC ProC440+uPA, and Stem Cell IFNα-2b were computed from the Daudi apoptosis assay results and are provided below in Table 6.

TABLE 6

| EC50: Daudi Apoptosis Assay | | | |
|---|---|---|---|
| | ProC440 (ACC) | ProC440 (ACC) + uPA | Stem Cell IFNα-2b |
| EC50 | 264.2 | 0.1842 | 0.3530 |

Cleavage with uPa at the expected site in the CM was confirmed by Mass spectrometry analysis (FIGS. 14A-14B). In addition to sensitivity to uPa activation, ProC440 is cleaved by MMP4 (FIGS. 14A-14B). Analysis by Mass spectrometry identified a MMP14 cleavage site at the C-terminal extremity of IFNα, near the cleavable moiety (FIG. 14B). Protease activation with MMP14 restored activity to a level that is comparable to the recombinant cytokine. All together, this indicates that ACC ProC440 can recover full activity after cleavage of intrinsic and engineered cleavable moieties by at least uPa and MMP14.

ACC ProC657 (N IFNα2b 0AA 1204DNIdL 0AA IgG4 KiHSS) was also prepared by recombinant methods. The 1$^{st}$ monomer construct of this ACC is a polypeptide having the amino acid sequence of SEQ ID NO: 314 and a signal sequence at its N-terminus. The 1$^{st}$ monomer construct of this ACC comprises, from N-terminus to C-terminus, a signal sequence, a mature cytokine protein that corresponds to human interferon alpha-2b (SEQ ID NO: 1), a cleavable moiety having the amino acid sequence of SEQ ID NO: 68, and a dimerization domain corresponding to human IgG Fc with a knob mutation (SEQ ID NO: 315). The 2$^{nd}$ monomer construct of this ACC is a polypeptide having the amino acid sequence of SEQ ID NO: 322 and a signal sequence at its N-terminus. The 2$^{nd}$ monomer construct has, from N-terminus to C-terminus, a signal sequence, a stub moiety (SEQ ID NO: 317), and a dimerization domain corresponding to human IgG Fc with a hole mutation (SEQ ID NO: 316).

The activity of ProC657 was tested in vitro using IFN-responsive HEK293 cells as previously described. The activity of ProC657 was reduced as compare to Stem Cell IFNα-2b or uPa-activated ProC440 but increased as compared to ProC440 (FIG. 15). Thus, the present disclosure provides different structures of ACCs that make it possible to modulate levels of reduction in activity in the ACCs.

Example 7: In Vivo Antiproliferative Activity of ACCs

The anti-proliferative effects of IFNα-2b-containing ACC ProC440 was tested in vivo using the Daudi xenograft tumor model. Beige/SCID mice were implanted subcutaneously with 10×10⁶ Daudi cells in serum-free medium (1:1 Matrigel). When the average tumor volume reached ~60-120 mm³, mice were randomized and dosed once a week for 5 weeks with ProC440. Body weights and tumor measurements were recorded twice weekly for the duration of the study. The data in FIG. 16 shows that IFNα-2b-containing ACC ProC440 induced complete tumor regression at a dose as low as 0.1 mg/kg and slowed-down tumor growth at a dose of 0.02 (top) and the anti-proliferative effects of Sylatron® are shown for comparison (bottom).

Example 8: In Vivo Tolerability Activity of ACCs

Human IFNα-2b cross react with hamster IFNa receptor and has been previously shown to be active in Hamster (Altrock et al, Journal of Interferon Research, 1986). To assess the tolerability of IFNα-2b-containing ACC ProC440, Syrian Gold Hamsters were dosed with a starting dose of 0.4 mg/kg. Animals received one dose of test article and kept on study up to 7 days post dose, unless non tolerated toxicities (DLT means dose limiting toxicities) were identified. The starting dose (0.4 mg/kg ("mpk")) represents an equivalent dose of INFα-con (recombinant interferon alpha, a non-naturally occurring type-I interferon manufactured by Amgen under the name Infergen®) expected to induce body weight loss, decreased food consumption and bone marrow suppression in a hamster (125 gr). (In cynomolgus monkeys (cyno), 0.1 mg/kg/day of INFα-con has been associated with body weight lost, decreased food consumption and bone marrow suppression (equal to 1.25-2.5×10⁷ U for a 125 gram hamster).) If the starting dose was tolerated, animals were moved up to a "medium dose" of 2 mg/kg and received three doses of test article unless not tolerated. If tolerated, animals were moved up to a "high dose" of 10 mg/kg and received three doses of test article unless not tolerated. If tolerated, animals were moved up to a "higher dose" of 15 mg/kg. At each stage, if the test dose was not tolerated, the animal was moved down to the next lower dose. If the starting dose was not tolerated, the animal was moved down to a "lower dose" of 0.08 mg/kg. Animals were dosed with an ACC having a N- to C-terminus structure of DD-CM-CP dimers (ProC286). As a negative control, animals were dosed with a human IgG4. The negative control did not induce any toxicity in the animals, as expected.

ProC286 (ChIgG4 5AA 1204DNIdL IFNα2b) was also prepared by recombinant methods. The 1ˢᵗ and 2ⁿᵈ monomer constructs were identical, with each being a polypeptide having the amino acid sequence of SEQ ID NO: 320 and a signal sequence at its N-terminus. Each of the 1ˢᵗ and 2ⁿᵈ monomer constructs comprises, from N-terminus to C-terminus, a signal sequence, a dimerization domain corresponding to human IgG Fc (SEQ ID NO: 3), a linker (SEQ ID NO: 321) a cleavable moiety having the amino acid sequence of SEQ ID NO: 100, a linker (SEQ ID NO: 2), and a mature cytokine protein that corresponds to human interferon alpha-2b (SEQ ID NO: 1).

ProC291 (NhIgG4 5AA 1204DNIdL IFNα2b) was also prepared by recombinant methods. The 1ˢᵗ and 2ⁿᵈ monomer constructs were identical. Each of the 1ˢᵗ and 2ⁿᵈ monomer constructs comprises, from N-terminus to C-terminus, a mature cytokine protein that corresponds to human interferon alpha-2b (SEQ ID NO: 1), a linker (SEQ ID NO: 321), a CM (SEQ ID NO: 100), a linker (GGGS), and a human IgG4 Fc region including the full hinge sequence (SEQ ID NO: 4).

Figure 17B:
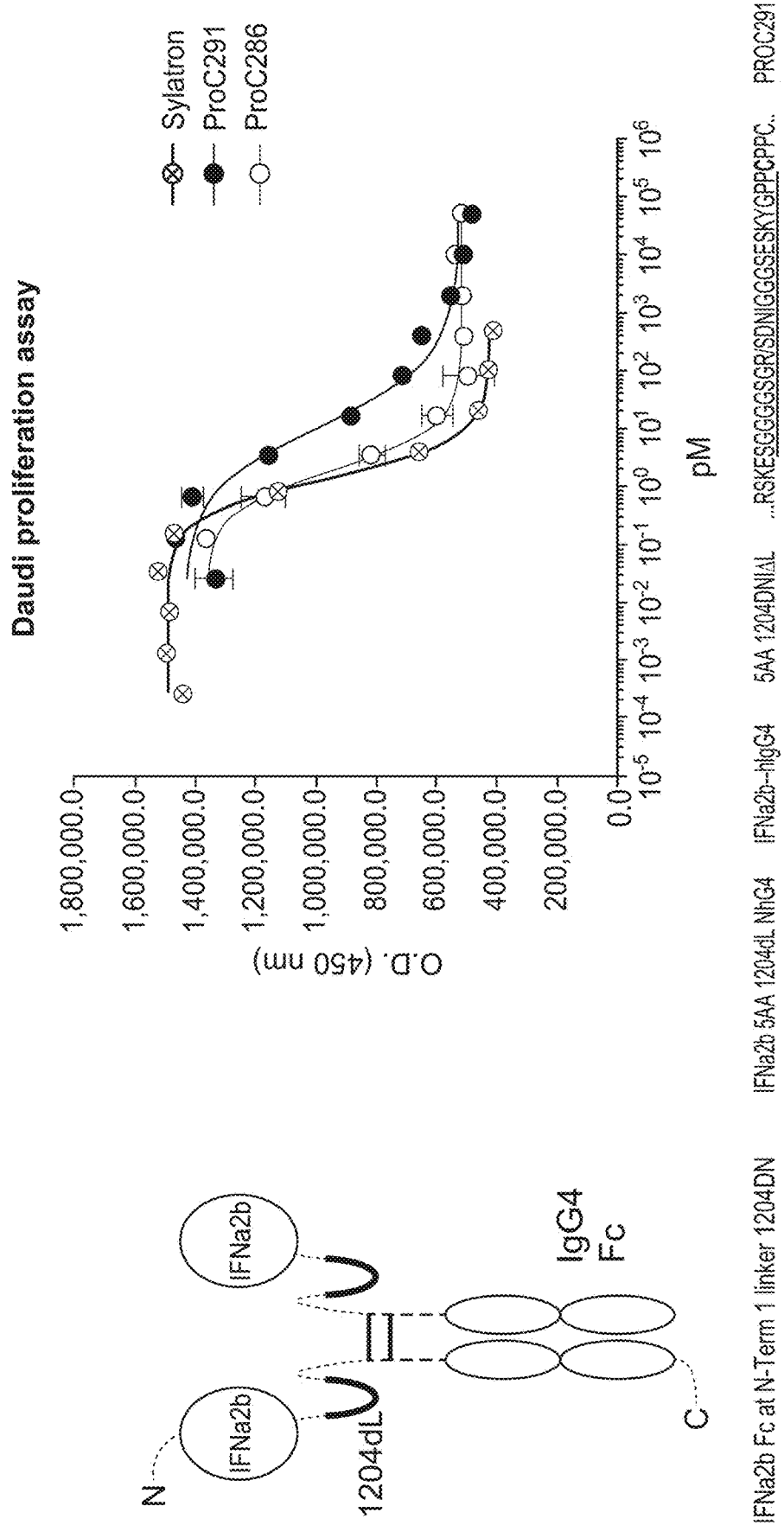
FIG. 17B depicts the structure of ProC291 and the activity of ProC291 compared to the activity of Sylatron® in the Daudi apotosis assay. ProC291 showed significantly reduced activity compared to Sylatron® and ProC286.
Figure 20:
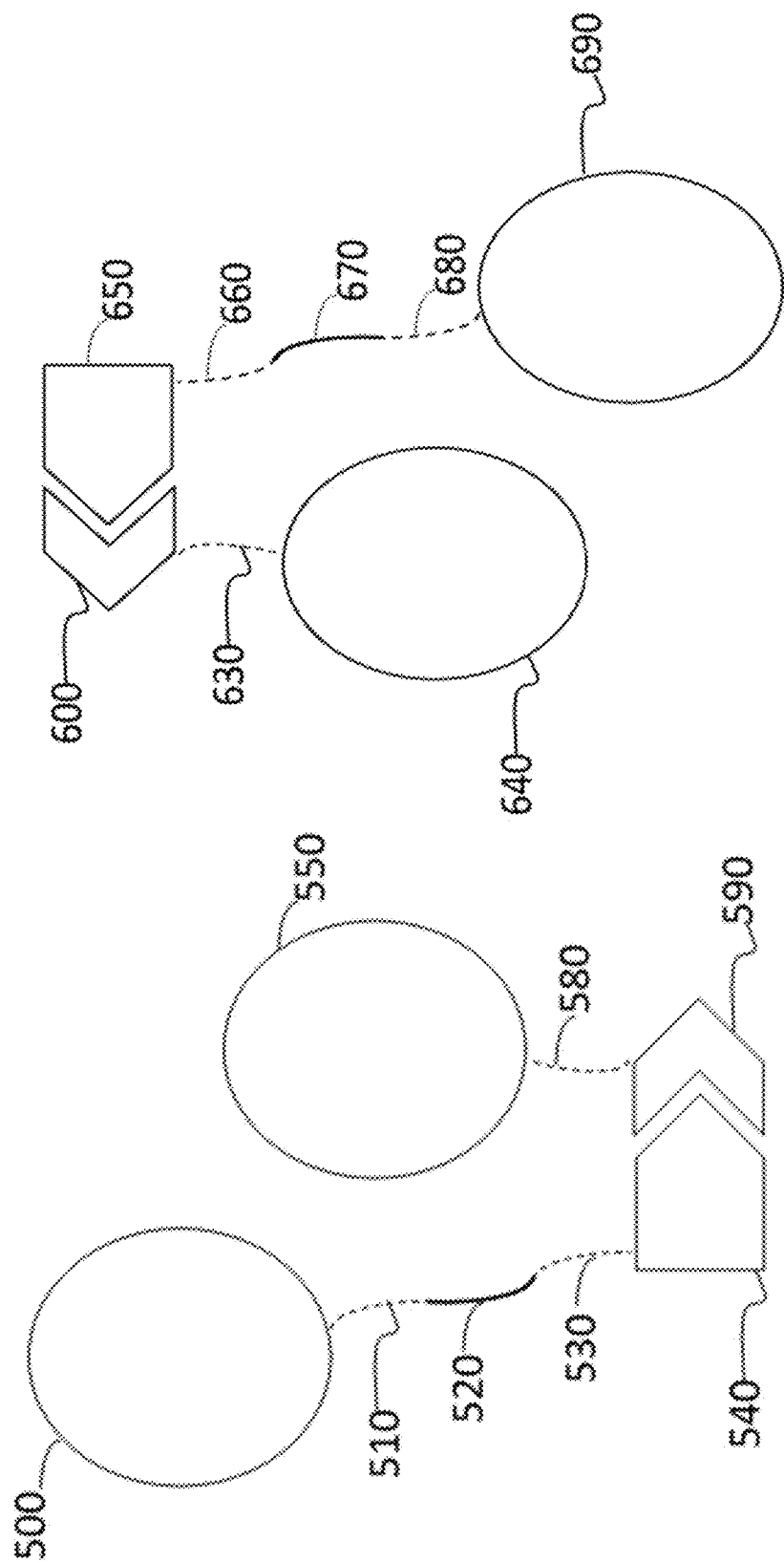
FIG. 20A is a schematic of an illustrative activatable cytokine construct comprising a first and second monomer construct that bind to each other by non-covalent means via first and second dimerization domains DD1 540 and DD2 590, respectively. The first monomer construct comprises, from N-terminus to C-terminus, a first mature cytokine protein CP1 500, a first optional linker 510, a first cleavable moiety CM1 520, a second optional linker 530, and a first dimerization domain DD1 540. The second monomer construct comprises, from N-terminus to C-terminus, a second mature cytokine protein CP2 550, a third optional linker 560, and a second dimerization domain DD2 590.
FIG. 20B is a schematic of an illustrative activatable cytokine construct comprising a first and second monomer construct that bind to each other by non-covalent means via first and second dimerization domains DD1 600 and DD2 650, respectively. The first monomer construct comprises, from N-terminus to C-terminus, a first dimerization domain DD1 600, a first optional linker 630 and a first mature cytokine protein CP1 640. The second monomer construct comprises, from N-terminus to C-terminus, a second dimerization domain DD2 650, a second optional linker 660, a cleavable moiety CM 670, a third optional linker 680, and a second mature cytokine protein CP2 690.
Figure 21:
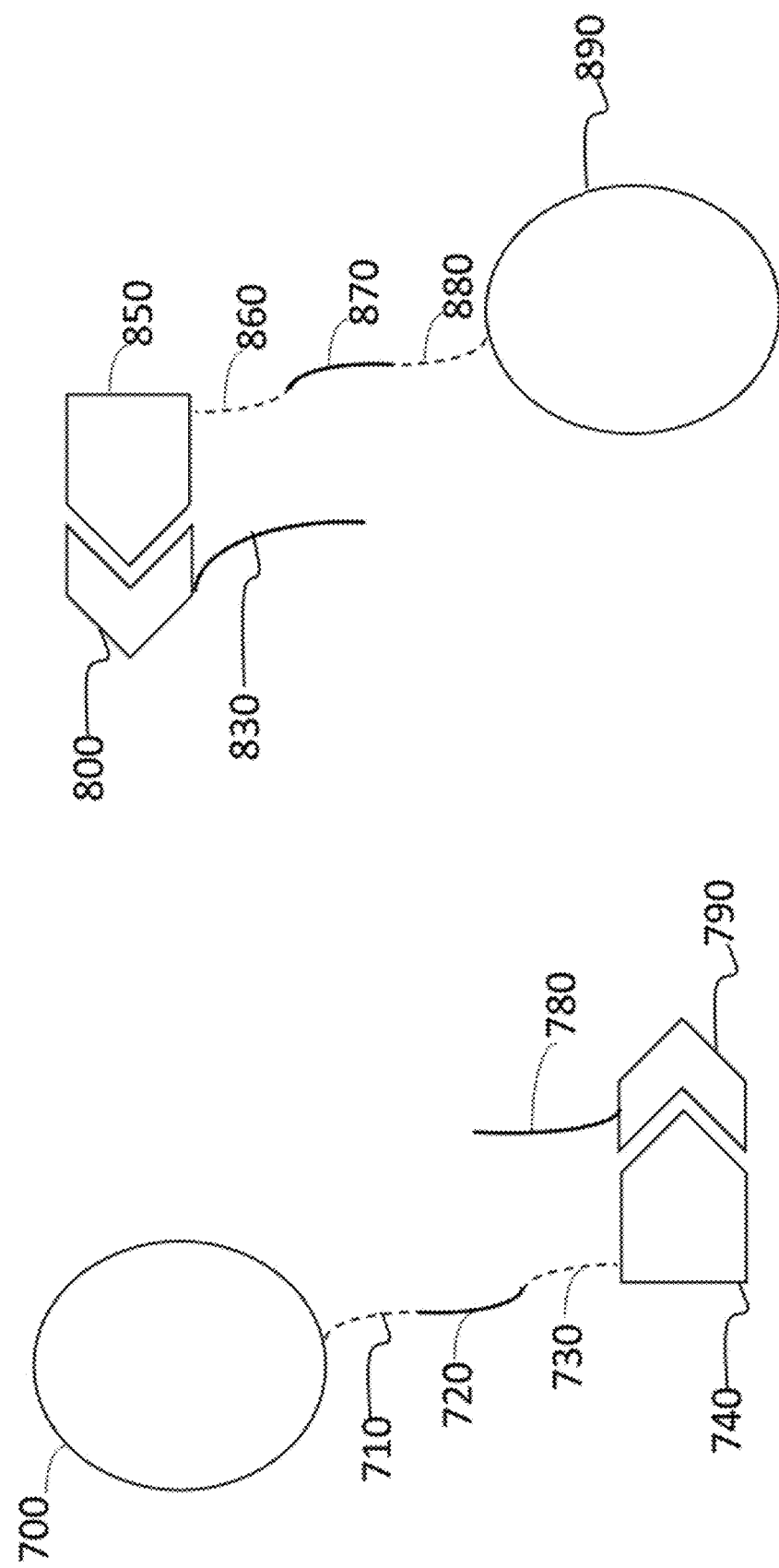
FIG. 21A is a schematic of an illustrative activatable cytokine construct comprising a first and second monomer construct that bind to each other by non-covalent means via first and second dimerization domains DD1 740 and DD2 790, respectively. The first monomer construct comprises, from N-terminus to C-terminus, a first mature cytokine protein CP 700, a first optional linker 710, a first cleavable moiety CM1 720, a second optional linker 730, and a first dimerization domain DD1 740. The second monomer construct comprises, from N-terminus to C-terminus, a polypeptide or protein that lacks cytokine activity 780, and a second dimerization domain DD2 790. The polypeptide or protein that lacks cytokine activity 780 may, for example, be a truncated cytokine protein that lacks cytokine activity, a mutated cytokine protein that lacks cytokine activity, a stub sequence, or a polypeptide sequence that binds with high affinity to CP 700 and reduces the cytokine activity of the second moiety as compared to the control level of the second moiety. The DD1 740 and the DD2 790 may be the same or different.
FIG. 21B is a schematic of an illustrative activatable cytokine construct comprising a first and second monomer construct that bind to each other by non-covalent means via first and second dimerization domains DD1 800 and DD2 850, respectively. The first monomer construct comprises, from N-terminus to C-terminus, a first dimerization domain DD1 800 and a polypeptide or protein that lacks cytokine activity 830. The second monomer construct comprises, from N-terminus to C-terminus, a second dimerization domain DD2 850, a first optional linker 860, a cleavable moiety CM 870, a second optional linker 880, and a mature cytokine protein CP 890. The polypeptide or protein that lacks cytokine activity 830 may, for example, be a truncated cytokine protein that lacks cytokine activity, a mutated cytokine protein that lacks cytokine activity, a stub sequence, or a polypeptide sequence that binds with high affinity to CP 700 and reduces the cytokine activity of the second moiety as compared to the control level of the second moiety. The DD1 800 and the DD2 850 may be the same or different.

The activity of ProC286 and ProC291 were compared to the activity of Sylatron® (PEG-IFN-alpha2b) in the Daudi apotosis assay (FIGS. 17A-17B). In this assay, ProC286 and Sylatron® showed similar levels of activity as shown in FIG. 17A This indicates that ProC286 has similar activity to commercially-available pegylated IFN-alpha2b, and could be used as surrogate Sylatron® control to evaluate the tolerability of IFNα-2b in the hamster study. ProC291 showed reduced activity compared to ProC286 and Sylatron®, indicating that the structural orientation of the IFN N-terminal to the Fc was important for reduction in activity. That is, when the DD is a pair of Fc domains, positioning the cytokine N-terminal to the DD (as in ProC291) may provide greater reduction of cytokine activity than when the cytokine is positioned C-terminal to the DD (as in ProC286).

Figure 23:
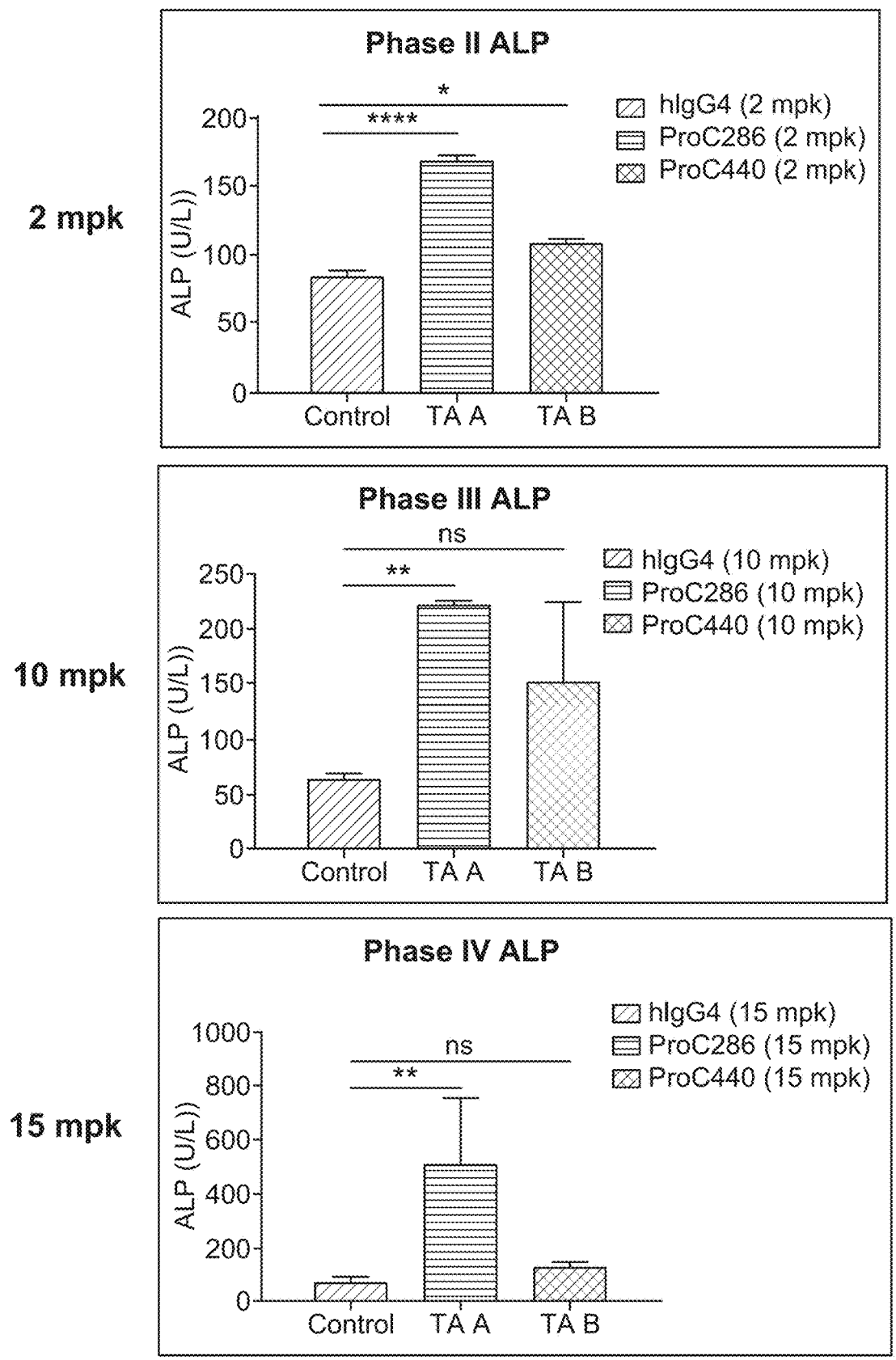
FIG. 23 shows the clinical chemistry outcomes (Alkaline phosphatase, Alanine transaminase, and Aspartate transaminase) in Syrian Gold Hamsters dosed with 2 mpk, 10 mpk, and 15 mpk of control hIgG4, ProC286, or ProC440.
Figure 23:
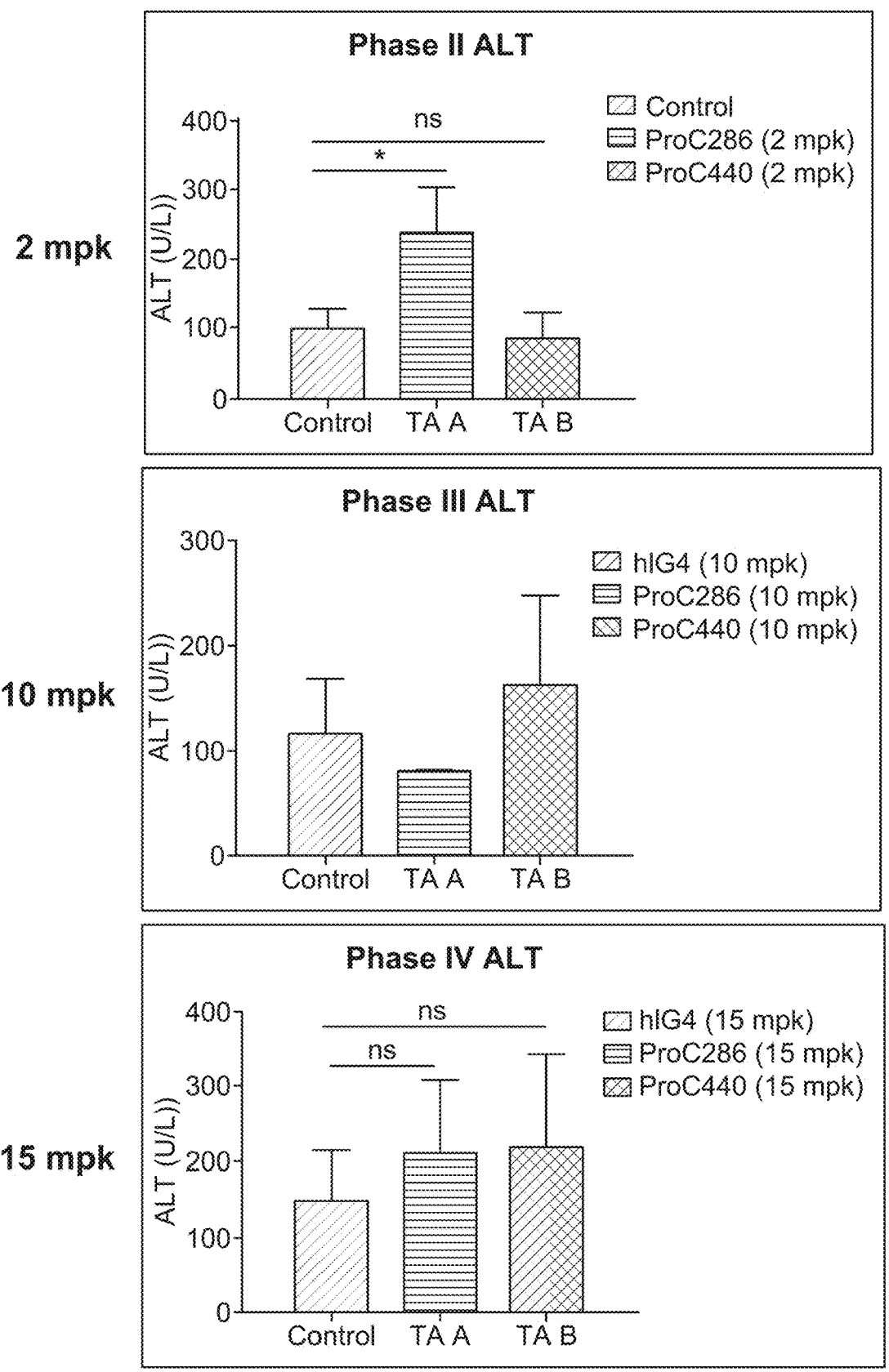
Figure 23:
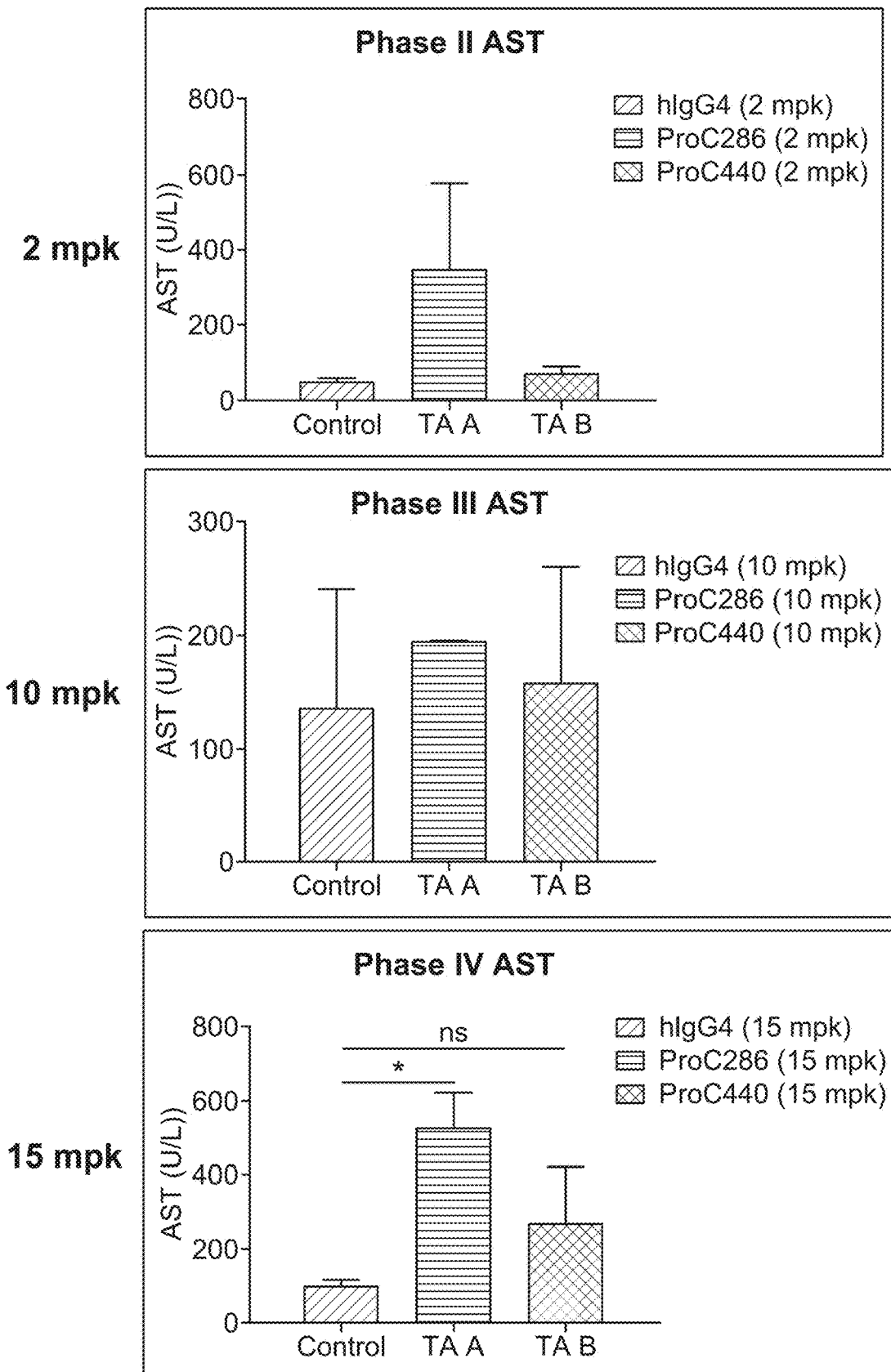
Figure 24:
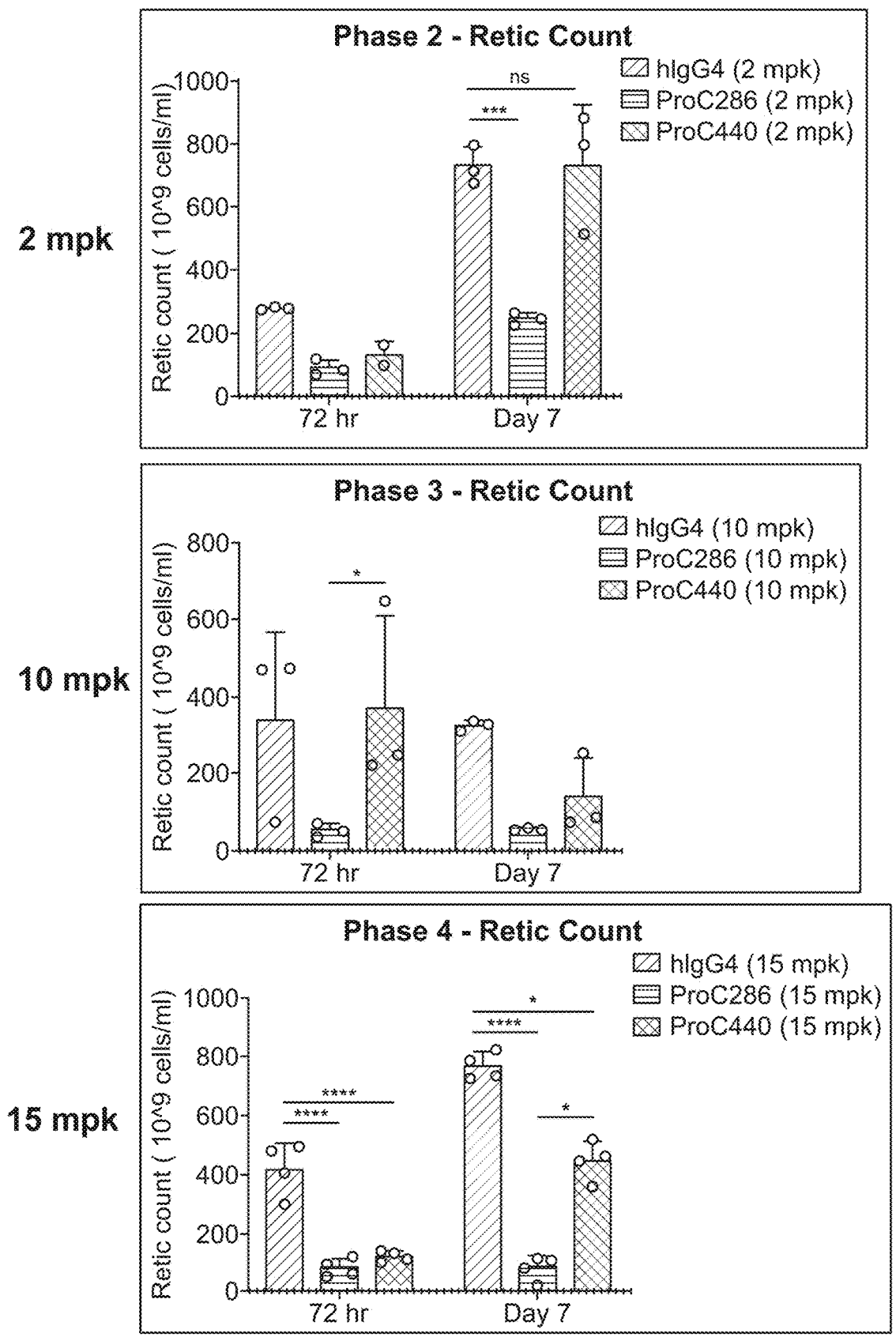
FIG. 24 shows the hematology analysis outcomes (Reticulocyte, Neutrophil, and White Blood Cells (WBC) counts) in Syrian Gold Hamsters dosed with 2 mpk, 10 mpk, and 15 mpk of control hIgG4, ProC286, or ProC440.
Figure 24:
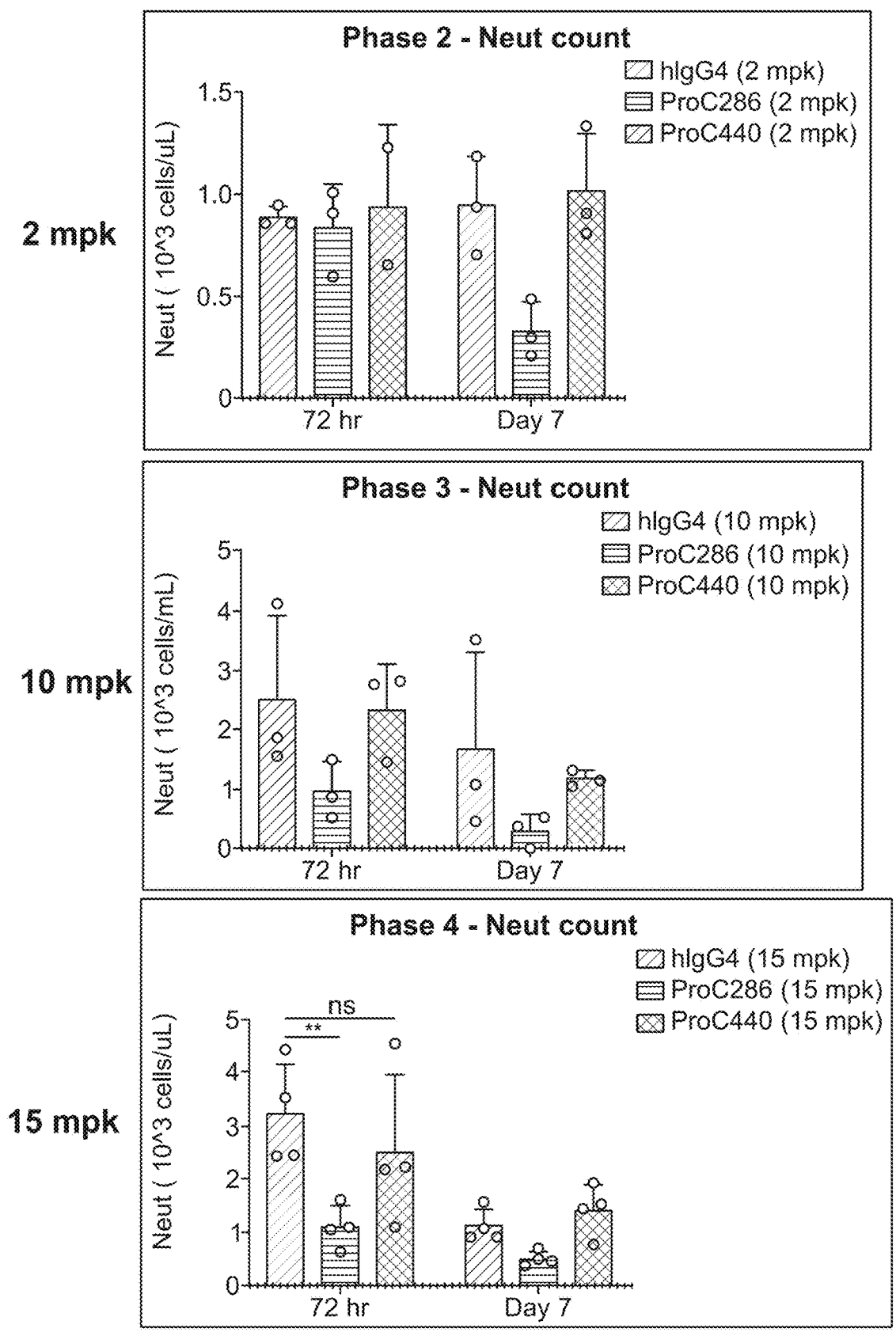
Figure 24:
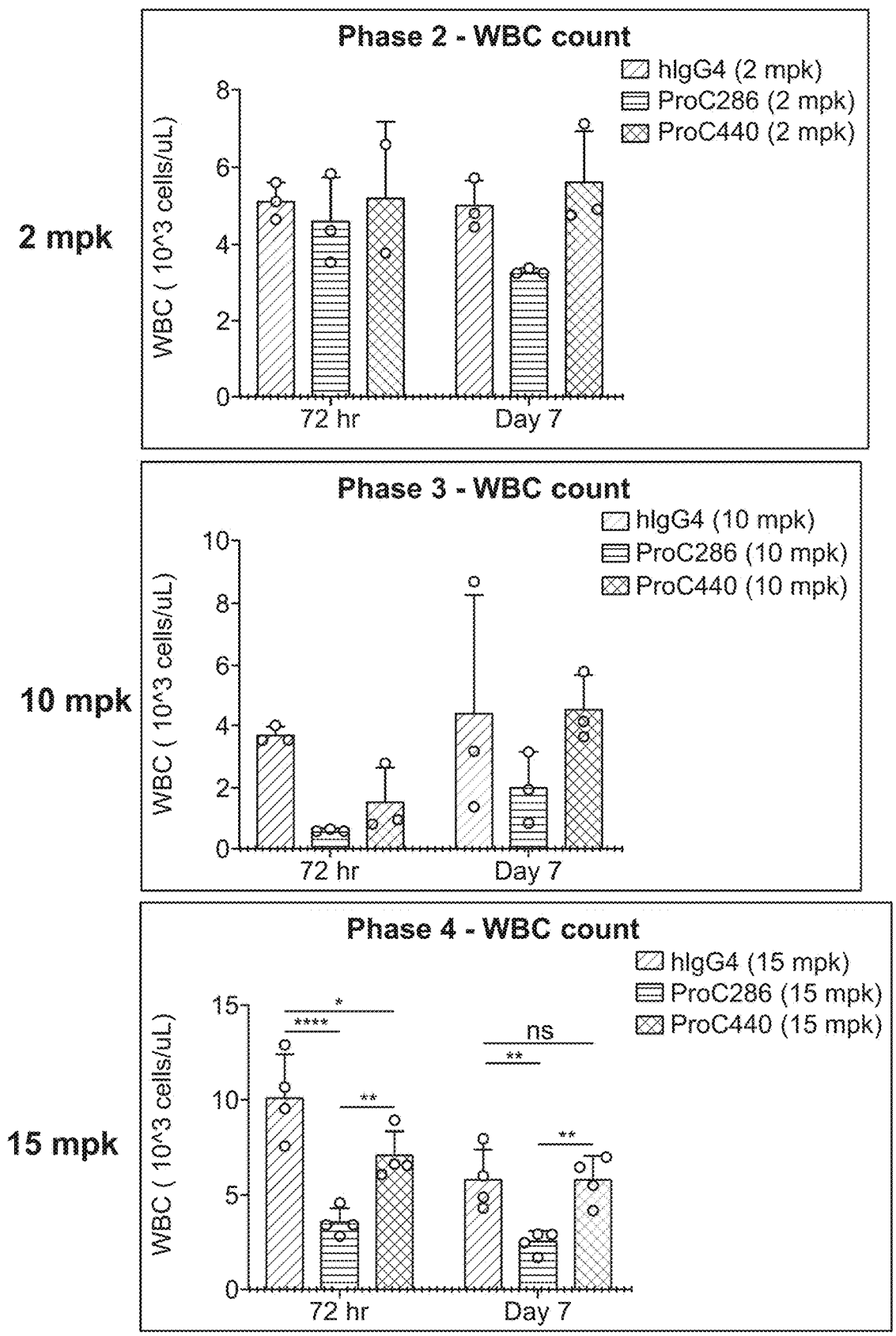

Animals were dosed on day 1 with the 0.4 mg/kg starting dose. Animals were kept on study for one week, unless a non-tolerated dose (DLT) was reached. Clinical observations, body weights & temperatures were measured prior to dosing, and at 6 h, 24 h, 72 h, and 7 d post-dose for each animal. Blood samples for Hematology and Chemistry analysis were collected at 72 h, 7 d post-dose for each animal. Hematology and Chemistry analysis were performed right after sampling. For the Hematology analysis, blood smear, differential white blood cell count, hematocrit, hemoglobin, mean corpuscular hemoglobin, mean corpuscular volume, platelet count, red blood cell (erythrocyte) count, red blood cell distribution width, reticulocyte count and white blood cell (leukocyte) count were evaluated. The clinical chemistry panel included measurement of alanine aminotransferase, albumin, albumin/globulin ratio, alkaline phosphatase, aspartate aminotransferase, calcium, chloride, cholesterol, creatine kinase, creatine, gamma glutamytransferase, globulin, glucose, inorganic phosphorus, potassium, sodium, total bilirubin, total protein, triglycerides, urea, nitrogen, and C-reactive protein. The evidence of toxicities in the tolerability study are summarized in FIGS. 22-24.

Figure 22:
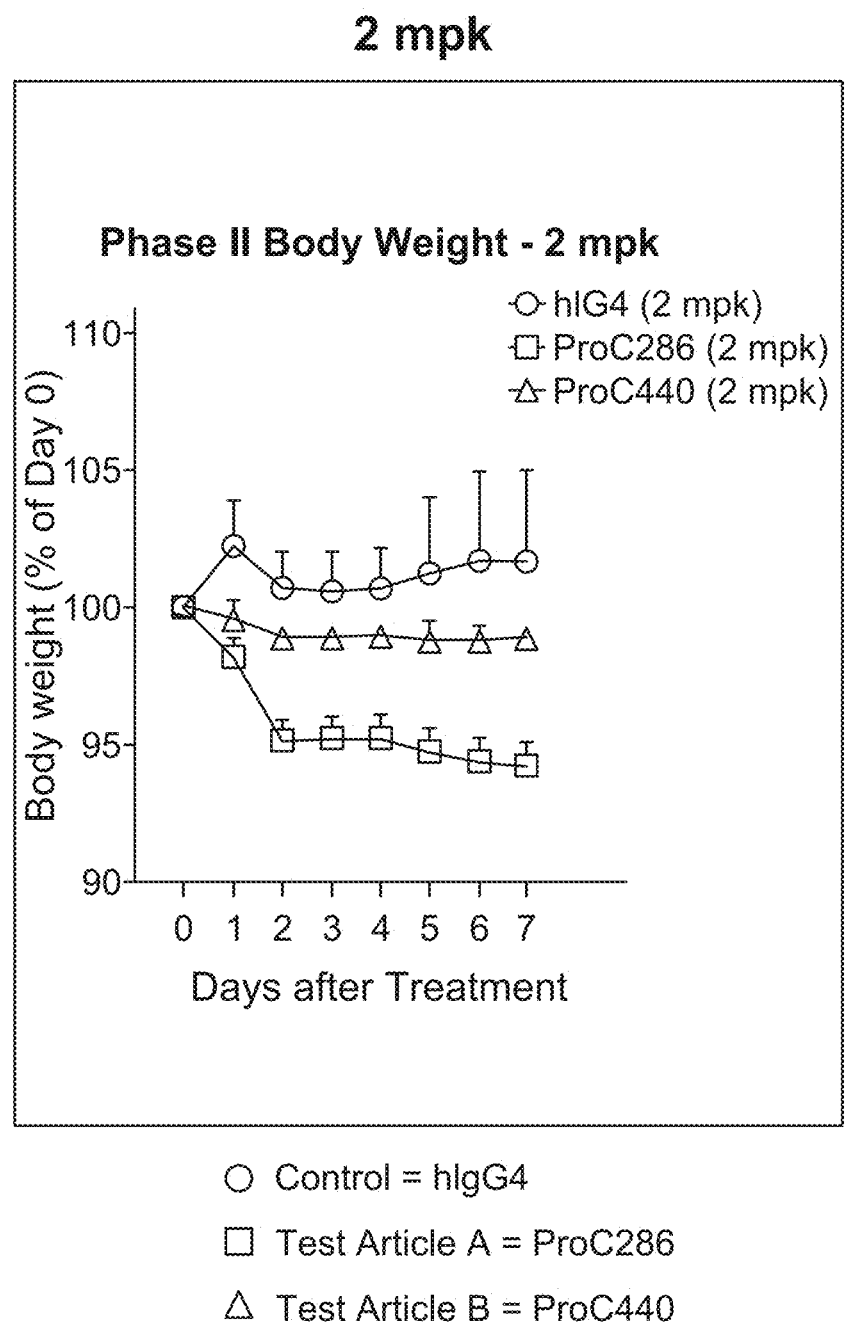
FIG. 22 shows the animal weight loss when dosed with 2 mpk, 10 mpk, and 15 mpk of control hIgG4, ProC286, or ProC440 over treatment periods in Syrian Gold Hamsters.
Figure 22:
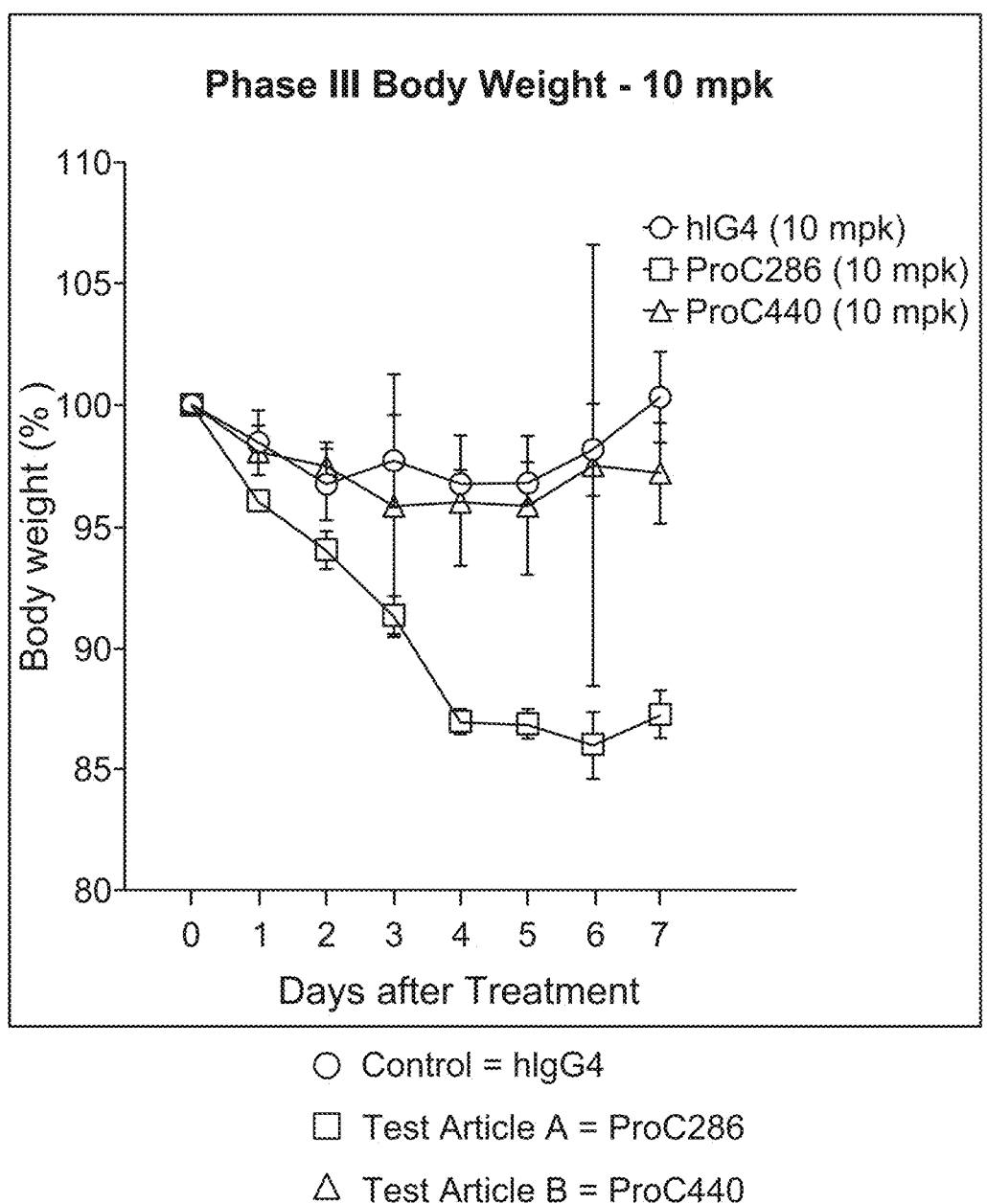
Figure 22:
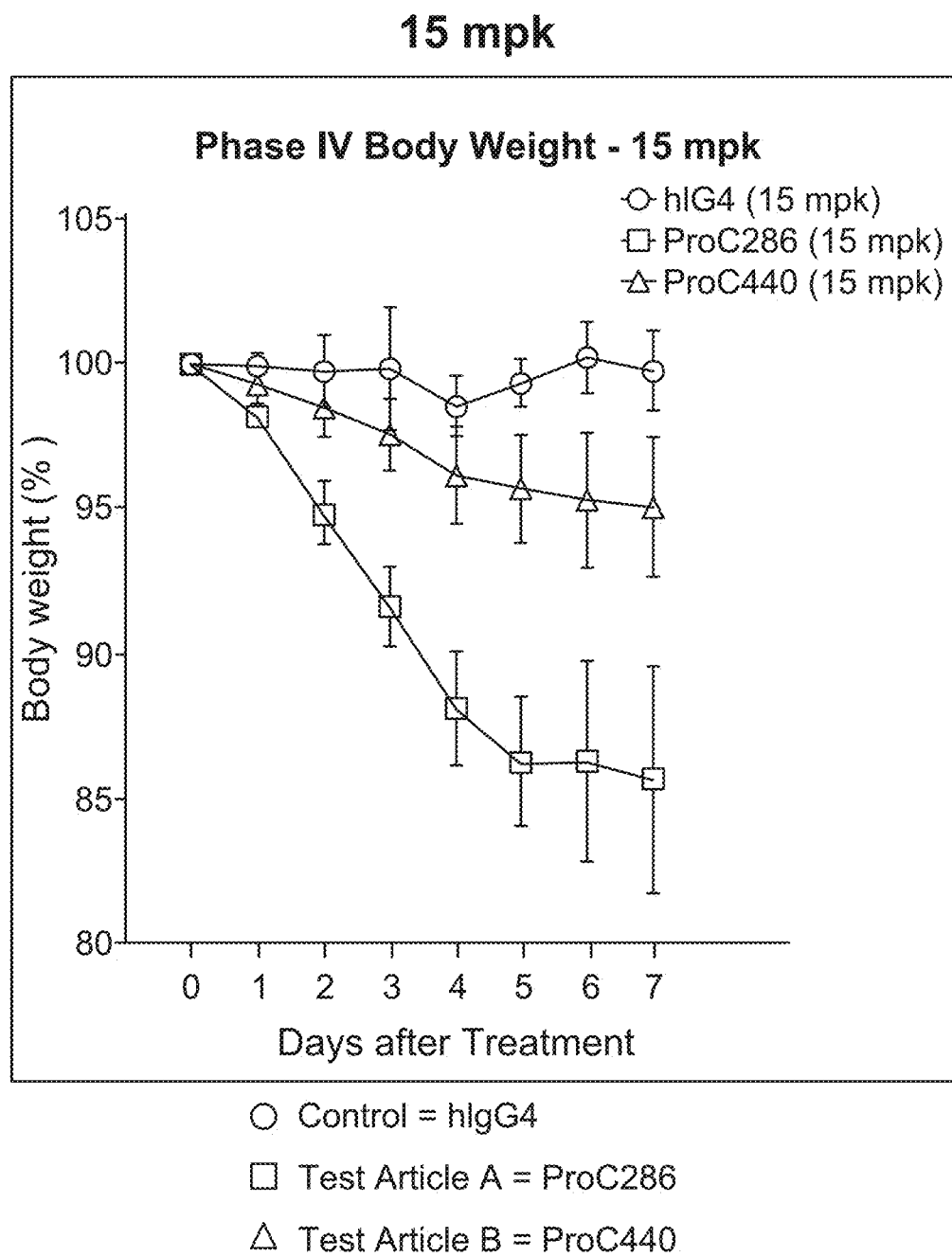

Overall, animals dosed with the unmasked ProC286 constructs showed on average 5% body weight loss at when dosed at 2 mpk, and 15% body weight loss when dosed at 10 mpk and 15 mpk (FIG. 22). One animal dosed with ProC286 at 15 mpk showed 20% body weight loss 7 days post-dose (end of study). This is considered a non-tolerated dose. In contrast, animals dosed with ProC440 at 2 mpk and 10 mpk did not show body weight loss.

Animals dosed with ProC440 at 15 mpk showed on average 5% body weight loss (FIG. 22). This indicates that ACCs of the present disclosure with a dimerized structure of, starting at the N-terminus, CP-CM-DD unexpectedly limits IFNα-2b mediated bodyweight loss. Without wishing to be bound by theory, it is believed that positioning the interferon N-terminal of the DD and using a relatively short LR inhibits cytokine activity in the context of ProC440, reducing the toxicity of the interferon in comparison to PEGylated IFNα-2b (Sylatron®) or ProC286.

In terms of clinical chemistry, animals dosed with ProC286 showed significant elevation of Alkaline Phosphatase (ALP) at all doses (0.4 mpk, 2 mpk, 10 mpk and 15 mpk), 7 days post-dose (end of study) (FIG. 23). No significant increase of ALP was measured when animals were dosed with 10 mpk or 15 mpk of ProC440 (FIG. 23). Elevation of ALT is a marker of liver toxicity. IFNα-2b has been shown to induce liver toxicities. This indicates that ACCs of the present disclosure with a dimerized structure of, starting at the N-terminus, CP-CM-DD unexpectedly limits IFNα-2b mediated liver toxicities.

In terms of hematology, 3 days post-dose and 7 days post-dose (end of study), animals dosed with ProC286 at 2 mpk, 10 mpk and 15 mpk showed significant reduction level of Reticulocyte count, Neutrophil count and White Blood Cells (WBC) count (FIG. 24). These reductions are reminiscent of IFNα-2b mediated bone-marrow toxicities. Three days post-dose, animals dosed with ProC440 showed reduction level of Reticulocyte count, Neutrophil count and White Blood Cells (WBC) count (FIG. 24). Overall, the reduction level of hematopoetic cells observed in animals dosed with ProC440 is not as significant as the reduction levels observed in animals dosed with ProC286. At 7 days post-dose (end of study), in animals dosed with ProC440, the overall level of Reticulocyte count, Neutrophil count and White Blood Cells (WBC) count is back to normal levels, or to a similar level that what observed in animals dosed with the negative control IgG4 (FIG. 24). In animals dosed with ProC286, the level of Reticulocyte count, Neutrophil count and White Blood Cells (WBC) count remains low. This indicates that ACCs of the present disclosure with a dimerized structure of, starting at the N-terminus, CP-CM-DD unexpectedly limits IFNα-2b mediated bone marrow toxicities.

Example 4. In Vitro Characterization of Additional Cytokine Constructs

Additional activatable cytokine constructs were also prepared by recombinant methods. The 1$^{st}$ and 2$^{nd}$ monomer constructs of these ACCs were identical. Each of the 1$^{st}$ and 2$^{nd}$ monomer constructs comprises, from N-terminus to C-terminus, a signal sequence from a mouse IgG kappa signal sequence (residues 1-20 of SEQ ID NO: 309), a mature cytokine protein that corresponds to human interferon alpha-2b (SEQ ID NO: 1), a cleavable moiety (CM) having the amino acid sequence of SEQ ID NO: 100, and a dimerization domain corresponding to human IgG4 S228P Fc (comprising SEQ ID NO: 3). In addition, these ACCs include or not a linker having the amino acid sequence SGGGG between the CP and the CM. These ACCs include or not a linker having the amino acid sequence GGGS between the CM and DD. These ACCs also contain or not portions of the hinge of the DD that are N-terminal to Cysteine 226. These additional activable cytokines constructs are described in Table 6 (see SEQ ID Nos: 336 to 342 and SEQ ID NO: 313).

TABLE 6

Activable cytokines having different lengths of amino acid sequences between CPand Cysteine 226 of human IgG

| Name | Alternative Name | Linker between CP and CM | Linker between CM and DD | Fc Hinge N-terminal residues | LINKING REGION LENGTH |
|---|---|---|---|---|---|
| ProC288 | IFNa2b 1204DNI 011 Fc | SGGGG | absent | absent | 12 |
| ProC289 | IFNa2b 1204DNI 3AA Fc | SGGGG | absent | GPP | 15 |
| ProC290 | IFNa2b 1204DNI 7AA Fc | SGGGG | absent | ESKYGPP | 19 |
| ProC291 | IFNa2b 1204DNI 11AA Fc | SGGGG | GGGS | ESKYGPP | 23 |
| ProC440 | N IFNa2b 0 1204DNIdL 0AA Fc | absent | absent | absent | 7 |
| ProC441 | N IFNa2b 0 1204DNIdL 3AA Fc | absent | absent | GPP | 10 |
| ProC442 | N IFNa2b 0 1204DNIdL 7AA Fc | absent | absent | ESKYGPP | 14 |
| ProC443 | N IFNa2b 0 1204DNIdL 11AA Fc | absent | GGGS | ESKYGPP | 18 |

The activity of ProC440, an ACC with no flexible linker and an Fc region truncated to Cys226, and the activity of additional ACCs containing various linkers and Fc region sequences was tested in vitro using IFN-responsive HEK293 cells and Daudi cells as previously described. In both assays, the activity (e.g., anti-proliferative effects) of ProC440 was reduced as compared to all other ACCs containing various additional sequences between the cytokine and the first amino acid that binds the DD to the corresponding second monomer (i.e., Cys226). EC50 values for the ACCs were computed from the IFNα/β assay results and are provided below in Table 7.

TABLE 7

| EC50: IFNα/β Reporter Assay | | | | | | | | |
|---|---|---|---|---|---|---|---|---|
| | Pro C288 | Pro C289 | Pro C290 | Pro C291 | Pro C440 | Pro C441 | Pro C442 | Pro C443 |
| EC50 | 34.34 | 17.93 | 10.33 | 8.743 | 41.37 | 6.28 | 6.637 | 1.687 |

EC50 values for the ACCs were computed from the Daudi apoptosis assay results and are provided below in Table 8.

TABLE 8

| EC50: Daudi Apoptosis Assay | | | | | | | | |
|---|---|---|---|---|---|---|---|---|
| | Pro C288 | Pro C289 | Pro C290 | Pro C291 | Pro C440 | Pro C441 | Pro C442 | Pro C443 |
| EC50 | 112.8 | 64.55 | 23.04 | 13.39 | 2078 | 1053 | 642.9 | 478 |

The data in Tables 7-8 also shows that the activity of the (uncleaved) ACCs could be modulated by varying the length of the amino acid sequences between the cytokine and Cys226 of the DD.

Without wishing to be bound by theory, based on the results presented herein, the inventors envisage that positioning a cytokine N-terminal of the DD and using a relatively short LR inhibits cytokine activity for cytokines in addition to the interferon-alpha cytokines exemplified in the foregoing specific examples. As described above, the invention described herein encompasses activatable cytokine constructs that include various cytokine proteins discussed herein. As non-limiting examples, the CP used in the ACCs of the invention may be any of those listed in SEQ ID NOs: 101 to 209, and variants thereof. In particular, monomeric cytokines are suited to use in the ACCs described herein. Based on the results provided herein, it is believed that the ACCs of the invention will exhibit reduced cytokine activity relative to the corresponding wild type cytokine, and that upon cleavage of the ACC by the relevant protease(s), the cleavage product will recover cytokine activity similar to that of the corresponding wild type cytokine.

Example Sequences

| SEQ ID NO. | NAME | SEQUENCE |
|---|---|---|
| 1 | Human Interferon-alpha-2b | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMIRSF SLSTNLQESLRSKE |
| 2 | Linker | GGGS |
| 3 | Human IgG4 Fc Region with S228P mutation, truncated to Cys226 | CPPCPAPEFLGGPSVFLFPPKPKDTLMISRTPEVTCVV VDVSQEDPEVQFNWYVDGVEVHNAKTKPREEQFNSTYR VVSVLTVLHQDWLNGKEYKCKVSNKGLPSSIEKTISKA KGQPREPQVYTLPPSQEEMTKNQVSLTCLVKGFYPSDI AVEWESNGQPENNYKTTPPVLDSDGSFFLYSRLTVD KSRWQQGNVFSCSVMHEALHNHYTQKSLSLS |
| 4 | Human IgG4 Fc Human IgG4 Fc Region with S228P mutation and full hinge region | ESKYGPPCPPCPAPEFLGGPSVFLFPPKPKDTLMISRT PEVTCVVVDVSQEDPEVQFNWYVDGVEVHNAKTKPREE QFNSTYRVVSVLTVLHQDWLNGKEYKCKVSNKGLPSSI EKTISKAKGQPREPQVYTLPPSQEEMTKNQVSLTCLVK GFYPSDIAVEWESNGQPENNYKTTPPVLDSDGSFFLYS RLTVDKSRWQQGNVFSCSVMHEALHNHYTQKSLSLS |
| 5 | CM | LSGRSDNH |
| 6 | CM | TGRGPSWV |
| 7 | CM | PLTGRSGG |
| 8 | CM | TARGPSFK |
| 9 | CM | NTLSGRSENHSG |
| 10 | CM | NTLSGRSGNHGS |
| 11 | CM | TSTSGRSANPRG |
| 12 | CM | TSGRSANP |
| 13 | CM | VHMPLGFLGP |
| 14 | CM | AVGLLAPP |

-continued

| SEQ ID NO. | NAME | SEQUENCE |
|---|---|---|
| 15 | CM | AQNLLGMV |
| 16 | CM | QNQALRMA |
| 17 | CM | LAAPLGLL |
| 18 | CM | STFPFGMF |
| 19 | CM | ISSGLLSS |
| 20 | CM | PAGLWLDP |
| 21 | CM | VAGRSMRP |
| 22 | CM | VVPEGRRS |
| 23 | CM | ILPRSPAF |
| 24 | CM | MVLGRSLL |
| 25 | CM | QGRAITFI |
| 26 | CM | SPRSIMLA |
| 27 | CM | SMLRSMPL |
| 28 | CM | ISSGLLSGRSDNH |
| 29 | CM | AVGLLAPPGGLSGRSDNH |
| 30 | CM | ISSGLLSSGGSGGSLSGRSDNH |
| 31 | CM | LSGRSGNH |
| 32 | CM | SGRSANPRG |
| 33 | CM | LSGRSDDH |
| 34 | CM | LSGRSDIH |
| 35 | CM | LSGRSDQH |
| 36 | CM | LSGRSDTH |
| 37 | CM | LSGRSDYH |
| 38 | CM | LSGRSDNP |
| 39 | CM | LSGRSANP |
| 40 | CM | LSGRSANI |
| 41 | CM | LSGRSDNI |
| 42 | CM | MIAPVAYR |
| 43 | CM | RPSPMWAY |
| 44 | CM | WATPRPMR |
| 45 | CM | FRLLDWQW |
| 46 | CM | ISSGL |
| 47 | CM | ISSGLLS |
| 48 | CM | ISSGLL |
| 49 | CM | ISSGLLSGRSANPRG |
| 50 | CM | AVGLLAPPTSGRSANPRG |
| 51 | CM | AVGLLAPPSGRSANPRG |
| 52 | CM | ISSGLLSGRSDDH |

-continued

| SEQ ID NO. | NAME | SEQUENCE |
|---|---|---|
| 53 | CM | ISSGLLSGRSDIH |
| 54 | CM | ISSGLLSGRSDQH |
| 55 | CM | ISSGLLSGRSDTH |
| 56 | CM | ISSGLLSGRSDYH |
| 57 | CM | ISSGLLSGRSDNP |
| 58 | CM | ISSGLLSGRSANP |
| 59 | CM | ISSGLLSGRSANI |
| 60 | CM | AVGLLAPPGGLSGRSDDH |
| 61 | CM | AVGLLAPPGGLSGRSDIH |
| 62 | CM | AVGLLAPPGGLSGRSDQH |
| 63 | CM | AVGLLAPPGGLSGRSDTH |
| 64 | CM | AVGLLAPPGGLSGRSDYH |
| 65 | CM | AVGLLAPPGGLSGRSDNP |
| 66 | CM | AVGLLAPPGGLSGRSANP |
| 67 | CM | AVGLLAPPGGLSGRSANI |
| 68 | CM | ISSGLLSGRSDNI |
| 69 | CM | AVGLLAPPGGLSGRSDNI |
| 70 | CM | GLSGRSDNHGGAVGLLAPP |
| 71 | CM | GLSGRSDNHGGVHMPLGFLGP |
| 72 | CM | LSGRSDNHGGVHMPLGFLGP |
| 73 | CM | ISSGLSS |
| 74 | CM | PVGYTSSL |
| 75 | CM | DWLYWPGI |
| 76 | CM | LKAAPRWA |
| 77 | CM | GPSHLVLT |
| 78 | CM | LPGGLSPW |
| 79 | CM | MGLFSEAG |
| 80 | CM | SPLPLRVP |
| 81 | CM | RMHLRSLG |
| 82 | CM | LLAPSHRA |
| 83 | CM | GPRSFGL |
| 84 | CM | GPRSFG |
| 85 | CM | SARGPSRW |
| 86 | CM | GGWHTGRN |
| 87 | CM | HTGRSGAL |
| 88 | CM | AARGPAIH |
| 89 | CM | RGPAFNPM |
| 90 | CM | SSRGPAYL |
| 91 | CM | RGPATPIIVI |

-continued

| SEQ ID NO. | NAME | SEQUENCE |
|---|---|---|
| 92 | CM | RGPA |
| 93 | CM | GGQPSGMWGW |
| 94 | CM | FPRPLGITGL |
| 95 | CM | SPLTGRSG |
| 96 | CM | SAGFSLPA |
| 97 | CM | LAPLGLQRR |
| 98 | CM | SGGPLGVR |
| 99 | CM | PLGL |
| 100 | CM | SGRSDNI |
| 101 | Human Interferon alpha-2a | CDLPQTHSLGSRRTLMLLAQMRKISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE |
| 102 | Rat Interferon alpha-2 | CDLPHTHNLRNKRAFTLLAQMRRLSPVSCLKDRKDFGF PLEKVDGQQIQKAQAIPVLHELTQQILSLFTSKESSTA WDASLLDSFCNDLQQQLSGLQACLMQQVGVQESPLTQE DSLLAVREYFHRITVYLREKKHSPCAWEVVRAEVWRAL SSSANLLGRLREERNES |
| 103 | Mouse Interferon alpha-2 | CDLPHTYNLRNKRALKVLAQMRRLPFLSCLKDRQDFGF PLEKVDNQQIQKAQAIPVLRDLTQQTLNLFTSKASSAA WNATLLDSFCNDLHQQLNDLQTCLMQQVGVQEPPLTQE DALLAVRKYFHRITVYLREKKHSPCAWEVVRAEVWRAL SSSVNLLPRLSEEKE |
| 104 | Human Interferon Alpha-2b | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE |
| 105 | Human Interferon Alpha-n3 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKECDLPQTHSLGSRRTLMLLAQMRRIS LFSCLKDRHDFGFPQEEFGNQFQKAETIPVLHEMIQQI FNLFSTKDSSAAWDETLLDKFYTELYQQLNDLEACVIQ GVGVTETPLMNEDSILAVRKYFQRITLYLKEKKYSPCA WEVVRAEIMRSFSLSTNLQESLRSKECDLPQTHSLGSR RTLMLLAQMRRISLFSCLKDRRDFGFPQEEFGNQFQKA ETIPVLHEMIQQIFNLFSTKDSSAAWDETLLDKFYTEL YQQLNDLEACVIQGVGVTETPLMNEDSILAVRKYFQRI TLYLKEKKYSPCAWEVVRAEIMRSFSLSTNLQESLRSK E |
| 106 | Human Interferon beta-1a | MSYNLLGFLQRSSNFQCQKLLWQLNGRLEYCLKDRMNF DIPEEIKQLQQFQKEDAALTIYEMLQNIFAIFRQDSSS TGWNETIVENLLANVYHQINHLKTVLEEKLEKEDFTRG KLMSSLHLKRYYGRILHYLKAKEYSHCAWTIVRVEILR NFYFINRLTGYLRN |
| 107 | Human Interferon beta-1b | SYNLLGFLQRSSNFQSQKLLWQLNGRLEYCLKDRMNFD IPEEIKQLQQFQKEDAALTIYEMLQNIFAIFRQDSSST GWNETIVENLLANVYHQINHLKTVLEEKLEKEDFTRGK LMSSLHLKRYYGRILHYLKAKEYSHCAWTIVRVEILRN FYFINRLTGYLRN |
| 108 | Mouse Interferon-Beta | MNNRWILHAAFLLCFSTTALSINYKQLQLQERTNIRKC QELLEQLNGKINLTYRADFKIPMEMTEKMQKSYTAFAI QEMLQNVFLVFRNNFSSTGWNETIVRLLDELHQQTVF LKTVLEEKQEERLTWEMSSTALHLKSYYWRVQRYLKLM KYNSYAWMVVRAEIFRNFLIIRRLTRNFQN |

-continued

| SEQ ID NO. | NAME | SEQUENCE |
|---|---|---|
| 109 | Rat Interferon-Beta | MANRWTLHIAFLLCFSTTALSIDYKQLQFRQSTSIRTC QKLLRQLNGRLNLSYRTDFKIPMEVMHPSQMEKSYTAF AIQVMLQNVFLVFRSNFSSTGWNETIVESLLDELHQQT ELLEIILKEKQEERLTWVTSTTTLGLKSYYWRVQRYLK DKKYNSYAWMVVRAEVFRNFSIILRLNRNFQN |
| 110 | Human Interferon Omega | MCDLPQNHGLLSRNTLVLLHQMRRISPFLCLKDRRDFR FPQEMVKGSQLQKAHVMSVLHEMLQQIFSLFHTERSS AAWNMTLLDQLHTGLHQQLQHLETCLLQVVGEGESA GAISSPALTLRRYFQGIRVYLKEKKYSDCAWEVVRMEI MKSLFLSTNMQERLRSKDRDLGSS |
| 111 | Human IL-1 alpha | MAKVPDMFEDLKNCYSENEEDSSSIDHLSLNQKSFYHV SYGPLHEGCMDQSVSLSISETSKTSKLTFKESMVVVAT NGKVLKKRRLSLSQSITDDDLEAIANDSEEEIIKPRSA PFSFLSNVKYNFMRIIKYEFILNDALNQSIIRANDQYL TAAALHNLDEAVKFDMGAYKSSKDDAKITVILRISKTQ LYVTAQDEDQPVLLKEMPEIPKTITGSETNLLFFWETH GTKNYFTSVAHPNLFIATKQDYWVCLAGGPPSITDFQI LENQA |
| 112 | Mouse IL-1 alpha | MAKVPDLFEDLKNCYSENEDYSSAIDHLSLNQKSFYDA SYGSLHETCTDQFVSLRTSETSKMSNFTFKESRVTVSA TSSNGKILKKRRLSFSETFTEDDLQSITHDLEETIQPR SAPYTYQSDLRYKLMKLVRQKFVMNDSLNQTIYQDVDK HYLSTTWLNDLQQEVKFDMYAYSSGGDDSKYPVTLKIS DSQLFVSAQGEDQPVLLKELPETPKLITGSETDLIFFW KSINSKNYFTSAAYPELFIATKEQSRVHLARGLPSMTD FQIS |
| 113 | Human IL-1 beta | MAEVPELASEMMAYYSGNEDDLFFEADGPKQMKCSFQD LDLCPLDGGIQLRISDHHYSKGFRQAASVVVAMDKLRK MLVPCPQTFQENDLSTFFPFIFEEEPIFFDTWDNEAYV HDAPVRSLNCTLRDSQQKSLVMSGPYELKALHLQGQDM EQQVVFSMSFVQGEESNDKIPVALGLKEKNLYLSCVLK DDKPTLQLESVDPKNYPKKKMEKRFVFNKIEINNKLEF ESAQFPNWYISTSQAENIVIPVFLGGTKGGQDITDFTM QFVSS |
| 114 | Mouse IL-1 beta | MATVPELNCEMPPFDSDENDLFFEVDGPQKMKGCFQTF DLGCPDESIQLQISQQHINKSFRQAVSLIVAVEKLWQL PVSFPWTFQDEDMSTFFSFIFEEEPILCDSWDDDDNLL VCDVPIRQLHYRLRDEQQKSLVLSDPYELKALHLNGQN INQQVIFSMSFVQGEPSNDKIPVALGLKGKNLYLSCVM KDGTPTLQLESVDPKQYPKKKMEKRFVFNKIEVKSKVE FESAEFPNWYISTSQAEHKPVFLGNNSGQDIIDFTMES VSS |
| 115 | Human IL-1RA | MEICRGLRSHLITLLLFLFHSETICRPSGRKSSKMQAF RIWDVNQKTFYLRNNQLVAGYLQGPNVNLEEKIDVVPI EPHALFLGIEGGKMCLSCVKSGDETRLQLEAVNITDLS ENRKQDKRFAFIRSDSGPTTSFESAACPGWFLCTAMEA DQPVSLTNMPDEGVMVTKFYFQEDE |
| 116 | Mouse IL-1RA | MEICWGPYSHLISLLLILLFHSEAACRPSGKRPCKMQA FRIWDTNQKTFYLRNNQLIAGYLQGPNIKLEEKIDMVP IDLHSVFLGIEGGKLCLSCAKSGDDIKLQLEEVNITDL SKNKEEDKRFTFIRSEKGPTTSFESAACPGWFLCTTLE ADRPVSLTNTPEEPLIVTKFYFQEDQ |
| 117 | Human IL-18 | MAAEPVEDNCINFVAMKFIDNTLYFIAEDDENLESDYF GKLESKLSVIRNLNDQVLFIDQGNRPLFEDMTDSDCRD NAPRTIFIISMYKDSQPRGMAVTISVKCEKISTLSCEN KIISFKEMNPPDNIKDTKSDIIFFQRSVPGHDNKMQFE SSSYEGYFLACEKERDLFKLILKKEDELGDRSIMFTVQ NED |
| 118 | Mouse IL-18 | MAAMSEDSCVNFKEMMFIDNTLYFIPEENGDLESDNFG RLHCTTAVIRNINDQVLFVDKRQPVFEDMTDIDQSASE PQTRLIIYMYKDSEVRGLAVTLSVKDSKMSTLSCKNKI ISFEEMDPPENIDDIQSDLIFFQKRVPGHNKMEFESSL YEGHFLACQKEDDAFKLILKKKDENGDKSVMFTLTNLH QS |

-continued

| SEQ ID NO. | NAME | SEQUENCE |
|---|---|---|
| 119 | Human IL-2 | MYRMQLLSCIALSLALVTNSAPTSSSTKKTQLQLEHLL<br>LDLQMILNGINNYKNPKLTRMLTFKFYMPKKATELKHL<br>QCLEEELKPLEEVLNLAQSKNFHLRPRDLISNINVIVL<br>ELKGSETTFMCEYADETATIVEFLNRWITFCQSIIS |
| 120 | Mouse IL-2 | MYSMQLASCVTLTLVLLVNSAPTSSSTSSSTAEAQQQQ<br>QQQQQQQQHLEQLLMDLQELLSRMENYRNLKLPRMLTF<br>KFYLPKQATELKDLQCLEDELGPLRHVLDLTQSKSFQL<br>EDAENFISNIRVTVVKLKGSDNTFECQFDDESATVVDF<br>LRRWIAFCQSITSTSPQ |
| 121 | Human IL-4 | MGLTSQLLPPLFFLLACAGNFVHGHKCDITLQEIIKTL<br>NSLTEQKTLCTELTVTDIFAASKNTTEKETFCRAATVL<br>RQFYSHHEKDTRCLGATAQQFHRHKQLIRFLKRLDRNL<br>WGLAGLNSCPVKEANQSTLENFLERLKTIIVIREKYSK<br>CSS |
| 122 | Mouse IL-4 | MGLNPQLVVILLFFLECTRSHIHGCDKNHLREIIGILN<br>EVTGEGTPCTEMDVPNVLTATKNTTESELVCRASKVLR<br>IFYLKHGKTPCLKKNSSVLMELQRLFRAFRCLDSSISC<br>TMNESKSTSLKDFLESLKSIMQMDYS |
| 123 | Human IL-7 | MFHVSFRYIFGLPPLILVLLPVASSDCDIEGKDGKQYE<br>SVLMVSIDQLLDSMKEIGSNCLNNEFNFFKRHICDANK<br>EGMFLFRAARKLRQFLKMNSTGDFDLHLLKVSEGTTIL<br>LNCTGQVKGRKPAALGEAQPTKSLEENKSLKEQKKLND<br>LCFLKRLLQEIKTCWNKILMGTKEH |
| 124 | Mouse IL-7 | MFHVSFRYIFGIPPLILVLLPVTSSECHIKDKEGKAYE<br>SVLMISIDELDKMTGTDSNCPNNEPNFFRKHVCDDTKE<br>AAFLNRAARKLKQFLKMNISEEFNVHLLTVSQGTQTLV<br>NCTSKEEKNVKEQKKNDACFLKRLLREIKTCWNKILKG<br>SI |
| 125 | Human IL-9 | MLLAMVLTSALLLCSVAGQGCPTLAGILDINFLINKMQ<br>EDPASKCHCSANVTSCLCLGIPSDNCTRPCFSERLSQM<br>TNTTMQTRYPLIFSRVKKSVEVLKNNKCPYFSCEQPCN<br>QTTAGNALTFLKSLLEIFQKEKMRGMRGKI |
| 126 | Mouse IL-9 | MLVTYILASVLLFSSVLGQRCSTTWGIRDTNYLIENLK<br>DDPPSKCSCSGNVTSCLCLSVPTDDCTTPCYREGLLQL<br>TNATQKSRLLPVFHRVKRIVEVLKNITCPSFSCEKPCN<br>QTMAGNTLSFLKSLLGTFQKTEMQRQKSRP |
| 127 | Human IL-13 | MHPLLNPLLLALGLMALLLTTVIALTCLGGFASPGPVP<br>PSTALRELIEELVNITQNQKAPLCNGSMVWSINLTAGM<br>YCAALESLINVSGCSAIEKTQRMLSGFCPHKVSAGQFS<br>SLHVRDTKIEVAQFVKDLLLHLKKLFREGRFN |
| 128 | Mouse IL-13 | MALWVTAVLALACLGGLAAPGPVPRSVSLPLTLKELIE<br>ELSNITQDQTPLCNGSMVWSVDLAAGGFCVALDSLTNI<br>SNCNAIYRTQRILHGLCNRKAPTTVSSLPDTKIEVAHF<br>ITKLLSYTKQLFRHGPF |
| 129 | Human IL-15 | MRISKPHLRSISIQCYLCLLLNSHFLTEAGIHVFILGC<br>FSAGLPKTEANWVNVISDLKKIEDLIQSMHIDATLYTE<br>SDVHPSCKVTAMKCFLLELQVISLESGDASIHDTVENL<br>IILANNSLSSNGNVTESGCKECEELEEKNIKEFLQSFV<br>HIVQMFINTS |
| 130 | Mouse IL-15 | MKILKPYMRNTSISCYLCFLLNSHFLTEAGIHVFILGC<br>VSVGLPKTEANWIDVRYDLEKIESLIQSIHIDTTLYTD<br>SDFHPSCKVTANINCFLLELQVILHEYSNMTLNETVRN<br>VLYLANSTLSSNKNVAESGCKECEELEEKTFTEFLQSF<br>IRIVQMFINTS |
| 131 | Human IL-3 | MSRLPVLLLLQLLVRPGLQAPMTQTTPLKTSWVNCSNM<br>IDEIITHLKQPPLPLLDFNNLNGEDQDILMENNLRRPN<br>LEAFNRAVKSLQNASAIESILKNLLPCLPLATAAPTRH<br>PIHIKDGDWNEFRRKLTFYLKTLENAQAQQTTLSLAIF |
| 132 | Mouse IL-3 | MVLASSTTSIHTMLLLLLMLFHLGLQASISGRDTHRLT<br>RTLNCSSIVKEIIGKLPEPELKTDDEGPSLRNKSFRRV<br>NLSKFVESQGEVDPEDRYVIKSNLQKLNCCLPTSANDS<br>ALPGVFIRDLDDFRKKLRFYMVHLNDLETVLTSRPPQP<br>ASGSVSPNRGTVEC |

-continued

| SEQ ID NO. | NAME | SEQUENCE |
|---|---|---|
| 133 | Human IL-5 | MRIVILLHLSLLALGAAVYVAIPTEIPTSALVKETLAL<br>LSTHRTLLIANETLRIPVPVHKNHQLCTEEIFQGIGTL<br>ESQTVQGGTVERLFKNLSLIKKYIDGQKKKCGEERRRV<br>NQFLDYLQEFLGVIVINTEWIIES |
| 134 | Mouse IL-5 | MRRMLLHLSVLTLSCVWATAMEIPMSTVVKETLTQLSA<br>HRALLTSNETMRLPVPTHKNHQLCIGEIFQGLDILKNQ<br>TVRGGTVEMLFQNLSLIKKYIDRQKEKCGEERRRTRQF<br>LDYLQEFLGVMSTEWAMEG |
| 135 | Human GM-CSF | MWLQSLLLLGTVACSISAPARSPSPSTQPWEHVNAIQE<br>ARRLLNLSRDTAAEMNETVEVISEMFDLQEPTCLQTRL<br>ELYKQGLRGSLTKLKGPLTMMASHYKQHCPPTPETSCA<br>TQIITFESFKENLKDFLLVIPFDCWEPVQE |
| 136 | Mouse GM-CSF | MWLQNLLFLGIVVYSLSAPTRSPITVTRPWKHVEAIKE<br>ALNLLDDMPVTLNEEVEVVSNEFSFKKLTCVQTRLKIF<br>EQGLRGNFTKLKGALNIVITASYYQTYCPPTPETDCET<br>QVTTYADFIDSLKTFLTDIPFECKKPGQK |
| 137 | Human IL-6 | MNSFSTSAFGPVAFSLGLLLVLPAAFPAPVPPGEDSKD<br>VAAPHRQPLTSSERIDKQIRYILDGISALRKETCNKSN<br>MCESSKEALAENNLNLPKMAEKDGCFQSGFNEETCLVK<br>IITGLLEFEVYLEYLQNRFESSEEQARAVQMSTKVLIQ<br>FLQKKAKNLDAITTPDPTTNASLLTKLQAQNQWLQDMT<br>THLILRSFKEFLQSSLRALRQM |
| 138 | Mouse IL-6 | MKFLSARDFHPVAFLGLMLVTTTAFPTSQVRRGDFTED<br>TTPNRPVYTTSQVGGLITHVLWEIVEMRKELCNGNSDC<br>MNNDDALAENNLKLPEIQRNDGCYQTGYNQEICLLKIS<br>SGLLEYHSYLEYMKNNLKDNKKDKARVLQRDTETLIHI<br>FNQEVKDLHKIVLPTPISNALLTDKLESQKEWLRTKTI<br>QFILKSLEEFLKVTLRSTRQT |
| 139 | Human IL-11 | MNCVCRLVLVVLSLWPDTAVAPGPPPGPPRVSPDPRAE<br>LDSTVLLTRSLLADTRQLAAQLRDKFPADGDHNLDSLP<br>TLAMSAGALGALQLPGVLTRLRADLLSYLRHVQWLRRA<br>GGSSLKTLEPELGTLQARLDRLLRRLQLLMSRLALPQP<br>PPDPPAPPLAPPSSAWGGIRAAHAILGGLHLTLDWAVR<br>GLLLLKTRL |
| 140 | Mouse IL-11 | MNCVCRLVLVVLSLWPDRVVAPGPPAGSPRVSSDPRAD<br>LDSAVLLTRSLLADTRQLAAQMRDKFPADGDHSLDSLP<br>TLAMSAGTLGSLQLPGVLTRLRVDLMSYLRHVQWLRRA<br>GGPSLKTLEPELGALQARLERLLRRLQLLMSRLALPQA<br>APDQPVIPLGPPASAWGSIRAAHAILGGLHLTLDWAVR<br>GLLLLKTRL |
| 141 | Human G-CSF | MAGPATQSPMKLMALQLLLWHSALWTVQEATPLGPASS<br>LPQSFLLKCLEQVRKIQGDGAALQEKLVSECATYKLCH<br>PEELVLLGHSLGIPWAPLSSCPSQALQLAGCLSQLHSG<br>LFLYQGLLQALEGISPELGPTLDTLQLDVADFATTIWQ<br>QMEELGMAPALQPTQGAMPAFASAFQRRAGGVLVASHL<br>QSFLEVSYRVLRHLAQP |
| 142 | Mouse G-CSF | MAQLSAQRRMKLMALQLLLWQSALWSGREAVPLVTVSA<br>LPPSLPLPRSFLLKSLEQVRKIQASGSVLLEQLCATYK<br>LCHPEELVLLGHSLGIPKASLSGCSSQALQQTQCLSQL<br>HSGLCLYQGLLQALSGISPALAPTLDLLQLDVANFATT<br>IWQQMENLGVAPTVQPTQSAMPAFTSAFQRRAGGVLAI<br>SYLQGFLETARLALHHLA |
| 143 | Human IL-12 alpha | MCPARSLLLVATLVLLDHLSLARNLPVATPDPGMFPCL<br>HESQNLLRAVSNMLQKARQTLEFYPCTSEEIDHEDITK<br>DKTSTVEACLPLELTKNESCLNSRETSFITNGSCLASR<br>KTSFMMALCLSSIYEDLKMYQVEFKTMNAKLLMDPKRQ<br>IFLDQNMLAVIDELMQALNFNSETVPQKSSLEEPDFYK<br>TKIKLCILLHAFRIRAVTIDRVMSYLNAS |
| 144 | Human IL-12 beta | MCHQQLVISWFSLVFLASPLVAIWELKKDVYVVELDWY<br>PDAPGEMVVLTCDTPEEDGITWTLDQSSEVLGSGKTLT<br>IQVKEFGDAGQYTCHKGGEVLSHSLLLLHKKEDGIWST<br>DILKDQKEPKNKTFLRCEAKNYSGRFTCWWLTTISTDL<br>TFSVKSSRGSSDPQGVTCGAATLSAERVRGDNKEYEYS<br>VECQEDSACPAAEESLPIEVMVDAVHKLKYENYTSSFF<br>IRDIIKPDPPKNLQLKPLKNSRQVEVSWEYPDTWSTPH |

-continued

| SEQ ID NO. | NAME | SEQUENCE |
|---|---|---|
| | | SYFSLTFCVQVQGKSKREKKDRVFTDKTSATVICRKNA SISVRAQDRYYSSSWSEWASVPCS |
| 145 | Mouse IL-12 beta | MCPQKLTISWFAIVLLVSPLMAMWELEKDVYVVEVDWT PDAPGETVNLTCDTPEEDDITWTSDQRHGVIGSGKTLT ITVKEFLDAGQYTCHKGGETLSHSHLLLHKKENGIWST EILKNFKNKTFLKCEAPNYSGRFTCSWLVQRNMDLKFN IKSSSSSPDSRAVTCGMASLSAEKVTLDQRDYEKYSVS CQEDVTCPTAEETLPIELALEARQQNKYENYSTSFFIR DIIKPDPPKNLQMKPLKNSQVEVSWEYPDSWSTPHSYF SLKFFVRIQRKKEKMKETEEGCNQKGAFLVEKTSTEVQ CKGGNVCVQADRYYNSSCSKWACVPCRVRS |
| 146 | Mouse IL-12 alpha | MCQSRYLLFLATLALLNHLSLARVIPVSGPARCLSQSR NLLKTTDDMVKTAREKLKHYSCTAEDIDHEDITRDQTS TLKTCLPLELHKNESCLATRETSSTTRGSCLPPQKTSL MMTLCLGSIYEDLKMYQTEFQAINAALQNHNHQQIILD KGMLVAIDELMQSLNHNGETLRQKPPVGEADPYRVKMK LCILLHAFSTRVVTINRVMGYLSSA |
| 147 | Human LIF | MKVLAAGVVPLLLVLHWKHGAGSPLPITPVNATCAIRH PCHNNLMNQIRSQLAQLNGSANALFILYYTAQGEPFPN NLDKLCGPNVTDFPPFHANGTEKAKLVELYRIVVYLGT SLGNITRDQKILNPSALSLHSKLNATADILRGLLSNVL CRLCSKYHVGHVDVTYGPDTSGKDVFQKKKLGCQLLGK YKQIIAVLAQAF |
| 148 | Mouse LIF | MKVLAAGIVPLLLLVLHWKHGAGSPLPITPVNATCAIR HPCHGNLMNQIKNQLAQLNGSANALFISYYTAQGEPFP NNVEKLCAPNMTDFPSFHGNGTEKTKLVELYRMVAYLS ASLTNITRDQKVLNPTAVSLQVKLNATIDVMRGLLSNV LCRLCNKYRVGHVDVPPVPDHSDKEAFQRKKLGCQLLG TYKQVISVVVQAF |
| 149 | Human OSM | MGVLLTQRTLLSLVLALLFPSMASMAAIGSCSKEYRVL LGQLQKQTDLMQDTSRLLDPYIRIQGLDVPKLREHCRE RPGAFPSEETLRGLGRRGFLQTLNATLGCVLHRLADLE QRLPKAQDLERSGLNIEDLEKLQMARPNILGLRNNIYC MAQLLDNSDTAEPTKAGRGASQPPTPTPASDAFQRKLE GCRFLHGYHRFMHSVGRVFSKWGESPNRSRRHSPHQAL RKGVRRTRPSRKGKRLMTRGQLPR |
| 150 | Mouse OSM | MQTRLLRTLLSLTLSLLILSMALANRGCSNSSSQLLSQ LQNQANLTGNTESLLEPYIRLQNLNTPDLRAACTQHSV AFPSEDTLRQLSKPHFLSTVYTTLDRVLYQLDALRQKF LKTPAFPKLDSARHNILGIRNNVFCMARLLNHSLEIPE PTQTDSGASRSTTTPDVFNTKIGSCGFLWGYHRFMGSV GRVFREWDDGSTRSRRQSPLRARRKGTRRIRVRHKGTR RIRVRRKGTRRIWVRRKGSRKIRPSRSTQSPTTRA |
| 151 | Human IL-10 | MHSSALLCCLVLLTGVRASPGQGTQSENSCTHFPGNLP NMLRDLRDAFSRVKTFFQMKDQLDNLLLKESLLEDFKG YLGCQALSEMIQFYLEEVMPQAENQDPDIKAHVNSLGE NLKTLRLRLRRCHRFLPCENKSKAVEQVKNAFNKLQEK GIYKAMSEFDIFINYIEAYMTMKIRN |
| 152 | Mouse IL-10 | MPGSALLCCLLLLTGMRISRGQYSREDNNCTHFPVGQS HMLLELRTAFSQVKTFFQTKDQLDNILLTDSLMQDFKG YLGCQALSEMIQFYLVEVMPQAEKHGPEIKEHLNSLGE KLKTLRMRLRRCHRFLPCENKSKAVEQVKSDFNKLQDQ GVYKAMNEFDIFINCIEAYMMIKMKS |
| 153 | Human IL-20 | MKASSLAFSLLSAAFYLLWTPSTGLKTLNLGSCVIATN LQEIRNGFSEIRGSVQAKDGNIDIRILRRTESLQDTKP ANRCCLLRHLLRLYLDRVFKNYQTPDHYTLRKISSLAN SFLTIKKDLRLCHARMTCHCGEEAMKKYSQILSHFEKL EPQAAVVKALGELDILLQWMEETE |
| 154 | Mouse IL-20 | MKGFGLAFGLFSAVGFLLWTPLTGLKTLHLGSCVITAN LQAIQKEFSEIRDSVQAEDTNIDIRILRTTESLKDIKS LDRCCFLRHLVRFYLDRVFKVYQTPDHHTLRKISSLAN SFLIIKKDLSVCHSHMACHCGEEAMEKYNQILSHFIEL ELQAAVVKALGELGILLRWMEEML |
| 155 | Human IL-14 | MKNQDKKNGAAKQSNPKSSPGQPEAGPEGAQERPSQAA PAVEAEGPGSSQAPRKPEGAQARTAQSGALRDVSEELS RQLEDILSTYCVDNNQGGPGEDGAQGEPAEPEDAEKSR |

| SEQ ID NO. | NAME | SEQUENCE |
|---|---|---|
| | | TYVARNGEPEPTPVVNGEKEPSKGDPNTEEIRQSDEVG
DRDHRRPQEKKKAKGLGKEITLLMQTLNTLSTPEEKLA
ALCKKYAELLEEHRNSQKQMKLLQKKQSQLVQEKDHLR
GEHSKAVLARSKLESLCRELQRHNRSLKEEGVQRAREE
EEKRKEVTSHFQVTLNDIQLQMEQHNERNSKLRQENME
LAERLKKLIEQYELREEHIDKVFKHKDLQQQLVDAKLQ
QAQEMLKEAEERHQREKDFLLKEAVESQRWICELMKQQ
ETHLKQQLALYTEKFEEFQNTLSKSSEVFTTFKQEMEK
MTKKIKKLEKETTMYRSRWESSNKALLEMAEEKTVRDK
ELEGLQVKIQRLEKLCRALQTERNDLNKRVQDLSAGGQ
GSLTDSGPERRPEGPGAQAPSSPRVTEAPCYPGAPSTE
ASGQTGPQEPTSARA |
| 156 | Mouse IL-14 | MKNQDKKNGPAKHSNSKGSPGQREAGPEGAHGRPRQTA
PGAEAEGSTSQAPGKTEGARAKAAQPGALCDVSEELSR
QLEDILSTYCVDNNQGGPAEEGAQGEPTEPEDTEKSRT
YAARNGEPEPGIPVVNGEKETSKGEPGTEEIRASDEVG
DRDHRRPQEKKKAKGLGKEITLLMQTLNTLSTPEEKLA
ALCKKYAELLEEHRNSQKQMKLLQKKQSQLVQEKDHLR
GEHSKAVLARSKLESLCRELQRHNRSLKEEGVQRAREE
EEKRKEVTSHFQVTLNDIQLQMEQHNERNSKLRQENME
LAERLKKLIEQYELREEHIDKVFKHKDLQQQLVDAKLQ
QAQEMLKEAEERHQREKEFLLKEAVESQRMCELMKQQE
THLKQQLALYTEKFEEFQNTLSKSSEVFTTFKQEMEKM
TKKIKKLEKETTMYRSRWESSNKALLEMAEEKTVRDKE
LEGLQVKIQRLEKLCRALQTERNDLNKRVQDLTAGGIT
DIGSERRPEATTASKEQGVESPGAQPASSPRATDAPCC
SGAPSTGTAGQTGPGEPTPATA |
| 157 | Human IL-16 | MESHSRAGKSRKSAKFRSISRSLMLCNAKTSDDGSSPD
EKYPDPFEISLAQGKEGIFHSSVQLADTSEAGPSSVPD
LALASEAAQLQAAGNDRGKTCRRIFFMKESSTASSREK
PGKLEAQSSNFLFPKACHQRARSNSTSVNPYCTREIDF
PMTKKSAAPTDRQPYSLCSNRKSLSQQLDCPAGKAAGT
SRPTRSLSTAQLVQPSGGLQASVISNIVLMKGQAKGLG
FSIVGGKDSIYGPIGIYVKTIFAGGAAAADGRLQEGDE
ILELNGESMAGLTHQDALQKFKQAKKGLLTLTVRTRLT
APPSLCSHLSPPLCRSLSSSTCITKDSSSFALESPSAP
ISTAKPNYRIMVEVSLQKEAGVGLGIGLCSVPYFQCIS
GIFVHTLSPGSVAHLDGRLRCGDEIVEISDSPVHCLTL
NEVYTILSHCDPGPVPIIVSRHPDPQVSEQQLKEAVAQ
AVENTKFGKERHQWSLEGVKRLESSWHGRPTLEKEREK
NSAPPHRRAQKVMIRSSSDSSYMSGSPGGSPGSGSAEK
PSSDVDISTHSPSLPLAREPVVLSIASSRLPQESPPLP
ESRDSHPPLRLKKSFEIVRKPMSSKPKPPPRKYFKSDS
DPQKSLEERENSSCSSGHTPPTCGQEARELLPLLLPQE
DTAGRSPSASAGCPGPGIGPQTKSSTEGEPGWRRASPV
TQTSPIKHPLLKRQARMDYSFDTTAEDPWVRISDCIKN
LFSPIMSENHGHMPLQPNASLNEEEGTQGHPDGTPPKL
DTANGTPKVYKSADSSTVKKGPPVAPKPAWFRQSLKGL
RNRASDPRGLPDPALSTQPAPASREHLGSHIRASSSSS
SIRQRISSFETFGSSQLPDKGAQRLSLQPSSGEAAKPL
GKHEEGRFSGLLGRGAAPTLVPQQPEQVLSSGSPAASE
ARDPGVSESPPPGRQPNQKTLPPGPDPLLRLLSTQAEE
SQGPVLKMPSQRARSFPLTRSQSCETKLLDEKTSKLYS
ISSQVSSAVMKSLLCLPSSISCAQTPCIPKEGASPTSS
SNEDSAANGSAETSALDTGFSLNLSELREYTEGLTEAK
EDDDGDHSSLQSGQSVISLLSSEELKKLIEEVKVLDEA
TLKQLDGIHVTILHKEEGAGLGFSLAGGADLENKVITV
HRVFPNGLASQEGTIQKGNEVLSINGKSLKGTTHHDAL
AILRQAREPRQAVIVTRKLTPEAMPDLNSSTDSAASAS
AASDVSVESTAEATVCTVTLEKMSAGLGFSLEGGKGSL
HGDKPLTINRIFKGAASEQSETVQPGDEILQLGGTAMQ
GLTRFEAWNIIKALPDGPVTIVRRKSLQSKETTAAGD
S |
| 158 | Mouse IL-16 | MEPHGHSGKSRKSTKFRSISRSLILCNAKTSDDGSSPD
EKYPDPFETSLCQGKEGFFHSSMQLADTFEAGLSNIPD
LALASDSAQLAAAGSDRGKHCRKMFFMKESSSTSSKEK
SGKPEAQSSSFLFPKACHQRTRSNSTSVNPYSAGEIDF
PMTKKSAAPTDRQPYSLCSNRKSLSQQLDYPILGTARP
TRSLSTAQLGQLSGGLQASVISNIVLMKGQAKGLGFSI
VGGKDSIYGPIGIYVKSIFAGGAAAADGRLQEGDEILE
LNGESMAGLTHQDALQKFKQAKKGLLTLTVRTRLTTPP
SLCSHLSPPLCRSLSSSTCGAQDSSPFSLESPASPAST
AKPNYRIMVEVSLKKEAGVGLGIGLCSIPYFQCISGIF
VHTLSPGSVAHLDGRLRCGDEIVEINDSPVHCLTLNEV |

-continued

| SEQ ID NO. | NAME | SEQUENCE |
|---|---|---|
| | | YTILSHCDPGPVPIIVSRHPDPQVSEQQLKEAVAQAVE
GVKFGKDRHQWSLEGVKRLESSWHGRPTLEKEREKHSA
PPHRRAQKIMVRSSSDSSYMSGSPGGSPCSAGAEPQPS
EREGSTHSPSLSPGEEQEPCPGVPSRPQQESPPLPESL
ERESHPPLRLKKSFEILVRKPTSSKPKPPPRKYFKNDS
EPQKKLEEKEKVTDPSGHTLPTCSQETRELLPLLLQED
TAGRAPCTAACCPGPAASTQTSSSTEGESRRSASPETP
ASPGKHPLLKRQARMDYSFDITAEDPWVRISDCIKNLF
SPIMSENHSHTPLQPNTSLGEEDGTQGCPEGGLSKMDA
ANGAPRVYKSADGSTVKKGPPVAPKPAWFRQSLKGLRN
RAPDPRRPPEVASAIQPTPVSRDPPGPQPQASSSIRQR
ISSFENFGSSQLPDRGVQRLSLQPSSGETTKFPGKQDG
GRFSGLLGQGATVTAKHRQTEVESMSTTFPNSSEVRDP
GLPESPPPGQRPSTKALSPDPLLRLLTTQSEDTQGPGL
KMPSQRARSFPLTRTQSCETKLLDEKASKLYSISSQLS
SAVMKSLLCLPSSVSCGQITCIPKERVSPKSPCNNSSA
AEGFGEAMASDTGFSLNLSELREYSEGLTEPGETEDRN
HCSSQAGQSVISLLSAEELEKLIEEVRVLDEATLKQLD
SIHVTILHKEEGAGLGFSLAGGADLENKVITVHRVFPN
GLASQEGTIQKGNEVLSINGKSLKGATHNDALAILRQA
RDPRQAVIVTRRTTVEATHDLNSSTDSAASASAASDIS
VESKEATVCTVTLEKTSAGLGFSLEGGKGSLHGDKPLT
INRIFKGTEQGEMVQPGDEILQLAGTAVQGLTRFEAWN
VIKALPDGPVTIVIRRTSLQCKQTTASADS |
| 159 | Human IL-17 | MTPGKTSLVSLLLLLSLEAIVKAGITIPRNPGCPNSED
KNFPRTVMVLNIHNRNTNTNPKRSSDYYNRSTSPWNL
HRNEDPERYPSVIWEAKCRHLGCINADGNVDYHMNSVP
IQQEILVLRREPPHCPNSFRLEKILVSVGCTCVTPIVH
HVA |
| 160 | Mouse IL-17 | MSPGRASSVSLMLLLLLSLAATVKAAAIIPQSSACPNT
EAKDFLQNVKVNLKVFNSLGAKVSSRRPSDYLNRSTSP
WTLHRNEDPDRYPSVIWEAQCRHQRCVNAEGKLDHHMN
SVLIQQEILVLKREPESCPFTFRVEKMLVGVGCTCVAS
IVRQAA |
| 161 | Human CD154 | MIETYNQTSPRSAATGLPISMKIFMYLLTVFLITQMIG
SALFAVYLHRRLDKIEDERNLHEDFVFMKTIQRCNTGE
RSLSLLNCEEIKSQFEGFVKDIMLNKEETKKENSFEMQ
KGDQNPQIAAHVISEASSKTTSVLQWAEKGYYTMSNNL
VTLENGKQLTVKRQGLYYIYAQVTFCSNREASSQAPFI
ASLCLKSPGRFERILLRAANTHSSAKPCGQQSIHLGGV
FELQPGASVFVNVTDPSQVSHGTGFTSFGLLKL |
| 162 | Mouse CD154 | MIETYSQPSPRSVATGLPASMKIFMYLLTVFLITQMIG
SVLFAVYLHRRLDKVEEEVNLHEDFVFIKKLKRCNKGE
GSLSLLNCEEMRRQFEDLVKDITLNKEEKKENSFEMQR
GDEDPQIAAHVVSEANSNAASVLQWAKKGYYTMKSNLV
MLENGKQLTVKREGLYYVYTQVTFCSNREPSSQRPFIV
GLWLKPSSGSERILLKAANTHSSSQLCEQQSVHLGGVF
ELQAGASVFVNVTEASQVIHRVGFSSFGLLKL |
| 163 | Human LT-beta | MGALGLEGRGGRLQGRGSLLLAVAGATSLVTLLLAVPI
TVLAVLALVPQDQGGLVTETADPGAQQQGLGFQKLPE
EEPETDLSPGLPAAHLIGAPLKGQGLGWETTKEQAFLT
SGTQFSDAEGLALPQDGLYYLYCLVGYRGRAPPGGGDP
QGRSVTLRSSLYRAGGAYGPGTPELLLEGAETVTPVLD
PARRQGYGPLWYTSVGFGGLVQLRRGERVYVNISHPDM
VDFARGKTFFGAVMVG |
| 164 | Mouse LT-beta | MGTRGLQGLGGRPQGRGCLLLAVAGATSLVTLLLAVPI
TVLAVLALVPQDQGRRVEKIIGSGAQAQKRLDDSKPSC
ILPSPSSLSETPDPRLHPQRSNASRNLASTSQGPVAQS
SREASAWMTILSPAADSTPDPGVQQLPKGEPETDLNPE
LPAAHLIGAWMSGQGLSWEASQEEAFLRSGAQFSPTHG
LALPQDGVYYLYCHVGYRGRTPPAGRSRARSLTLRSAL
YRAGGAYGRGSPELLLEGAETVTPVVDPIGYGSLWYTS
VGFGGLAQLRSGERVYVNISHPDMVDYRRGKTFFGAVM
VG |
| 165 | Human TNF-alpha | STESMIRDVELAEEEALPKKTGGPQGSRRCLFLSLFSFL
IVAGATTLFCLLHFGVIGPQREEFPRDLSLISPLAQAV
RSSSRTPSDKPVAHVVANPQAEGQLQWLNRRANALLAN
GVELRDNQLVVPSEGLYLIYSQVLFKGQGCPSTHVLLT
HTISRIAVSYQTKVNLLSAIKSPCQRETPEGAEAKPWY
EPIYLGGVFQLEKGDRLSAEINRPDYLDFAESGQVYFG
IIAL |

-continued

| SEQ ID NO. | NAME | SEQUENCE |
|---|---|---|
| 166 | Mouse TNF-alpha | NHQVEEQLEWLSQRANALLANGMDLKDNQLVVPADGLY LVYSQVLFKGQGCPDYVLLTHTVSRFAISYQEKVNLLS AVKSPCPKDTPEGAELKPWYEPIYLGGVFQLEKGDQLS AEVNLPKYLDFAESGQVYFGVIAL |
| 167 | Human TNF-beta | MTPPERLFLPRVCGTTLHLLLLGLLLVLLPGAQGLPGV GLTPSAAQTARQHPKMHLAHSTLKPAAHLIGDPSKQNS LLWRANTDRAFLQDGFSLSNNSLLVPTSGIYFVYSQVV FSGKAYSPKATSSPLYLAHEVQLFSSQYPFHVPLLSSQ KMVYPGLQEPWLHSMYHGAAFQLTQGDQLSTHTDGI PHLVLSPSTVFFGAFAL |
| 168 | Human 4-1BBL | MEYASDASLDPEAPWPPAPRARACRVLPWALVAGLLLL LLLAAACAVFLACPWAVSGARASPGSAASPRLREGPEL SPDDPAGLLDLRQGMFAQLVAQNVLLIDGPLSWYSDPG LAGVSLTGGLSYKEDTKELVVAKAGVYYVFFQLELRRV VAGEGSGSVSLALHLQPLRSAAGAAALALTVDLPPASS EARNSAFGFQGRLLHLSAGQRLGVHLHTEARARHAWQL TQGATVLGLFRVTPEIPAGLPSPRSE |
| 169 | Mouse 4-1BBL | MDQHTLDVEDTADARHPAGTSCPSDAALLRDTGLLADA ALLSDTVRPTNAALPTDAAYPAVNVRDREAAWPPALNF CSRHPKLYGLVALVLLLLIAACVPIFTRTEPRPALTIT TSPNLGTRENNADQVTPVSHIGCPNTTQQGSPVFAKLL AKNQASLCNTTLNWHSQDGAGSSYLSQGLRYEEDKKEL VVDSPGLYYVFLELKLSPTFTNTGHKVQGWVSLVLQAK PQVDDFDNLALTVELFPCSMENKLVDRSWSQLLLLKAG HRLSVGLRAYLHGAQDAYRDWELSYPNTTSFGLFLVKP DNPWE |
| 170 | Human APRIL | AVLTQKQKKQHSVLHLVPINATSKDDSDVTEVMWQPAL RRGRGLQAQGYGVRIQDAGVYLLYSQVLFQDVTFTMGQ VVSREGQGRQETLFRCIRSMPSHPDRAYNSCYSAGVFH LHQGDILSVIIPRARAKLNLSPHGTFLGFVKL |
| 171 | Mouse APRIL | MPASSPGHMGGSVREPALSVALWLSWGAVLGAVTCAVA LLIQQTELQSLRREVSRLQRSGGPSQKQGERPWQSLWE QSPDVLEAWKDGAKSRRRRAVLTQKHKKKHSVLHLVPV NITSKADSDVTEVMWQPVLRRGRGLEAQGDIVRVWDTG IYLLYSQVLFHDVTFTMGQVVSREGQGRRETLFRCIRS MPSDPDRAYNSCYSAGVFHLHQGDIITVKIPRANAKLS LSPHGTFLGFVKL |
| 172 | Human CD70 | MPEEGSGCSVRRRPYGCVLRAALVPLVAGLVICLVVCI QRFAQAQQQLPLESLGWDVAELQLNHTGPQQDPRLYWQ GGPALGRSFLHGPELDKGQLRIHRDGIYMVHIQVTLAI CSSTTASRHHPTTLAVGICSPASRSISLLRLSFHQGCT IASQRLTPLARGDTLCTNLTGTLLPSRNTDETFFGVQW VRP |
| 173 | Mouse CD70 | MPEEGRPCPWVRWSGTAFQRQWPWLLLVVFITVFCCWF HCSGLLSKQQQRLLEHPEPHTAELQLNLTVPRKDPTLR WGAGPALGRSFTHGPELEEGHLRIHQDGLYRLHIQVTL ANCSSPGSTLQHRATLAVGICSPAAHGISLLRGRFGQD CTVALQRLTYLVHGDVLCTNLTPLLPSRNADETFFGV QWICP |
| 174 | Human CD153 | MDPGLQQALNGMAPPGDTAMHVPAGSVASHLGTTSRSY FYLTTATLALCLVFTVATIMVLVVQRTDSIPNSPDNVP LKGGNCSEDLLCILKRAPFKKSWAYLQVAKHLNKTKLS WNKDGILHGVRYQDGNLVIQFPGLYFIICQLQFLVQCP NNSVDLKLELLINKHIKKQALVTVCESGMQTKHVYQNL SQFLLDYLQVNTTISVNVDTFQYIDTSTFPLENVLSIF LYSNSD |
| 175 | Mouse CD153 | MEPGLQQAGSCGAPSPDPAMQVQPGSVASPWRSTRPWR STSRSYFYLSTTALVCLVVAVAIILVLVVQKKDSTPNT TEKAPLKGGNCSEDLFCTLKSTPSKKSWAYLQVSKHLN NTKLSWNEDGTIHGLIYQDGNLIVQFPGLYFIVCQLQF LVQCSNHSVDLTLQLLINSKIKKQTLVTVCESGVQSKN IYQNLSQFLLHYLQVNSTISVRVDNFQYVDTNTFPLDN VLSVFLYSSSD |
| 176 | Human CD178 | MQQPFNYPYPQIYWVDSSASSPWAPPGTVLPCPTSVPR RPGQRRPPPPPPPPPLPPPPPPPLPPLPLPPLKKRGN HSTGLCLLVMFFMVLVALVGLGLGMFQLFHLQKELAEL |

| SEQ ID NO. | NAME | SEQUENCE |
|---|---|---|
| | | RESTSQMHTASSLEKQIGHPSPPPEKKELRKVAHLTGK SNSRSMPLEWEDTYGIVLLSGVKYKKGGLVINETGLYF VYSKVYFRGQSCNNLPLSHKVYMRNSKYPQDLVMMEGK MMSYCTTGQMWARSSYLGAVFNLTSADHLYVNVSELSL VNFEESQTFFGLYKL |
| 177 | Mouse CD178 | MQQPMNYPCPQIFWVDSSATSSWAPPGSVFPCPSCGPR GPDQRRPPPPPPPVSPLPPSQPLPLPPLTPLKKKDHN TNLWLPVVFFMVLVALVGMGLGMYQLFHLQKELAELRE FTNQSLKVSSFEKQIANPSTPSEKKEPRSVAHLTGNPH SRSIPLEWEDTYGTALISGVKYKKGGLVINETGLYFVY SKVYFRGQSCNNQPLNHKVYMRNSKYPEDLVLMEEKRL NYCTTGQIWAHSSYLGAVFNLTSADHLYVNISQLSLIN FEESKTFFGLYKL |
| 178 | Human GITRL | MTLHPSPITCEFLFSTALISPKMCLSHLENIVIPLSHS RTQGAQRSSWKLWLFCSIVMLLFLCSFSWLIFIFLQLE TAKEPCMAKFGPLPSKWQMASSEPPCVNKVSDWKLEIL QNGLYLIYGQVAPNANYNDVAPFEVRLYKNKDMIQTLT NKSKIQNVGGTYELHVGDTIDLIFNSEHQVLKNNTYWG IILLANPQFIS |
| 179 | Mouse GITRL | MEEMPLRESSPQRAERCKKSWLLCIVALLLMLLCSLGT LIYTSLKPTAIESCMVKFELSSSKWHMTSPKPHCVNTT SDGKLKILQSGTYLIYGQVIPVDKKYIKDNAPFVVQIY KKNDVLQTLMNDFQILPIGGVYELHAGDNIYLKFNSKD HIQKTNTYWGIILMPDLPFIS |
| 180 | Human LIGHT | MEESVVRPSVFVVDGQTDIPFTRLGRSHRRQSCSVARV GLGLLLLLMGAGLAVQGWFLLQLHWRLGEMVTRLPDGP AGSWEQLIQERRSHEVNPAAHLTGANSSLTGSGGPLLW ETQLGLAFLRGLSYHDGALVVTKAGYYYIYSKVQLGGV GCPLGLASTITHGLYKRTPRYPEELELLVSQQSPCGRA TSSSRVWWDSSFLGGVVHLEAGEKVVVRVLDERLVRLR DGTRSYFGAFMV |
| 181 | Mouse LIGHT | MESVVQPSVFVVDGQTDIPFRRLEQNHRRRRCGTVQVS LALVLLLGAGLATQGWFLLRLHQRLGDIVAHLPDGGKG SWEKLIQDQRSHQANPAAHLTGANASLIGIGGPLLWET RLGLAFLRGLTYHDGALVTMEPGYYYVYSKVQLSGVGC PQGLANGLPITHGLYKRTSRYPKELELLVSRRSPCGRA NSSRVWWDSSFLGGVVHLEAGEEVVVRVPGNRLVRPRD GTRSYFGAFMV |
| 182 | Human OX40L | MERVQPLEENVGNAARPRFERNKLLLVASVIQGLGLLL CFTYICLHFSALQVSHRYPRIQSIKVQFTEYKKEKGFI LTSQKEDEIMKVQNNSVIINCDGFYLISLKGYFSQEVN ISLHYQKDEEPLFQLKKVRSVNSLMVASLTYKDKVYLN VTTDNTSLDDFHVNGGELILIHQNPGEFCVL |
| 183 | Mouse OX40L | MEGEGVQPLDENLENGSRPRFKWKKTLRLVVSGIKGAG MLLCFIYVCLQLSSSPAKDPPIQRLRGAVTRCEDGQLF ISSYKNEYQTMEVQNNSVVIKCDGLYIIYLKGSFFQEV KIDLHFREDHNPISIPMLNDGRRIVFTVVASLAFKDKV YLTVNAPDTLCEHLQINDGELIVVQLTPGYCAPEGSYH STVNQVP |
| 184 | Human TALL-1 | MDDSTEREQSRLTSCLKKREEMKLKECVSILPRKESPS VRSSKDGKLLAATLLLALLSCCLTVVSFYQVAALQGDL ASLRAELQGHHAEKLPAGAGAPKAGLEEAPAVTAGLKI FEPPAPGEGNSSQNSRNKRAVQGPEETVTQDCLQLIAD SETPTIQKGSYTFVPWLLSFKRGSALEEKENKILVKET GYFFIYGQVLYTDKTYAMGHLIQRKKVHVFGDELSLVT LFRCIQNMPETLPNNSCYSAGIAKLEEGDELQLAIPRE NAQISLDGDVTFFGALKLL |
| 185 | Mouse TALL-1 | MAMAFCPKDQYWDSSRKSCVSCALTCSQRSQRTCTDFC KFINCRKEQGRYYDHLLGACVSCDSTCTQHPQQCAHFC EKRPRSQANLQPELGRPQAGEVEVRSDNSGRHQGSEHG PGLRLSSDQLTLYCTLGVCLCAIFCCFLVALASFLRRR GEPLPSQPAGPRGSQANSPHAHRPVTEACDEVTASPQP VETCSFCFPERSSPTQESAPRSLGIHGFAGTAAPQPCM RATVGGLGVLRASTGDARPAT |
| 186 | Human TRAIL | MAMMEVQGGPSLGQTCVLIVIFTVLLQSLCVAVTYVYF TNELKQMQDKYSKSGIACFLKEDDSYWDPNDEESMNSP CWQVKWQLRQLVRKMILRTSEETISTVQEKQQNISPLV |

| SEQ ID NO. | NAME | SEQUENCE |
|---|---|---|
| | | RERGPQRVAAHITGTRGRSNTLSSPNSKNEKALGRKIN SWESSRSGHSFLSNLHLRNGELVIHEKGFYYIYSQTYF RFQEEIKENTKNDKQMVQYIYKYTSYPDPILLMKSARN SCWSKDAEYGLYSIYQGGIFELKENDRIFVSVTNEHLI DMDHEASFFGAFLVG |
| 187 | Mouse TRAIL | MPSSGALKDLSFSQHFRMMVICIVLLQVLLQAVSVAVT YMYFTNEMKQLQDNYSKIGLACFSKTDEDFWDSTDGEI LNRPCLQVKRQLYQLIEEVTLRTFQDTISTVPEKQLST PPLPRGGRPQKVAAHITGITRRSNSALIPISKDGKTLG QKIESWESSRKGHSFLNHVLFRNGELVIEQEGLYYIYS QTYFRFQEAEDASKMVSKDKVRTKQLVQYIYKYTSYPD PIVLMKSARNSCWSRDAEYGLYSIYQGGLFELKKNDRI FVSVTNEHLMDLDQEASFFGAFLIN |
| 188 | Human TWEAK | MAARRSQRRRGRRGEPGTALLVPLALGLGLALACLGLL LAVVSLGSRASLSAQEPAQEELVAEEDQDPSELNPQTE ESQDPAPFLNRLVRPRRSAPKGRKTARRAIAAHYEVH PRPGQDGAQAGVDGTVSGWEEARINSSSPLRYNRQIGE FIVTRAGLYYLYCQVHFDEGKAVYLKLDLLVDGVLALR CLEEFSATAASSLGPQLRLCQVSGLLALRPGSSLRIRT LPWAHLKAAPFLTYFGLFQVH |
| 189 | Mouse TWEAK | MASAWPRSLPQILVLGFGLVLMRAAAGEQAPGTSPCSS GSSWSADLDKCMDCASCPARPHSDFCLGCAAAPPAHFR LLWPILGGALSLVLVLALVSSFLVWRRCRRREKFTTPI EETGGEGCPGVALIQ |
| 190 | Human TRANCE | MRRASRDYTKYLRGSEEMGGGPGAPHEGPLHAPPPPAP HQPPAASRSMFVALLGLGLGQVVCSVALFFYFRAQMDP NRISEDGTHCIYRILRLHENADFQDTTLESQDTKLIPD SCRRIKQAFQGAVQKELQHIVGSQHIRAEKAMVDGSWL DLAKRSKLEAQPFAHLTINATDIPSGSHKVSLSSWYHD RGWAKISNMTFSNGKLIVNQDGFYYLYANICFRHHETS GDLATEYLQLMVYVTKTSIKIPSSHTLMKGGSTKYWSG NSEFHFYSINVGGFFKLRSGEEISIEVSNPSLLDPDQD ATYFGAFKVRDID |
| 191 | Mouse TRANCE | MRRASRDYGKYLRSSEEMGSGPGVPHEGPLHPAPSAPA PAPPPAASRSMFLALLGLGLGQVVCSIALFLYFRAQMD PNRISEDSTHCFYRILRLHENADLQDSTLESEDTLPDS CRRMKQAFQGAVQKELQHIVGPQRFSGAPAMMEGSWLD VAQRGKPEAQPFAHLTINAASIPSGSHKVTLSSWYHDR GWAKISNMTLSNGKLRVNQDGFYYLYANICFRHHETSG SVPTDYLQLMVYVVKTSIKIPSSHNLMKGGSTKNWSGN SEFHFYSINVGGFFKLRAGEEISIQVSNPSLLDPDQDA TYFGAFKVQDID |
| 192 | Human TGF-beta1 | MPPSGLRLLLLLLPLLWLLVLTPGRPAAGLSTCKTIDM ELVKRKRIEAIRGQILSKLRLASPPSQGEVPPGPLPEA VLALYNSTRDRVAGESAEPEPEPEADYYAKEVTRVLMV ETHNEIYDKFKQSTHSIYMFFNTSELREAVPEPVLLSR AELRLLRLKLKVEQHVELYQKYSNNSWRYLSNRLLAPS DSPEWLSFDVTGVVRQWLSRGGEIEGFRLSAHCSCDSR DNTLQVDINGFTTGRRGDLATIHGMNRPFLLLMATPLE RAQHLQSSRHRRALDTNYCFSSTEKNCCVRQLYIDFRK DLGWKWIHEPKGYHANFCLGPCPYIWSLDTQYSKVLAL YNQHNPGASAAPCCVPQALEPLPIVYYVGRKPKVEQLS NMIVRSCKCS |
| 193 | Mouse TGF-beta1 | MPPSGLRLLPLLLPLPWLLVLTPGRPAAGLSTCKTIDM ELVKRKRIEAIRGQILSKLRLASPPSQGEVPPGPLPEA VLALYNSTRDRVAGESADPEPEPEADYYAKEVTRVLMV DRNNAIYEKTKDISHSIYMFFNTSDIREAVPEPPLLSR AELRLQRLKSSVEQHVELYQKYSNNSWRYLGNRLLTPT DTPEWLSFDVTGVVRQWLNQGDGIQGFRFSAHCSCDSK DNKLHVEINGISPKRRGDLGTIHDMNRPFLLLMATPLE RAQHLSSRHRRALDTNYCFSSTEKNCCVRQLYIDFRK DLGWKWIHEPKGYHANFCLGPCPYIWSLDTQYSKVLAL YNQHNPGASASPCCVPQALEPLPIVYYVGRKPKVEQLS NMIVRSCKCS |
| 194 | Human TGF-beta2 | MHYCVLSAFLILHLVTVALSLSTCSTLDMDQFMRKRIE AIRGQILSKLKLTSPPEDYPEPEEVPPEVISIYNSTRD LLQEKASRRAAACERERSDEEYYAKEVYKIDMPPFFPS ENAIPPTFYRPYFRIVRFDVSAMEKNASNLVKAEFRVF RLQNPKARVPEQRIELYQILKSKDLTSPTQRYIDSKVV |

-continued

| SEQ ID NO. | NAME | SEQUENCE |
|---|---|---|
| | | KTRAEGEWLSFDVTDAVHEWLHHKDRNLGFKISLHCPC CTFVPSNNYIIPNKSEELEARFAGIDGTSTYTSGDQKT IKSTRKKNSGKTPHLLLMLLPSYRLESQQTNRRKKRAL DAAYCFRNVQDNCCLRPLYIDFKRDLGWKWIHEPKGYN ANFCAGACPYLWSSDTQHSRVLSLYNTINPEASASPCC VSQDLEPLTILYYIGKTPKIEQLSNMIVKSCKCS |
| 195 | Mouse TGF-beta2 | MHYCVLSTFLLLHLVPVALSLSTCSTLDMDQFMRKRIE AIRGQILSKLKLTSPPEDYPEPDEVPPEVISIYNSTRD LLQEKASRRAAACERERSDEEYYAKEVYKIDMPSHLPS ENAIPPTFYRPYFRIVRFDVSTMEKNASNLVKAEFRVF RLQNPKARVAEQRIELYQILKSKDLTSPTQRYIDSKVV KTRAEGEWLSFDVTDAVQEWLHHKDRNLGFKISLHCPC CTFVPSNNYIIPNKSEELEARFAGIDGTSTYASGDQKT IKSTRKKTSGKTPHLLLMLLPSYRLESQQSSRRKKRAL DAAYCFRNVQDNCCLRPLYIDFKRDLGWKWIHEPKGYN ANFCAGACPYLWSSDTQHTKVLSLYNTINPEASASPCC VSQDLEPLTILYYIGNTPKIEQLSNMIVKSCKCS |
| 196 | Human TGF-beta3 | MKMHLQRALVVLALLNFATVSLSLSTCTTLDFGHIKKK RVEAIRGQILSKLRLTSPPEPTVMTHVPYQVLALYNST RELLEEMHGEREEGCTQENTESEYYAKEIHKFDMIQGL AEHNELAVCPKGITSKVFRFNVSSVEKNRTNLFRAEFR VLRVPNPSSKRNEQRIELFQILRPDEHIAKQRYIGGKN LPTRGTAEWLSFDVTDTVREWLLRRESNLGLEISIHCP CHTFQPNGDILENIHEVMEIKFKGVDNEDDHGRGDLGR LKKQKDHHNPHLILMMIPPHRLDNPGQGGQRKKRALDT NYCFRNLEENCCVRPLYIDFRQDLGWKWVHEPKGYYAN FCSGPCPYLRSADTTHSTVLGLYNTLNPEASASPCCVP QDLEPLTILYYVGRTPKVEQLSNMVVKSCKCS |
| 197 | Mouse TGF-beta3 | MHLQRALVVLALLNLATISLSLSTCTTLDFGHIKKKRV EAIRGQILSKLRLTSPPEPSVMTHVPYQVLALYNSTRE LLEEMHGEREEGCTQETSESEYYAKEIHKFDMIQGLAE HNELAVCPKGITSKVFRFNVSSVEKNGTNLFRAEFRVL RVPNPSSKRTEQRIELFQILRPDEHIAKQRYIGGKNLP TRGTAEWLSFDVTDTVREWLLRRESNLGLEISIHCPCH TFQPNGDILENVHEVMEIKFKGVDNEDDHGRGDLGRLK KQKDHHNPHLILMMIPPHRLDSPGQGSQRKKRALDTNY CFRNLEENCCVRPLYIDFRQDLGWKWVHEPKGYYANFC SGPCPYLRSADTTHSTVLGLYNTLNPEASASPCCVPQD LEPLTILYYVGRTPKVEQLSNMVVKSCKCS |
| 198 | Human EPO | MGVHECPAWLWLLLSLLSLPLGLPVLGAPPRLICDSRV LERYLLEAKEAENITTGCAEHCSLNENITVPDTKVNFY AWKRMEVGQQAVEVWQGLALLSEAVLRGQALLVNSSQP WEPLQLHVDKAVSGLRSLTTLLRALGAQKEAISPPDAA SAAPLRTITADTFRKLFRVYSNFLRGKLKLYTGEACRT GDR |
| 199 | Mouse EPO | MGVPERPTLLLLLSLLLIPLGLPVLCAPPRLICDSRVL ERYILEAKEAENVTMGCAEGPRLSENITVPDTKVNFYA WKRMEVEEQAIEVWQGLSLLSEAILQAQALLANSSQPP ETLQLHIDKAISGLRSLTSLLRVLGAQKELMSPPDTTP PAPLRTLTVDTFCKLFRVYANFLRGKLKLYTGEVCRRG DR |
| 200 | Human TPO | MELTELLLVVMLLLTARLTLSSPAPPACDLRVLSKLLR DSHVLHSRLSQCPEVHPLPTPVLLPAVDFSLGEWKTQM EETKAQDILGAVTLLLEGVMAARGQLGPTCLSSLLGQL SGQVRLLLGALQSLLGTQLPPQGRTTAHKDPNAIFLSF QHLLRGKVRFLMLVGGSTLCVRRAPPTTAVPSRTSLVL TLNELPNRTSGLLETNFTASARTTGSGLLKWQQGFRAK IPGLLNQTSRSLDQIPGYLNRIHELLNGTRGLFPGPSR RTLGAPDISSGTSDTGSLPPNLQPGYSPSPTHPPTGQY TLFPLPPTLPTPVVQLHPLLPDPSAPTPTPTSPLLNTS YTHSQNLSQEG |
| 201 | Mouse TPO | MELTDLLLAAMLLAVARLTLSSPVAPACDPRLLNKLLR DSHLLHSRLSQCPDVDPLSIPVLLPAVDFSLGEWKTQT EQSKAQDILGAVSLLLEGVMAARGQLEPSCLSSLLGQL SGQVRLLLGALQGLLGTQLPLQGRTTAHKDPNALFLSL QQLLRGKVRFLLLVEGPTLCVRRTLPTTAVPSSTSQLL TLNKFPNRTSGLLETNFSVTARTAGPGLLSRLQGFRVK ITPGQLNQTSRSPVQISGYLNRTHGPVNGTHGLFAGTS |

-continued

| SEQ ID NO. | NAME | SEQUENCE |
|---|---|---|
| | | LQTLEASDISPGAFNKGSLAFNLQGGLPPSPSLAPDGH TPFPPSPALPTTHGSPPQLHPLFPDPSTTMPNSTAPHP VTMYPHPRNLSQET |
| 202 | Human FLT-3L | MTVLAPAWSPTTYLLLLLLLSSGLSGTQDCSFQHSPIS SDFAVKIRELSDYLLQDYPVTVASNLQDEELCGGLWRL VLAQRWMERLKTVAGSKMQGLLERVNTEIHFVTKCAFQ PPPSCLRFVQTNISRLLQETSEQLVALKPWITRQNFSR CLELQCQPDSSTLPPPWSPRPLEATAPTAPQPPLLLLL LLPVGLLLLAAAWCLHWQRTRRRTPRPGEQVPPVPSPQ DLLLVEH |
| 203 | Mouse FLT-3L | MTVLAPAWSPNSSLLLLLLLLSPCLRGTPDCYFSHSPI SSNFKVKFRELTDHLLKDYPVTVAVNLQDEKHCKALWS LFLAQRWIEQLKTVAGSKMQTLLEDVNTEIHFVTSCTF QPLPECLRFVQTNISHLLKDTCTQLLALKPCIGKACQN FSRCLEVQCQPDSSTLLPPRSPIALEATELPEPRPRQL LLLLLLLLPLTLVLLAAAWGLRWQRARRRGELHPGVPL PSHIP |
| 204 | Human SCF | MKKTQTWILTCIYLQLLLFNPLVKTEGICRNRVTNNVK DVTKLVANLPKDYMITLKYVPGMDVLPSHCWISEMVVQ LSDSLTDLLDKFSNISEGLSNYSIIDKLVNIVDDLVEC VKENSSKDLKKSFKSPEPRLFTPEEFFRIFNRSIDAFK DFVVASETSDCVVSSTLSPEKDSRVSVTKPFMLPPVAA SSLRNDSSSSNRKAKNPPGDSSLHWAAMALPALFSLII GFAFGALYWKKRQPSLTRAVENIQINEEDNEISMLQEK EREFQEV |
| 205 | Mouse SCF | MKKTQTWIITCIYLQLLLFNPLVKTKEICGNPVTDNVK DITKLVANLPNDYMITLNYVAGMDVLPSHCWLRDMVIQ LSLSLTTLLDKFSNISEGLSNYSIIDKLGKIVDDLVLC MEENAPKNIKESPKRPETRSFTPEEFFSIFNRSIDAFK DFMVASDTSDCVLSSTLGPEKDSRVSVTKPFMLPPVAA SSLRNDSSSSNRKAAKAPEDSGLQWTAMALPALISLVI GFAFGALYWKKKQSSLTRAVENIQINEEDNEISMLQQK EREFQEV |
| 206 | Human M-CSF | MTAPGAAGRCPPTTWLGSLLLLVCLLASRSITEEVSEY CSHMIGSGHLQSLQRLIDSQMETSCQITFEFVDQEQLK DPVCYLKKAFLLVQDIMEDTMRFRDNTPNAIAIVQLQE LSLRLKSCFTKDYEEHDKACVRTFYETPLQLLEKVKNV FNETKNLLDKDWNIFSKNCNNSFAECSSQDVVTKPDCN CLYPKAIPSSDPASVSPHQPLAPSMAPVAGLTWEDSEG TEGSSLLPGEQPLHTVDPGSAKQRPPRSTCQSFEPPET PVVKDSTIGGSPQPRPSVGAFNPGMEDILDSAMGTNWV PEEASGEASEIPVPQGTELSPSRPGGGSMQTEPARPSN FLSASSPLPASAKGQQPADVTGTALPRVGPVRPTGQDW NHTPQKTDHPSALLRDPPEPGSPRISSLRPQGLSNPST LSAQPQLSRSHSSGSVLPLGELEGRRSTRDRRSPAEPE GGPASEGAARPLPRFNSVPLTDTGHERQSEGSFSPQLQ ESVFHLLVPSVILVLLAVGGLLFYRWRRRSHQEPQRAD SPLEQPEGSPLTQDDRQVELPV |
| 207 | Mouse M-CSF | MTARGAAGRCPSSTWLGSRLLLVCLLMSRSIAKEVSEH CSHMIGNGHLKVLQQLIDSQMETSCQIAFEFVDQEQLD DPVCYLKKAFFLVQDIIDETMRFKDNTPNANATERLQE LSNNLNSCFTKDYEEQNKACVRTFHETPLQLLEKIKNF FNETKNLLEKDWNIFTKNCNNSFAKCSSRDVVTKPDCN CLYPKATPSSDPASASPHQPPAPSMAPLAGLAWDDSQR TEGSSLLPSELPLRIEDPGSAKQRPPRSTCQTLESTEQ PNHGDRLTEDSQPHPSAGGPVPGVEDILESSLGTNWVL EEASGEASEGFLTQEAKFSPSTPVGGSIQAETDRPRAL SASPFPKSTEDQKPVDITDRPLTEVNPMRPIGQTQNNT PEKTDGTSTLREDHQEPGSPHIATPNPQRVSNSATPVA QLLLPKSHSWGIVLPLGELEGKRSTRDRRSPAELEGGS ASEGAARPVARFNSIPLTDTGHVEQHEGSSDPQIPESV FHLLVPGIILVLLTVGGLLFYKWKWRSHRDPQTLDSSV GRPEDSSLTQDEDRQVELPV |
| 208 | Human MSP | MGWLPLLLLLTQCLGVPGQRSPLNDFQVLRGTELQHLL HAVVPGPWQEDVADAEECAGRCGPLMDCRAFHYNVSSH GCQLLPWTQHSPHTRLRRSGRCDLFQKKDYVRTCIMNN GVGYRGTMATTVGGLPCQAWSHKFPNDHKYTPTLRNGL EENFCRNPDGDPGGPWCYTTDPAVRFQSCGIKSCREAA CVWCNGEEYRGAVDRTESGRECQRWDLQHPHQHPFEPG KFLDQGLDDNYCRNPDGSERPWCYTTDPQIEREFCDLP |

-continued

| SEQ ID NO. | NAME | SEQUENCE |
|---|---|---|
| | | RCGSEAQPRQEATTVSCFRGKGEGYRGTANTTTAGVPC<br>QRWDAQIPHQHRFTPEKYACKDLRENFCRNPDGSEAPW<br>CFTLRPGMRAAFCYQIRRCTDDVRPQDCYHGAGEQYRG<br>TVSKTRKGVQCQRWSAETPHKPQFTFTSEPHAQLEENF<br>CRNPDGDSHGPWCYTMDPRTPFDYCALRRCADDQPPSI<br>LDPPDQVQFEKCGKRVDRLDQRRSKLRVVGGHPGNSPW<br>TVSLRNRQGQHFCGGSLVKEQWILTARQCFSSCHMPLT<br>GYEVWLGTLFQNPQHGEPSLQRVPVAKMVCGPSGSQLV<br>LLKLERSVTLNQRVALICLPPEWYVVPPGTKCEIAGWG<br>ETKGTGNDTVLNVALLNVISNQECNIKHRGRVRESEMC<br>TEGLLAPVGACEGDYGGPLACFTHNCWVLEGIIIPNRV<br>CARSRWPAVFTRVSVFVDWIHKVMRLG |
| 209 | Mouse MSP | MGLPLPLLQSSLLLMLLLRLSAASTNLNWQCPRIPYAA<br>SRDFSVKYVVPSFSAGGRVQATAAYEDSTNSAVFVATR<br>NHLHVLGPDLQFIENLTTGPIGNPGCQTCASCGPGPHG<br>PPKDTDTLVLVMEPGLPALVSCGSTLQGRCFLHELEPR<br>GKALHLAAPACLFSANNNKPEACTDCVASPLGTRVTVV<br>EQGHASYFYVASSLDPELAASFSPRSVSIRRLKSDTSG<br>FQPGFPSLSVLPKYLASYLIKYVYSFHSGDFVYFLTVQ<br>PISVTSPPSALHTRLVRLNAVEPEIGDYRELVLDCHFA<br>PKRRRRGAPEGTQPYPVLQAAHSAPVDAKLAVELSISE<br>GQEVLFGVFVTVKDGGSGMGPNSVVCAFPIYHLNILIE<br>EGVEYCCHSSNSSSLLSRGLDFFQTPSFCPNPPGGEAS<br>GPSSRCHYFPLMVHASFTRVDLFNGLLGSVKVTALHVT<br>RLGNVTVAHMGTVDGRVLQVEIARSLNYLLYVSNFSLG<br>SSGQPVHRDVSRLGNDLLFASGDQVFKVPIQGPGCREI<br>FLTCWRCLRAQRFMGCGWCGDRCDRQKECPGSWQQDHC<br>PPEISEFYPHSGPLRGTTRLTLCGSNFYLRPDDVVPEG<br>THQITVGQSPCRLLPKDSSSPRPGSLKEFIQELECELE<br>PLVTQAVGTTNISLVITNMPAGKHFRVEGISVQEGFSF<br>VEPVLTSIKPDFGPRAGGTYLTLEGQSLSVGTSRAVLV<br>NGTQCRLEQVNEEQILCVTPPGAGTARVPLHLQIGGAE<br>VPGSWTFHYKEDPIVLDISPKCGYSGSHIMIHQHLTS<br>AWHFTLSFHDGQSTVESRCAGQFVEQQQRRCRLPEYVV<br>RNPQGWATGNLSVWGDGAAGFTLPGFRFLPPPSPLRAG<br>LVELKPEEHSVKVEYVGLGAVADCVTVNMTVGGEVCQH<br>ELRGDVVICPLPPSLQLGKDGVPLQVCDGGCHILSQV<br>VRSSPGRASQRILLIALLVLILLVAVLAVALIFNSRRR<br>KKQLGAHSLSPTTLSDINDTASGAPNHEESSESRDGTS<br>VPLLRTESIRLQDLDRMLLAEVKDVLIPHEQVVIHTDQ<br>VIGKGHFGVVYHGEYTDGAQNQTHCAIKSLSRITEVQE<br>VEAFLREGLLMRGLHHPNILALIGIMLPPEGLPRVLLP<br>YMRHGDLLHFIRSPQRNPTVKDLVSFGLQVACGMEYLA<br>EQKFVHRDLAARNCMLDESFTVKVADFGLARGVLDKEY<br>YSVRQHRHARLPVKWMALESLQTYRFTTKSDVWSFGVL<br>LWELLTRGAPPYPHIDPFDLSHFLAQGRRLPQPEYCPD<br>SLYHVMLRCWEADPAARPTFRALVLEVKQVVASLLGDH<br>YVQLTAAYVNVGPRAVDDGSVPPEQVQPSPQHCRSTSK<br>PRPLSEPPLPT |
| 210 | Linker | GSSGGSGGSGG |
| 211 | Linker | GGGSGGGS |
| 212 | Linker | GGGSGGGSGGGS |
| 213 | Linker | GGGGSGGGGSGGGGS |
| 214 | Linker | GGGGSGGGGSGGGGSGGGGSGGGGS |
| 215 | Linker | GGGGSGGGGS |
| 216 | Linker | (GGGGS)n |
| 217 | Linker | GGGGSGS |
| 218 | Linker | GGGGSGGGGSGGGGSGS |
| 219 | Linker | GGSLDPKGGGGS |
| 220 | Linker | PKSCDKTHTCPPCPAPELLG |
| 221 | Linker | SKYGPPCPPCPAPEFLG |
| 222 | Linker | GKSSGSGSESKS |

-continued

| SEQ ID NO. | NAME | SEQUENCE |
|---|---|---|
| 223 | Linker | GSTSGSGKSSEGKG |
| 224 | Linker | GSTSGSGKSSEGSGSTKG |
| 225 | Linker | GSTSGSGKPGSGEGSTKG |
| 226 | Linker | GSTSGSGKPGSSEGST |
| 227 | Linker | (GSGGS)n |
| 228 | Linker | (GGGS)n |
| 229 | Linker | GGSG |
| 230 | Linker | GGSGG |
| 231 | Linker | GSGSG |
| 232 | Linker | GSGGG |
| 233 | Linker | GGGSG |
| 234 | Linker | GSSSG |
| 235 to 244 | (Intentionally Omitted) | (Intentionally Omitted) |
| 245 | Linker | GPQGTAGQ |
| 246 to 249 | (Intentionally Omitted) | (Intentionally Omitted) |
| 250 | Linker | YGAGLGW |
| 251 to 262 | (Intentionally Omitted) | (Intentionally Omitted) |
| 263 | CM | APRSALAHGLF |
| 264 | CM | AQNLLGMY |
| 265 | CM | LSGRSDNHGGAVGLLAPP |
| 266 | CM | VHMPLGFLGPGGLSGRSDNH |
| 267 | CM | LSGRSDNHGGVHMPLGFLGP |
| 268 | CM | LSGRSDNHGGSGGSISSGLLSS |
| 269 | CM | ISSGLLSSGGSGGSLSGRSGNH |
| 270 | CM | LSGRSDNHGGSGGSQNQALRMA |
| 271 | CM | QNQALRMAGGSGGSLSGRSDNH |
| 272 | CM | LSGRSGNHGGSGGSQNQALRMA |
| 273 | CM | QNQALRMAGGSGGSLSGRSGNH |
| 274 | CM | ISSGLLSGRSGNH |
| 275 | CM | AVGLLAPPGGTSTSGRSANPRG |
| 276 | CM | TSTSGRSANPRGGAVGLLAPP |
| 277 | CM | VHMPLGFLGPGGTSTSGRSANPRG |
| 278 | CM | TSTSGRSANPRGGVHMPLGFLGP |
| 279 | CM | LSGRSGNHGGSGGSISSGLLSS |
| 280 | Cleavable Sequence | PRFKIIGG |
| 281 | Cleavable Sequence | PRFRIIGG |
| 282 | Cleavable Sequence | SSRHRRALD |

-continued

| SEQ ID NO. | NAME | SEQUENCE |
|---|---|---|
| 283 | Cleavable Sequence | RKSSIIIRMRDVVL |
| 284 | Cleavable Sequence | SSSFDKGKYKKGDDA |
| 285 | Cleavable Sequence | SSSFDKGKYKRGDDA |
| 286 | Cleavable Sequence | IEGR |
| 287 | Cleavable Sequence | IDGR |
| 288 | Cleavable Sequence | GGSIDGR |
| 289 | Cleavable Sequence | PLGLWA |
| 290 | Cleavable Sequence | GPQGIAGQ |
| 291 | Cleavable Sequence | GPQGLLGA |
| 292 | Cleavable Sequence | GIAGQ |
| 293 | Cleavable Sequence | GPLGIAGI |
| 294 | Cleavable Sequence | GPEGLRVG |
| 295 | Cleavable Sequence | YGAGLGVV |
| 296 | Cleavable Sequence | AGLGVVER |
| 297 | Cleavable Sequence | AGLGISST |
| 298 | Cleavable Sequence | EPQALAMS |
| 299 | Cleavable Sequence | QALAMSAI |
| 300 | Cleavable Sequence | AAYHLVSQ |
| 301 | Cleavable Sequence | MDAFLESS |
| 302 | Cleavable Sequence | ESLPVVAV |
| 303 | Cleavable Sequence | SAPAVESE |
| 304 | Cleavable Sequence | DVAQFVLT |
| 305 | Cleavable Sequence | VAQFVLT |
| 306 | Cleavable Sequence | VAQFVLTE |
| 307 | Cleavable Sequence | AQFVLTEG |
| 308 | Cleavable Sequence | PVQPIGPQ |
| 309 | IFN-α2b-1204dL-hIgG4 | METDTLLLWVLLLWVPGSTGCDLPQTHSLGSRRTLMLL AQMRRISLFSCLKDRHDFGFPQEEFGNQFQKAETIPVL HEMIQQIFNLFSTKDSSAAWDETLLDKFYTELYQQLND LEACVIQGVGVTETPLMKEDSILAVRKYFQRITLYLKE KKYSPCAWEVVRAEIMRSFSLSTNLQESLRSKESGRSD NIGGGSESKYGPPCPPCPAPEFLGGPSVFLFPPKPKDT LMISRTPEVTCVVVDVSQEDPEVQFNWYVDGVEVHNAK TKPREEQFNSTYRVVSVLTVLHQDWLNGKEYKCKVSNK GLPSSIEKTISKAKGQPREPQVYTLPPSQEEMTKNQVS LTCLVKGFYPSDIAVEWESNGQPENNYKTTPPVLDSDG SFFLYSRLTVDKSRWQQGNVFSCSVMHEALHNHYTQKS LSLS |
| 310 | IFN-α-1204dL-hIgG4 (polynucleotide) | ATGGAAACCGACACACTGCTGCTGTGGGTGCTGCTTTT GTGGGTGCCAGGATCCACAGGCTGTGATCTGCCTCAAA CGCATTCATTGGGGTCCAGGCGCACGCTTATGTTGCTT GCACAGATGAGGAGAATATCACTTTTCTCTTGCTTGAA GGACCGCCACGATTTTGGCTTTCCGCAGGAAGAGTTCG GTAACCAGTTCCAAAAGGCAGAGACAATCCCCGTTTTG CATGAGATGATCCAACAGATCTTTAACCTGTTTTCAAC CAAGGATAGCAGCGCAGCGTGGGATGAGACACTGCTTG ACAAGTTTTACACCGAGCTCTATCAGCAACTTAATGAT CTCGAAGCCTGCGTAATTCAAGGAGTAGGCGTTACAGA GACACCTTTGATGAAGGAGGATTCCATCCTTGCAGTAA |

-continued

| SEQ ID NO. | NAME | SEQUENCE |
|---|---|---|
| | | GAAAATACTTCCAGAGGATCACCCTCTACCTCAAAGAA
AAGAAATACTCCCCATGCGCGTGGGAAGTAGTGCGAGC
TGAAATAATGCGGAGCTTTTCTTTGTCAACTAATCTCC
AAGAATCTCTGAGAAGCAAGGAGTCAGGTAGGTCTGAT
AATATCGGGGGAGGTTCTGAATCTAAGTACGGCCCTCC
TTGTCCTCCATGTCCTGCTCCAGAGTTTCTCGGAGGCC
CCTCCGTGTTCCTGTTTCCTCCAAAGCCTAAGGACACC
CTGATGATCAGCAGAACCCCTGAAGTGACCTGCGTGGT
GGTCGACGTTTCACAAGAGGACCCCGAGGTGCAGTTCA
ATTGGTACGTGGACGGCGTGGAAGTGCACAACGCCAAG
ACCAAGCCTAGAGAGGAACAGTTCAACAGCACCTACAG
AGTGGTGTCCGTGCTGACCGTGCTGCACCAGGATTGGC
TGAACGGCAAAGAGTACAAGTGCAAGGTGTCCAACAAG
GGCCTGCCTAGCAGCATCGAGAAAACCATCAGCAAGGC
CAAGGGCCAGCCAAGGGAACCCCAGGTTTACACACTGC
CACCTAGCCAAGAGGAAATGACCAAGAACCAGGTGTCC
CTGACCTGCCTGGTCAAGGGCTTTTACCCCTCCGATAT
CGCCGTGGAATGGGAGAGCAATGGCCAGCCTGAGAACA
ACTACAAGACCACACCTCCTGTGCTGGACAGCGACGGC
TCATTCTTCCTGTACAGCAGACTGACCGTGGACAAGAG
CAGATGGCAGCAGGGCAACGTGTTCAGCTGCAGCGTGA
TGCACGAGGCCCTGCACAACCACTACACCCAGAAGTCT
CTGAGCCTGAGCTGA |
| 311 | IFN-α2b-1490DNI-hIgG4 | METDTLLLWVLLLWVPGSTGCDLPQTHSLGSRRTLMLH
EMIQQIFNLFSTKDSSAAWDETLLDKFYTELYQQLNDL
EACVIQGVGVTETPLMKEDSILAVRKYFQRITLYLKEK
KYSPCAWEVVRAEIMRSFSLSTNLQESLRSKEISSGLL
SGRSDNIGGGSESKYGPPCPPCPAPEFLGGPSVFLFPP
KPKDTLMISRTPEVTCVVVDVSQEDPEVQFNWYVDGVE
VHNAKTKPREEQFNSTYRVVSVLTVLHQDWLNGKEYKC
KVSNKGLPSSIEKTISKAKGQPREPQVYTLPPSQEEMT
KNQVSLTCLVKGFYPSDIAVEWESNGQPENNYKTTPPV
LDSDGSFFLYSRLTVDKSRWQQGNVFSCSVMHEALHNH
YTQKSLSLS |
| 312 | IFN-α2b-1490DNI-(polynucleotide) | ATGGAAACCGACACACTGCTGCTGTGGGTGCTGCTTTT
GTGGGTGCCAGGATCCACAGGCTGTGATCTGCCTCAAA
CGCATTCATTGGGTCCAGGCGCACGCTTATGTTGCTT
GCACAGATGAGGAGAATATCACTTTTTCTCTTGCTTGAA
GGACCGCCACGATTTTGGCTTTCCGCAGGAAGAGTTCG
GTAACCAGTTCCAAAAGGCAGAGACAATCCCCGTTTTG
CATGAGATGATCCAACAGATCTTTAACCTGTTTTCAAC
CAAGGATAGCAGCGCAGCGTGGGATGAGACACTGCTTG
ACAAGTTTTACACCGAGCTCTATCAGCAACTTAATGAT
CTCGAAGCCTGCGTAATTCAAGGAGTAGGCGTTACAGA
GACACCTTTGATGAAGGAGGATTCCATCCTTGCAGTAA
GAAAATACTTCCAGAGGATCACCCTCTACCTCAAAGAA
AAGAAATACTCCCCATGCGCGTGGGAAGTAGTGCGAGC
TGAAATAATGCGGAGCTTTTCTTTGTCAACTAATCTCC
AAGAATCTCTGAGAAGCAAGGAGATTAGTTCTGGCCTG
CTGTCAGGTAGGTCTGATAATATCGGGGGAGGTTCTGA
ATCTAAGTACGGCCCTCCTTGTCCTCCATGTCCTGCTC
CAGAGTTTCTCGGAGGCCCCTCCGTGTTCCTGTTTCCT
CCAAAGCCTAAGGACACCCTGATGATCAGCAGAACCCC
TGAAGTGACCTGCGTGGTGGTCGACGTTTCACAAGAGG
ACCCCGAGGTGCAGTTCAATTGGTACGTGGACGGCGTG
GAAGTGCACAACGCCAAGACCAAGCCTAGAGAGGAACA
GTTCAACAGCACCTACAGAGTGGTGTCCGTGCTGACCG
TGCTGCACCAGGATTGGCTGAACGGCAAAGAGTACAAG
TGCAAGGTGTCCAACAAGGGCCTGCCTAGCAGCATCGA
GAAAACCATCAGCAAGGCCAAGGGCCAGCCAAGGGAAC
CCCAGGTTTACACACTGCCACCTAGCCAAGAGGAAATG
ACCAAGAACCAGGTGTCCCTGACCTGCCTGGTCAAGGG
CTTTTACCCCTCCGATATCGCCGTGGAATGGGAGAGCA
ATGGCCAGCCTGAGAACAACTACAAGACCACACCTCCT
GTGCTGGACAGCGACGGCTCATTCTTCCTGTACAGCAG
ACTGACCGTGGACAAGAGCAGATGGCAGCAGGGCAACG
TGTTCAGCTGCAGCGTGATGCACGAGGCCCTGCACAAC
CACTACACCCAGAAGTCTCTGAGCCTGAGCTGA |
| 313 | ProC440 without signal sequence | CDLPQTHSLGSRRTLMLLAQMRRISLFSCLKDRHINGF
PQEEFGNQFQKAETIPVLHEMIQQIFNLFSTKDSSAAW
DETLLDKFYTELYQQLNDLEACVIQGVGVTETPLMKED
SILAVRKYFQRITLYLKEKKYSPCAWEVVRAEIMRSFS
LSTNLQESLRSKESGRSDNICPPCPAPEFLGGPSVFLF
PPKPKDTLMISRTPEVTCVVVDVSQEDPEVQFNWYVDG |

-continued

| SEQ ID NO. | NAME | SEQUENCE |
|---|---|---|
| | | VEVHNAKTKPREEQFNSTYRVVSVLTVLHQDWLNGKEY KCKVSNKGLPSSIEKTISKAKGQPREPQVYTLPPSQEE MTKNQVSLTCLVKGFYPSDIAVEWESNGQPENNYKTTP PVLDSDGSFFLYSRLTVDKSRWQQGNVFSCSVMHEALH NHYTQKSLSLS |
| 314 | PROC657 first monomer (knob mutation) without signal sequence | CDLPQTHSLGSRRTLMLLAQMRRISLFSCLKDRHINGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKESGRSDNICPPCPAPEFEGGPSVFLF PPKPKDTLMISRTPEVTCVVVDVSQEDPEVQFNWYVDG VEVHNAKTKPREEQFNSTYRVVSVLTVLHQDWLNGKEY KCKVSNKGLPSSIEKTISKAKGQPREPQVYTLPPCQEE MTKNQVSLWCLVKGFYPSDIAVEWESNGQPENNYKTTP PVLDSDGSFFLYSRLTVDKSRWQEGNVFSCSVMHEALH NHYTQKSLSLSLG |
| 315 | human IgG Fc with a knob mutation | CPPCPAPEFEGGPSVFLFPPKPKDTLMISRTPEVTCVV VDVSQEDPEVQFNWYVDGVEVHNAKTKPREEQFNSTYR VVSVLTVLHQDWLNGKEYKCKVSNKGLPSSIEKTISKA KGQPREPQVYTLPPCQEEMTKNQVSLWCLVKGFYPSDI AVEWESNGQPENNYKTTPPVLDSDGSFFLYSRLTVDKS RWQEGNVFSCSVMHEALHNHYTQKSLSLSLG |
| 316 | human IgG Fc with a hole mutation | CPPCPAPEFEGGPSVFLFPPKPKDTLMISRTPEVTCVV VDVSQEDPEVQFNWYVDGVEVHNAKTKPREEQFNSTYR VVSVLTVLHQDWLNGKEYKCKVSNKGLPSSIEKTISKA KGQPREPQVCTLPPSQEEMTKNQVSLSCAVKGFYPSDI AVEWESNGQPENNYKTTPPVLDSDGSFFLVSRLTVDKS RWQEGNVFSCSVMHEALHNRFTQKSLSLSLG |
| 317 | stub moiety | SDNI |
| 318 | Linker | GSSGGS |
| 319 | Linker | ESKY |
| 320 | ProC286 without signal sequence | ESKYGPPCPPCPAPEFLGGPSVFLFPPKPKDTLMISRT PEVTCVVVDVSQEDPEVQFNWYVDGVEVHNAKTKPREE QFNSTYRVVSVLTVLHQDWLNGKEYKCKVSNKGLPSSI EKTISKAKGQPREPQVYTLPPSQEEMTKNQVSLTCLVK GFYPSDIAVEWESNGQPENNYKTTPPVLDSDGSFFLYS RLTVDKSRWQQGNVFSCSVMHEALHNHYTQKSLSLSSG GGGSGRSDNIGGGSCDLPQTHSLGSRRTLMLLAQMRRI SLFSCLKDRHDFGFPQEEFGNQFQKAETIPVLHEMIQQ IFNLFSTKDSSAAWDETLLDKFYTELYQQLNDLEACVI QGVGVTETPLMKEDSILAVRKYFQRITLYLKEKKYSPC AWEVVRAEIMRSFSLSTNLQESLRSKE |
| 321 | Linker | SGGG |
| 322 | PROC657 second monomer (hole mutation) without signal sequence | SDNICPPCPAPEFEGGPSVFLFPPKPKDTLMISRTPEV TCVVVDVSQEDPEVQFNWYVDGVEVHNAKTKPREEQFN STYRVVSVLTVLHQDWLNGKEYKCKVSNKGLPSSIEKT ISKAKGQPREPQVCTLPPSQEEMTKNQVSLSCAVKGFY PSDIAVEWESNGQPENNYKTTPPVLDSDGSFFLVSRLT VDKSRWQEGNVFSCSVMHEALHNRFTQKSLSLSLG |
| 323 | PRO859 sequence without signal sequence | CDLPQTHSLGSRRTLMLLAQMRKISLFSCLKDRHDFGF PQEEFGNQFQKAETIPVLHEMIQQIFNLFTTKDSSAAW DEDLLDKFCTELYQQLNDLEACVMQEERVGETPLMNVD SILAVKKYFRRITLYLTEKKYSPCAWEVVRAEIMRSLS LSTNLQERLRRKELSGRSDNICPPCPAPEFLGGPSVFL FPPKPKDTLMISRTPEVTCVVVDVSQEDPEVQFNWYVD GVEVHNAKTKPREEQFNSTYRVVSVLTVLHQDWLNGKE YKCKVSNKGLPSSIEKTISKAKGQPREPQVYTLPPSQE EMTKNQVSLTCLVKGFYPSDIAVEWESNGQPENNYKTT PPVLDSDGSFFLYSRLTVDKSRWQQGNVFSCSVMHEAL HNHYTQKSLSLS |
| 324 | Universal IFN-alpha A/D sequence | CDLPQTHSLGSRRTLMLLAQMRKISLFSCLKDRHDFGF PQEEFGNQFQKAETIPVLHEMIQQIFNLFTTKDSSAAW DEDLLDKFCTELYQQLNDLEACVMQEERVGETPLMNVD SILAVKKYFRRITLYLTEKKYSPCAWEVVRAEIMRSLS LSTNLQERLRRKE |

-continued

| SEQ ID NO. | NAME | SEQUENCE |
|---|---|---|
| 325 | Interferon beta, Chain A, human (1AU1) | MSYNLLGFLQRSSNFQCQKLLWQLNGRLEYCLKDRMNF DIPEEIKQLQQFQKEDAALTIYEMLQNIFAIFRQDSSS TGWNETIVENLLANVYHQINHLKTVLEEKLEKEDFTRG KLMSSLHLKRYYGRILHYLKAKEYSHCAWTIVRVEILR NFYFINRLTGYLRN |
| 326 | IFNB_CHICK Q90873.1 | MTANHQSPGMHSILLLLLLPALTTTFSCNHLRHQDANF SWKSLQLLQNTAPPPPQPCPQQDVTFPFPETLLKSKDK KQAAITTLRILQHLFNMLSSPHTPKHWIDRTRHSLLNQ IQHYIFIFILEQCFVNQGTRSQRRGPRNAHLSINKYFR SIHNFLQHNNYSACTWDHVRLQARDCFRHVDTLIQWMK SRAPLTASSKRLNTQ |
| 327 | IFNA3_CANLF O97945.1 | MALPCSFSVALVLLSCHSLCCLACHLPDTHSLRNWRVL TLLGQMRRLSASSCDHYTTDFAFPKELFDGQRLQEAQA LSVVHVMTQKVFHLFCTNTSSAPWNMTLLEELCSGLSE QLDDLDACPLQEAGLAETPLMHEDSTLRTYFQRISLYL QDRNHSPCAWEMVRAEIGRSFFSLTILQERVRRRK |
| 328 | IFN_ANAPL P51526.1 | MPGPSAPPPPAIYSALALLLLLTPPANAFSCSPLRLHD SAFAWDSLQLLRNMAPSPTQPCPQQHAPCSFPDTLLDT NDTQQAAHTALHLLQHLFDTLSSPSTPAHWLHTARHDL LNQLQHHIHHLERCFPADAARLHRRGPRNLHLSINKYF GCIQHFLQNHTYSPCAWDHVRLEAHACFQRIHRLTRTM R |
| 329 | IFNAH_BOVIN P49878.1 | MAPAWSFLLALLLLSCNAICSLGCHLPHTHSLPNRRVL TLLRQLRRVSPSSCLQDRNDFAFPQEALGGSQLKAQA ISVLHEVTQHTFQLFSTEGSAAAWDESLLDKLRAALDQ QLTDLQACLRQEEGLRGAPLLKEDASLAVRKYFHRLTL YLREKRHNPCAWEVVRAEVMRAFSSSTNLQERFRRKD |
| 330 | IFNA1_CHICK P42165.1 | MAVPASPQHPRGYGILLLTLLLKALATTASACNHLRPQ DATFSHDSLQLLRDMAPTLPQLCPQHNASCSFNDTILD TSNTRQADKTTHDILQHLFKILSSPSTPAHWNDSQRQS LLNRIHRYTQHLEQCLDSSDTRSRTRWPRNLHLTIKKH FSCLHTFLQDNDYSACAWEHVRLQARAWFLHIHNLTGN TRT |
| 331 | IFNA_FELCA P35849.1 | MALPSSFLVALVALGCNSVCSLGCDLPQTHGLLNRRAL TLLGQMRRLPASSCQKDRNDFAFPQDVFGGDQSHKAQA LSVVHVTNQKIFHFFCTEASSSAAWNTTLLEEFCTGLD RQLTRLEACVLQEVEEGEAPLTNEDIHPEDSILRNYFQ RLSLYLQEKKYSPCAWEIVRAEIMRSLYYSSTALQKRL RSEK |
| 332 | interferon-beta-1 [Sus scrofa] AAA31056.1 | MANKCILQIALLMCFSTTALSMSYDVLRYQQRSSNLAC QKLLGQLPGTPQYCLEDRIVINFEVPEEIMQPPQFQKE DAVLIIHEMLQQIFGILRRNFSSTGWNETVIKTILVEL DGQMDDLETILEEIMEEENFPRGDMTILHLKKYYLSIL QYLKSKEYRSCAWTVVQVEILRNFSFLNRLTDYLRN |
| 333 | IFNB2_BOVIN P01576.1 | MTHRCLLQMVLLLCFSTTALSRSYSLLRFQQRRSLALC QKLLRQLPSTPQHCLEARMDFQMPEEMKQAQQFQKEDA ILVIYEMLQQIFNILTRDFSSTGWSETIIEDLLEELYE QMNHLEPIQKEIMQKQNSTMGDTTVLHLRKYYFNLVQY LKSKEYNRCAWTVVRVQILRNFSFLTRLTGYLRE |
| 334 | A Chain A, INTERFERON-ALPHA 2B 1RH2 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMNED SILAVRKYFQRITLYLKEKKYSPCAWEVVRAEIIVIRS FSLSTNLQESLRSKE |
| 335 | Linker | SGGGG |
| 336 | ProC288 without signal sequence | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIIVIRS FSLSTNLQESLRSKESGGGGSGRSDNICPPCPAPEFLG GPSVFLFPPKPKDTLMISRTPEVTCVVVDVSQEDPEVQ FNWYVDGVEVHNAKTKPREEQFNSTYRVVSVLTVLHQD WLNGKEYKCKVSNKGLPSSIEKTISKAKGQPREPQVYT LPPSQEEMTKNQVSLTCLVKGFYPSDIAVEWESNGQPE NNYKTTPPVLDSDGSFFLYSRLTVDKSRWQQGNVFSCS VMHEALHNHYTQKSLSLS |

-continued

| SEQ ID NO. | NAME | SEQUENCE |
|---|---|---|
| 337 | ProC289 without signal sequence | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKESGGGGSGRSDNIGPPCPPCPAPEFL GGPSVFLFPPKPKDTLMISRTPEVTCVVVDVSQEDPEV QFNWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIAVEWESNGQP ENNYKTTPPVLDSDGSFFLYSRLTVDKSRWQQGNVFSC SVMHEALHNHYTQKSLSLS |
| 338 | ProC290 without signal sequence | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKESGGGGSGRSDNIESKYGPPCPPCPA PEFLGGPSVFLFPPKPKDTLMISRTPEVTCVVVDVSQE DPEVQFNWYVDGVEVHNAKTKPREEQFNSTYRVVSVLT VLHQDWLNGKEYKCKVSNKGLPSSIEKTISKAKGQPRE PQVYTLPPSQEEMTKNQVSLTCLVKGFYPSDIAVEWES NGQPENNYKTTPPVLDSDGSFFLYSRLTVDKSRWQQGN VFSCSVMHEALHNHYTQKSLSLS |
| 339 | ProC291 without signal sequence | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKESGGGGSGRSDNIGGGSESKYGPPCP PCPAPEFLGGPSVFLFPPKPKDTLMISRTPEVTCVVVD VSQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLTCLVKGFYPSDIAV EWESNGQPENNYKTTPPVLDSDGSFFLYSRLTVDKSRW QQGNVFSCSVMHEALHNHYTQKSLSLS |
| 340 | ProC441 without signal sequence | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKESGRSDNIGPPCPPCPAPEFLGGPSV FLFPPKPKDTLMISRTPEVTCVVVDVSQEDPEVQFNWY VDGVEVHNA |
| 341 | ProC442 without signal sequence | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSF SLSTNLQESLRSKESGRSDNIESKYGPPCPPCPAPEFL GGPSVFLFPPKPKDTLMISRTPEVTCVVVDVSQEDPEV QFNWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIAVEWESNGQP ENNYKTTPPVLDSDGSFFLYSRLTVDKSRWQQGNVFSC SVMHEALHNHYTQKSLSLS |
| 342 | ProC443 without signal sequence | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKESGRSDNIGGGSESKYGPPCPPCPAP EFLGGPSVFLFPPKPKDTLMISRTPEVTCVVVDVSQED PEVQFNWYVDGVEVHNAKTKPREEQFNSTYRVVSVLTV LHQDWLNGKEYKCKVSNKGLPSSIEKTISKAKGQPREP QVYTLPPSQEEMTKNQVSLTCLVKGFYPSDIAVEWESN GQPENNYKTTPPVLDSDGSFFLYSRLTVDKSRWQQGNV FSCSVMHEALHNHYTQKSLSLS |
| 343 | Signal sequence | MRAWIFFLLCLAGRALA |
| 344 | Signal sequence | MALTFALLVALLVLCKSSCSVG |
| 345 | Signal sequence | METDTLLLWVLLLWVPGSTG |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An activatable cytokine construct (ACC) comprising a first monomer construct and a second monomer construct, wherein:
   (a) the first monomer construct comprises a first mature cytokine protein (CP1), a first cleavable moiety (CM1), and a first dimerization domain (DD1);
   (b) the second monomer construct comprises a second mature cytokine protein (CP2), a second cleavable moiety (CM2), and a second dimerization domain (DD2);
   (c) the first monomer construct is a polypeptide comprising, in an N- to C-terminal direction, the CP1, the CM1, and the DD1 and the first monomer construct is characterized in that the CP1 and the DD1 are linked by a Linking Region of no more than 18 amino acids such that the Linking Region of no more than 18 amino acids includes the CM1, further wherein:
      the CP1 is a mature interferon;
      (d) further wherein:
         (i) the second monomer construct is the same as the first monomer construct, and
         (ii) the DD1 and the DD2 are a pair of human IgG Fc domains;
   (e) the DD1 and the DD2 are covalently bound to each other via at least one disulfide bond thereby forming a dimer of the first monomer construct and the second monomer construct; and
   (f) the ACC is characterized by having a reduced level of interferon activity as compared to a corresponding control interferon.

2. The ACC of claim 1, wherein the CP1 is a mature human interferon alpha.

3. The ACC of claim 2, wherein the mature interferon is mature interferon alpha-2b.

4. The ACC of claim 3, wherein the mature interferon comprises a sequence that is at least 95% identical to SEQ ID NO: 1.

5. The ACC of claim 3, wherein the mature interferon alpha comprises the sequence of SEQ ID NO: 1.

6. The ACC of claim 1, wherein the CM1 and the CM2 each comprises no more than 7 amino acids.

7. The ACC of claim 1, wherein each of the CM1 and the CM2 is independently cleavable by a urokinase (uPa) and/or a matrix metalloproteinase (MMP).

8. The ACC of claim 1, wherein the CM1 and the CM2 each comprises a sequence that is at least 85% identical to SEQ ID NO: 100.

9. The ACC of claim 1, wherein the CM1 and the CM2 each comprises a sequence selected from the group consisting of SEQ ID NO: 41, SEQ ID NO: 68, and SEQ ID NO: 100.

10. The ACC of claim 1, wherein the DD1 and the DD2 are a pair of human IgG4 Fc domains.

11. The ACC of claim 1, wherein the DD1 and the DD2 are a pair of human IgG1 or IgG4 Fc domains truncated at the N-terminus to Cysteine 226 as numbered by EU numbering.

12. The ACC of claim 10, wherein the human IgG4 Fc domains comprise a S228P mutation as numbered by EU numbering.

13. The ACC of claim 1, wherein the DD1 and the DD2 each comprises a sequence that is at least 95% identical to SEQ ID NO: 3.

14. The ACC of claim 1, wherein the DD1 and the DD2 each comprises the sequence of SEQ ID NO: 3.

15. The ACC of claim 1, wherein the first and second monomer constructs are covalently bound to each other via at least two disulfide bonds.

16. The ACC of claim 1, wherein the first and second monomer constructs are covalently bound to each other via at least three disulfide bonds.

17. The ACC of claim 1, wherein the first and second monomer constructs are covalently bound to each other via at least four disulfide bonds.

18. The ACC of claim 1, wherein each of the first and second monomer constructs comprises a sequence that is at least 95% identical to SEQ ID NO: 313.

19. An activatable cytokine construct (ACC) comprising a first monomer construct and a second monomer construct, wherein:
   (a) the first monomer construct comprises a first mature cytokine protein (CP1), a first cleavable moiety (CM1), and a first dimerization domain (DD1);
   (b) the second monomer construct comprises a second mature cytokine protein (CP2), a second cleavable moiety (CM2), and a second dimerization domain (DD2);
   (c) the first monomer construct is a polypeptide comprising, in an N- to C-terminal direction, the CP1, the CM1, and the DD1, further wherein:
      (i) each of the first monomer construct and the second monomer construct comprises a Linking Region comprising no more than 18 amino acids, and
      (ii) the CP1 is a mature interferon;
      (d) further wherein:
         (i) the second monomer construct is the same as the first monomer construct, and
         (ii) the DD1 and the DD2 are a pair of human IgG Fc domains;
   (e) the DD1 and the DD2 are covalently bound to each other via at least one disulfide bond thereby forming a dimer of the first monomer construct and the second monomer construct; and
   (f) the ACC is characterized by having a reduced level of interferon activity as compared to a corresponding control interferon, wherein each of the first and second monomer constructs comprises SEQ ID NO: 313.

20. An activatable cytokine construct (ACC) comprising a first monomer construct and a second monomer construct, wherein:
  (a) the first monomer construct comprises a first mature cytokine protein (CP1), a first cleavable moiety (CM1), and a first dimerization domain (DD1) in an N- to C-terminal direction, wherein the CP1 and the CM1 directly abut each other and the CM1 and the DD1 directly abut each other;
  (b) the second monomer construct comprises a second mature cytokine protein (CP2), a second cleavable moiety (CM2), and a second dimerization domain (DD2) in an N- to C-terminal direction, wherein the CP2 and the CM2 directly abut each other and the CM2 and the DD2 directly abut each other;
  (c)
    wherein the CP1 is a mature interferon and
    the CM1 comprises a sequence that is at least 85% identical to SEQ ID: 100,
  (d) further wherein:
    (i) the second monomer construct is the same as the first monomer construct, and
    (ii) the DD1 and DD2 are a pair of human IgG1 or IgG4 Fc domains;
  (e) the DD1 and the DD2 are covalently bound to each other via at least one disulfide bond thereby forming a dimer of the first monomer construct and the second monomer construct; and
  (f) the ACC is characterized by having a reduced level of interferon alpha activity as compared to the interferon alpha activity of PEGylated interferon alpha-2b.

21. An activatable cytokine construct (ACC) that includes a first monomer construct and a second monomer construct, wherein:
  (a) the first monomer construct comprises a first mature cytokine protein (CP1), a first cleavable moiety (CM1), and a first dimerization domain (DD1),
    wherein the CM1 is positioned between the CP1 and the DD1 and the first monomer construct is characterized in that the CP1 and the DD1 are linked by a Linking Region of no more than 18 amino acids such that the Linking Region of no more than 18 amino acids includes the CM1; and
  (b) the second monomer construct comprises a second mature cytokine protein (CP2), a second cleavable moiety (CM2), and a second dimerization domain (DD2), wherein the CM2 is positioned between the CP2 and the DD2 and the second monomer construct is characterized in that the CP2 and the DD2 are linked by a Linking Region of no more than 18 amino acids such that the Linking Region of no more than 18 amino acids includes the CM2; or
  (a) the first monomer construct comprises a first mature cytokine protein (CP1), a first dimerization domain (DD1), and
  (b) the second monomer construct comprises a second mature cytokine protein (CP2), a cleavable moiety (CM), and a second dimerization domain (DD2), wherein the CM is positioned between the CP2 and the DD2, wherein the CM functions as a substrate for a protease and the second monomer construct is characterized in that the CP2 and the DD2 are linked by a Linking Region of no more than 18 amino acids such that the Linking Region of no more than 18 amino acids includes the CM2; or
  (a) the first monomer construct comprises a first mature cytokine protein (CP1), a cleavable moiety (CM), and a first dimerization domain (DD1), wherein the CM is positioned between the CP1 and the DD1 and the first monomer construct is characterized in that the CP1 and the DD1 are linked by a Linking Region of no more than 18 amino acids such that the Linking Region of no more than 18 amino acids includes the CM1, and
  (b) the second monomer construct comprises a second mature cytokine protein (CP2), and a second dimerization domain (DD2),
  wherein the CM functions as a substrate for a protease; or
  (a) the first monomer construct comprises a first mature cytokine protein (CP1), and a first dimerization domain (DD1), and
  (b) the second monomer construct comprises a second mature cytokine protein (CP2), and a second dimerization domain (DD2), wherein the CP1, the CP2, or both CP1 and CP2 include(s) an amino acid sequence that functions as a substrate for a protease and the first monomer construct is characterized in that the CP1 and the DD1 are linked by a Linking Region of no more than 18 amino acids and the second monomer construct is characterized in that the CP2 and the DD2 are linked by a Linking Region of no more than 18 amino acids;
  wherein CP1 and CP2 are mature interfereons;
  wherein the DD1 and the DD2 bind each other thereby forming a dimer of the first monomer construct and the second monomer construct;
  wherein the ACC is characterized by having a reduced level of CP1 or CP2 activity as compared to a control level of the CP1 or CP2 activity, and
  wherein the first monomer construct and the second monomer construct have a structure, wherein CP1 and CP2 are N-terminal to DD1 and DD2, respectively, in each construct.

22. The ACC of claim 21, wherein the DD1 and the DD2 are a pair of Fc domains.

23. The ACC of claim 22, wherein the pair of Fc domains is a pair of human Fc domains.

24. The ACC of claim 23, wherein the human Fc domains are human IgG1 Fc domains, human IgG2 Fc domains, human IgG3 Fc domains, or human IgG4 Fc domains.

25. The ACC of claim 24, wherein the human Fc domains are human IgG4 Fc domains.

26. The ACC of claim 23, wherein the human Fc domains comprise a sequence that is at least 90% identical to SEQ ID NO: 3, SEQ ID NO: 315, or SEQ ID NO: 316.

27. The ACC of claim 23, wherein the human Fc domains comprise SEQ ID NO: 3, SEQ ID NO: 315, or SEQ ID NO: 316.

28. The ACC of claim 21, wherein the CP1 and/or CP2 comprises a sequence that is at least 95% identical to SEQ ID NO: 1.

29. The ACC of claim 21, wherein the CP1 and/or CP2 comprises a sequence of SEQ ID NO: 1.

* * * * *